United States Patent
Baileykobayashi et al.

(10) Patent No.: US 11,313,862 B2
(45) Date of Patent: Apr. 26, 2022

(54) METHOD FOR DIAGNOSING AMYOTROPHIC LATERAL SCLEROSIS USING SIGNAL PEPTIDE AS INDICATOR

(71) Applicants: TOAGOSEI CO., LTD., Tokyo (JP); NATIONAL UNIVERSITY CORPORATION NAGOYA UNIVERSITY, Aichi (JP)

(72) Inventors: Nahoko Baileykobayashi, Tsukuba (JP); Makoto Sawada, Nagoya (JP); Tetsuhiko Yoshida, Tsukuba (JP)

(73) Assignees: Toagosei Co., Ltd., Tokyo (JP); National University Corporation Nagoya University, Nagoya (JP)

( * ) Notice: Subject to any disclaimer, the term of this patent is extended or adjusted under 35 U.S.C. 154(b) by 279 days.

(21) Appl. No.: 16/081,247

(22) PCT Filed: Mar. 2, 2017

(86) PCT No.: PCT/JP2017/008332
§ 371 (c)(1),
(2) Date: Aug. 30, 2018

(87) PCT Pub. No.: WO2017/150681
PCT Pub. Date: Sep. 8, 2017

(65) Prior Publication Data
US 2019/0094236 A1    Mar. 28, 2019

(30) Foreign Application Priority Data
Mar. 3, 2016 (JP) .............................. JP2016-041054

(51) Int. Cl.
*G01N 33/68* (2006.01)
*G01N 27/62* (2021.01)
(Continued)

(52) U.S. Cl.
CPC ......... *G01N 33/6818* (2013.01); *G01N 27/62* (2013.01); *G01N 33/6848* (2013.01);
(Continued)

(58) Field of Classification Search
CPC ........... G01N 33/6818; G01N 33/6851; G01N 33/6896; G01N 33/6848; G01N 27/62;
(Continued)

(56) References Cited

U.S. PATENT DOCUMENTS

2003/0143191 A1 * 7/2003 Bell .................... A61P 31/18
424/85.1
2003/0208058 A1 * 11/2003 Fiscella .................. A61P 15/08
536/23.5
(Continued)

FOREIGN PATENT DOCUMENTS

EP    1522856 A1 * 4/2005 ........... C07K 14/595
JP    5069804        8/2012
(Continued)

OTHER PUBLICATIONS

Japanese Office Action dated Feb. 18, 2021 in JP Application No. 2018-503408.
(Continued)

*Primary Examiner* — Jesse P Frumkin
(74) *Attorney, Agent, or Firm* — Occhiuti & Rohlicek LLP

(57) ABSTRACT

The method for aiding ALS detection provided by the present invention includes determining a profile of signal peptides contained in a bodily fluid from a test subject, and comparing the signal peptide profile thus determined for the test subject with a previously-determined profile of signal peptides in a bodily fluid from a healthy subject. The presence of a difference between the signal peptide profile of the test subject and the signal peptide profile of the healthy
(Continued)

subject at a specific molecular weight is then associated with the test subject's suffering from or developing ALS.

12 Claims, 1 Drawing Sheet

Specification includes a Sequence Listing.

(51) Int. Cl.
  *G16H 50/30* (2018.01)
  *G16H 50/20* (2018.01)
  *C07K 7/00* (2006.01)

(52) U.S. Cl.
  CPC ..... *G01N 33/6851* (2013.01); *G01N 33/6896* (2013.01); *G16H 50/20* (2018.01); *G16H 50/30* (2018.01); *C07K 7/00* (2013.01); *G01N 2800/28* (2013.01)

(58) Field of Classification Search
  CPC .... G01N 2800/28; G01N 27/623; C07K 7/00; Y02A 90/10; G06F 19/30; G06F 19/32; G06F 19/34; G06Q 50/22; G06Q 50/24; G16H 50/00; G16H 50/20; G16H 50/30; G16H 50/50; G16H 50/70; G16H 50/80
  See application file for complete search history.

(56) References Cited

U.S. PATENT DOCUMENTS

| | | | | |
|---|---|---|---|---|
| 2004/0266674 | A1* | 12/2004 | Mills | C07K 14/472 |
| | | | | 435/69.3 |
| 2005/0118586 | A1* | 6/2005 | Bejanin | C07K 14/47 |
| | | | | 435/6.16 |
| 2005/0208619 | A1* | 9/2005 | Rosen | A61P 35/02 |
| | | | | 435/69.1 |
| 2005/0244904 | A1 | 11/2005 | Ng | |
| 2005/0266467 | A1* | 12/2005 | Roy | G01N 33/564 |
| | | | | 435/6.12 |
| 2007/0298998 | A1* | 12/2007 | Paige | G01N 33/6896 |
| | | | | 514/17.7 |
| 2008/0145941 | A1* | 6/2008 | Bateman | A61K 49/0004 |
| | | | | 436/71 |
| 2013/0196924 | A1* | 8/2013 | Bucci | C07K 14/472 |
| | | | | 514/17.7 |
| 2013/0316366 | A1* | 11/2013 | Yu | G01N 33/582 |
| | | | | 435/7.2 |
| 2014/0328824 | A1* | 11/2014 | Porgador | A61P 25/28 |
| | | | | 424/94.61 |
| 2017/0082579 | A1 | 3/2017 | Sawada | |
| 2017/0088593 | A1* | 3/2017 | Ildefonso | A61K 38/1709 |

FOREIGN PATENT DOCUMENTS

| | | | |
|---|---|---|---|
| JP | 5422785 | 12/2013 | |
| WO | WO-0136432 A2 * | 5/2001 | ............... A61P 1/00 |
| WO | 2005042761 | 5/2005 | |
| WO | 2015178249 | 11/2015 | |
| WO | 2016032319 | 3/2016 | |

OTHER PUBLICATIONS

Butterfield, D. Allan, Liqing Gu, Fabio Di Domenico, and Rena AS Robinson. "Mass spectrometry and redox proteomics: applications in disease." Mass spectrometry reviews 33, No. 4 (2014): 277-301.

* cited by examiner

METHOD FOR DIAGNOSING AMYOTROPHIC LATERAL SCLEROSIS USING SIGNAL PEPTIDE AS INDICATOR

CROSS REFERENCE TO RELATED APPLICATIONS

This application is a National Phase under 35 USC 371 of International Application No. PCT/JP2017/008332 filed on Mar. 2, 2017, which claims priority to Japanese Application No. 2016-041054 filed on Mar. 3, 2016, the contents of which are hereby incorporated by reference in their entirety.

TECHNICAL FIELD

The present invention relates to a method for diagnosing amyotrophic lateral sclerosis using a signal peptide as an indicator.

The priority claim for this application is based on Japanese Patent Application No. 2016-041054 filed on Mar. 3, 2016, and the entire contents of that Japanese application are herein incorporated by reference.

BACKGROUND ART

Neurodegenerative diseases are diseases involving impairment of specific nerves, and are characterized by symptoms of reduced cognitive function, ataxia, and involuntary movement. Such neurodegenerative diseases include Alzheimer's disease, Parkinson's disease, amyotrophic lateral sclerosis (ALS) and the like.

Amyotrophic lateral sclerosis (hereunder also called ALS) is a progressive neurodegenerative disease involving selective impairment of motor nerves (upper motor nerves, lower motor nerves). Typically, systemic muscle atrophy and muscle weakness (that is, impaired motor function) occur. The principal clinical symptoms of ALS include spasms, tendon hyperreflexia, fasciculation, gait disturbance, language disorder (articulation disorder), swallowing disorder, respiratory disorder and the like.

ALS is generally diagnosed based on the presence or absence and rate of progress of such clinical symptoms of ALS, and by excluding other diseases that impair motor function and the like. For example, it is diagnosed by an appropriate combination of nerve conduction testing, electromyography, muscle biopsy, neuroimaging (CT, MRI or the like), blood testing, spinal fluid testing and the like.

CITATION LIST

Patent Literature

Patent Literature 1: Japanese Patent No. 5069804
Patent Literature 2: Japanese Patent No. 5422785

SUMMARY OF INVENTION

Technical Problem

However, early ALS and atypical ALS may be difficult to distinguish from other diseases involving impaired motor function. Moreover, because ALS is a rare disease, some physicians (typically family doctors) may have little experience with diagnosing (or treating) ALS patients, and may be unaccustomed to diagnosis. For these reasons, a highly accurate diagnosis of ALS may be difficult even when ALS diagnosis is attempted based on a combination of multiple tests as described above. Even specialists run the risk of overlooking ALS or misdiagnosing another disease as ALS.

When ALS is overlooked (diagnosed as another disease), not only is treatment for ALS delayed, but unnecessary treatment (such as surgery, medication or the like) may be performed. When another disease (typically, another disease involving impaired motor function) is misdiagnosed as ALS, moreover, the opportunity to treat the original disease appropriately may be lost.

Furthermore, the aforementioned neuroimaging (CT or MRI for example) requires specialized and expensive medical equipment, and can only be performed at a limited number of medical facilities. Judging the results of such imaging is also an advanced skill. And because there are also few specialists (or medical facilities) familiar with ALS diagnosis (or treatment), visiting such a medical facility in order to check for ALS represents a serious burden for the patient (suspected ALS sufferer).

Because ALS is difficult to diagnose, moreover, a long time may elapse between the original recognition of symptoms by the patient (suspected ALS sufferer) or the initial diagnosis and the definite ALS diagnosis. Consequently, in some cases it is difficult to initiate early treatment (care) for ALS.

Under these circumstances, there has been demand in recent years for the identification and use of biomarkers that can provide useful information for ALS diagnosis. The specificity and sensitivity of diagnosis can be expected to improve when ALS is diagnosed with such biomarkers. It is also expected that by diagnosing ALS with such biomarkers, it will be possible to shorten the time required for ALS diagnosis.

For example, Patent Literature 1 describes a method using a urinary metabolite (tPGDM) of prostaglandin D2 as an ALS biomarker. Although there has been much research of this kind into the identification and use of biomarkers useful for ALS diagnosis, however, none has yet been incorporated into routine clinical testing due to problems of accuracy, reliability and the like.

It is an object of the present invention to provide a new method that can aid in the detection of ALS, as well as a biomarker for use in this method. It is another object to provide an ALS testing composition and ALS testing kit for use in this method for aiding detection of ALS.

Solution to Problem

Focusing on signal peptides in a bodily fluid, the inventors carried out intensive studies on the signal peptides present in the bodily fluid with the aim of establishing methods of diagnosing ALS using such signal peptides as indicators. As a result, we discovered differences in the presence and absence and abundance of specific signal peptides between the bodily fluids of ALS patients and the bodily fluids of healthy subjects. We then perfected the present invention after finding that useful data for diagnosing ALS could be obtained by using these specific signal peptides as indicators.

First, the inventors discovered that the profiles of signal peptides in the bodily fluids of ALS patients differed from the profiles of signal peptides in the bodily fluids of healthy subjects. Therefore, the first embodiment of the present invention provides a method for aiding ALS detection, the method including determining a profile of signal peptides in the molecular weight range of 1000 to 3500 from signal peptides contained in a bodily fluid from a test subject, and comparing the signal peptide profile thus determined for the test subject with a previously-determined profile of signal peptides in a bodily fluid from a healthy subject. In this method, the presence of a difference between the signal peptide profile of the test subject and the signal peptide profile of the healthy subject at any of the following molecular weights is associated with the test subject's suffering from or developing ALS (typically, the difference suggests that the test subject suffers from or has developed ALS):
1405.71±2, 1406.49±2, 1409.40±2, 1410.97±2, 1418.70±2, 1426.68±2, 1437.62±2, 1445.77±2, 1451.61±2, 1456.44±2, 1458.88±2, 1466.24±2, 1468.86±2, 1472.12±2, 1476.87±2, 1482.60±2, 1493.58±2, 1495.42±2, 1496.52±2, 1497.16±2, 1498.88±2, 1502.40±2, 1505.52±2, 1508.76±2, 1510.50±2, 1516.64±2, 1521.93±2, 1529.32±2, 1530.37±2, 1533.52±2, 1539.36±2, 1544.22±2, 1553.72±2, 1555.72±2, 1560.24±2, 1566.20±2, 1567.20±2, 1567.74±2, 1575.70±2, 1578.07±2, 1580.91±2, 1589.58±2, 1592.55±2, 1597.25±2, 1608.53±2, 1609.36±2, 1610.62±2, 1616.12±2, 1629.15±2, 1639.39±2, 1640.36±2, 1646.58±2, 1655.72±2, 1657.97±2, 1659.24±2, 1660.46±2, 1662.16±2, 1679.09±2, 1682.54±2, 1683.12±2, 1687.34±2, 1688.14±2, 1691.08±2, 1691.75±2, 1694.76±2, 1695.74±2, 1700.65±2, 1702.19±2, 1705.53±2, 1708.77±2, 1712.10±2, 1714.63±2, 1715.56±2, 1719.51±2, 1721.61±2, 1726.31±2, 1737.85±2, 1739.71±2, 1743.69±2, 1761.79±2, 1769.93±2, 1774.13±2, 1775.70±2, 1786.39±2, 1788.03±2, 1790.80±2, 1796.23±2, 1797.49±2, 1800.34±2, 1801.79±2, 1804.45±2, 1810.72±2, 1812.31±2, 1813.77±2, 1817.26±2, 1818.66±2, 1819.34±2, 1819.93±2, 1821.71±2, 1822.73±2, 1829.48±2, 1831.81±2, 1832.41±2, 1836.18±2, 1837.33±2, 1840.84±2, 1849.81±2, 1854.68±2, 1858.34±2, 1864.19±2, 1866.06±2, 1875.28±2, 1876.50±2, 1878.25±2, 1890.21±2, 1891.32±2, 1893.00±2, 1904.69±2, 1911.46±2, 1913.68±2, 1916.02±2, 1919.35±2, 1927.13±2, 1931.84±2, 1934.86±2, 1935.52±2, 1936.83±2, 1937.87±2, 1941.22±2, 1944.97±2, 1948.39±2, 1952.47±2, 1957.80±2, 1962.82±2, 1969.82±2, 1972.54±2, 1975.58±2, 1976.51±2, 1977.70±2, 1979.29±2, 1988.46±2, 1991.91±2, 1995.37±2, 2009.91±2, 2011.18±2, 2013.86±2, 2023.97±2, 2027.73±2, 2030.95±2, 2032.69±2, 2039.29±2, 2043.12±2, 2045.68±2, 2051.76±2, 2055.50±2, 2059.05±2, 2062.98±2, 2065.57±2, 2066.09±2, 2074.03±2, 2075.32±2, 2079.80±2, 2083.74±2, 2084.36±2, 2085.85±2, 2089.53±2, 2092.25±2, 2092.80±2, 2097.03±2, 2099.42±2, 2111.39±2, 2113.10±2, 2115.77±2, 2120.37±2, 2126.55±2, 2137.63±2, 2139.15±2, 2140.48±2, 2143.42±2, 2146.46±2, 2149.85±2, 2151.02±2, 2160.22±2, 2161.68±2, 2167.09±2, 2167.78±2, 2168.75±2, 2173.75±2, 2177.51±2, 2179.25±2, 2184.93±2, 2185.65±2, 2186.28±2, 2190.18±2, 2191.02±2, 2192.84±2, 2196.47±2, 2199.82±2, 2201.22±2, 2204.02±2, 2207.10±2, 2211.58±2, 2216.77±2, 2218.45±2, 2219.30±2, 2220.56±2, 2222.74±2, 2226.96±2, 2228.22±2, 2231.60±2, 2239.71±2, 2244.01±2, 2251.78±2, 2254.83±2, 2256.53±2, 2261.91±2, 2266.45±2, 2268.58±2, 2274.97±2, 2276.04±2, 2278.67±2, 2281.09±2, 2285.01±2, 2289.43±2, 2290.85±2, 2292.35±2, 2295.92±2, 2296.92±2, 2301.71±2, 2302.50±2, 2303.21±2, 2305.43±2, 2307.22±2, 2314.24±2, 2314.81±2, 2317.68±2, 2325.30±2, 2327.73±2, 2341.14±2, 2342.87±2, 2344.45±2, 2351.97±2, 2353.99±2, 2355.29±2, 2357.54±2, 2367.75±2, 2375.59±2, 2378.35±2, 2380.39±2, 2393.64±2, 2402,11±2, 2404.01±2, 2406.49±2, 2412.79±2, 2414.25±2, 2415.20±2, 2416.30±2, 2431.13±2, 2434.36±2, 2438.19±2, 2439.22±2, 2444.37±2, 2451.90±2, 2453.96±2, 2455.44±2, 2456.62±2, 2459.43±2, 2462.31±2, 2464.16±2, 2470.97±2, 2478.17±2, 2479.28±2, 2484.18±2, 2500.40±2, 2502.64±2, 2504.73±2, 2507.42±2, 2509.21±2, 2515.26±2, 2517.43±2, 2519.07±2, 2527.31±2, 2531.06±2, 2532.26±2, 2546.08±2, 2554.96±2, 2559.48±2, 2564.01±2, 2571.26±2, 2578.45±2, 2581.25±2, 2583.37±2, 2584.81±2, 2587.01±2, 2588.90±2, 2593.68±2, 2596.11±2, 2603.33±2, 2608.20±2, 2613.31±2, 2614.91±2, 2622.46±2, 2629.26±2, 2633.69±2, 2634.61±2, 2640.51±2, 2641.73±2, 2652.85±2, 2655.08±2, 2665.15±2, 2670.00±2, 2682.80±2, 2696.41±2, 2697.73±2, 2698.27±2, 2699.82±2, 3302.01±2, 3303.21±2, 3309.84±2, 3323.89±2, 3330.34±2, 3337.92±2, 3366.84±2, 3370.39±2, 3378.18±2, 3380.43±2 and 3384.77±2.

In this Description, a "signal peptide profile" is a data set relating to the presence of multiple signal peptides within a specific molecular weight range (whether the signal peptides are present, and the abundance thereof). Typically, the multiple signal peptides are distinguished (classified) based on their molecular weights.

Such a signal peptide profile can be determined by mass spectrometry for example, and represented as a mass spectrum. A signal peptide profile can also be determined by another analysis method based on the physiochemical properties or biochemical properties of the signal peptides. For example, the signal peptides can be determined based on differences in their electrophoretic properties in two-dimensional electrophoresis, and represented in the form of multiple spots confirmed on the two-dimensional electrophoresis gel. Alternatively, the signal peptide profile can be determined by immunological methods using antibodies to the signal peptides (preferably using a protein microarray capable of analyzing multiple proteins simultaneously).

This signal peptide profile need not include data relating to all signal peptides present within a specific molecular weight range, and need only include data relating to signal peptides having molecular weights that are subject to comparison. Thus, the signal peptide profile includes data relating to 2 or 3 or more, or at least 5, or at least 10, or at least 20, or at least 30, or at least 40, or at least 50, or at least 60, or at least 70, or at least 80, or at least 90, or at least 100 signal peptides.

With the method for aiding ALS detection disclosed here, useful data for determining whether or not a test subject suffers from or has developed ALS can be obtained by a simple method in which a profile of signal peptides contained in a bodily fluid from the test subject is determined, and this signal peptide profile is compared with the aforementioned signal peptide profile from a healthy subject. This method for aiding ALS detection can be used favorably for predicting, diagnosing (early diagnosis) and initiating treatment for ALS, and as a follow-up indicator after the start of treatment (typically, as an indicator for determining the effects of treatment).

Because this method is an in vitro test using a bodily fluid collected from a test subject, it does not require that the subject (patient) personally appear at a facility capable of obtaining the signal peptide profile from the bodily fluid. Thus, the method for aiding ALS detection described here can be implemented at many medical facilities.

Moreover, with this method the likelihood that a test subject suffers from or has developed ALS is indicated as the result of a comprehensive analysis of the determined signal peptide profile. Therefore, this method can provide highly reliable data for purposes of ALS diagnosis.

The inventors have confirmed that the likelihood that a test subject suffers from or has developed ALS is greater when certain signal peptides specified by specific molecular weights are more abundant in the signal peptide profile of the test subject. That is, in a preferred embodiment of the method for aiding ALS detection disclosed here as the first embodiment, an increase in the abundance of a signal peptide specified by any of the following molecular weights in the signal peptide profile of the test subject in comparison with the signal peptide profile of the healthy subject is associated with the test subject's suffering from or developing ALS (typically, suggests that the test subject suffers from or has developed ALS):
1405.71±2, 1406.49±2, 1409.40±2, 1410.97±2, 1418.70±2, 1426.68±2, 1437.62±2, 1445.77±2, 1451.61±2, 1456.44±2, 1458.88±2, 1466.24±2, 1468.86±2, 1472.12±2, 1476.87±2, 1482.60±2, 1493.58±2, 1495.42±2, 1496.52±2, 1498.88±2, 1502.40±2, 1505.52±2, 1508.76±2, 1510.50±2, 1516.64±2, 1521.93±2, 1529.32±2, 1530.37±2, 1533.52±2, 1539.36±2, 1544.22±2, 1553.72±2, 1555.72±2, 1560.24±2, 1566.20±2, 1567.20±2, 1575.70±2, 1578.07±2, 1580.91±2, 1589.58±2, 1592.55±2, 1597.25±2, 1608.53±2, 1609.36±2, 1610.62±2, 1616.12±2, 1629.15±2, 1639.39±2, 1640.36±2, 1646.58±2, 1655.72±2, 1657.97±2, 1659.24±2, 1660.46±2, 1662.16±2, 1679.09±2, 1682.54±2, 1683.12±2, 1687.34±2, 1688.14±2, 1691.08±2, 1691.75±2, 1694.76±2, 1695.74±2, 1700.65±2, 1702.19±2, 1708.77±2, 1712.10±2, 1714.63±2, 1715.56±2, 1719.51±2, 1721.61±2, 1726.31±2, 1737.85±2, 1739.71±2, 1743.69±2, 1761.79±2, 1769.93±2, 1774.13±2, 1775.70±2, 1786.39±2, 1788.03±2, 1790.80±2, 1796.23±2, 1797.49±2, 1800.34±2, 1801.79±2, 1804.45±2, 1810.72±2, 1812.3±21, 1813.77±2, 1817.26±2, 1818.66±2, 1819.93±2, 1821.71±2, 1822.73±2, 1829.48±2, 1832.41±2, 1836.18±2, 1837.33±2, 1840.84±2, 1849.81±2, 1854.68±2, 1858.34±2, 1864.19±2, 1866.06±2, 1875.28±2, 1876.50±2, 1878.25±2, 1890.21±2, 1891.32±2, 1893.00±2, 1904.69±2, 1911.46±2, 1913.68±2, 1916.02±2, 1919.35±2, 1927.13±2, 1931.84±2, 1934.86±2, 1936.83±2, 1937.87±2, 1941.22±2, 1944.97±2, 1948.39±2, 1952.47±2, 1957.80±2, 1962.82±2, 1969.82±2, 1972.54±2, 1975.58±2, 1976.51±2, 1977.70±2, 1979.29±2, 1988.46±2, 1991.91±2, 1995.37±2, 2009.91±2, 2011.18±2, 2013.86±2, 2023.97±2, 2027.73±2, 2030.95±2, 2032.69±2, 2039.29±2, 2043.12±2, 2045.68±2, 2051.76±2, 2059.05±2, 2062.98±2, 2066.09±2, 2074.03±2, 2075.32±2, 2079.80±2, 2083.74±2, 2085.85±2, 2089.53±2, 2092.80±2, 2097.03±2, 2099.42±2, 2111.39±2, 2113.10±2, 2115.77±2, 2120.37±2, 2126.55±2, 2137.63±2, 2139.15±2, 2143.42±2, 2146.46±2, 2149.85±2, 2151.02±2, 2160.22±2, 2161.68±2, 2167.09±2, 2168.75±2, 2173.75±2, 2177.51±2, 2179.25±2, 2185.65±2, 2186.28±2, 2190.18±2, 2191.02±2, 2192.84±2, 2196.47±2, 2199.82±2, 2201.22±2, 2204.02±2, 2207.10±2, 2211.58±2, 2216.77±2, 2218.45±2, 2219.30±2, 2220.56±2, 2222.74±2, 2226.96±2, 2228.22±2, 2231.60±2, 2239.71±2, 2244.01±2, 2251.78±2, 2254.83±2, 2256.53±2, 2261.91±2, 2266.45±2, 2268.58±2, 2274.97±2, 2276.04±2, 2278.67±2, 2281.09±2, 2285.01±2, 2289.43±2, 2290.85±2, 2292.35±2, 2295.92±2, 2296.92±2, 2301.71±2, 2302.50±2, 2303.21±2, 2305.43±2, 2307.22±2, 2314.24±2, 2317.68±2, 2325.30±2, 2341.14±2, 2342.87±2, 2344.45±2, 2351.97±2, 2353.99±2, 2355.29±2, 2357.54±2, 2367.75±2, 2375.59±2, 2378.35±2, 2380.39±2, 2393.64±2, 2402.11±2, 2404.01±2, 2406.49±2, 2412.79±2, 2414.25±2, 2415.20±2, 2416.30±2, 2431.13±2, 2434.36±2, 2438.19±2, 2439.22±2, 2444.37±2, 2451.90±2, 2453.96±2, 2455.44±2, 2456.62±2, 2459.43±2, 2462.31±2, 2464.16±2, 2470.97±2, 2478.17±2, 2479.28±2, 2484.18±2, 2500.40±2, 2502.64±2, 2504.73±2, 2507.42±2, 2509.21±2, 2515.26±2, 2517.43±2, 2519.07±2, 2527.31±2, 2531.06±2, 2532.26±2, 2546.08±2, 2554.96±2, 2559.48±2, 2564.01±2, 2571.26±2, 2578.45±2, 2581.25±2, 2583.37±2, 2584.81±2, 2587.01±2, 2588.90±2, 2593.68±2, 2596.11±2, 2603.33±2, 2608.20±2, 2613.31±2, 2614.91±2, 2622.46±2, 2629.26±2, 2633.69±2, 2634.61±2, 2640.51±2, 2641.73±2, 2652.85±2, 2655.08±2, 2665.15±2, 2670.00±2, 2682.80±2, 2696.41±2, 2698.27±2, 2699.82±2, 3302.01±2, 3303.21±2, 3323.89±2, 3330.34±2, 3337.92±2, 3366.84±2, 3370.39±2, 3378.18±2, 3380.43±2 and 3384.77±2.

The inventors have also confirmed that in the signal peptide profile of a test subject, the likelihood that the test subject suffers from or has developed ALS is greater when certain signal peptides specified by specific molecular weights are less abundant. That is, in a preferred embodiment of the method for aiding ALS detection disclosed here as the first embodiment, a decrease in the abundance of a signal peptide specified by any of the following molecular weights in the signal peptide profile of the test subject in comparison with the signal peptide profile of the healthy subject is associated with the test subject's suffering from or developing ALS (typically, suggests that the test subject suffers from or has developed ALS):
1497.16±2, 1567.74±2, 1705.53±2, 1819.34±2, 1831.81±2, 1935.52±2, 2055.50±2, 2065.57±2, 2084.36±2, 2092.25±2, 2140.48±2, 2167.78±2, 2184.93±2, 2314.81±2, 2327.73±2, 2697.73±2 and 3309.84±2.

In a preferred embodiment of the method for aiding ALS detection disclosed here as the first embodiment, the signal peptide profile is tested (determined) with a mass spectrometer.

Comprehensive analysis of signal peptides in a bodily fluid can be accomplished easily and with high accuracy by using a mass spectrometer. That is, a profile of signal peptides in the bodily fluid can be determined easily and with high accuracy by using a mass spectrometer.

Patent Literature 2 describes a method for using mass spectrometry to detect cancer, but does not describe detecting ALS.

In another preferred embodiment of the method for aiding ALS detection disclosed here as the first embodiment, the method includes immobilizing a bodily fluid from a test subject on a thermoplastic resin before the signal peptide profile is determined, and the profile of signal peptides present in the bodily fluid immobilized on the thermoplastic resin is determined by matrix assisted laser desorption/ionization-time of flight mass spectrometry (MALDI-TOFMS).

Conventionally, it was believed that when mass spectrometry is performed by irradiating a sample immobilized on a thermoplastic resin with an ionizing laser, the thermoplastic resin on which the sample is immobilized is ionized together with the sample, reducing the accuracy of the mass spectrometry. However, the inventors' researches have confirmed that ionization of signal peptides can be promoted and accurate mass spectrometry can be accomplished by performing mass spectrometry with the bodily fluid to be analyzed immobilized on a thermoplastic resin.

That is, even when a bodily fluid contains signal peptides that are difficult to ionize, a signal peptide profile that includes these signal peptides can be determined favorably by analysis using MALDI-TOFMS with the bodily fluid immobilized on a thermoplastic resin.

After further research into signal peptide profiles in the bodily fluids of ALS patients, the inventors confirmed that body fluids from ALS patients and body fluids from healthy subjects differ in the degree of abundance of specific signal peptides.

Thus, the second embodiment of the present invention provides a method for aiding ALS detection, the method including testing the presence or absence of an ALS-associated signal peptide in a bodily fluid from a test subject or the degree of abundance of the ALS-associated signal peptide when present.

The ALS-associated signal peptide is a signal peptide the presence or absence or degree of abundance of which in a bodily fluid from an ALS patient differs from the presence or absence or reference level set for degree of abundance of the same signal peptide in a bodily fluid from a healthy subject. The molecular weight of this ALS-associated signal peptide is:
1405.71±2, 1406.49±2, 1409.40±2, 1410.97±2, 1418.70±2, 1426.68±2, 1437.62±2, 1445.77±2, 1451.61±2, 1456.44±2, 1458.88±2, 1466.24±2, 1468.86±2, 1472.12±2, 1476.87±2, 1482.60±2, 1493.58±2, 1495.42±2, 1496.52±2, 1497.16±2, 1498.88±2, 1502.40±2, 1505.52±2, 1508.76±2, 1510.50±2, 1516.64±2, 1521.93±2, 1529.32±2, 1530.37±2, 1533.52±2, 1539.36±2, 1544.22±2, 1553.72±2, 1555.72±2, 1560.24±2, 1566.20±2, 1567.20±2, 1567.74±2, 1575.70±2, 1578.07±2, 1580.91±2, 1589.58±2, 1592.55±2, 1597.25±2, 1608.53±2, 1609.36±2, 1610.62±2, 1616.12±2, 1629.15±2, 1639.39±2, 1640.36±2, 1646.58±2, 1655.72±2, 1657.97±2, 1659.24±2, 1660.46±2, 1662.16±2, 1679.09±2, 1682.54±2, 1683.12±2, 1687.34±2, 1688.14±2, 1691.08±2, 1691.75±2, 1694.76±2, 1695.74±2, 1700.65±2, 1702.19±2, 1705.53±2, 1708.77±2, 1712.10±2, 1714.63±2, 1715.56±2, 1719.51±2, 1721.61±2, 1726.31±2, 1737.85±2, 1739.71±2, 1743.69±2, 1761.79±2, 1769.93±2, 1774.13±2, 1775.70±2, 1786.39±2, 1788.03±2, 1790.80±2, 1796.23±2, 1797.49±2, 1800.34±2, 1801.79±2, 1804.45±2, 1810.72±2, 1812.31±2, 1813.77±2, 1817.26±2, 1818.66±2, 1819.34±2, 1819.93±2, 1821.71±2, 1822.73±2, 1829.48±2, 1831.81±2, 1832.41±2, 1836.18±2, 1837.33±2, 1840.84±2, 1849.81±2, 1854.68±2, 1858.34±2, 1864.19±2, 1866.06±2, 1875.28±2, 1876.50±2, 1878.25±2, 1890.21±2, 1891.32±2, 1893.00±2, 1904.69±2, 1911.46±2, 1913.68±2, 1916.02±2, 1919.35±2, 1927.13±2, 1931.84±2, 1934.86±2, 1935.52±2, 1936.83±2, 1937.87±2, 1941.22±2, 1944.97±2, 1948.39±2, 1952.47±2, 1957.80±2, 1962.82±2, 1969.82±2, 1972.54±2, 1975.58±2, 1976.51±2, 1977.70±2, 1979.29±2, 1988.46±2, 1991.91±2, 1995.37±2, 2009.91±2, 2011.18±2, 2013.86±2, 2023.97±2, 2027.73±2, 2030.95±2, 2032.69±2, 2039.29±2, 2043.12±2, 2045.68±2, 2051.76±2, 2055.50±2, 2059.05±2, 2062.98±2, 2065.57±2, 2066.09±2, 2074.03±2, 2075.32±2, 2079.80±2, 2083.74±2, 2084.36±2, 2085.85±2, 2089.53±2, 2092.25±2, 2092.80±2, 2097.03±2, 2099.42±2, 2111.39±2, 2113.10±2, 2115.77±2, 2120.37±2, 2126.55±2, 2137.63±2, 2139.15±2, 2140.48±2, 2143.42±2, 2146.46±2, 2149.85±2, 2151.02±2, 2160.22±2, 2161.68±2, 2167.09±2, 2167.78±2, 2168.75±2, 2173.75±2, 2177.51±2, 2179.25±2, 2184.93±2, 2185.65±2, 2186.28±2, 2190.18±2, 2191.02±2, 2192.84±2, 2196.47±2, 2199.82±2, 2201.22±2, 2204.02±2, 2207.10±2, 2211.58±2, 2216.77±2, 2218.45±2, 2219.30±2, 2220.56±2, 2222.74±2, 2226.96±2, 2228.22±2, 2231.60±2, 2239.71±2, 2244.01±2, 2251.78±2, 2254.83±2, 2256.53±2, 2261.91±2, 2266.45±2, 2268.58±2, 2274.97±2, 2276.04±2, 2278.67±2, 2281.09±2, 2285.01±2, 2289.43±2, 2290.85±2, 2292.35±2, 2295.92±2, 2296.92±2, 2301.71±2, 2302.50±2, 2303.21±2, 2305.43±2, 2307.22±2, 2314.24±2, 2314.81±2, 2317.68±2, 2325.30±2, 2327.73±2, 2341.14±2, 2342.87±2, 2344.45±2, 2351.97±2, 2353.99±2, 2355.29±2, 2357.54±2, 2367.75±2, 2375.59±2, 2378.35±2, 2380.39±2, 2393.64±2, 2402.11±2, 2404.01±2, 2406.49±2, 2412.79±2, 2414.25±2, 2415.20±2, 2416.30±2, 2431.13±2, 2434.36±2, 2438.19±2, 2439.22±2, 2444.37±2, 2451.90±2, 2453.96±2, 2455.44±2, 2456.62±2, 2459.43±2, 2462.31±2, 2464.16±2, 2470.97±2, 2478.17±2, 2479.28±2, 2484.18±2, 2500.40±2, 2502.64±2, 2504.73±2, 2507.42±2, 2509.21±2, 2515.26±2, 2517.43±2, 2519.07±2, 2527.31±2, 2531.06±2, 2532.26±2, 2546.08±2, 2554.96±2, 2559.48±2, 2564.01±2, 2571.26±2, 2578.45±2, 2581.25±2, 2583.37±2, 2584.81±2, 2587.01±2, 2588.90±2, 2593.68±2, 2596.11±2, 2603.33±2, 2608.20±2, 2613.31±2, 2614.91±2, 2622.46±2, 2629.26±2, 2633.69±2, 2634.61±2, 2640.51±2, 2641.73±2, 2652.85±2, 2655.08±2, 2665.15±2, 2670.00±2, 2682.80±2, 2696.41±2, 2697.73±2, 2698.27±2, 2699.82±2, 3302.01±2, 3303.21±2, 3309.84±2, 3323.89±2, 3330.34±2, 3337.92±2, 3366.84±2, 3370.39±2, 3378.18±2, 3380.43±2 or 3384.77±2.

With this method, the likelihood that a test subject suffers from or has developed ALS can be easily investigated by a simple method in which the presence or absence of the ALS-associated signal peptide, or the abundance thereof when present, is tested in a bodily fluid from the test subject. This method for aiding ALS detection can be used favorably for predicting, diagnosing (early diagnosis) and initiating treatment for ALS, and as a follow-up indicator after the start of treatment (typically, as an indicator for determining the effects of treatment).

Because this method is an in vitro test method using a bodily fluid collected from a test subject, it does not require that the subject (patient) personally appear at a facility capable of testing the presence or absence or degree of abundance of the signal peptide in the bodily fluid. Thus, the method for aiding ALS detection described here can be implemented at many medical facilities.

In a preferred embodiment of the method for aiding ALS detection disclosed here as the second embodiment, an amino acid sequence constituting the ALS-associated signal peptide is any of amino acid sequences represented by SEQ ID Nos: 1 to 1580.

A signal peptide comprising any of the amino acid sequences represented by SEQ ID Nos: 1 to 1580 is a typical example of a signal peptide corresponding to the molecular weight of the ALS-associated signal peptide. That is, the signal peptides comprising the amino acid sequences represented by SEQ ID Nos: 1 to 1580 above are suitable as the ALS-associated signal peptide.

The ALS-associated signal peptide disclosed here is a signal peptide the presence or absence or degree of abundance of which in a bodily fluid from an ALS patient has been confirmed by the inventors to differ from a reference level set based on the presence or absence and degree of abundance of the same signal peptide in a bodily fluid from a healthy subject. Thus, this ALS-associated signal peptide can be used as a biomarker for diagnosing ALS.

That is, another aspect of the present invention provides a biomarker for use in diagnosing ALS. This biomarker is a signal peptide comprising any of the amino acid sequences represented by SEQ ID Nos: 1 to 1580.

In another preferred embodiment of the method for aiding ALS detection disclosed here as the second embodiment, the degree of abundance of any of the ALS-associated signal peptides having the following molecular weights out of the tested ALS-associated signal peptides in the bodily fluid from the test subject is confirmed to be high in comparison with the reference level:
1405.71±2, 1406.49±2, 1409.40±2, 1410.97±2, 1418.70±2, 1426.68±2, 1437.62±2, 1445.77±2, 1451.61±2, 1456.44±2, 1458.88±2, 1466.24±2, 1468.86±2, 1472.12±2, 1476.87±2, 1482.60±2, 1493.58±2, 1495.42±2, 1496.52±2, 1498.88±2, 1502.40±2, 1505.52±2, 1508.76±2, 1510.50±2, 1516.64±2, 1521.93±2, 1529.32±2, 1530.37±2, 1533.52±2, 1539.36±2, 1544.22±2, 1553.72±2, 1555.72±2, 1560.24±2, 1566.20±2, 1567.20±2, 1575.70±2, 1578.07±2, 1580.91±2, 1589.58±2, 1592.55±2, 1597.25±2, 1608.531±2, 1609.36±2, 1610.62±2, 1616.12±2, 1629.15±2, 1639.39±2, 1640.36±2, 1646.58±2, 1655.72±2, 1657.97±2, 1659.24±2, 1660.46±2, 1662.16±2, 1679.09±2, 1682.54±2, 1683.12±2, 1687.34±2, 1688.14±2, 1691.08±2, 1691.75±2, 1694.76±2, 1695.74±2, 1700.65±2, 1702.19±2, 1708.77±2, 1712.10±2, 1714.63±2, 1715.56±2, 1719.51±2, 1721.61±2, 1726.31±2, 1737.85±2, 1739.71±2, 1743.69±2, 1761.79±2, 1769.93±2, 1774.13±2, 1775.70±2, 1786.39±2, 1788.03±2, 1790.80±2, 1796.23±2, 1797.49±2, 1800.34±2, 1801.79±2, 1804.45±2, 1810.72±2, 1812.3±21, 1813.77±2, 1817.26±2, 1818.66±2, 1819.93±2, 1821.71±2, 1822.73±2, 1829.48±2, 1832.41±2, 1836.18±2, 1837.33±2, 1840.84±2, 1849.81±2, 1854.68±2, 1858.34±2, 1864.19±2, 1866.06±2, 1875.28±2, 1876.50±2, 1878.25±2, 1890.21±2, 1891.32±2, 1893.00±2, 1904.69±2, 1911.46±2, 1913.68±2, 1916.02±2, 1919.35±2, 1927.13±2, 1931.84±2, 1934.86±2, 1936.83±2, 1937.87±2, 1941.22±2, 1944.97±2, 1948.39±2, 1952.47±2, 1957.80±2, 1962.82±2, 1969.82±2, 1972.54±2, 1975.58±2, 1976.51±2, 1977.70±2, 1979.29±2, 1988.46±2, 1991.91±2, 1995.37±2, 2009.91±2, 2011.18±2, 2013.86±2, 2023.97±2, 2027.73±2, 2030.95±2, 2032.69±2, 2039.29±2, 2043.12±2, 2045.68±2, 2051.76±2, 2059.05±2, 2062.98±2, 2066.09±2, 2074.03±2, 2075.32±2, 2079.80±2, 2083.74±2, 2085.85±2, 2089.53±2, 2092.80±2, 2097.03±2, 2099.42±2, 2111.39±2, 2113.10±2, 2115.77±2, 2120.37±2, 2126.55±2, 2137.63±2, 2139.15±2, 2143.42±2, 2146.46±2, 2149.85±2, 2151.02±2, 2160.22±2, 2161.68±2, 2167.09±2, 2168.75±2, 2173.75±2, 2177.51±2, 2179.25±2, 2185.65±2, 2186.28±2, 2190.18±2, 2191.02±2, 2192.84±2, 2196.47±2, 2199.82±2, 2201.22±2, 2204.02±2, 2207.10±2, 2211.58±2, 2216.77±2, 2218.45±2, 2219.30±2, 2220.56±2, 2222.74±2, 2226.96±2, 2228.22±2, 2231.60±2, 2239.71±2, 2244.01±2, 2251.78±2, 2254.83±2, 2256.53±2, 2261.91±2, 2266.45±2, 2268.58±2, 2274.97±2, 2276.04±2, 2278.67±2, 2281.09±2, 2285.01±2, 2289.43±2, 2290.85±2, 2292.35±2, 2295.92±2, 2296.92±2, 2301.71±2, 2302.50±2, 2303.21±2, 2305.43±2, 2307.22±2, 2314.24±2, 2317.68±2, 2325.30±2, 2341.14±2, 2342.87±2, 2344.45±2, 2351.97±2, 2353.99±2, 2355.29±2, 2357.54±2, 2367.75±2, 2375.59±2, 2378.35±2, 2380.39±2, 2393.64±2, 2402.11±2, 2404.01±2, 2406.49±2, 2412.79±2, 2414.25±2, 2415.20±2, 2416.30±2, 2431.13±2, 2434.36±2, 2438.19±2, 2439.22±2, 2444.37±2, 2451.90±2, 2453.96±2, 2455.44±2, 2456.62±2, 2459.43±2, 2462.31±2, 2464.16±2, 2470.97±2, 2478.17±2, 2479.28±2, 2484.18±2, 2500.40±2, 2502.64±2, 2504.73±2, 2507.42±2, 2509.21±2, 2515.26±2, 2517.43±2, 2519.07±2, 2527.31±2, 2531.06±2, 2532.26±2, 2546.08±2, 2554.96±2, 2559.48±2, 2564.01±2, 2571.26±2, 2578.45±2, 2581.25±2, 2583.37±2, 2584.81±2, 2587.01±2, 2588.90±2, 2593.68±2, 2596.11±2, 2603.33±2, 2608.20±2, 2613.31±2, 2614.91±2, 2622.46±2, 2629.26±2, 2633.69±2, 2634.61±2, 2640.51±2, 2641.73±2, 2652.85±2, 2655.08±2, 2665.15±2, 2670.00±2, 2682.80±2, 2696.41±2, 2698.27±2, 2699.82±2, 3302.01±2, 3303.21±2, 3323.89±2, 3330.34±2, 3337.92±2, 3366.84±2, 3370.39±2, 3378.18±2, 3380.43±2 and 3384.77±2.

In a preferred embodiment, an amino acid sequence of the ALS-associated signal peptide is any of amino acid sequences represented by SEQ ID Nos: 1 to 16, 21 to 27, 29 to 46, 53 to 67, 72 to 87, 94 to 108, 118 to 172, 179 to 243, 248 to 295, 297 to 304, 307 to 317, 320 to 333, 337 to 354, 359 to 422, 424, 425, 430 to 585, 587 to 593, 595 to 605, 607 to 693, 696, 699 to 777, 786 to 902, 906 to 914, 918 to 945, 947 to 983, 990 to 1029, 1042 to 1201, 1208 to 1217, 1230 to 1566, 1569 to 1571 and 1574 to 1580.

This ALS-associated signal peptide is a signal peptide the abundance of which in a bodily fluid from an ALS patient has been confirmed by the inventors to be greater than its reference level. Consequently, if the abundance of this ALS-associated signal peptide is found to be greater than the reference level in a bodily fluid from a test subject, this abundance is associated with the test subject's suffering from or having developed ALS (typically, it suggests that the test subject suffers from or has developed ALS).

In another preferred embodiment of the method for aiding ALS detection disclosed here as the second embodiment, the method further includes confirming that the degree of abundance of any of the ALS-associated signal peptides having the following molecular weights out of the tested ALS-associated signal peptides in the bodily fluid from the test subject is low in comparison with a reference level set based on the degree of abundance of the same signal peptide in a bodily fluid from a healthy subject:
1497.16±2, 1567.74±2, 1705.53±2, 1819.34±2, 1831.81±2, 1935.52±2, 2055.50±2, 2065.57±2, 2084.36±2, 2092.25±2, 2140.48±2, 2167.78±2, 2184.93±2, 2314.81±2, 2327.73±2, 2697.73±2 and 3309.84±2.

In a preferred embodiment, an amino acid sequence of the ALS-associated signal peptide is any of amino acid sequences represented by SEQ ID Nos: 68, 69, 296, 357, 429, 903 to 905, 1223 to 1229, 1572 and 1573.

This ALS-associated signal peptide is a signal peptide the abundance of which in a bodily fluid from an ALS patient has been confirmed by the inventors to be lower than its reference level. Consequently, if the abundance of this ALS-associated signal peptide is found to be lower than the reference level in a bodily fluid from a test subject, this abundance is associated with the test subject's suffering from or having developed ALS (typically, it suggests that the test subject suffers from or has developed ALS).

Moreover, in another preferred embodiment of the method for aiding ALS detection disclosed here as the second embodiment, at least the degree of abundance of an ALS-associated signal peptide with a molecular weight of 1502.40±2, 1521.93±2, 1629.15±2, 1682.54±2, 1691.75±2, 1705.53±2, 1821.71±2, 1836.18±2, 1948.39±2, 2011.18±2, 2092.80±2, 2099.42±2, 2177.51±2, 2179.25±2, 2186.28±2, 2211.58±2, 2226.96±2, 2254.83±2, 2278.67±2, 2290.85±2, 2292.35±2, 2502.64±2, 2640.51±2, 2698.27±2 or 3330.34±2 is tested.

In an especially preferred embodiment, an amino acid sequence constituting the ALS-associated signal peptide is any of the amino acid sequences represented by SEQ ID Nos: 1 to 180.

This ALS-associated signal peptide is a signal peptide the presence or absence or degree of abundance of which in a bodily fluid from an ALS patient has been confirmed by the inventors to be dramatically different from the presence or absence or degree of abundance of the same signal peptide in a bodily fluid from a healthy subject (typically, from the reference level). Consequently, useful and highly reliable data for judging whether a test subject suffers from or has developed ALS can be obtained by testing whether or not the ALS-associated signal peptide is present in a bodily fluid from the test subject, or by testing the degree of abundance of the ALS-associated signal peptide when it is present.

In another preferred embodiment of the method for aiding ALS detection disclosed here as the second embodiment, at least 10 kinds of ALS-associated signal peptides having molecular weights differing by at least 3 from each other are tested in the bodily fluid from the test subject.

By testing multiple ALS-associated signal peptides with different molecular weights, it is possible to obtain even more reliable (accurate) data for judging whether a test subject suffers from or has developed ALS.

Moreover, in another preferred embodiment of the method for aiding ALS detection disclosed here as the second embodiment, the presence or absence or degree of abundance of the ALS-associated signal peptide in the bodily fluid from the test subject is tested with a mass spectrometer.

The presence or absence and degree of abundance of multiple ALS-associated signal peptides can be tested efficiently using such a mass spectrometer.

In another preferred embodiment of the method for aiding ALS detection disclosed here as the second embodiment, the method includes immobilizing the bodily fluid on a thermoplastic resin before the presence or absence and degree of abundance of the ALS-associated signal peptide in the bodily fluid is tested, and the presence or absence and degree of abundance of the ALS-associated signal peptide in the bodily fluid immobilized on the thermoplastic resin is determined by matrix assisted laser desorption/ionization-time of flight mass spectrometly (MALDI-TOFMS).

The presence or absence and degree of abundance of even a difficult-to-ionize signal peptide can be analyzed with a high degree of accuracy by fixing the bodily fluid on the thermoplastic resin and using MALDI-TOFMS to investigate the ALS-associated signal peptide in the immobilize bodily fluid.

Moreover, in another preferred embodiment of the method for aiding ALS detection disclosed here as the first or second embodiment, the bodily fluid is a cerebrospinal fluid.

The cerebrospinal fluid has few contaminants. Because the cerebrospinal fluid circulates continuously through the brain and spinal column, moreover, it easily reflects changes in the environment of the nervous system (typically the central nervous system). Consequently, the cerebrospinal fluid is a suitable subject for testing signal peptide profiles, and also for testing the presence or absence or degree of abundance of ALS-associated signal peptides.

Another aspect of the present invention provides a composition for use in detecting ALS (hereunder also called an "ALS testing composition"). An ALS testing composition of one embodiment disclosed herein includes a synthetic peptide comprising any of amino acid sequences represented by SEQ ID Nos: 1 to 1580, and one or two or more carriers.

Another aspect of the present invention provides a kit for use in detecting ALS (hereunder also called an "ALS testing kit"). An ALS kit of one embodiment disclosed herein includes a synthetic peptide comprising any of amino acid sequences represented by SEQ ID Nos: 1 to 1580, and a support for immobilizing (carrying) the synthetic peptide or a bodily fluid from a test subject.

The synthetic peptide contained in the ALS testing composition and ALS testing kit is an artificially synthesized peptide comprising the same amino acid sequence as a signal peptide that is one of the ALS-associated signal peptides discovered by the inventors. Consequently, this synthetic peptide can be used as a standard substance or a control (typically a positive control) in a method for aiding ALS detection. Thus, a method for aiding ALS detection can be implemented with a high degree of reliability using the composition or kit disclosed here.

In a preferred embodiment of the ALS testing kit disclosed here, the support is made of a thermoplastic resin.

Fixing the synthetic peptide on a thermoplastic resin support allows the peptide to be analyzed (measured) favorably by mass spectrometry (typically MALDI-TOFMS) using MALDI (matrix assisted laser desorption/ionization) as the ionization method even if the peptide is one that is difficult to ionize. Consequently, this ALS testing kit is especially desirable when mass spectrometry (typically MALDI-TOFMS) using MALDI (matrix assisted laser desorption/ionization) as the ionization method is used as the method for aiding ALS detection.

DESCRIPTION OF EMBODIMENTS

Figure 1:
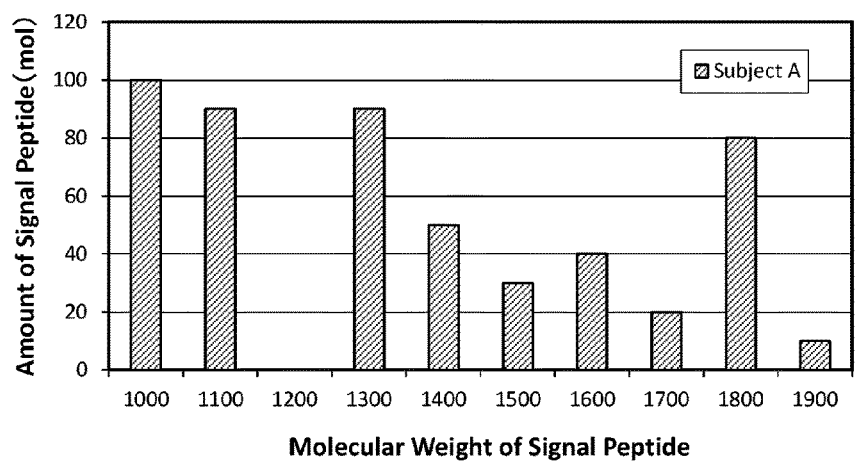
FIG. 1 is a graph showing a typical example of a signal peptide profile; this graph schematically shows a profile of signal peptides presumed to be present in a bodily fluid from a virtual subject A; and the molecular weights of the signal peptides are shown on the horizontal axis, and the amount (mol) of each signal peptide on the vertical axis.

Preferred embodiments of the present invention are explained below. Matters other than those specifically mentioned in this Description (such as the molecular weights and amino acid sequences of the ALS-associated signal peptides disclosed here) that are necessary for implementing the present invention (such as methods for analyzing signal peptides in a bodily fluid, peptide chemical synthesis methods, and general matters associated with the preparation of testing compositions containing peptides) can be understood as design matters by those skilled in the art based on prior art in the fields of cell engineering, physiology, medicine, pharmacology, organic chemistry, biochemistry, genetic engineering, protein engineering, molecular biology, genetics and the like. The present invention can be implemented based on the content disclosed in this Description and technical common knowledge in these fields. In the explanations below, in some cases amino acids are represented by 1-letter abbreviations based on the rules of nomenclature for amino acids as given in the IUPAC-IUB guidelines (but are represented by 3-letter abbreviations in the sequence tables).

The entire contents of all literature cited in this Description are incorporated by reference in this Description.

In this Description, a "synthetic peptide" is not a peptide whose peptide chain exists stably and independently by itself in nature, but rather a peptide fragment that has been manufactured by artificial chemical synthesis or biosynthesis (that is, production based on genetic engineering), and can exist stably in a specific composition (such as an ALS testing composition or ALS testing kit used to detect ALS).

In this Description, moreover, the term "peptide" refers to an amino acid polymer having multiple peptide bonds, and encompasses those called polypeptides and oligopeptides according to the number of constituent amino acid residues. Typically, it refers to those with relatively low molecular weights comprising not more than 50 (preferably not more than 30, such as not more than 20) total amino acid residues.

In this Description, "amino acid residue" is a term encompassing the N-terminal amino acid and C-terminal amino acid of the peptide chain, except where otherwise specified.

The amino acid sequences described in this Description are always N-terminal on the left side and C-terminal on the right.

The terms "healthy" and "normal" are used synonymously in the present Description. These terms signify the healthy state of an individual who exhibits no clinical symptoms of ALS and has not been diagnosed with ALS. That is, in the present Description a "healthy subject", "healthy person" or "normal subject" means the same as a "healthy individual" or "normal individual", meaning that the individual exhibits no clinical symptoms of ALS and has not been diagnosed with ALS. In the present Description, a "healthy subject" is a "healthy person", meaning a test subject used as a comparative subject in the inventions disclosed here.

The "healthy subject" is preferably one who does not suffer from and has not developed any other disease that causes impaired motor function (such as spinal muscular atrophy, multifocal neuropathy, post-polio syndrome or multiple sclerosis), and more preferably is one who also does not suffer from and has not developed any other neurodegenerative disease (such as Alzheimer's disease or Parkinson's disease).

Moreover, the "healthy subject" is preferably one who resembles the test subject in such background factors as race, age, sex and the like.

In this Description, the "degree of abundance of a signal peptide" is not limited to the absolute quantitative value of the signal peptide in a bodily fluid, but also includes the relative quantitative value of the signal peptide. For example, it may means that the abundance of the signal peptide is greater or less than the abundance thereof in a specific bodily fluid (typically, a bodily fluid from a healthy subject), or that it is greater or less than a specific reference value (typically, a reference value determined from the degree of abundance of the signal peptide in a bodily fluid from a healthy subject).

In this Description, moreover, the "±2" in "M±2" designating a specific molecular weight M indicates an error range that may occur due to the analytic equipment, analytic methods and measurement conditions and differences in these. An error range of "±2" has been set based on the error range that may occur in mass spectrometry using general-purpose MALDI-TOFMS, but the error range is not limited to this, and another value (such as ±1 or +3) can also be set appropriately depending on the analytic equipment, analytic methods and measurement conditions.

First Embodiment

Focusing on signal peptides in a bodily fluid, the inventors first conducted exhaustive research into bodily fluids from ALS patients and bodily fluids from healthy subjects, including a comprehensive analysis of signal peptides present in these bodily fluids. Considering the fact that the signal peptide profiles of bodily fluids from ALS patients differ from the signal peptide profiles of bodily fluids from healthy subjects, we perfected a method for aiding ALS detection based on differences between these signal peptide profiles.

That is, in the method for aiding ALS detection disclosed here as the first embodiment, the presence of a difference between a profile of signal peptides contained in a bodily fluid from a test subject and a profile of signal peptides contained in a bodily fluid from a healthy subject at a specific molecular weight or weights is associated with the test subject's suffering from or developing ALS (typically, the difference suggests that the test subject suffers from or has developed ALS, by for example indicating an increased likelihood that the test subject suffers from or has developed ALS).

Specifically, the method for aiding ALS detection disclosed as the first embodiment includes:

(i) determining a profile of signal peptides in the molecular weight range of 1000 to 3500 from signal peptides contained in a bodily fluid from a test subject; and (ii) comparing the signal peptide profile thus determined for the test subject with a signal peptide profile previously determined in a bodily fluid from a healthy subject.

In this method for aiding ALS detection, the presence of a difference between the signal peptide profile of the test subject and the signal peptide profile of the healthy subject at any of the following molecular weights is associated with the test subject's suffering from or developing ALS (typically, the difference suggests that the test subject suffers from or has developed ALS):

1405.71±2, 1406.49±2, 1409.40±2, 1410.97±2, 1418.70±2, 1426.68±2, 1437.62±2, 1445.77±2, 1451.61±2, 1456.44±2, 1458.88±2, 1466.24±2, 1468.86±2, 1472.12±2, 1476.87±2, 1482.60±2, 1493.58±2, 1495.42±2, 1496.52±2, 1497.16±2, 1498.88±2, 1502.40±2, 1505.52±2, 1508.76±2, 1510.50±2, 1516.64±2, 1521.93±2, 1529.32±2, 1530.37±2, 1533.52±2, 1539.36±2, 1544.22±2, 1553.72±2, 1555.72±2, 1560.24±2, 1566.20±2, 1567.20±2, 1567.74±2, 1575.70±2, 1578.07±2, 1580.91±2, 1589.58±2, 1592.55±2, 1597.25±2, 1608.53±2, 1609.36±2, 1610.62±2, 1616.12±2, 1629.15±2, 1639.39±2, 1640.36±2, 1646.58±2, 1655.72±2, 1657.97±2, 1659.24±2, 1660.46±2, 1662, 16±2, 1679.09±2, 1682.54±2, 1683.12±2, 1687.34±2, 1688.14±2, 1691.08±2, 1691.75±2, 1694.76±2, 1695.74±2, 1700.65±2, 1702.19±2, 1705.53±2, 1708.77±2, 1712.10±2, 1714.63±2, 1715.56±2, 1719.51±2, 1721.61±2, 1726.31±2, 1737.85±2, 1739.71±2, 1743.69±2, 1761.79±2, 1769.93±2, 1774.13±2, 1775.70±2, 1786.39±2, 1788.03±2, 1790.80±2, 1796.23±2, 1797.49±2, 1800.34±2, 1801.79±2, 1804.45±2, 1810.72±2, 1812.31±2, 1813.77±2, 1817.26±2, 1818.66±2, 1819.34±2, 1819.93±2, 1821.71±2, 1822.73±2, 1829.48±2, 1831.81±2, 1832.41±2, 1836.18±2, 1837.33±2, 1840.84±2, 1849.81±2, 1854.68±2, 1858.34±2, 1864.19±2, 1866.06±2, 1875.28±2, 1876.50±2, 1878.25±2, 1890.21±2, 1891.32±2, 1893.00±2, 1904.69±2, 1911.46±2, 1913.68±2, 1916.02±2, 1919.35±2, 1927.13±2, 1931.84±2, 1934.86±2, 1935.52±2, 1936.83±2, 1937.87±2, 1941.22±2, 1944.97±2, 1948.39±2, 1952.47±2, 1957.80±2, 1962.82±2, 1969.82±2, 1972.54±2, 1975.58±2, 1976.51±2, 1977.70±2, 1979.29±2, 1988.46±2, 1991.91±2, 1995.37±2, 2009.91±2, 2011.18±2, 2013.86±2, 2023.97±2, 2027.73±2, 2030.95±2, 2032.69±2, 2039.29±2, 2043.12±2, 2045.68±2, 2051.76±2, 2055.50±2, 2059.05±2, 2062.98±2, 2065.57±2, 2066.09±2, 2074.03±2, 2075.32±2, 2079.80±2, 2083.74±2, 2084.36±2, 2085.85±2, 2089.53±2, 2092.25±2, 2092.80±2, 2097.03±2, 2099.42±2, 2111.39±2, 2113.10±2, 2115.77±2, 2120.37±2, 2126.55±2, 2137.63±2, 2139.15±2, 2140.48±2, 2143.42±2, 2146.46±2, 2149.85±2, 2151.02±2, 2160.22±2, 2161.68±2, 2167.09±2, 2167.78±2, 2168.75±2, 2173.75±2, 2177.51±2, 2179.25±2, 2184.93±2, 2185.65±2, 2186.28±2, 2190.18±2, 2191.02±2, 2192.84±2, 2196.47±2, 2199.82±2, 2201.22±2, 2204.02±2, 2207.10±2, 2211.58±2, 2216.77±2, 2218.45±2, 2219.30±2, 2220.56±2, 2222.74±2, 2226.96±2, 2228.22±2, 2231.60±2, 2239.71±2, 2244.01±2, 2251.78±2, 2254.83±2, 2256.53±2, 2261.91±2, 2266.45±2, 2268.58±2, 2274.97±2, 2276.04±2, 2278.67±2, 2281.09±2, 2285.01±2, 2289.43±2, 2290.85±2, 2292.35±2, 2295.92±2, 2296.92±2, 2301.71±2, 2302.50±2, 2303.21±2, 2305.43±2, 2307.22±2, 2314.24±2, 2314.81±2, 2317.68±2, 2325.30±2, 2327.73±2, 2341.14±2, 2342.87±2, 2344.45±2, 2351.97±2, 2353.99±2, 2355.29±2, 2357.54±2, 2367.75±2, 2375.59±2, 2378.35±2, 2380.39±2, 2393.64±2, 2402.11±2, 2404.01±2, 2406.49±2, 2412.79±2, 2414.25±2, 2415.20±2, 2416.30±2, 2431.13±2, 2434.36±2, 2438.19±2, 2439.22±2, 2444.37±2, 2451.90±2, 2453.96±2, 2455.44±2, 2456.62±2, 2459.43±2, 2462.31±2, 2464.16±2, 2470.97±2, 2478.17±2, 2479.28±2, 2484.18±2, 2500.40±2, 2502.64±2, 2504.73±2, 2507.42±2, 2509.21±2, 2515.26±2, 2517.43±2, 2519.07±2, 2527.31±2, 2531.06±2, 2532.26±2, 2546.08±2, 2554.96±2, 2559.48±2, 2564.01±2, 2571.26±2, 2578.45±2, 2581.25±2, 2583.37±2, 2584.81±2, 2587.01±2, 2588.90±2, 2593.68±2, 2596.11±2, 2603.33±2, 2608.20±2, 2613.31±2, 2614.91±2, 2622.46±2, 2629.26±2, 2633.69±2, 2634.61±2, 2640.51±2, 2641.73±2, 2652.85±2, 2655.08±2, 2665.15±2, 2670.00±2, 2682.80±2, 2696.41±2, 2697.73±2, 2698.27±2, 2699.82±2, 3302.01±2, 3303.21±2, 3309.84±2, 3323.89±2, 3330.34±2, 3337.92±2, 3366.84±2, 3370.39±2, 3378.18±2, 3380.43±2 and 3384.77±2.

In a profile of signal peptides in a bodily fluid from an ALS patient, a signal peptide specified by any of the following molecular weights is more abundant than in the signal peptide profile of a healthy subject:
1405.71±2, 1406.49±2, 1409.40±2, 1410.97±2, 1418.70±2, 1426.68±2, 1437.62±2, 1445.77±2, 1451.61±2, 1456.44±2, 1458.88±2, 1466.24±2, 1468.86±2, 1472.12±2, 1476.87±2, 1482.60±2, 1493.58±2, 1495.42±2, 1496.52±2, 1498.88±2, 1502.40±2, 1505.52±2, 1508.76±2, 1510.50±2, 1516.64±2, 1521.93±2, 1529.32±2, 1530.37±2, 1533.52±2, 1539.36±2, 1544.22±2, 1553.72±2, 1555.72±2, 1560.24±2, 1566.20±2, 1567.20±2, 1575.70±2, 1578.07±2, 1580.91±2, 1589.58±2, 1592.55±2, 1597.25±2, 1608.53±2, 1609.36±2, 1610.62±2, 1616.12±2, 1629.15±2, 1639.39±2, 1640.36±2, 1646.58±2, 1655.72±2, 1657.97±2, 1659.24±2, 1660.46±2, 1662.16±2, 1679.09±2, 1682.54±2, 1683.12±2, 1687.34±2, 1688.14±2, 1691.08±2, 1691.75±2, 1694.76±2, 1695.74±2, 1700.65±2, 1702.19±2, 1708.77±2, 1712.10±2, 1714.63±2, 1715.56±2, 1719.51±2, 1721.61±2, 1726.31±2, 1737.85±2, 1739.71±2, 1743.69±2, 1761.79±2, 1769.93±2, 1774.13±2, 1775.70±2, 1786.39±2, 1788.03±2, 1790.80±2, 1796.23±2, 1797.49±2, 1800.34±2, 1801.79±2, 1804.45±2, 1810.72±2, 1812.3±21, 1813.77±2, 1817.26±2, 1818.66±2, 1819.93±2, 1821.71±2, 1822.73±2, 1829.48±2, 1832.41±2, 1836.18±2, 1837.33±2, 1840.84±2, 1849.81±2, 1854.68±2, 1858.34±2, 1864.19±2, 1866.06±2, 1875.28±2, 1876.50±2, 1878.25±2, 1890.21±2, 1891.32±2, 1893.00±2, 1904.69±2, 1911.46±2, 1913.68±2, 1916.02±2, 1919.35±2, 1927.13±2, 1931.84±2, 1934.86±2, 1936.83±2, 1937.87±2, 1941.22±2, 1944.97±2, 1948.39±2, 1952.47±2, 1957.80±2, 1962.82±2, 1969.82±2, 1972.54±2, 1975.58±2, 1976.51±2, 1977.70±2, 1979.29±2, 1988.46±2, 1991.91±2, 1995.37±2, 2009.91±2, 2011.18±2, 2013.86±2, 2023.97±2, 2027.73±2, 2030.95±2, 2032.69±2, 2039.29±2, 2043.12±2, 2045.68±2, 2051.76±2, 2059.05±2, 2062.98±2, 2066.09±2, 2074.03±2, 2075.32±2, 2079.80±2, 2083.74±2, 2085.85±2, 2089.53±2, 2092.80±2, 2097.03±2, 2099.42±2, 2111.39±2, 2113.10±2, 2115.77±2, 2120.37±2, 2126.55±2, 2137.63±2, 2139.15±2, 2143.42±2, 2146.46±2, 2149.85±2, 2151.02±2, 2160.22±2, 2161.68±2, 2167.09±2, 2168.75±2, 2173.75±2, 2177.51±2, 2179.25±2, 2185.65±2, 2186.28±2, 2190.18±2, 2191.02±2, 2192.84±2, 2196.47±2, 2199.82±2, 2201.22±2, 2204.02±2, 2207.10±2, 2211.58±2, 2216.77±2, 2218.45±2, 2219.30±2, 2220.56±2, 2222.74±2, 2226.96±2, 2228.22±2, 2231.60±2, 2239.71±2, 2244.01±2, 2251.78±2, 2254.83±2, 2256.53±2, 2261.91±2, 2266.45±2, 2268.58±2, 2274.97±2, 2276.04±2, 2278.67±2, 2281.09±2, 2285.01±2, 2289.43±2, 2290.85±2, 2292.35±2, 2295.92±2, 2296.92±2, 2301.71±2, 2302.50±2, 2303.21±2, 2305.43±2, 2307.22±2, 2314.24±2, 2317.68±2, 2325.30±2, 2341.14±2, 2342.87±2, 2344.45±2, 2351.97±2, 2353.99±2, 2355.29±2, 2357.54±2, 2367.75±2, 2375.59±2, 2378.35±2, 2380.39±2, 2393.64±2, 2402.11±2, 2404.01±2, 2406.49±2, 2412.79±2, 2414.25±2, 2415.20±2, 2416.30±2, 2431.13±2, 2434.36±2, 2438.19±2, 2439.22±2, 2444.37±2, 2451.90±2, 2453.96±2, 2455.44±2, 2456.62±2, 2459.43±2, 2462.31±2, 2464.16±2, 2470.97±2, 2478.17±2, 2479.28±2, 2484.18±2, 2500.40±2, 2502.64±2, 2504.73±2, 2507.42±2, 2509.21±2, 2515.26±2, 2517.43±2, 2519.07±2, 2527.31±2, 2531.06±2, 2532.26±2, 2546.08±2, 2554.96±2, 2559.48±2, 2564.01±2, 2571.26±2, 2578.45±2, 2581.25±2, 2583.37±2, 2584.81±2, 2587.01±2, 2588.90±2, 2593.68±2, 2596.11±2, 2603.33±2, 2608.20±2, 2613.31±2, 2614.91±2, 2622.46±2, 2629.26±2, 2633.69±2, 2634.61±2, 2640.51±2, 2641.73±2, 2652.85±2, 2655.08±2, 2665.15±2, 2670.00±2, 2682.80±2, 2696.41±2, 2698.27±2, 2699.82±2, 3302.01±2, 3303.21±2, 3323.89±2, 3330.34±2, 3337.92±2, 3366.84±2, 3370.39±2, 3378.18±2, 3380.43±2 and 3384.77±2.

That is, the fact that the abundance of a signal peptide specified by any of these molecular weights is greater in the signal peptide profile of a test subject than in the signal peptide profile of a healthy subject reflects a strong likelihood that the test subject suffers from or has developed ALS.

Moreover, in a profile of signal peptides in a bodily fluid from an ALS patient, a signal peptide specified by any of the following molecular weights is less abundant than in the signal peptide profile of a healthy subject:
1497.16±2, 1567.74±2, 1705.53±2, 1819.34±2, 1831.81±2, 1935.52±2, 2055.50±2, 2065.57±2, 2084.36±2, 2092.25±2, 2140.48±2, 2167.78±2, 2184.93±2, 2314.81±2, 2327.73±2, 2697.73±2 and 3309.84±2.

That is, the fact that a signal peptide specified by any of these molecular weights is less abundant in the signal peptide profile of a test subject than in the signal peptide profile of a healthy subject reflects a strong likelihood that the test subject suffers from or has developed ALS.

FIG. 1 shows a typical example of a signal peptide profile of a subject A. As shown in FIG. 1, a signal peptide profile can be represented as a bar graph, with the molecular weights of the signal peptides presumed to be present in the bodily fluid of a subject A shown on the horizontal axis, and the amounts of these signal peptides on the vertical axis.

Figure 2:
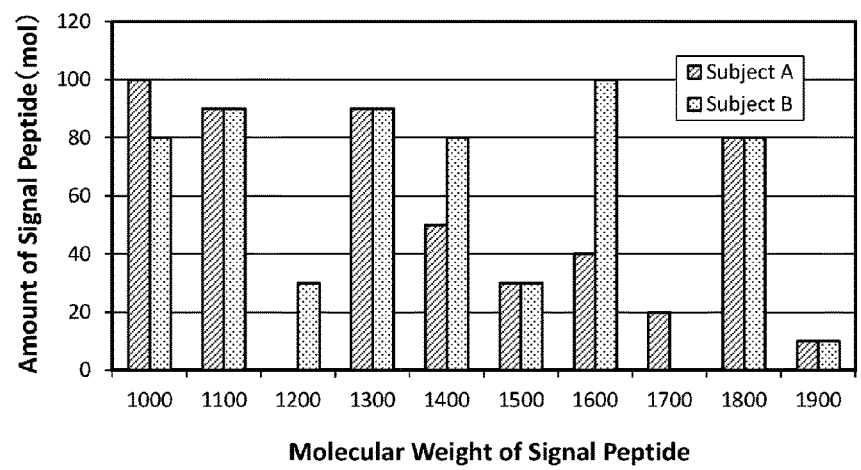
FIG. 2 is a graph displaying the signal peptide profile of subject A from FIG. 1 together with the signal peptide profile of a subject B, which was determined separately from the signal peptide profile of the subject A: the molecular weights of the signal peptides are shown on the horizontal axis and the abundance (mol) of each signal peptides on the vertical axis; and as in the case of the subject A, the signal peptide profile of the subject B displayed on this graph is a profile of signal peptides presumed to be present in a bodily fluid from a virtual subject B.

FIG. 2 displays two signal peptide profiles, the signal peptide profile of the subject A from FIG. 1 together with the signal peptide profile of a subject B, which was determined separately from the signal peptide profile of the subject A. When the signal peptide profile of the subject A and the signal peptide profile of the subject B are in the relationship shown in FIG. 2, the signal peptide profile of the subject A differs from the signal peptide profile of the subject B at molecular weights of 1000, 1200, 1400, 1600 and 1700. Specifically, the signal peptides specified by the molecular weights 1000 and 1700 are more abundant in the signal peptide profile of the subject A than in the signal peptide profile of the subject B, while the signal peptides specified by the molecular weights 1200, 1400 and 1600 are less abundant in the signal peptide profile of the subject A than in the signal peptide profile of the subject B.

In the method for aiding ALS detection disclosed here, to obtain data about a test subject's suffering from or developing ALS (typically, data suggesting that the test subject suffers from or has developed ALS, such as data showing an increased likelihood that the test subject suffers from or has developed ALS), it is sufficient to compare the signal peptide profile of the test subject with the signal peptide profile of a healthy subject, and confirm at least one difference at the aforementioned specific molecular weights (typically, an increase or decrease in the abundance of at least one of the signal peptides specified by the specific molecular weights). From the standpoint of obtaining data for determining more reliably (with greater accuracy) whether a test subject suffers from ALS, it is desirable to confirm that the signal peptide of the test subject differs from the signal peptide profile of a healthy subject at multiple (2 or 3 or more, or preferably at least 10, or more preferably at least 20) molecular weights selected from the aforementioned specific molecular weights (typically, that the signal peptides specified by these specific molecular weights are more or less abundant than in a healthy subject).

A profile of signal peptides in a bodily fluid can be determined by a known method (qualitative measurement method) capable of confirming the presence or absence of signal peptides specified by the target molecular weights. Preferably, it is determined by a method (quantitative measurement method) capable of measuring the amounts of the signal peptides specified by the target molecular weights.

In a preferred embodiment, the signal peptide profile is determined by analysis using a mass spectrometer. That is, this signal peptide profile is preferably determined by mass spectrometry. Typically, a signal peptide profile can be determined efficiently by mass spectrometry because multiple signal peptides can be analyzed simultaneously.

A mass spectrum of signal peptides present in a bodily fluid can be obtained by using mass spectrometry to measure a bodily fluid subject to analysis. This mass spectrum is a spectrum obtained by isolating the signal peptides present in the bodily fluid according to their mass to charge ratios (m/z), and can be used as the aforementioned signal peptide profile.

The mass spectrometry is not particularly limited, and may be selected appropriately from the conventional mass spectrometry methods of LC-MS (liquid chromatography-mass spectrometry), ESI-MS (electrospray ionization mass spectrometry) and MALDI-TOFMS (matrix assisted laser desorption/ionization-time of flight mass spectrometry). In other words, the ionization methods and ion detection methods in mass spectrometry are not particularly limited. For example, the conventional methods of EI (electron ionization), CI (chemical ionization), FAB (fast atom bombardment), ESI (electrospray ionization), APCI (atmospheric pressure chemical ionization), ICP (inductively coupled plasma) and MALDI (matrix assisted laser desorption/ionization) can be selected appropriately as ionization methods. For the method of detecting the ionized molecules, a conventional detection method such as magnetic sector, quadrupole (Q), ion trap (IT), Fourier-transform ion cyclotron resonance (FT-ICR), accelerator mass spectrometry (AMS) or time-of-flight (TOF) detection or a tandem method combining these detection methods can be selected appropriately.

In an especially preferred embodiment, analysis is performed by mass spectrometry using MALDI (matrix assisted laser desorptionlionization) (hereunder also called MALDI MS). With MALDI MS, it is typically possible to analyze large molecules that are difficult to ionize (for example, biological molecules such as proteins and peptides). Moreover, MALDI MS is also suited to analyzing signal peptides in a bodily fluid because it is typically capable of analyzing micro samples and samples with low purity in many cases. In mass spectrometry using MALDI, the ionized molecules are typically analyzed (detected) by time-of-flight mass spectrometry (TOFMS). That is, MALDI-TOFMS can preferably be adopted for mass spectrometry.

When signal peptides in a bodily fluid are analyzed by such MALDI MS (typically MALDI-TOFMS), the bodily fluid is preferably immobilized on a thermoplastic resin. The signal peptides typically tend to have low ionization efficiency because they are often highly hydrophobic molecules having many hydrophobic amino acids. Ionization of the signal peptides can be promoted by immobilizing them on a thermoplastic resin. Moreover, immobilizing the bodily fluid on a thermoplastic resin can improve the accuracy of signal peptide analysis because it can suppress ionization of contaminants contained in the bodily fluid.

A conventional known resin material can be used as the thermoplastic resin for immobilizing the bodily fluid, without any particular limitations. For example, a resin material made primarily of a polyolefin resin such as polyethylene or polypropylene, an acrylic resin such as polymethyl methacrylate, an ethylene-vinyl acetate copolymer resin (EVA), a polyvinyl chloride resin or a polyester resin can be used. To promote ionization of the signal peptides while suppressing ionization of contaminants, an ethylene-vinyl acetate copolymer resin can be used by preference.

In a preferred embodiment, the bodily fluid to be analyzed is immobilized on a thermoplastic resin that has been molded into a film shape or sheet shape (typically, a thermoplastic film). The thickness of this thermoplastic resin film is not particularly limited, but may be about 50 μm to 200 μm (typically about 100 μm) for example.

The matrix used when analyzing signal peptides in a bodily fluid by the MALDI MS (typically MALDI-TOFMS) method is not particularly limited, and a conventional known matrix used in mass spectrometry by MALDI may be selected appropriately. Examples include sinapinic acid (3,5-dimethoxy-4-hydroxycinnamic acid), CHCA (α-cyano-4-hydroxycinnamic acid), ferulic acid (trans-4-hydroxy-3-methoxvcinnamic acid), gentisic acid. DHBA (2,5-dihydroxybenzoic acid), HPA (3-hydroxypicolinic acid), dithranol (1,8-dihydroxy-9,10-dihydroanthracen-9-one) and the like. Sinapinic acid is suitable as a matrix in mass spectrometry of high molecular weight molecules, and is also a suitable matrix for mass spectrometry of peptides and proteins. Consequently, sinapinic acid can be used favorably as a matrix in mass spectrometry of signal peptides.

In a preferred embodiment, multiple mass spectrometric analyses are repeatedly performed independently of one another on the target bodily fluid. Signal peptides contained in a bodily fluid can be accurately assayed by statistically processing the results of such multiple mass spectrometric analyses.

For example, the abundance of a signal peptide present in a bodily fluid can be confirmed by calculating the frequency with which the presence of the target signal peptide is detected in multiple mass spectrometric analyses (detection frequency), and taking this frequency, as the quantitative value of the signal peptide. Alternatively, in cases in which the target signal peptide can be quantified by a single mass spectrometric analysis, an average value or median value calculated from the results (quantitative values) of multiple mass spectrometric analyses can be used favorably as the quantitative value of the signal peptide.

Because the accuracy of the assay is greater the more times mass spectrometry is repeated, mass spectrometry is preferably repeated at least 50 times for example (preferably at least 100 times, or more preferably at least 200 times, or still more preferably at least 300) times).

For example, the abundance of a signal peptide in a bodily fluid can be confirmed by the following methods when MALDI MS is adopted as the method of mass spectrometry.

First, the bodily fluid to be analyzed is exposed multiple times (such as at least 50 times, or preferably at least 100 times, or more preferably at least 200 times, or still more preferably at least 300 times) to an ionizing laser. Mass spectrometry (preferably TOFMS) is performed for each laser exposure, and the presence (detection) or absence of a molecule of the target molecular weight (that is, a signal peptide of the target molecular weight) is confirmed. The frequency with which a molecule of the target molecular weight is detected (detection frequency) in these multiple MALDI MS analyses is then calculated, and this frequency is given as the abundance of the signal peptide to thereby confirm the abundance of the target signal peptide.

In another preferred embodiment, the signal peptide profile may be determined by immunological methods. Typically, immunological methods are methods in which the amount of an antigen is assessed by performing an antigen-antibody reaction between an antigen (or fragment thereof) and an antibody that reacts specifically with that antigen to thereby form an immune complex, and detecting (imaging) the antibody. That is, the signal peptide profile can be determined by methods using antibodies that react specifically with the target signal peptides or fragments thereof.

A conventional known method may be adopted as the immunological method without any particular limitations as long as it can detect the target signal peptide Examples include EIA, radioimmunoassay (RIA), fluorescence immunoassay (FIA), chemiluminescence immunoassay (CLIA), gel precipitation reaction, immunoturbidimetric methods, particle agglutination reaction methods and the like.

Either a method (direct method) using an antibody that has been somehow labeled in advance (labeled primary antibody) or a method (indirect method) using a labeled secondary antibody that specifically recognizes an antibody (that is, primary antibody) to the signal peptide may be used favorably as the immunological method.

A labeling compound commonly used by those skilled in the art in the field of diagnosis by immunological methods such as ELISA may be used as the labeling substance for the antibody (primary antibody or secondary antibody). Examples include radioactive isotopes such as $^3$H, $^{14}$C, $^{131}$I and $^{99m}$Tc; enzymes such as β-galactosidase, β-glucosidase, alkaline phosphatase, peroxidase and malate dehydrogenase; fluorescent substances such as fluorescamine and fluorescein isothiocyanate; and luminescent substances such as luciferin, luminol derivatives, isoluminol derivatives and the like.

Labeling of the antibody with these labeling substances can be accomplished by conventional known methods, and detailed explanations are omitted because these methods are not a feature of the present invention.

The antibody used in the immunological method may be any capable of detecting the target signal peptide, without any particular limitations. For example, it may be a monoclonal antibody, polyclonal antibody, single chain antibody, chimera antibody or the like. The immune animal (antibody-producing animal, host, source) and constant domain of the immunoglobulin (also called the isotype or class) are also not particularly limited. For example, the antibody may be obtained by immunizing a mouse, rat, rabbit, horse, cow, goat, sheep, pig or the like, and may be any of IgG, IgM, IgA, IgE and IgD (preferably IgG).

These antibodies may be prepared by conventional known methods, and detailed explanations are omitted because these methods are not a feature of the present invention.

A composition, kit or protein array (typically a protein microarray) containing an antibody capable of detecting a target signal peptide is also provided by another aspect of the present invention.

The profile of signal peptides contained in a bodily fluid from a healthy subject may be any profile of signal peptides in a bodily fluid collected from at least one healthy subject who does not suffer from and has not developed ALS. However the profiles of signal peptides in bodily fluids are subject to differences among individuals (individual differences) even among healthy subjects. Consequently, the profile of signal peptides contained in a bodily fluid from a healthy subject is preferably determined comprehensively from the profiles of signal peptides contained in bodily fluids from multiple (2 or 3 or more, or preferably at least 5, or more preferably at least 10) healthy subjects.

This profile of signal peptides in a bodily fluid from a healthy subject is preferably determined by methods similar to those used to determine the signal peptide profile of the test subject.

In the method for aiding ALS detection disclosed here, the signal peptide profile of the test subject and the signal peptide profile of the healthy subject can be compared by comparing at least one of the aforementioned specific molecular weights at which deviations from the profile of signal peptides in a bodily fluid from a healthy subject indicate that a test subject suffers from or has developed ALS.

Data about the likelihood (typically, an increase or decrease in the likelihood) that a test subject suffers from or has developed ALS can be obtained more reliably (accurately) if more molecular weights that are among the specific molecular weights at which deviations from the profile of signal peptides in a bodily fluid from a healthy subject indicate that a test subject suffers from or has developed ALS are included in the signal peptide profile of the test subject in comparison with the signal peptide profile of the healthy subject. That is, preferably the signal peptide profile of the test subject and the signal peptide profile of the healthy subject are compared with respect to 2 or 3 or more (preferably at least 10, or more preferably at least 20) of the specific molecular weights at which deviations from the profile of signal peptides in a bodily fluid from a healthy subject indicate that a test subject suffers from or has developed ALS.

In the method for aiding ALS detection disclosed here, when the signal peptide profile of a test subject and the signal peptide profile of a healthy subject are compared with a focus on specific molecular weights, the likelihood that the test subject suffers from or has developed ALS (typically, an increase in such likelihood) can be indicated with greater accuracy the greater the frequency of differences at the specific molecular weights being compared.

That is, from the standpoint of obtaining more reliable (accurate) data about the likelihood that a test subject suffers from or has developed ALS (typically, an increase in such likelihood), it is desirable to confirm that the signal peptide profile of the test subject and the signal peptide profile of the healthy subject differ at 60% or more (preferably at least 70%, or more preferably at least 80%, or still more preferably at least 95%) of the specific molecular weights that are compared when comparing the signal peptide profile of the test subject with the signal peptide profile of the healthy subject.

Second Embodiment

The inventors compared and studied the profiles of signal peptides contained in bodily fluids from ALS patients and the profiles of signal peptides contained in bodily fluids from healthy subjects in more detail. We then found that the presence and absence and degree of abundance of specific signal peptides (that is, ALS-associated signal peptides) were different in bodily fluids from ALS patients and healthy subjects. We then perfected a method for aiding ALS detection using such a specific signal peptide (that is, ALS-associated signal peptide) as an indicator.

That is, in the method for aiding ALS detection disclosed here as the second embodiment, the presence of a difference between the presence or absence or degree of abundance of the ALS-associated signal peptide in a bodily fluid from a test subject and the presence or absence of the same ALS-associated signal peptide in a bodily fluid from a healthy subject or a reference level set for degree of abundance thereof is associated with the test subject's suffering from or developing ALS (typically, the difference suggests that the test subject suffers from or has developed ALS, by for example indicating an increased likelihood that the test subject suffers from or has developed ALS).

Specifically, the method for aiding ALS detection disclosed here as the second embodiment includes:

(i) testing whether one or two or more ALS signal peptides are present in a bodily fluid from a test subject, or testing the degree of abundance of the ALS-associated signal peptide or peptides when present.

In this method for aiding ALS detection, the molecular weight of the ALS-associated signal peptide is.
1405.71±2, 1406.49±2, 1409.40±2, 1410.97±2, 1418.70±2, 1426.68±2, 1437.62±2, 1445.77±2, 1451.61±2, 1456.44±2, 1458.88±2, 1466.24±2, 1468.86±2, 1472.12±2, 1476.87±2, 1482.60±2, 1493.58±2, 1495.42±2, 1496.52±2, 1497.16±2, 1498.88±2, 1502.402, 1505.52±2, 1508.76±2, 1510.50±2, 1516.64±2, 1521.93±2, 1529.32±2, 1530.37±2, 1533.52±2, 1539.36±2, 1544.22±2, 1553.72±2, 1555.72±2, 1560.24±2, 1566.20±2, 1567.20±2, 1567.74±2, 1575.70±2, 1578.07±2, 1580.91±2, 1589.58±2, 1592.55±2, 1597.25±2, 1608.53±2, 1609.36±2, 1610.62±2, 1616.12±2, 1629.15±2, 1639.39±2, 1640.36±2, 1646.58±2, 1655.72±2, 1657.97±2, 1659.24±2, 1660.46±2, 1662.16±2, 1679.09±2, 1682.54±2, 1683.12±2, 1687.34±2, 1688.14±2, 1691.08±2, 1691.75±2, 1694.76±2, 1695.74±2, 1700.65±2, 1702.19±2, 1705.53±2, 1708.77±2, 1712.10±2, 1714.63±2, 1715.56±2, 1719.51±2, 1721.61±2, 1726.31±2, 1737.85±2, 1739.71±2, 1743.69±2, 1761.79±2, 1769.93±2, 1774.13±2, 1775.70±2, 1786.39±2, 1788.03±2, 1790.80±2, 1796.23±2, 1797.49±2, 1800.34±2, 1801.79±2, 1804.45±2, 1810.72±2, 1812.31±2, 1813.77±2, 1817.26±2, 1818.66±2, 1819.34±2, 1819.93±2, 1821.71±2, 1822.73±2, 1829.48±2, 1831.81±2, 1832.41±2, 1836.18±2, 1837.33±2, 1840.84±2, 1849.81±2, 1854.68±2, 1858.34±2, 1864.19±2, 1866.06±2, 1875.28±2, 1876.50±2, 1878.25±2, 1890.21±2, 1891.32±2, 1893.00±2, 1904.69±2, 1911.46±2, 1913.68±2, 1916.02±2, 1919.35±2, 1927.13±2, 1931.84±2, 1934.86±2, 1935.52±2, 1936.83±2, 1937.87±2, 1941.22±2, 1944.97±2, 1948.39±2, 1952.47±2, 1957.80±2, 1962.82±2, 1969.82±2, 1972.54±2, 1975.58±2, 1976.51±2, 1977.70±2, 1979.29±2, 1988.46±2, 1991.91±2, 1995.37±2, 2009.91±2, 2011.18±2, 2013.86±2, 2023.97±2, 2027.73±2, 2030.95±2, 2032.69±2, 2039.29±2, 2043.12±2, 2045.68±2, 2051.76±2, 2055.50±2, 2059.05±2, 2062.98±2, 2065.57±2, 2066.09±2, 2074.03±2, 2075.32±2, 2079.80±2, 2083.74±2, 2084.36±2, 2085.85±2, 2089.53±2, 2092.25±2, 2092.80±2, 2097.03±2, 2099.42±2, 2111.39±2, 2113.10±2, 2115.77±2, 2120.37±2, 2126.55±2, 2137.63±2, 2139.15±2, 2140.48±2, 2143.42±2, 2146.46±2, 2149.85±2, 2151.02±2, 2160.22±2, 2161.68±2, 2167.09±2, 2167.78±2, 2168.75±2, 2173.75±2, 2177.51±2, 2179.25±2, 2184.93±2, 2185.65±2, 2186.28±2, 2190.18±2, 2191.02±2, 2192.84±2, 2196.47±2, 2199.82±2, 2201.22±2, 2204.02±2, 2207.10±2, 2211.58±2, 2216.77±2, 2218.45±2, 2219.30±2, 2220.56±2, 2222.74±2, 2226.96±2, 2228.22±2, 2231.60±2, 2239, 71±2, 2244.01±2, 2251.78±2, 2254.83±2, 2256.53±2, 2261.91±2, 2266.45±2, 2268.58±2, 2274.97±2, 2276.04±2, 2278.67±2, 2281.09±2, 2285.01±2, 2289.43±2, 2290.85±2, 2292.35±2, 2295.92±2, 2296.92±2, 2301.71±2, 2302.50±2, 2303.21±2, 2305.43±2, 2307.22±2, 2314.24±2, 2314.81±2, 2317.68±2, 2325.30±2, 2327.73±2, 2341.14±2, 2342.87±2, 2344.45±2, 2351.97±2, 2353.99±2, 2355.29±2, 2357.54±2, 2367.75±2, 2375.59±2, 2378.35±2, 2380.39±2, 2393.64±2, 2402.11±2, 2404.01±2, 2406.49±2, 2412.79±2, 2414.25±2, 2415.20±2, 2416.30±2, 2431.13±2, 2434.36±2, 2438.19±2, 2439.22±2, 2444.37±2, 2451.90±2, 2453.96±2, 2455.44±2, 2456.62±2, 2459.43±2, 2462.31±2, 2464.16±2, 2470.97±2, 2478.17±2, 2479.28±2, 2484.18±2, 2500.40±2, 2502.64±2, 2504.73±2, 2507.42±2, 2509.21±2, 2515.26±2, 2517.43±2, 2519.07±2, 2527.31±2, 2531.06±2, 2532.26±2, 2546.08±2, 2554.96±2, 2559.48±2, 2564.01±2, 2571.26±2, 2578.45±2, 2581.25±2, 2583.37±2, 2584.81±2, 2587.01±2, 2588.90±2, 2593.68±2, 2596.11±2, 2603.33±2, 2608.20±2, 2613.31±2, 2614.91±2, 2622.46±2, 2629.26±2, 2633.69±2, 2634.61±2, 2640.51±2, 2641.73±2, 2652.85±2, 2655.08±2, 2665.15±2, 2670.00±2, 2682.80±2, 2696.41±2, 2697.73±2, 2698.27±2, 2699.82±2, 3302.01±2, 3303.21±2, 3309.84±2, 3323.89±2, 3330.34±2, 3337.92±2, 3366.84±2, 3370.39±2, 3378.18±2, 3380.43±2 or 3384.77±2.

The signal peptides specified by these molecular weights are signal peptides the presence or absence or degree of abundance of which in bodily fluids from ALS patients has been confirmed by the inventors to differ from the presence or absence or reference levels set based on degree of abundance of the same signal peptides in bodily fluids from healthy subjects.

A typical example of the ALS-associated signal peptide disclosed here is a signal peptide comprising any of the amino acid sequences represented by SEQ ID Nos: 1 to 1580.

In the method for aiding ALS detection disclosed here as the second embodiment, the presence or absence and degree of abundance of the ALS-associated signal peptide can be tested by methods similar to those used to determine the profile of signal peptides in a bodily fluid in the first embodiment. Consequently, detailed explanations of these testing methods are omitted.

The reference level can be set based on test results obtained by testing the presence or absence, or the degree of abundance when present, of the target signal peptide in a bodily fluid collected from at least one healthy subject who does not suffer from (has not developed) ALS. However, the presence or absence (or abundance) of target signal peptides m bodily fluids is subject to differences among individuals (individual differences) even among healthy subjects. Consequently, the reference level is preferably determined comprehensively based on the results of testing of bodily fluids from multiple (2 or 3 or more, or preferably at least 5, or more preferably at least 10) healthy subjects.

The methods for testing the bodily fluids collected from the healthy subjects are preferably similar to those used to test the presence or absence or degree of abundance of the ALS-associated signal peptide in a bodily fluid from a test subject.

When one healthy subject is tested as a control, the reference level can be determined using the test results from the single healthy subject as the reference level.

When multiple healthy subjects are tested as control subjects, on the other hand, the reference level can be determined by appropriate statistical processing of the test results from the multiple healthy subjects. The methods of this statistical processing are not particularly limited. For example, the average (or median) of the test results from multiple healthy subjects can be calculated, and this average (or median) value can be set as the upper or lower limit of the reference level. Alternatively, the value of a predetermined multiple of the average (or median) value can be set as the upper or lower limit of the reference level. For example, a multiple of 1.5 times, 2 times, 3 times or 5 times the average (or median value) or a multiple of 0.8 times, or 0.5 times, or 0.3 times the average (or median) value can be the upper or lower limit of the reference level.

Alternatively, a suitable numerical range that includes the average (or median) value can also be set as the reference level. For example, a statistical tolerance range or a range of predetermined multiples can be set as the reference level, or a range up to a number 1 times, or 1.5 times, or 2 times, or 3 times, or 5 times the standard deviation (or standard error) from the average (or median) value can be set as the reference level. A numerical range of ±10%, or ±20%, or ±30%, or ±40%, or ±50% or ±60% of the average (or median) value can also be set as the reference level for example.

A suitable cutoff (or threshold) value can also be calculated and used as the reference level. This cutoff (or threshold) value can be set at a value at which an ALS patient can be distinguished from a healthy patient with a predetermined sensitivity and/or specificity (such as at least 50%, or at least 60%, or at least 70%, or at least 80%, or at least 90%, or at least 95%, or at least 98%). This cutoff (or threshold) value can be calculated by conventional known statistical methods, and can be determined at will from a comparison of the abundance distributions of the signal peptide in a healthy subject group and an ALS patient group.

For example, it can be set using an ROC curve (receiver operating characteristic curve). An ROC curve is a graph showing the ALS detection sensitivity on the vertical axis and the false positive rate (that is. "1-specificity") on the horizontal axis. To set the cutoff value, an appropriate reference value is set for the abundance of the target signal peptide, and an ROC curve can then be obtained by continuously varying this reference value and plotting the resulting changes in the sensitivity and false-positive rate. A value that can be expected to yield the desired sensitivity and specificity can then be set as the cutoff value based on the resulting ROC curve.

"Sensitivity" in an ALS patient group means the rate (true positive rate) at which the ALS patient group is judged as positive when the abundance of a signal peptide is set to a predetermined value (the reference value), while "specificity" in a healthy subject group means the rate (true negative rate) at which the healthy subject group is judged as negative when the abundance of a signal peptide is set to a predetermined value (the reference value).

Alternatively, the 5th percentile value (preferably the 1st percentile value) or the 95th percentile value (preferably 99th percentile value) of the abundance of the signal peptide in the healthy subject group or ALS patient group can be set as the cutoff value.

In the method for aiding ALS detection disclosed here, data about a test subject's suffering from or developing ALS (typically, data suggesting that the test subject suffers from or has developed ALS, such as data regarding the likelihood that the test subject suffers from or has developed ALS) can be obtained by testing the presence or absence or degree of abundance of at least one kind of ALS-associated signal peptide in a bodily fluid from the test subject. From the standpoint of improving the reliability (typically accuracy) of the data obtained by this method, it is desirable to test for 2 or 3 or more, or preferably at least 10, or still more preferably at least 20 ALS-associated signal peptides. When testing for multiple ALS-associated signal peptides, moreover, the molecular weights of these ALS-associated signal peptides preferably differ by at least 3 (more preferably by at least 5) from each other.

In the method for aiding ALS detection disclosed here, the presence of a difference between the test results for at least one kind of tested ALS-associated signal peptide (that is, difference in the presence or absence of the ALS-associated signal peptide in a bodily fluid from a test subject, or in the abundance of the signal peptide in a bodily fluid from a test subject) and the reference level of that ALS-associated signal peptide is associated with the test subject's suffering from or developing ALS (typically, suggests that the test subject suffers from or has developed ALS).

That is, in a preferred embodiment of the method for aiding ALS detection disclosed here the results of a test of a bodily fluid from the test subject (that is, presence or absence of one or two or more ALS-associated signal peptides m the bodily fluid from the test subject, or degree of abundance when such ALS-associated signal peptides are present) are compared with the reference levels of the corresponding ALS-associated signal peptides.

In the method for aiding ALS detection disclosed here, the likelihood that the test subject suffers from or has developed ALS (typically, an increase in this likelihood) is indicated more reliably (accurately) the greater the frequency with which the degree of abundance (or presence or absence) of these ALS-associated signal peptides in the bodily fluid from the test subject differs from the reference levels when the results of a test of the bodily fluid from the test subject are compared with the reference levels of the corresponding ALS-associated signal peptides.

That is, from the standpoint of obtaining highly reliable (highly accurate) data about the likelihood that a test subject suffers from or has developed ALS (typically, an increase in this likelihood), it is desirable to confirm that at least 60% (preferably at least 70%, or more preferably at least 80%, or still more preferably at least 95%) of the tested ALS-associated signal peptides differ from the reference levels for those signal peptides.

In other words, in the method for aiding ALS detection disclosed here the likelihood that a test subject does not suffer from or has not developed ALS (typically, a decrease in the likelihood that the test subject suffers from or has developed ALS) is indicated more reliably (accurately) the lower the frequency with which the degree of abundance (or presence or absence) of these ALS-associated signal peptides in the bodily fluid from the test subject differs from the reference levels when the results of a test of the bodily fluid from the test subject are compared with the reference levels of the corresponding ALS-associated signal peptides.

That is, from the standpoint of obtaining highly reliable (high accurate) data about the likelihood that a test subject does not suffer from and has not developed ALS (typically, a decrease in the likelihood that the test subject suffers from or has developed ALS), it is desirable to confirm that at least 60% (preferably at least 70%, or more preferably at least 80%, or still more preferably at least 95%) of the tested ALS-associated signal peptides are within the reference levels for those signal peptides.

In a preferred embodiment of the method for aiding ALS detection disclosed here, at least any of the ALS-associated signal peptides having the molecular weights 1502.40±2, 1521.93±2, 1629.15±2, 1682.54±2, 1691.75±2, 1705.53±2, 1821.71±2, 1836.18±2, 1948.39±2, 2011.18±2, 2092.80±2, 2099.42±2, 2177.51±2, 2179.25±2, 2186.28±2, 2211.58±2, 2226.96±2, 2254.83±2, 2278.67±2, 2290.85±2, 2292.35±2, 2502.64±2, 2640.51±2, 2698.27±2 and 3330.34±2 is tested as an ALS-associated signal peptide. More preferably, at least any of the ALS-associated signal peptides comprising the amino acid sequences represented by SEQ ID Nos: 1 to 180 is tested. In other words, preferred ALS-associated signal peptides for testing by the method for aiding ALS detection disclosed here include at least any of the ALS-associated signal peptides having molecular weights of 1629.17±2, 1767.38±2, 1900.43±2, 1933.29±2, 1966.96±2, 1996.12±2, 2187.30±2, 2196.08±2, 2196.64±2 and 2240.20±2 (preferably, at least any of the ALS-associated signal peptides comprising the amino acid sequences represented by SEQ ID Nos: 1 to 180).

These ALS-associated signal peptides are ALS-associated signal peptides the presence or absence or degree of abundance of which in bodily fluids from ALS patients has been confirmed by the inventors to be dramatically different from the reference levels. Consequently, the reliability (typically accuracy) of data obtained by the method for aiding ALS detection disclosed here (that is, data associated with a test subject's suffering from or developing ALS, typically data suggesting that the test subject suffers from or has developed ALS, such as data regarding the likelihood that the test subject suffers from or has developed ALS) can be improved by testing the presence or absence or degree of abundance when present of at least one kind (preferably 2 or 3 or more kinds, or more preferably at least 5 kinds, or still more preferably at least 10 kinds) of these ALS-associated signal peptides in a bodily fluid from a test subject.

In a preferred embodiment of the method for aiding ALS detection disclosed here, the abundance of a signal peptide capable of distinguishing ALS patients from healthy subjects with high sensitivity and/or high specificity is tested. For example, preferably the AUC (area under the curve) of the ROC curves is calculated, and the abundance of a signal peptide with a large AUC is tested (that is, the abundance of that signal peptide is compared with the reference level thereof). The AUC is the area under the ROC curve, and it is known that indicators with greater AUCs are better indicators for detecting diseases with high diagnostic ability (predictive ability).

In a preferred embodiment of the method for aiding ALS detection disclosed here, specific ALS-associated signal peptides are tested to confirm that the degree of abundance of those signal peptides in a bodily fluid from a test subject is higher than the reference levels. These specific ALS-associated signal peptides, the abundance of which in a bodily fluid from a test subject is tested to confirm that it is higher than the reference levels, are also called "ALS positive signal peptides" below.

These ALS positive signal peptides are typically the ALS-associated signal peptides specified by the molecular weights:
1405.71±2, 1406.49±2, 1409.40±2, 1410.97±2, 1418.70±2, 1426.68±2, 1437.62±2, 1445.77±2, 1451.61±2, 1456.44±2, 1458.88±2, 1466.24±2, 1468.86±2, 1472.12±2, 1476.87±2, 1482.60±2, 1493.58±2, 1495.42±2, 1496.52±2, 1498.88±2, 1502.40±2, 1505.52±2, 1508.76±2, 1510.50±2, 1516.64±2, 1521.93±2, 1529.32±2, 1530.37±2, 1533.52±2, 1539.36±2, 1544.22±2, 1553.72±2, 1555.72±2, 1560.24±2, 1566.20±2, 1567.20±2, 1575.70±2, 1578.07±2, 1580.91±2, 1589.58±2, 1592.55±2, 1597.25±2, 1608.53±2, 1609.36±2, 1610.62±2, 1616.12±2, 1629.15±2, 1639.39±2, 1640.36±2, 1646.58±2, 1655.72±2, 1657.97±2, 1659.24±2, 1660.46±2, 1662.16±2, 1679.09±2, 1682.54±2, 1683.12±2, 1687.34±2, 1688.14±2, 1691.08±2, 1691.75±2, 1694.76±2, 1695.74±2, 1700.65±2, 1702.19±2, 1708.77±2, 1712.10±2, 1714.63±2, 1715.56±2, 1719.51±2, 1721.61±2, 1726.31±2, 1737.85±2, 1739.71±2, 1743.69±2, 1761.79±2, 1769.93±2, 1774.13±2, 1775.70±2, 1786.39±2, 1788.03±2, 1790.80±2, 1796.23±2, 1797.49±2, 1800.34±2, 1801.79±2, 1804.45±2, 1810.72±2, 1812.3±21, 1813.77±2, 1817.26±2, 1818.66±2, 1819.93±2, 1821.71±2, 1822.73±2, 1829.48±2, 1832.41±2, 1836.18±2, 1837.33±2, 1840.84±2, 1849.81±2, 1854.68±2, 1858.34±2, 1864.19±2, 1866.06±2, 1875.28±2, 1876.50±2, 1878.25±2, 1890.21±2, 1891.32±2, 1893.00±2, 1904.69±2, 1911.46±2, 1913.68±2, 1916.02±2, 1919.35±2, 1927.13±2, 1931.84±2, 1934.86±2, 1936.83±2, 1937.87±2, 1941.22±2, 1944.97±2, 1948.39±2, 1952.47±2, 1957.80±2, 1962.82±2, 1969.82±2, 1972.54±2, 1975.58±2, 1976.51±2, 1977.70±2, 1979.29±2, 1988.46±2, 1991.91±2, 1995.37±2, 2009.91±2, 2011.18±2, 2013.86±2, 2023.97±2, 2027.73±2, 2030.95±2, 2032.69±2, 2039.29±2, 2043.12±2, 2045.68±2, 2051.76±2, 2059.05±2, 2062.98±2, 2066.09±2, 2074.03±2, 2075.32±2, 2079.80±2, 2083.74±2, 2085.85±2, 2089.53±2, 2092.80±2, 2097.03±2, 2099.42±2, 2111.39±2, 2113.10±2, 2115.77±2, 2120.37±2, 2126.55±2, 2137.63±2, 2139.15±2, 2143.42±2, 2146.46±2, 2149.85±2, 2151.02±2, 2160.22±2, 2161.68±2, 2167.09±2, 2168.75±2, 2173.75±2, 2177.51±2, 2179.25±2, 2185.65±2, 2186.28±2, 2190.18±2, 2191.02±2, 2192.84±2, 2196.47±2, 2199.82±2, 2201.22±2, 2204.02±2, 2207.10±2, 2211.58±2, 2216.77±2, 2218.45±2, 2219.30±2, 2220.56±2, 2222.74±2, 2226.96±2, 2228.22±2, 2231.60±2, 2239.71±2, 2244.01±2, 2251.78±2, 2254.83±2, 2256.53±2, 2261.91±2, 2266.45±2, 2268.58±2, 2274.97±2, 2276.04±2, 2278.67±2, 2281.09±2, 2285.01±2, 2289.43±2, 2290.85±2, 2292.35±2, 2295.92±2, 2296.92±2, 2301.71±2, 2302.50±2, 2303.21±2, 2305.43±2, 2307.22±2, 2314.24±2, 2317.68±2, 2325.30±2, 2341.14±2, 2342.87±2, 2344.45±2, 2351.97±2, 2353.99±2, 2355.29±2, 2357.54±2, 2367.75±2, 2375.59±2, 2378.35±2, 2380.39±2, 2393.64±2, 2402.11±2, 2404.01±2, 2406.49±2, 2412.79±2, 2414.25±2, 2415.20±2, 2416.30±2, 2431.13±2, 2434.36±2, 2438.19±2, 2439.22±2, 2444.37±2, 2451.90±2, 2453.96±2, 2455.44±2, 2456.62±2, 2459.43±2, 2462.31±2, 2464.16±2, 2470.97±2, 2478.17±2, 2479.28±2, 2484.18±2, 2500.40±2, 2502.64±2, 2504.73±2, 2507.42±2, 2509.21±2, 2515.26±2, 2517.43±2, 2519.07±2, 2527.31±2, 2531.06±2, 2532.26±2, 2546.08±2, 2554.96±2, 2559.48±2, 2564.01±2, 2571.26±2, 2578.45±2, 2581.25±2, 2583.37±2, 2584.81±2, 2587.01±2, 2588.90±2, 2593.68±2, 2596.11±2, 2603.33±2, 2608.20±2, 2613.31±2, 2614.91±2, 2622.46±2, 2629.26±2, 2633.69±2, 2634.61±2, 2640.51±2, 2641.73±2, 2652.85±2, 2655.08±2, 2665.15±2, 2670.00±2, 2682.80±2, 2696.41±2, 2698.27±2, 2699.82±2, 3302.01±2, 3303.21±2, 3323.89±2, 3330.34±2, 3337.92±2, 3366.84±2, 3370.39±2, 3378.18±2, 3380.43±2 or 3384.77±2.

In a preferred embodiment, these ALS positive signal peptides comprise any of the amino acid sequences represented by SEQ ID Nos: 1 to 16, 21 to 27, 29 to 46, 53 to 67, 72 to 87, 94 to 108, 118 to 172, 179 to 243, 248 to 295, 297 to 304, 307 to 317, 320 to 333, 337 to 354, 359 to 422, 424, 425, 430 to 585, 587 to 593, 595 to 605, 607 to 693, 696, 699 to 777, 786 to 902, 906 to 914, 918 to 945, 947 to 983, 990 to 1029, 1042 to 1201, 1208 to 1217, 1230 to 1566, 1569 to 1571 and 1574 to 1580.

These ALS positive signal peptides are a subset of the ALS-associated signal peptides, and are signal peptides the abundance of which in bodily fluids from ALS patients has been confirmed by the inventors to be higher than the reference levels. That is, the fact that the abundance of any ALS positive signal peptide in a bodily fluid from a test subject exceeds the reference level reflects a strong likelihood that the test subject suffers from or has developed ALS.

In a preferred embodiment of the method for aiding ALS detection disclosed here, specific ALS-associated signal peptides are tested to confirm that the degree of abundance of those signal peptides in a bodily fluid from a test subject is lower than the reference levels. These specific ALS-associated signal peptides, the abundance of which in a bodily fluid from a test subject is tested to confirm that it is lower than the reference levels, are also called "ALS negative signal peptides" below.

These ALS negative signal peptides are typically the ALS-associated signal peptides specified by the following molecular weights:
1497.16±2, 1567.74±2, 1705.53±2, 1819.34±2, 1831.81±2, 1935.52±2, 2055.50±2, 2065.57±2, 2084.36±2, 2092.25±2, 2140.48±2, 2167.78±2, 2184.93±2, 2314.81±2, 2327.73±2, 2697.73±2 or 3309.84±2.

In a preferred embodiment, these ALS negative signal peptides comprise any of the amino acid sequences represented by SEQ ID Nos: 68, 69, 296, 357, 429, 903 to 905, 1223 to 1229, 1572 and 1573.

These ALS negative signal peptides are a subset of the ALS-associated signal peptides, and are signal peptides the abundance of which in bodily fluids from ALS patients has been confirmed by the inventors to be lower than the reference levels. That is, the fact that the abundance of any ALS negative signal peptide in a bodily fluid from a test subject is smaller than the reference level reflects a strong likelihood that the test subject suffers from or has developed ALS.

To confirm a strong likelihood that the test subject suffers from or has developed ALS, it is desirable to test the degree of abundance of the ALS positive signal peptides in a bodily fluid from the test subject (or the presence or absence of the ALS positive signal peptides in a bodily fluid from the test subject).

To confirm a strong likelihood that the test subject does not suffer from and has not developed ALS, on the other hand, it is desirable to test the degree of abundance of the ALS negative signal peptides in a bodily fluid from the test subject (or the presence or absence of the ALS negative signal peptides in a bodily fluid from the test subject).

In the method for aiding ALS detection disclosed here as the first or second embodiment, the bodily fluid is not particularly limited as long as it is one that can be used as an object of testing in in vitro testing to aid disease detection (diagnosis), and biological samples collected in advance from test subjects, such as cerebrospinal fluid, blood, plasma, serum, lymph fluid, ascites, saliva, synovial fluid, semen, tears, sweat, urine and the like, may be used as is or after being prepared with suitable diluents and the like. It is more desirable to use cerebrospinal fluid, blood, serum or plasma, and cerebrospinal fluid is especially desirable.

The bodily fluid may also be pre-treated in advance to isolate the signal peptides from a biological sample obtained from a test subject (to increase the abundance of the signal peptides).

<Biomarker>

A signal peptide the degree of abundance (or presence or absence) of which in bodily fluids from ALS patients is significantly different from the degree of abundance (or presence or absence) thereof in bodily fluids from healthy subjects, and which can be used to detect (diagnose) ALS by using the degree of abundance of the signal peptide as an indicator, can be used as a biomarker for diagnosing ALS (hereunder also called an ALS biomarker).

"Significantly different" in this Description may mean that the significance level in a statistically significant difference test is 5%. That is, the difference can be judged to be significant if the p value obtained from statistically significant difference testing is p<0.05. Conventional known testing methods such as a t-test (for example, Student's t-test) or U test (Mann-Whitney's U test) may be applied to statistically significant difference testing, with no particular limitations.

The signal peptides designated as ALS-associated signal peptides in the second embodiment of the method for aiding ALS detection (including the ALS positive signal peptides and ALS negative signal peptides) are all signal peptides which have been confirmed by the inventors to have p values of p<0.05 according to a U test (Mann-Whitney's U test) in a comparison of abundance in bodily fluids from ALS patients with abundance in bodily fluids from healthy subjects. Consequently, these ALS-associated signal peptides can be used favorably as ALS biomarkers.

That is, a typical example of the ALS biomarker provided by the present invention is a signal peptide comprising any of the amino acid sequences represented by SEQ ID Nos: 1 to 1580.

Of these ALS-associated signal peptides, the signal peptides having molecular weights of 1502.40±2, 1521.93±2, 1629.15±2, 1682.54±2, 1691.75±2, 1705.53±2, 1821.71±2, 1836.18±2, 1948.39±2, 2011.18±2, 2092.80±2, 2099.42±2, 2177.51±2, 2179.25±2, 2186.28±2, 2211.58±2, 2226.96±2, 2254.83±2, 2278.67±2, 2290.85±2, 2292.35±2, 2502.64±2, 2640.51±2, 2698.27±2 or 3330.34±2 (typically, signal peptides comprising amino acid sequences represented by SEQ ID Nos: 1 to 180) are all signal peptides which have been confirm by the inventors to have p values of p<0.01 according to a U test (Mann-Whitney's U test) in a comparison of abundance in bodily fluids from ALS patients with abundance in bodily fluids from healthy subjects. Consequently, these ALS-associated signal peptides are especially desirable for use as ALS biomarkers.

An ALS positive signal peptide (typically, a signal peptide comprising any of the amino acid sequences represented by SEQ ID Nos: 1 to 16, 21 to 27, 29 to 46, 53 to 67, 72 to 87, 94 to 108, 118 to 172, 179 to 243, 248 to 295, 297 to 304, 307 to 317, 320 to 333, 337 to 354, 359 to 422, 424, 425, 430 to 585, 587 to 593, 595 to 605, 607 to 693, 696, 699 to 777, 786 to 902, 906 to 914, 918 to 945, 947 to 983, 990 to 1029, 1042 to 1201, 1208 to 1217, 1230 to 1566, 1569 to 1571 and 1574 to 1580) can also be used favorably as a biomarker (hereunder also called a positive biomarker) for which an increase in the abundance of the signal peptide is associated with the onset or development of ALS (typically, suggests the onset or development of ALS, such as for example an increased likelihood of the onset or development of ALS).

Furthermore, an ALS negative signal peptide (typically, a signal peptide comprising any of the amino acid sequences represented by SEQ ID Nos: 68, 69, 296, 357, 429, 903 to 905, 1223 to 1229, 1572 and 1573) can also be used favorably as a biomarker (hereunder also called a negative biomarker) for which a decrease in the abundance of the signal peptide is associated with the onset or development of ALS (typically, suggests the onset or development of ALS, such as for example an increased likelihood of the onset or development of ALS).

The present invention also provides an artificially synthesized peptide (hereunder also called a synthetic marker peptide) comprising any of the amino acid sequences constituting the aforementioned ALS diagnostic biomarkers.

This synthetic marker peptide can be used favorably as a control (typically a positive control) or a standard substance (typically, as an internal standard substance or external standard substance) in a method for aiding ALS detection. This synthetic marker peptide can also be used favorably for the purpose of calibrating equipment used in a method for aiding ALS detection.

That is, a typical example of the synthetic marker peptide provided by the present invention is an artificially synthesized peptide comprising any of the amino acid sequences represented by SEQ ID Nos: 1 to 1580.

A synthetic marker peptide comprising any of the amino acid sequences constituting the aforementioned positive biomarkers may also be called a "synthetic positive marker peptide" below. Similarly, a synthetic marker peptide comprising any of the amino acid sequences constituting the aforementioned negative biomarkers may also be called a "synthetic negative marker peptide".

Moreover, the present invention also provides a peptide set formed of a combination of 2 or 3 or more (preferably at least 5, or more preferably at least 10, or still more preferably at least 20) synthetic marker peptides selected from the synthetic marker peptides disclosed here. The combination of synthetic marker peptides can be selected appropriately so as to correspond to the ALS biomarkers of interest in the method for aiding ALS detection.

This peptide set can be used favorably when multiple signal peptides are of interest simultaneously in the method for aiding ALS detection (or when multiple molecular weights are of interest simultaneously in a signal peptide profile).

The peptide set disclosed here may be a set of peptides selected from the aforementioned synthetic positive marker peptides, or a set of peptides selected from the aforementioned synthetic negative marker peptides.

The peptide set may also be a set of peptides selected from the synthetic marker peptides corresponding to the ALS-associated signal peptides (that is, ALS biomarkers) having molecular weights of 1502.40±2, 1521.93±2, 1629.15±2, 1682.54±2, 1691.75±2, 1705.53±2, 1821.71±2, 1836.18±2, 1948.39±2, 2011.18±2, 2092.80±2, 2099.42±2, 2177.51±2, 2179.25±2, 2186.28±2, 2211.58±2, 2226.96±2, 2254.83±2, 2278.67±2, 2290.85±2, 2292.35±2, 2502.64±2, 2640.51±2, 2698.27±2 or 3330.34±2 (typically, the synthetic marker peptides comprising amino acid sequences represented by SEQ ID Nos: 1 to 180).

The peptide set may also be a set of peptides selected from the synthetic marker peptides corresponding to ALS-associated signal peptides (that is, ALS biomarkers) within a specific molecular weight range. That is, it may be a set of peptides selected from the synthetic marker peptides corresponding to ALS-associated signal peptides (that is, ALS biomarkers) having molecular weights of at least 1000 and less than 2000, or at least 2000 and less than 2500, or at least 2500 and less than 3000, or at least 3000 and less than 3500 for example.

The synthetic marker peptides disclosed here can be easily manufactured based on common chemical synthesis methods. For example, either a conventional known solid-phase synthesis method or liquid-phase synthesis method may be adopted. Solid-phase synthesis using Boc (t-butyloxycarbonyl) or Fmoc (9-fluorenylmethyloxycarbonyl) as the protective group of the amino group is desirable.

For the synthetic marker peptides disclosed here, peptide chains having the desired amino acid sequences and modified (C-terminal amidated, etc.) parts can be synthesized by solid-phase synthesis using a commercial peptide synthesizer (available for example from Intavis AG, Protein Technologies, Inc. or the like).

A synthetic marker peptide can also be synthesized based on genetic engineering techniques. That is, a polynucleotide (typically DNA) having a nucleotide sequence (including ATG initiation codon) coding for the amino acid sequence of a desired synthetic marker peptide is synthesized. A recombinant vector carrying a gene expression construct comprising the synthesized polynucleotide (DNA) together with various regulatory elements for expressing the amino acid sequence in host cells (including promoters, ribosome binding sites, terminators, enhancers, and various cis-elements for controlling the expression level) is then constructed according to the host cells.

This recombinant vector is then introduced into specific host cells (such as yeast, insect or plant cells) by ordinary methods, and the host cells or a tissue or individual organism containing those cells are cultured under specific conditions. The target peptide can thus be expressed and produced in cells. The peptide can then be isolated from the host cells (or from medium when it is excreted), and refolded, purified or the like as necessary to obtain the target synthetic marker peptide.

Methods conventionally used in the field can be adopted as the methods for constructing a recombinant vector and introducing the resulting vector into host cells and the like, and detailed explanations are omitted because these methods themselves are not a particular feature of the present invention.

For example, a fusion protein expression system can be used for efficient and large-scale production in host cells. That is, a gene (DNA) coding for the amino acid sequence of a target synthetic marker peptide is chemically synthesized, and the synthesized gene is introduced into a favorable site of a suitable fusion protein expression vector (for example, the pET series provided by Novagen Inc., and GST (glutathione S-transferase) fusion protein expression vectors such as the pGEX series provided by Amersham Biosciences). Host cells (typically E. coli) are then transformed with the resulting vector. The resulting transformant is cultured to obtain the target fusion protein. Next, the protein is extracted and purified. The resulting purified fusion protein is then cleaved with a specific enzyme (protease), and a released target peptide fragment (designed synthetic marker peptide) is collected by a method such as affinity chromatography. This can also be refolded by suitable methods as necessary. The synthetic marker peptide disclosed here can be manufactured using such a conventional known fusion protein expression system (for example, a GST/His system provided by Amersham Biosciences for example).

Template DNA (that is, a synthetic gene fragment containing a nucleotide sequence coding for the amino acid sequence of a synthetic marker peptide) for use in a cell-free protein synthesis system can also be constructed, and a target polypeptide can be synthesized in vitro with a so-called cell-free protein synthesis system using various compounds necessary for peptide synthesis (ATP, RNA polymerase, amino acids, etc.). The papers of Shimzu et al (Shimizu et al., Nature Biotechnology, 19, 751-755 (2001)) and Madin et al (Madin et al., Proc. Natl. Acad. Sci. USA, 97(2), 559-564 (2000)) for example may be consulted with respect to cell-free protein synthesis systems. Based on the techniques described in these papers, many companies have already commissioned polypeptide products at the time of filing of this application, and cell-free protein synthesis kits (for example, the PROTEIOS™ Wheat Germ Cell-free Protein Synthesis Kit available from CellFree Sciences Co., Ltd. in Japan) are commercially available.

A single- or double-stranded polynucleotide comprising a nucleotide sequence coding for the synthetic marker peptide disclosed here and/or a nucleotide sequence complementary to that sequence can be easily manufactured (synthesized) by conventional known methods. That is, a nucleotide sequence corresponding to the amino acid sequence of a synthetic marker peptide can be easily determined and provided by selecting codons corresponding to each amino acid residue constituting a designed amino acid sequence. Once the nucleotide sequence has been determined, a (single-stranded) polynucleotide corresponding to the desired nucleotide sequence can then be easily obtained with a DNA synthesizer or the like. Furthermore, the resulting single-stranded DNA can then be used as a template to obtain a target double-stranded DNA by various enzymatic synthesis techniques (typically PCR). Moreover, a polynucleotide may be in the form of either DNA or RNA (mRNA or the like). DNA may be provided in either double-stranded or single-stranded form. In the case of single-stranded DNA, it may be either a coding strand (sense strand) or a non-coding strand (antisense strand) complementary to the sense strand.

As discussed above, the resulting polynucleotide can be used in various host cells and cell-free protein synthesis systems as a material for constructing a recombinant gene (expression cassette) for synthetic marker peptide production.

The synthetic marker peptide disclosed here may also be in the form of a salt. For example, it is possible to use an acid addition salt of the peptide obtained by an addition reaction performed by ordinary methods with a commonly used inorganic or organic acid. Other salts (such as metal salts) are also possible. Thus, the "peptides" described in this Description and in the claims encompass salts of peptides.

<ALS Testing Composition>

The ALS testing composition provided by the present invention includes at least one of the aforementioned synthetic marker peptides. This composition can be used as a control (typically a positive control) or an indicator substance in a method for aiding ALS detection for example. In other words, the present invention provides a comparative composition (typically a positive control composition) and a standard substance composition in a method for aiding ALS detection.

The ALS testing composition disclosed here may contain 2 or 3 or more of the aforementioned synthetic marker peptides. That is, the ALS testing composition may contain the synthetic marker peptide set described above.

Like conventional in vitro diagnostic agents (in vitro testing agents) and peptide preparations, the ALS testing composition disclosed here may contain various components in addition to the synthetic marker peptide that is the principal component. In addition to the synthetic marker peptide, it may normally contain at least one kind of accessory component capable of maintaining the peptide stably (typically, without denaturing or decomposition). This accessory component may differ depending on the use and form (mode of use) of the ALS testing composition, but examples include various pharmacologically (medically) acceptable carriers. A carrier that is commonly used as a diluent, excipient or the like in conventional in vitro diagnostic agents (in vitro testing agents) is preferred.

For example, saline and various pharmacologically acceptable buffers may be included as solvents, or in other words carriers. Typical examples include water, physiological buffers (such as phosphate-buffered saline (PBS)), and various organic solvents. Other examples include aqueous solutions of alcohols (such as ethanol) at suitable concentrations, glycerol, and non-drying oils such as olive oil, as well as liposomes. Various excipients such as sugars (dextrin, lactose, etc.) may also be included. In addition, preservatives, stabilizers, pH adjusters and other agents as well as various fillers, bulking agents, binders, humectants, surfactants, colorants, perfumes and the like may be added as in conventional diagnostic agents and peptide preparations.

The form of the ALS testing composition is not particularly limited. Examples of typical forms include liquids, suspensions, emulsions, aerosols, foams, granules, powders, pills, capsules, ointments, aqueous gels and the like. The composition may also be in the form of a freeze-dried composition or granules that are dissolved in saline or a suitable buffer (such as PBS) before use to prepare a liquid.

The processes for preparing agents (compositions) in various forms using the synthetic marker peptide (principal component) and various carriers (accessory components) may be based on conventional known methods, and detailed explanations are omitted because such preparation methods are not themselves a feature of the present invention. Sources of detailed information about formulations include Comprehensive Medicinal Chemistry, Corwin Hansch Ed., Pergamon Press (1990). The entire contents of this text are incorporated by reference in this Description.

<ALS Testing Kit>

The present invention provides an ALS testing kit for use in a method for aiding ALS detection. This kit includes at least one of the aforementioned synthetic marker peptides.

The ALS testing kit may also comprising 2 or 3 or more of the synthetic marker peptides. That is, the ALS testing kit may include the synthetic marker peptide set described above.

The reagents and instruments included in this kit may be selected appropriately according to the types of testing methods (typically, the methods for analyzing the degree of abundance (or presence or absence) of signal peptides in a bodily fluid, or the methods for determining signal peptide profiles in a bodily fluid) and the detection and measurement equipment (normally a commercial device is used, and suitable chemicals and instruments (substrates, etc.) are selected according to the user's manual). For example, in addition to the synthetic marker peptide and various carriers (including solvents such as saline) constituting the aforementioned ALS testing composition, these may include diluents (typically various buffers) for diluting the synthetic marker peptides or bodily fluid to be measured, and a matrix for MALDI MS and the like.

A preferred embodiment of the ALS testing kit disclosed herein is a kit provided with a plurality of the ALS testing composition, containing mutually different synthetic marker peptides. For example, this may be a kit provided with an ALS testing composition containing at least one of the synthetic positive marker peptides and an ALS testing composition containing at least one of the synthetic negative marker peptides.

A preferred embodiment of the ALS testing kit disclosed here may be provided with a substrate for immobilizing (carrying) the synthetic marker peptide or bodily fluid.

For example, this may be a kit comprising a synthetic marker peptide that has been immobilized (carried) in advance on a substrate. Alternatively, the kit may be provided with a substrate separately from the synthetic marker peptide, and the synthetic marker peptide may be carried (immobilized) on the substrate at the time of use.

The bodily fluid to be measured (that is, a bodily fluid from a test subject) may be immobilized a substrate that is the same as or different from the substrate on which the synthetic marker peptide is immobilized, and either may be selected depending on the detection method.

Typically, the substrate may be made of various polymer compounds (such as agarose and cellulose) and synthetic resins (such as polystyrene, polypropylene and polycarbonate), or a ceramic material such as glass. The substrate may be in the shape of a plate, beads, or a membrane, stick or test tube or the like depending on the intended use, without any particular limitations. The method of carrying (immobilized) the peptide on the substrate may be similar to conventional methods, without any particular limitations. For example, a conventional known physical adsorption method, covalent binding method, ionic binding method, crosslinking method or the like may be adopted.

A kit provided with a substrate having a surface made of thermoplastic resin for immobilizing (carrying) the synthetic marker peptide or bodily fluid (or preferably a substrate made of thermoplastic resin) can be used favorably in a testing method (method for aiding ALS detection) using MALDI MS. In this case, the substrate is preferably in a film, sheet, plate, membrane, stick or chip form. The peptide may then be carried on the substrate by heating and melting the thermoplastic resin.

A preferred embodiment of the ALS testing kit disclosed here is a kit provided with an ALS testing chip comprising at least one of the synthetic marker peptides immobilized (carried) on a film-shaped or plate-shaped substrate. In this substrate, the surface that carries the synthetic marker peptide is made of a thermoplastic resin.

In other words, the present invention provides an ALS testing chip comprising at least one of the synthetic marker peptides immobilized (carried) on a film-shaped or plate-shaped substrate, wherein the surface of the substrate that carries the synthetic marker peptide is made of a thermoplastic resin.

In a preferred embodiment of this ALS testing chip, 2 or 3 or more (preferably at least 5, or more preferably at least 10, or still more preferably at least 20) different synthetic marker peptides are immobilized on the same substrate. Typically, this may include the synthetic marker peptides constituting the synthetic marker peptide set described above, immobilized on the same substrate.

In an ALS testing chip comprising multiple synthetic marker peptides immobilized on the same substrate, the multiple synthetic marker peptides may be immobilized on the same spot on the same substrate, or may be immobilized on different spots independently of one another. For example, the synthetic marker peptides constituting the synthetic marker peptide set described above may all be immobilized together on the same spot.

One preferred example of the ALS testing kit disclosed here is a kit provided with multiple ALS testing chips having different synthetic marker peptides immobilized thereon. For example, this may be a kit provided with an ALS testing chip having at least one of the aforementioned synthetic positive marker peptides immobilized thereon, and an ALS testing chip having at least one of the aforementioned synthetic negative marker peptides immobilized thereon.

Some examples of the present invention are explained below, but the intent is not to limit the invention to what is shown in the examples.

Example 1

Profiles of signal peptides contained in bodily fluids were determined for bodily fluids obtained from a healthy subject group and an ALS patient group. In this example, the signal peptide profiles in the bodily fluids were determined by comprehensive analysis using MALDI-TOFMS. The specific procedures are given below.

In this example, cerebrospinal fluid collected from 5 healthy subjects and cerebrospinal fluid collected from 5 ALS patients (all Hispanic) was used for the samples. Commercial samples were purchased and used for all the cerebrospinal fluid samples. The characteristics (sex, race, disease stage, etc.) of the cerebrospinal fluid donors in each group are shown in Table 1.

TABLE 1

|  | ALS patient group | Healty subject group |
|---|---|---|
| Number of subjects | 5 | 5 |
| Age (±SD) | 54.6 ± 4.7 | 76 ± 12.5 |
| Sex (%) |  |  |
| Male | 3 (60%) | 2 (40%) |
| Female | 2 (40%) | 3 (60%) |

Each cerebrospinal fluid sample was mixed with a matrix and immobilized on a substrate.

The cerebrospinal fluid sample and matrix liquid were first mixed at a volume ratio of 1:1. The matrix liquid included sinapinic acid (CHCA) as the matrix, contained at a concentration of 5 mg/mL in a 50 vol % acetonitrile aqueous solution containing 0.1 vol % trifluoracetic acid (0.1% TFA/50% ACN aqueous solution).

The matrix liquid was mixed with the cerebrospinal fluid sample to obtain a mixed matrix-cerebrospinal fluid sample, 2 µL of which was then dropped onto a substrate, and vacuum dried. A measurement plate commonly used in MALDI MS was covered with an EVA film for use as the substrate. That is, in the substrate for immobilizing the bodily fluid in this example the surface for immobilizing the bodily fluid was made of a thermoplastic resin.

The measurement sample thus prepared was subjected to mass spectrometry.

An AXIMA (registered trademark) Performance, manufactured by Shimadzu Corporation was used as the mass spectrometer (MALDI-TOFMS). For the measurement conditions, the laser source was a N2 encapsulated laser ($\lambda$=337.1 nm), the acceleration voltage was +20 kV, the delay withdrawal was optimized at m/z 2200, and the flight mode was set to Liner mode. The measurement equipment was calibrated by the external standard method, using Antiotensin 11 (m/z 1046.54), ACTH fragment 18-39 (m/z 2465.20) and Insulin (m/z 5730.61) as the calibrants (calibration standards). Each cerebrospinal fluid sample was exposed 200 times to laser light, and a mass spectrum was obtained for each laser exposure.

The mass spectra obtained separately for each laser exposure were integrated and averaged to obtain a representative mass spectrum for each cerebrospinal fluid sample.

The mass spectra obtained separately for each of the 200 laser exposures were also compared, the number of times that each peak was detected in the 200 mass spectra was integrated, and the integrated value was given as the peak value. That is, if a peak at m/z 1000 was detected 100 times in the 200 mass spectra separately obtained from the 200 laser exposures, the peak value of this peak is 100.

The peaks detected in the representative mass spectrum obtained above reflect the presence of signal peptides corresponding to the m/z values of these peaks in the measured cerebrospinal fluid sample. That is, the profile of signal peptides in this cerebrospinal fluid is represented qualitatively by this representative mass spectrum. Consequently, a profile of signal peptides present in a bodily fluid (cerebrospinal fluid) can be obtained as a representative mass spectrum by the method disclosed here.

The peak values obtained above reflect the degree of abundance of signal peptides corresponding to the m/z values of these peaks in the measured cerebrospinal fluid sample. That is, the data set relating to these peak values quantitatively shows a profile of the signal peptides present in the cerebrospinal fluid. Consequently, a profile of signal peptides present in a bodily fluid (cerebrospinal fluid) can be determined as a data set relating to peak values by the method disclosed here.

Example 2

Comparison of ALS Patient Group and Healthy Subject Group

The peak values of each peak obtained in Example 1 above were then subjected to statistically significant difference testing between the ALS patient group and healthy subject group. A two-tail test was performed using a U test (Mann-Whitney's U test) as the statistically significant difference test. In this significant difference test, the significance level was set at 5% (that is, the difference was significant when the P value was $p<0.05$).

As a result, significant differences were found at 327 peaks between the ALS patient group and the healthy subject group. The results are shown in Tables 2 to 9.

TABLE 2

| m/z of each peak | ALS patient group (n = 5) | | Healty subject group (n = 5) | | P value |
|---|---|---|---|---|---|
| | Average of Peak value | Standard Deviation of Peak value | Average of Peak value | Standard Deviation of Peak value | |
| 1405.71 | 18.52 | 7.11 | 2.46 | 3.63 | 0.012 |
| 1406.49 | 14.74 | 10.74 | 1.98 | 2.79 | 0.037 |
| 1409.4 | 12.67 | 11.48 | 0.52 | 1.04 | 0.011 |
| 1410.97 | 13.64 | 10.65 | 0.29 | 0.49 | 0.021 |
| 1418.7 | 19.21 | 4.66 | 1.41 | 2.29 | 0.012 |
| 1426.68 | 14.43 | 11 | 1.62 | 1.2 | 0.012 |
| 1437.62 | 12.9 | 11.16 | 0.24 | 0.53 | 0.018 |
| 1445.77 | 15.91 | 8.36 | 0.15 | 0.15 | 0.012 |
| 1451.61 | 13.22 | 11.15 | 0.67 | 1.48 | 0.02 |
| 1456.44 | 21.13 | 7.06 | 5.28 | 4.26 | 0.022 |
| 1458.88 | 15.68 | 10.99 | 3 | 1.91 | 0.037 |
| 1466.24 | 10.79 | 12.66 | 0.68 | 0.92 | 0.036 |
| 1468.86 | 11.77 | 12.49 | 1.41 | 1.37 | 0.037 |
| 1472.12 | 12.44 | 11.92 | 1 | 1.13 | 0.022 |
| 1476.87 | 14.66 | 11.33 | 2.38 | 1.56 | 0.037 |
| 1482.6 | 14.57 | 10 | 0.46 | 0.65 | 0.011 |
| 1493.58 | 11.7 | 12.23 | 0.81 | 1.19 | 0.021 |
| 1495.42 | 16.07 | 9.07 | 1.01 | 0.96 | 0.012 |
| 1496.52 | 14.02 | 10.19 | 0.1 | 0.18 | 0.011 |
| 1497.16 | 0 | 0 | 11.07 | 12.18 | 0.025 |
| 1498.88 | 17.66 | 7.54 | 1.3 | 0.93 | 0.012 |
| 1502.4 | 14.46 | 9.71 | 0 | 0 | 0.007 |
| 1505.52 | 13.38 | 10.64 | 0 | 0 | 0.025 |
| 1508.76 | 12.31 | 11.92 | 0.84 | 0.83 | 0.012 |
| 1510.5 | 11.67 | 11.96 | 0.24 | 0.44 | 0.011 |
| 1516.64 | 15.99 | 9.7 | 1.72 | 1.91 | 0.021 |
| 1521.93 | 17.23 | 6.98 | 0.49 | 1.11 | 0.01 |
| 1529.32 | 20.03 | 6.8 | 3.65 | 3.32 | 0.012 |
| 1530.37 | 15.81 | 10.04 | 2.36 | 3.32 | 0.036 |
| 1533.52 | 18.55 | 8.74 | 3.3 | 1.79 | 0.012 |
| 1539.36 | 8.56 | 13.71 | 0.95 | 0.91 | 0.021 |
| 1544.22 | 13.28 | 11.31 | 0.86 | 0.8 | 0.012 |
| 1553.72 | 18.64 | 4.89 | 0.76 | 1.16 | 0.011 |

TABLE 2-continued

| m/z of each peak | ALS patient group (n = 5) | | Healty subject group (n = 5) | | P value |
|---|---|---|---|---|---|
| | Average of Peak value | Standard Deviation of Peak value | Average of Peak value | Standard Deviation of Peak value | |
| 1555.72 | 17.22 | 8.27 | 1.65 | 2.29 | 0.012 |
| 1560.24 | 11.35 | 12.12 | 0.18 | 0.17 | 0.012 |
| 1566.2 | 17.31 | 9.39 | 3.18 | 3.47 | 0.037 |
| 1567.2 | 13 | 11.17 | 0.35 | 0.29 | 0.012 |
| 1567.74 | 0 | 0 | 9.65 | 12.91 | 0.025 |
| 1575.7 | 8.34 | 13.65 | 0.49 | 0.45 | 0.022 |
| 1578.07 | 14.78 | 9.99 | 0.65 | 0.71 | 0.022 |
| 1580.91 | 11.16 | 12.23 | 0.18 | 0.27 | 0.012 |
| 1589.58 | 14.46 | 11.19 | 2.91 | 4.07 | 0.037 |
| 1592.55 | 12.42 | 11.42 | 0.12 | 0.17 | 0.036 |
| 1597.25 | 12.6 | 11.59 | 0.59 | 0.83 | 0.034 |
| 1608.53 | 15.61 | 9.27 | 0.71 | 0.53 | 0.012 |

TABLE 3

| m/z of each peak | ALS patient group (n = 5) | | Healty subject group (n = 5) | | P value |
|---|---|---|---|---|---|
| | Average of Peak value | Standard Deviation of Peak value | Average of Peak value | Standard Deviation of Peak value | |
| 1609.36 | 17.26 | 8.87 | 2.78 | 3.91 | 0.021 |
| 1610.62 | 10.76 | 12.52 | 0.34 | 0.67 | 0.011 |
| 1616.12 | 12.26 | 11.9 | 0.82 | 1.25 | 0.037 |
| 1629.15 | 14.42 | 9.75 | 0 | 0 | 0.007 |
| 1639.39 | 15.21 | 10.12 | 1.25 | 0.95 | 0.012 |
| 1640.36 | 12.8 | 11.57 | 0.8 | 1.09 | 0.012 |
| 1646.58 | 12.08 | 11.63 | 0.09 | 0.13 | 0.02 |
| 1655.72 | 10.01 | 12.84 | 0.21 | 0.24 | 0.012 |
| 1657.97 | 16.51 | 8.46 | 0.88 | 0.88 | 0.012 |
| 1659.24 | 12.16 | 12.32 | 1.43 | 1.1 | 0.022 |
| 1660.46 | 14.36 | 10.99 | 1.63 | 1.7 | 0.012 |
| 1662.16 | 13.58 | 11.28 | 1.13 | 0.94 | 0.022 |
| 1679.09 | 10.56 | 12.66 | 0.4 | 0.59 | 0.011 |
| 1682.54 | 0 | 0 | 11.88 | 11.7 | 0.007 |
| 1683.12 | 10.63 | 12.63 | 0.47 | 0.97 | 0.011 |
| 1687.34 | 15.02 | 10.3 | 1.38 | 1.63 | 0.022 |
| 1688.14 | 14.3 | 10.85 | 1.94 | 3.44 | 0.021 |
| 1691.08 | 9.87 | 13.1 | 0.63 | 0.25 | 0.012 |
| 1691.75 | 13.75 | 10.76 | 0.67 | 1.5 | 0.01 |
| 1694.76 | 8.92 | 13.35 | 0.3 | 0.42 | 0.012 |
| 1695.74 | 17.83 | 9.31 | 3.4 | 2.86 | 0.022 |
| 1700.65 | 18.09 | 10.14 | 4.59 | 2.89 | 0.022 |
| 1702.19 | 16.77 | 9.97 | 3.87 | 4.66 | 0.037 |
| 1705.53 | 0 | 0 | 12.1 | 11.55 | 0.007 |
| 1708.77 | 18.34 | 6.6 | 1.4 | 1.47 | 0.012 |
| 1712.1 | 13.54 | 11.39 | 1.4 | 1.74 | 0.021 |
| 1714.63 | 18.87 | 6.55 | 2.08 | 2.42 | 0.012 |
| 1715.56 | 8.75 | 13.44 | 0.34 | 0.48 | 0.022 |
| 1719.51 | 14.88 | 10.19 | 1.04 | 1.21 | 0.012 |
| 1721.61 | 13.63 | 10.66 | 0.29 | 0.41 | 0.011 |
| 1726.31 | 17.89 | 5.35 | 0.16 | 0.23 | 0.011 |
| 1737.85 | 8.98 | 13.39 | 0.44 | 0.27 | 0.012 |
| 1739.71 | 13.09 | 11.19 | 0.48 | 0.47 | 0.012 |
| 1743.69 | 14.66 | 10.55 | 1.46 | 2.21 | 0.021 |
| 1761.79 | 12.77 | 11.81 | 1.15 | 1.13 | 0.036 |
| 1769.93 | 11.5 | 12.04 | 0.19 | 0.31 | 0.034 |
| 1774.13 | 15.63 | 9.75 | 2.04 | 3.81 | 0.034 |
| 1775.7 | 11.75 | 12.47 | 1.48 | 1.86 | 0.036 |
| 1786.39 | 18.18 | 6.32 | 1.08 | 1.48 | 0.012 |
| 1788.03 | 15.91 | 9.68 | 2.09 | 3.43 | 0.021 |
| 1790.8 | 17.61 | 8.59 | 2.35 | 2.41 | 0.022 |
| 1796.23 | 13.53 | 11.16 | 0.87 | 0.62 | 0.012 |
| 1797.49 | 13.64 | 10.53 | 0.13 | 0.3 | 0.045 |

TABLE 4

| m/z of each peak | ALS patient group (n = 5) | | Healty subject group (n = 5) | | P value |
|---|---|---|---|---|---|
| | Average of Peak value | Standard Deviation of Peak value | Average of Peak value | Standard Deviation of Peak value | |
| 1800.34 | 11.53 | 12.32 | 0.77 | 0.99 | 0.037 |
| 1801.79 | 19.12 | 6.24 | 2 | 1.68 | 0.012 |
| 1804.45 | 14.95 | 9.7 | 0.52 | 0.9 | 0.012 |
| 1810.72 | 17.28 | 8.69 | 2.18 | 2.65 | 0.012 |
| 1812.31 | 11.69 | 12.38 | 1.21 | 1.75 | 0.037 |
| 1813.77 | 11.17 | 12.33 | 0.4 | 0.57 | 0.011 |
| 1817.26 | 14.56 | 10.68 | 1.6 | 2.42 | 0.037 |
| 1818.66 | 15.13 | 9.54 | 0.5 | 0.55 | 0.012 |
| 1819.34 | 0 | 0 | 10.94 | 12.26 | 0.025 |
| 1819.93 | 15.36 | 9.47 | 0.79 | 1.57 | 0.021 |
| 1821.71 | 9.79 | 12.93 | 0.18 | 0.4 | 0.01 |
| 1822.73 | 16.54 | 9.56 | 1.95 | 0.75 | 0.012 |
| 1829.48 | 16.71 | 8.07 | 0.72 | 0.31 | 0.012 |
| 1831.81 | 0 | 0 | 12.62 | 11.2 | 0.025 |
| 1832.41 | 16.39 | 8.85 | 1.17 | 1.4 | 0.036 |
| 1836.18 | 13.91 | 10.66 | 0.71 | 1.6 | 0.01 |
| 1837.33 | 12.8 | 11.63 | 0.96 | 1.46 | 0.034 |
| 1840.84 | 17.83 | 7.23 | 1.37 | 1.84 | 0.012 |
| 1849.81 | 16.31 | 8.56 | 0.78 | 0.94 | 0.012 |
| 1854.68 | 10.29 | 12.76 | 0.33 | 0.51 | 0.02 |
| 1858.34 | 15.47 | 9.73 | 1.38 | 2.5 | 0.02 |
| 1864.19 | 15.39 | 9.58 | 1.02 | 2.02 | 0.021 |
| 1866.06 | 16.93 | 7.69 | 0.68 | 0.92 | 0.012 |
| 1875.28 | 20.32 | 8.92 | 5.87 | 3.88 | 0.012 |
| 1876.5 | 15.8 | 8.92 | 0.57 | 0.79 | 0.011 |
| 1878.25 | 11.11 | 12.48 | 0.77 | 1.6 | 0.022 |
| 1890.21 | 14.46 | 10.69 | 1.24 | 1.23 | 0.022 |
| 1891.32 | 16.73 | 8.57 | 1.36 | 1.98 | 0.012 |
| 1893 | 12.88 | 11.73 | 1.3 | 1.91 | 0.021 |
| 1904.69 | 10.97 | 12.61 | 0.76 | 0.9 | 0.036 |
| 1911.46 | 15.01 | 10.23 | 1.28 | 1.61 | 0.021 |
| 1913.68 | 12.44 | 11.6 | 0.49 | 1.1 | 0.018 |
| 1916.02 | 13.23 | 11.62 | 1.36 | 1.39 | 0.012 |
| 1919.35 | 11.81 | 12.26 | 1.01 | 1.36 | 0.036 |
| 1927.13 | 15.89 | 9.35 | 1.45 | 2.71 | 0.021 |
| 1931.84 | 15.79 | 9.39 | 1.12 | 1.48 | 0.012 |
| 1934.86 | 10.44 | 12.73 | 0.42 | 0.52 | 0.012 |
| 1935.52 | 0 | 0 | 10.03 | 12.73 | 0.025 |
| 1936.83 | 11.56 | 12.14 | 0.44 | 0.5 | 0.012 |
| 1937.87 | 13.44 | 11.15 | 0.83 | 1.19 | 0.02 |
| 1941.22 | 13.64 | 11.15 | 1.46 | 2.83 | 0.036 |
| 1944.97 | 16.26 | 8.99 | 1.12 | 1.02 | 0.012 |
| 1948.39 | 14.14 | 10.46 | 0.68 | 1.52 | 0.01 |

TABLE 5

| m/z of each peak | ALS patient group (n = 5) | | Healty subject group (n = 5) | | P value |
|---|---|---|---|---|---|
| | Average of Peak value | Standard Deviation of Peak value | Average of Peak value | Standard Deviation of Peak value | |
| 1952.47 | 9.64 | 13.11 | 0.52 | 1.1 | 0.034 |
| 1957.8 | 13.48 | 11.34 | 1.29 | 1.83 | 0.022 |
| 1962.82 | 12.86 | 11.1 | 0.11 | 0.17 | 0.02 |
| 1969.82 | 13.06 | 11.39 | 0.75 | 0.69 | 0.037 |
| 1972.54 | 14.07 | 10.6 | 0.79 | 1.51 | 0.02 |
| 1975.58 | 14.44 | 11.13 | 2.17 | 2.64 | 0.036 |
| 1976.51 | 15.44 | 8.94 | 0.21 | 0.16 | 0.012 |
| 1977.7 | 18.15 | 5.95 | 0.81 | 1.29 | 0.011 |
| 1979.29 | 17.91 | 8.07 | 2.05 | 1.59 | 0.012 |
| 1988.46 | 10.26 | 12.94 | 0.89 | 1.61 | 0.036 |
| 1991.91 | 15.83 | 10.12 | 2.06 | 2.04 | 0.022 |
| 1995.37 | 13.93 | 11.89 | 2.54 | 1.57 | 0.012 |
| 2009.91 | 9.15 | 13.38 | 0.63 | 0.71 | 0.012 |
| 2011.18 | 15.18 | 9.21 | 0.22 | 0.49 | 0.01 |
| 2013.86 | 15.43 | 9.51 | 0.84 | 1.17 | 0.012 |
| 2023.97 | 15.46 | 9.58 | 1.12 | 2.13 | 0.022 |
| 2027.73 | 14.44 | 10.22 | 0.59 | 0.83 | 0.02 |
| 2030.95 | 8.71 | 13.39 | 0.16 | 0.25 | 0.021 |
| 2032.69 | 11.23 | 12.49 | 0.8 | 1 | 0.037 |
| 2039.29 | 13.14 | 11.83 | 1.6 | 1.4 | 0.022 |
| 2043.12 | 11.85 | 12.27 | 1 | 0.98 | 0.022 |
| 2045.68 | 16.29 | 8.32 | 0.51 | 0.59 | 0.012 |
| 2051.76 | 14.74 | 10.29 | 0.98 | 0.92 | 0.012 |
| 2055.5 | 0 | 0 | 11.24 | 12.08 | 0.025 |
| 2059.05 | 15.21 | 10.15 | 1.32 | 1.18 | 0.022 |
| 2062.98 | 11.11 | 12.3 | 0.26 | 0.35 | 0.012 |
| 2065.57 | 0 | 0 | 10.08 | 12.71 | 0.025 |
| 2066.09 | 13.21 | 11.14 | 0.64 | 1.43 | 0.045 |
| 2074.03 | 11.32 | 12.41 | 0.78 | 1.3 | 0.036 |
| 2075.32 | 13.91 | 11.57 | 2.17 | 2.23 | 0.022 |
| 2079.8 | 13.24 | 11.26 | 1.12 | 2.5 | 0.045 |
| 2083.74 | 12.61 | 11.38 | 0.27 | 0.36 | 0.012 |
| 2084.36 | 0 | 0 | 10.58 | 12.45 | 0.025 |
| 2085.85 | 12.16 | 11.79 | 0.45 | 0.57 | 0.012 |
| 2089.53 | 14.41 | 10.19 | 0.5 | 0.46 | 0.012 |
| 2092.25 | 0 | 0 | 9.48 | 13 | 0.025 |
| 2092.8 | 14.13 | 10.37 | 0.49 | 1.09 | 0.01 |
| 2097.03 | 16.11 | 9.45 | 1.55 | 1.8 | 0.012 |
| 2099.42 | 13.41 | 10.65 | 0.05 | 0.11 | 0.01 |
| 2111.39 | 12.66 | 11.22 | 0.06 | 0.13 | 0.045 |
| 2113.1 | 11.8 | 11.83 | 0.15 | 0.33 | 0.045 |
| 2115.77 | 11.56 | 12.19 | 0.64 | 1.44 | 0.018 |
| 2120.37 | 10.94 | 12.56 | 0.61 | 0.72 | 0.036 |

TABLE 6

| m/z of each peak | ALS patient group (n = 5) | | Healty subject group (n = 5) | | P value |
|---|---|---|---|---|---|
| | Average of Peak value | Standard Deviation of Peak value | Average of Peak value | Standard Deviation of Peak value | |
| 2126.55 | 14.45 | 10.57 | 1.34 | 2.38 | 0.021 |
| 2137.63 | 12.11 | 11.72 | 0.29 | 0.65 | 0.045 |
| 2139.15 | 14.29 | 11 | 1.54 | 1.52 | 0.022 |
| 2140.48 | 0 | 0 | 14.5 | 9.67 | 0.025 |
| 2143.42 | 15.78 | 8.68 | 0.31 | 0.39 | 0.012 |
| 2146.46 | 10.69 | 12.61 | 0.44 | 0.67 | 0.02 |
| 2149.85 | 15.66 | 9.55 | 1.08 | 1.01 | 0.012 |
| 2151.02 | 16.96 | 8.15 | 1.11 | 1.2 | 0.012 |
| 2160.22 | 16.02 | 10.27 | 2.41 | 1.96 | 0.012 |
| 2161.68 | 16.24 | 9.44 | 3.12 | 5.3 | 0.037 |
| 2167.09 | 11.99 | 11.67 | 0.08 | 0.17 | 0.045 |
| 2167.78 | 0 | 0 | 10.14 | 12.68 | 0.025 |
| 2168.75 | 16.82 | 8.6 | 1.52 | 2.18 | 0.022 |
| 2173.75 | 15.3 | 9.38 | 0.5 | 0.46 | 0.012 |
| 2177.51 | 13.11 | 10.87 | 0.04 | 0.1 | 0.01 |
| 2179.25 | 13.79 | 10.3 | 0 | 0 | 0.007 |
| 2184.93 | 0 | 0 | 8.03 | 13.59 | 0.025 |
| 2185.65 | 17.02 | 8.64 | 2.21 | 3.65 | 0.02 |
| 2186.28 | 12.04 | 11.64 | 0.07 | 0.15 | 0.01 |
| 2190.18 | 17.63 | 9.55 | 4.45 | 5.03 | 0.037 |
| 2191.02 | 15.85 | 9.19 | 0.95 | 1.39 | 0.012 |
| 2192.84 | 10.27 | 12.87 | 0.6 | 0.93 | 0.034 |
| 2196.47 | 12.26 | 13.06 | 3.48 | 2.47 | 0.037 |
| 2199.82 | 7.28 | 13.87 | 0.06 | 0.14 | 0.045 |
| 2201.54 | 15.64 | 9.44 | 1.75 | 3.92 | 0.045 |
| 2204.02 | 12.87 | 11.59 | 0.93 | 1.22 | 0.022 |
| 2207.1 | 10.33 | 13.07 | 1.12 | 1.09 | 0.037 |
| 2211.58 | 9.55 | 13.03 | 0.16 | 0.35 | 0.01 |
| 2216.77 | 11.9 | 12.08 | 1.09 | 2.43 | 0.045 |
| 2218.45 | 12.89 | 11.41 | 0.61 | 0.61 | 0.012 |
| 2219.3 | 9.82 | 13.04 | 0.47 | 0.54 | 0.022 |
| 2220.56 | 15.97 | 8.47 | 0.33 | 0.73 | 0.011 |
| 2222.74 | 15.38 | 9.45 | 0.68 | 0.67 | 0.037 |
| 2226.96 | 13.64 | 10.43 | 0 | 0 | 0.007 |

TABLE 6-continued

| m/z of each peak | ALS patient group (n = 5) | | Healty subject group (n = 5) | | P value |
|---|---|---|---|---|---|
| | Average of Peak value | Standard Deviation of Peak value | Average of Peak value | Standard Deviation of Peak value | |
| 2228.22 | 11.05 | 12.39 | 0.36 | 0.33 | 0.022 |
| 2231.6 | 12.95 | 11.48 | 0.9 | 1.56 | 0.034 |
| 2239.71 | 15.94 | 10.12 | 3.29 | 4.74 | 0.021 |
| 2244.01 | 11.58 | 12.41 | 1.06 | 1.33 | 0.022 |
| 2251.78 | 17.76 | 7.91 | 1.67 | 0.83 | 0.012 |
| 2254.83 | 13.06 | 11.1 | 0.34 | 0.77 | 0.01 |
| 2256.53 | 9.59 | 13.02 | 0.18 | 0.22 | 0.036 |
| 2261.91 | 11.86 | 11.84 | 0.22 | 0.49 | 0.045 |
| 2266.45 | 10.84 | 12.31 | 0 | 0 | 0.025 |

TABLE 7

| m/z of each peak | ALS patient group (n = 5) | | Healty subject group (n = 5) | | P value |
|---|---|---|---|---|---|
| | Average of Peak value | Standard Deviation of Peak value | Average of Peak value | Standard Deviation of Peak value | |
| 2268.58 | 11.8 | 11.9 | 0.28 | 0.62 | 0.045 |
| 2274.97 | 17.37 | 9 | 2.85 | 3.5 | 0.012 |
| 2276.04 | 14.63 | 10.78 | 1.57 | 1.44 | 0.022 |
| 2278.67 | 13.07 | 10.91 | 0.05 | 0.11 | 0.01 |
| 2281.09 | 15.63 | 8.94 | 0.39 | 0.33 | 0.012 |
| 2285.01 | 13.18 | 11.26 | 0.66 | 0.46 | 0.012 |
| 2289.43 | 15.08 | 10.59 | 1.91 | 2.09 | 0.021 |
| 2290.85 | 15.26 | 8.91 | 0 | 0 | 0.007 |
| 2292.35 | 15.68 | 8.52 | 0.07 | 0.15 | 0.01 |
| 2295.92 | 11.62 | 12.26 | 0.75 | 0.92 | 0.012 |
| 2296.92 | 15.92 | 9.12 | 0.92 | 1.07 | 0.012 |
| 2301.71 | 15.29 | 9.96 | 1.16 | 1.05 | 0.012 |
| 2302.5 | 15.74 | 9.65 | 2.06 | 3.86 | 0.034 |
| 2303.21 | 15.81 | 9.36 | 2.75 | 5.54 | 0.034 |
| 2305.43 | 11.28 | 12.72 | 1.85 | 2.78 | 0.036 |
| 2307.22 | 13.15 | 11.21 | 0.57 | 0.58 | 0.012 |
| 2314.24 | 12.27 | 11.44 | 0 | 0 | 0.025 |
| 2314.81 | 0 | 0 | 6.91 | 13.97 | 0.025 |
| 2317.68 | 12.65 | 11.96 | 1.41 | 1.79 | 0.012 |
| 2325.3 | 13.5 | 10.97 | 0.58 | 0.62 | 0.012 |
| 2327.73 | 0 | 0 | 13.86 | 10.25 | 0.025 |
| 2341.14 | 8.23 | 13.52 | 0 | 0 | 0.025 |
| 2342.87 | 14.75 | 10.25 | 0.97 | 1.09 | 0.012 |
| 2344.45 | 14.88 | 9.81 | 0.56 | 0.76 | 0.011 |
| 2351.97 | 8.05 | 13.65 | 0.21 | 0.31 | 0.036 |
| 2353.99 | 10.18 | 12.97 | 0.68 | 0.62 | 0.012 |
| 2355.29 | 11.95 | 11.65 | 0 | 0 | 0.025 |
| 2357.54 | 12.83 | 11.27 | 0.31 | 0.37 | 0.012 |
| 2367.75 | 8.79 | 13.38 | 0.21 | 0.16 | 0.012 |
| 2375.59 | 16.84 | 7.96 | 0.77 | 0.53 | 0.012 |
| 2378.35 | 17.59 | 5.88 | 0.14 | 0.18 | 0.012 |
| 2380.39 | 12.54 | 11.36 | 0.16 | 0.22 | 0.036 |
| 2393.64 | 14.63 | 10.45 | 1.15 | 1.5 | 0.021 |
| 2402.11 | 13.69 | 11.13 | 1.02 | 0.87 | 0.012 |
| 2404.01 | 12.36 | 11.63 | 0.43 | 0.97 | 0.045 |
| 2406.49 | 10.31 | 12.82 | 0.48 | 0.47 | 0.012 |
| 2412.79 | 11.91 | 11.73 | 0.08 | 0.11 | 0.011 |
| 2414.25 | 12.04 | 11.82 | 0.42 | 0.93 | 0.045 |
| 2415.2 | 14.72 | 11 | 2.06 | 1.95 | 0.036 |
| 2416.3 | 11.46 | 11.98 | 0.04 | 0.1 | 0.045 |
| 2431.13 | 11.53 | 11.93 | 0.02 | 0.05 | 0.045 |
| 2434.36 | 12.09 | 11.84 | 0.45 | 0.44 | 0.012 |
| 2438.19 | 12.48 | 11.3 | 0 | 0 | 0.025 |

TABLE 8

| m/z of each peak | ALS patient group (n = 5) | | Healty subject group (n = 5) | | P value |
|---|---|---|---|---|---|
| | Average of Peak value | Standard Deviation of Peak value | Average of Peak value | Standard Deviation of Peak value | |
| 2439.22 | 14.23 | 11.01 | 1.68 | 2.33 | 0.036 |
| 2444.37 | 15.32 | 10 | 1.43 | 2.07 | 0.02 |
| 2451.9 | 11.22 | 12.61 | 1.01 | 0.89 | 0.012 |
| 2453.96 | 12.77 | 11.19 | 0.14 | 0.32 | 0.045 |
| 2455.44 | 11.77 | 11.81 | 0.07 | 0.13 | 0.011 |
| 2456.62 | 13.13 | 12.1 | 2.18 | 1.92 | 0.037 |
| 2459.43 | 14.58 | 10.19 | 0.71 | 0.91 | 0.022 |
| 2462.31 | 11.23 | 12.3 | 0.42 | 0.92 | 0.011 |
| 2464.16 | 14.92 | 9.62 | 0.41 | 0.92 | 0.045 |
| 2470.97 | 16.04 | 8.93 | 0.9 | 1.45 | 0.012 |
| 2478.17 | 14.5 | 9.78 | 0.11 | 0.22 | 0.011 |
| 2479.28 | 12.83 | 11.59 | 0.87 | 1.13 | 0.012 |
| 2484.18 | 11.41 | 12.37 | 1.03 | 2.16 | 0.02 |
| 2500.4 | 14.96 | 10.06 | 1.04 | 1.62 | 0.012 |
| 2502.64 | 12.63 | 11.35 | 0.25 | 0.55 | 0.01 |
| 2504.73 | 13.85 | 11.3 | 2.16 | 3.43 | 0.036 |
| 2507.42 | 12.35 | 11.8 | 0.67 | 0.81 | 0.012 |
| 2509.21 | 12.62 | 11.63 | 0.72 | 1.1 | 0.034 |
| 2515.26 | 7.42 | 13.8 | 0 | 0 | 0.025 |
| 2517.43 | 14.9 | 10.1 | 2.54 | 5.24 | 0.034 |
| 2519.07 | 10.26 | 12.62 | 0 | 0 | 0.045 |
| 2527.31 | 13.31 | 10.83 | 0.19 | 0.31 | 0.02 |
| 2531.06 | 13.3 | 11.17 | 0.73 | 1.22 | 0.012 |
| 2532.26 | 12.23 | 11.49 | 0.03 | 0.06 | 0.045 |
| 2546.08 | 11.84 | 12.04 | 0.54 | 0.3 | 0.012 |
| 2554.96 | 17.74 | 7.11 | 1.16 | 1.58 | 0.011 |
| 2559.48 | 16.87 | 7.83 | 0.76 | 1.21 | 0.011 |
| 2564.01 | 11.96 | 11.64 | 0 | 0 | 0.025 |
| 2571.26 | 10.51 | 13.07 | 1.36 | 1.29 | 0.012 |
| 2578.45 | 11.97 | 11.86 | 0.36 | 0.53 | 0.011 |
| 2581.25 | 17.06 | 7.54 | 0.68 | 0.67 | 0.012 |
| 2583.37 | 10.49 | 12.5 | 0 | 0 | 0.025 |
| 2584.81 | 10.46 | 12.62 | 0.22 | 0.27 | 0.036 |
| 2587.01 | 10.27 | 12.8 | 0.43 | 0.71 | 0.021 |
| 2588.9 | 13.86 | 10.42 | 0.22 | 0.23 | 0.036 |
| 2593.68 | 10.56 | 12.71 | 0.53 | 0.65 | 0.012 |
| 2596.11 | 10.96 | 12.47 | 0.42 | 0.43 | 0.012 |
| 2603.33 | 14.88 | 9.7 | 0.43 | 0.49 | 0.012 |
| 2608.2 | 12.5 | 11.6 | 0.54 | 0.97 | 0.021 |
| 2613.31 | 11.35 | 12.02 | 0 | 0 | 0.025 |
| 2614.91 | 17.74 | 7.82 | 1.77 | 2.13 | 0.012 |
| 2622.46 | 11.81 | 11.97 | 0.38 | 0.41 | 0.037 |
| 2629.26 | 16.2 | 8.49 | 0.6 | 0.94 | 0.012 |

TABLE 9

| m/z of each peak | ALS patient group (n = 5) | | Healty subject group (n = 5) | | P value |
|---|---|---|---|---|---|
| | Average of Peak value | Standard Deviation of Peak value | Average of Peak value | Standard Deviation of Peak value | |
| 2633.69 | 12.5 | 11.29 | 0 | 0 | 0.025 |
| 2634.61 | 11.98 | 12.32 | 1.25 | 1.12 | 0.037 |
| 2640.51 | 14.35 | 10.12 | 0.38 | 0.85 | 0.01 |
| 2641.73 | 11.99 | 11.95 | 0.56 | 0.82 | 0.021 |
| 2652.85 | 11.63 | 12.24 | 0.71 | 0.81 | 0.037 |
| 2655.08 | 13.38 | 10.94 | 0.4 | 0.44 | 0.012 |
| 2665.15 | 13.49 | 10.66 | 0.15 | 0.22 | 0.012 |
| 2670 | 10.97 | 12.24 | 0 | 0 | 0.025 |
| 2682.8 | 19.8 | 3.15 | 1.29 | 0.95 | 0.012 |
| 2696.41 | 14.64 | 10.04 | 0.57 | 0.64 | 0.012 |
| 2697.73 | 0 | 0 | 10.33 | 12.58 | 0.025 |
| 2698.27 | 14.67 | 9.53 | 0.02 | 0.04 | 0.01 |
| 2699.82 | 15.12 | 9.45 | 0.43 | 0.92 | 0.02 |
| 3302.01 | 9.88 | 12.8 | 0 | 0 | 0.025 |
| 3303.21 | 9.87 | 13.04 | 0.54 | 0.7 | 0.037 |
| 3309.84 | 0 | 0 | 11.35 | 12.02 | 0.025 |
| 3323.89 | 9.89 | 12.8 | 0.01 | 0.02 | 0.045 |

TABLE 9-continued

| | ALS patient group (n = 5) | | Healty subject group (n = 5) | | |
|---|---|---|---|---|---|
| m/z of each peak | Average of Peak value | Standard Deviation of Peak value | Average of Peak value | Standard Deviation of Peak value | P value |
| 3330.34 | 12.91 | 11.2 | 0.31 | 0.7 | 0.01 |
| 3337.92 | 11.26 | 12.12 | 0.08 | 0.18 | 0.045 |
| 3366.84 | 12.53 | 11.27 | 0 | 0 | 0.025 |
| 3370.39 | 7.79 | 13.7 | 0.06 | 0.12 | 0.045 |
| 3378.18 | 9.31 | 13.07 | 0 | 0 | 0.025 |
| 3380.43 | 11.84 | 11.96 | 0.47 | 1.05 | 0.045 |
| 3384.77 | 9.63 | 12.99 | 0.15 | 0.25 | 0.034 |

As shown in Tables 2 to 9, 327 peaks were identified at which there were significant differences in the peak values between the ALS patient group and the healthy subject group (peaks of m/z 1405.71, 1406.49, 1409.40, 1410.97, 1418.70, 1426.68, 1437.62, 1445.77, 1451.61, 1456.44, 1458.88, 1466.24, 1468.86, 1472.12, 1476.87, 1482.60, 1493.58, 1495.42, 1496.52, 1497.16, 1498.88, 1502.40, 1505.52, 1508.76, 1510.50, 1516.64, 1521.93, 1529.32, 1530.37, 1533.52, 1539.36, 1544.22, 1553.72, 1555.72, 1560.24, 1566.20, 1567.20, 1567.74, 1575.70, 1578.07, 1580.91, 1589.58, 1592.55, 1597.25, 1608.53, 1609.36, 1610.62, 1616.12, 1629.15, 1639.39, 1640.36, 1646.58, 1655.72, 1657.97, 1659.24, 1660.46, 1662.16, 1679.09, 1682.54, 1683.12, 1687.34, 1688.14, 1691.08, 1691.75, 1694.76, 1695.74, 1700.65, 1702.19, 1705.53, 1708.77, 1712.10, 1714.63, 1715.56, 1719.51, 1721.61, 1726.31, 1737.85, 1739.71, 1743.69, 1761.79, 1769.93, 1774.13, 1775.70, 1786.39, 1788.03, 1790.80, 1796.23, 1797.49, 1800.34, 1801.79, 1804.45, 1810.72, 1812.31, 1813.77, 1817.26, 1818.66, 1819.34, 1819.93, 1821.71, 1822.73, 1829.48, 1831.81, 1832.41, 1836.18, 1837.33, 1840.84, 1849.81, 1854.68, 1858.34, 1864.19, 1866.06, 1875.28, 1876.50, 1878.25, 1890.21, 1891.32, 1893.00, 1904.69, 1911.46, 1913.68, 1916.02, 1919.35, 1927.13, 1931.84, 1934.86, 1935.52, 1936.83, 1937.87, 1941.22, 1944.97, 1948.39, 1952.47, 1957.80, 1962.82, 1969.82, 1972.54, 1975.58, 1976.51, 1977.70, 1979.29, 1988.46, 1991.91, 1995.37, 2009.91, 2011.18, 2013.86, 2023.97, 2027.73, 2030.95, 2032.69, 2039.29, 2043.12, 2045.68, 2051.76, 2055.50, 2059.05, 2062.98, 2065.57, 2066.09, 2074.03, 2075.32, 2079.80, 2083.74, 2084.36, 2085.85, 2089.53, 2092.25, 2092.80, 2097.03, 2099.42, 2111.39, 2113.10, 2115.77, 2120.37, 2126.55, 2137.63, 2139.15, 2140.48, 2143.42, 2146.46, 2149.85, 2151.02, 2160.22, 2161.68, 2167.09, 2167.78, 2168.75, 2173.75, 2177.51, 2179.25, 2184.93, 2185.65, 2186.28, 2190.18, 2191.02, 2192.84, 2196.47, 2199.82, 2201.22, 2204.02, 2207.10, 2211.58, 2216.77, 2218.45, 2219.30, 2220.56, 2222.74, 2226.96, 2228.22, 2231.60, 2239.71, 2244.01, 2251.78, 2254.83, 2256.53, 2261.91, 2266.45, 2268.58, 2274.97, 2276.04, 2278.67, 2281.09, 2285.01, 2289.43, 2290.85, 2292.35, 2295.92, 2296.92, 2301.71, 2302.50, 2303.21, 2305.43, 2307.22, 2314.24, 2314.81, 2317.68, 2325.30, 2327.73, 2341.14, 2342.87, 2344.45, 2351.97, 2353.99, 2355.29, 2357.54, 2367.75, 2375.59, 2378.35, 2380.39, 2393.64, 2402.11, 2404.01, 2406.49, 2412.79, 2414.25, 2415.20, 2416.30, 2431.13, 2434.36, 2438.19, 2439.22, 2444.37, 2451.90, 2453.96, 2455.44, 2456.62, 2459.43, 2462.31, 2464.16, 2470.97, 2478.17, 2479.28, 2484.18, 2500.40, 2502.64, 2504.73, 2507.42, 2509.21, 2515.26, 2517.43, 2519.07, 2527.31, 2531.06, 2532.26, 2546.08, 2554.96, 2559.48, 2564.01, 2571.26, 2578.45, 2581.25, 2583.37, 2584.81, 2587.01, 2588.90, 2593.68, 2596.11, 2603.33, 2608.20, 2613.31, 2614.91, 2622.46, 2629.26, 2633.69, 2634.61, 2640.51, 2641.73, 2652.85, 2655.08, 2665.15, 2670.00, 2682.80, 2696.41, 2697.73, 2698.27, 2699.82, 3302.01, 3303.21, 3309.84, 3323.89, 3330.34, 3337.92, 3366.84, 3370.39, 3378.18, 3380.43 and 3384.77). That is, these results show that the signal peptides having molecular weights corresponding to the m/z values of the 327 peaks whose peak values differed significantly between the ALS patient group and healthy subject group are ALS-associated signal peptides.

These results also show that the signal peptides having molecular weights corresponding to the m/z values of the 327 peaks whose peak values differed significantly between the ALS patient group and healthy subject group (that is, the ALS-associated signal peptides) are signal peptides (that is, ALS biomarkers) that can be used to distinguish between ALS patients and healthy subjects by indicating the degree of abundance of these signal peptides in a bodily fluid.

These results also show that the signal peptide profiles of the ALS patients and the signal peptides profiles of the healthy subjects determined in Example 2 differ at all of the m/z values of the 327 peaks (or the molecular weights corresponding to the m/z values of these peaks). That is, these results confirm that data indicating the likelihood that a test subject suffers from or has developed ALS can be obtained by determining a profile of signal peptides present in a bodily fluid collected from a test subject, and comparing the m/z values of these 327 peaks (or the molecular weights corresponding to the m/z values of these peaks) in the signal peptide profile of the test subject and the signal peptide profile of a healthy subject.

These results also confirm that data indicating the likelihood that a test subject suffers from or has developed ALS can be obtained by testing the degree of abundance of any signal peptide with a molecular weight corresponding to any of these 327 peak m/z values in a bodily fluid collected from a test subject, and comparing this with the degree of abundance of the same signal peptide in a bodily fluid from a healthy subject.

Moreover, as shown in Tables 2 to 9, the peak values of the peaks at the following m/z values (310 peaks) were significantly higher in the ALS patient group than in the healthy subject group. These results indicate the signal peptides having molecular weights corresponding to the m/z values of these 310 peaks are ALS positive signal peptides (that is, positive biomarkers):

1405.71, 1406.49, 1409.40, 1410.97, 1418.70, 1426.68, 1437.62, 1445.77, 1451.61, 1456.44, 1458.88, 1466.24, 1468.86, 1472.12, 1476.87, 1482.60, 1493.58, 1495.42, 1496.52, 1498.88, 1502.40, 1505.52, 1508.76, 1510.50, 1516.64, 1521.93, 1529.32, 1530.37, 1533.52, 1539.36, 1544.22, 1553.72, 1555.72, 1560.24, 1566.20, 1567.20, 1575.70, 1578.07, 1580.91, 1589.58, 1592.55, 1597.25, 1608.53, 1609.36, 1610.62, 1616.12, 1629.15, 1639.39, 1640.36, 1646.58, 1655.72, 1657.97, 1659.24, 1660.46, 1662.16, 1679.09, 1682.54, 1683.12, 1687.34, 1688.14, 1691.08, 1691.75, 1694.76, 1695.74, 1700.65, 1702.19, 1708.77, 1712.10, 1714.63, 1715.56, 1719.51, 1721.61, 1726.31, 1737.85, 1739.71, 1743.69, 1761.79, 1769.93, 1774.13, 1775.70, 1786.39, 1788.03, 1790.80, 1796.23, 1797.49, 1800.34, 1801.79, 1804.45, 1810.72, 1812.31, 1813.77, 1817.26, 1818.66, 1819.93, 1821.71, 1822.73, 1829.48, 1832.41, 1836.18, 1837.33, 1840.84, 1849.81, 1854.68, 1858.34, 1864.19, 1866.06, 1875.28, 1876.50, 1878.25, 1890.21, 1891.32, 1893.00, 1904.69, 1911.46, 1913.68, 1916.02, 1919.35, 1927.13, 1931.84, 1934.86, 1936.83, 1937.87, 1941.22, 1944.97, 1948.39, 1952.47, 1957.80, 1962.82, 1969.82, 1972.54, 1975.58, 1976.51, 1977.70, 1979.29, 1988.46, 1991.91, 1995.37, 2009.91, 2011.18, 2013.86, 2023.97, 2027.73, 2030.95, 2032.69, 2039.29, 2043.12, 2045.68, 2051.76, 2059.05, 2062.98, 2066.09, 2074.03, 2075.32, 2079.80, 2083.74, 2085.85, 2089.53, 2092.80, 2097.03, 2099.42, 2111.39, 2113.10, 2115.77, 2120.37, 2126.55, 2137.63, 2139.15, 2143.42, 2146.46, 2149.85, 2151.02, 2160.22, 2161.68, 2167.09, 2168.75, 2173.75, 2177.51, 2179.25, 2185.65, 2186.28, 2190.18, 2191.02, 2192.84, 2196.47, 2199.82, 2201.22, 2204.02, 2207.10, 2211.58, 2216.77, 2218.45, 2219.30, 2220.56, 2222.74, 2226.96, 2228.22, 2231.60, 2239.71, 2244.01, 2251.78, 2254.83, 2256.53, 2261.91, 2266.45, 2268.58, 2274.97, 2276.04, 2278.67, 2281.09, 2285.01, 2289.43, 2290.85, 2292.35, 2295.92, 2296.92, 2301.71, 2302.50, 2303.21, 2305.43, 2307.22, 2314.24, 2317.68, 2325.30, 2341.14, 2342.87, 2344.45, 2351.97, 2353.99, 2355.29, 2357.54, 2367.75, 2375.59, 2378.35, 2380.39, 2393.64, 2402.11, 2404.01, 2406.49, 2412.79, 2414.25, 2415.20, 2416.30, 2431.13, 2434.36, 2438.19, 2439.22, 2444.37, 2451.90, 2453.96, 2455.44, 2456.62, 2459.43, 2462.31, 2464.16, 2470.97, 2478.17, 2479.28, 2484.18, 2500.40, 2502.64, 2504.73, 2507.42, 2509.21, 2515.26, 2517.43, 2519.07, 2527.31, 2531.06, 2532.26, 2546.08, 2554.96, 2559.48, 2564.01, 2571.26, 2578.45, 2581.25, 2583.37, 2584.81, 2587.01, 2588.90, 2593.68, 2596.11, 2603.33, 2608.20, 2613.31, 2614.91, 2622.46, 2629.26, 2633.69, 2634.61, 2640.51, 2641.73, 2652.85, 2655.08, 2665.15, 2670.00, 2682.80, 2696.41, 2698.27, 2699.82, 3302.01, 3303.21, 3323.89, 3330.34, 3337.92, 3366.84, 3370.39, 3378.18, 3380.43 and 3384.77.

Furthermore, as shown in Tables 2 to 9, the peak values of the peaks at the following m/z values (17 peaks) were significantly lower in the ALS patient group than in the healthy subject group. These results indicate the signal peptides having molecular weights corresponding to the m/z values of these 17 peaks are ALS negative signal peptides (that is, negative biomarkers):
1497.16, 1567.74, 1705.53, 1819.34, 1831.81, 1935.52, 2055.50, 2065.57, 2084.36, 2092.25, 2140.48, 2167.78, 2184.93, 2314.81, 2327.73, 2697.73 and 3309.84.

Moreover, as shown in Tables 2 to 9, the peak values of the peaks at m/z values of 1502.40, 1521.93, 1629.15, 1682.54, 1691.75, 1705.53, 1821.71, 1836.18, 1948.39, 2011.18, 2092.80, 2099.42, 2177.51, 2179.25, 2186.28, 2211.58, 2226.96, 2254.83, 2278.67, 2290.85, 2292.35, 2502.64, 2640.51, 2698.27 and 3330.34 (25 peaks) were dramatically different (p≤0.01) in the ALS patient group in comparison with the healthy subject group. These results indicate that the signal peptides having molecular weights corresponding to the m/z values of these 25 peaks are signal peptides that can distinguish ALS patients from healthy subjects with a high degree of accuracy (reliability) when the degree of abundance of the signal peptides in a bodily fluid is used as an indicator.

That is, these results confirm that highly reliable (highly accurate) data indicating a strong possibility that a test subject suffers from or has developed ALS can be obtained by determining a profile of signal peptides in a bodily fluid collected from the test subject if the signal peptide profile of the test subject differs from the signal peptide profile of a healthy subject at a m/z value at any of these 25 peaks (or a molecular weight corresponding to any of these peak m/z values).

In other words, we confirmed that highly reliable (highly accurate) data indicating whether or not there is a strong likelihood that a test subject suffers from or has developed ALS can be obtained by testing the degree of abundance of any of the signal peptides having molecular weights corresponding to these 25 peak m/z values in a bodily fluid collected from a test subject, and comparing it with the degree of abundance of the same signal peptide in a bodily fluid from a healthy subject.

Example 3

Specifying Signal Peptides

Signal peptides were specified corresponding to the 327 peaks identified in Example 2 having peak values that were significantly different between an ALS patient group and a healthy subject group. That is, the m/z values of each peak were compared with the molecular weights of known signal peptides, and if the molecular weight of a signal peptide was within m/z±2 of a target peak, it was specified as a signal peptide corresponding to the target peak. The results are shown in Tables 10 to 44.

As shown in Tables 10 to 44, the signal peptides comprising the amino acid sequences represented by SEQ ID Nos: 1 to 1580 were specified as the ALS-associated signal peptides (that is, ALS biomarkers) disclosed here.

These results indicate that data for aiding ALS detection (diagnosis) can be obtained (typically. ALS can be diagnosed) by using as an indicator the degree of abundance of a signal peptide comprising any of the amino acid sequences represented by SEQ ID Nos: 1 to 1580.

TABLE 10

| Signal Peptide | | | |
|---|---|---|---|
| Amino acid sequence | SEQ ID No. | MW | m/z of the corresponding peak |
| MLTVALLALLCASASG | 181 | 1533.9 | 1533.52 |
| MNLLLILTFVAAAVA | 182 | 1559.97 | 1560.24 |
| MRLILPVGLIATTLA | 183 | 1582.02 | 1580.91 |
| MLRVLVGAVLPAMLL | 184 | 1596.11 | 1597.25 |
| MLLPLLLLLPMCWA | 1 | 1627.18 | 1629.15 |
| MLLILLSVALLALSSA | 2 | 1628.09 | 1629.15 |
| MLLILLSVALLALSSA | 3 | 1628.09 | 1629.15 |
| MYALFLLASLLGAALA | 185 | 1638.04 | 1639.39 |
| MRGLLVLSVLLGAVFG | 186 | 1645.08 | 1646.58 |
| MLPLWTLSLLLGAVAG | 187 | 1655.07 | 1655.72 |
| MKLPLLLALLFGAVSA | 188 | 1657.13 | 1657.97, 1655.72 |
| MIRTLLLSTLVAGALS | 189 | 1659.06 | 1659.24, 1660.46, 1657.97 |
| MIRTLLLSTLVAGALS | 190 | 1659.06 | 1659.24, 1660.46, 1657.97 |
| MLLILLSVALLAFSSA | 191 | 1662.1 | 1662.16, 1660.46 |
| MKVSAVLLCLLLMTAA | 192 | 1677.2 | 1679.09 |
| MLAATVLTLALLGNAHA | 193 | 1680.04 | 1679.09 |
| MLFLLLPLLAVLPGDG | 4 | 1682.14 | 1682.54, 1683.12 |

TABLE 10-continued

Signal Peptide

| Amino acid sequence | SEQ ID No. | MW | m/z of the corresponding peak |
|---|---|---|---|
| MTAEFLSLLCLGLCLG | 5 | 1684.1 | 1683.12, 1682.54 |
| MGTWILFACLLGAAFA | 194 | 1685.07 | 1683.12 |
| MALFGALFLALLAGAHA | 195 | 1687.08 | 1687.34, 1688.14 |
| MKWLLLLGLVALSEC | 196 | 1689.15 | 1687.34, 1688.14, 1691.08 |
| MLLSVPLLLGLLGLAVA | 6 | 1693.2 | 1691.75, 1694.76 |
| MGAPRSLLLALAAGLAVA | 197 | 1695.1 | 1695.74, 1694.76 |
| MLAVGCALLAALLAAPGAA | 198 | 1697.13 | 1695.74 |
| MLGVLVLGALALAGLGFP | 199 | 1712.17 | 1712.1 |
| MALRVLLLTALTLCHG | 200 | 1725.18 | 1726.31 |
| MLALLCSCLLLAAGASDA | 201 | 1736.13 | 1737.85 |
| MKRVLVLLLAVAFGHA | 202 | 1738.21 | 1737.85, 1739.71 |
| MSLVLLSLAALCRSAVP | 203 | 1744.18 | 1743.69 |
| MVPVLLSLLLLLGPAVP | 204 | 1745.28 | 1743.69 |
| MRLTVLCAVCLLPGSLA | 205 | 1760.24 | 1761.79 |
| MALDYLLLLLLASAVAA | 206 | 1761.19 | 1761.79 |
| MVWKVAVFLSVALGIGA | 207 | 1761.2 | 1761.79 |
| MSLSAFTLFLALIGGTSG | 208 | 1786.12 | 1786.39, 1788.03 |
| MLCLLLTLGVALVCGVPA | 209 | 1786.32 | 1786.39, 1788.03 |
| MRSAAVLALLLCAGQVTA | 210 | 1788.2 | 1786.39, 1788.03 |
| MFRLWLLLAGLCGLLA | 211 | 1790.3 | 1790.8 |
| MWFLTTLLLWVPVDG | 212 | 1791.18 | 1790.8 |
| MRSTILLFCLLGSTRS | 213 | 1798.19 | 1796.23, 1797.49 |
| MARILLLFLPGLVAVCA | 214 | 1800.34 | 1800.34, 1801.79 |
| MVAAVLLGLSWLCSPLGA | 215 | 1801.24 | 1800.34, 1801.79 |
| MAGPSLACCLLGLLALTSA | 216 | 1805.24 | 1804.45 |
| MLLAMVLTSALLLCSVAG | 217 | 1806.31 | 1804.45 |
| MQPSSLLPLALCLLAAPA | 218 | 1809.26 | 1810.72 |
| MWCIVLFSLLAWVYA | 219 | 1815.26 | 1813.77 |
| MKPLLLAVSLGLIAALQA | 7 | 1822.32 | 1822.73, 1821.71 |
| MKAAVLTLAVLFLTGSQA | 8 | 1834.25 | 1832.41, 1836.18 |
| MWLQSLLLLGTVACSIS | 9 | 1835.25 | 1836.18 |

TABLE 11

| Signal Peptide Amino acid sequence | SEQ ID No. | MW | m/z of the corresponding peak |
|---|---|---|---|
| MKFFLLLFTIGFCWA | 10 | 1837.31 | 1837.33, 1836.18 |
| MKFFLLLFTIGFCWA | 11 | 1837.31 | 1837.33, 1836.18 |
| MLRRALLCLAVAALVRA | 220 | 1840.37 | 1840.84 |
| MKALIVLGLVLLSVTVQG | 221 | 1854.37 | 1854.68 |
| MALLFLLPLVMQGVSRA | 222 | 1859.36 | 1858.34 |
| MTTLLWVFVTLRVITA | 223 | 1864.32 | 1864.19, 1866.06 |
| MGSGLPLVLLLTLLGSSHG | 224 | 1865.26 | 1866.06, 1864.19 |
| MGTQEGWCLLLCLALSGA | 225 | 1866.24 | 1866.06 |
| MKLLTGLVFCSLVLGVSS | 226 | 1867.34 | 1866.06 |
| MSALGAVIALLLWGQLFA | 227 | 1874.31 | 1875.28 |
| MKWMVVVLVCLQLLEA | 228 | 1875.42 | 1875.28, 1876.5 |
| MLLKTVLLLGHVAQVLM | 229 | 1879.44 | 1878.25 |
| MKLLAATVLLLTICSLEG | 230 | 1889.38 | 1890.21, 1891.32 |
| MRACISLVLAVLCGLAWA | 231 | 1890.39 | 1890.21, 1891.32 |
| MKLAALLGLCVALSCSSAAA | 232 | 1893.35 | 1893 |
| MQPFLLLLAFLLTPGAGT | 233 | 1903.35 | 1904.69 |
| MGLAWGLGVLFLMHVCGT | 234 | 1905.36 | 1904.69 |

TABLE 11-continued

Signal Peptide

| Amino acid sequence | SEQ ID No. | MW | m/z of the corresponding peak |
|---|---|---|---|
| MWSGWWLWPLVAVCTA | 235 | 1906.29 | 1904.69 |
| MFALGLPFLVLLVASVES | 236 | 1906.35 | 1904.69 |
| MLPPGTATLLTLLLAAGSLG | 237 | 1910.34 | 1911.46 |
| MQPLLLLLAFLLPTGAEA | 238 | 1911.37 | 1911.46 |
| MVWKWMPLLLLLVCVA | 239 | 1915.53 | 1916.02, 1913.68 |
| MWVPVVFLTLSVTWIGA | 240 | 1919.36 | 1919.35 |
| MAWSLGSWLGGCLLVSALG | 241 | 1921.3 | 1919.35 |
| MWLLVSVILISRISSVGG | 242 | 1930.38 | 1931.84 |
| MKLASGFLVLWLSLGGGLA | 243 | 1933.38 | 1934.86, 1931.84 |
| MKVLLRLICFIALLISS | 244 | 1933.53 | 1934.86, 1931.84, 1935.52 |
| MKVLWAALLVTFLAGCQA | 245 | 1935.42 | 1935.52, 1934.86, 1936.83 |
| MKALIAALLLITLQYSCA | 246 | 1936.44 | 1934.86, 1935.52, 1936.83, 1937.87 |
| MNSGVCLCVLMAVLAAGALT | 247 | 1937.42 | 1935.52, 1936.83, 1937.87 |
| MEAVAVAAAVGVLLLAGAGGAAG | 248 | 1939.3 | 1941.22, 1937.87 |
| MKLVNIWLLLLVVLLCG | 249 | 1940.56 | 1941.22 |
| MQALVLLLCIGALLGHSSC | 250 | 1942.42 | 1941.22 |
| MGAPACALALCVAVAIVAGASS | 251 | 1946.37 | 1944.97 |
| MHLLLFQLLVLLPLGKT | 12 | 1949.51 | 1948.39 |
| MGLQACLLGLFALILSGKC | 252 | 1951.47 | 1952.47 |
| MRAWIFFLLCLAGRALA | 253 | 1952.45 | 1952.47 |
| MLLFVLTCLLAVFPAIST | 254 | 1952.48 | 1952.47 |
| MKWVWALLLLAALGSGRA | 255 | 1956.42 | 1957.8 |
| MKSLILLAILAALAVVTLC | 256 | 1956.56 | 1957.8 |
| MIWYILIIGILLPQSLA | 257 | 1957.49 | 1957.8 |
| MWRSLGLALALCLLPSGGT | 258 | 1959.4 | 1957.8 |
| MPALGWAVAAILMLQTAMA | 259 | 1959.45 | 1957.8 |
| MRLFTGIVFCSLVMGVTS | 260 | 1961.43 | 1962.82 |
| MDYLLMIFSLLFVACQG | 261 | 1964.43 | 1962.82 |

TABLE 12

Signal Peptide

| Amino acid sequence | SEQ ID No. | MW | m/z of the corresponding peak |
|---|---|---|---|
| MQPTLLLSLLGAVGLAAVNS | 262 | 1968.38 | 1969.82 |
| MALSWVLTVLSLLPLLEA | 263 | 1969.45 | 1969.82 |
| MALSWVLTVLSLLPLLEA | 264 | 1969.45 | 1969.82 |
| MVEMLPTAILLVLAVSVVA | 265 | 1969.51 | 1969.82 |
| MDILCSTLLLLTVPSGVLS | 266 | 1975.43 | 1975.58, 1976.51 |
| MARAPLGVLLLLGLLGRGVG | 267 | 1976.5 | 1975.58, 1976.51, 1977.7 |
| MLPLCLVAALLLAAGPGPSLG | 268 | 1977.49 | 1975.58, 1976.51, 1977.7, 1979.29 |

TABLE 12-continued

Signal Peptide

| Amino acid sequence | SEQ ID No. | MW | m/z of the corresponding peak |
|---|---|---|---|
| MRTLAILAAILLVALQAQA | 269 | 1980.48 | 1979.29 |
| MRTLAILAAILLVALQAQA | 270 | 1980.48 | 1979.29 |
| MWLFHTLLCIASLALLAA | 271 | 1987.49 | 1988.46 |
| MVLHLLLFLLLTPQGGHS | 272 | 1989.45 | 1988.46 |
| MVMLLLLLSALAGLFGAAEG | 273 | 1990.49 | 1991.91 |
| MKSVLLLTTLLVPAHLVAA | 274 | 1990.52 | 1991.91 |
| MARAPPLLAALTALLAAAAAGG | 275 | 1991.42 | 1991.91 |
| MALLLTTVIALTCLGGFASP | 276 | 1992.46 | 1991.91 |
| MRGLAVLLTVALATLLAPGAG | 277 | 2008.49 | 2009.91 |
| MQPILLLLAFLLLPRADA | 278 | 2008.54 | 2009.91 |
| MEKLLCFLVLTSLSHAFG | 13 | 2009.45 | 2009.91, 2011.18 |
| MAAALALVAGVLSGAVLPLWS | 14 | 2010.47 | 2009.91, 2011.18 |
| MKGLAAALLVLVCTMALCSC | 15 | 2011.6 | 2009.91, 2011.18 |
| MNLAISIALLLTVLQVSRG | 16 | 2012.48 | 2011.18, 2013.86 |
| MFLKAVVLTLALVAVAGARA | 279 | 2014.54 | 2013.86 |
| MGFWILAILTILMYSTAA | 280 | 2015.5 | 2013.86 |
| MKSLVLLLCLAQLWGCHS | 281 | 2015.52 | 2013.86 |
| MRGPSGALWLLLALRTVLG | 282 | 2024.5 | 2023.97 |
| MFFWCACCLMVAWRVSA | 283 | 2024.52 | 2023.97 |
| MYGKIIFVLLLSGIVSISA | 284 | 2024.53 | 2023.97 |
| MSCPVPACCALLLVLGLCRA | 285 | 2033.61 | 2032.69 |
| MKLVFLVLLFLGALGLCLA | 286 | 2034.68 | 2032.69 |
| MYGKIIFVLLLSAIVSISA | 287 | 2038.56 | 2039.29 |
| MVALPMVLVLLLVLSRGES | 288 | 2040.59 | 2039.29 |
| MRFMTLLFLTALAGALVCA | 289 | 2042.59 | 2043.12 |
| MARPLCTLLLLMATLAGALA | 290 | 2043.62 | 2043.12 |
| MWLLLTMASLISVLGTTHG | 291 | 2044.5 | 2043.12, 2045.68 |
| MAPLRPLLILALLAWVALA | 292 | 2045.64 | 2045.68 |
| MALTAHPSCLLALLVAGLAQG | 293 | 2050.51 | 2051.76 |
| MALLFSLILAICTRPGFLA | 294 | 2050.59 | 2051.76 |
| IFASLLRAVIASICVVSSMA | 295 | 2051.53 | 2051.76 |
| MGDHLDLLLGVVLMAGPVFG | 296 | 2054.49 | 2055.5 |
| MPLGLLWLGLALLGALHAQA | 297 | 2058.56 | 2059.05 |
| MQLFLLLCLVLLSPQGASL | 298 | 2059.6 | 2059.05 |
| MTCSPLLLTLLIHCTGSWA | 299 | 2060.52 | 2059.05 |
| MRLLVLLWGCLLLPGYEA | 300 | 2060.59 | 2059.05 |
| MISPVLILFSSFLCHVAIA | 301 | 2061.57 | 2062.98 |

TABLE 12-continued

Signal Peptide

| Amino acid sequence | SEQ ID No. | MW | m/z of the corresponding peak |
|---|---|---|---|
| MRLLAKIICLMLWAICVA | 302 | 2061.74 | 2062.98 |
| MWLCPLALNLILMAASGAAC | 303 | 2062.59 | 2062.98 |

TABLE 13

Signal Peptide

| Amino acid sequence | SEQ ID No. | MW | m/z of the corresponding peak |
|---|---|---|---|
| MAQHLSTLLLLLATLAVALA | 304 | 2063.57 | 2062.98 |
| MAWASRLGLLLALLLPVVGA | 305 | 2064.6 | 2062.98, 2065.57, 2066.09 |
| MRGATRVSIMLLLVTVSDC | 306 | 2065.54 | 2065.57, 2066.09 |
| MKTLLLLLLVLLELGEAQG | 307 | 2067.6 | 2066.09 |
| MTPPRLFWVWLLVAGTQG | 308 | 2072.5 | 2074.03 |
| MNCRELPLTLWVLISVST | 309 | 2075.51 | 2074.03, 2075.32 |
| MSVKGMAIALAVILCATVVQG | 310 | 2075.61 | 2074.03, 2075.32 |
| MRALLLLGFLLVSLESTLS | 311 | 2076.57 | 2075.32 |
| MAARALCMLGLVLALLSSSSA | 312 | 2078.57 | 2079.8 |
| MERASCLLLLLLPLVHVSA | 313 | 2078.6 | 2079.8 |
| MERGLPLLCAVLALVLAPAGA | 314 | 2078.6 | 2079.8 |
| MKLITILFLCSRLLLSLT | 315 | 2078.69 | 2079.8 |
| MALVLEIFTLLASICWVSA | 316 | 2080.57 | 2079.8 |
| MIILIYLFLLLWEDTQG | 317 | 2081.54 | 2079.8 |
| MLLLFLLFEGLCCPGENTA | 318 | 2084.53 | 2083.74, 2084.36, 2085.85 |
| MWLCPLALNLILMAASGAVC | 319 | 2090.65 | 2089.53, 2092.25 |
| MGRLQLVVLGLTCCWAVASA | 17 | 2091.58 | 2092.25, 2092.8 |
| MKVSVAALSCLMLVAVLGSQA | 18 | 2091.61 | 2092.25, 2092.8 |
| MRLLPRLLLLLLLVFPAT | 19 | 2092.74 | 2092.25, 2092.8 |
| MKVSVAALSCLMLVTALGSQA | 20 | 2093.59 | 2092.25, 2092.8 |
| MQGPPLLTAAHLLCVCTAALA | 21 | 2094.58 | 2092.8 |
| MKLAVTLTLVTLALCCSSASA | 320 | 2096.59 | 2097.03 |
| MYGKIIFVLLLSEIVSISA | 321 | 2096.6 | 2097.03 |
| MALPFALLMALVVLSCKSSC | 22 | 2097.68 | 2097.03, 2099.42 |
| MNQLSFLLFLIATTRGWS | 23 | 2098.49 | 2097.03, 2099.42 |
| MAAAMPLALLVLLLLGPGGWC | 322 | 2110.71 | 2111.39 |
| MWATQGLAVALALSVLPGSRA | 323 | 2112.52 | 2111.39, 2113.1 |
| MNVLLGSVVIFATFVTLCNA | 324 | 2112.57 | 2111.39, 2113.1 |

TABLE 13-continued

Signal Peptide

| Amino acid sequence | SEQ ID No. | MW | m/z of the corresponding peak |
|---|---|---|---|
| MAWPLCTLLLLLATQAVALA | 325 | 2112.66 | 2111.39, 2113.1 |
| MFSMRIVCLVLSVVGTAWT | 326 | 2113.62 | 2113.1 |
| MAWQGLVLAACLLMFPSTTA | 327 | 2124.6 | 2126.55 |
| MATSMGLLLLLLLLTQPGAG | 328 | 2126.68 | 2126.55 |
| MLLLPLPLLLFLLCSRAEA | 329 | 2126.73 | 2126.55 |
| MARPHPWWLCVLGTLVGLS | 330 | 2136.6 | 2137.63 |
| MSAVLLLALLGFILPLPGVQA | 331 | 2136.71 | 2137.63 |
| MARGAALALLLFGLLGVLVAAP | 332 | 2137.7 | 2137.63, 2139.15 |
| MKILILGIFLFLCSTPAWA | 333 | 2137.71 | 2137.63, 2139.15 |
| MRLPAQLLGLLMLWVPGSSG | 334 | 2139.65 | 2139.15, 2140.48 |
| MKWVTFISLLFLFSSAYS | 335 | 2140.57 | 2139.15, 2140.48 |
| MSLFPSLPLLLLSMVAASYS | 336 | 2140.62 | 2139.15, 2140.48 |
| MASHRLLLLCLAGLVFVSEA | 337 | 2143.63 | 2143.42 |
| MDWTWRILFLVAAATGAHS | 338 | 2146.49 | 2146.46 |
| MNKPLLWISVLTSLLEAFA | 339 | 2146.62 | 2146.46 |
| MKFLAVLVLLGVSIFLVSAQ | 340 | 2148.72 | 2149.85 |
| MFCPLKULLPVLLDYSLG | 341 | 2148.73 | 2149.85 |
| MDPRLPAWALVLLGPALVFA | 342 | 2150.65 | 2149.85, 2151.02 |

TABLE 14

| Signal Peptide Amino acid sequence | SEQ ID No. | MW | m/z of the corresponding peak |
|---|---|---|---|
| MLLWSLLVIFDAVTEQADS | 343 | 2151.5 | 2149.85, 2151.02 |
| MEHKEVVLLLLLFLKSAAP | 344 | 2151.68 | 2149.85, 2151.02 |
| MAWTPLFLFLLTCCPGGSNS | 345 | 2158.58 | 2160.22 |
| MRLLLALLGVLLSVPGPPVLS | 346 | 2158.76 | 2160.22 |
| MSGARSKLALFLCGCYVVALG | 347 | 2159.65 | 2160.22 |
| MEPWPLLLLFSLCSAGLVLG | 348 | 2159.67 | 2160.22 |
| MSRLPVLLLLQLLVRPGLQ | 349 | 2159.75 | 2160.22, 2161.68 |
| MDWTWRVFCLLAVAPGAHS | 350 | 2160.54 | 2160.22, 2161.68 |
| MEMLQGLLLLLLSMGGAWA | 351 | 2160.72 | 2160.22, 2161.68 |
| MKSFLLVVNALALTLPFLAV | 352 | 2160.73 | 2160.22, 2161.68 |
| MKLMVLVFTIGLTLLLGVQA | 353 | 2160.79 | 2160.22, 2161.68 |
| MDLRQFLMCLSLCTAFALS | 354 | 2163.65 | 2161.68 |
| MIFLTALPLFWIMISASRG | 355 | 2167.7 | 2167.09, 2167.78, 2168.75 |
| MLPCLVVLLAALLSLRLGSDA | 356 | 2168.72 | 2167.09, 2167.78, 2168.75 |
| MTPGALLMLLGALGAPLAPGVRG | 24 | 2176.71 | 2177.51 |
| MQAAWLLGALVVPQLLGFGHG | 25 | 2178.62 | 2177.51, 2179.25 |
| MEKIPVSAFLLLVALSYTLA | 26 | 2179.69 | 2179.25 |
| MHSFPPLLLLLFWGVVSHS | 27 | 2180.64 | 2179.25 |
| MILFKQATYFISLFATVSC | 357 | 2183.65 | 2184.93 |
| MAPLALHLLVLVPILLSLVAS | 358 | 2183.81 | 2184.93, 2185.65 |
| MMLHSALGLCLLLVTVSSNLA | 28 | 2186.71 | 2184.93, 2185.65, 2186.28 |
| MVVALRYVWPLLLCSPCLL | 359 | 2189.81 | 2190.18, 2191.02 |
| MRAPGCGRLVLPLLLLAAAALA | 360 | 2190.78 | 2190.18, 2191.02 |
| MRLFLWNAVLTLFVTSLIG | 361 | 2194.71 | 2192.84, 2196.47 |

TABLE 14-continued

| Signal Peptide Amino acid sequence | SEQ ID No. | MW | m/z of the corresponding peak |
|---|---|---|---|
| MALPVTALLLPLALLLHAARP | 362 | 2194.79 | 2192.84, 2196.47 |
| MIFLLLMLSLELQLHQIAA | 363 | 2197.77 | 2196.47 |
| MRGMKLLGALLALAALLQGAVS | 364 | 2197.77 | 2196.47 |
| MKLVSVALMYLGSLAFLGADT | 365 | 2200.68 | 2199.82, 2201.22 |
| MGPLMVLFCLLFLYPGLADS | 366 | 2200.74 | 2199.82, 2201.22 |
| MKALLALPLLLLLSTPPCAPQ | 367 | 2203.81 | 2204.22 |
| MIASQFLSALTLVLLIKESGA | 368 | 2205.68 | 2204.22, 2207.1 |
| MGLSTVPDLLLPLVLLELLVG | 369 | 2205.76 | 2204.22, 2207.1 |
| MKTLQSTLLLLLLVPLIKPA | 370 | 2205.85 | 2204.22, 2207.1 |
| MALLLALSLLVLWTSPAPTLS | 29 | 2210.74 | 2211.58 |
| MAARLLLLGILLLLLPLPVPA | 30 | 2210.92 | 2211.58 |
| MSACRSFAVAICILEISILTA | 31 | 2212.71 | 2211.58 |
| MKWVESIFLIFLLNFTES | 371 | 2217.65 | 2216.77, 2218.45, 2219.3 |
| MAPVAVWAALAVGLELWAAAHA | 372 | 2218.64 | 2216.77, 2218.45, 2219.3, 2220.56 |
| MRWALLVLLAFLSPASQKSS | 373 | 2218.69 | 2216.77, 2218.45, 2219.3, 2220.56 |
| MKGFTATLFLWTUFPSCSG | 374 | 2220.67 | 2219.3, 2220.56 |
| MGTSLLCWMALCLLGADHADT | 375 | 2222.64 | 2222.74 |
| MELSWHVVFIALLSFSCWG | 32 | 2225.65 | 2226.96 |
| MGAMTQLLAGVFLAFLALATEG | 33 | 2225.69 | 2226.96 |
| MYRMQLLSCIALSLALVTNS | 34 | 2227.72 | 2226.96, 2228.22 |
| MGLGPVFLLLAGIFPFAPPGAAA | 35 | 2227.74 | 2226.96, 2228.22 |
| MEHSTFLSGLVLATLLSQVSP | 376 | 2230.6 | 2231.6 |

TABLE 15

| Signal Peptide Amino acid sequence | SEQ ID No. | MW | m/z of the corresponding peak |
|---|---|---|---|
| MKTLQFFFLFCCWKAICC | 377 | 2232.82 | 2231.6 |
| MVLQTQVFISLLLWISGAYG | 378 | 2239.7 | 2239.71 |
| MVLQTQVFISLLLWISGAYG | 379 | 2239.7 | 2239.71 |
| MVLQTQVFISLLLWISGAYG | 380 | 2239.7 | 2239.71 |
| MMWPMHTPLLLLTALMVAVA | 381 | 2239.88 | 2239.71 |
| MSPFLYLVLLVLGLHATIHC | 382 | 2240.79 | 2239.71 |
| MRPAFALCLLWQALWPGPGGG | 383 | 2241.7 | 2239.71 |
| MEAPAQLLFLLLLWLPDTTG | 384 | 2242.7 | 2244.01 |
| MEAPAQLLFLLLLWLPDTTG | 385 | 2242.7 | 2244.01 |
| MWATLPLLCAGAWLLGVPVCGA | 386 | 2242.78 | 2244.01 |
| MVRLPLQCVLWGCLLTAVHP | 387 | 2249.82 | 2251.78 |

TABLE 15-continued

| Amino acid sequence | SEQ ID No. | Signal Peptide MW | m/z of the corresponding peak |
|---|---|---|---|
| MNQTAILICCLIFLTLSGIQG | 388 | 2252.77 | 2251.78 |
| MIPARFAGVLLALALILPGTLC | 36 | 2253.88 | 2254.83 |
| MAQGVLWILLGLLLWSDPGTA | 37 | 2254.72 | 2254.83, 2256.53 |
| MILNKALLLGALALTAVMSPCGG | 389 | 2257.84 | 2256.53 |
| MWRCPLGLLLLLPLAGHLALG | 390 | 2257.87 | 2256.53 |
| MRPADLLQLVLLLDLPRDLG | 391 | 2261.75 | 2261.91 |
| MKASAALLCLLLTAAAFSPQGLA | 392 | 2261.77 | 2261.91 |
| MRLLILALLGICSLTAYIVEG | 393 | 2262.84 | 2261.91 |
| MKVVPSLLLSVLLAQVWLVPG | 394 | 2262.87 | 2261.91 |
| MAAAGQLCLLYLSAGLLSRLGAA | 395 | 2263.74 | 2261.91 |
| MEQGKGLAVLILAIILLQGTLA | 396 | 2265.82 | 2266.45 |
| MALPFVLLMALVVLNCKSICS | 397 | 2265.92 | 2266.45 |
| MRLLWGLIWASSFFTLSLQ | 398 | 2269.73 | 2268.58 |
| MRLLWGLIWASSFFTLSLQ | 399 | 2269.73 | 2268.58 |
| MMGLSLASAVLLASLLSLHLGTA | 400 | 2269.79 | 2268.58 |
| MSLLVVSMACVGFFLLQGAWP | 401 | 2269.81 | 2268.58 |
| MSDLLSVFLHLLLLFKLVAP | 402 | 2269.86 | 2268.58 |
| MKVTGIFLLSALALLSLSGNTGA | 38 | 2277.75 | 2276.04, 2278.67 |
| MASRWAVQLLLVAAWSMGCGE | 39 | 2279.72 | 2278.67, 2281.09 |
| MKLLHVFLLFLCFHLRFC | 403 | 2280.92 | 2281.09 |
| MRPSGTAGAALLALLAALCPASRA | 404 | 2282.75 | 2281.09 |
| MTNKCLLQIALLLCFSTTALS | 405 | 2284.82 | 2285.01 |
| MDMWTALLILQALLLPSLADG | 406 | 2285.79 | 2285.01 |
| MGSQVHLLSFLLLWISDTRA | 407 | 2287.7 | 2289.43 |
| MGSPGMVLGLLVQIWALQEASS | 408 | 2287.72 | 2289.43 |
| MILNKALLLGALALTTVMSPCGG | 409 | 2287.86 | 2289.43 |
| MAELPGPFLCGALLGFLCLSGLA | 40 | 2293.83 | 2292.35 |
| MGLFMIIAILLFQKPTVTEQ | 41 | 2293.85 | 2292.35 |
| MEAPAAGLFLLLLLGTWAPAPGS | 410 | 2296.75 | 2295.92, 2296.92 |
| MGPWGWKLRWTVALLLAAAGT | 411 | 2298.78 | 2296.92 |
| MFSLKTLPFLLLLHVQISKA | 412 | 2299.89 | 2301.71 |
| MLGQVVTLILLLLLKVYQGKG | 413 | 2299.93 | 2301.71 |
| MVYKTLFALCILTAGWRVQS | 414 | 2300.81 | 2301.71, 2302.5 |
| MQIELSTCFFLCLLRFCFS | 415 | 2301.82 | 2301.71, 2302.5, 2303.21 |
| MVPPKLHVLFCLCGCLAVVYP | 416 | 2302.94 | 2301.71, 2302.5, 2303.21 |

TABLE 16

| Signal Peptide Amino acid sequence | SEQ ID No. | MW | m/z of the corresponding peak |
|---|---|---|---|
| MKSIYFVAGLFVMLVQGSWQ | 417 | 2304.79 | 2303.21, 2305.43 |
| MILNKALMLGALALTTVMSPCGG | 418 | 2305.9 | 2305.43, 2307.22 |
| MILNKALMLGALALTTVMSPCGG | 419 | 2305.9 | 2305.43, 2307.22 |
| MILNKALMLGALALTTVMSPCGG | 420 | 2305.9 | 2305.43, 2307.22 |
| MQMSPALTCLVLGLALVFGEGSA | 421 | 2308.79 | 2307.22 |
| MRALWVLGLCCVLLTFGSVRA | 422 | 2308.89 | 2307.22 |
| MMWTWALWMLPSLCKFSLA | 423 | 2315.9 | 2314.24, 2314.81, 2317.68 |
| MTAAAGSAGRAAVPLLLCALLAPGGA | 424 | 2323.8 | 2325.3 |
| MWKRWLALALALVAVAWVRA | 425 | 2324.9 | 2325.3 |
| MRLSVCLLMVSLALCCYQAHA | 426 | 2325.91 | 2325.3, 2327.73 |
| MALTFALLVALLVLSCKSSCSVG | 427 | 2326.9 | 2325.3, 2327.73 |
| MDAMKRGLCCVLLLCGAVFVSP | 428 | 2326.94 | 2325.3, 2327.73 |
| MASRLTLLTLLLLLLAGDRASS | 429 | 2328.84 | 2327.73 |
| MLLAWVQAFLVSNMLLAEAYG | 430 | 2340.82 | 2341.14 |
| MRLSVCLLLLTLALCCYRANA | 431 | 2340.95 | 2341.14, 2342.87 |
| MTSSRLWFSLLLAAAFAGRATA | 432 | 2341.76 | 2341.14, 2342.87 |
| MEAPAQLLFLLLLWLPDTTR | 433 | 2341.84 | 2341.14, 2342.87 |
| MKWKALFTAAILQAQLPITEA | 434 | 2344.84 | 2342.87, 2344.45 |
| MEIKHLLFLVAAACLLPMLSM | 435 | 2345.02 | 2344.45 |
| MPRPRLLAALCGALLCAPSLLVA | 436 | 2349.98 | 2351.97 |
| MASPFALLMVLVVLSCKSSCSLG | 437 | 2356.94 | 2357.54 |
| MKVSAALLCLLLIAATFIPQGLA | 438 | 2357.98 | 2357.54 |
| MGHPPLLPLLLLLHTCVPASWG | 439 | 2365.92 | 2367.75 |
| MRLSWFRVLTVLSICLSAVAT | 440 | 2366.91 | 2367.75 |
| MGLPRLVCAFLLAACCCCPRVAG | 441 | 2368.01 | 2367.75 |
| MESRVLLRTFCLIFGLGAVWG | 442 | 2368.88 | 2367.75 |
| MVGKMWPVLWTLCAVRVTVDA | 443 | 2375.93 | 2375.59 |
| MRVLSGTSLMLCSLLLLLQALC | 444 | 2379.03 | 2378.35 |
| MQVSTAALAVLLCTMALCNQVLS | 445 | 2380.92 | 2380.39 |
| MLGPCMLLLLLLLGLRLQLSLG | 446 | 2381.12 | 2380.39 |
| MARRSVLYFILLNALINKGQA | 447 | 2391.9 | 2393.64 |
| MRRLLEPCWWILFLKITSS | 448 | 2392.95 | 2393.64 |
| MLLLARCLLLVLVSSLLVCSGLA | 449 | 2401.11 | 2402.11 |
| MDTSPLCFSILLVLCIFIQSSA | 450 | 2401.92 | 2402.11 |
| MERMLPLLALGLLAAGFCPAVLC | 451 | 2403.06 | 2402.11, 2404.01 |
| MLWLFQSLLFVFCFGPGNVVS | 452 | 2404.91 | 2404.01, 2406.49 |
| MGTGGRRGAAAAPLLVAVAALLLGAAG | 453 | 2405.89 | 2404.01, 2406.49 |
| MLSCRLQCALAALSIVLALGCVTG | 454 | 2407 | 2406.49 |

TABLE 16-continued

| Signal Peptide | | | m/z |
|---|---|---|---|
| Amino acid sequence | SEQ ID No. | MW | of the corresponding peak |
| MKPVWVATLLWMLLLVPRLGA | 455 | 2408.09 | 2406.49 |
| MKLCVTVLSLLMLVAAFCSPALS | 456 | 2411.08 | 2412.79 |
| MAQSLALSLLILVLAFGIPRTQG | 457 | 2412.96 | 2412.79, 2414.25 |
| MALKNKFSCLWILGLCLVATTS | 458 | 2412.99 | 2412.79, 2414.25 |
| MELWGAYLLLCLFSLLTQVTT | 459 | 2415.93 | 2414.25, 2415.2, 2416.3 |
| MFSFVDLRLLLLLAATALLTHG | 460 | 2415.96 | 2414.25, 2415.2, 2416.3 |
| MKVSEAALSLLVLILIITSASRS | 461 | 2415.96 | 2414.25, 2415.2, 2416.3 |
| MAGCVPLLQGLVLVALHRVEPS | 462 | 2415.98 | 2414.25, 2415.2, 2416.3 |

TABLE 17

| Signal Peptide | | | m/z |
|---|---|---|---|
| Amino acid sequence | SEQ ID No. | MW | of the corresponding peak |
| MARSLVCLGVIILLSAFSGPGVRG | 463 | 2416.97 | 2415.2, 2416.3 |
| MPSSVSWGILLLAGLCCLVPVSLA | 464 | 2430.02 | 2431.13 |
| MAQHHLWILLLCLQTWPEAAG | 465 | 2431.9 | 2431.13 |
| MSRTAYTVGALLLLLGTLLPAAEG | 466 | 2431.92 | 2431.13 |
| MGVPRPQPWALGLLLFLLPGSLG | 467 | 2433 | 2431.13, 2434.36 |
| MPSPGTVCSLLLLGMLWLDLAMA | 468 | 2433.04 | 2431.13, 2434.36 |
| MDMRVLAQLLGLLLLCFPGARC | 469 | 2434.08 | 2434.36 |
| MDMRVPAQLLGLLLLWLPGAKC | 470 | 2439.08 | 2438.19, 2439.22 |
| MNKLLCCALVFLDISIKWTTQ | 471 | 2441 | 2439.22 |
| MANLGCWMLVLFVATWSDLGLC | 472 | 2443.98 | 2444.37 |
| MLQGPGSLLLLFLASHCCLGSARG | 473 | 2444.95 | 2444.37 |
| MARRAGGARMFGSLLLFALLAAGV | 474 | 2450 | 2451.9 |
| MMKTLLLFVGLLLTWESGQVLG | 475 | 2450.04 | 2451.9 |
| MRVLGGRCGALLACLLLVLPVSEA | 476 | 2455.08 | 2453.96, 2455.96, 2456.62 |
| MRGANAWAPLCLLLAAATQLSRQ | 477 | 2455.92 | 2453.96, 2455.96, 2456.62 |
| MGELMAFLLPLIIVLMVKHSDS | 478 | 2458.07 | 2456.62, 2459.43 |
| MAGPLRAPLLLLAILAVALAVSPAAG | 479 | 2470.1 | 2470.97 |
| MTPWLGLIVLLGSWSLGDWGAEA | 480 | 2472.88 | 2470.97 |
| MFARMSDLHVLLLMALVGKTACG | 481 | 2478.09 | 2478.17, 2479.28 |
| MAPFEPLASGILLLLWLIAPSRA | 482 | 2480.05 | 2478.17, 2479.28 |
| MPMGSLQPLATLYLLGMLVASCLG | 483 | 2480.1 | 2478.17, 2479.28 |
| MAHRPPSPALASVLLALLLSGAARA | 484 | 2484 | 2484.18 |
| MKGPPTFCSLLLLSLLLSPDPTAA | 485 | 2486.02 | 2484.18 |
| MGKNKLLHPSLVLLLLVLLPTDA | 486 | 2499.14 | 2500.4 |
| MDRGTLPLAVALLLASCSLSPTSLA | 42 | 2500.99 | 2500.4, 2502.64 |
| MPGFLVRILPLLLVLLLLGPTRG | 43 | 2502.23 | 2500.4, 2502.64 |

TABLE 17-continued

| Signal Peptide Amino acid sequence | SEQ ID No. | MW | m/z of the corresponding peak |
|---|---|---|---|
| MKPIQKLLAGLILLTWCVEGCSS | 44 | 2504.1 | 2502.64, 2504.73 |
| MGLGARGAWAALLLGTLQVLALLGAA | 487 | 2508.06 | 2507.42, 2509.21 |
| MARLQTALLVVLVLLAVALQATEA | 488 | 2508.1 | 2507.42, 2509.21 |
| MAGPPRLLLLPLLLALARGLPGALA | 489 | 2508.19 | 2507.42, 2509.21 |
| MDHLGASLWPQVGSLCLLLAGAAW | 490 | 2509.97 | 2509.21 |
| MGPPHSGPGGVRVGALLLLGVLGLVSG | 491 | 2511.02 | 2509.21 |
| MLTLQTWLVQALFIFLTTESTG | 492 | 2513.97 | 2515.26 |
| MERGAGAKLLPLLLLLRATGFTCA | 493 | 2516.1 | 2515.26, 2517.43 |
| MARSFSLLMVVLVLSYKSICSLG | 494 | 2518.13 | 2517.43, 2519.07 |
| MGIPMGKSMLVLLTFLAFASCCIA | 495 | 2518.21 | 2517.43, 2519.07 |
| MGSGPRGALSLLLLLLAPPSRPAAGC | 496 | 2519.06 | 2517.43, 2519.07 |
| MQIITTALVCLLLAGMWPEDVDS | 497 | 2520.01 | 2519.07 |
| MPLLLYTCLLWLPTSGLWTVQA | 498 | 2520.09 | 2519.07 |
| MQLPLALCLVCLLVHTAFRVVEG | 499 | 2526.15 | 2527.31 |
| MDMRVPAQLLGLLLLWLRGARC | 500 | 2526.16 | 2527.31 |
| MAVMAPRTLVLLLSGALALTQTWA | 501 | 2528.11 | 2527.31 |
| MAVMAPRTLVLLLSGALALTQTWA | 502 | 2528.11 | 2527.31 |
| MAVMAPRTLVLLLSGALALTQTWA | 503 | 2528.11 | 2527.31 |
| MAVMAPRTLVLLLSGALALTQTWA | 504 | 2528.11 | 2527.31 |
| MAVMAPRTLVLLLSGALALTQTWA | 505 | 2528.11 | 2527.31 |

TABLE 18

| Signal Peptide Amino acid sequence | SEQ ID No. | MW | m/z of the corresponding peak |
|---|---|---|---|
| MAVMAPRTLVLLLSGALALTQTWA | 506 | 2528.11 | 2527.31 |
| MAVMAPRTLVLLLSGALALTQTWA | 507 | 2528.11 | 2527.31 |
| MAVMAPRTLVLLLSGALALTQTWA | 508 | 2528.11 | 2527.31 |
| MKSIILFVLSLLLILEKQAAVMG | 509 | 2531.24 | 2531.06, 2532.26 |
| MGRGLLRGLWPLHIVLWTRIAS | 510 | 2546.12 | 2546.08 |
| MGLTSQLLPPLFFLLACAGNFVHG | 511 | 2547.07 | 2546.08 |
| MRIHYLLFALLFLFLVPVPGHG | 512 | 2554.18 | 2554.96 |
| MARLGNCSLTWAALIILLLPGSLE | 513 | 2556.12 | 2554.96 |
| MAFDVSCFFWVVLFSAGCKVITS | 514 | 2558.07 | 2559.48 |
| MQRGAALCLRLWLCLGLLDGLVSG | 515 | 2559.14 | 2559.48 |
| MLPPAIHFYLLPLACILMKSCLA | 516 | 2559.29 | 2559.48 |
| MCPRAARAPATLLLALGAVLWPAAGA | 517 | 2562.13 | 2564.01 |
| MKASSLAFSLLSAAFYLLWTPSTG | 518 | 2563.01 | 2564.01 |

TABLE 18-continued

| Signal Peptide Amino acid sequence | SEQ ID No. | MW | m/z of the corresponding peak |
|---|---|---|---|
| MAPRGCIVAVFAIFCISRLLCSHG | 519 | 2565.17 | 2564.01 |
| MAPAMESPTLLCVALLFFAPDGVLA | 520 | 2578.14 | 2578.45 |
| MSFPCKFVASFLLIFNVSSKGAVS | 521 | 2580.1 | 2578.45, 2581.25 |
| MRVMAPQALLLLLSGALALIETWA | 522 | 2582.2 | 2581.25, 2583.37 |
| MMSFVQKGSWLLLALLHPTIILA | 523 | 2583.23 | 2581.25, 2583.37, 2584.81 |
| MRVTAPRTVLLLLSGALALTETWA | 524 | 2584.12 | 2583.37, 2584.81 |
| MRVTAPRTVLLLLSGALALTETWA | 525 | 2584.12 | 2583.37, 2584.81 |
| MRVMAPRALLLLLSGGLALTETWA | 526 | 2584.18 | 2583.37, 2584.81 |
| MRVMAPRALLLLLSGGLALTETWA | 527 | 2584.18 | 2583.37, 2584.81 |
| MLVMAPRTVLLLLSAALALTETWA | 528 | 2585.2 | 2583.37, 2584.81, 2587.01 |
| MLVMAPRTVLLLLSAALALTETWA | 529 | 2585.2 | 2583.37, 2584.81, 2587.01 |
| MLVMAPRTVLLLLSAALALTETWA | 530 | 2585.2 | 2583.37, 2584.81, 2587.01 |
| MLVMAPRTVLLLLSAALALTETWA | 531 | 2585.2 | 2583.37, 2584.81, 2587.01 |
| MLVMAPRTVLLLLSAALALTETWA | 532 | 2585.2 | 2583.37, 2584.81, 2587.01 |
| MLVMAPRTVLLLLSAALALTETWA | 533 | 2585.2 | 2583.37, 2584.81, 2587.01 |
| MLVMAPRTVLLLLSAALALTETWA | 534 | 2585.2 | 2583.37, 2584.81, 2587.01 |
| MLVMAPRTVLLLLSAALALTETWA | 535 | 2585.2 | 2583.37, 2584.81, 2587.01 |
| MLVMAPRTVLLLLSAALALTETWA | 536 | 2585.2 | 2583.37, 2584.81, 2587.01 |
| MARKSNLPVLLVPFLLCQALVRC | 537 | 2585.27 | 2583.37, 2584.81, 2587.01 |
| MRGTPKTHLLAFSLLCLLSKVRT | 538 | 2586.2 | 2584.81, 2587.01 |
| MKYTSYILAFQLCIVLGSLGCYC | 539 | 2590.17 | 2588.9 |
| MRLPRRAALGLLPLLLLLPPAPEA | 540 | 2592.27 | 2593.68 |
| MQTPRASPPRPALLLLLLLLGGAHG | 541 | 2593.17 | 2593.68 |
| MGSRAELCTLLGGFSFLLLLIPGEG | 542 | 2595.11 | 2593.68, 2596.11 |
| MAAAAATKILLCLPLLLLLSGWSRA | 543 | 2597.26 | 2596.11 |
| MALWMRLLPLLALLALWGPDPAAA | 544 | 2604.25 | 2603.33 |
| MRQTLPCIYFWGGLLPFGMLCAS | 545 | 2605.19 | 2603.33 |
| MKENVASATVFTLLLFLNTCLLNG | 546 | 2613.13 | 2613.31, 2614.91 |
| MGNSCYNIVATLLLVLNFERTRS | 547 | 2615.06 | 2613.31, 2614.91 |
| MEKKCTLYFLVLLPFFMILVTA | 548 | 2621.34 | 2622.46 |
| MAPSSPRPALPALLVLLGALFPGPGNA | 549 | 2628.17 | 2629.26 |
| MRQSHQLPLVGLLLFSFIPSQLC | 550 | 2628.19 | 2629.26 |
| MRVMAPRTLILLLSGALALTETWA | 551 | 2628.23 | 2629.26 |

TABLE 19

| Signal Peptide Amino acid sequence | SEQ ID No. | MW | m/z of the corresponding peak |
|---|---|---|---|
| MRVMAPRTLILLLSGALALTETWA | 552 | 2628.23 | 2629.26 |
| MRVMAPRTLILLLSGALALTETWA | 553 | 2628.23 | 2629.26 |
| MRVMAPRTLILLLSGALALTETWA | 554 | 2628.23 | 2629.26 |
| MRVMAPRTLLLLLSGALALTETWA | 555 | 2628.23 | 2629.26 |
| MRVMAPRTLILLLSGALALTETWA | 556 | 2628.23 | 2629.26 |
| MRVMAPRTLILLLSGALALTETWA | 557 | 2628.23 | 2629.26 |
| MRVMAPRTLILLLSGALALTETWA | 558 | 2628.23 | 2629.26 |
| MRVMAPRTLILLLSGALALTETWA | 559 | 2628.23 | 2629.26 |
| MAAVVAATRWWQLLLVLSAAGMGASG | 560 | 2631.15 | 2629.26 |
| MAGPAIHTAPMLFLVLLLPLELSLA | 561 | 2632.3 | 2633.69 |
| MLGARLRLWVCALCSVCSMSVLRA | 45 | 2639.31 | 2640.51 |
| MGQPSLTWMLMVVVASWFITTAAT | 46 | 2642.18 | 2640.51, 2641.73 |
| MSEVPVARVWLVLLLLTVQVGVTAG | 562 | 2651.25 | 2652.85 |
| MALPPGPAALRHTLLLLPALLSSGWG | 563 | 2653.22 | 2652.85, 2655.08 |
| MASSPWGCVCGLLLLLLPLLGTGPALG | 564 | 2653.29 | 2652.85, 2655.08 |
| MDMRVPAQLLGLLLLWLRRVRC | 565 | 2653.35 | 2652.85, 2655.08 |
| MLVMAPRTVLLLLWGAVALTETWA | 566 | 2656.28 | 2655.08 |
| MAVTDSLSRAATVLATVLLLSFGSVAA | 567 | 2665.14 | 2665.15 |
| MSAPKLLSLGCIFFPLLLFQQARA | 568 | 2665.29 | 2665.15 |
| MRVTAPRTVLLLLWGAVALTETWA | 569 | 2669.22 | 2670 |
| MRVTAPRTVLLLLWGAVALTETWA | 570 | 2669.22 | 2670 |
| MRVTAPRTVLLLLWGAVALTETWA | 571 | 2669.22 | 2670 |
| MRVTAPRTVLLLLWGAVALTETWA | 572 | 2669.22 | 2670 |
| MRVTAPRTVLLLLWGAVALTETWA | 573 | 2669.22 | 2670 |
| MRVTAPRTVLLLLWGAVALTETWA | 574 | 2669.22 | 2670 |
| MRVTAPRTVLLLLWGAVALTETWA | 575 | 2669.22 | 2670 |
| MGAGATGRAMDGPRLLLLLLLGVSLGGA | 576 | 2681.25 | 2682.8 |
| MYLWLKLLAFGFAFLDTEVFVTG | 577 | 2682.22 | 2682.8 |
| MRVTAPRTLLLLLWGAVALTETWA | 578 | 2683.25 | 2682.8 |
| MRVTAPRTLLLLLWGAVALTETWA | 579 | 2683.25 | 2682.8 |
| MRVTAPRTLLLLLWGAVALTETWA | 580 | 2683.25 | 2682.8 |
| MRVTAPRTLLLLLWGAVALTETWA | 581 | 2683.25 | 2682.8 |
| MRVTAPRTLLLLLWGAVALTETWA | 582 | 2683.25 | 2682.8 |
| MRVTAPRTLLLLLWGAVALTETWA | 583 | 2683.25 | 2682.8 |
| MRVTAPRTLLLLLWGAVALTETWA | 584 | 2683.25 | 2682.8 |
| MAGLMTIVTSLLFLGVCAHHIIPTGS | 585 | 2683.28 | 2682.8 |
| MAAGSRTSLLLAFGLLCLSWLQEGSA | 586 | 2696.17 | 2696.41, 2697.73 |
| MRVTAPRTLLLLLWGALALTETWA | 47 | 2697.28 | 2696.41, 2697.73, 2698.27 |

TABLE 19-continued

| Signal Peptide | | | m/z |
|---|---|---|---|
| Amino acid sequence | SEQ ID No. | MW | of the corresponding peak |
| MRVTAPRTLLLLLWGALALTETWA | 48 | 2697.28 | 2696.41, 2697.73, 2698.27 |
| MRVTAPRTLLLLLWGALALTETWA | 49 | 2697.28 | 2696.41, 2697.73, 2698.27 |
| MRVTAPRTLLLLLWGALALTETWA | 50 | 2697.28 | 2696.41, 2697.73, 2698.27 |
| MRVTAPRTLLLLLWGALALTETWA | 51 | 2697.28 | 2696.41, 2697.73, 2698.27 |
| MAAASRSASGWALLLLVALWQQRAAG | 52 | 2699.17 | 2697.73, 2698.27, 2699.82 |
| MALKVLLEQEKTFFTLLVLLGYLSCKVTC | 587 | 3305.1 | 3303.21 |
| MESRGPLATSRLLLLLLLLLRHTRQGWA | 53 | 3329.06 | 3330.34 |

TABLE 20

| Signal Peptide | | | m/z |
|---|---|---|---|
| Amino acid sequence | SEQ ID No. | MW | of the corresponding peak |
| VVFLTLSVTWIGA | 588 | 1405.7 | 1405.71, 1406.49 |
| VVFLTLSVTWIGA | 589 | 1405.7 | 1405.71, 1406.49 |
| VVFLTLSVTWIGA | 590 | 1405.7 | 1405.71, 1406.49 |
| MGSRFLLVLLSGAS | 591 | 1450.77 | 1451.61 |
| MLRLYVLVMGVSA | 592 | 1451.86 | 1451.61 |
| MRALAVLSVTLVMA | 593 | 1474.9 | 1476.87 |
| MALLLLSLGLSLIAA | 594 | 1498.94 | 1497.16, 1498.88 |
| MNRVLCAPAAGAVRA | 595 | 1499.83 | 1498.88 |
| MNPLLILAFVGAAVA | 596 | 1499.88 | 1498.88 |
| MKTLFLGVTLGLAAA | 597 | 1505.89 | 1505.52 |
| MKTLFLGVTLGLAAA | 598 | 1505.89 | 1505.52 |
| MQSRLLLLGAPGGHG | 599 | 1506.79 | 1508.76, 1505.52 |
| MLLLPLLLPVLGAGS | 600 | 1506.96 | 1508.76, 1505.52 |
| MKLGLLCALLSLLAG | 601 | 1515.99 | 1516.64 |
| MILPLHNLGNGVRS | 54 | 1520.82 | 1521.93 |
| MAPPLLLLLASGAAA | 55 | 1521.93 | 1521.93 |
| MLGITVLAALLACASS | 602 | 1533.92 | 1533.52 |
| MRTLLTILTVGSLAA | 603 | 1559.94 | 1560.24 |
| MRLLTLLGLLCGSVA | 604 | 1560 | 1560.24 |
| MGLLLLVLILTPSLA | 605 | 1567.05 | 1566.2 |
| MGLTLLLLLLLGLEG | 606 | 1569.03 | 1567.74, 1567.2 |
| MVPLVPALVMLGLVAG | 607 | 1580.08 | 1580.91 |
| MKIIILLGFLGATLS | 608 | 1590.05 | 1589.58 |
| MKVLLLTGLGALFFA | 609 | 1594.04 | 1592.55 |
| MLLATLLLLLLGGALA | 610 | 1596.1 | 1597.25 |
| MAMGLFRVCLVVVTA | 611 | 1610.09 | 1610.62, 1609.36, 1608.53 |
| MKLLVILLFSGLITG | 612 | 1618.1 | 1616.12 |

TABLE 20-continued

| Signal Peptide Amino acid sequence | SEQ ID No. | MW | m/z of the corresponding peak |
|---|---|---|---|
| MLLILLSVALLALSSA | 56 | 1628.09 | 1629.15 |
| MLLILLSVALLALSSA | 57 | 1628.09 | 1629.15 |
| MTLRLLVAALCAGILA | 58 | 1629.11 | 1629.15 |
| MMLRLLSSLLLVAVA | 59 | 1630.14 | 1629.15 |
| MMLRLLSSLLLVAVA | 60 | 1630.14 | 1629.15 |
| MVLLLLVAIPLLVHS | 61 | 1631.14 | 1629.15 |
| MLPLLLGLLGPAACWA | 613 | 1639.1 | 1639.39, 1640.36 |
| MRVLACLLAALVGIQA | 614 | 1642.11 | 1640.36 |
| MLLVLLSVVLLALSSA | 615 | 1642.12 | 1640.36 |
| MTVFLSFAFLAAILT | 616 | 1645.04 | 1646.36 |
| MNFILFIFIPGVFS | 617 | 1645.04 | 1646.36 |
| MNYSPGLVSLILLLL | 618 | 1646.07 | 1646.36 |
| MELRVLLCWASLAAA | 619 | 1647.04 | 1646.36 |
| MAAPALLLLALLLPVGA | 620 | 1647.14 | 1646.36 |
| MVLAQGLLSMALLALC | 621 | 1647.15 | 1646.36 |
| MAAQAAAAQAAAAQAAQA | 622 | 1656.84 | 1655.72, 1657.97 |
| MKTGLFFLCLLGTAAA | 623 | 1657.08 | 1655.72, 1657.97 |
| MPVTFALLLLLGQATA | 624 | 1659.07 | 1657.97, 1659.24, 1660.46 |
| MSVPLLKIGVVLSTMA | 625 | 1659.13 | 1657.97, 1659.24, 1660.46 |

TABLE 21

| Signal Peptide Amino acid sequence | SEQ ID No. | MW | m/z of the corresponding peak |
|---|---|---|---|
| MAILPLLLCLLPLAPA | 626 | 1662.22 | 1662.16, 1660.46 |
| MQARALLLAALAALALA | 62 | 1681.12 | 1682.54, 1683.12 |
| MDAPARLLAPLLLLCA | 63 | 1681.14 | 1682.54, 1683.12 |
| MKLLLWACIVCVAFA | 64 | 1681.21 | 1682.54, 1683.12 |
| MGSRCALALAVLSALLC | 65 | 1692.15 | 1691.75, 1691.08 |
| MACAAVMIPGLLRCSVG | 66 | 1692.17 | 1691.75, 1691.08 |
| MKRLVCVLLVCSSAVA | 67 | 1692.19 | 1691.75, 1691.08 |
| MNLSLVLAAFCLGIASA | 627 | 1694.09 | 1694.76, 1695.74 |
| MGGAGILLLLLAGAGVVVA | 628 | 1695.15 | 1694.76 |
| MWPLALVIASLTLALS | 629 | 1699.13 | 1700.65 |
| MLRGTLLCAVLGLLRA | 630 | 1700.19 | 1700.65, 1702.19 |
| MAAGVVFLALSAQLLQA | 631 | 1703.08 | 1702.19 |
| MAAGVVFLALSAQLLQA | 632 | 1703.08 | 1702.19 |
| MHLLPALAGVLATLVLA | 633 | 1703.17 | 1702.19 |

TABLE 21-continued

| Signal Peptide Amino acid sequence | SEQ ID No. | MW | m/z of the corresponding peak |
|---|---|---|---|
| MKPPFLLALVVCSVVS | 634 | 1703.19 | 1702.19 |
| MALLLVSLLAFLSLGSG | 68 | 1705.14 | 1705.53 |
| MNPTLILAAFCLGIASA | 69 | 1706.11 | 1705.53 |
| MPWPLLLLLAVSGAQT | 635 | 1710.12 | 1708.77, 1712.1 |
| MLLLGILTLAFAGRTAG | 636 | 1718.14 | 1719.51 |
| MDVLFVAIFAVPLILG | 637 | 1718.18 | 1719.51 |
| MFVLLYVTSFAICASG | 638 | 1722.1 | 1721.61 |
| MARTRDRVRLLLLL | 639 | 1726.17 | 1726.31 |
| MKFTIVFAGLLGVFLA | 640 | 1727.19 | 1726.31 |
| MRIAVICFCLLGITCA | 641 | 1727.26 | 1726.31 |
| MSSSSWLLLSLVAVTAA | 642 | 1736.06 | 1737.85 |
| MAPKLITVLCLGFCLN | 643 | 1736.24 | 1737.85 |
| MAVLFLLLFLCGTPQA | 644 | 1737.21 | 1737.85 |
| MRLALLWALGLLGAGSP | 645 | 1739.16 | 1739.71, 1737.85 |
| MVGCGVAVLCLWVSCGAA | 646 | 1739.18 | 1739.71, 1737.85 |
| MAFLGLFSLLVLQSMA | 647 | 1741.19 | 1739.71 |
| MLGSLGLWALLPTAVEA | 648 | 1742.11 | 1743.69 |
| MKKLMVVLSLIAAAWA | 649 | 1745.27 | 1743.69 |
| MWPLVAALLLGSACCGSA | 650 | 1763.18 | 1761.79 |
| MPLSPGLLLLLLSGATAT | 651 | 1768.19 | 1769.93 |
| MGWLFLKVLLAGVSFS | 652 | 1768.2 | 1769.93 |
| MGAAGLLGVFLALVAPGVL | 653 | 1769.23 | 1769.93 |
| MGLLLLVPLLLLPGSYG | 654 | 1769.27 | 1769.93 |
| MIAFLLTSVLMIPHAGG | 655 | 1771.22 | 1769.93 |
| MKATIILLLLAQVSWA | 656 | 1771.24 | 1769.93 |
| MAARAVFLALSAQLLQA | 657 | 1774.16 | 1774.13, 1775.7 |
| MWTLVSWVALTAGLVAG | 658 | 1775.15 | 1775.7, 1774.13 |
| MSQVMSSPLLAGGHAVSL | 659 | 1785.12 | 1786.39 |
| MLLPALLFGMAWALADG | 660 | 1790.23 | 1790.8 |
| MVLLCLFLASLAATPRA | 661 | 1790.27 | 1790.8 |
| MWFLTTLLLWVPVDG | 662 | 1791.19 | 1790.8 |
| MWFLTTLLLWVPVDG | 663 | 1791.19 | 1790.8 |

TABLE 22

| Signal Peptide Amino acid sequence | SEQ ID No. | MW | m/z of the corresponding peak |
|---|---|---|---|
| MLLLLLLLPLLWGTKG | 664 | 1794.36 | 1796.23 |
| MSAVGLVLLVLALRLRA | 665 | 1795.31 | 1796.23 |

TABLE 22-continued

| Signal Peptide Amino acid sequence | SEQ ID No. | MW | m/z of the corresponding peak |
|---|---|---|---|
| MLPRLLLLICAPLCEP | 666 | 1795.35 | 1796.23 |
| MLARALLLCAVLALSHT | 667 | 1796.28 | 1796.23, 1797.49 |
| MRLHLLLLLALCGAGTT | 668 | 1796.28 | 1796.23, 1797.49 |
| LSKQQASQVLVRKRR | 669 | 1797.14 | 1796.23, 1797.49 |
| MWPLTALLLLVPSSGQA | 670 | 1797.19 | 1796.23, 1797.49 |
| MAGLAARLVLLAGAAALASG | 671 | 1797.2 | 1796.23, 1797.49 |
| MWLFFGITGLLTAALSG | 672 | 1798.18 | 1796.23, 1797.49 |
| MAVPARTCGASRPGPART | 673 | 1799.11 | 1797.49, 1800.34 |
| MWAQLLLGMLALSPAIA | 674 | 1799.28 | 1797.49, 1800.34 |
| MDFGLALLLAGLLGLLLG | 675 | 1800.28 | 1800.34, 1801.79 |
| MRTLLLVLWLATRGSA | 676 | 1801.23 | 1800.34, 1801.79 |
| MVPHLLLLCLLPLVRA | 677 | 1801.38 | 1800.34, 1801.79 |
| MFLLLALLTELGRLQA | 678 | 1802.26 | 1800.34, 1801.79 |
| MWLLGPLCLLLSSAAES | 679 | 1804.21 | 1804.45 |
| MLLGWASLLLCAFRLP | 680 | 1804.3 | 1804.45 |
| MALRHLALLAGLLVGVAS | 681 | 1805.26 | 1804.45 |
| MPLQLLLLLILLGPGNS | 682 | 1805.3 | 1804.45 |
| MTFGTVLLLSVLASYHG | 683 | 1809.16 | 1810.72 |
| MRLLFLAVLRPHTGNA | 684 | 1809.21 | 1810.72 |
| MLQGLLPVSLLLSVAVSA | 685 | 1811.26 | 1810.72, 1812.31 |
| MALGACGLLLLLAVPGVSL | 686 | 1811.33 | 1810.72, 1812.31 |
| MRIMLLFTAILAFSLA | 687 | 1811.33 | 1810.72, 1812.31 |
| MPPPPPLLLLTVLVVAAA | 688 | 1812.34 | 1810.72, 1812.31, 1813.77 |
| MCLLSSSAASDLAATSLTA | 689 | 1813.08 | 1812.31, 1813.77 |
| MSKQQASQVLVRKRR | 690 | 1815.18 | 1813.77 |
| MRALVLLLSLFLLGGQA | 691 | 1815.3 | 1813.77, 1817.26 |
| MKIITYFCIWAVAWA | 692 | 1816.27 | 1817.26 |
| MLVIWILTLALRLCAS | 693 | 1816.35 | 1817.26 |
| MVLLRLLVFLFAPVVS | 694 | 1817.36 | 1817.26, 1818.66, 1819.34 |
| MAPRPLLLLLLLGGSAA | 695 | 1819.33 | 1818.66, 1819.34, 1819.93 |
| MITFLPLLLGLSLGCTGA | 70 | 1820.29 | 1818.66, 1819.34, 1819.93, 1821.71 |
| MLAVLYLLVKTAKLGTS | 71 | 1821.3 | 1819.34, 1819.93, 1821.71 |
| MAPPAARLALLSAAALTLA | 72 | 1822.25 | 1821.71, 1822.73 |
| MRPLLGLLLVFAGCTFA | 73 | 1822.31 | 1821.71, 1822.73 |
| MLLFALLLAMELPLVAA | 696 | 1829.39 | 1829.48 |
| MPPLLAPLLCLALLPALA | 697 | 1830.42 | 1829.48, 1831.81, 1832.41 |
| MHAALAGPLLAALLATARA | 698 | 1832.25 | 1831.81, 1832.41 |
| MPSLLLLFTAALLSSWA | 74 | 1834.26 | 1832.41, 1836.18 |

TABLE 22-continued

| Signal Peptide Amino acid sequence | SEQ ID No. | MW | m/z of the corresponding peak |
|---|---|---|---|
| MAFRQALQLAACGLAGGSA | 75 | 1836.17 | 1836.18, 1837.33 |
| MPLLLLLPLLWAGALAM | 76 | 1836.42 | 1836.18, 1837.33 |
| MGARGALLLALLLARAGLG | 77 | 1837.31 | 1836.18, 1837.33 |
| MAAAVVLAAGLRAARRAVA | 699 | 1838.26 | 1837.33 |
| MGVQAGLFGMLGFLGVALG | 700 | 1838.27 | 1837.33 |
| MLSLLVWILTLSDTFS | 701 | 1839.23 | 1840.84, 1837.33 |

TABLE 23

| Signal Peptide Amino acid sequence | SEQ ID No. | MW | m/z of the corresponding peak |
|---|---|---|---|
| MVPPVWTLLLLVGAALF | 702 | 1840.35 | 1840.84 |
| MAPKLLLLLCLFSGLHA | 703 | 1840.37 | 1840.84 |
| MRDLPLTSLALVLSALGA | 704 | 1841.25 | 1840.84 |
| MPMDLILVVWFCVCTA | 705 | 1841.36 | 1840.84 |
| MKGILVAGITAVLVAAVES | 706 | 1842.28 | 1840.84 |
| MARGSALLLASLLLAAALS | 707 | 1842.28 | 1840.84 |
| MKAAGILTLIGCLVTGAES | 708 | 1848.26 | 1849.81 |
| MKAAGILTLIGCLVTGAES | 709 | 1848.26 | 1849.81 |
| MWLPPALLLLSLSGCFS | 710 | 1848.31 | 1849.81 |
| MARKALKLASWTSMALA | 711 | 1849.3 | 1849.81 |
| MLHLLALFLHCLPLASG | 712 | 1849.34 | 1849.81 |
| MWRVLFLLSGLGGLRM | 713 | 1849.34 | 1849.81 |
| MRPGPALLLLGVGLSLSVG | 714 | 1850.3 | 1849.81 |
| MDWTWRILFLVAAATG | 715 | 1851.2 | 1849.81 |
| MLPPWTLGLLLLATVRG | 716 | 1851.33 | 1849.81 |
| MLLRGVLLALQALQLAGA | 717 | 1851.33 | 1849.81 |
| MGAIGLLWLLPLLLSTAA | 718 | 1853.34 | 1854.68 |
| MACPGFLWALVISTCLE | 719 | 1854.29 | 1854.68 |
| MWLPALVLATLAASAAWA | 720 | 1856.26 | 1854.68 |
| MGSLMLLFVETTRNSSA | 721 | 1857.18 | 1858.34 |
| MNYSLHLAFVCLSLFT | 722 | 1859.25 | 1858.34 |
| MTAPWVALALLWGSLCAG | 723 | 1860.28 | 1858.34 |
| MAPAPVTLLAPGAASSMSCS | 724 | 1862.22 | 1864.19 |
| MTSSLLLAFLLLAPTTVA | 725 | 1862.31 | 1864.19 |
| MGSCARLLLLWGCTVVAA | 726 | 1864.33 | 1864.19, 1866.06 |
| MAAAGAAVARSPGIGAGPALR | 727 | 1865.19 | 1864.19, 1866.06 |
| MKILCIFLTFVFTVSC | 728 | 1865.4 | 1866.06, 1864.19 |

TABLE 23-continued

| Signal Peptide Amino acid sequence | SEQ ID No. | MW | m/z of the corresponding peak |
|---|---|---|---|
| MRLLVAPLLLAWVAGATA | 729 | 1866.35 | 1866.06 |
| MKPLLLAISLSLIAALQA | 730 | 1866.38 | 1866.06 |
| MLFLQFLLLALLLPGGD | 731 | 1874.36 | 1875.28 |
| MAGSLTGLLLLQAVSWASG | 732 | 1875.22 | 1875.28, 1876.5 |
| LGLCWVFLVALLRGVLC | 733 | 1875.42 | 1875.28, 1876.5 |
| MKLFWLLFTIGFCWA | 734 | 1876.36 | 1875.28, 1876.5, 1878.25 |
| MALRRLGAALLLLPLLAA | 735 | 1876.43 | 1875.28, 1876.5, 1878.25 |
| MIPAVVLLLLLLVEQAAA | 736 | 1877.41 | 1878.25, 1876.5 |
| MPPMLWLLLHFAAPALG | 737 | 1878.38 | 1878.25, 1876.5 |
| MALLALLLVVALPRVWT | 738 | 1879.43 | 1878.25 |
| MQEAIILLALLGAMSGGEA | 739 | 1888.28 | 1890.21 |
| MGTLPWLLAFFILGLQA | 740 | 1891.35 | 1890.21, 1891.32, 1893 |
| MLTTLLPILLLSGWAFC | 741 | 1892.4 | 1891.32, 1893 |
| MAPARLFALLLFFVGGVA | 742 | 1893.37 | 1893 |
| MLKALFLTMLTLALVKS | 743 | 1893.47 | 1893 |
| MLLWILLLETSLCFAAG | 744 | 1894.37 | 1893 |
| MAPLALVGVTLLLAAPPCSG | 745 | 1894.38 | 1893 |
| MRGLGTCLATLAGLLLTAAG | 746 | 1903.34 | 1904.69 |
| MVAATVAAAWLLLWAAACA | 747 | 1903.35 | 1904.69 |

TABLE 24

| Signal Peptide Amino acid sequence | SEQ ID No. | MW | m/z of the corresponding peak |
|---|---|---|---|
| MLLLSLTLSLVLLGSSWG | 748 | 1903.36 | 1904.69 |
| MKASVVLSLLGYLVVPSGA | 749 | 1904.35 | 1904.69 |
| MLLLLLLLPPLLCGRVGA | 750 | 1905.53 | 1904.69 |
| MWPRLAFCCWGLALVSG | 751 | 1910.36 | 1911.46 |
| MTALPGPLWLLGLALCALG | 752 | 1910.42 | 1911.46 |
| MLVAGLLLWASLLTGAWP | 753 | 1912.37 | 1911.46, 1913.68 |
| MRVFCVGLLLFSVTWAA | 754 | 1913.38 | 1911.46, 1913.68 |
| MLGIWIVAFLFFGTSRG | 755 | 1915.33 | 1913.68, 1916.02 |
| MKPQFVGILLSSLLGAALG | 756 | 1915.37 | 1913.68, 1916.02 |
| MLSLLLLALPVLASRAYA | 757 | 1915.42 | 1913.68, 1916.02 |
| MVPDTACVLLLTLAALGASG | 758 | 1916.34 | 1916.02 |
| MARAQALVLALTFQLCAP | 759 | 1917.37 | 1916.02, 1919.35 |
| MARAQALVLALTFQLCAP | 760 | 1917.37 | 1916.02, 1919.35 |
| MTTQLGPALVLGVALCLGCG | 761 | 1917.39 | 1916.02, 1919.35 |
| MGLKALCLGLLCVLFVSH | 762 | 1917.48 | 1916.02, 1919.35 |

TABLE 24-continued

| Signal Peptide Amino acid sequence | SEQ ID No. | MW | m/z of the corresponding peak |
|---|---|---|---|
| MKVHMLVGVLVMVGFTVG | 763 | 1917.48 | 1916.02, 1919.35 |
| MDLWQLLLTLALAGSSDA | 764 | 1918.24 | 1919.35 |
| MWVPVVFLTLSVTWIGA | 765 | 1919.36 | 1919.35 |
| MWVPVVFLTLSVTWIGA | 766 | 1919.36 | 1919.35 |
| MWVPVVFLTLSVTWIGA | 767 | 1919.36 | 1919.35 |
| MWVPVVFLTLSVTWIGA | 768 | 1919.36 | 1919.35 |
| MRVYIFLCLMCWVRS | 769 | 1920.47 | 1919.35 |
| MTAGAGVLLLLLSLSGALRA | 770 | 1927.38 | 1927.13 |
| MKFFMVLLPASLASTSLA | 771 | 1927.4 | 1927.13 |
| MRAAGTLLAFCCLVLSTTG | 772 | 1928.37 | 1927.13 |
| MLCSLLLCECLLLVAGYA | 773 | 1928.48 | 1927.13 |
| MWLLVSVILISRISSVGG | 774 | 1930.39 | 1931.84 |
| MKFILLWALLNLTVALA | 775 | 1930.47 | 1931.84 |
| MKTLAGLVLGLVIFDAAVT | 776 | 1932.4 | 1931.84 |
| MGPGVLLLLLVATAWHGQG | 777 | 1933.35 | 1931.84, 1934.86 |
| MARVPPVGALLLLRGSRQ | 778 | 1934.39 | 1934.86, 1935.52 |
| MLLLFSVILISWVSTVGG | 779 | 1935.4 | 1934.86, 1935.52, 1936.83 |
| MWQLWASLCCLLVLANA | 780 | 1935.41 | 1934.86, 1935.52, 1936.83 |
| MLMLFVFGVLLHEVSLS | 781 | 1935.43 | 1934.86, 1935.52, 1936.83 |
| MRSLLLLSAFCLLEAALA | 782 | 1935.43 | 1934.86, 1935.52, 1936.83 |
| MQQRGLAIVALAVCAALHA | 783 | 1936.38 | 1934.86, 1935.52, 1936.83, 1937.87 |
| MGARGALLLALLLARAGLR | 784 | 1936.44 | 1934.86, 1935.52, 1936.83, 1937.87 |
| MPLALTLLLLSGLGAPGGWG | 785 | 1937.38 | 1935.52, 1936.83, 1937.87 |
| MAAAGLVAVAAAAEYSGTVASG | 786 | 1938.19 | 1936.83, 1937.87 |
| MTIALLGFAIFLLHCATC | 787 | 1938.45 | 1936.83, 1937.87 |
| MIAISAVSSALLFSLLCEA | 788 | 1939.37 | 1937.87, 1941.22 |
| MWGLLLALAAFAPAVGPALG | 789 | 1939.4 | 1937.87, 1941.22 |
| MGGPRALLAALWALEAAGTA | 790 | 1940.3 | 1941.22 |
| MNGLSLSELCCLCCPPCPG | 791 | 1940.41 | 1941.22 |
| MWGRLWPLLLSILTATA | 792 | 1942.4 | 1941.22 |
| MLNLLLLALPVLASRAYA | 793 | 1942.44 | 1941.22 |

TABLE 25

| Signal Peptide Amino acid sequence | SEQ ID No. | MW | m/z of the corresponding peak |
|---|---|---|---|
| MLNLLLLALPVLASRAYA | 794 | 1942.44 | 1941.22 |
| MIHLGHILFLLLLPVAAA | 795 | 1942.49 | 1941.22 |

TABLE 25-continued

| Signal Peptide Amino acid sequence | SEQ ID No. | MW | m/z of the corresponding peak |
|---|---|---|---|
| MASHRLLLLCLAGLVFVS | 796 | 1943.45 | 1944.97 |
| MHYPTALLFLILANGAQA | 797 | 1944.33 | 1944.97 |
| MQHIFAFFCTGFLGAVVG | 798 | 1945.34 | 1944.97 |
| MRPFFLLCFALPGLLHA | 78 | 1946.46 | 1944.97, 1948.39 |
| MLLWPLLLLLLLPTLA | 79 | 1946.6 | 1944.97, 1948.39 |
| MYLSICCCFLLWAPALT | 80 | 1948.47 | 1948.39 |
| MLRILCLALCSLLTGTRA | 81 | 1948.49 | 1948.39 |
| MLLWASLLAFAPVCGQSAA | 82 | 1949.37 | 1948.39 |
| CMTALTVTLMVLSSPLALS | 799 | 1951.45 | 1952.47 |
| MGLIWLLLLSLLEPGWP | 800 | 1951.45 | 1952.47 |
| MAARPGPLWLLGLTLCALG | 801 | 1953.45 | 1952.47 |
| MPWTILLFAAGSLAIPAPS | 802 | 1956.38 | 1957.8 |
| MAPPTGVLSSLLLLVTIAGC | 803 | 1956.44 | 1957.8 |
| MSTMRLLTLALLFSCSVA | 804 | 1957.46 | 1957.8 |
| MSISSALAMVFMGAKGNTAA | 805 | 1958.36 | 1957.8 |
| MKLHCCLFTLVASIIVPA | 806 | 1959.52 | 1957.8 |
| MLTPPLLLLLPLLSALVAA | 807 | 1959.55 | 1957.8 |
| MLLFSVLLLLSLVTGTQL | 808 | 1961.48 | 1962.82 |
| MELVLVFLCSLLAPMVLA | 809 | 1962.56 | 1962.82 |
| MAPWLQLLSLLGLLPGAVA | 810 | 1963.46 | 1962.82 |
| MFLLLTALQVLAIAMTQS | 811 | 1964.47 | 1962.82 |
| MALLVLGLVSCTFFLAVNG | 812 | 1968.46 | 1969.82 |
| MSLLLLLLLVSYYVGTLG | 813 | 1968.47 | 1969.82 |
| MSATTACWPAFTVLGEARG | 814 | 1969.27 | 1969.82 |
| MEKILFYLFLIGIAVKA | 815 | 1969.51 | 1969.82 |
| MRAPLLPPAPVVLSLLILG | 816 | 1970.54 | 1969.82 |
| MGSPVSHLLAGFCVWVVLG | 817 | 1972.41 | 1972.54 |
| MAPAFLLLLLLWPQGCVS | 818 | 1972.49 | 1972.54 |
| MLLLINVILTLWVSCANG | 819 | 1973.48 | 1972.54 |
| MRRAWILLTLGLVACVSA | 820 | 1973.48 | 1972.54 |
| MLKTFTVLLFCIRMSLG | 821 | 1973.54 | 1972.54 |
| MWILALSLFQSFANVFS | 822 | 1974.36 | 1975.58 |
| MAGVVHVSLAALLLLPMAPA | 823 | 1974.51 | 1975.58 |
| MLQLWKLVLLCGVLTGTS | 824 | 1975.49 | 1975.58, 1976.51 |
| MKTLPVLVLSLTLLLTVFS | 825 | 1975.51 | 1975.58, 1976.51 |
| MTLLLLPLLLASLLASCSC | 826 | 1975.55 | 1975.58, 1976.51 |
| MRLGSPGLLFLLFSSLRA | 827 | 1978.43 | 1976.51, 1977.7, 1979.29 |
| MILLAVLFLCFISSYSAS | 828 | 1978.45 | 1976.51, 1977.7, 1979.29 |

TABLE 25-continued

| Signal Peptide Amino acid sequence | SEQ ID No. | MW | m/z of the corresponding peak |
|---|---|---|---|
| MLLLLLPLLWGRERAEG | 829 | 1980.45 | 1979.29 |
| MRTIAILAAILLVALQAQA | 830 | 1980.49 | 1979.29 |
| MWLSPSLLLLILPGYSIA | 831 | 1987.48 | 1988.46 |
| MLPLLAALLAAACPLPPVRG | 832 | 1987.55 | 1988.46 |
| MWGRLLLWPLVLGFSLS | 833 | 1988.47 | 1988.46 |
| MWSLLLCGLSIALPLSVTA | 834 | 1988.49 | 1988.46 |

TABLE 26

| Signal Peptide Amino acid sequence | SEQ ID No. | MW | m/z of the corresponding peak |
|---|---|---|---|
| MKSVLLLTTLLVPAHLVAA | 835 | 1990.53 | 1991.91 |
| MKGARLFVLLSSLWSGGIG | 836 | 1992.42 | 1991.91 |
| MKALMLLTLSVLLCWVSA | 837 | 1992.59 | 1991.91 |
| MWLPLVLLLAVLLLAVLC | 838 | 1993.68 | 1991.91, 1995.37 |
| MRAGPGPTVTLALVLAVAWA | 839 | 1994.43 | 1995.37 |
| MAGIPGLLFLLFFLLCAVG | 840 | 1995.57 | 1995.37 |
| MVLSLTGLIAFSFLQATLA | 841 | 1996.44 | 1995.37 |
| MLLWLLLLILTPGREQS | 842 | 1996.49 | 1995.37 |
| MVLLLVILIPVLVSSAGTSA | 843 | 1996.53 | 1995.37 |
| MPALGPALLQALWAGWVLT | 844 | 2008.46 | 2009.91 |
| MKFVPCLLLVTLSCLGTLG | 845 | 2008.59 | 2009.91 |
| MRFLAATFLLLALSTAAQA | 83 | 2009.45 | 2009.91, 2011.18 |
| MKALGAVLLALLLCGRPGRG | 84 | 2009.56 | 2009.91, 2011.18 |
| MVPSAGQLALFALADPPVAAA | 85 | 2010.39 | 2009.91, 2011.18 |
| MSLLLSFYLLGLLVSSGQA | 86 | 2012.44 | 2011.18, 2013.86 |
| MLGCGIPALGLLLLLQGSADG | 87 | 2012.47 | 2011.18, 2013.86 |
| MFPLRALWLVWALLGVAG | 846 | 2013.53 | 2013.86 |
| MFLSILVALCLWLHLALG | 847 | 2013.59 | 2013.86 |
| MVLLRVLILLLSWAAGMGG | 848 | 2013.59 | 2013.86 |
| MKLLPSVVLKLFLAAVLSA | 849 | 2013.6 | 2013.86 |
| MEPLRLLILLFVTELSGA | 850 | 2015.49 | 2013.86 |
| MVLLTAVLLLLAAYAGPAQS | 851 | 2015.49 | 2013.86 |
| MCCWPLLLLWGLLPGTAAG | 852 | 2015.54 | 2013.86 |
| MRWTIVILLCFCKAAEL | 853 | 2022.62 | 2023.97 |
| MLNVSGLFVLLCGLLVSSSA | 854 | 2023.49 | 2023.97 |
| MVPAWLWLLCVSVPQALP | 855 | 2023.54 | 2023.97 |
| MGAVLRSLLACSFCVLLRA | 856 | 2023.56 | 2023.97 |
| MKLLSLVAVVGCLLVPPAEA | 857 | 2023.58 | 2023.97 |

TABLE 26-continued

| Signal Peptide Amino acid sequence | SEQ ID No. | MW | m/z of the corresponding peak |
|---|---|---|---|
| MDSWFILVLLGSGLICVSA | 858 | 2024.48 | 2023.97 |
| MGPAWLWLLGTGILASVHC | 859 | 2025.47 | 2023.97 |
| MLFWVLGLLILCGFLWT | 860 | 2025.6 | 2023.97 |
| METLLGGLLAFGMAFAVVDA | 861 | 2026.45 | 2027.73 |
| MRTLTILTAVLLVALQAKA | 862 | 2026.56 | 2027.73 |
| MYELLVLFMLIQPQSMA | 863 | 2027.55 | 2027.73 |
| MVRCLGPALLLLLLGSASS | 864 | 2027.57 | 2027.73 |
| MELALLCGLVVMAGVIPIQG | 865 | 2027.59 | 2027.73 |
| MAWFALYLLSLLWATAGT | 866 | 2028.45 | 2027.73 |
| MWQIVFFTLSCDLVLAAA | 867 | 2028.47 | 2027.73 |
| MVLCWLLLLVMALPPGTTG | 868 | 2028.62 | 2027.73 |
| MGFLGTGTWILVLVLPIQA | 869 | 2029.52 | 2027.73, 2030.95 |
| MEVTCLLLLALIPFHCRG | 870 | 2029.57 | 2027.73, 2030.95 |
| MVWCLGLAVLSLVISQGADG | 871 | 2032.46 | 2030.95, 2032.69 |
| MMHLRLFCILLAAVSGAEG | 872 | 2032.53 | 2030.95, 2032.69 |
| MSPSPTALFCLGLCLGRVPA | 873 | 2033.51 | 2032.69 |
| MSMLFYTLITAFLIGIQA | 874 | 2033.53 | 2032.69 |
| MLPCLALLLLMELSVCTVA | 875 | 2033.66 | 2032.69 |

TABLE 27

| Signal Peptide Amino acid sequence | SEQ ID No. | MW | m/z of the corresponding peak |
|---|---|---|---|
| MRQGLLVLALVLVLVLVLA | 876 | 2033.68 | 2032.69 |
| MDFLLALVLVSSLYLQAAA | 877 | 2038.48 | 2039.29 |
| MNCQQLWLGFLLPMTVSG | 878 | 2038.49 | 2039.29 |
| MYGKIIFVLLLSAIVSISA | 879 | 2038.57 | 2039.29 |
| MYGKIIFVLLLSAIVSISA | 880 | 2038.57 | 2039.29 |
| MPPFLITLFLFHSCCLR | 881 | 2038.58 | 2039.29 |
| MAARVAAVRAAAWLLLGAATG | 882 | 2040.47 | 2039.29 |
| MFLWLFLILSALISSTNA | 883 | 2040.5 | 2039.29 |
| MEPLCPLLLVGFSLPLARA | 884 | 2040.57 | 2039.29 |
| MKSPHVLVFLCLLVALVTG | 885 | 2040.61 | 2039.29 |
| MRPLLCALAGLALLCAVGALA | 886 | 2040.64 | 2039.29 |
| MQACMVPGLALCLLLGPLAGA | 887 | 2042.63 | 2043.12 |
| MAWTKYQLFLAGLMLVTG | 888 | 2043.53 | 2043.12 |
| MTLLPGLLFLTWLHTCLA | 889 | 2043.57 | 2043.12 |
| MKAPIPHLILLYATFTQS | 890 | 2044.49 | 2043.12, 2045.68 |

TABLE 27-continued

| Signal Peptide Amino acid sequence | SEQ ID No. | MW | m/z of the corresponding peak |
|---|---|---|---|
| MRANDALQVLGLLFSLARG | 891 | 2045.44 | 2045.68 |
| MKRLLLLFLFFITFSSA | 892 | 2047.58 | 2045.68 |
| MKPLVLLVALLLWPSSVPA | 893 | 2047.62 | 2045.68 |
| MQLVILRVTIFLPWCFA | 894 | 2050.61 | 2051.76 |
| MRAPLCLLLLVAHAVDMLA | 895 | 2050.63 | 2051.76 |
| MGIVCAQCSFILLLSIIRA | 896 | 2051.62 | 2051.76 |
| MAPSLWKGLVGIGLFALAHA | 897 | 2052.52 | 2051.76 |
| MGLGLLLPLLLLWTRGTQG | 898 | 2052.56 | 2051.76 |
| MIPVELLLCYLLLHPVDA | 899 | 2052.58 | 2051.76 |
| MLPGRLCWVPLLLALGVGSG | 900 | 2052.58 | 2051.76 |
| MRSEALLLYFTLLHFAGA | 901 | 2053.46 | 2051.76 |
| MAGTGLLALRTLPGPSWVRG | 902 | 2053.46 | 2051.76 |
| MLRTSGLALLALVSAVGPSQA | 903 | 2055.47 | 2055.5 |
| MDFWLWPLYFLPVSGAL | 904 | 2055.47 | 2055.5 |
| MVGLLLFFFPAIFLEVSL | 905 | 2056.59 | 2055.5 |
| MTRALCSALRQALLLLAAAA | 906 | 2057.56 | 2059.05 |
| MRLLLLLLVAASAMVRSEA | 907 | 2057.6 | 2059.05 |
| MLPGCIFLMILLIPQVKE | 908 | 2058.69 | 2059.05 |
| MRLAVLFSGALLGLLAAQGTG | 909 | 2059.51 | 2059.05 |
| MRLLAWLIFLANWGGARA | 910 | 2059.51 | 2059.05 |
| MALGLLIAVPLLLQAAPRGAA | 911 | 2059.59 | 2059.05 |
| MTCSPLLLTLLIHCTGSWA | 912 | 2060.54 | 2059.05 |
| MFQTGGLIVFYGLLAQTMA | 913 | 2061.5 | 2062.98 |
| MGSGRVPGLCLLVLLVHARA | 914 | 2062.58 | 2062.98 |
| MMLNLVRYVCVLGNMVHA | 915 | 2063.61 | 2062.98, 2065.57 |
| MVPRISAAIFIFELLGSNS | 916 | 2065.47 | 2065.57, 2066.09 |
| MVLLWLTLLLIALPCLLQ | 917 | 2066.73 | 2065.57, 2066.09 |
| MDSRQAAALLVLLLIDGGC | 918 | 2072.52 | 2074.03 |
| MCAFPWLLLLLLQEGSQ | 919 | 2075.57 | 2075.32, 2074.03 |
| MSALWLLLGLLALMDLSES | 920 | 2076.55 | 2075.32 |
| MRALVLLGCLLASLLFSGQA | 921 | 2076.6 | 2075.32 |

TABLE 28

| Signal Peptide Amino acid sequence | SEQ ID No. | MW | m/z of the corresponding peak |
|---|---|---|---|
| MKKFFTVAILAGSVLSTAHG | 922 | 2078.51 | 2079.8 |
| MALVLILQLLTLWPLCHT | 923 | 2078.66 | 2079.8 |
| MKLALLLPWACCCLCGSALA | 924 | 2080.7 | 2079.8 |

TABLE 28-continued

| Signal Peptide Amino acid sequence | SEQ ID No. | MW | m/z of the corresponding peak |
|---|---|---|---|
| MIVLLLFALLWMVEGVFS | 925 | 2081.66 | 2079.8 |
| MHSWERLAVLVLLGAAACAA | 926 | 2082.52 | 2083.74, 2084.36 |
| MPHTLWMVWVLGVIISLS | 927 | 2082.61 | 2083.74, 2084.36 |
| MGIGCWRNPLLLLIALVLS | 928 | 2082.65 | 2083.74, 2084.36 |
| MAILMLSLQLILLLIPSIS | 929 | 2082.73 | 2083.74, 2084.36 |
| MTPACPLLLSVILSLRLATA | 930 | 2083.63 | 2083.74, 2084.36 |
| MLLALALLLAFLPPASQKSS | 931 | 2084.6 | 2083.74, 2084.36, 2085.85 |
| MGRPLLLPLLPLLLPPAFL | 932 | 2084.73 | 2083.74, 2084.36, 2085.85 |
| MAFLPSWVCVLVGSFSASLA | 933 | 2085.52 | 2083.74, 2084.36, 2085.85 |
| MGPHFTLLCAALAGCLLPAEG | 934 | 2085.55 | 2083.74, 2084.36, 2085.85 |
| MGVLGRVLLWLQLCALTQA | 935 | 2085.61 | 2083.74, 2084.36, 2085.85 |
| MLQGTCSVLLLWGILGAIQA | 936 | 2087.58 | 2085.85, 2089.53 |
| MNGLSLSELCCLFCCPPCPG | 937 | 2087.58 | 2085.85, 2089.53 |
| MNGLSLSELCCLFCCPPCPG | 938 | 2087.58 | 2085.85, 2089.53 |
| MALPSLLLLVAALAGGVRPPGA | 939 | 2087.6 | 2085.85, 2089.53 |
| MPALRPLLPLLLLLRLTSG | 940 | 2087.69 | 2085.85, 2089.53 |
| MRPRLWLLLAAQLTVLHG | 941 | 2088.6 | 2089.53 |
| MSWAPVLLMLFVYCTGCGP | 942 | 2088.61 | 2089.53 |
| MAGIFYFALFSCLFGICDA | 943 | 2089.53 | 2089.53 |
| MELLPLWLCLGFHFLTVG | 944 | 2089.6 | 2089.53 |
| MTWLVLLGTLLCMLRVGLG | 945 | 2089.71 | 2089.53 |
| MSDLGAVISLLLWGRQLFA | 946 | 2090.52 | 2089.53, 2092.25 |
| MIVFIFLAMGLSLENEYT | 88 | 2091.52 | 2089.53, 2092.25, 2092.8 |
| MFGTLLLYCFFLATVPALA | 89 | 2091.61 | 2092.25, 2092.8 |
| MWPLTVPPPLLLLLCSGLAG | 90 | 2091.66 | 2092.25, 2092.8 |
| MPVIAGGILAALLLLIVWLC | 91 | 2091.78 | 2092.25, 2092.8 |
| MAGPERWGPLLLCLLQAAPG | 92 | 2093.55 | 2092.25, 2092.8 |
| MGISTVILEMCLLWGQVLS | 93 | 2093.61 | 2092.25, 2092.8 |
| MRDSACWSQRKDELLQQ | 94 | 2094.36 | 2092.8 |
| MGGPRAWALLCLGLLLPGGGAA | 95 | 2094.58 | 2092.8 |
| MSLMVVSMACVGVLLAAGGLAT | 96 | 2094.66 | 2092.8 |
| MTKALLIYLVSSFLALNQA | 947 | 2096.56 | 2097.03 |
| MRGELWLLVLVLREAARA | 948 | 2096.57 | 2097.03 |
| MLPFLFFSTLFSSIFTEA | 97 | 2098.49 | 2097.03, 2099.42 |
| MTPQLLLALVLWASCPPCSG | 98 | 2100.6 | 2099.42 |
| MPAGRAARTCALLALCLLGAGA | 99 | 2100.61 | 2099.42 |
| MIPGNRMLMVVLLCQVLLG | 100 | 2100.76 | 2099.42 |
| MRAALWTLGLGPLLLNLWA | 949 | 2109.61 | 2111.39 |

TABLE 28-continued

| Signal Peptide Amino acid sequence | SEQ ID No. | MW | m/z of the corresponding peak |
|---|---|---|---|
| MLPQQVGFVCAVLALVCCASG | 950 | 2109.63 | 2111.39 |
| MRLGPRTAALGLLLLCAAAAGA | 951 | 2110.62 | 2111.39 |
| MKFSPAHYLLPLLPALVLS | 952 | 2110.64 | 2111.39 |
| MMLSWKQLILLSFIGCLGG | 953 | 2110.68 | 2111.39 |
| MARAMAAAWPLLLVALLVLS | 954 | 2110.71 | 2111.39 |

TABLE 29

| Signal Peptide Amino acid sequence | SEQ ID No. | MW | m/z of the corresponding peak |
|---|---|---|---|
| MKILVALAVFFLVSTQLFA | 955 | 2111.67 | 2111.39, 2113.1 |
| MAPRALPGSAVLAAAVFVGGAVS | 956 | 2112.53 | 2111.39, 2113.1 |
| MERVTLALLLLAGLTALEAN | 957 | 2112.56 | 2111.39, 2113.1 |
| MHPQVVILSLILHLADSVAG | 958 | 2113.55 | 2113.1 |
| MAFCALTIVALYILSLKDQ | 959 | 2113.62 | 2113.1 |
| MVRPYPLIYFLFLPLGAC | 960 | 2113.66 | 2113.1 |
| MTERRRALSLAAVVDSINL | 961 | 2115.49 | 2115.77 |
| MKPLLETLYLLGMLVPGGLG | 962 | 2115.68 | 2115.77 |
| MVSQALRLLCLLLGLQGCLA | 963 | 2115.7 | 2115.77 |
| MGRPLLLPLLLLLQPPAFL | 964 | 2115.74 | 2115.77 |
| MKLLLLALPMLVLLPQVIP | 965 | 2115.85 | 2115.77 |
| MLCCCPLADALLIFLETGSC | 966 | 2116.64 | 2115.77 |
| MEKSIWLLACLAWVLPTGS | 967 | 2118.59 | 2120.37 |
| MSRVVSLLLGAALLCGHGAFC | 968 | 2118.62 | 2120.37 |
| MGWTWRILFLVVIAAGAQS | 969 | 2119.56 | 2120.37 |
| MAAPVPWACCAVLAAAAAVVYA | 970 | 2119.61 | 2120.37 |
| MWGLVRLLLAWLGGWGCMG | 971 | 2119.65 | 2120.37 |
| MLGVLELLLLGAAWLAGPARG | 972 | 2121.62 | 2120.37 |
| MLLLLLLPLLWGRERVEG | 973 | 2121.66 | 2120.37 |
| MATSMGLLLLLLLLLTQPGAG | 974 | 2126.7 | 2126.55 |
| MRGCLRLALLCALPWLLLA | 975 | 2126.77 | 2126.55 |
| MWVLGIAATFCGLFLLPGFA | 976 | 2127.65 | 2126.55 |
| MLLLWVSVVAALALAVLAPGAG | 977 | 2135.69 | 2137.63 |
| MACLGFLLPVGFLLLISTVAG | 978 | 2135.71 | 2137.63 |
| MASLGLLLLLLLTALPPLWS | 979 | 2135.73 | 2137.63 |
| MVLLSILRILFLCELVLF | 980 | 2135.8 | 2137.63 |
| MSPAPRPSRCLLLPLLTLGT | 981 | 2136.66 | 2137.63 |
| MRLLWKLVILLPLINSSAG | 982 | 2137.71 | 2137.63, 2139.15 |

TABLE 29-continued

| Signal Peptide Amino acid sequence | SEQ ID No. | MW | m/z of the corresponding peak |
|---|---|---|---|
| MRFVVALVLLNVAAAGAVPLL | 983 | 2137.71 | 2137.63, 2139.15 |
| MQHSLVFFFAVILHLSHL | 984 | 2139.6 | 2137.63, 2139.15, 2140.48 |
| MATSWGTVFFMLVVSCVCSA | 985 | 2139.61 | 2137.63, 2139.15, 2140.48 |
| MALPSRILLWKLVLLQSSA | 986 | 2139.68 | 2139.15, 2140.48 |
| MIWYVATFIASVIGTRGLAA | 987 | 2140.58 | 2139.15, 2140.48 |
| MGHLWLLGIWGLCGLLLCAA | 988 | 2140.71 | 2139.15, 2140.48 |
| MQSHLAPLACAAAAGRAGGSCQA | 989 | 2142.47 | 2140.48, 2143.42 |
| MHYCVLSAFLILHLVTVAL | 990 | 2143.69 | 2143.42 |
| MLLLLLPSLLLLLLLPGPGSG | 991 | 2143.79 | 2143.42 |
| MSPLLFGAGLVVLNLVTSARS | 992 | 2145.6 | 2146.46 |
| MLLGQLSTLLCLLSGALPTGSG | 993 | 2145.62 | 2146.46 |
| MWTLKSSLVLLLCLTCSYA | 994 | 2145.68 | 2146.46 |
| MWTLKSSLVLLLCLTCSYA | 995 | 2145.68 | 2146.46 |
| MGSLVLTLCALFCLAAYLVSG | 996 | 2145.68 | 2146.46 |
| MRLPWELLVLQSFILCLA | 997 | 2145.71 | 2146.46 |
| MEMFTFLLTCIFLPLLRG | 998 | 2145.73 | 2146.46 |
| MTRCALLLLMVLMLGRVLV | 999 | 2145.88 | 2146.46 |
| MDWTWRILFLVAAATGAHS | 1000 | 2146.5 | 2146.46 |

TABLE 30

| Signal Peptide Amino acid sequence | SEQ ID No. | MW | m/z of the corresponding peak |
|---|---|---|---|
| MWWRVLSLLAWFPLQEA | 1001 | 2146.59 | 2146.46 |
| MLRQLLLAALCLAGPPAPARA | 1002 | 2146.7 | 2146.46 |
| MTLFPVLLFLVAGLLPSFPA | 1003 | 2146.71 | 2146.46 |
| MGTARWLALGSLFALAGLLEG | 1004 | 2147.57 | 2146.46 |
| MNGLSLSELCCLFCYPPCPG | 1005 | 2147.62 | 2146.46 |
| MVPKADSGAFLLLFLLVLTV | 1006 | 2147.7 | 2146.46 |
| MLRFYLFISLLCLSRSDA | 1007 | 2148.62 | 2149.85 |
| MDAAFLLVLGLLAQSLCLSLG | 1008 | 2148.66 | 2149.85 |
| MMSFLLGAILTLLWAPTAQA | 1009 | 2148.66 | 2149.85 |
| MNGNLDGWVVVLAAPLLPAAQ | 1010 | 2149.54 | 2149.85, 2151.02 |
| MRRQWGALLLGALLCAHAVA | 1011 | 2150.65 | 2149.85, 2151.02 |
| MGPRAKTISSLFFLLWVLA | 1012 | 2150.66 | 2149.85, 2151.02 |
| MGGLEPCSRLLLLPLLLAVSG | 1013 | 2152.7 | 2151.02 |
| MAPAVTRLLFLQLVLGPTLV | 1014 | 2152.72 | 2151.02 |
| METLGALLVLEFLLLSPVEA | 1015 | 2158.63 | 2160.22 |
| MASSLTCTGVIWALLSFLCAA | 1016 | 2158.64 | 2160.22 |

TABLE 30-continued

| Signal Peptide Amino acid sequence | SEQ ID No. | MW | m/z of the corresponding peak |
|---|---|---|---|
| MAVGKFLLGSLLLLSLQLGQG | 1017 | 2158.68 | 2160.22 |
| MWQLLAAACWMLLLGSMYG | 1018 | 2158.71 | 2160.22 |
| MGTGGSLLCGCSLVLSCLCPSAS | 1019 | 2159.62 | 2160.22 |
| MWLYLAAFVGLYYLLHW | 1020 | 2159.63 | 2160.22 |
| MDWTWRILFLVAAATGTHA | 1021 | 2160.53 | 2160.22, 2161.68 |
| DLRVATVTLMLAILSSSLAEG | 1022 | 2160.56 | 2160.22, 2161.68 |
| MLNNLLLFSLQISLIGTTLG | 1023 | 2161.64 | 2161.68 |
| MAAGLARLLLLLGLSAGGPAPAGA | 1024 | 2161.64 | 2161.68 |
| MRPGTALQAVLLAVLLVGLRA | 1025 | 2162.72 | 2161.68 |
| MVLQTQVFISLLLWISGASG | 1026 | 2163.61 | 2161.68 |
| MRLGLLSVALLFVGSSHLYS | 1027 | 2163.61 | 2161.68 |
| MSSTLPALLCVGLCLSQRISA | 1028 | 2163.66 | 2161.68 |
| MAVAPLRGALLLWQLLAAGGAA | 1029 | 2163.66 | 2161.68 |
| MRGPGHPLLLGLLLVLGPSPE | 1030 | 2166.66 | 2167.09, 2167.78 |
| MEQIWLLLLLTIRVLPGSA | 1031 | 2166.7 | 2167.09, 2167.78 |
| MATVRASLRGALLLLLAVAGVA | 1032 | 2166.71 | 2167.09, 2167.78 |
| MPRVSAPLVLLPAWLVMVAC | 1033 | 2166.79 | 2167.09, 2167.78, 2168.75 |
| MGGRVFLAFCVWLTLPGAET | 1034 | 2168.61 | 2167.09, 2167.78, 2168.75 |
| MEFGLSWVFLVALLRGVQC | 1035 | 2168.66 | 2167.09, 2167.78, 2168.75 |
| MRVGGAFHLLLVCLSPALLSA | 1036 | 2168.7 | 2167.09, 2167.78, 2168.75 |
| MAQSRVLLLLLLPPQLHL | 1037 | 2168.76 | 2167.09, 2167.78, 2168.75 |
| MALRAPALLPLLLLLLPLRA | 1038 | 2168.85 | 2167.09, 2167.78, 2168.75 |
| MDPKGLLSLTFVLFLSLAFG | 1039 | 2169.66 | 2167.78, 2168.75 |
| MVWRLVLLALWVWPSTQA | 1040 | 2169.67 | 2167.78, 2168.75 |
| MDLLWMPLLLVAACVSAVHS | 1041 | 2169.71 | 2167.78, 2168.75 |
| MWGFLVLKARWLVTPVRT | 1042 | 2173.7 | 2173.75 |
| MEWPARLCGLWALLLCAGGGG | 1043 | 2174.65 | 2173.75 |
| MHGGQGPLLLLLLLAVCLGAQG | 1044 | 2174.71 | 2173.75 |
| MFAVVFFILSLMTCQPGVTA | 101 | 2175.71 | 2177.51, 2173.75 |
| MKYVFYLGVLAGTFFFADS | 102 | 2176.57 | 2177.51 |

TABLE 31

| Signal Peptide Amino acid sequence | SEQ ID No. | MW | m/z of the corresponding peak |
|---|---|---|---|
| MLLWTAVLLFVPCVGKTVW | 103 | 2176.76 | 2177.51 |
| MATLSFVFLLLGAVSWPPASA | 104 | 2178.63 | 2177.51, 2179.25 |
| MNNLSFSELCCLFCCPPCPG | 105 | 2178.65 | 2177.51, 2179.25 |

TABLE 31-continued

| Amino acid sequence | SEQ ID No. | MW | Signal Peptide m/z of the corresponding peak |
|---|---|---|---|
| MVATKTFALLLLSLFLAVGLG | 106 | 2178.75 | 2177.51, 2179.25 |
| MNSLVSWQLLLFLCATHFG | 107 | 2180.62 | 2179.25 |
| MKLLLLTLTVLLLLSQLTPG | 108 | 2180.81 | 2179.25 |
| MRSSLTMVGTLWAFLSLVTA | 109 | 2184.65 | 2184.93, 2185.65, 2186.28 |
| MASLVSLELGLLLAVLVVTATA | 110 | 2184.71 | 2184.93, 2185.65, 2186.28 |
| MKAFHTFCVVLLVFGSVSEA | 111 | 2185.64 | 2184.93, 2185.65, 2186.28 |
| MGGTLAWTLLLPLLLRESDS | 112 | 2186.6 | 2184.93, 2185.65, 2186.28 |
| MEFVRALWLGLALALGPGSAGG | 113 | 2186.61 | 2184.93, 2185.65, 2186.28 |
| MRTLFNLLWLALACSPVHT | 114 | 2186.68 | 2184.93, 2185.65, 2186.28 |
| MKILVAFLVVLTIFGIQSHG | 115 | 2186.74 | 2184.93, 2185.65, 2186.28 |
| MEPHLLGLLLGLLLGGTRVLA | 116 | 2186.74 | 2184.93, 2185.65, 2186.28 |
| MRRCRWAALALGLLRLCLA | 117 | 2186.79 | 2184.93, 2185.65, 2186.28 |
| MKFLIFAFFGGVHLLSLCSG | 118 | 2187.7 | 2186.28 |
| MMLLILFLVIICSHISVNQ | 119 | 2187.81 | 2186.28 |
| MTCSPLLLTLLIHCTGSWAQ | 1045 | 2188.67 | 2190.18 |
| MVFLKFFCMSFFCHLCQG | 1046 | 2188.76 | 2190.18 |
| MLMPLCGLLWWWCCCSG | 1047 | 2188.78 | 2190.18 |
| MARLLGLCAWARKSVRLASS | 1048 | 2189.68 | 2190.18, 2191.02 |
| MDWNWRILFLVVIAAGAQS | 1049 | 2190.6 | 2190.18, 2191.02 |
| MQGPLLLPGLCFLLSLFGAVT | 1050 | 2190.74 | 2190.18, 2191.02 |
| MEGKWLLCMLLVLGTAIVEA | 1051 | 2190.77 | 2190.18, 2191.02 |
| MGALARALLLPLLAQWLLRA | 1052 | 2190.77 | 2190.18, 2191.02 |
| MAGPWTFTLLCGLLAATLIQA | 1053 | 2191.69 | 2190.18, 2191.02, 2192.84 |
| MGFCLALAWTLLVGAWTPLGA | 1054 | 2191.69 | 2190.18, 2191.02, 2192.84 |
| MYRRKSGWTGCAITCSPCTA | 1055 | 2192.6 | 2191.02, 2192.84 |
| MPFSVSWGVLLLAGLCCLVPS | 1056 | 2192.74 | 2191.02, 2192.84 |
| MALLPVLFLVTVLLPSLPAEG | 1057 | 2193.76 | 2192.84 |
| MFQQFQASCLVLFFLVGFA | 1058 | 2196.67 | 2196.47 |
| MALAALMIALGSLGLHTWQAQ | 1059 | 2196.67 | 2196.47 |
| MAGAVSLLGVVGLLLVSALSGVLG | 1060 | 2196.73 | 2196.47 |
| MDTSRLGVLLSLPVLLQLATG | 1061 | 2197.67 | 2196.47 |
| MSPSGRLCLLTIVGLILPTRG | 1062 | 2197.74 | 2196.47 |
| MAAAAWLQVLPVILLLLGAHP | 1063 | 2197.76 | 2196.47 |
| MKRLPLLVVFSTLLNCSYT | 1064 | 2198.72 | 2199.82 |
| MRGVSCLQVLLLLVLGAAGTQG | 1065 | 2199.71 | 2199.82, 2201.22 |
| MGLLASAGLLLLLVIGHPRSLG | 1066 | 2201.75 | 2199.82, 2201.22 |
| MQRWTLWAAAFLTLHSAQA | 1067 | 2202.57 | 2201.22, 2204.02 |
| MAFRTICVLVGVFICSICVK | 1068 | 2202.85 | 2201.22, 2204.02 |

TABLE 31-continued

| Signal Peptide | | | m/z |
|---|---|---|---|
| Amino acid sequence | SEQ ID No. | MW | of the corresponding peak |
| MAFYSCCWVLLALTWHTSA | 1069 | 2203.64 | 2204.02 |
| MHLIDYLLLLLVGLLALSHG | 1070 | 2204.75 | 2204.02 |
| MGFPAAALLCALCCGLLAPAARA | 1071 | 2204.78 | 2204.02 |
| MKAWGTVVVTLATLMVVTVDA | 1072 | 2205.71 | 2204.02, 2207.1 |
| MLCLGWIFLWLVAGERIKG | 1073 | 2205.76 | 2204.02, 2207.1 |

TABLE 32

| Signal Peptide | | | m/z |
|---|---|---|---|
| Amino acid sequence | SEQ ID No. | MW | of the corresponding peak |
| MAQLFLPLLAALVLAQAPAALA | 1074 | 2206.77 | 2207.1 |
| MLLCTARLVGLQLLISCCWA | 1075 | 2207.82 | 2207.1 |
| MGAAARLSAPRALVLWAALGAAA | 1076 | 2208.66 | 2207.1 |
| MACRCLSFLLMGTFLSVSQT | 1077 | 2208.72 | 2207.1 |
| MNLVICVLLLSIWKNNCMT | 1078 | 2208.81 | 2207.1 |
| MMLQHLVIFCLGLVVQNFC | 1079 | 2208.81 | 2207.1 |
| MCPGALWVALPLLSLLAGSLQG | 120 | 2210.74 | 2211.58 |
| MLAEWGACLLLAVALLGPGLQA | 121 | 2210.74 | 2211.58 |
| MRGTRLALLALVLAACGELAPA | 122 | 2210.74 | 2211.58 |
| MMKRAAAAAVGGALAVGAVPVVLS | 123 | 2210.74 | 2211.58 |
| MEACVSSLLVLALGALSVGSSFG | 124 | 2211.63 | 2211.58 |
| MAVRALKLLTTLLAVVAAASQA | 125 | 2211.74 | 2211.58 |
| MPVPALCLLWALAMVTRPASA | 126 | 2211.79 | 2211.58 |
| MSNSVPLLCFWSLCYCFAAG | 127 | 2212.67 | 2211.58 |
| MAGGRCGPQLTALLAAWIAAVAA | 128 | 2212.67 | 2211.58 |
| MPGPLGLLCFLALGLLGSAGPSGA | 129 | 2212.71 | 2211.58 |
| MSACRSFAVAICILEISILTA | 130 | 2212.73 | 2211.58 |
| METLCLRASFWLALVGCVIS | 131 | 2212.73 | 2211.58 |
| MRLGLCVVALVLSWTHLTIS | 132 | 2212.75 | 2211.58 |
| MAPRTLWSCYLCCLLTAAAGA | 1080 | 2215.72 | 2216.77 |
| MAPPQVLAFGLLLAAATATFAAA | 1081 | 2216.68 | 2216.77, 2218.45 |
| MSPHPTALLGLVLCLAQTIHT | 1082 | 2216.7 | 2216.77, 2218.45 |
| MQLLGLLSILWMLKSSPGATG | 1083 | 2216.74 | 2216.77, 2218.45 |
| MGWRAAGALLLALLLHGRLLA | 1084 | 2216.77 | 2216.77, 2218.45 |
| MGWRAAGALLLALLLHGRLLA | 1085 | 2216.77 | 2216.77, 2218.45 |
| MGPGRCLLTALLLLALAPPPEA | 1086 | 2217.77 | 2216.77, 2218.45, 2219.3 |
| MAPHWAVWLLAARLWGLGIG | 1087 | 2218.7 | 2216.77, 2218.45, 2219.3, 2220.56 |
| MFRTAVMMAASLALTGAVVAHA | 1088 | 2219.73 | 2218.45, 2219.3, 2220.56 |
| MTPIVTVLICLGLSLGPRTHV | 1089 | 2220.77 | 2219.3, 2220.56, 2220.56, 2222.74 |

TABLE 32-continued

| Signal Peptide Amino acid sequence | SEQ ID No. | MW | m/z of the corresponding peak |
|---|---|---|---|
| MAPQTLLPVLVLCVLLLQAQG | 1090 | 2220.82 | 2219.3, 2220.56, 2222.74 |
| MRVPAQLLGLLLLWLPGARC | 1091 | 2220.82 | 2219.3, 2220.56, 2222.74 |
| MKALIFAAAGLLLLLPTFCQS | 1092 | 2221.8 | 2220.56, 2222.74 |
| MGRAGAAAVIPGLALLWAVGLGSA | 1093 | 2222.69 | 2222.74 |
| MLRLLRPLLLLLLLPPPGSP | 1094 | 2222.9 | 2222.74 |
| MASVFHYFLLVLVFLDTHA | 1095 | 2223.67 | 2222.74 |
| MHFQAFWLCLGLLFISINA | 1096 | 2224.72 | 2222.74 |
| MPLPWSLALPLLLSWVAGGFG | 133 | 2225.73 | 2226.96 |
| MWPSQLLIFMMLLAPIIHA | 134 | 2225.86 | 2226.96 |
| MGPSTPLLILFLLSWSGPLQG | 135 | 2227.7 | 2226.96, 2228.22 |
| MNSLSWGAANAVLLLLLAWA | 136 | 2227.7 | 2226.96, 2228.22 |
| MALGTTLRASLLLLGLLTEGLA | 137 | 2227.74 | 2226.96, 2228.22 |
| MMRTCVLLSAVLWCLTGVQC | 138 | 2227.84 | 2226.96, 2228.22 |
| MIRKLFIVLLLLLVTIEEA | 139 | 2227.87 | 2226.96, 2228.22 |
| MHLLGPWLLLLVLEYLAFS | 140 | 2228.77 | 2226.96, 2228.22 |
| MGLGRVLLFLAVAFPFAPPAAA | 1097 | 2229.76 | 2228.22, 2231.6 |
| MRLIRNIYIFCSIVMTAEG | 1098 | 2230.75 | 2231.6 |

TABLE 33

| Signal Peptide Amino acid sequence | SEQ ID No. | MW | m/z of the corresponding peak |
|---|---|---|---|
| MTLGSPRKGLLMLLMALVTQG | 1099 | 2230.83 | 2231.6 |
| MAGAPGPLRLALLLLGMVGRAGP | 1100 | 2231.8 | 2231.6 |
| MGPAPLPLLLGLFLPALWRR | 1101 | 2231.83 | 2231.6 |
| MSPHLTALLGLVLCLAQTIHT | 1102 | 2232.74 | 2231.6 |
| MAQALPWLLLWMGAGVLPAHG | 1103 | 2232.75 | 2231.6 |
| MGKPWLRALQLLLLLGASWA | 1104 | 2237.79 | 2239.71 |
| MVAGTRCLLALLLPQVLLGGAAG | 1105 | 2237.81 | 2239.71 |
| MNILMLTFIICGLLTRVTKG | 1106 | 2237.87 | 2239.71 |
| MRRLLLVTSLVVVLLWEAGA | 1107 | 2239.8 | 2239.71 |
| MAPSAWAICWLLGGLLLHGGSS | 1108 | 2240.68 | 2239.71 |
| MVTRAGAGTAVAGAVVVALLSAALA | 1109 | 2240.7 | 2239.71 |
| MTARAWASWRSSALLLLLVP | 1110 | 2242.72 | 2244.01 |
| MAAHLLPICALFLTLLDMAQG | 1111 | 2242.8 | 2244.01 |
| MPPAAPARLALALGLGLWLGALA | 1112 | 2243.79 | 2244.01 |
| MALHIHEACILLLVIPGLVTS | 1113 | 2243.81 | 2244.01 |
| MQAPRAALVFALVIALVPVGRG | 1114 | 2249.8 | 2251.78 |

TABLE 33-continued

| Signal Peptide Amino acid sequence | SEQ ID No. | MW | m/z of the corresponding peak |
|---|---|---|---|
| MNLCLSALLFFLVILLPSGKG | 1115 | 2249.86 | 2251.78 |
| MPALWLGCCLCFSLLLPAARA | 1116 | 2249.86 | 2251.78 |
| MKPGGFWLHLTLLGASLPAALG | 1117 | 2250.74 | 2251.78 |
| MAAMASLGALALLLLSSLSRCSA | 1118 | 2250.78 | 2251.78 |
| MLSGVWFLSVLTVAGILQTES | 1119 | 2251.67 | 2251.78 |
| MGLRPGIFLLELLLLLGQGTP | 1120 | 2251.81 | 2251.78 |
| MLAPLFLCCLRNLFRKLIS | 1121 | 2251.9 | 2251.78 |
| MFESFNVPGLYIAVQAVLALA | 141 | 2253.69 | 2251.78, 2254.83 |
| MQPVMLALWSLLLLWGLATP | 142 | 2253.85 | 2254.83 |
| MPLKHYLLLLVGCQAWGAGLA | 143 | 2254.79 | 2254.83, 2256.53 |
| MAGVRARAPLPLALLLSLPAAPG | 144 | 2255.8 | 2254.83, 2256.53 |
| MLLPQLCWLPLLAGLLPPVPA | 145 | 2255.91 | 2254.83, 2256.53 |
| MQIPRAALLPLLLLLAAPASA | 1122 | 2256.87 | 2256.53 |
| MRLLCGLWLWLSLLKVLQA | 1123 | 2256.9 | 2256.53 |
| MSLTVVSMACVGFFLLQGAWP | 1124 | 2257.77 | 2256.53 |
| MKLLFPIFASLMLQYQVNT | 1125 | 2257.79 | 2256.53 |
| MVPSAGQLALFALGIVLAACQAL | 1126 | 2257.79 | 2256.53 |
| MLRLGLCAAALLCVCRPGAVRA | 1127 | 2257.89 | 2256.53 |
| MVFSLKVILFLSLLLSPVLK | 1128 | 2260.94 | 2261.91 |
| MLMLMLVAAVTMWLRPLVTA | 1129 | 2260.97 | 2261.91 |
| MTSQRSPLAPLLLLSLHGVAAS | 1130 | 2262.7 | 2261.91 |
| MAARGSGPRALRLLLLVQLVAG | 1131 | 2262.8 | 2261.91 |
| MLGARAWLGRVLLLPRAGAGLA | 1132 | 2262.8 | 2261.91 |
| MRLLILALLGICSLTAYIVEG | 1133 | 2262.85 | 2261.91 |
| MRLLALAAAALLARAPAPEVCAA | 1134 | 2263.8 | 2261.91 |
| MNIILEILLLLITIIYSYL | 1135 | 2264.88 | 2266.45 |
| MAAAPLLLLLLVPVPLLPLLA | 1136 | 2265.02 | 2266.45 |
| MLSHGAGLALWITLSLLQTGLA | 1137 | 2266.74 | 2266.45, 2268.58 |
| MELAALCRWGLLLALLPPGAAS | 1138 | 2266.8 | 2266.45, 2268.58 |
| MPLSSHLLPALVLFLAGSSGWA | 1139 | 2267.72 | 2266.45, 2268.58 |

TABLE 34

| Signal Peptide Amino acid sequence | SEQ ID No. | MW | m/z of the corresponding peak |
|---|---|---|---|
| MALAALMIALGSLGLHTWQAQA | 1140 | 2267.75 | 2266.45, 2268.58 |
| MPRGFTWLRYLGIFLGVALG | 1141 | 2267.77 | 2266.45, 2268.58 |
| MSLASGPGPGWLLFSFGMGLVSG | 1142 | 2268.69 | 2268.58 |
| MKMHLQRALVVLALLNFATV | 1143 | 2268.87 | 2268.58 |

TABLE 34-continued

| Signal Peptide Amino acid sequence | SEQ ID No. | MW | m/z of the corresponding peak |
|---|---|---|---|
| MRIFAVFIFMTYWHLLNA | 1144 | 2273.8 | 2274.97 |
| MHVHVCVCLCVCIYTSSCVCA | 1145 | 2273.87 | 2274.97 |
| MLVNFILRCGLLLVTLSLAIA | 1146 | 2273.92 | 2274.97 |
| MVPAAGALLWVLLLNLGPRAAGA | 1147 | 2274.8 | 2274.97, 2276.04 |
| MKLVTIFLLVTISLCSYSATA | 1148 | 2274.82 | 2274.97, 2276.04 |
| MRLSLPLLLLLLGAWAIPGGLG | 1149 | 2274.89 | 2274.97, 2276.04 |
| MALMFTGHLLFLALLMFAFS | 1150 | 2274.89 | 2274.97, 2276.04 |
| MRTLWMALCALSRLWPGAQA | 1151 | 2275.8 | 2274.97, 2276.04 |
| MKALRLSASALFCLLLINGLGA | 1152 | 2275.85 | 2274.97, 2276.04 |
| MSLFGLLLLTSALAGQRQGTQA | 146 | 2276.69 | 2274.97, 2276.04, 2278.67 |
| MSGAPTAGAALMLCAATAVLLSAQG | 147 | 2276.73 | 2274.97, 2276.04, 2278.67 |
| MGLQFSQVISICWAAMGSLYA | 148 | 2276.73 | 2274.97, 2276.04, 2278.67 |
| MPGAAEALPTVTVTLVAGAVPPASG | 149 | 2277.67 | 2276.04, 2278.67 |
| MRPRKAFLLLLLLGLVQLLA | 150 | 2278.97 | 2278.67 |
| MARSATLAAAALALCLLLAPPGLA | 151 | 2279.84 | 2278.67, 2281.09 |
| MESLLLPVLLLLAILWTQAAA | 152 | 2279.86 | 2278.67, 2281.09 |
| MEGAPPGSLALRLLLFVALPASG | 1153 | 2280.76 | 2281.09 |
| MSSFGYRTLTVALFTLICCPG | 1154 | 2280.76 | 2281.09 |
| MPPFLITLFLFHSCCLRANG | 1155 | 2280.81 | 2281.09 |
| MVTSSFPISVAVFALITLQVGT | 1156 | 2281.74 | 2281.09 |
| MDHCGALFLCLCLLTLQNATT | 1157 | 2281.77 | 2281.09 |
| MLPWTALGLALSLRLALARSGA | 1158 | 2281.8 | 2281.09 |
| MKVLPASGLAVFLIMALTFSTA | 1159 | 2281.85 | 2281.09 |
| MRALLALCLLLGWLRWGPAGA | 1160 | 2281.87 | 2281.09 |
| MMAAGAALALALWLLMPPVEVGG | 1161 | 2282.87 | 2281.09 |
| MSALRPLLLLLLPLCPGPGPGPG | 1162 | 2282.89 | 2281.09 |
| MALLTNLLPLCCLALLALPAQS | 1163 | 2282.91 | 2281.09 |
| MQFQLTLFLHLGWLSYSKA | 1164 | 2283.72 | 2285.01 |
| MVGTKAWVFSFLVLEVTSVLG | 1165 | 2283.76 | 2285.01 |
| MRMCTPIRGLLMALAVMFGTA | 1166 | 2283.95 | 2285.01 |
| MGRARRFQWPLLLLWAAAAG | 1167 | 2284.77 | 2285.01 |
| MTNKCLLQIALLLCFSTTALS | 1168 | 2284.84 | 2285.01 |
| MSLLLPPLALLLLLAALVAPATA | 1169 | 2285.95 | 2285.01 |
| MKYSCCALVLAVLGTELLGSLC | 1170 | 2287.86 | 2289.43 |
| MIISHFPKCVAVFALLALSVGA | 1171 | 2287.86 | 2289.43 |
| MSLMVVSMACVGFFLLQGAWP | 1172 | 2287.87 | 2289.43 |
| MSLMVVSMACVGFFLLQGAWP | 1173 | 2287.87 | 2289.43 |
| MSLMVVSMACVGFFLLQGAWP | 1174 | 2287.87 | 2289.43 |

TABLE 34-continued

| Signal Peptide | | | m/z |
|---|---|---|---|
| Amino acid sequence | SEQ ID No. | MW | of the corresponding peak |
| MRRLPRALLLQLRLALLVAA | 1175 | 2287.94 | 2289.43 |
| MDTRNKAQLLVLLTLLSVLF | 1176 | 2288.83 | 2289.43 |
| MGAMAYPLLLCLLLAQLGLGAVG | 153 | 2288.91 | 2289.43, 2290.85 |
| MGPPLPLLLLLLLLLPPRVLP | 154 | 2289.04 | 2289.43, 2290.85 |

TABLE 35

| Signal Peptide | | | m/z |
|---|---|---|---|
| Amino acid sequence | SEQ ID No. | MW | of the corresponding peak |
| MSGNWVHPGQILIWAIWVLA | 155 | 2291.75 | 2290.85, 2292.35 |
| MRRWAWAAVVVLLGPQLVLL | 156 | 2291.88 | 2290.85, 2292.35 |
| MRLPDVOLWLVLLWALVRA | 157 | 2292.87 | 2292.35 |
| MRCALALSALLLLLSTPPLLPS | 158 | 2293.91 | 2292.35 |
| MAGQRVLLLVGFLLPGVLLSEA | 1177 | 2296.85 | 2295.92, 2296.92 |
| MVSWGRFICLVVVTMATLSLA | 1178 | 2297.88 | 2295.92, 2296.92 |
| MSSGDPAHLGLCLWLWLGATLG | 1179 | 2298.72 | 2296.92 |
| MKIPVLPAVVLLSLLVLHSAQG | 1180 | 2298.91 | 2296.92 |
| MFLATLSFLLPFAHPFGTVSC | 1181 | 2299.79 | 2301.71 |
| MQLLGLLGLLWMLKASPWATG | 1182 | 2299.88 | 2301.71 |
| MDWPHNLLFLLTISIFLGLG | 1183 | 2300.8 | 2301.71, 2302.5 |
| MTARGLALGLLLLLLCPAQVFS | 1184 | 2300.9 | 2301.71, 2302.5 |
| MNCVCRLVLVVLSLWPDTAVA | 1185 | 2302.86 | 2301.71, 2302.5, 2303.21 |
| MSRSATLLLCLLGCHVWKAVT | 1186 | 2302.86 | 2301.71, 2302.5, 2303.21 |
| MATWALLLLAAMLLGNPGLVFS | 1187 | 2302.88 | 2301.71, 2302.5, 2303.21 |
| MPSWIGAVILPLLGLLLSLPAGA | 1188 | 2302.9 | 2301.71, 2302.5, 2303.21 |
| MAGRGGSALLALCGALAACGWLLGA | 1189 | 2303.81 | 2302.5, 2303.21, 2305.43 |
| MWTALVLIWIFSLSLSESHA | 1190 | 2304.74 | 2303.21, 2305.43 |
| MFKCWSVVLVLGFIFLESEG | 1191 | 2304.8 | 2303.21, 2305.43 |
| MMWRPSVLLLLLLLRHGAQG | 1192 | 2304.9 | 2303.21, 2305.43 |
| MLMPVHFLLLLLLLLGGPRTG | 1193 | 2304.98 | 2303.21, 2305.43 |
| MSLMVISMACVGFFLLQGAWT | 1194 | 2305.88 | 2305.43, 2307.22 |
| MSLMVISMACVGFFLLQGAWT | 1195 | 2305.88 | 2305.43, 2307.22 |
| MSLMVISMACVGFFLLQGAWT | 1196 | 2305.88 | 2305.43, 2307.22 |
| MGWLTRIVCLFWGVLLTARA | 1197 | 2306.87 | 2305.43, 2307.22 |
| MAREMTILGSAVLTLLLAGYLA | 1198 | 2307.85 | 2307.22 |
| MSAAWIPALGLGVCLLLLPGPAGS | 1199 | 2307.85 | 2307.22 |
| MAAATASPRSLLVLLQVVVLALA | 1200 | 2307.87 | 2307.22 |
| MAPGMSGRGGAALLCLSALLAHASG | 1201 | 2312.77 | 2314.24 |

TABLE 35-continued

| Signal Peptide Amino acid sequence | SEQ ID No. | MW | m/z of the corresponding peak |
|---|---|---|---|
| MGRRDAQLLAALLVLGLCALAGS | 1202 | 2312.83 | 2314.24, 2314.81 |
| MKAQTALSFFLILITSLSGSQG | 1203 | 2313.75 | 2314.24, 2314.81 |
| MSRRSMLLAWALPSLLRLGAA | 1204 | 2313.87 | 2314.24, 2314.81 |
| MRLRFWLLIWLLLGFISH | 1205 | 2314.92 | 2314.24, 2314.81 |
| MRLRFWLLIWLLLGFISH | 1206 | 2314.92 | 2314.24, 2314.81 |
| MDTKLMCLLFFFSLPPLLVS | 1207 | 2315.94 | 2314.24, 2314.81, 2317.68 |
| MALWRGSAYAGFLALAVGCVFL | 1208 | 2316.82 | 2317.68 |
| MKFLLLVLAALGFLTQVIPASA | 1209 | 2316.92 | 2317.68 |
| MVGAMWKVIVSLVLLMPGPCDG | 1210 | 2316.95 | 2317.68 |
| MPPPRLLFFLLFLTPMEVR | 1211 | 2317.94 | 2317.68 |
| MAGVGAAALSLLLHLGALALAAGAEG | 1212 | 2318.77 | 2317.68 |
| MKLTFFLGLLALISCFTPSES | 1213 | 2318.83 | 2317.68 |
| MKVFKFIGLMILLTSAFSAGSG | 1214 | 2318.88 | 2317.68 |
| MQPLWLCWALWVLPLASPGAA | 1215 | 2323.86 | 2325.3 |
| MRRAPSLVLFFLVALCGRGNC | 1216 | 2323.88 | 2325.3 |
| MALPYHIFLFTVLLPSFTLT | 1217 | 2324.86 | 2325.3 |
| MASMAAVLTWALALLSAFSATQA | 1218 | 2325.78 | 2325.3, 2327.73 |

TABLE 36

| Signal Peptide Amino acid sequence | SEQ ID No. | MW | m/z of the corresponding peak |
|---|---|---|---|
| VMAPRTLVLLLSGALALTQTWA | 1219 | 2325.85 | 2325.3, 2327.73 |
| MSSNTMLQKTLLILISFSVVT | 1220 | 2326.85 | 2325.3, 2327.73 |
| MGRRALLLLLLSFLAPWATIA | 1221 | 2326.92 | 2325.3, 2327.73 |
| MTTSPILQLLLRLSLCGLLLQ | 1222 | 2326.94 | 2325.3, 2327.73 |
| MWSHLNRLLFWSIFSSVTC | 1223 | 2327.76 | 2327.73 |
| MKHLWFFLLLVAAPRWVLS | 1224 | 2327.91 | 2327.73 |
| MKHLWFFLLLVAAPRWVLS | 1225 | 2327.91 | 2327.73 |
| MKHLWFFLLLVAAPRWVLS | 1226 | 2327.91 | 2327.73 |
| MPLWVFFFVILTLSNSSHCS | 1227 | 2328.79 | 2327.73 |
| MVGQRVLLLVAFLLSGVLLSEA | 1228 | 2328.89 | 2327.73 |
| MVLLHWCLLWLLFPLSSRT | 1229 | 2328.92 | 2327.73 |
| MTDKSIVILSLMVFHSSFING | 1230 | 2339.81 | 2341.14 |
| MPFRLLIPLGLLCALLPQHHG | 1231 | 2339.95 | 2341.14 |
| MSLMVVSMARVGFFLLQGAWP | 1232 | 2340.91 | 2341.14, 2342.87 |
| MVHVARLLLLLTFFLRTDA | 1233 | 2342.92 | 2341.14, 2342.87, 2344.45 |
| MDSWTFCCVSLCILVAKHTDA | 1234 | 2343.8 | 2342.87, 2344.45 |
| MAGASRLLFLWLGCFCVSLAQG | 1235 | 2343.87 | 2342.87, 2344.45 |

TABLE 36-continued

| Signal Peptide Amino acid sequence | SEQ ID No. | MW | m/z of the corresponding peak |
|---|---|---|---|
| MEASRWWLLVTVLMAGAHCVA | 1236 | 2344.86 | 2342.87, 2344.45 |
| MDPKQTTLLCLVLCLGQRIQA | 1237 | 2344.9 | 2344.45 |
| MPGVARLPLLLGLLLLPRPGRP | 1238 | 2350.01 | 2351.97 |
| MRTYRYFLLLFWVGQPYP | 1239 | 2350.82 | 2351.97 |
| MSRPGTATPALALVLLAVTLAGVGA | 1240 | 2350.85 | 2351.97 |
| MRVALGMLWLLALAWPPQARG | 1241 | 2350.93 | 2351.97 |
| MGSSSFLVLMVSLVLVTLVAVEG | 1242 | 2351.9 | 2351.97 |
| MGFLSPIYVIFFFFGVKVHC | 1243 | 2351.91 | 2351.97 |
| MWPLWLCWALWVLPLAGPGAA | 1244 | 2351.91 | 2351.97 |
| MVRIWTTIMIVLILLLRIGP | 1245 | 2352.08 | 2351.97, 2353.99 |
| MGPVRLGILLFLFLAVHEAWA | 1246 | 2353.91 | 2351.97, 2353.99, 2355.29 |
| MKLWVSALLMAWFGVLSCVQA | 1247 | 2353.95 | 2351.97, 2353.99, 2355.29 |
| MRVFLLCAYILLLMVSQLRA | 1248 | 2354.04 | 2353.99, 2355.29 |
| MSAPRLLISIIIMVSASSSSCMG | 1249 | 2354.91 | 2353.99, 2355.29 |
| MLRYLLKTLLQMNLFADSLA | 1250 | 2354.91 | 2353.99, 2355.29 |
| MGRRRLLVWLCAVAALLSGAQA | 1251 | 2355.91 | 2353.99, 2355.29, 2357.54 |
| MKPPLLVFIVCLLWLKDSHC | 1252 | 2356.01 | 2355.29, 2357.54 |
| MRPAALRGALLGCLCLALLCLGGA | 1253 | 2357.02 | 2355.29, 2357.54 |
| MDLLQFLAFLFVLLLSGMGATG | 1254 | 2357.91 | 2357.54 |
| MVFAFWKVFLILSCLAGQVSV | 1255 | 2358.94 | 2357.54 |
| MGGMKYIFSLLFFLLLEGGKT | 1256 | 2365.93 | 2367.75 |
| MELGCWTQLGLTFLQLLLISS | 1257 | 2366.87 | 2367.75 |
| MKIAVLFCFFLLIIFQTDFG | 1258 | 2366.96 | 2367.75 |
| MILIPRMLLVLFLLLPILSSA | 1259 | 2367.13 | 2367.75 |
| MGAPLAVALGALHYLALFLQLGGA | 1260 | 2367.89 | 2367.75 |
| MKTLPLFVCICALSACFSFSEG | 1261 | 2367.91 | 2367.75 |
| MRLWSWVLHLGLLSAALGCGLA | 1262 | 2367.91 | 2367.75 |
| MSAPSLRARAAGLGLLLCAVLGRA | 1263 | 2367.92 | 2367.75 |
| MGIRGMLRAAVILLLIRTWLA | 1264 | 2368.04 | 2367.75 |

TABLE 37

| Signal Peptide Amino acid sequence | SEQ ID No. | MW | m/z of the corresponding peak |
|---|---|---|---|
| MAGWPGAGPLCVLGGAALGVCLAGVAG | 1265 | 2368.88 | 2367.75 |
| MAEAGLRGWLLWALLLRLAQS | 1266 | 2368.88 | 2367.75 |
| MALVRALVCCLLTAWHCRSGLG | 1267 | 2373.97 | 2375.59 |
| MCSRVPLLLPLLLLLALGPGVQG | 1268 | 2374.04 | 2375.59 |

TABLE 37-continued

| Signal Peptide Amino acid sequence | SEQ ID No. | MW | m/z of the corresponding peak |
|---|---|---|---|
| MAAEWASRFWLWATLLIPAAA | 1269 | 2375.82 | 2375.59 |
| MQIPQAPWPVVWAVLQLGWR | 1270 | 2375.87 | 2375.59 |
| MTLTLSVLICLGLSVGPRTCVQA | 1271 | 2375.95 | 2375.59 |
| MWKVSALLFVLGSASLWVLAEG | 1272 | 2377.88 | 2378.35 |
| MMCLKILRISLAILAGWALCSA | 1273 | 2378.08 | 2378.35 |
| MPGIKRILTVTILALCLPSPGNA | 1274 | 2378.98 | 2378.35, 2380.39 |
| MGAPFVWALGLLMLQMLLFVAG | 1275 | 2379.04 | 2378.35, 2380.39 |
| MDPECAQLLPALCAVLVDPRQP | 1276 | 2379.85 | 2378.35, 2380.39 |
| MTNVYSLDGILVFGLLFVCTCA | 1277 | 2379.89 | 2378.35, 2380.39 |
| MSRQLLPVLLLLLLRASCPWG | 1278 | 2380.01 | 2378.35, 2380.39 |
| MRPHLSPPLQQLLLPVLLACAA | 1279 | 2381.98 | 2380.39 |
| MMCPLWRLLIFLGLLALPLAP | 1280 | 2382.13 | 2380.39 |
| MLLTLIILLPVVSKFSFVSLSA | 1281 | 2392.03 | 2393.64 |
| MLSKVLPVLLGILLILQSRVEG | 1282 | 2392.03 | 2393.64 |
| MRGSGPRGAGRRRPPSGGGDTPIT | 1283 | 2393.68 | 2393.64 |
| MELQAARACFALLWGCALAAAAAA | 1284 | 2393.89 | 2393.64 |
| MGPSSCLLLILIPLLQLINPGST | 1285 | 2393.98 | 2393.64 |
| MVFLVACALHIALDLLPRLER | 1286 | 2393.99 | 2393.64 |
| MGFHFCIWIIFLLPPPCKKC | 1287 | 2394.08 | 2393.64 |
| MGAARLLPNLTLCLQLLILCCQ | 1288 | 2401.07 | 2402.11 |
| MRHGVAWALLVAAALGLGARGVRG | 1289 | 2402.9 | 2402.11, 2404.01 |
| MLTRLVLSAHLSSTTSPPWTHA | 1290 | 2406.79 | 2406.49 |
| MGRHLALLLLLLLFQHFGDS | 1291 | 2407.95 | 2406.49 |
| MGSSRLAALLLPLLLIVIDLSDS | 1292 | 2410.95 | 2412.79 |
| MEHKEVVLLLLLFLKSAPTET | 1293 | 2411.93 | 2412.79 |
| MRRPAAVPLLLLLCFGSQRAKA | 1294 | 2412.01 | 2412.79 |
| MLHVEMLTLVFLVLWMCVFS | 1295 | 2412.09 | 2412.79 |
| MASCLALRMALLLVSGVLAPAVLT | 1296 | 2414.09 | 2412.79, 2414.25, 2415.2 |
| MRVTLATIAWMVSFVSNYSHT | 1297 | 2414.84 | 2414.25, 2415.2, 2416.3 |
| METQELRGALALLLLCFFTSAS | 1298 | 2414.88 | 2414.25, 2415.2, 2416.3 |
| MKMKSQATMICCLVFFLSTEC | 1299 | 2415.05 | 2414.25, 2415.2, 2416.3 |
| MDWTWRVFCLLAVAPGVHSQV | 1300 | 2415.87 | 2414.25, 2415.2, 2416.3 |
| MARRGPGWRPLLLLVLLAGAAQG | 1301 | 2416.97 | 2415.2, 2416.3 |
| MRAARAAPLLQLLLLLGPWLEA | 1302 | 2417.01 | 2415.2, 2416.3 |
| MARHLLLPLVMLVISPIPGAFQ | 1303 | 2417.07 | 2415.2, 2416.3 |
| MMRAVWEALAALAAVACLVGAVRG | 1304 | 2430.01 | 2431.13 |
| MEPAVSLAVCALLFLLWVRLKG | 1305 | 2430.07 | 2431.13 |
| MNLRLCVQALLLLWLSLTAVCG | 1306 | 2431.07 | 2431.13 |

TABLE 37-continued

| Signal Peptide | | | m/z |
|---|---|---|---|
| Amino acid sequence | SEQ ID No. | MW | of the corresponding peak |
| MPGPWLLLALALTLNLTGVPGGRA | 1307 | 2431.97 | 2431.13 |
| MAGGSATTWGYPVALLLLVATLGLG | 1308 | 2432.91 | 2431.13, 2434.36 |
| MECLYYFLGFLLLAARLPLDA | 1309 | 2432.98 | 2431.13, 2434.36 |
| MKMRFLGLVVCLVLWTLHSEG | 1310 | 2433.05 | 2431.13, 2434.36 |

TABLE 38

| Signal Peptide | | | m/z |
|---|---|---|---|
| Amino acid sequence | SEQ ID No. | MW | of the corresponding peak |
| MKGRGMLVLLLHAVVLGLPSAWA | 1311 | 2433.07 | 2431.13, 2434.36 |
| MTPILTVLICLGLSLGPRTHVQA | 1312 | 2434.01 | 2434.36 |
| MTPILTVLICLGLSLGPRTHVQA | 1313 | 2434.01 | 2434.36 |
| MKDMPLRIHVLLGLAITTLVQA | 1314 | 2434.05 | 2434.36 |
| MTCWLCVLSLPLLLLPAAPPPAGG | 1315 | 2434.08 | 2434.36 |
| MLRAGWLRGAAALALLLAARVVAA | 1316 | 2435.03 | 2434.36 |
| MKENYCLQAALVCLGMLCHSHA | 1317 | 2435.97 | 2434.36 |
| MGAAAVRWHLCVLLALGTRGRLA | 1318 | 2436 | 2434.36 |
| MPYFTRLILFLFCLMVLVES | 1319 | 2436.09 | 2434.36 |
| MPRCRWLSLILLTIPLALVAR | 1320 | 2436.12 | 2434.36 |
| MLRDVRGRRRAGAALVGVLVAEA | 1321 | 2436.92 | 2438.19 |
| MRPRSALPRLLLPLLLLPAAGPA | 1322 | 2437.08 | 2438.19 |
| MAGAWLRWGLLLWAGLLASSAHG | 1323 | 2437.9 | 2438.19, 2439.22 |
| MASYLYGVLFAVGLCAPIYCVSP | 1324 | 2437.98 | 2438.19, 2439.22 |
| MPLLPSTVGLAGLLFWAGQAVNAL | 1325 | 2439.95 | 2438.19, 2439.22 |
| VLHCTKSCTCHKQCTYFKFY | 1326 | 2440.92 | 2439.22 |
| MLPAATASLLGPLLTACALLPFAQG | 1327 | 2441 | 2439.22 |
| MMGLFPRTTGALAIFVVVILVHG | 1328 | 2443.06 | 2444.37 |
| MWSWKCLLFWAVLVTATLCTA | 1329 | 2444.03 | 2444.37 |
| MPRWLLLSLTFAGLFPLRRR | 1330 | 2444.04 | 2444.37 |
| MAKFGVHRILLLAISLTKCLES | 1331 | 2444.05 | 2444.37 |
| MFSHLPFDCVLLLLLLLTRS | 1332 | 2445.08 | 2444.37 |
| MDLPRGLVVAWALSLWPGFTDT | 1333 | 2445.87 | 2444.37 |
| MKSPRRTTLCLMFIVIYSSKA | 1334 | 2446.05 | 2444.37 |
| MMPAQYALTSSLVLLVLLSTARA | 1335 | 2450.01 | 2451.9 |
| MVSAAAPSLLILLLLLLGSVPATDA | 1336 | 2450.02 | 2451.9 |
| MRSRLPPALAALGAALLLSSIEAE | 1337 | 2450.93 | 2451.9 |
| MEQRPRGCAAVAAALLLVLLGARA | 1338 | 2451 | 2451.9 |
| MSRLSRSLLWAATCLGVLCVLSA | 1339 | 2451.02 | 2451.9 |
| MVCSAAPLLLLATTLPLLGSPVAQA | 1340 | 2451.04 | 2451.9 |

TABLE 38-continued

| Signal Peptide Amino acid sequence | SEQ ID No. | MW | m/z of the corresponding peak |
|---|---|---|---|
| MILNWKLLGILVLCLHTRGISG | 1341 | 2451.09 | 2451.9 |
| MAPYPCGCHILLLLFCCLAAARA | 1342 | 2451.11 | 2451.9 |
| MIIMVIIFLVLLFWENEVND | 1343 | 2452.02 | 2451.9, 2453.96 |
| MKLHSLISVLLLFVTLIPKGKT | 1344 | 2452.13 | 2451.9, 2453.96 |
| MIMFPLFGKISLGILIFVLIEG | 1345 | 2452.15 | 2451.9, 2453.96 |
| MTPILTVLICLGLSLGPRTRVQA | 1346 | 2453.06 | 2451.9, 2453.96 |
| MPSPPGLRALWLCAALCASRRAGG | 1347 | 2454.98 | 2453.96, 2455.44, 2456.62 |
| MNLWLLACLVAGFLGAWAPAVHT | 1348 | 2454.99 | 2453.96, 2455.44, 2456.62 |
| MRTQSLLLLGALLAVGSQLPAVFG | 1349 | 2455.99 | 2455.44, 2456.62 |
| MGRRMRGAAATAGLWLLALGSLLA | 1350 | 2457.01 | 2455.44, 2456.62 |
| MPRATALGALVSLLLLLPLPRGAGG | 1351 | 2458.06 | 2456.62, 2459.43 |
| MVARVGLLLRALQLLLWGHLDA | 1352 | 2459.05 | 2459.43 |
| MDPQCTMGLSNILFVMAFLLSGA | 1353 | 2460 | 2459.43 |
| MAETLFWTPLLVVLLAGLGDTEA | 1354 | 2460.92 | 2459.43, 2462.31 |
| MGPWSRSLSALLLLLQVSSWLC | 1355 | 2460.99 | 2459.43, 2462.31 |
| MAHVRGLQLPGCLALAALCSLVHS | 1356 | 2461.02 | 2459.43, 2462.31 |

TABLE 39

| Signal Peptide Amino acid sequence | SEQ ID No. | MW | m/z of the corresponding peak |
|---|---|---|---|
| MKLCSLAVLVPIVLFCEQHVFA | 1357 | 2461.1 | 2459.43, 2462.31 |
| MAAALWGFFPVLLLLLSGDVQS | 1358 | 2462 | 2462.31 |
| MILQAHLHSLCLLMLYLATGYG | 1359 | 2462.05 | 2462.31 |
| MQAACWYVLFLLQPTVYLVTC | 1360 | 2463.03 | 2462.31, 2464.16 |
| MLGMNMLLITLFLLLPLSMLKG | 1361 | 2463.26 | 2462.31, 2464.16 |
| MILANVFCLFFFLDETLRSLA | 1362 | 2463.99 | 2462.31, 2464.16 |
| MAAVRGAPLLSCLLALLALCPGGRP | 1363 | 2464.11 | 2462.31, 2464.16 |
| MAGTVRTACLVVAMLLSLDFPGQA | 1364 | 2465 | 2464.16 |
| MDLIRGVLLRLLLLASSLGPGAVS | 1365 | 2465.05 | 2464.16 |
| METGALRRPQLLPLLLLLCGGCP | 1366 | 2465.09 | 2464.16 |
| MESWWGLPCLAFLCFLMHARG | 1367 | 2469.02 | 2470.97 |
| MGRVGYWTLLVLPALLVWRGPA | 1368 | 2469.04 | 2470.97 |
| MLRKGCCVELLLLLVAAELPLGGG | 1369 | 2469.12 | 2470.97 |
| MKGSRALLLVALTLFCICRMATG | 1370 | 2469.15 | 2470.97 |
| MQGLLFSTLLLAGLAQFCCRVQG | 1371 | 2470.02 | 2470.97 |
| MPGRTWELCLLLLLGLGLGSQEA | 1372 | 2470.99 | 2470.97 |
| MASDLIRTILVVALISKLGTAVDA | 1373 | 2471 | 2470.97 |

TABLE 39-continued

| Signal Peptide Amino acid sequence | SEQ ID No. | MW | m/z of the corresponding peak |
|---|---|---|---|
| MWCASPVAVVAFCAGLLVSHPVLT | 1374 | 2472.04 | 2470.97 |
| MLINKLWLLLVTLCLTEELAAA | 1375 | 2472.1 | 2470.97 |
| MRGAARLGRPGRSCLPGPALRAAAA | 1376 | 2476.97 | 2478.17 |
| MERIVICLMVIFLGTLVHKSSS | 1377 | 2477.1 | 2478.17 |
| MSPLWWGFLLSCLGCKILPGAQG | 1378 | 2478.05 | 2478.17, 2479.28 |
| MRPPGFRNFLLLASSLLFAGLSA | 1379 | 2478.99 | 2478.17, 2479.28 |
| MSPPLLKLGAVLSTMAMISNWMS | 1380 | 2479.09 | 2478.17, 2479.28 |
| MRLRPLPLVWPGLLQLLFCDS | 1381 | 2480.13 | 2478.17, 2479.28 |
| MVSVPTTWCSVALALLVALHEGKG | 1382 | 2483 | 2484.18 |
| MDRRMWGAHVFCVLSPLPTVLG | 1383 | 2486.03 | 2484.18 |
| MNKHFLFLFLLYCLIVAVTSL | 1384 | 2486.13 | 2484.18 |
| MVVLNPMTLGIYLQLFFLSIVS | 1385 | 2499.12 | 2500.4 |
| MAIHKALVMCLGLPLFLFPGAWA | 1386 | 2500.18 | 2500.4 |
| MAWQMMQLLLLALVTAAGSAQPR | 159 | 2501.08 | 2500.4, 2502.64 |
| MRVLFFVFGVLSLMFTVPPGRS | 160 | 2501.1 | 2500.4, 2502.64 |
| MDMFPLTWVFLALYFSRHQV | 161 | 2502 | 2500.4, 2502.64 |
| MPMASPQTLVLYLLVLAVTEAWG | 162 | 2504.06 | 2502.64, 2504.73 |
| MLLWVQQALLALLLPTLLAQGEA | 1387 | 2506.09 | 2504.73, 2507.42 |
| MRRRLWLGLAWLLLARAPDAAG | 1388 | 2507.05 | 2507.42 |
| MRKTRLWGLLWMLFVSELRA | 1389 | 2507.11 | 2507.42 |
| MKFYSLLLCSLLFSFPFLCHP | 1390 | 2507.13 | 2507.42 |
| MAVESQGGRPLVLGLLLCVLGPVVS | 1391 | 2508.09 | 2507.42, 2509.21 |
| MKAPAVLAPGILVLLFTLVQRSNG | 1392 | 2509.1 | 2507.42, 2509.21 |
| MKLLKLTGFIFFLFFLTESLT | 1393 | 2510.12 | 2509.21 |
| MRGSQEVLLMWLLVLAVGGTEHA | 1394 | 2511.01 | 2509.21 |
| MKMLTRLQVLTLALFSKGFLLS | 1395 | 2511.18 | 2509.21 |
| MAAATRGCRPWGSLLGLLGLVSAAAA | 1396 | 2514.02 | 2515.26 |
| MAAATRGCRPWGSLLGLLGLVSAAAA | 1397 | 2514.02 | 2515.26 |
| MGAPSACRTLVLALAAMLVVPQAET | 1398 | 2514.08 | 2515.26 |

TABLE 40

| Signal Peptide Amino acid sequence | SEQ ID No. | MW | m/z of the corresponding peak |
|---|---|---|---|
| MAGLGASLHVWGWLMLGSCLLARA | 1399 | 2514.08 | 2515.26 |
| MASLGQILFWSIISIIILAGAIA | 1400 | 2515.14 | 2515.26 |
| MGQLCWLPLLAPLLLLRPPGVQS | 1401 | 2516.16 | 2515.26, 2517.43 |
| MCLTDEWGFLFFFFLGVPEA | 1402 | 2516.97 | 2515.26, 2517.43 |
| MRTHTRGAPSVFFIYLLCFVSA | 1403 | 2517.02 | 2515.26, 2517.43 |

TABLE 40-continued

| Signal Peptide Amino acid sequence | SEQ ID No. | MW | m/z of the corresponding peak |
|---|---|---|---|
| MSDLLSIYSAPVVVSTVLHMLQI | 1404 | 2517.05 | 2515.26, 2517.43 |
| MFLSKPSVYICLFTCVLQLSHS | 1405 | 2517.08 | 2515.26, 2517.43, 2519.07 |
| MYLETRRAIFVFWIFLQVQG | 1406 | 2518.03 | 2517.43, 2519.07 |
| MPRKQPAGCIFLLTFLGLSGLVGT | 1407 | 2520.1 | 2519.07 |
| MRPRRPLVFMSLVCALLNTCQA | 1408 | 2520.16 | 2519.07 |
| MDPKYFILILFCGHLNNTFFS | 1409 | 2521 | 2519.07 |
| MRGHPSLLLLYMALTTCLDTSPS | 1410 | 2521.02 | 2519.07 |
| MGYCQGVSQVAVVLLMFPKEKEA | 1411 | 2528.06 | 2527.31 |
| MGGRVFLVFLAFCVWLTLPGAET | 1412 | 2528.08 | 2527.31 |
| MAVMAPRTLVLLLSGALALTQTWA | 1413 | 2528.12 | 2527.31 |
| MAVMAPRTLVLLLSGALALTQTWA | 1414 | 2528.12 | 2527.31 |
| MAVMAPRTLVLLLSGALALTQTWA | 1415 | 2528.12 | 2527.31 |
| MAVMAPRTLVLLLSGALALTQTWA | 1416 | 2528.12 | 2527.31 |
| MAVMAPRTLVLLLSGALALTQTWA | 1417 | 2528.12 | 2527.31 |
| MAVMAPRTLVLLLSGALALTQTWA | 1418 | 2528.12 | 2527.31 |
| MAVMAPRTLVLLLSGALALTQTWA | 1419 | 2528.12 | 2527.31 |
| MAVMAPRTLVLLLSGALALTQTWA | 1420 | 2528.12 | 2527.31 |
| MAVMAPRTLVLLLSGALALTQTWA | 1421 | 2528.12 | 2527.31 |
| MAVMAPRTLVLLLSGALALTQTWA | 1422 | 2528.12 | 2527.31 |
| MAVMAPRTLVLLLSGALALTQTWA | 1423 | 2528.12 | 2527.31 |
| MAVMAPRTLVLLLSGALALTQTWA | 1424 | 2528.12 | 2527.31 |
| MRIAVLLFAIFFFMSQVLPARG | 1425 | 2528.17 | 2527.31 |
| MRIAVLLFAIFFFMSQVLPARG | 1426 | 2528.17 | 2527.31 |
| MWHLKLCAVLMIFLLLLGQIDG | 1427 | 2528.23 | 2527.31 |
| MEPRALVTALSLGLSLCSLGLLVTA | 1428 | 2529.11 | 2527.31, 2531.06 |
| MRLHLLLLILLLFSILLSPVRG | 1429 | 2531.28 | 2531.06, 2532.26 |
| MLSQLAMLQGSLLLWATMSVAQQ | 1430 | 2533.12 | 2532.26 |
| MPAGVPMSTYLKMFAASLLAMCAGA | 1431 | 2533.17 | 2532.26 |
| MQSPWKILTVAPLFLLLSLQSSA | 1432 | 2544.1 | 2546.08 |
| MQPPSLLLLLLLLLLLCVSVVRP | 1433 | 2544.34 | 2546.08 |
| MRTPQLALLQVFFLVFPDGVRP | 1434 | 2545.09 | 2546.08 |
| MARQPPPPWVHAAFLLCLLSLGGA | 1435 | 2546.1 | 2546.08 |
| MQFRLFSFAUILNCMDYSHC | 1436 | 2553.09 | 2554.96 |
| MGSRGQGLLLAYCLLLAFASGLVLS | 1437 | 2554.12 | 2554.96 |
| MFLATLYFALPLLDLLLSAEVSGG | 1438 | 2555.08 | 2554.96 |
| MQRLVLLLAISLLLYQDLPVRS | 1439 | 2555.17 | 2554.96 |
| MRLWKAVVVTLAFMSVDICVTTA | 1440 | 2555.17 | 2554.96 |
| MRKPAAGFLPSLLKVLLLPLAPAAA | 1441 | 2559.25 | 2559.48 |

TABLE 40-continued

| Signal Peptide | | | m/z |
|---|---|---|---|
| Amino acid sequence | SEQ ID No. | MW | of the corresponding peak |
| MQAAVAVSVPFLLLCVLGTCPPARC | 1442 | 2560.21 | 2559.48 |
| MSRLRALLGLGLLVAGSRVPRIKS | 1443 | 2564.19 | 2564.01 |
| MRIAVLFFTIFFFMSQVLPAKG | 1444 | 2564.2 | 2564.01 |

TABLE 41

| Signal Peptide | | | m/z |
|---|---|---|---|
| Amino acid sequence | SEQ ID No. | MW | of the corresponding peak |
| MLPCASCLPGSLLLWALLLLLLGSA | 1445 | 2569.28 | 2571.26 |
| MKPWILLLVMFISGVVMLLPVLG | 1446 | 2570.4 | 2571.26 |
| MTRGRAWGMRRAAAGAGGARAAGPTGG | 1447 | 2571.94 | 2571.26 |
| MSRKIEGFLLLLLFGYEATLGLS | 1448 | 2572.11 | 2571.26 |
| MPPFLLLEAVCVFLFSRVPPSLP | 1449 | 2573.21 | 2571.26 |
| MGVRVHVVAASALLYFILLSGTRC | 1450 | 2577.16 | 2578.45 |
| MVLAAPLLLGFLLLALELRPRGEA | 1451 | 2577.22 | 2578.45 |
| MMAGMKIQLVCMLLLAFSSWSLC | 1452 | 2577.33 | 2578.45 |
| MPRPGTMALCLLTLVLSLLPPQAAA | 1453 | 2578.25 | 2578.45 |
| MMQLLQLLLGLLGPGGYLFLLGDC | 1454 | 2579.23 | 2578.45 |
| MRELVNIPLVHILTLVAFSGTEK | 1455 | 2581.12 | 2581.25 |
| MAAFPHKIIFFLVCSTLTHVAFS | 1456 | 2581.15 | 2581.25 |
| MRQAGRAALLAALLLLVQLCPGSSQ | 1457 | 2581.15 | 2581.25 |
| MKLDMTGDCMPVLVLMAAVLTVTGA | 1458 | 2581.25 | 2581.25 |
| MAPLLPIRTLPLILILLALLSPGAA | 1459 | 2581.33 | 2581.25 |
| MALARGSRQLGALVWGACLCVLVHG | 1460 | 2582.16 | 2581.25, 2583.37 |
| MWMFSWLCAILIILAIAGMNTIA | 1461 | 2583.29 | 2583.37, 2584.81 |
| MDILVPLLQLLVLLLTLPLHLMA | 1462 | 2583.37 | 2583.37, 2584.81 |
| MRVTAPRTVLLLLSGALALTETWA | 1463 | 2584.12 | 2583.37, 2584.81 |
| MRVTAPRTVLLLLSGALALTETWA | 1464 | 2584.12 | 2583.37, 2584.81 |
| MRVTAPRTVLLLLSGALALTETWA | 1465 | 2584.12 | 2583.37, 2584.81 |
| MRVTAPRTVLLLLSGALALTETWA | 1466 | 2584.12 | 2583.37, 2584.81 |
| MRVMAPRALLLLLSGGLALTETWA | 1467 | 2584.19 | 2583.37, 2584.81 |
| MRVMAPRALLLLLSGGLALTETWA | 1468 | 2584.19 | 2583.37, 2584.81 |
| MRVMAPRALLLLLSGGLALTETWA | 1469 | 2584.19 | 2583.37, 2584.81 |
| MRVMAPRALLLLLSGGLALTETWA | 1470 | 2584.19 | 2583.37, 2584.81 |
| MGASRDRGLAALWCLGLLGGLARVAG | 1471 | 2585.1 | 2583.37, 2584.81, 2587.01 |
| MAVMAPRTLVLLLSGALALTQTWAG | 1472 | 2585.18 | 2583.37, 2584.81, 2587.01 |
| MAVMAPRTLVLLLSGALALTQTWAG | 1473 | 2585.18 | 2583.37, 2584.81, 2587.01 |
| MAVMAPRTLVLLLSGALALTQTWAG | 1474 | 2585.18 | 2583.37, 2584.81, 2587.01 |

TABLE 41-continued

| Signal Peptide Amino acid sequence | SEQ ID No. | MW | m/z of the corresponding peak |
|---|---|---|---|
| MEACCLLQLPQRLLLLGAAALTATA | 1475 | 2585.2 | 2583.37, 2584.81, 2587.01 |
| MLVMAPRTVLLLLSAALALTETWA | 1476 | 2585.22 | 2583.37, 2584.81, 2587.01 |
| MLVMAPRTVLLLLSAALALTETWA | 1477 | 2585.22 | 2583.37, 2584.81, 2587.01 |
| MLVMAPRTVLLLLSAALALTETWA | 1478 | 2585.22 | 2583.37, 2584.81, 2587.01 |
| MLVMAPRTVLLLLSAALALTETWA | 1479 | 2585.22 | 2583.37, 2584.81, 2587.01 |
| MLVMAPRTVLLLLSAALALTETWA | 1480 | 2585.22 | 2583.37, 2584.81, 2587.01 |
| MALKWTSVLLLIHLGCYFSSGSCG | 1481 | 2587.13 | 2587.01, 2588.9 |
| MGSGGDSLLGGRGSLPLLLLLIMGGMA | 1482 | 2587.17 | 2587.01, 2588.9 |
| MAGAGGGLGVWGNLVLLGLCSWTGARA | 1483 | 2588.06 | 2587.01, 2588.9 |
| MHVAEVAVNVILLLSMGWTSDSLC | 1484 | 2589.1 | 2588.9 |
| MLTRNCLSLLLWVLFDGGLLTPL | 1485 | 2589.21 | 2588.9 |
| MAPAQRPLLPLLLLLLPLPPPPFA | 1486 | 2589.32 | 2588.9 |
| MAAIRMGKLTTMPAGLIYASVSVHA | 1487 | 2590.18 | 2588.9 |
| MKVLGRSFFWVLFPVLPWAVQA | 1488 | 2592.19 | 2593.68 |
| MRQKAVSLFLCYLLLFTCSGVEA | 1489 | 2593.18 | 2593.68 |
| MPPPRTGRGLLWLGLVLSSVCVALG | 1490 | 2593.2 | 2593.68 |

TABLE 42

| Signal Peptide Amino acid sequence | SEQ ID No. | MW | m/z of the corresponding peak |
|---|---|---|---|
| MLFRNRFLLLLALAALLAFVSLS | 1491 | 2593.26 | 2593.68 |
| MLPLPSCSLPILLLFLLPSVPIES | 1492 | 2593.28 | 2593.68 |
| MKAMPWNWTCLLSHLLMVGMGSS | 1493 | 2594.21 | 2593.68, 2596.11 |
| MALGKVLAMALVLALAVLGSLSPGARA | 1494 | 2594.27 | 2593.68, 2596.11 |
| MVPSSPRALFLLLLILACPEPRAS | 1495 | 2595.22 | 2593.68, 2596.11 |
| MCRIAGALRTLLPLLAALLQASVEA | 1496 | 2595.22 | 2593.68, 2596.11 |
| MNNFRATILFWAAAAWAKSGKPSG | 1497 | 2596.01 | 2596.11 |
| MHLRLISWLFIILNFMEYIGS | 1498 | 2597.19 | 2596.11 |
| MKLANWYWLSSAVLATYGFLVVA | 1499 | 2604.11 | 2603.33 |
| MTMCSGARLALLVYGIIMHSSVYS | 1500 | 2604.18 | 2603.33 |
| MGLRSHHLSLGLLLLFLLPAECLG | 1501 | 2604.23 | 2603.33 |
| MGTARIAPGLALLLCCPVLSSAYALV | 1502 | 2604.24 | 2603.33 |
| MDAQTWPVGFRCLLLLALVGSARS | 1503 | 2605.13 | 2603.33 |
| MYREWVVVNVFMMLYVQLVQG | 1504 | 2605.19 | 2603.33 |
| MSSRIARALALVVTLLHLTRLALS | 1505 | 2606.22 | 2608.2 |
| MARGPGLAPPPLRLPLLLLVLAAVTG | 1506 | 2607.29 | 2608.2 |
| MGSLSNYALLQLTLTAFLTILVQP | 1507 | 2608.14 | 2608.2 |
| MAAPTPARPVLTHLLVALFGMGSWA | 1508 | 2608.17 | 2608.2 |

TABLE 42-continued

| Signal Peptide | | m/z | |
|---|---|---|---|
| Amino acid sequence | SEQ ID No. | MW | of the corresponding peak |
| MKIQLFFFILHFWVTILPARS | 1509 | 2608.24 | 2608.2 |
| MELRPWLLWVVAATGTLVLLAADA | 1510 | 2610.16 | 2608.2 |
| MARAGWTSPVPLCVCLLLTCGFAEA | 1511 | 2610.19 | 2608.2 |
| MKGGCVSQWKAAAGFLFCVMVFASA | 1512 | 2610.19 | 2608.2 |
| MCAERLGQFMTLALVLATFDPARG | 1513 | 2612.14 | 2613.31 |
| MLSFVDTRTLLLLAVTLCLATCQS | 1514 | 2613.21 | 2613.31, 2614.91 |
| MRTAPSLRRCVCLLLAAILDLARG | 1515 | 2613.26 | 2613.31, 2614.91 |
| MKPATGLWVWVSLLVAAGTVQPSDS | 1516 | 2614.06 | 2613.31, 2614.91 |
| MGIFLVYVGFVFFSVLYVQQGLS | 1517 | 2614.15 | 2613.31, 2614.91 |
| MPSLPAPPAPLLLLGLLLLGSRPARG | 1518 | 2621.28 | 2622.46 |
| MRKHVLAASFSMLSLLVIMGDTDS | 1519 | 2623.16 | 2622.46 |
| MNVDAEASMAVISLLFLAVMYVVH | 1520 | 2624.19 | 2622.46 |
| MSPPPLLQPLLLLLPLLNVEPSGAT | 1521 | 2624.23 | 2622.46 |
| MRVMAPRTLILLLSGALALTETWA | 1522 | 2628.25 | 2629.26 |
| MRVMAPRTLILLLSGALALTETWA | 1523 | 2628.25 | 2629.26 |
| MRVMAPRTLILLLSGALALTETWA | 1524 | 2628.25 | 2629.26 |
| MRVMAPRTLILLLSGALALTETWA | 1525 | 2628.25 | 2629.26 |
| MRVMAPRTLILLLSGALALTETWA | 1526 | 2628.25 | 2629.26 |
| MTSCGQQSLNVLAVLFSLLFSAVLS | 1527 | 2629.14 | 2629.26 |
| MATRSVLLALVVLNLLFYVPPGRS | 1528 | 2630.24 | 2629.26 |
| MARFLTLCTWLLLLGPGLLATVRA | 1529 | 2630.31 | 2629.26 |
| MHTLTGFSLVSLLSFGYLSWDWA | 1530 | 2632.04 | 2633.69 |
| MHWGTLCGFLWLWPYLFYVQA | 1531 | 2632.15 | 2633.69 |
| MRAVPLPAPLLPLLLLALLAAPAARA | 1532 | 2633.37 | 2633.69, 2634.61 |
| MVVMAPRTLFLLLSGALTLTETWA | 1533 | 2635.23 | 2633.69, 2634.61 |
| MISSVKLNLILVLSLSTMHVFWC | 1534 | 2635.3 | 2633.69, 2634.61 |
| MDVRALPWLPWLLWLLCRGGGDA | 163 | 2639.19 | 2640.51 |
| MDTTAAAALPAFVALLLLSPWPLLGS | 164 | 2640.19 | 2640.51, 2641.73 |

TABLE 43

| Signal Peptide | | m/z | |
|---|---|---|---|
| Amino acid sequence | SEQ ID No. | MW | of the corresponding peak |
| MARLGALLLAAALGALLSFALLAAAVAS | 165 | 2640.28 | 2640.51, 2641.73 |
| MARHGLPLLPLLSLLVGAWLKLGNG | 166 | 2640.28 | 2640.51, 2641.73 |
| MTAWILLPVSLSAFSITGIWTVYA | 167 | 2641.17 | 2640.51, 2641.73 |
| MRVTAPRTVLLLLSGALALTETWAG | 168 | 2641.18 | 2640.51, 2641.73 |
| MMNMSLPFLWSLLTLLIFAEVNG | 169 | 2641.26 | 2640.51, 2641.73 |

TABLE 43-continued

| Signal Peptide Amino acid sequence | SEQ ID No. | MW | m/z of the corresponding peak |
|---|---|---|---|
| MARPDPSAPPSLLLLLAQLVGRAAA | 170 | 2642.21 | 2640.51, 2641.73 |
| MLVMAPRTVLLLLSAALALTETWAG | 171 | 2642.27 | 2640.51, 2641.73 |
| MLVMAPRTVLLLLSAALALTETWAG | 172 | 2642.27 | 2640.51, 2641.73 |
| MKTFTWTLGVLFFLLVDTGHCRG | 1535 | 2643.17 | 2641.73 |
| MASVAWAVLKVLLLLPTQTWSPVGA | 1536 | 2652.24 | 2652.85 |
| MASVAWAVLKVLLLLPTQTWSPVGA | 1537 | 2652.24 | 2652.85 |
| MRWLWPLAVSLAVILAVGLSRVSGG | 1538 | 2652.25 | 2652.85 |
| MAAASAGATRLLLLLLMAVAAPSRARG | 1539 | 2653.26 | 2652.85, 2655.08 |
| MGTRGAVMPPPMWGLLGCCFVCAWA | 1540 | 2655.32 | 2655.08 |
| MKPALLPWALLLLATALGPGPGPTADA | 1541 | 2656.23 | 2655.08 |
| MQKIMHISVLLSPVLWGLIFGVSS | 1542 | 2656.3 | 2655.08 |
| MHPDLGPLCTLLYVTLTILCSSVSS | 1543 | 2664.21 | 2665.15 |
| MSLMVVSMACVGFFLLEGPWPHVGG | 1544 | 2665.27 | 2665.15 |
| MEPRLFCWTTLFLLAGWCLPGLP | 1545 | 2665.29 | 2665.15 |
| MKCTAREWLRVTTVLFMARAIPA | 1546 | 2665.29 | 2665.15 |
| MPPAGLRRAAPLTAIALLVLGAPLVLA | 1547 | 2666.36 | 2665.15 |
| MEALLLGAGLLLGAYVLVYYNLVKA | 1548 | 2668.28 | 2670 |
| MKITSTSCICPVLVCLCFVQRCYG | 1549 | 2668.36 | 2670 |
| MRVTAPRTVLLLLWGAVALTETWA | 1550 | 2669.23 | 2670 |
| MRVTAPRTVLLLLWGAVALTETWA | 1551 | 2669.23 | 2670 |
| MRVTAPRTVLLLLWGAVALTETWA | 1552 | 2669.23 | 2670 |
| MARAGWTGLLPLYVCLLLTCGFAKA | 1553 | 2669.32 | 2670 |
| MAGPGSPRRASRGASALLAAALLYAALG | 1554 | 2670.14 | 2670 |
| MLGIWTLLPLVLTSVARLSSKSVNA | 1555 | 2670.26 | 2670 |
| MVLAFQLVSFTYIWILKPNVCA | 1556 | 2670.32 | 2670 |
| MDSLPRLTSVLTLLFSGLWHLGLT | 1557 | 2671.2 | 2670 |
| MAHTFRGCSLAFMFIITWLLIKA | 1558 | 2671.34 | 2670 |
| MQKLQLCVYIYLFMLIVAGPVDL | 1559 | 2671.37 | 2670 |
| MSQAWVPGLAPTLLFSLLAGPQKIAA | 1560 | 2681.24 | 2682.8 |
| MYFLTPILVAILCILVVWIFKNA | 1561 | 2681.43 | 2682.8 |
| MQGAQEASASEMLPLLLPLLWAGALA | 1562 | 2682.2 | 2682.8 |
| MPGPPALRRRLLLLLLVLLIAGSAGA | 1563 | 2682.41 | 2682.8 |
| MRVTAPRTLLLLLWGAVALTETWA | 1564 | 2683.26 | 2682.8 |
| MVAWRSAFLVCLAFSLATLVQRGSG | 1565 | 2684.23 | 2682.8 |
| CLKFPGGSCMAALTVTLMVLSSPLALA | 1566 | 2695.37 | 2696.41 |
| MAAGSRTSLLLAFGLLCLSWLQEGSA | 1567 | 2696.19 | 2696.41, 2697.73 |
| MAAGSRTSLLLAFGLLCLSWLQEGSA | 1568 | 2696.19 | 2696.41, 2697.73 |
| MATSTGRWLLLRLALFGFLWEASG | 173 | 2697.2 | 2696.41, 2697.73, 2698.27 |

TABLE 43-continued

| Signal Peptide | | | m/z |
|---|---|---|---|
| Amino acid sequence | SEQ ID No. | MW | of the corresponding peak |
| MAWGGVHTCCFHLCCCCSWPQGAVP | 174 | 2697.26 | 2696.41, 2697.73, 2698.27 |
| MRVTAPRTLLLLLWGALALTETWA | 175 | 2697.29 | 2696.41, 2697.73, 2698.27 |
| MGGPAAPRGAGRLRALLLALVVAGIPAGA | 176 | 2697.29 | 2696.41, 2697.73, 2698.27 |

TABLE 44

| Signal Peptide | | | m/z |
|---|---|---|---|
| Amino acid sequence | SEQ ID No. | MW | of the corresponding peak |
| MLAASIFRPTLLLCWLAAPWPTQP | 177 | 2697.31 | 2696.41, 2697.73, 2698.27 |
| MRQRLLPSVTSLLLVALLFPGSSQA | 178 | 2698.27 | 2696.41, 2697.73, 2698.27, 2699.82 |
| MYSFNTLRLYLWETIVFFSLAASKEAEA | 1569 | 3301.81 | 3302.01, 3303.21 |
| MEPGPTAAQRRCSLPPWLPLGLLLWSGLALG | 1570 | 3301.97 | 3302.01, 3303.21 |
| MKTQRDGHSLGRWSLVLLLLGLVMPLAIIA | 1571 | 3303.09 | 3302.01, 3303.21 |
| MSPVRRWGSPCLFPLQLFSLCWVLSVAQS | 1572 | 3308.99 | 3309.84 |
| MCFPKVLSDDMKKLKARMVMLLPTSAQGLG | 1573 | 3310.15 | 3309.84 |
| MCPSEMGTLWHHWSPVLISLAALFSKVTEG | 179 | 3328.93 | 3330.34 |
| MAPRARRRRPLFALLLLCALLARLQVALQ | 180 | 3331.2 | 3330.34 |
| MLRGISQLPAVATMSWVLLPVLWLIVQTQA | 1574 | 3336.12 | 3337.92 |
| MRRISLTSSPVRLLLFLLLLLIALEIMVGG | 1575 | 3339.25 | 3337.92 |
| MCSYYHMKKRSVSGCNITIFAVMFSHLSAG | 1576 | 3370.03 | 3370.39 |
| MNWELLLWLLVLCALLLLLVQLLRFLRA | 1577 | 3380.35 | 3380.43 |
| MKCLGKRRGQAAAFLPLCWLFLKILQPGHS | 1578 | 3384.19 | 3384.77 |
| MKTKLNIYNMQFLLFVFLVWDPARLVLA | 1579 | 3385.19 | 3384.77 |
| MAWKSSVIMQMGRFLLLVILFLPREMTSS | 1580 | 3386.22 | 3384.77 |

Example 3

Peptide Synthesis

Synthetic peptides comprising the amino acid sequences represented by SEQ ID Nos: 1 to 180 described above were synthesized by solid-phase synthesis (Fmoc method) using a commercial peptide synthesizer (manufactured by Intavis AG) according to the manual. In the explanation below, these synthetic peptides are called peptides 1 to 180. Regarding the mode of use of the peptide synthesizer, detailed explanations are omitted because this is not a feature of the invention.

Example 4

Preparation of Liquid Composition

The synthetic peptides (synthetic marker peptides) of peptides 1 to 180 above were each dissolved in 0.1% TFA/50% ACN aqueous solution to a peptide concentration of 1 μmol/mL, to obtain liquid compositions (ALS testing compositions) having the synthetic marker peptides disclosed here as principal components.

Example 5

Preparation of ALS Testing Chips

ALS testing chips were prepared comprising the synthetic peptides (synthetic marker peptides) of peptides 1 to 180 above immobilized on substrates. For the substrate, EVA film was affixed to a measurement plate commonly used in MALDI MS. That is, this was a plate-shaped substrate in which the surface on which the synthetic marker peptide was immobilized was made of thermoplastic resin.

Each ALS testing composition was first diluted 100 times with 0.1% TFA/50% ACN aqueous solution, to prepare a synthetic marker peptide dilution. This synthetic marker peptide dilution was then mixed at a volume ratio of 1:1 with matrix liquid. A 0.1% TFA/50% ACN aqueous solution containing 5 mg/mL sinapinic acid (CHCA) was used as the matrix liquid.

2 μL of the mixed solution obtained by mixing this matrix liquid with the synthetic marker peptide dilution was then dripped onto the substrate, and vacuum dried to prepare an ALS testing chip.

INDUSTRIAL APPLICABILITY

As discussed above, data about whether a test subject suffers from or has developed ALS (typically, data showing whether there is a strong likelihood that the test subject suffers from or has developed ALS) can be obtained by the method for aiding ALS detection disclosed here. That is, ALS can be detected with a high degree of accuracy by the method for aiding ALS detection disclosed here. Consequently, the method for aiding ALS detection disclosed here can be used favorably for predicting, diagnosing (early diagnosis) and initiating treatment for ALS, and as a follow-up indicator after the start of treatment (typically, as an indicator for determining the effects of treatment).

Moreover, the ALS biomarker disclosed here can be used favorably as an indicator for detecting (diagnosing) with a high degree of accuracy whether a test subject suffers from or has developed ALS. That is, the synthetic marker peptide disclosed here (or an ALS testing composition, ALS testing kit or ALS testing chip containing the synthetic marker peptide) can be used favorably for the purpose of detecting (diagnosing) ALS with a high degree of accuracy.

(Sequence Listing Free Text)

SEQ ID Nos: 1 to 1580 Peptides

---

The invention claimed is:

1. A method for aiding detection of amyotrophic lateral sclerosis (ALS), the method comprising:
   analyzing to determine a presence or an absence of an ALS-associated signal peptide in a bodily fluid from a test subject or analyzing to determine a degree of abundance of the ALS-associated signal peptide when present, and
   comparing the presence or the absence of the ALS-associated signal peptide or the degree of abundance of the ALS-associated signal peptide in the bodily fluid from the test subject with a reference level that has been set based on results obtained by having determined the presence or the absence of the ALS-associated signal peptide, or by having determined the degree of abundance of the ALS-associated signal peptide in a bodily fluid from at least one healthy subject, wherein
   a molecular weight of the ALS-associated signal peptide is:

1405.71±2, 1406.49±2, 1409.40±2, 1410.97±2, 1418.70±2, 1426.68±2, 1437.62±2, 1445.77±2, 1451.61±2, 1456.44±2, 1458.88±2, 1466.24±2, 1468.86±2, 1472.12±2, 1476.87±2, 1482.60±2, 1493.58±2, 1495.42±2, 1496.52±2, 1497.16±2, 1498.88±2, 1502.40±2, 1505.52±2, 1508.76±2, 1510.50±2, 1516.64±2, 1521.93±2, 1529.32±2, 1530.37±2, 1533.52±2, 1539.36±2, 1544.22±2, 1553.72±2, 1555.72±2, 1560.24±2, 1566.20±2, 1567.20±2, 1567.74±2, 1575.70±2, 1578.07±2, 1580.91±2, 1589.58±2, 1592.55±2, 1597.25±2, 1608.53±2, 1609.36±2, 1610.62±2, 1616.12±2, 1629.15±2, 1639.39±2, 1640.36±2, 1646.58±2, 1655.72±2, 1657.97±2, 1659.24±2, 1660.46±2, 1662.16±2, 1679.09±2, 1682.54±2, 1683.12±2, 1687.34±2, 1688.14±2, 1691.08±2, 1691.75±2, 1694.76±2, 1695.74±2, 1700.65±2, 1702.19±2, 1705.53±2, 1708.77±2, 1712.10±2, 1714.63±2, 1715.56±2, 1719.51±2, 1721.61±2, 1726.31±2, 1737.85±2, 1739.71±2, 1743.69±2, 1761.79±2, 1769.93±2, 1774.13±2, 1775.70±2, 1786.39±2, 1788.03±2, 1790.80±2, 1796.23±2, 1797.49±2, 1800.34±2, 1801.79±2, 1804.45±2, 1810.72±2, 1812.31±2, 1813.77±2, 1817.26±2, 1818.66±2, 1819.34±2, 1819.93±2, 1821.71±2, 1822.73±2, 1829.48±2, 1831.81±2, 1832.41±2, 1836.18±2, 1837.33±2, 1840.84±2, 1849.81±2, 1854.68±2, 1858.34±2, 1864.19±2, 1866.06±2, 1875.28±2, 1876.50±2, 1878.25±2, 1890.21±2, 1891.32±2, 1893.00±2, 1904.69±2, 1911.46±2, 1913.68±2, 1916.02±2, 1919.35±2, 1927.13±2, 1931.84±2, 1934.86±2, 1935.52±2, 1936.83±2, 1937.87±2, 1941.22±2, 1944.97±2, 1948.39±2, 1952.47±2, 1957.80±2, 1962.82±2, 1969.82±2, 1972.54±2, 1975.58±2, 1976.51±2, 1977.70±2, 1979.29±2, 1988.46±2, 1991.91±2, 1995.37±2, 2009.91±2, 2011.18±2, 2013.86±2, 2023.97±2, 2027.73±2, 2030.95±2, 2032.69±2, 2039.29±2, 2043.12±2, 2045.68±2, 2051.76±2, 2055.50±2, 2059.05±2, 2062.98±2, 2065.57±2, 2066.09±2, 2074.03±2, 2075.32±2, 2079.80±2, 2083.74±2, 2084.36±2, 2085.85±2, 2089.53±2, 2092.25±2, 2092.80±2, 2097.03±2, 2099.42±2, 2111.39±2, 2113.10±2, 2115.77±2, 2120.37±2, 2126.55±2, 2137.63±2, 2139.15±2, 2140.48±2, 2143.42±2, 2146.46±2, 2149.85±2, 2151.02±2, 2160.22±2, 2161.68±2, 2167.09±2, 2167.78±2, 2168.75±2, 2173.75±2, 2177.51±2, 2179.25±2, 2184.93±2, 2185.65±2, 2186.28±2, 2190.18±2, 2191.02±2, 2192.84±2, 2196.47±2, 2199.82±2, 2201.22±2, 2204.02±2, 2207.10±2, 2211.58±2, 2216.77±2, 2218.45±2, 2219.30±2, 2220.56±2, 2222.74±2, 2226.96±2, 2228.22±2, 2231.60±2, 2239.71±2, 2244.01±2, 2251.78±2, 2254.83±2, 2256.53±2, 2261.91±2, 2266.45±2, 2268.58±2, 2274.97±2, 2276.04±2, 2278.67±2, 2281.09±2, 2285.01±2, 2289.43±2, 2290.85±2, 2292.35±2, 2295.92±2, 2296.92±2, 2301.71±2, 2302.50±2, 2303.21±2, 2305.43±2, 2307.22±2, 2314.24±2, 2314.81±2, 2317.68±2, 2325.30±2, 2327.73±2, 2341.14±2, 2342.87±2, 2344.45±2, 2351.97±2, 2353.99±2, 2355.29±2, 2357.54±2, 2367.75±2, 2375.59±2, 2378.35±2, 2380.39±2, 2393.64±2, 2402.11±2, 2404.01±2, 2406.49±2, 2412.79±2, 2414.25±2, 2415.20±2, 2416.30±2, 2431.13±2, 2434.36±2, 2438.19±2, 2439.22±2, 2444.37±2, 2451.90±2, 2453.96±2, 2455.44±2, 2456.62±2, 2459.43±2, 2462.31±2, 2464.16±2, 2470.97±2, 2478.17±2, 2479.28±2, 2484.18±2, 2500.40±2, 2502.64±2, 2504.73±2, 2507.42±2, 2509.21±2, 2515.26±2, 2517.43±2, 2519.07±2, 2527.31±2, 2531.06±2, 2532.26±2, 2546.08±2, 2554.96±2, 2559.48±2, 2564.01±2, 2571.26±2, 2578.45±2, 2581.25±2, 2583.37±2, 2584.81±2, 2587.01±2, 2588.90±2, 2593.68±2, 2596.11±2, 2603.33±2, 2608.20±2, 2613.31±2, 2614.91±2, 2622.46±2, 2629.26±2, 2633.69±2, 2634.61±2, 2640.51±2, 2641.73±2, 2652.85±2, 2655.08±2, 2665.15±2, 2670.00±2, 2682.80±2, 2696.41±2, 2697.73±2, 2698.27±2, 2699.82±2, 3302.01±2, 3303.21±2, 3309.84±2, 3323.89±2, 3330.34±2, 3337.92±2, 3366.84±2, 3370.39±2, 3378.18±2, 3380.43±2 or 3384.77±2, wherein the degree of abundance of any of the ALS-associated signal peptides having the following molecular weights out of the tested ALS-associated signal peptides in the bodily fluid from the test subject is confirmed to be high in comparison with the reference level:

1405.71±2, 1406.49±2, 1409.40±2, 1410.97±2, 1418.70±2, 1426.68±2, 1437.62±2, 1445.77±2, 1451.61±2, 1456.44±2, 1458.88±2, 1466.24±2, 1468.86±2, 1472.12±2, 1476.87±2, 1482.60±2, 1493.58±2, 1495.42±2, 1496.52±2, 1498.88±2, 1502.40±2, 1505.52±2, 1508.76±2, 1510.50±2, 1516.64±2, 1521.93±2, 1529.32±2, 1530.37±2, 1533.52±2, 1539.36±2, 1544.22±2, 1553.72±2, 1555.72±2, 1560.24±2, 1566.20±2, 1567.20±2, 1575.70±2, 1578.07±2, 1580.91±2, 1589.58±2, 1592.55±2, 1597.25±2, 1608.53±2, 1609.36±2, 1610.62±2, 1616.12±2, 1629.15±2, 1639.39±2, 1640.36±2, 1646.58±2, 1655.72±2, 1657.97±2, 1659.24±2, 1660.46±2, 1662.16±2, 1679.09±2, 1682.54±2, 1683.12±2, 1687.34±2, 1688.14±2, 1691.08±2, 1691.75±2, 1694.76±2, 1695.74±2, 1700.65±2, 1702.19±2, 1708.77±2, 1712.10±2, 1714.63±2, 1715.56±2, 1719.51±2, 1721.61±2, 1726.31±2, 1737.85±2, 1739.71±2, 1743.69±2, 1761.79±2, 1769.93±2, 1774.13±2, 1775.70±2, 1786.39±2, 1788.03±2, 1790.80±2, 1796.23±2, 1797.49±2, 1800.34±2, 1801.79±2, 1804.45±2, 1810.72±2, 1812.3±21, 1813.77±2, 1817.26±2, 1818.66±2, 1819.93±2, 1821.71±2, 1822.73±2, 1829.48±2, 1832.41±2, 1836.18±2, 1837.33±2, 1840.84±2, 1849.81±2, 1854.68±2, 1858.34±2, 1864.19±2, 1866.06±2, 1875.28±2, 1876.50±2, 1878.25±2, 1890.21±2, 1891.32±2, 1893.00±2, 1904.69±2, 1911.46±2, 1913.68±2, 1916.02±2, 1919.35±2, 1927.13±2, 1931.84±2, 1934.86±2, 1936.83±2, 1937.87±2, 1941.22±2, 1944.97±2, 1948.39±2, 1952.47±2, 1957.80±2, 1962.82±2, 1969.82±2, 1972.54±2, 1975.58±2, 1976.51±2, 1977.70±2, 1979.29±2, 1988.46±2, 1991.91±2, 1995.37±2, 2009.91±2, 2011.18±2, 2013.86±2, 2023.97±2, 2027.73±2, 2030.95±2, 2032.69±2, 2039.29±2, 2043.12±2, 2045.68±2, 2051.76±2, 2059.05±2, 2062.98±2, 2066.09±2, 2074.03±2, 2075.32±2, 2079.80±2, 2083.74±2, 2085.85±2, 2089.53±2, 2092.80±2, 2097.03±2, 2099.42±2, 2111.39±2, 2113.10±2, 2115.77±2, 2120.37±2, 2126.55±2, 2137.63±2, 2139.15±2, 2143.42±2, 2146.46±2, 2149.85±2, 2151.02±2, 2160.22±2, 2161.68±2, 2167.09±2, 2168.75±2, 2173.75±2, 2177.51±2, 2179.25±2, 2185.65±2, 2186.28±2, 2190.18±2, 2191.02±2, 2192.84±2, 2196.47±2, 2199.82±2, 2201.22±2, 2204.02±2, 2207.10±2, 2211.58±2, 2216.77±2, 2218.45±2, 2219.30±2, 2220.56±2, 2222.74±2, 2226.96±2, 2228.22±2, 2231.60±2, 2239.71±2, 2244.01±2, 2251.78±2, 2254.83±2, 2256.53±2, 2261.91±2, 2266.45±2, 2268.58±2, 2274.97±2, 2276.04±2, 2278.67±2, 2281.09±2, 2285.01±2, 2289.43±2, 2290.85±2, 2292.35±2, 2295.92±2, 2296.92±2, 2301.71±2, 2302.50±2, 2303.21±2, 2305.43±2, 2307.22±2, 2314.24±2, 2317.68±2, 2325.30±2, 2341.14±2, 2342.87±2, 2344.45±2, 2351.97±2, 2353.99±2, 2355.29±2, 2357.54±2, 2367.75±2, 2375.59±2, 2378.35±2, 2380.39±2, 2393.64±2, 2402.11±2, 2404.01±2, 2406.49±2, 2412.79±2, 2414.25±2, 2415.20±2, 2416.30±2, 2431.13±2, 2434.36±2, 2438.19±2, 2439.22±2, 2444.37±2, 2451.90±2, 2453.96±2, 2455.44±2, 2456.62±2, 2459.43±2, 2462.31±2, 2464.16±2, 2470.97±2, 2478.17±2, 2479.28±2, 2484.18±2, 2500.40±2, 2502.64±2, 2504.73±2, 2507.42±2, 2509.21±2, 2515.26±2, 2517.43±2, 2519.07±2, 2527.31±2, 2531.06±2, 2532.26±2, 2546.08±2, 2554.96±2, 2559.48±2, 2564.01±2, 2571.26±2, 2578.45±2, 2581.25±2, 2583.37±2, 2584.81±2, 2587.01±2, 2588.90±2, 2593.68±2, 2596.11±2, 2603.33±2, 2608.20±2, 2613.31±2, 2614.91±2, 2622.46±2, 2629.26±2, 2633.69±2, 2634.61±2, 2640.51±2, 2641.73±2, 2652.85±2, 2655.08±2, 2665.15±2, 2670.00±2, 2682.80±2, 2696.41±2, 2698.27±2, 2699.82±2, 3302.01±2, 3303.21±2, 3323.89±2, 3330.34±2, 33317.92±2, 3366.84±2, 3370.39±2, 3378.18±2, 3380.43±2 and 3384.77±2, wherein the presence or the absence or the degree of abundance of the ALS-associated signal peptide in the bodily fluid from the test subject is tested with a mass spectrometer, wherein further comprising:

immobilizing the bodily fluid on a thermoplastic resin before the presence or the absence and the degree of abundance of the ALS-associated signal peptide in the bodily fluid is tested, and wherein the presence or the absence and the degree of abundance of the ALS-associated signal peptide in the bodily fluid immobilized on the thermoplastic resin is determined by matrix assisted laser desorption/ionization-time of flight mass spectrometry.

2. The method according to claim 1, wherein an amino acid sequence of the ALS-associated signal peptide is any of amino acid sequences represented by SEQ ID Nos: 1 to 16, 21 to 27, 29 to 46, 53 to 67, 72 to 87, 94 to 108, 118 to 172, 179 to 243, 248 to 295, 297 to 304, 307 to 317, 320 to 333, 337 to 354, 359 to 422, 424, 425, 430 to 585, 587 to 593, 595 to 605, 607 to 693, 696, 699 to 777, 786 to 902, 906 to 914, 918 to 945, 947 to 983, 990 to 1029, 1042 to 1201, 1208 to 1217, 1230 to 1566, 1569 to 1571 and 1574 to 1580.

3. The method according to claim 1, wherein at least the degree of abundance of an ALS-associated signal peptide with a molecular weight of 1502.40±2, 1521.93±2, 1629.15±2, 1682.54±2, 1691.75±2, 1705.53±2, 1821.71±2, 1836.18±2, 1948.39±2, 2011.18±2, 2092.80±2, 2099.42±2, 2177.51±2, 2179.25±2, 2186.28±2, 2211.58±2, 2226.96±2, 2254.83±2, 2278.67±2, 2290.85±2, 2292.35±2, 2502.64±2, 2640.51±2, 2698.27±2 or 3330.34±2 is tested.

4. The method according to claim 3, wherein an amino acid sequence constituting the ALS-associated signal peptide is any of amino acid sequences represented by SEQ ID Nos: 1 to 180.

5. The method according to claim 1, wherein at least 10 kinds of ALS-associated signal peptides having molecular weights differing by at least 3 from each other are tested in the bodily fluid from the test subject.

6. The method according to claim 1, wherein the bodily fluid is a cerebrospinal fluid.

7. A method for aiding detection of amyotrophic lateral sclerosis (ALS), the method comprising:

analyzing to determine a presence or an absence of an ALS-associated signal peptide in a bodily fluid from a test subject or analyzing to determine a degree of abundance of the ALS-associated signal peptide when present, and comparing the presence or the absence of the ALS-associated signal peptide or the degree of abundance of the ALS-associated signal peptide in the bodily fluid from the test subject with a reference level that has been set based on results obtained by having determined the presence or the absence of the ALS-associated signal peptide, or by having determined the degree of abundance of the ALS-associated signal peptide in a bodily fluid from at least one healthy subject, wherein a molecular weight of the ALS-associated signal peptide is:

1405.71±2, 1406.49±2, 1409.40±2, 1410.97±2, 1418.70±2, 1426.68±2, 1437.62±2, 1445.77±2, 1451.61±2, 1456.44±2, 1458.88±2, 1466.24±2, 1468.86±2, 1472.12±2, 1476.87±2, 1482.60±2, 1493.58±2, 1495.42±2, 1496.52±2, 1497.16±2, 1498.88±2, 1502.40±2, 1505.52±2, 1508.76±2, 1510.50±2, 1516.64±2, 1521.93±2, 1529.32±2, 1530.37±2, 1533.52±2, 1539.36±2, 1544.22±2, 1553.72±2, 1555.72±2, 1560.24±2, 1566.20±2, 1567.20±2, 1567.74±2, 1575.70±2, 1578.07±2, 1580.91±2, 1589.58±2, 1592.55±2, 1597.25±2, 1608.53±2, 1609.36±2, 1610.62±2, 1616.12±2, 1629.15±2, 1639.39±2, 1640.36±2, 1646.58±2, 1655.72±2, 1657.97±2, 1659.24±2, 1660.46±2, 1662.16±2, 1679.09±2, 1682.54±2, 1683.12±2, 1687.34±2, 1688.14±2, 1691.08±2, 1691.75±2, 1694.76±2, 1695.74±2, 1700.65±2, 1702.19±2, 1705.53±2, 1708.77±2, 1712.10±2, 1714.63±2, 1715.56±2, 1719.51±2, 1721.61±2, 1726.31±2, 1737.85±2, 1739.71±2, 1743.69±2, 1761.79±2, 1769.93±2, 1774.13±2, 1775.70±2, 1786.39±2, 1788.03±2, 1790.80±2, 1796.23±2, 1797.49±2, 1800.34±2, 1801.79±2, 1804.45±2, 1810.72±2, 1812.31±2, 1813.77±2, 1817.26±2, 1818.66±2, 1819.34±2, 1819.93±2, 1821.71±2, 1822.73±2, 1829.48±2, 1831.81±2, 1832.41±2, 1836.18±2, 1837.33±2, 1840.84±2, 1849.81±2, 1854.68±2, 1858.34±2, 1864.19±2, 1866.06±2, 1875.28±2, 1876.50±2, 1878.25±2, 1890.21±2, 1891.32±2, 1893.00±2, 1904.69±2, 1911.46±2, 1913.68±2, 1916.02±2, 1919.35±2, 1927.13±2, 1931.84±2, 1934.86±2, 1935.52±2, 1936.83±2, 1937.87±2, 1941.22±2, 1944.97±2, 1948.39±2, 1952.47±2, 1957.80±2, 1962.82±2, 1969.82±2, 1972.54±2, 1975.58±2, 1976.51±2, 1977.70±2, 1979.29±2, 1988.46±2, 1991.91±2, 1995.37±2, 2009.91±2, 2011.18±2, 2013.86±2, 2023.97±2, 2027.73±2, 2030.95±2, 2032.69±2, 2039.29±2, 2043.12±2, 2045.68±2, 2051.76±2, 2055.50±2, 2059.05±2, 2062.98±2, 2065.57±2, 2066.09±2, 2074.03±2, 2075.32±2, 2079.80±2, 2083.74±2, 2084.36±2, 2085.85±2, 2089.53±2, 2092.25±2, 2092.80±2, 2097.03±2, 2099.42±2, 2111.39±2, 2113.10±2, 2115.77±2, 2120.37±2, 2126.55±2, 2137.63±2, 2139.15±2, 2140.48±2, 2143.42±2, 2146.46±2, 2149.85±2, 2151.02±2, 2160.22±2, 2161.68±2, 2167.09±2, 2167.78±2, 2168.75±2, 2173.75±2, 2177.51±2, 2179.25±2, 2184.93±2, 2185.65±2, 2186.28±2, 2190.18±2, 2191.02±2, 2192.84±2, 2196.47±2, 2199.82±2, 2201.22±2, 2204.02±2, 2207.10±2, 2211.58±2, 2216.77±2, 2218.45±2, 2219.30±2, 2220.56±2, 2222.74±2, 2226.96±2, 2228.22±2, 2231.60±2, 2239.71±2, 2244.01±2, 2251.78±2, 2254.83±2, 2256.53±2, 2261.91±2, 2266.45±2, 2268.58±2, 2274.97±2, 2276.04±2, 2278.67±2, 2281.09±2, 2285.01±2, 2289.43±2, 2290.85±2, 2292.35±2, 2295.92±2, 2296.92±2, 2301.71±2, 2302.50±2, 2303.21±2, 2305.43±2, 2307.22±2, 2314.24±2, 2314.81±2, 2317.68±2, 2325.30±2, 2327.73±2, 2341.14±2, 2342.87±2, 2344.45±2, 2351.97±2, 2353.99±2, 2355.29±2, 2357.54±2, 2367.75±2, 2375.59±2, 2378.35±2, 2380.39±2, 2393.64±2, 2402.11±2, 2404.01±2, 2406.49±2, 2412.79±2, 2414.25±2, 2415.20±2, 2416.30±2, 2431.13±2, 2434.36±2, 2438.19±2, 2439.22±2, 2444.37±2, 2451.90±2, 2453.96±2, 2455.44±2, 2456.62±2, 2459.43±2, 2462.31±2, 2464.16±2, 2470.97±2, 2478.17±2, 2479.28±2, 2484.18±2, 2500.40±2, 2502.64±2, 2504.73±2, 2507.42±2, 2509.21±2, 2515.26±2, 2517.43±2, 2519.07±2, 2527.31±2, 2531.06±2, 2532.26±2, 2546.08±2, 2554.96±2, 2559.48±2, 2564.01±2, 2571.26±2, 2578.45±2, 2581.25±2, 2583.37±2, 2584.81±2, 2587.01±2, 2588.90±2, 2593.68±2, 2596.11±2, 2603.33±2, 2608.20±2, 2613.31±2, 2614.91±2, 2622.46±2, 2629.26±2, 2633.69±2, 2634.61±2, 2640.51±2, 2641.73±2, 2652.85±2, 2655.08±2, 2665.15±2, 2670.00±2, 2682.80±2, 2696.41±2, 2697.73±2, 2698.27±2, 2699.82±2, 3302.01±2, 3303.21±2, 3309.84±2, 3323.89±2, 3330.34±2, 3337.92±2, 3366.84±2, 3370.39±2, 3378.18±2, 3380.43±2 or 3384.77±2, wherein further comprising:
confirming that the degree of abundance of any of the ALS-associated signal peptides having the following molecular weights out of the tested ALS-associated signal peptides in the bodily fluid from the test subject is low in comparison with the reference level:
1497.16±2, 1567.74±2, 1705.53±2, 1819.34±2, 1831.81±2, 1935.52±2, 2055.50±2, 2065.57±2, 2084.36±2, 2092.25±2, 2140.48±2, 2167.78±2, 2184.93±2, 2314.81±2, 2327.73±2, 2697.73±2 and 3309.84±2, wherein the presence or the absence or the degree of abundance of the ALS-associated signal peptide in the bodily fluid from the test subject is tested with a mass spectrometer, wherein further comprising:
immobilizing the bodily fluid on a thermoplastic resin before the presence or the absence and the degree of abundance of the ALS-associated signal peptide in the bodily fluid is tested, and wherein the presence or the absence and the degree of abundance of the ALS-associated signal peptide in the bodily fluid immobilized on the thermoplastic resin is determined by matrix assisted laser desorption/ionization-time of flight mass spectrometry.

8. The method according to claim 7, wherein an amino acid sequence of the ALS-associated signal peptide is any of amino acid sequences represented by SEQ ID Nos: 68, 69, 296, 357, 429, 903 to 905, 1223 to 1229, 1572 and 1573.

9. The method according to claim 7, wherein at least the degree of abundance of an ALS-associated signal peptide with a molecular weight of 1502.40±2, 1521.93±2, 1629.15±2, 1682.54±2, 1691.75±2, 1705.53±2, 1821.71±2, 1836.18±2, 1948.39±2, 2011.18±2, 2092.80±2, 2099.42±2, 2177.51±2, 2179.25±2, 2186.28±2, 2211.58±2, 2226.96±2, 2254.83±2, 2278.67±2, 2290.85±2, 2292.35±2, 2502.64±2, 2640.51±2, 2698.27±2 or 3330.34±2 is tested.

10. The method according to claim 9, wherein an amino acid sequence constituting the ALS-associated signal peptide is any of amino acid sequences represented by SEQ ID Nos: 1 to 180.

11. The method according to claim 7, wherein at least 10 kinds of ALS-associated signal peptides having molecular weights differing by at least 3 from each other are tested in the bodily fluid from the test subject.

12. The method according to claim 7, wherein the bodily fluid is a cerebrospinal fluid.

\* \* \* \* \*

SEQUENCE LISTING

```
<160> NUMBER OF SEQ ID NOS: 1580

<210> SEQ ID NO 1
<211> LENGTH: 14
<212> TYPE: PRT
<213> ORGANISM: Homo sapiens

<400> SEQUENCE: 1

Met Leu Leu Pro Leu Leu Leu Leu Leu Pro Met Cys Trp Ala
1               5                   10

<210> SEQ ID NO 2
<211> LENGTH: 16
<212> TYPE: PRT
<213> ORGANISM: Homo sapiens

<400> SEQUENCE: 2

Met Leu Leu Ile Leu Leu Ser Val Ala Leu Leu Ala Leu Ser Ser Ala
1               5                   10                  15

<210> SEQ ID NO 3
<211> LENGTH: 16
<212> TYPE: PRT
<213> ORGANISM: Homo sapiens

<400> SEQUENCE: 3

Met Leu Leu Ile Leu Leu Ser Val Ala Leu Leu Ala Leu Ser Ser Ala
1               5                   10                  15

<210> SEQ ID NO 4
<211> LENGTH: 16
<212> TYPE: PRT
<213> ORGANISM: Homo sapiens

<400> SEQUENCE: 4

Met Leu Phe Leu Leu Leu Pro Leu Leu Ala Val Leu Pro Gly Asp Gly
1               5                   10                  15

<210> SEQ ID NO 5
<211> LENGTH: 16
<212> TYPE: PRT
<213> ORGANISM: Homo sapiens

<400> SEQUENCE: 5

Met Thr Ala Glu Phe Leu Ser Leu Leu Cys Leu Gly Leu Cys Leu Gly
1               5                   10                  15

<210> SEQ ID NO 6
<211> LENGTH: 17
```

-continued

```
<212> TYPE: PRT
<213> ORGANISM: Homo sapiens

<400> SEQUENCE: 6

Met Leu Leu Ser Val Pro Leu Leu Leu Gly Leu Leu Gly Leu Ala Val
1               5                   10                  15

Ala

<210> SEQ ID NO 7
<211> LENGTH: 18
<212> TYPE: PRT
<213> ORGANISM: Homo sapiens

<400> SEQUENCE: 7

Met Lys Pro Leu Leu Leu Ala Val Ser Leu Gly Leu Ile Ala Ala Leu
1               5                   10                  15

Gln Ala

<210> SEQ ID NO 8
<211> LENGTH: 18
<212> TYPE: PRT
<213> ORGANISM: Homo sapiens

<400> SEQUENCE: 8

Met Lys Ala Ala Val Leu Thr Leu Ala Val Leu Phe Leu Thr Gly Ser
1               5                   10                  15

Gln Ala

<210> SEQ ID NO 9
<211> LENGTH: 17
<212> TYPE: PRT
<213> ORGANISM: Homo sapiens

<400> SEQUENCE: 9

Met Trp Leu Gln Ser Leu Leu Leu Leu Gly Thr Val Ala Cys Ser Ile
1               5                   10                  15

Ser

<210> SEQ ID NO 10
<211> LENGTH: 15
<212> TYPE: PRT
<213> ORGANISM: Homo sapiens

<400> SEQUENCE: 10

Met Lys Phe Phe Leu Leu Leu Phe Thr Ile Gly Phe Cys Trp Ala
1               5                   10                  15

<210> SEQ ID NO 11
<211> LENGTH: 15
<212> TYPE: PRT
<213> ORGANISM: Homo sapiens

<400> SEQUENCE: 11

Met Lys Phe Phe Leu Leu Leu Phe Thr Ile Gly Phe Cys Trp Ala
1               5                   10                  15

<210> SEQ ID NO 12
<211> LENGTH: 17
<212> TYPE: PRT
<213> ORGANISM: Homo sapiens

<400> SEQUENCE: 12
```

```
Met His Leu Leu Leu Phe Gln Leu Leu Val Leu Pro Leu Gly Lys
1               5                   10                  15

Thr

<210> SEQ ID NO 13
<211> LENGTH: 18
<212> TYPE: PRT
<213> ORGANISM: Homo sapiens

<400> SEQUENCE: 13

Met Glu Lys Leu Leu Cys Phe Leu Val Leu Thr Ser Leu Ser His Ala
1               5                   10                  15

Phe Gly

<210> SEQ ID NO 14
<211> LENGTH: 21
<212> TYPE: PRT
<213> ORGANISM: Homo sapiens

<400> SEQUENCE: 14

Met Ala Ala Ala Leu Ala Leu Val Ala Gly Val Leu Ser Gly Ala Val
1               5                   10                  15

Leu Pro Leu Trp Ser
            20

<210> SEQ ID NO 15
<211> LENGTH: 20
<212> TYPE: PRT
<213> ORGANISM: Homo sapiens

<400> SEQUENCE: 15

Met Lys Gly Leu Ala Ala Ala Leu Leu Val Leu Val Cys Thr Met Ala
1               5                   10                  15

Leu Cys Ser Cys
            20

<210> SEQ ID NO 16
<211> LENGTH: 19
<212> TYPE: PRT
<213> ORGANISM: Homo sapiens

<400> SEQUENCE: 16

Met Asn Leu Ala Ile Ser Ile Ala Leu Leu Leu Thr Val Leu Gln Val
1               5                   10                  15

Ser Arg Gly

<210> SEQ ID NO 17
<211> LENGTH: 20
<212> TYPE: PRT
<213> ORGANISM: Homo sapiens

<400> SEQUENCE: 17

Met Gly Arg Leu Gln Leu Val Val Leu Gly Leu Thr Cys Cys Trp Ala
1               5                   10                  15

Val Ala Ser Ala
            20

<210> SEQ ID NO 18
<211> LENGTH: 21
<212> TYPE: PRT
<213> ORGANISM: Homo sapiens
```

-continued

```
<400> SEQUENCE: 18

Met Lys Val Ser Val Ala Ala Leu Ser Cys Leu Met Leu Val Ala Val
1               5                   10                  15

Leu Gly Ser Gln Ala
            20

<210> SEQ ID NO 19
<211> LENGTH: 18
<212> TYPE: PRT
<213> ORGANISM: Homo sapiens

<400> SEQUENCE: 19

Met Arg Leu Leu Pro Arg Leu Leu Leu Leu Leu Leu Leu Val Phe Pro
1               5                   10                  15

Ala Thr

<210> SEQ ID NO 20
<211> LENGTH: 21
<212> TYPE: PRT
<213> ORGANISM: Homo sapiens

<400> SEQUENCE: 20

Met Lys Val Ser Val Ala Ala Leu Ser Cys Leu Met Leu Val Thr Ala
1               5                   10                  15

Leu Gly Ser Gln Ala
            20

<210> SEQ ID NO 21
<211> LENGTH: 21
<212> TYPE: PRT
<213> ORGANISM: Homo sapiens

<400> SEQUENCE: 21

Met Gln Gly Pro Pro Leu Leu Thr Ala Ala His Leu Leu Cys Val Cys
1               5                   10                  15

Thr Ala Ala Leu Ala
            20

<210> SEQ ID NO 22
<211> LENGTH: 20
<212> TYPE: PRT
<213> ORGANISM: Homo sapiens

<400> SEQUENCE: 22

Met Ala Leu Pro Phe Ala Leu Leu Met Ala Leu Val Val Leu Ser Cys
1               5                   10                  15

Lys Ser Ser Cys
            20

<210> SEQ ID NO 23
<211> LENGTH: 18
<212> TYPE: PRT
<213> ORGANISM: Homo sapiens

<400> SEQUENCE: 23

Met Asn Gln Leu Ser Phe Leu Leu Phe Leu Ile Ala Thr Thr Arg Gly
1               5                   10                  15

Trp Ser

<210> SEQ ID NO 24
<211> LENGTH: 23
```

<212> TYPE: PRT
<213> ORGANISM: Homo sapiens

<400> SEQUENCE: 24

Met Thr Pro Gly Ala Leu Leu Met Leu Leu Gly Ala Leu Gly Ala Pro
1               5                   10                  15

Leu Ala Pro Gly Val Arg Gly
            20

<210> SEQ ID NO 25
<211> LENGTH: 21
<212> TYPE: PRT
<213> ORGANISM: Homo sapiens

<400> SEQUENCE: 25

Met Gln Ala Ala Trp Leu Leu Gly Ala Leu Val Val Pro Gln Leu Leu
1               5                   10                  15

Gly Phe Gly His Gly
            20

<210> SEQ ID NO 26
<211> LENGTH: 20
<212> TYPE: PRT
<213> ORGANISM: Homo sapiens

<400> SEQUENCE: 26

Met Glu Lys Ile Pro Val Ser Ala Phe Leu Leu Leu Val Ala Leu Ser
1               5                   10                  15

Tyr Thr Leu Ala
            20

<210> SEQ ID NO 27
<211> LENGTH: 19
<212> TYPE: PRT
<213> ORGANISM: Homo sapiens

<400> SEQUENCE: 27

Met His Ser Phe Pro Pro Leu Leu Leu Leu Leu Phe Trp Gly Val Val
1               5                   10                  15

Ser His Ser

<210> SEQ ID NO 28
<211> LENGTH: 21
<212> TYPE: PRT
<213> ORGANISM: Homo sapiens

<400> SEQUENCE: 28

Met Met Leu His Ser Ala Leu Gly Leu Cys Leu Leu Leu Val Thr Val
1               5                   10                  15

Ser Ser Asn Leu Ala
            20

<210> SEQ ID NO 29
<211> LENGTH: 21
<212> TYPE: PRT
<213> ORGANISM: Homo sapiens

<400> SEQUENCE: 29

Met Ala Leu Leu Leu Ala Leu Ser Leu Leu Val Leu Trp Thr Ser Pro
1               5                   10                  15

Ala Pro Thr Leu Ser
            20

```
<210> SEQ ID NO 30
<211> LENGTH: 21
<212> TYPE: PRT
<213> ORGANISM: Homo sapiens

<400> SEQUENCE: 30

Met Ala Ala Arg Leu Leu Leu Gly Ile Leu Leu Leu Leu Pro
1               5                   10                  15

Leu Pro Val Pro Ala
            20

<210> SEQ ID NO 31
<211> LENGTH: 21
<212> TYPE: PRT
<213> ORGANISM: Homo sapiens

<400> SEQUENCE: 31

Met Ser Ala Cys Arg Ser Phe Ala Val Ala Ile Cys Ile Leu Glu Ile
1               5                   10                  15

Ser Ile Leu Thr Ala
            20

<210> SEQ ID NO 32
<211> LENGTH: 19
<212> TYPE: PRT
<213> ORGANISM: Homo sapiens

<400> SEQUENCE: 32

Met Glu Leu Ser Trp His Val Val Phe Ile Ala Leu Leu Ser Phe Ser
1               5                   10                  15

Cys Trp Gly

<210> SEQ ID NO 33
<211> LENGTH: 22
<212> TYPE: PRT
<213> ORGANISM: Homo sapiens

<400> SEQUENCE: 33

Met Gly Ala Met Thr Gln Leu Leu Ala Gly Val Phe Leu Ala Phe Leu
1               5                   10                  15

Ala Leu Ala Thr Glu Gly
            20

<210> SEQ ID NO 34
<211> LENGTH: 20
<212> TYPE: PRT
<213> ORGANISM: Homo sapiens

<400> SEQUENCE: 34

Met Tyr Arg Met Gln Leu Leu Ser Cys Ile Ala Leu Ser Leu Ala Leu
1               5                   10                  15

Val Thr Asn Ser
            20

<210> SEQ ID NO 35
<211> LENGTH: 23
<212> TYPE: PRT
<213> ORGANISM: Homo sapiens

<400> SEQUENCE: 35

Met Gly Leu Gly Pro Val Phe Leu Leu Leu Ala Gly Ile Phe Pro Phe
```

```
1               5                   10                  15

Ala Pro Pro Gly Ala Ala Ala
            20

<210> SEQ ID NO 36
<211> LENGTH: 22
<212> TYPE: PRT
<213> ORGANISM: Homo sapiens

<400> SEQUENCE: 36

Met Ile Pro Ala Arg Phe Ala Gly Val Leu Leu Ala Leu Ala Leu Ile
1               5                   10                  15

Leu Pro Gly Thr Leu Cys
            20

<210> SEQ ID NO 37
<211> LENGTH: 21
<212> TYPE: PRT
<213> ORGANISM: Homo sapiens

<400> SEQUENCE: 37

Met Ala Gln Gly Val Leu Trp Ile Leu Leu Gly Leu Leu Leu Trp Ser
1               5                   10                  15

Asp Pro Gly Thr Ala
            20

<210> SEQ ID NO 38
<211> LENGTH: 23
<212> TYPE: PRT
<213> ORGANISM: Homo sapiens

<400> SEQUENCE: 38

Met Lys Val Thr Gly Ile Phe Leu Leu Ser Ala Leu Ala Leu Leu Ser
1               5                   10                  15

Leu Ser Gly Asn Thr Gly Ala
            20

<210> SEQ ID NO 39
<211> LENGTH: 21
<212> TYPE: PRT
<213> ORGANISM: Homo sapiens

<400> SEQUENCE: 39

Met Ala Ser Arg Trp Ala Val Gln Leu Leu Val Ala Ala Trp Ser
1               5                   10                  15

Met Gly Cys Gly Glu
            20

<210> SEQ ID NO 40
<211> LENGTH: 23
<212> TYPE: PRT
<213> ORGANISM: Homo sapiens

<400> SEQUENCE: 40

Met Ala Glu Leu Pro Gly Pro Phe Leu Cys Gly Ala Leu Leu Gly Phe
1               5                   10                  15

Leu Cys Leu Ser Gly Leu Ala
            20

<210> SEQ ID NO 41
<211> LENGTH: 20
<212> TYPE: PRT
```

<213> ORGANISM: Homo sapiens

<400> SEQUENCE: 41

Met Gly Leu Phe Met Ile Ile Ala Ile Leu Phe Gln Lys Pro Thr
1               5                   10                  15
Val Thr Glu Gln
            20

<210> SEQ ID NO 42
<211> LENGTH: 25
<212> TYPE: PRT
<213> ORGANISM: Homo sapiens

<400> SEQUENCE: 42

Met Asp Arg Gly Thr Leu Pro Leu Ala Val Ala Leu Leu Leu Ala Ser
1               5                   10                  15
Cys Ser Leu Ser Pro Thr Ser Leu Ala
            20                  25

<210> SEQ ID NO 43
<211> LENGTH: 23
<212> TYPE: PRT
<213> ORGANISM: Homo sapiens

<400> SEQUENCE: 43

Met Pro Gly Phe Leu Val Arg Ile Leu Pro Leu Leu Leu Val Leu Leu
1               5                   10                  15
Leu Leu Gly Pro Thr Arg Gly
            20

<210> SEQ ID NO 44
<211> LENGTH: 23
<212> TYPE: PRT
<213> ORGANISM: Homo sapiens

<400> SEQUENCE: 44

Met Lys Pro Ile Gln Lys Leu Leu Ala Gly Leu Ile Leu Leu Thr Trp
1               5                   10                  15
Cys Val Glu Gly Cys Ser Ser
            20

<210> SEQ ID NO 45
<211> LENGTH: 24
<212> TYPE: PRT
<213> ORGANISM: Homo sapiens

<400> SEQUENCE: 45

Met Leu Gly Ala Arg Leu Arg Leu Trp Val Cys Ala Leu Cys Ser Val
1               5                   10                  15
Cys Ser Met Ser Val Leu Arg Ala
            20

<210> SEQ ID NO 46
<211> LENGTH: 24
<212> TYPE: PRT
<213> ORGANISM: Homo sapiens

<400> SEQUENCE: 46

Met Gly Gln Pro Ser Leu Thr Trp Met Leu Met Val Val Val Ala Ser
1               5                   10                  15
Trp Phe Ile Thr Thr Ala Ala Thr
            20

<210> SEQ ID NO 47
<211> LENGTH: 24
<212> TYPE: PRT
<213> ORGANISM: Homo sapiens

<400> SEQUENCE: 47

Met Arg Val Thr Ala Pro Arg Thr Leu Leu Leu Leu Trp Gly Ala
1               5                   10                  15

Leu Ala Leu Thr Glu Thr Trp Ala
            20

<210> SEQ ID NO 48
<211> LENGTH: 24
<212> TYPE: PRT
<213> ORGANISM: Homo sapiens

<400> SEQUENCE: 48

Met Arg Val Thr Ala Pro Arg Thr Leu Leu Leu Leu Trp Gly Ala
1               5                   10                  15

Leu Ala Leu Thr Glu Thr Trp Ala
            20

<210> SEQ ID NO 49
<211> LENGTH: 24
<212> TYPE: PRT
<213> ORGANISM: Homo sapiens

<400> SEQUENCE: 49

Met Arg Val Thr Ala Pro Arg Thr Leu Leu Leu Leu Trp Gly Ala
1               5                   10                  15

Leu Ala Leu Thr Glu Thr Trp Ala
            20

<210> SEQ ID NO 50
<211> LENGTH: 24
<212> TYPE: PRT
<213> ORGANISM: Homo sapiens

<400> SEQUENCE: 50

Met Arg Val Thr Ala Pro Arg Thr Leu Leu Leu Leu Trp Gly Ala
1               5                   10                  15

Leu Ala Leu Thr Glu Thr Trp Ala
            20

<210> SEQ ID NO 51
<211> LENGTH: 24
<212> TYPE: PRT
<213> ORGANISM: Homo sapiens

<400> SEQUENCE: 51

Met Arg Val Thr Ala Pro Arg Thr Leu Leu Leu Leu Trp Gly Ala
1               5                   10                  15

Leu Ala Leu Thr Glu Thr Trp Ala
            20

<210> SEQ ID NO 52
<211> LENGTH: 26
<212> TYPE: PRT
<213> ORGANISM: Homo sapiens

<400> SEQUENCE: 52

```
Met Ala Ala Ala Ser Arg Ser Ala Ser Gly Trp Ala Leu Leu Leu Leu
1               5                   10                  15

Val Ala Leu Trp Gln Gln Arg Ala Ala Gly
            20                  25
```

<210> SEQ ID NO 53
<211> LENGTH: 29
<212> TYPE: PRT
<213> ORGANISM: Homo sapiens

<400> SEQUENCE: 53

```
Met Glu Ser Arg Gly Pro Leu Ala Thr Ser Arg Leu Leu Leu Leu Leu
1               5                   10                  15

Leu Leu Leu Leu Leu Arg His Thr Arg Gln Gly Trp Ala
            20                  25
```

<210> SEQ ID NO 54
<211> LENGTH: 14
<212> TYPE: PRT
<213> ORGANISM: Homo sapiens

<400> SEQUENCE: 54

```
Met Ile Leu Pro Leu His Asn Leu Gly Asn Gly Val Arg Ser
1               5                   10
```

<210> SEQ ID NO 55
<211> LENGTH: 16
<212> TYPE: PRT
<213> ORGANISM: Homo sapiens

<400> SEQUENCE: 55

```
Met Ala Pro Pro Leu Leu Leu Leu Leu Ala Ser Gly Ala Ala Ala
1               5                   10                  15
```

<210> SEQ ID NO 56
<211> LENGTH: 16
<212> TYPE: PRT
<213> ORGANISM: Homo sapiens

<400> SEQUENCE: 56

```
Met Leu Leu Ile Leu Leu Ser Val Ala Leu Leu Ala Leu Ser Ser Ala
1               5                   10                  15
```

<210> SEQ ID NO 57
<211> LENGTH: 16
<212> TYPE: PRT
<213> ORGANISM: Homo sapiens

<400> SEQUENCE: 57

```
Met Leu Leu Ile Leu Leu Ser Val Ala Leu Leu Ala Leu Ser Ser Ala
1               5                   10                  15
```

<210> SEQ ID NO 58
<211> LENGTH: 16
<212> TYPE: PRT
<213> ORGANISM: Homo sapiens

<400> SEQUENCE: 58

```
Met Thr Leu Arg Leu Leu Val Ala Ala Leu Cys Ala Gly Ile Leu Ala
1               5                   10                  15
```

<210> SEQ ID NO 59
<211> LENGTH: 15
<212> TYPE: PRT

<213> ORGANISM: Homo sapiens

<400> SEQUENCE: 59

Met Met Leu Arg Leu Leu Ser Ser Leu Leu Val Ala Val Ala
1               5                   10                  15

<210> SEQ ID NO 60
<211> LENGTH: 15
<212> TYPE: PRT
<213> ORGANISM: Homo sapiens

<400> SEQUENCE: 60

Met Met Leu Arg Leu Leu Ser Ser Leu Leu Val Ala Val Ala
1               5                   10                  15

<210> SEQ ID NO 61
<211> LENGTH: 15
<212> TYPE: PRT
<213> ORGANISM: Homo sapiens

<400> SEQUENCE: 61

Met Val Leu Leu Leu Leu Val Ala Ile Pro Leu Leu Val His Ser
1               5                   10                  15

<210> SEQ ID NO 62
<211> LENGTH: 17
<212> TYPE: PRT
<213> ORGANISM: Homo sapiens

<400> SEQUENCE: 62

Met Gln Ala Arg Ala Leu Leu Leu Ala Ala Leu Ala Ala Leu Ala Leu
1               5                   10                  15

Ala

<210> SEQ ID NO 63
<211> LENGTH: 16
<212> TYPE: PRT
<213> ORGANISM: Homo sapiens

<400> SEQUENCE: 63

Met Asp Ala Pro Ala Arg Leu Leu Ala Pro Leu Leu Leu Cys Ala
1               5                   10                  15

<210> SEQ ID NO 64
<211> LENGTH: 15
<212> TYPE: PRT
<213> ORGANISM: Homo sapiens

<400> SEQUENCE: 64

Met Lys Leu Leu Leu Trp Ala Cys Ile Val Cys Val Ala Phe Ala
1               5                   10                  15

<210> SEQ ID NO 65
<211> LENGTH: 17
<212> TYPE: PRT
<213> ORGANISM: Homo sapiens

<400> SEQUENCE: 65

Met Gly Ser Arg Cys Ala Leu Ala Leu Ala Val Leu Ser Ala Leu Leu
1               5                   10                  15

Cys

<210> SEQ ID NO 66

```
<211> LENGTH: 17
<212> TYPE: PRT
<213> ORGANISM: Homo sapiens

<400> SEQUENCE: 66

Met Ala Cys Ala Ala Val Met Ile Pro Gly Leu Leu Arg Cys Ser Val
1               5                   10                  15
Gly

<210> SEQ ID NO 67
<211> LENGTH: 16
<212> TYPE: PRT
<213> ORGANISM: Homo sapiens

<400> SEQUENCE: 67

Met Lys Arg Leu Val Cys Val Leu Leu Val Cys Ser Ser Ala Val Ala
1               5                   10                  15

<210> SEQ ID NO 68
<211> LENGTH: 17
<212> TYPE: PRT
<213> ORGANISM: Homo sapiens

<400> SEQUENCE: 68

Met Ala Leu Leu Leu Val Ser Leu Leu Ala Phe Leu Ser Leu Gly Ser
1               5                   10                  15
Gly

<210> SEQ ID NO 69
<211> LENGTH: 17
<212> TYPE: PRT
<213> ORGANISM: Homo sapiens

<400> SEQUENCE: 69

Met Asn Pro Thr Leu Ile Leu Ala Ala Phe Cys Leu Gly Ile Ala Ser
1               5                   10                  15
Ala

<210> SEQ ID NO 70
<211> LENGTH: 18
<212> TYPE: PRT
<213> ORGANISM: Homo sapiens

<400> SEQUENCE: 70

Met Ile Thr Phe Leu Pro Leu Leu Leu Gly Leu Ser Leu Gly Cys Thr
1               5                   10                  15
Gly Ala

<210> SEQ ID NO 71
<211> LENGTH: 17
<212> TYPE: PRT
<213> ORGANISM: Homo sapiens

<400> SEQUENCE: 71

Met Leu Ala Val Leu Tyr Leu Leu Val Lys Thr Ala Lys Leu Gly Thr
1               5                   10                  15
Ser

<210> SEQ ID NO 72
<211> LENGTH: 19
<212> TYPE: PRT
<213> ORGANISM: Homo sapiens
```

```
<400> SEQUENCE: 72

Met Ala Pro Pro Ala Ala Arg Leu Ala Leu Leu Ser Ala Ala Ala Leu
1               5                   10                  15

Thr Leu Ala

<210> SEQ ID NO 73
<211> LENGTH: 17
<212> TYPE: PRT
<213> ORGANISM: Homo sapiens

<400> SEQUENCE: 73

Met Arg Pro Leu Leu Gly Leu Leu Leu Val Phe Ala Gly Cys Thr Phe
1               5                   10                  15

Ala

<210> SEQ ID NO 74
<211> LENGTH: 17
<212> TYPE: PRT
<213> ORGANISM: Homo sapiens

<400> SEQUENCE: 74

Met Pro Ser Leu Leu Leu Leu Phe Thr Ala Ala Leu Leu Ser Ser Trp
1               5                   10                  15

Ala

<210> SEQ ID NO 75
<211> LENGTH: 19
<212> TYPE: PRT
<213> ORGANISM: Homo sapiens

<400> SEQUENCE: 75

Met Ala Phe Arg Gln Ala Leu Gln Leu Ala Ala Cys Gly Leu Ala Gly
1               5                   10                  15

Gly Ser Ala

<210> SEQ ID NO 76
<211> LENGTH: 17
<212> TYPE: PRT
<213> ORGANISM: Homo sapiens

<400> SEQUENCE: 76

Met Pro Leu Leu Leu Leu Leu Pro Leu Leu Trp Ala Gly Ala Leu Ala
1               5                   10                  15

Met

<210> SEQ ID NO 77
<211> LENGTH: 19
<212> TYPE: PRT
<213> ORGANISM: Homo sapiens

<400> SEQUENCE: 77

Met Gly Ala Arg Gly Ala Leu Leu Leu Ala Leu Leu Leu Ala Arg Ala
1               5                   10                  15

Gly Leu Gly

<210> SEQ ID NO 78
<211> LENGTH: 17
<212> TYPE: PRT
<213> ORGANISM: Homo sapiens
```

<400> SEQUENCE: 78

Met Arg Pro Phe Phe Leu Leu Cys Phe Ala Leu Pro Gly Leu Leu His
1               5                   10                  15

Ala

<210> SEQ ID NO 79
<211> LENGTH: 17
<212> TYPE: PRT
<213> ORGANISM: Homo sapiens

<400> SEQUENCE: 79

Met Leu Leu Trp Pro Leu Leu Leu Leu Leu Leu Leu Pro Thr Leu
1               5                   10                  15

Ala

<210> SEQ ID NO 80
<211> LENGTH: 17
<212> TYPE: PRT
<213> ORGANISM: Homo sapiens

<400> SEQUENCE: 80

Met Tyr Leu Ser Ile Cys Cys Cys Phe Leu Leu Trp Ala Pro Ala Leu
1               5                   10                  15

Thr

<210> SEQ ID NO 81
<211> LENGTH: 18
<212> TYPE: PRT
<213> ORGANISM: Homo sapiens

<400> SEQUENCE: 81

Met Leu Arg Ile Leu Cys Leu Ala Leu Cys Ser Leu Leu Thr Gly Thr
1               5                   10                  15

Arg Ala

<210> SEQ ID NO 82
<211> LENGTH: 19
<212> TYPE: PRT
<213> ORGANISM: Homo sapiens

<400> SEQUENCE: 82

Met Leu Leu Trp Ala Ser Leu Leu Ala Phe Ala Pro Val Cys Gly Gln
1               5                   10                  15

Ser Ala Ala

<210> SEQ ID NO 83
<211> LENGTH: 19
<212> TYPE: PRT
<213> ORGANISM: Homo sapiens

<400> SEQUENCE: 83

Met Arg Phe Leu Ala Ala Thr Phe Leu Leu Leu Ala Leu Ser Thr Ala
1               5                   10                  15

Ala Gln Ala

<210> SEQ ID NO 84
<211> LENGTH: 20
<212> TYPE: PRT
<213> ORGANISM: Homo sapiens

<400> SEQUENCE: 84

```
Met Lys Ala Leu Gly Ala Val Leu Leu Ala Leu Leu Leu Cys Gly Arg
1               5                   10                  15

Pro Gly Arg Gly
            20
```

<210> SEQ ID NO 85
<211> LENGTH: 21
<212> TYPE: PRT
<213> ORGANISM: Homo sapiens

<400> SEQUENCE: 85

```
Met Val Pro Ser Ala Gly Gln Leu Ala Leu Phe Ala Leu Ala Asp Pro
1               5                   10                  15

Pro Val Ala Ala Ala
            20
```

<210> SEQ ID NO 86
<211> LENGTH: 19
<212> TYPE: PRT
<213> ORGANISM: Homo sapiens

<400> SEQUENCE: 86

```
Met Ser Leu Leu Leu Ser Phe Tyr Leu Leu Gly Leu Leu Val Ser Ser
1               5                   10                  15

Gly Gln Ala
```

<210> SEQ ID NO 87
<211> LENGTH: 21
<212> TYPE: PRT
<213> ORGANISM: Homo sapiens

<400> SEQUENCE: 87

```
Met Leu Gly Cys Gly Ile Pro Ala Leu Gly Leu Leu Leu Leu Leu Gln
1               5                   10                  15

Gly Ser Ala Asp Gly
            20
```

<210> SEQ ID NO 88
<211> LENGTH: 18
<212> TYPE: PRT
<213> ORGANISM: Homo sapiens

<400> SEQUENCE: 88

```
Met Ile Val Phe Ile Phe Leu Ala Met Gly Leu Ser Leu Glu Asn Glu
1               5                   10                  15

Tyr Thr
```

<210> SEQ ID NO 89
<211> LENGTH: 19
<212> TYPE: PRT
<213> ORGANISM: Homo sapiens

<400> SEQUENCE: 89

```
Met Phe Gly Thr Leu Leu Leu Tyr Cys Phe Phe Leu Ala Thr Val Pro
1               5                   10                  15

Ala Leu Ala
```

<210> SEQ ID NO 90
<211> LENGTH: 20
<212> TYPE: PRT
<213> ORGANISM: Homo sapiens -continued

<400> SEQUENCE: 90

Met Trp Pro Leu Thr Val Pro Pro Leu Leu Leu Leu Leu Cys Ser
1               5                   10                  15

Gly Leu Ala Gly
            20

<210> SEQ ID NO 91
<211> LENGTH: 21
<212> TYPE: PRT
<213> ORGANISM: Homo sapiens

<400> SEQUENCE: 91

Met Pro Val Ile Ala Gly Gly Ile Leu Ala Leu Leu Leu Leu Ile
1               5                   10                  15

Val Val Val Leu Cys
            20

<210> SEQ ID NO 92
<211> LENGTH: 20
<212> TYPE: PRT
<213> ORGANISM: Homo sapiens

<400> SEQUENCE: 92

Met Ala Gly Pro Glu Arg Trp Gly Pro Leu Leu Leu Cys Leu Leu Gln
1               5                   10                  15

Ala Ala Pro Gly
            20

<210> SEQ ID NO 93
<211> LENGTH: 19
<212> TYPE: PRT
<213> ORGANISM: Homo sapiens

<400> SEQUENCE: 93

Met Gly Ile Ser Thr Val Ile Leu Glu Met Cys Leu Leu Trp Gly Gln
1               5                   10                  15

Val Leu Ser

<210> SEQ ID NO 94
<211> LENGTH: 17
<212> TYPE: PRT
<213> ORGANISM: Homo sapiens

<400> SEQUENCE: 94

Met Arg Asp Ser Ala Cys Trp Ser Gln Arg Lys Asp Glu Leu Leu Gln
1               5                   10                  15

Gln

<210> SEQ ID NO 95
<211> LENGTH: 22
<212> TYPE: PRT
<213> ORGANISM: Homo sapiens

<400> SEQUENCE: 95

Met Gly Gly Pro Arg Ala Trp Ala Leu Leu Cys Leu Gly Leu Leu Leu
1               5                   10                  15

Pro Gly Gly Gly Ala Ala
            20

<210> SEQ ID NO 96

```
<211> LENGTH: 22
<212> TYPE: PRT
<213> ORGANISM: Homo sapiens

<400> SEQUENCE: 96

Met Ser Leu Met Val Val Ser Met Ala Cys Val Gly Val Leu Leu Ala
1               5                   10                  15

Ala Gly Gly Leu Ala Thr
            20

<210> SEQ ID NO 97
<211> LENGTH: 18
<212> TYPE: PRT
<213> ORGANISM: Homo sapiens

<400> SEQUENCE: 97

Met Leu Pro Phe Leu Phe Phe Ser Thr Leu Phe Ser Ser Ile Phe Thr
1               5                   10                  15

Glu Ala

<210> SEQ ID NO 98
<211> LENGTH: 20
<212> TYPE: PRT
<213> ORGANISM: Homo sapiens

<400> SEQUENCE: 98

Met Thr Pro Gln Leu Leu Leu Ala Leu Val Leu Trp Ala Ser Cys Pro
1               5                   10                  15

Pro Cys Ser Gly
            20

<210> SEQ ID NO 99
<211> LENGTH: 22
<212> TYPE: PRT
<213> ORGANISM: Homo sapiens

<400> SEQUENCE: 99

Met Pro Ala Gly Arg Ala Ala Arg Thr Cys Ala Leu Leu Ala Leu Cys
1               5                   10                  15

Leu Leu Gly Ala Gly Ala
            20

<210> SEQ ID NO 100
<211> LENGTH: 19
<212> TYPE: PRT
<213> ORGANISM: Homo sapiens

<400> SEQUENCE: 100

Met Ile Pro Gly Asn Arg Met Leu Met Val Val Leu Leu Cys Gln Val
1               5                   10                  15

Leu Leu Gly

<210> SEQ ID NO 101
<211> LENGTH: 20
<212> TYPE: PRT
<213> ORGANISM: Homo sapiens

<400> SEQUENCE: 101

Met Phe Ala Val Val Phe Phe Ile Leu Ser Leu Met Thr Cys Gln Pro
1               5                   10                  15

Gly Val Thr Ala
            20
```

<210> SEQ ID NO 102
<211> LENGTH: 19
<212> TYPE: PRT
<213> ORGANISM: Homo sapiens

<400> SEQUENCE: 102

Met Lys Tyr Val Phe Tyr Leu Gly Val Leu Ala Gly Thr Phe Phe Phe
1               5                   10                  15

Ala Asp Ser

<210> SEQ ID NO 103
<211> LENGTH: 19
<212> TYPE: PRT
<213> ORGANISM: Homo sapiens

<400> SEQUENCE: 103

Met Leu Leu Trp Thr Ala Val Leu Leu Phe Val Pro Cys Val Gly Lys
1               5                   10                  15

Thr Val Trp

<210> SEQ ID NO 104
<211> LENGTH: 21
<212> TYPE: PRT
<213> ORGANISM: Homo sapiens

<400> SEQUENCE: 104

Met Ala Thr Leu Ser Phe Val Phe Leu Leu Leu Gly Ala Val Ser Trp
1               5                   10                  15

Pro Pro Ala Ser Ala
            20

<210> SEQ ID NO 105
<211> LENGTH: 20
<212> TYPE: PRT
<213> ORGANISM: Homo sapiens

<400> SEQUENCE: 105

Met Asn Asn Leu Ser Phe Ser Glu Leu Cys Cys Leu Phe Cys Cys Pro
1               5                   10                  15

Pro Cys Pro Gly
            20

<210> SEQ ID NO 106
<211> LENGTH: 21
<212> TYPE: PRT
<213> ORGANISM: Homo sapiens

<400> SEQUENCE: 106

Met Val Ala Thr Lys Thr Phe Ala Leu Leu Leu Leu Ser Leu Phe Leu
1               5                   10                  15

Ala Val Gly Leu Gly
            20

<210> SEQ ID NO 107
<211> LENGTH: 19
<212> TYPE: PRT
<213> ORGANISM: Homo sapiens

<400> SEQUENCE: 107

Met Asn Ser Leu Val Ser Trp Gln Leu Leu Leu Phe Leu Cys Ala Thr
1               5                   10                  15

His Phe Gly

<210> SEQ ID NO 108
<211> LENGTH: 20
<212> TYPE: PRT
<213> ORGANISM: Homo sapiens

<400> SEQUENCE: 108

Met Lys Leu Leu Leu Thr Leu Thr Val Leu Leu Leu Ser Gln
1               5                   10                  15

Leu Thr Pro Gly
            20

<210> SEQ ID NO 109
<211> LENGTH: 20
<212> TYPE: PRT
<213> ORGANISM: Homo sapiens

<400> SEQUENCE: 109

Met Arg Ser Ser Leu Thr Met Val Gly Thr Leu Trp Ala Phe Leu Ser
1               5                   10                  15

Leu Val Thr Ala
            20

<210> SEQ ID NO 110
<211> LENGTH: 22
<212> TYPE: PRT
<213> ORGANISM: Homo sapiens

<400> SEQUENCE: 110

Met Ala Ser Leu Val Ser Leu Glu Leu Gly Leu Leu Leu Ala Val Leu
1               5                   10                  15

Val Val Thr Ala Thr Ala
            20

<210> SEQ ID NO 111
<211> LENGTH: 20
<212> TYPE: PRT
<213> ORGANISM: Homo sapiens

<400> SEQUENCE: 111

Met Lys Ala Phe His Thr Phe Cys Val Val Leu Leu Val Phe Gly Ser
1               5                   10                  15

Val Ser Glu Ala
            20

<210> SEQ ID NO 112
<211> LENGTH: 20
<212> TYPE: PRT
<213> ORGANISM: Homo sapiens

<400> SEQUENCE: 112

Met Gly Gly Thr Leu Ala Trp Thr Leu Leu Leu Pro Leu Leu Leu Arg
1               5                   10                  15

Glu Ser Asp Ser
            20

<210> SEQ ID NO 113
<211> LENGTH: 22
<212> TYPE: PRT
<213> ORGANISM: Homo sapiens

```
<400> SEQUENCE: 113

Met Glu Phe Val Arg Ala Leu Trp Leu Gly Leu Ala Leu Ala Leu Gly
1               5                   10                  15

Pro Gly Ser Ala Gly Gly
            20

<210> SEQ ID NO 114
<211> LENGTH: 19
<212> TYPE: PRT
<213> ORGANISM: Homo sapiens

<400> SEQUENCE: 114

Met Arg Thr Leu Phe Asn Leu Leu Trp Leu Ala Leu Ala Cys Ser Pro
1               5                   10                  15

Val His Thr

<210> SEQ ID NO 115
<211> LENGTH: 20
<212> TYPE: PRT
<213> ORGANISM: Homo sapiens

<400> SEQUENCE: 115

Met Lys Ile Leu Val Ala Phe Leu Val Val Leu Thr Ile Phe Gly Ile
1               5                   10                  15

Gln Ser His Gly
            20

<210> SEQ ID NO 116
<211> LENGTH: 21
<212> TYPE: PRT
<213> ORGANISM: Homo sapiens

<400> SEQUENCE: 116

Met Glu Pro His Leu Leu Gly Leu Leu Gly Leu Leu Gly Gly
1               5                   10                  15

Thr Arg Val Leu Ala
            20

<210> SEQ ID NO 117
<211> LENGTH: 19
<212> TYPE: PRT
<213> ORGANISM: Homo sapiens

<400> SEQUENCE: 117

Met Arg Arg Cys Arg Trp Ala Ala Leu Ala Leu Gly Leu Leu Arg Leu
1               5                   10                  15

Cys Leu Ala

<210> SEQ ID NO 118
<211> LENGTH: 20
<212> TYPE: PRT
<213> ORGANISM: Homo sapiens

<400> SEQUENCE: 118

Met Lys Phe Leu Ile Phe Ala Phe Phe Gly Gly Val His Leu Leu Ser
1               5                   10                  15

Leu Cys Ser Gly
            20

<210> SEQ ID NO 119
<211> LENGTH: 19
```

```
<212> TYPE: PRT
<213> ORGANISM: Homo sapiens

<400> SEQUENCE: 119

Met Met Leu Leu Ile Leu Phe Leu Val Ile Ile Cys Ser His Ile Ser
1               5                   10                  15

Val Asn Gln

<210> SEQ ID NO 120
<211> LENGTH: 22
<212> TYPE: PRT
<213> ORGANISM: Homo sapiens

<400> SEQUENCE: 120

Met Cys Pro Gly Ala Leu Trp Val Ala Leu Pro Leu Leu Ser Leu Leu
1               5                   10                  15

Ala Gly Ser Leu Gln Gly
            20

<210> SEQ ID NO 121
<211> LENGTH: 22
<212> TYPE: PRT
<213> ORGANISM: Homo sapiens

<400> SEQUENCE: 121

Met Leu Ala Glu Trp Gly Ala Cys Leu Leu Ala Val Ala Leu Leu
1               5                   10                  15

Gly Pro Gly Leu Gln Ala
            20

<210> SEQ ID NO 122
<211> LENGTH: 22
<212> TYPE: PRT
<213> ORGANISM: Homo sapiens

<400> SEQUENCE: 122

Met Arg Gly Thr Arg Leu Ala Leu Leu Ala Leu Val Leu Ala Ala Cys
1               5                   10                  15

Gly Glu Leu Ala Pro Ala
            20

<210> SEQ ID NO 123
<211> LENGTH: 24
<212> TYPE: PRT
<213> ORGANISM: Homo sapiens

<400> SEQUENCE: 123

Met Met Lys Arg Ala Ala Ala Ala Val Gly Gly Ala Leu Ala Val
1               5                   10                  15

Gly Ala Val Pro Val Val Leu Ser
            20

<210> SEQ ID NO 124
<211> LENGTH: 23
<212> TYPE: PRT
<213> ORGANISM: Homo sapiens

<400> SEQUENCE: 124

Met Glu Ala Cys Val Ser Ser Leu Leu Val Leu Ala Leu Gly Ala Leu
1               5                   10                  15

Ser Val Gly Ser Ser Phe Gly
            20
```

-continued

<210> SEQ ID NO 125
<211> LENGTH: 22
<212> TYPE: PRT
<213> ORGANISM: Homo sapiens

<400> SEQUENCE: 125

Met Ala Val Arg Ala Leu Lys Leu Leu Thr Thr Leu Leu Ala Val Val
1               5                   10                  15

Ala Ala Ala Ser Gln Ala
            20

<210> SEQ ID NO 126
<211> LENGTH: 21
<212> TYPE: PRT
<213> ORGANISM: Homo sapiens

<400> SEQUENCE: 126

Met Pro Val Pro Ala Leu Cys Leu Leu Trp Ala Leu Ala Met Val Thr
1               5                   10                  15

Arg Pro Ala Ser Ala
            20

<210> SEQ ID NO 127
<211> LENGTH: 20
<212> TYPE: PRT
<213> ORGANISM: Homo sapiens

<400> SEQUENCE: 127

Met Ser Asn Ser Val Pro Leu Leu Cys Phe Trp Ser Leu Cys Tyr Cys
1               5                   10                  15

Phe Ala Ala Gly
            20

<210> SEQ ID NO 128
<211> LENGTH: 23
<212> TYPE: PRT
<213> ORGANISM: Homo sapiens

<400> SEQUENCE: 128

Met Ala Gly Gly Arg Cys Gly Pro Gln Leu Thr Ala Leu Leu Ala Ala
1               5                   10                  15

Trp Ile Ala Ala Val Ala Ala
            20

<210> SEQ ID NO 129
<211> LENGTH: 24
<212> TYPE: PRT
<213> ORGANISM: Homo sapiens

<400> SEQUENCE: 129

Met Pro Gly Pro Leu Gly Leu Leu Cys Phe Leu Ala Leu Gly Leu Leu
1               5                   10                  15

Gly Ser Ala Gly Pro Ser Gly Ala
            20

<210> SEQ ID NO 130
<211> LENGTH: 21
<212> TYPE: PRT
<213> ORGANISM: Homo sapiens

<400> SEQUENCE: 130

Met Ser Ala Cys Arg Ser Phe Ala Val Ala Ile Cys Ile Leu Glu Ile
1               5                   10                  15

Ser Ile Leu Thr Ala
            20

<210> SEQ ID NO 131
<211> LENGTH: 20
<212> TYPE: PRT
<213> ORGANISM: Homo sapiens

<400> SEQUENCE: 131

Met Glu Thr Leu Cys Leu Arg Ala Ser Phe Trp Leu Ala Leu Val Gly
1               5                   10                  15

Cys Val Ile Ser
            20

<210> SEQ ID NO 132
<211> LENGTH: 20
<212> TYPE: PRT
<213> ORGANISM: Homo sapiens

<400> SEQUENCE: 132

Met Arg Leu Gly Leu Cys Val Val Ala Leu Val Leu Ser Trp Thr His
1               5                   10                  15

Leu Thr Ile Ser
            20

<210> SEQ ID NO 133
<211> LENGTH: 21
<212> TYPE: PRT
<213> ORGANISM: Homo sapiens

<400> SEQUENCE: 133

Met Pro Leu Pro Trp Ser Leu Ala Leu Pro Leu Leu Ser Trp Val
1               5                   10                  15

Ala Gly Gly Phe Gly
            20

<210> SEQ ID NO 134
<211> LENGTH: 19
<212> TYPE: PRT
<213> ORGANISM: Homo sapiens

<400> SEQUENCE: 134

Met Trp Pro Ser Gln Leu Leu Ile Phe Met Met Leu Leu Ala Pro Ile
1               5                   10                  15

Ile His Ala

<210> SEQ ID NO 135
<211> LENGTH: 21
<212> TYPE: PRT
<213> ORGANISM: Homo sapiens

<400> SEQUENCE: 135

Met Gly Pro Ser Thr Pro Leu Leu Ile Leu Phe Leu Leu Ser Trp Ser
1               5                   10                  15

Gly Pro Leu Gln Gly
            20

<210> SEQ ID NO 136
<211> LENGTH: 21
<212> TYPE: PRT

<213> ORGANISM: Homo sapiens

<400> SEQUENCE: 136

Met Asn Ser Leu Ser Trp Gly Ala Ala Asn Ala Val Leu Leu Leu Leu
1               5                   10                  15

Leu Leu Ala Trp Ala
            20

<210> SEQ ID NO 137
<211> LENGTH: 22
<212> TYPE: PRT
<213> ORGANISM: Homo sapiens

<400> SEQUENCE: 137

Met Ala Leu Gly Thr Thr Leu Arg Ala Ser Leu Leu Leu Leu Gly Leu
1               5                   10                  15

Leu Thr Glu Gly Leu Ala
            20

<210> SEQ ID NO 138
<211> LENGTH: 20
<212> TYPE: PRT
<213> ORGANISM: Homo sapiens

<400> SEQUENCE: 138

Met Met Arg Thr Cys Val Leu Leu Ser Ala Val Leu Trp Cys Leu Thr
1               5                   10                  15

Gly Val Gln Cys
            20

<210> SEQ ID NO 139
<211> LENGTH: 19
<212> TYPE: PRT
<213> ORGANISM: Homo sapiens

<400> SEQUENCE: 139

Met Ile Arg Lys Leu Phe Ile Val Leu Leu Leu Leu Val Thr Ile
1               5                   10                  15

Glu Glu Ala

<210> SEQ ID NO 140
<211> LENGTH: 19
<212> TYPE: PRT
<213> ORGANISM: Homo sapiens

<400> SEQUENCE: 140

Met His Leu Leu Gly Pro Trp Leu Leu Leu Val Leu Glu Tyr Leu
1               5                   10                  15

Ala Phe Ser

<210> SEQ ID NO 141
<211> LENGTH: 21
<212> TYPE: PRT
<213> ORGANISM: Homo sapiens

<400> SEQUENCE: 141

Met Phe Glu Ser Phe Asn Val Pro Gly Leu Tyr Ile Ala Val Gln Ala
1               5                   10                  15

Val Leu Ala Leu Ala
            20

-continued

```
<210> SEQ ID NO 142
<211> LENGTH: 20
<212> TYPE: PRT
<213> ORGANISM: Homo sapiens

<400> SEQUENCE: 142

Met Gln Pro Val Met Leu Ala Leu Trp Ser Leu Leu Leu Trp Gly
1               5                   10                  15

Leu Ala Thr Pro
            20

<210> SEQ ID NO 143
<211> LENGTH: 21
<212> TYPE: PRT
<213> ORGANISM: Homo sapiens

<400> SEQUENCE: 143

Met Pro Leu Lys His Tyr Leu Leu Leu Val Gly Cys Gln Ala Trp
1               5                   10                  15

Gly Ala Gly Leu Ala
            20

<210> SEQ ID NO 144
<211> LENGTH: 23
<212> TYPE: PRT
<213> ORGANISM: Homo sapiens

<400> SEQUENCE: 144

Met Ala Gly Val Arg Ala Arg Ala Pro Leu Pro Leu Ala Leu Leu
1               5                   10                  15

Ser Leu Pro Ala Ala Pro Gly
            20

<210> SEQ ID NO 145
<211> LENGTH: 21
<212> TYPE: PRT
<213> ORGANISM: Homo sapiens

<400> SEQUENCE: 145

Met Leu Leu Pro Gln Leu Cys Trp Leu Pro Leu Leu Ala Gly Leu Leu
1               5                   10                  15

Pro Pro Val Pro Ala
            20

<210> SEQ ID NO 146
<211> LENGTH: 22
<212> TYPE: PRT
<213> ORGANISM: Homo sapiens

<400> SEQUENCE: 146

Met Ser Leu Phe Gly Leu Leu Leu Thr Ser Ala Leu Ala Gly Gln
1               5                   10                  15

Arg Gln Gly Thr Gln Ala
            20

<210> SEQ ID NO 147
<211> LENGTH: 25
<212> TYPE: PRT
<213> ORGANISM: Homo sapiens

<400> SEQUENCE: 147

Met Ser Gly Ala Pro Thr Ala Gly Ala Ala Leu Met Leu Cys Ala Ala
1               5                   10                  15
```

Thr Ala Val Leu Leu Ser Ala Gln Gly
            20                  25

<210> SEQ ID NO 148
<211> LENGTH: 21
<212> TYPE: PRT
<213> ORGANISM: Homo sapiens

<400> SEQUENCE: 148

Met Gly Leu Gln Phe Ser Gln Val Ile Ser Ile Cys Trp Ala Ala Met
1               5                   10                  15

Gly Ser Leu Tyr Ala
            20

<210> SEQ ID NO 149
<211> LENGTH: 25
<212> TYPE: PRT
<213> ORGANISM: Homo sapiens

<400> SEQUENCE: 149

Met Pro Gly Ala Ala Glu Ala Leu Pro Thr Val Thr Val Thr Leu Val
1               5                   10                  15

Ala Gly Ala Val Pro Pro Ala Ser Gly
            20                  25

<210> SEQ ID NO 150
<211> LENGTH: 20
<212> TYPE: PRT
<213> ORGANISM: Homo sapiens

<400> SEQUENCE: 150

Met Arg Pro Arg Lys Ala Phe Leu Leu Leu Leu Leu Gly Leu Val
1               5                   10                  15

Gln Leu Leu Ala
            20

<210> SEQ ID NO 151
<211> LENGTH: 24
<212> TYPE: PRT
<213> ORGANISM: Homo sapiens

<400> SEQUENCE: 151

Met Ala Arg Ser Ala Thr Leu Ala Ala Ala Leu Ala Leu Cys Leu
1               5                   10                  15

Leu Leu Ala Pro Pro Gly Leu Ala
            20

<210> SEQ ID NO 152
<211> LENGTH: 21
<212> TYPE: PRT
<213> ORGANISM: Homo sapiens

<400> SEQUENCE: 152

Met Glu Ser Leu Leu Leu Pro Val Leu Leu Leu Ala Ile Leu Trp
1               5                   10                  15

Thr Gln Ala Ala Ala
            20

<210> SEQ ID NO 153
<211> LENGTH: 23
<212> TYPE: PRT
<213> ORGANISM: Homo sapiens

```
<400> SEQUENCE: 153

Met Gly Ala Met Ala Tyr Pro Leu Leu Leu Cys Leu Leu Leu Ala Gln
1               5                   10                  15

Leu Gly Leu Gly Ala Val Gly
            20

<210> SEQ ID NO 154
<211> LENGTH: 21
<212> TYPE: PRT
<213> ORGANISM: Homo sapiens

<400> SEQUENCE: 154

Met Gly Pro Pro Leu Pro Leu Leu Leu Leu Leu Leu Leu Leu Leu Pro
1               5                   10                  15

Pro Arg Val Leu Pro
            20

<210> SEQ ID NO 155
<211> LENGTH: 20
<212> TYPE: PRT
<213> ORGANISM: Homo sapiens

<400> SEQUENCE: 155

Met Ser Gly Asn Trp Val His Pro Gly Gln Ile Leu Ile Trp Ala Ile
1               5                   10                  15

Trp Val Leu Ala
            20

<210> SEQ ID NO 156
<211> LENGTH: 20
<212> TYPE: PRT
<213> ORGANISM: Homo sapiens

<400> SEQUENCE: 156

Met Arg Arg Trp Ala Trp Ala Ala Val Val Leu Leu Gly Pro Gln
1               5                   10                  15

Leu Val Leu Leu
            20

<210> SEQ ID NO 157
<211> LENGTH: 19
<212> TYPE: PRT
<213> ORGANISM: Homo sapiens

<400> SEQUENCE: 157

Met Arg Leu Pro Asp Val Gln Leu Trp Leu Val Leu Trp Ala Leu
1               5                   10                  15

Val Arg Ala

<210> SEQ ID NO 158
<211> LENGTH: 22
<212> TYPE: PRT
<213> ORGANISM: Homo sapiens

<400> SEQUENCE: 158

Met Arg Cys Ala Leu Ala Leu Ser Ala Leu Leu Leu Leu Leu Ser Thr
1               5                   10                  15

Pro Pro Leu Leu Pro Ser
            20
```

```
<210> SEQ ID NO 159
<211> LENGTH: 23
<212> TYPE: PRT
<213> ORGANISM: Homo sapiens

<400> SEQUENCE: 159

Met Ala Trp Gln Met Met Gln Leu Leu Leu Ala Leu Val Thr Ala
1               5                   10                  15

Ala Gly Ser Ala Gln Pro Arg
            20

<210> SEQ ID NO 160
<211> LENGTH: 22
<212> TYPE: PRT
<213> ORGANISM: Homo sapiens

<400> SEQUENCE: 160

Met Arg Val Leu Phe Phe Val Phe Gly Val Leu Ser Leu Met Phe Thr
1               5                   10                  15

Val Pro Pro Gly Arg Ser
            20

<210> SEQ ID NO 161
<211> LENGTH: 20
<212> TYPE: PRT
<213> ORGANISM: Homo sapiens

<400> SEQUENCE: 161

Met Asp Met Phe Pro Leu Thr Trp Val Phe Leu Ala Leu Tyr Phe Ser
1               5                   10                  15

Arg His Gln Val
            20

<210> SEQ ID NO 162
<211> LENGTH: 23
<212> TYPE: PRT
<213> ORGANISM: Homo sapiens

<400> SEQUENCE: 162

Met Pro Met Ala Ser Pro Gln Thr Leu Val Leu Tyr Leu Leu Val Leu
1               5                   10                  15

Ala Val Thr Glu Ala Trp Gly
            20

<210> SEQ ID NO 163
<211> LENGTH: 23
<212> TYPE: PRT
<213> ORGANISM: Homo sapiens

<400> SEQUENCE: 163

Met Asp Val Arg Ala Leu Pro Trp Leu Pro Trp Leu Leu Trp Leu Leu
1               5                   10                  15

Cys Arg Gly Gly Gly Asp Ala
            20

<210> SEQ ID NO 164
<211> LENGTH: 26
<212> TYPE: PRT
<213> ORGANISM: Homo sapiens

<400> SEQUENCE: 164

Met Asp Thr Thr Ala Ala Ala Ala Leu Pro Ala Phe Val Ala Leu Leu
1               5                   10                  15
```

```
Leu Leu Ser Pro Trp Pro Leu Leu Gly Ser
            20                  25

<210> SEQ ID NO 165
<211> LENGTH: 28
<212> TYPE: PRT
<213> ORGANISM: Homo sapiens

<400> SEQUENCE: 165

Met Ala Arg Leu Gly Ala Leu Leu Ala Ala Ala Leu Gly Ala Leu
1               5                   10                  15

Leu Ser Phe Ala Leu Leu Ala Ala Ala Val Ala Ser
            20                  25

<210> SEQ ID NO 166
<211> LENGTH: 25
<212> TYPE: PRT
<213> ORGANISM: Homo sapiens

<400> SEQUENCE: 166

Met Ala Arg His Gly Leu Pro Leu Leu Pro Leu Leu Ser Leu Leu Val
1               5                   10                  15

Gly Ala Trp Leu Lys Leu Gly Asn Gly
            20                  25

<210> SEQ ID NO 167
<211> LENGTH: 24
<212> TYPE: PRT
<213> ORGANISM: Homo sapiens

<400> SEQUENCE: 167

Met Thr Ala Trp Ile Leu Leu Pro Val Ser Leu Ser Ala Phe Ser Ile
1               5                   10                  15

Thr Gly Ile Trp Thr Val Tyr Ala
            20

<210> SEQ ID NO 168
<211> LENGTH: 25
<212> TYPE: PRT
<213> ORGANISM: Homo sapiens

<400> SEQUENCE: 168

Met Arg Val Thr Ala Pro Arg Thr Val Leu Leu Leu Leu Ser Gly Ala
1               5                   10                  15

Leu Ala Leu Thr Glu Thr Trp Ala Gly
            20                  25

<210> SEQ ID NO 169
<211> LENGTH: 23
<212> TYPE: PRT
<213> ORGANISM: Homo sapiens

<400> SEQUENCE: 169

Met Met Asn Met Ser Leu Pro Phe Leu Trp Ser Leu Leu Thr Leu Leu
1               5                   10                  15

Ile Phe Ala Glu Val Asn Gly
            20

<210> SEQ ID NO 170
<211> LENGTH: 26
<212> TYPE: PRT
<213> ORGANISM: Homo sapiens
```

<400> SEQUENCE: 170

Met Ala Arg Pro Asp Pro Ser Ala Pro Pro Ser Leu Leu Leu Leu Leu
1               5                   10                  15

Leu Ala Gln Leu Val Gly Arg Ala Ala Ala
            20                  25

<210> SEQ ID NO 171
<211> LENGTH: 25
<212> TYPE: PRT
<213> ORGANISM: Homo sapiens

<400> SEQUENCE: 171

Met Leu Val Met Ala Pro Arg Thr Val Leu Leu Leu Ser Ala Ala
1               5                   10                  15

Leu Ala Leu Thr Glu Thr Trp Ala Gly
            20                  25

<210> SEQ ID NO 172
<211> LENGTH: 25
<212> TYPE: PRT
<213> ORGANISM: Homo sapiens

<400> SEQUENCE: 172

Met Leu Val Met Ala Pro Arg Thr Val Leu Leu Leu Ser Ala Ala
1               5                   10                  15

Leu Ala Leu Thr Glu Thr Trp Ala Gly
            20                  25

<210> SEQ ID NO 173
<211> LENGTH: 24
<212> TYPE: PRT
<213> ORGANISM: Homo sapiens

<400> SEQUENCE: 173

Met Ala Thr Ser Thr Gly Arg Trp Leu Leu Leu Arg Leu Ala Leu Phe
1               5                   10                  15

Gly Phe Leu Trp Glu Ala Ser Gly
            20

<210> SEQ ID NO 174
<211> LENGTH: 25
<212> TYPE: PRT
<213> ORGANISM: Homo sapiens

<400> SEQUENCE: 174

Met Ala Trp Gly Gly Val His Thr Cys Cys Phe His Leu Cys Cys Cys
1               5                   10                  15

Cys Ser Trp Pro Gln Gly Ala Val Pro
            20                  25

<210> SEQ ID NO 175
<211> LENGTH: 24
<212> TYPE: PRT
<213> ORGANISM: Homo sapiens

<400> SEQUENCE: 175

Met Arg Val Thr Ala Pro Arg Thr Leu Leu Leu Leu Leu Trp Gly Ala
1               5                   10                  15

Leu Ala Leu Thr Glu Thr Trp Ala
            20

<210> SEQ ID NO 176
<211> LENGTH: 29
<212> TYPE: PRT
<213> ORGANISM: Homo sapiens

<400> SEQUENCE: 176

Met Gly Gly Pro Ala Ala Pro Arg Gly Ala Gly Arg Leu Arg Ala Leu
1               5                   10                  15

Leu Leu Ala Leu Val Val Ala Gly Ile Pro Ala Gly Ala
            20                  25

<210> SEQ ID NO 177
<211> LENGTH: 24
<212> TYPE: PRT
<213> ORGANISM: Homo sapiens

<400> SEQUENCE: 177

Met Leu Ala Ala Ser Ile Phe Arg Pro Thr Leu Leu Leu Cys Trp Leu
1               5                   10                  15

Ala Ala Pro Trp Pro Thr Gln Pro
            20

<210> SEQ ID NO 178
<211> LENGTH: 25
<212> TYPE: PRT
<213> ORGANISM: Homo sapiens

<400> SEQUENCE: 178

Met Arg Gln Arg Leu Leu Pro Ser Val Thr Ser Leu Leu Leu Val Ala
1               5                   10                  15

Leu Leu Phe Pro Gly Ser Ser Gln Ala
            20                  25

<210> SEQ ID NO 179
<211> LENGTH: 30
<212> TYPE: PRT
<213> ORGANISM: Homo sapiens

<400> SEQUENCE: 179

Met Cys Pro Ser Glu Met Gly Thr Leu Trp His His Trp Ser Pro Val
1               5                   10                  15

Leu Ile Ser Leu Ala Ala Leu Phe Ser Lys Val Thr Glu Gly
            20                  25                  30

<210> SEQ ID NO 180
<211> LENGTH: 29
<212> TYPE: PRT
<213> ORGANISM: Homo sapiens

<400> SEQUENCE: 180

Met Ala Pro Arg Ala Arg Arg Arg Pro Leu Phe Ala Leu Leu Leu
1               5                   10                  15

Leu Cys Ala Leu Leu Ala Arg Leu Gln Val Ala Leu Gln
            20                  25

<210> SEQ ID NO 181
<211> LENGTH: 16
<212> TYPE: PRT
<213> ORGANISM: Homo sapiens

<400> SEQUENCE: 181

Met Leu Thr Val Ala Leu Leu Ala Leu Leu Cys Ala Ser Ala Ser Gly

<210> SEQ ID NO 182
<211> LENGTH: 15
<212> TYPE: PRT
<213> ORGANISM: Homo sapiens

<400> SEQUENCE: 182

Met Asn Leu Leu Leu Ile Leu Thr Phe Val Ala Ala Ala Val Ala
1               5                   10                  15

<210> SEQ ID NO 183
<211> LENGTH: 15
<212> TYPE: PRT
<213> ORGANISM: Homo sapiens

<400> SEQUENCE: 183

Met Arg Leu Ile Leu Pro Val Gly Leu Ile Ala Thr Thr Leu Ala
1               5                   10                  15

<210> SEQ ID NO 184
<211> LENGTH: 15
<212> TYPE: PRT
<213> ORGANISM: Homo sapiens

<400> SEQUENCE: 184

Met Leu Arg Val Leu Val Gly Ala Val Leu Pro Ala Met Leu Leu
1               5                   10                  15

<210> SEQ ID NO 185
<211> LENGTH: 16
<212> TYPE: PRT
<213> ORGANISM: Homo sapiens

<400> SEQUENCE: 185

Met Tyr Ala Leu Phe Leu Leu Ala Ser Leu Leu Gly Ala Ala Leu Ala
1               5                   10                  15

<210> SEQ ID NO 186
<211> LENGTH: 16
<212> TYPE: PRT
<213> ORGANISM: Homo sapiens

<400> SEQUENCE: 186

Met Arg Gly Leu Leu Val Leu Ser Val Leu Leu Gly Ala Val Phe Gly
1               5                   10                  15

<210> SEQ ID NO 187
<211> LENGTH: 16
<212> TYPE: PRT
<213> ORGANISM: Homo sapiens

<400> SEQUENCE: 187

Met Leu Pro Leu Trp Thr Leu Ser Leu Leu Leu Gly Ala Val Ala Gly
1               5                   10                  15

<210> SEQ ID NO 188
<211> LENGTH: 16
<212> TYPE: PRT
<213> ORGANISM: Homo sapiens

<400> SEQUENCE: 188

Met Lys Leu Pro Leu Leu Leu Ala Leu Leu Phe Gly Ala Val Ser Ala
1               5                   10                  15

<210> SEQ ID NO 189
<211> LENGTH: 16
<212> TYPE: PRT
<213> ORGANISM: Homo sapiens

<400> SEQUENCE: 189

Met Ile Arg Thr Leu Leu Leu Ser Thr Leu Val Ala Gly Ala Leu Ser
1               5                   10                  15

<210> SEQ ID NO 190
<211> LENGTH: 16
<212> TYPE: PRT
<213> ORGANISM: Homo sapiens

<400> SEQUENCE: 190

Met Ile Arg Thr Leu Leu Leu Ser Thr Leu Val Ala Gly Ala Leu Ser
1               5                   10                  15

<210> SEQ ID NO 191
<211> LENGTH: 16
<212> TYPE: PRT
<213> ORGANISM: Homo sapiens

<400> SEQUENCE: 191

Met Leu Leu Ile Leu Leu Ser Val Ala Leu Leu Ala Phe Ser Ser Ala
1               5                   10                  15

<210> SEQ ID NO 192
<211> LENGTH: 16
<212> TYPE: PRT
<213> ORGANISM: Homo sapiens

<400> SEQUENCE: 192

Met Lys Val Ser Ala Val Leu Leu Cys Leu Leu Leu Met Thr Ala Ala
1               5                   10                  15

<210> SEQ ID NO 193
<211> LENGTH: 17
<212> TYPE: PRT
<213> ORGANISM: Homo sapiens

<400> SEQUENCE: 193

Met Leu Ala Ala Thr Val Leu Thr Leu Ala Leu Leu Gly Asn Ala His
1               5                   10                  15

Ala

<210> SEQ ID NO 194
<211> LENGTH: 16
<212> TYPE: PRT
<213> ORGANISM: Homo sapiens

<400> SEQUENCE: 194

Met Gly Thr Trp Ile Leu Phe Ala Cys Leu Leu Gly Ala Ala Phe Ala
1               5                   10                  15

<210> SEQ ID NO 195
<211> LENGTH: 17
<212> TYPE: PRT
<213> ORGANISM: Homo sapiens

<400> SEQUENCE: 195

Met Ala Leu Phe Gly Ala Leu Phe Leu Ala Leu Leu Ala Gly Ala His
1               5                   10                  15

Ala

<210> SEQ ID NO 196
<211> LENGTH: 15
<212> TYPE: PRT
<213> ORGANISM: Homo sapiens

<400> SEQUENCE: 196

Met Lys Trp Leu Leu Leu Gly Leu Val Ala Leu Ser Glu Cys
1               5                   10                  15

<210> SEQ ID NO 197
<211> LENGTH: 18
<212> TYPE: PRT
<213> ORGANISM: Homo sapiens

<400> SEQUENCE: 197

Met Gly Ala Pro Arg Ser Leu Leu Leu Ala Leu Ala Ala Gly Leu Ala
1               5                   10                  15

Val Ala

<210> SEQ ID NO 198
<211> LENGTH: 19
<212> TYPE: PRT
<213> ORGANISM: Homo sapiens

<400> SEQUENCE: 198

Met Leu Ala Val Gly Cys Ala Leu Leu Ala Ala Leu Leu Ala Ala Pro
1               5                   10                  15

Gly Ala Ala

<210> SEQ ID NO 199
<211> LENGTH: 18
<212> TYPE: PRT
<213> ORGANISM: Homo sapiens

<400> SEQUENCE: 199

Met Leu Gly Val Leu Val Leu Gly Ala Leu Ala Leu Ala Gly Leu Gly
1               5                   10                  15

Phe Pro

<210> SEQ ID NO 200
<211> LENGTH: 16
<212> TYPE: PRT
<213> ORGANISM: Homo sapiens

<400> SEQUENCE: 200

Met Ala Leu Arg Val Leu Leu Leu Thr Ala Leu Thr Leu Cys His Gly
1               5                   10                  15

<210> SEQ ID NO 201
<211> LENGTH: 18
<212> TYPE: PRT
<213> ORGANISM: Homo sapiens

<400> SEQUENCE: 201

Met Leu Ala Leu Leu Cys Ser Cys Leu Leu Leu Ala Ala Gly Ala Ser
1               5                   10                  15

Asp Ala

<210> SEQ ID NO 202
<211> LENGTH: 16

```
<212> TYPE: PRT
<213> ORGANISM: Homo sapiens

<400> SEQUENCE: 202

Met Lys Arg Val Leu Val Leu Leu Ala Val Ala Phe Gly His Ala
1               5                   10                  15

<210> SEQ ID NO 203
<211> LENGTH: 17
<212> TYPE: PRT
<213> ORGANISM: Homo sapiens

<400> SEQUENCE: 203

Met Ser Leu Val Leu Leu Ser Leu Ala Ala Leu Cys Arg Ser Ala Val
1               5                   10                  15

Pro

<210> SEQ ID NO 204
<211> LENGTH: 17
<212> TYPE: PRT
<213> ORGANISM: Homo sapiens

<400> SEQUENCE: 204

Met Val Pro Val Leu Leu Ser Leu Leu Leu Leu Leu Gly Pro Ala Val
1               5                   10                  15

Pro

<210> SEQ ID NO 205
<211> LENGTH: 17
<212> TYPE: PRT
<213> ORGANISM: Homo sapiens

<400> SEQUENCE: 205

Met Arg Leu Thr Val Leu Cys Ala Val Cys Leu Leu Pro Gly Ser Leu
1               5                   10                  15

Ala

<210> SEQ ID NO 206
<211> LENGTH: 17
<212> TYPE: PRT
<213> ORGANISM: Homo sapiens

<400> SEQUENCE: 206

Met Ala Leu Asp Tyr Leu Leu Leu Leu Leu Ala Ser Ala Val Ala
1               5                   10                  15

Ala

<210> SEQ ID NO 207
<211> LENGTH: 17
<212> TYPE: PRT
<213> ORGANISM: Homo sapiens

<400> SEQUENCE: 207

Met Val Trp Lys Val Ala Val Phe Leu Ser Val Ala Leu Gly Ile Gly
1               5                   10                  15

Ala

<210> SEQ ID NO 208
<211> LENGTH: 18
<212> TYPE: PRT
<213> ORGANISM: Homo sapiens
```

```
<400> SEQUENCE: 208

Met Ser Leu Ser Ala Phe Thr Leu Phe Leu Ala Leu Ile Gly Gly Thr
1               5                   10                  15

Ser Gly

<210> SEQ ID NO 209
<211> LENGTH: 18
<212> TYPE: PRT
<213> ORGANISM: Homo sapiens

<400> SEQUENCE: 209

Met Leu Cys Leu Leu Leu Thr Leu Gly Val Ala Leu Val Cys Gly Val
1               5                   10                  15

Pro Ala

<210> SEQ ID NO 210
<211> LENGTH: 18
<212> TYPE: PRT
<213> ORGANISM: Homo sapiens

<400> SEQUENCE: 210

Met Arg Ser Ala Ala Val Leu Ala Leu Leu Leu Cys Ala Gly Gln Val
1               5                   10                  15

Thr Ala

<210> SEQ ID NO 211
<211> LENGTH: 16
<212> TYPE: PRT
<213> ORGANISM: Homo sapiens

<400> SEQUENCE: 211

Met Phe Arg Leu Trp Leu Leu Leu Ala Gly Leu Cys Gly Leu Leu Ala
1               5                   10                  15

<210> SEQ ID NO 212
<211> LENGTH: 15
<212> TYPE: PRT
<213> ORGANISM: Homo sapiens

<400> SEQUENCE: 212

Met Trp Phe Leu Thr Thr Leu Leu Leu Trp Val Pro Val Asp Gly
1               5                   10                  15

<210> SEQ ID NO 213
<211> LENGTH: 16
<212> TYPE: PRT
<213> ORGANISM: Homo sapiens

<400> SEQUENCE: 213

Met Arg Ser Thr Ile Leu Leu Phe Cys Leu Leu Gly Ser Thr Arg Ser
1               5                   10                  15

<210> SEQ ID NO 214
<211> LENGTH: 17
<212> TYPE: PRT
<213> ORGANISM: Homo sapiens

<400> SEQUENCE: 214

Met Ala Arg Ile Leu Leu Leu Phe Leu Pro Gly Leu Val Ala Val Cys
1               5                   10                  15

Ala
```

<210> SEQ ID NO 215
<211> LENGTH: 18
<212> TYPE: PRT
<213> ORGANISM: Homo sapiens

<400> SEQUENCE: 215

Met Val Ala Ala Val Leu Leu Gly Leu Ser Trp Leu Cys Ser Pro Leu
1               5                   10                  15

Gly Ala

<210> SEQ ID NO 216
<211> LENGTH: 19
<212> TYPE: PRT
<213> ORGANISM: Homo sapiens

<400> SEQUENCE: 216

Met Ala Gly Pro Ser Leu Ala Cys Cys Leu Leu Gly Leu Leu Ala Leu
1               5                   10                  15

Thr Ser Ala

<210> SEQ ID NO 217
<211> LENGTH: 18
<212> TYPE: PRT
<213> ORGANISM: Homo sapiens

<400> SEQUENCE: 217

Met Leu Leu Ala Met Val Leu Thr Ser Ala Leu Leu Leu Cys Ser Val
1               5                   10                  15

Ala Gly

<210> SEQ ID NO 218
<211> LENGTH: 18
<212> TYPE: PRT
<213> ORGANISM: Homo sapiens

<400> SEQUENCE: 218

Met Gln Pro Ser Ser Leu Leu Pro Leu Ala Leu Cys Leu Leu Ala Ala
1               5                   10                  15

Pro Ala

<210> SEQ ID NO 219
<211> LENGTH: 15
<212> TYPE: PRT
<213> ORGANISM: Homo sapiens

<400> SEQUENCE: 219

Met Trp Cys Ile Val Leu Phe Ser Leu Leu Ala Trp Val Tyr Ala
1               5                   10                  15

<210> SEQ ID NO 220
<211> LENGTH: 17
<212> TYPE: PRT
<213> ORGANISM: Homo sapiens

<400> SEQUENCE: 220

Met Leu Arg Arg Ala Leu Leu Cys Leu Ala Val Ala Ala Leu Val Arg
1               5                   10                  15

Ala

<210> SEQ ID NO 221
<211> LENGTH: 18

```
<212> TYPE: PRT
<213> ORGANISM: Homo sapiens

<400> SEQUENCE: 221

Met Lys Ala Leu Ile Val Leu Gly Leu Val Leu Leu Ser Val Thr Val
1               5                   10                  15

Gln Gly

<210> SEQ ID NO 222
<211> LENGTH: 17
<212> TYPE: PRT
<213> ORGANISM: Homo sapiens

<400> SEQUENCE: 222

Met Ala Leu Leu Phe Leu Leu Pro Leu Val Met Gln Gly Val Ser Arg
1               5                   10                  15

Ala

<210> SEQ ID NO 223
<211> LENGTH: 16
<212> TYPE: PRT
<213> ORGANISM: Homo sapiens

<400> SEQUENCE: 223

Met Thr Thr Leu Leu Trp Val Phe Val Thr Leu Arg Val Ile Thr Ala
1               5                   10                  15

<210> SEQ ID NO 224
<211> LENGTH: 19
<212> TYPE: PRT
<213> ORGANISM: Homo sapiens

<400> SEQUENCE: 224

Met Gly Ser Gly Leu Pro Leu Val Leu Leu Leu Thr Leu Leu Gly Ser
1               5                   10                  15

Ser His Gly

<210> SEQ ID NO 225
<211> LENGTH: 18
<212> TYPE: PRT
<213> ORGANISM: Homo sapiens

<400> SEQUENCE: 225

Met Gly Thr Gln Glu Gly Trp Cys Leu Leu Leu Cys Leu Ala Leu Ser
1               5                   10                  15

Gly Ala

<210> SEQ ID NO 226
<211> LENGTH: 18
<212> TYPE: PRT
<213> ORGANISM: Homo sapiens

<400> SEQUENCE: 226

Met Lys Leu Leu Thr Gly Leu Val Phe Cys Ser Leu Val Leu Gly Val
1               5                   10                  15

Ser Ser

<210> SEQ ID NO 227
<211> LENGTH: 18
<212> TYPE: PRT
<213> ORGANISM: Homo sapiens
```

<400> SEQUENCE: 227

Met Ser Ala Leu Gly Ala Val Ile Ala Leu Leu Leu Trp Gly Gln Leu
1               5                   10                  15

Phe Ala

<210> SEQ ID NO 228
<211> LENGTH: 16
<212> TYPE: PRT
<213> ORGANISM: Homo sapiens

<400> SEQUENCE: 228

Met Lys Trp Met Val Val Leu Val Cys Leu Gln Leu Leu Glu Ala
1               5                   10                  15

<210> SEQ ID NO 229
<211> LENGTH: 17
<212> TYPE: PRT
<213> ORGANISM: Homo sapiens

<400> SEQUENCE: 229

Met Leu Leu Lys Thr Val Leu Leu Gly His Val Ala Gln Val Leu
1               5                   10                  15

Met

<210> SEQ ID NO 230
<211> LENGTH: 18
<212> TYPE: PRT
<213> ORGANISM: Homo sapiens

<400> SEQUENCE: 230

Met Lys Leu Leu Ala Ala Thr Val Leu Leu Thr Ile Cys Ser Leu
1               5                   10                  15

Glu Gly

<210> SEQ ID NO 231
<211> LENGTH: 18
<212> TYPE: PRT
<213> ORGANISM: Homo sapiens

<400> SEQUENCE: 231

Met Arg Ala Cys Ile Ser Leu Val Leu Ala Val Leu Cys Gly Leu Ala
1               5                   10                  15

Trp Ala

<210> SEQ ID NO 232
<211> LENGTH: 20
<212> TYPE: PRT
<213> ORGANISM: Homo sapiens

<400> SEQUENCE: 232

Met Lys Leu Ala Ala Leu Leu Gly Leu Cys Val Ala Leu Ser Cys Ser
1               5                   10                  15

Ser Ala Ala Ala
            20

<210> SEQ ID NO 233
<211> LENGTH: 18
<212> TYPE: PRT
<213> ORGANISM: Homo sapiens

<400> SEQUENCE: 233

Met Gln Pro Phe Leu Leu Leu Leu Ala Phe Leu Leu Thr Pro Gly Ala
1               5                   10                  15

Gly Thr

<210> SEQ ID NO 234
<211> LENGTH: 18
<212> TYPE: PRT
<213> ORGANISM: Homo sapiens

<400> SEQUENCE: 234

Met Gly Leu Ala Trp Gly Leu Gly Val Leu Phe Leu Met His Val Cys
1               5                   10                  15

Gly Thr

<210> SEQ ID NO 235
<211> LENGTH: 16
<212> TYPE: PRT
<213> ORGANISM: Homo sapiens

<400> SEQUENCE: 235

Met Trp Ser Gly Trp Trp Leu Trp Pro Leu Val Ala Val Cys Thr Ala
1               5                   10                  15

<210> SEQ ID NO 236
<211> LENGTH: 18
<212> TYPE: PRT
<213> ORGANISM: Homo sapiens

<400> SEQUENCE: 236

Met Phe Ala Leu Gly Leu Pro Phe Leu Val Leu Leu Val Ala Ser Val
1               5                   10                  15

Glu Ser

<210> SEQ ID NO 237
<211> LENGTH: 20
<212> TYPE: PRT
<213> ORGANISM: Homo sapiens

<400> SEQUENCE: 237

Met Leu Pro Pro Gly Thr Ala Thr Leu Leu Thr Leu Leu Leu Ala Ala
1               5                   10                  15

Gly Ser Leu Gly
            20

<210> SEQ ID NO 238
<211> LENGTH: 18
<212> TYPE: PRT
<213> ORGANISM: Homo sapiens

<400> SEQUENCE: 238

Met Gln Pro Leu Leu Leu Leu Ala Phe Leu Leu Pro Thr Gly Ala
1               5                   10                  15

Glu Ala

<210> SEQ ID NO 239
<211> LENGTH: 16
<212> TYPE: PRT
<213> ORGANISM: Homo sapiens

<400> SEQUENCE: 239

Met Val Trp Lys Trp Met Pro Leu Leu Leu Leu Val Cys Val Ala
1               5                   10                  15

<210> SEQ ID NO 240
<211> LENGTH: 17
<212> TYPE: PRT
<213> ORGANISM: Homo sapiens

<400> SEQUENCE: 240

Met Trp Val Pro Val Val Phe Leu Thr Leu Ser Val Thr Trp Ile Gly
1               5                   10                  15

Ala

<210> SEQ ID NO 241
<211> LENGTH: 19
<212> TYPE: PRT
<213> ORGANISM: Homo sapiens

<400> SEQUENCE: 241

Met Ala Trp Ser Leu Gly Ser Trp Leu Gly Gly Cys Leu Leu Val Ser
1               5                   10                  15

Ala Leu Gly

<210> SEQ ID NO 242
<211> LENGTH: 18
<212> TYPE: PRT
<213> ORGANISM: Homo sapiens

<400> SEQUENCE: 242

Met Trp Leu Leu Val Ser Val Ile Leu Ile Ser Arg Ile Ser Ser Val
1               5                   10                  15

Gly Gly

<210> SEQ ID NO 243
<211> LENGTH: 19
<212> TYPE: PRT
<213> ORGANISM: Homo sapiens

<400> SEQUENCE: 243

Met Lys Leu Ala Ser Gly Phe Leu Val Leu Trp Leu Ser Leu Gly Gly
1               5                   10                  15

Gly Leu Ala

<210> SEQ ID NO 244
<211> LENGTH: 17
<212> TYPE: PRT
<213> ORGANISM: Homo sapiens

<400> SEQUENCE: 244

Met Lys Val Leu Leu Arg Leu Ile Cys Phe Ile Ala Leu Leu Ile Ser
1               5                   10                  15

Ser

<210> SEQ ID NO 245
<211> LENGTH: 18
<212> TYPE: PRT
<213> ORGANISM: Homo sapiens

<400> SEQUENCE: 245

Met Lys Val Leu Trp Ala Ala Leu Leu Val Thr Phe Leu Ala Gly Cys
1               5                   10                  15

Gln Ala

<210> SEQ ID NO 246
<211> LENGTH: 18
<212> TYPE: PRT
<213> ORGANISM: Homo sapiens

<400> SEQUENCE: 246

Met Lys Ala Leu Ile Ala Ala Leu Leu Leu Ile Thr Leu Gln Tyr Ser
1               5                   10                  15

Cys Ala

<210> SEQ ID NO 247
<211> LENGTH: 20
<212> TYPE: PRT
<213> ORGANISM: Homo sapiens

<400> SEQUENCE: 247

Met Asn Ser Gly Val Cys Leu Cys Val Leu Met Ala Val Leu Ala Ala
1               5                   10                  15

Gly Ala Leu Thr
            20

<210> SEQ ID NO 248
<211> LENGTH: 23
<212> TYPE: PRT
<213> ORGANISM: Homo sapiens

<400> SEQUENCE: 248

Met Glu Ala Val Ala Val Ala Ala Ala Val Gly Val Leu Leu Leu Ala
1               5                   10                  15

Gly Ala Gly Gly Ala Ala Gly
            20

<210> SEQ ID NO 249
<211> LENGTH: 17
<212> TYPE: PRT
<213> ORGANISM: Homo sapiens

<400> SEQUENCE: 249

Met Lys Leu Val Asn Ile Trp Leu Leu Leu Val Val Leu Leu Cys
1               5                   10                  15

Gly

<210> SEQ ID NO 250
<211> LENGTH: 19
<212> TYPE: PRT
<213> ORGANISM: Homo sapiens

<400> SEQUENCE: 250

Met Gln Ala Leu Val Leu Leu Leu Cys Ile Gly Ala Leu Leu Gly His
1               5                   10                  15

Ser Ser Cys

<210> SEQ ID NO 251
<211> LENGTH: 22
<212> TYPE: PRT
<213> ORGANISM: Homo sapiens

<400> SEQUENCE: 251

Met Gly Ala Pro Ala Cys Ala Leu Ala Leu Cys Val Ala Val Ala Ile
1               5                   10                  15

Val Ala Gly Ala Ser Ser

<210> SEQ ID NO 252
<211> LENGTH: 19
<212> TYPE: PRT
<213> ORGANISM: Homo sapiens

<400> SEQUENCE: 252

Met Gly Leu Gln Ala Cys Leu Leu Gly Leu Phe Ala Leu Ile Leu Ser
1               5                   10                  15

Gly Lys Cys

<210> SEQ ID NO 253
<211> LENGTH: 17
<212> TYPE: PRT
<213> ORGANISM: Homo sapiens

<400> SEQUENCE: 253

Met Arg Ala Trp Ile Phe Phe Leu Leu Cys Leu Ala Gly Arg Ala Leu
1               5                   10                  15

Ala

<210> SEQ ID NO 254
<211> LENGTH: 18
<212> TYPE: PRT
<213> ORGANISM: Homo sapiens

<400> SEQUENCE: 254

Met Leu Leu Phe Val Leu Thr Cys Leu Leu Ala Val Phe Pro Ala Ile
1               5                   10                  15

Ser Thr

<210> SEQ ID NO 255
<211> LENGTH: 18
<212> TYPE: PRT
<213> ORGANISM: Homo sapiens

<400> SEQUENCE: 255

Met Lys Trp Val Trp Ala Leu Leu Leu Leu Ala Ala Leu Gly Ser Gly
1               5                   10                  15

Arg Ala

<210> SEQ ID NO 256
<211> LENGTH: 19
<212> TYPE: PRT
<213> ORGANISM: Homo sapiens

<400> SEQUENCE: 256

Met Lys Ser Leu Ile Leu Leu Ala Ile Leu Ala Ala Leu Ala Val Val
1               5                   10                  15

Thr Leu Cys

<210> SEQ ID NO 257
<211> LENGTH: 17
<212> TYPE: PRT
<213> ORGANISM: Homo sapiens

<400> SEQUENCE: 257

Met Ile Trp Tyr Ile Leu Ile Ile Gly Ile Leu Leu Pro Gln Ser Leu
1               5                   10                  15

Ala

```
<210> SEQ ID NO 258
<211> LENGTH: 19
<212> TYPE: PRT
<213> ORGANISM: Homo sapiens

<400> SEQUENCE: 258

Met Trp Arg Ser Leu Gly Leu Ala Leu Ala Leu Cys Leu Leu Pro Ser
1               5                   10                  15

Gly Gly Thr

<210> SEQ ID NO 259
<211> LENGTH: 19
<212> TYPE: PRT
<213> ORGANISM: Homo sapiens

<400> SEQUENCE: 259

Met Pro Ala Leu Gly Trp Ala Val Ala Ala Ile Leu Met Leu Gln Thr
1               5                   10                  15

Ala Met Ala

<210> SEQ ID NO 260
<211> LENGTH: 18
<212> TYPE: PRT
<213> ORGANISM: Homo sapiens

<400> SEQUENCE: 260

Met Arg Leu Phe Thr Gly Ile Val Phe Cys Ser Leu Val Met Gly Val
1               5                   10                  15

Thr Ser

<210> SEQ ID NO 261
<211> LENGTH: 17
<212> TYPE: PRT
<213> ORGANISM: Homo sapiens

<400> SEQUENCE: 261

Met Asp Tyr Leu Leu Met Ile Phe Ser Leu Leu Phe Val Ala Cys Gln
1               5                   10                  15

Gly

<210> SEQ ID NO 262
<211> LENGTH: 20
<212> TYPE: PRT
<213> ORGANISM: Homo sapiens

<400> SEQUENCE: 262

Met Gln Pro Thr Leu Leu Leu Ser Leu Leu Gly Ala Val Gly Leu Ala
1               5                   10                  15

Ala Val Asn Ser
            20

<210> SEQ ID NO 263
<211> LENGTH: 18
<212> TYPE: PRT
<213> ORGANISM: Homo sapiens

<400> SEQUENCE: 263

Met Ala Leu Ser Trp Val Leu Thr Val Leu Ser Leu Leu Pro Leu Leu
1               5                   10                  15

Glu Ala
```

<210> SEQ ID NO 264
<211> LENGTH: 18
<212> TYPE: PRT
<213> ORGANISM: Homo sapiens

<400> SEQUENCE: 264

Met Ala Leu Ser Trp Val Leu Thr Val Leu Ser Leu Leu Pro Leu Leu
1               5                   10                  15

Glu Ala

<210> SEQ ID NO 265
<211> LENGTH: 19
<212> TYPE: PRT
<213> ORGANISM: Homo sapiens

<400> SEQUENCE: 265

Met Val Glu Met Leu Pro Thr Ala Ile Leu Leu Val Leu Ala Val Ser
1               5                   10                  15

Val Val Ala

<210> SEQ ID NO 266
<211> LENGTH: 19
<212> TYPE: PRT
<213> ORGANISM: Homo sapiens

<400> SEQUENCE: 266

Met Asp Ile Leu Cys Ser Thr Leu Leu Leu Leu Thr Val Pro Ser Gly
1               5                   10                  15

Val Leu Ser

<210> SEQ ID NO 267
<211> LENGTH: 20
<212> TYPE: PRT
<213> ORGANISM: Homo sapiens

<400> SEQUENCE: 267

Met Ala Arg Ala Pro Leu Gly Val Leu Leu Leu Leu Gly Leu Leu Gly
1               5                   10                  15

Arg Gly Val Gly
            20

<210> SEQ ID NO 268
<211> LENGTH: 21
<212> TYPE: PRT
<213> ORGANISM: Homo sapiens

<400> SEQUENCE: 268

Met Leu Pro Leu Cys Leu Val Ala Ala Leu Leu Leu Ala Ala Gly Pro
1               5                   10                  15

Gly Pro Ser Leu Gly
            20

<210> SEQ ID NO 269
<211> LENGTH: 19
<212> TYPE: PRT
<213> ORGANISM: Homo sapiens

<400> SEQUENCE: 269

Met Arg Thr Leu Ala Ile Leu Ala Ala Ile Leu Leu Val Ala Leu Gln
1               5                   10                  15

Ala Gln Ala

<210> SEQ ID NO 270
<211> LENGTH: 19
<212> TYPE: PRT
<213> ORGANISM: Homo sapiens

<400> SEQUENCE: 270

Met Arg Thr Leu Ala Ile Leu Ala Ala Ile Leu Leu Val Ala Leu Gln
1               5                   10                  15

Ala Gln Ala

<210> SEQ ID NO 271
<211> LENGTH: 18
<212> TYPE: PRT
<213> ORGANISM: Homo sapiens

<400> SEQUENCE: 271

Met Trp Leu Phe His Thr Leu Leu Cys Ile Ala Ser Leu Ala Leu Leu
1               5                   10                  15

Ala Ala

<210> SEQ ID NO 272
<211> LENGTH: 18
<212> TYPE: PRT
<213> ORGANISM: Homo sapiens

<400> SEQUENCE: 272

Met Val Leu His Leu Leu Leu Phe Leu Leu Leu Thr Pro Gln Gly Gly
1               5                   10                  15

His Ser

<210> SEQ ID NO 273
<211> LENGTH: 20
<212> TYPE: PRT
<213> ORGANISM: Homo sapiens

<400> SEQUENCE: 273

Met Val Met Leu Leu Leu Leu Leu Ser Ala Leu Ala Gly Leu Phe Gly
1               5                   10                  15

Ala Ala Glu Gly
            20

<210> SEQ ID NO 274
<211> LENGTH: 19
<212> TYPE: PRT
<213> ORGANISM: Homo sapiens

<400> SEQUENCE: 274

Met Lys Ser Val Leu Leu Leu Thr Thr Leu Leu Val Pro Ala His Leu
1               5                   10                  15

Val Ala Ala

<210> SEQ ID NO 275
<211> LENGTH: 22
<212> TYPE: PRT
<213> ORGANISM: Homo sapiens

<400> SEQUENCE: 275

Met Ala Arg Ala Pro Pro Leu Leu Ala Ala Leu Thr Ala Leu Leu Ala
1               5                   10                  15

Ala Ala Ala Ala Gly Gly
            20

<210> SEQ ID NO 276
<211> LENGTH: 20
<212> TYPE: PRT
<213> ORGANISM: Homo sapiens

<400> SEQUENCE: 276

Met Ala Leu Leu Leu Thr Thr Val Ile Ala Leu Thr Cys Leu Gly Gly
1               5                   10                  15

Phe Ala Ser Pro
            20

<210> SEQ ID NO 277
<211> LENGTH: 21
<212> TYPE: PRT
<213> ORGANISM: Homo sapiens

<400> SEQUENCE: 277

Met Arg Gly Leu Ala Val Leu Leu Thr Val Ala Leu Ala Thr Leu Leu
1               5                   10                  15

Ala Pro Gly Ala Gly
            20

<210> SEQ ID NO 278
<211> LENGTH: 18
<212> TYPE: PRT
<213> ORGANISM: Homo sapiens

<400> SEQUENCE: 278

Met Gln Pro Ile Leu Leu Leu Ala Phe Leu Leu Leu Pro Arg Ala
1               5                   10                  15

Asp Ala

<210> SEQ ID NO 279
<211> LENGTH: 20
<212> TYPE: PRT
<213> ORGANISM: Homo sapiens

<400> SEQUENCE: 279

Met Phe Leu Lys Ala Val Val Leu Thr Leu Ala Leu Val Ala Val Ala
1               5                   10                  15

Gly Ala Arg Ala
            20

<210> SEQ ID NO 280
<211> LENGTH: 18
<212> TYPE: PRT
<213> ORGANISM: Homo sapiens

<400> SEQUENCE: 280

Met Gly Phe Trp Ile Leu Ala Ile Leu Thr Ile Leu Met Tyr Ser Thr
1               5                   10                  15

Ala Ala

<210> SEQ ID NO 281
<211> LENGTH: 18
<212> TYPE: PRT
<213> ORGANISM: Homo sapiens

<400> SEQUENCE: 281

```
Met Lys Ser Leu Val Leu Leu Leu Cys Leu Ala Gln Leu Trp Gly Cys
1               5                   10                  15

His Ser

<210> SEQ ID NO 282
<211> LENGTH: 19
<212> TYPE: PRT
<213> ORGANISM: Homo sapiens

<400> SEQUENCE: 282

Met Arg Gly Pro Ser Gly Ala Leu Trp Leu Leu Leu Ala Leu Arg Thr
1               5                   10                  15

Val Leu Gly

<210> SEQ ID NO 283
<211> LENGTH: 17
<212> TYPE: PRT
<213> ORGANISM: Homo sapiens

<400> SEQUENCE: 283

Met Phe Phe Trp Cys Ala Cys Cys Leu Met Val Ala Trp Arg Val Ser
1               5                   10                  15

Ala

<210> SEQ ID NO 284
<211> LENGTH: 19
<212> TYPE: PRT
<213> ORGANISM: Homo sapiens

<400> SEQUENCE: 284

Met Tyr Gly Lys Ile Ile Phe Val Leu Leu Leu Ser Gly Ile Val Ser
1               5                   10                  15

Ile Ser Ala

<210> SEQ ID NO 285
<211> LENGTH: 20
<212> TYPE: PRT
<213> ORGANISM: Homo sapiens

<400> SEQUENCE: 285

Met Ser Cys Pro Val Pro Ala Cys Cys Ala Leu Leu Leu Val Leu Gly
1               5                   10                  15

Leu Cys Arg Ala
                20

<210> SEQ ID NO 286
<211> LENGTH: 19
<212> TYPE: PRT
<213> ORGANISM: Homo sapiens

<400> SEQUENCE: 286

Met Lys Leu Val Phe Leu Val Leu Leu Phe Leu Gly Ala Leu Gly Leu
1               5                   10                  15

Cys Leu Ala

<210> SEQ ID NO 287
<211> LENGTH: 19
<212> TYPE: PRT
<213> ORGANISM: Homo sapiens

<400> SEQUENCE: 287
```

Met Tyr Gly Lys Ile Ile Phe Val Leu Leu Ser Ala Ile Val Ser
1               5                   10                  15

Ile Ser Ala

<210> SEQ ID NO 288
<211> LENGTH: 19
<212> TYPE: PRT
<213> ORGANISM: Homo sapiens

<400> SEQUENCE: 288

Met Val Ala Leu Pro Met Val Leu Val Leu Leu Val Leu Ser Arg
1               5                   10                  15

Gly Glu Ser

<210> SEQ ID NO 289
<211> LENGTH: 19
<212> TYPE: PRT
<213> ORGANISM: Homo sapiens

<400> SEQUENCE: 289

Met Arg Phe Met Thr Leu Leu Phe Leu Thr Ala Leu Ala Gly Ala Leu
1               5                   10                  15

Val Cys Ala

<210> SEQ ID NO 290
<211> LENGTH: 20
<212> TYPE: PRT
<213> ORGANISM: Homo sapiens

<400> SEQUENCE: 290

Met Ala Arg Pro Leu Cys Thr Leu Leu Leu Met Ala Thr Leu Ala
1               5                   10                  15

Gly Ala Leu Ala
            20

<210> SEQ ID NO 291
<211> LENGTH: 19
<212> TYPE: PRT
<213> ORGANISM: Homo sapiens

<400> SEQUENCE: 291

Met Trp Leu Leu Leu Thr Met Ala Ser Leu Ile Ser Val Leu Gly Thr
1               5                   10                  15

Thr His Gly

<210> SEQ ID NO 292
<211> LENGTH: 19
<212> TYPE: PRT
<213> ORGANISM: Homo sapiens

<400> SEQUENCE: 292

Met Ala Pro Leu Arg Pro Leu Leu Ile Leu Ala Leu Leu Ala Trp Val
1               5                   10                  15

Ala Leu Ala

<210> SEQ ID NO 293
<211> LENGTH: 21
<212> TYPE: PRT
<213> ORGANISM: Homo sapiens

<400> SEQUENCE: 293

```
Met Ala Leu Thr Ala His Pro Ser Cys Leu Leu Ala Leu Leu Val Ala
1               5                   10                  15

Gly Leu Ala Gln Gly
            20

<210> SEQ ID NO 294
<211> LENGTH: 19
<212> TYPE: PRT
<213> ORGANISM: Homo sapiens

<400> SEQUENCE: 294

Met Ala Leu Leu Phe Ser Leu Ile Leu Ala Ile Cys Thr Arg Pro Gly
1               5                   10                  15

Phe Leu Ala

<210> SEQ ID NO 295
<211> LENGTH: 20
<212> TYPE: PRT
<213> ORGANISM: Homo sapiens

<400> SEQUENCE: 295

Ile Phe Ala Ser Leu Leu Arg Ala Val Ile Ala Ser Ile Cys Val Val
1               5                   10                  15

Ser Ser Met Ala
            20

<210> SEQ ID NO 296
<211> LENGTH: 20
<212> TYPE: PRT
<213> ORGANISM: Homo sapiens

<400> SEQUENCE: 296

Met Gly Asp His Leu Asp Leu Leu Gly Val Val Leu Met Ala Gly
1               5                   10                  15

Pro Val Phe Gly
            20

<210> SEQ ID NO 297
<211> LENGTH: 20
<212> TYPE: PRT
<213> ORGANISM: Homo sapiens

<400> SEQUENCE: 297

Met Pro Leu Gly Leu Leu Trp Leu Gly Leu Ala Leu Leu Gly Ala Leu
1               5                   10                  15

His Ala Gln Ala
            20

<210> SEQ ID NO 298
<211> LENGTH: 19
<212> TYPE: PRT
<213> ORGANISM: Homo sapiens

<400> SEQUENCE: 298

Met Gln Leu Phe Leu Leu Leu Cys Leu Val Leu Leu Ser Pro Gln Gly
1               5                   10                  15

Ala Ser Leu

<210> SEQ ID NO 299
<211> LENGTH: 19
<212> TYPE: PRT
<213> ORGANISM: Homo sapiens
```

```
<400> SEQUENCE: 299

Met Thr Cys Ser Pro Leu Leu Leu Thr Leu Leu Ile His Cys Thr Gly
1               5                   10                  15

Ser Trp Ala

<210> SEQ ID NO 300
<211> LENGTH: 18
<212> TYPE: PRT
<213> ORGANISM: Homo sapiens

<400> SEQUENCE: 300

Met Arg Leu Leu Val Leu Leu Trp Gly Cys Leu Leu Leu Pro Gly Tyr
1               5                   10                  15

Glu Ala

<210> SEQ ID NO 301
<211> LENGTH: 19
<212> TYPE: PRT
<213> ORGANISM: Homo sapiens

<400> SEQUENCE: 301

Met Ile Ser Pro Val Leu Ile Leu Phe Ser Ser Phe Leu Cys His Val
1               5                   10                  15

Ala Ile Ala

<210> SEQ ID NO 302
<211> LENGTH: 18
<212> TYPE: PRT
<213> ORGANISM: Homo sapiens

<400> SEQUENCE: 302

Met Arg Leu Leu Ala Lys Ile Ile Cys Leu Met Leu Trp Ala Ile Cys
1               5                   10                  15

Val Ala

<210> SEQ ID NO 303
<211> LENGTH: 20
<212> TYPE: PRT
<213> ORGANISM: Homo sapiens

<400> SEQUENCE: 303

Met Trp Leu Cys Pro Leu Ala Leu Asn Leu Ile Leu Met Ala Ala Ser
1               5                   10                  15

Gly Ala Ala Cys
            20

<210> SEQ ID NO 304
<211> LENGTH: 20
<212> TYPE: PRT
<213> ORGANISM: Homo sapiens

<400> SEQUENCE: 304

Met Ala Gln His Leu Ser Thr Leu Leu Leu Leu Leu Ala Thr Leu Ala
1               5                   10                  15

Val Ala Leu Ala
            20

<210> SEQ ID NO 305
<211> LENGTH: 20
<212> TYPE: PRT
```

<213> ORGANISM: Homo sapiens

<400> SEQUENCE: 305

Met Ala Trp Ala Ser Arg Leu Gly Leu Leu Ala Leu Leu Leu Pro
1               5                   10                  15

Val Val Gly Ala
            20

<210> SEQ ID NO 306
<211> LENGTH: 19
<212> TYPE: PRT
<213> ORGANISM: Homo sapiens

<400> SEQUENCE: 306

Met Arg Gly Ala Thr Arg Val Ser Ile Met Leu Leu Leu Val Thr Val
1               5                   10                  15

Ser Asp Cys

<210> SEQ ID NO 307
<211> LENGTH: 19
<212> TYPE: PRT
<213> ORGANISM: Homo sapiens

<400> SEQUENCE: 307

Met Lys Thr Leu Leu Leu Leu Leu Val Leu Leu Glu Leu Gly Glu
1               5                   10                  15

Ala Gln Gly

<210> SEQ ID NO 308
<211> LENGTH: 18
<212> TYPE: PRT
<213> ORGANISM: Homo sapiens

<400> SEQUENCE: 308

Met Thr Pro Pro Arg Leu Phe Trp Val Trp Leu Leu Val Ala Gly Thr
1               5                   10                  15

Gln Gly

<210> SEQ ID NO 309
<211> LENGTH: 18
<212> TYPE: PRT
<213> ORGANISM: Homo sapiens

<400> SEQUENCE: 309

Met Asn Cys Arg Glu Leu Pro Leu Thr Leu Trp Val Leu Ile Ser Val
1               5                   10                  15

Ser Thr

<210> SEQ ID NO 310
<211> LENGTH: 21
<212> TYPE: PRT
<213> ORGANISM: Homo sapiens

<400> SEQUENCE: 310

Met Ser Val Lys Gly Met Ala Ile Ala Leu Ala Val Ile Leu Cys Ala
1               5                   10                  15

Thr Val Val Gln Gly
            20

<210> SEQ ID NO 311
<211> LENGTH: 19

<212> TYPE: PRT
<213> ORGANISM: Homo sapiens

<400> SEQUENCE: 311

Met Arg Ala Leu Leu Leu Gly Phe Leu Leu Val Ser Leu Glu Ser
1               5                   10                  15

Thr Leu Ser

<210> SEQ ID NO 312
<211> LENGTH: 21
<212> TYPE: PRT
<213> ORGANISM: Homo sapiens

<400> SEQUENCE: 312

Met Ala Ala Arg Ala Leu Cys Met Leu Gly Leu Val Leu Ala Leu Leu
1               5                   10                  15

Ser Ser Ser Ser Ala
            20

<210> SEQ ID NO 313
<211> LENGTH: 19
<212> TYPE: PRT
<213> ORGANISM: Homo sapiens

<400> SEQUENCE: 313

Met Glu Arg Ala Ser Cys Leu Leu Leu Leu Leu Pro Leu Val His
1               5                   10                  15

Val Ser Ala

<210> SEQ ID NO 314
<211> LENGTH: 21
<212> TYPE: PRT
<213> ORGANISM: Homo sapiens

<400> SEQUENCE: 314

Met Glu Arg Gly Leu Pro Leu Leu Cys Ala Val Leu Ala Leu Val Leu
1               5                   10                  15

Ala Pro Ala Gly Ala
            20

<210> SEQ ID NO 315
<211> LENGTH: 18
<212> TYPE: PRT
<213> ORGANISM: Homo sapiens

<400> SEQUENCE: 315

Met Lys Leu Ile Thr Ile Leu Phe Leu Cys Ser Arg Leu Leu Leu Ser
1               5                   10                  15

Leu Thr

<210> SEQ ID NO 316
<211> LENGTH: 19
<212> TYPE: PRT
<213> ORGANISM: Homo sapiens

<400> SEQUENCE: 316

Met Ala Leu Val Leu Glu Ile Phe Thr Leu Leu Ala Ser Ile Cys Trp
1               5                   10                  15

Val Ser Ala

<210> SEQ ID NO 317

```
<211> LENGTH: 17
<212> TYPE: PRT
<213> ORGANISM: Homo sapiens

<400> SEQUENCE: 317

Met Ile Ile Leu Ile Tyr Leu Phe Leu Leu Trp Glu Asp Thr Gln
1               5                   10                  15

Gly

<210> SEQ ID NO 318
<211> LENGTH: 19
<212> TYPE: PRT
<213> ORGANISM: Homo sapiens

<400> SEQUENCE: 318

Met Leu Leu Leu Phe Leu Leu Phe Glu Gly Leu Cys Cys Pro Gly Glu
1               5                   10                  15

Asn Thr Ala

<210> SEQ ID NO 319
<211> LENGTH: 20
<212> TYPE: PRT
<213> ORGANISM: Homo sapiens

<400> SEQUENCE: 319

Met Trp Leu Cys Pro Leu Ala Leu Asn Leu Ile Leu Met Ala Ala Ser
1               5                   10                  15

Gly Ala Val Cys
            20

<210> SEQ ID NO 320
<211> LENGTH: 21
<212> TYPE: PRT
<213> ORGANISM: Homo sapiens

<400> SEQUENCE: 320

Met Lys Leu Ala Val Thr Leu Thr Leu Val Thr Leu Ala Leu Cys Cys
1               5                   10                  15

Ser Ser Ala Ser Ala
            20

<210> SEQ ID NO 321
<211> LENGTH: 19
<212> TYPE: PRT
<213> ORGANISM: Homo sapiens

<400> SEQUENCE: 321

Met Tyr Gly Lys Ile Ile Phe Val Leu Leu Leu Ser Glu Ile Val Ser
1               5                   10                  15

Ile Ser Ala

<210> SEQ ID NO 322
<211> LENGTH: 21
<212> TYPE: PRT
<213> ORGANISM: Homo sapiens

<400> SEQUENCE: 322

Met Ala Ala Ala Met Pro Leu Ala Leu Leu Val Leu Leu Leu Leu Gly
1               5                   10                  15

Pro Gly Gly Trp Cys
            20
```

<210> SEQ ID NO 323
<211> LENGTH: 21
<212> TYPE: PRT
<213> ORGANISM: Homo sapiens

<400> SEQUENCE: 323

Met Trp Ala Thr Gln Gly Leu Ala Val Ala Leu Ala Leu Ser Val Leu
1               5                   10                  15

Pro Gly Ser Arg Ala
            20

<210> SEQ ID NO 324
<211> LENGTH: 20
<212> TYPE: PRT
<213> ORGANISM: Homo sapiens

<400> SEQUENCE: 324

Met Asn Val Leu Leu Gly Ser Val Val Ile Phe Ala Thr Phe Val Thr
1               5                   10                  15

Leu Cys Asn Ala
            20

<210> SEQ ID NO 325
<211> LENGTH: 20
<212> TYPE: PRT
<213> ORGANISM: Homo sapiens

<400> SEQUENCE: 325

Met Ala Trp Pro Leu Cys Thr Leu Leu Leu Leu Ala Thr Gln Ala
1               5                   10                  15

Val Ala Leu Ala
            20

<210> SEQ ID NO 326
<211> LENGTH: 19
<212> TYPE: PRT
<213> ORGANISM: Homo sapiens

<400> SEQUENCE: 326

Met Phe Ser Met Arg Ile Val Cys Leu Val Leu Ser Val Val Gly Thr
1               5                   10                  15

Ala Trp Thr

<210> SEQ ID NO 327
<211> LENGTH: 20
<212> TYPE: PRT
<213> ORGANISM: Homo sapiens

<400> SEQUENCE: 327

Met Ala Trp Gln Gly Leu Val Leu Ala Ala Cys Leu Leu Met Phe Pro
1               5                   10                  15

Ser Thr Thr Ala
            20

<210> SEQ ID NO 328
<211> LENGTH: 21
<212> TYPE: PRT
<213> ORGANISM: Homo sapiens

<400> SEQUENCE: 328

Met Ala Thr Ser Met Gly Leu Leu Leu Leu Leu Leu Leu Leu Leu Thr
1               5                   10                  15

Gln Pro Gly Ala Gly
            20

<210> SEQ ID NO 329
<211> LENGTH: 19
<212> TYPE: PRT
<213> ORGANISM: Homo sapiens

<400> SEQUENCE: 329

Met Leu Leu Leu Pro Leu Pro Leu Leu Phe Leu Leu Cys Ser Arg
1               5                   10                  15

Ala Glu Ala

<210> SEQ ID NO 330
<211> LENGTH: 19
<212> TYPE: PRT
<213> ORGANISM: Homo sapiens

<400> SEQUENCE: 330

Met Ala Arg Pro His Pro Trp Trp Leu Cys Val Leu Gly Thr Leu Val
1               5                   10                  15

Gly Leu Ser

<210> SEQ ID NO 331
<211> LENGTH: 21
<212> TYPE: PRT
<213> ORGANISM: Homo sapiens

<400> SEQUENCE: 331

Met Ser Ala Val Leu Leu Leu Ala Leu Leu Gly Phe Ile Leu Pro Leu
1               5                   10                  15

Pro Gly Val Gln Ala
            20

<210> SEQ ID NO 332
<211> LENGTH: 22
<212> TYPE: PRT
<213> ORGANISM: Homo sapiens

<400> SEQUENCE: 332

Met Ala Arg Gly Ala Ala Leu Ala Leu Leu Phe Gly Leu Leu Gly
1               5                   10                  15

Val Leu Val Ala Ala Pro
            20

<210> SEQ ID NO 333
<211> LENGTH: 19
<212> TYPE: PRT
<213> ORGANISM: Homo sapiens

<400> SEQUENCE: 333

Met Lys Ile Leu Ile Leu Gly Ile Phe Leu Phe Leu Cys Ser Thr Pro
1               5                   10                  15

Ala Trp Ala

<210> SEQ ID NO 334
<211> LENGTH: 20
<212> TYPE: PRT
<213> ORGANISM: Homo sapiens

<400> SEQUENCE: 334

```
Met Arg Leu Pro Ala Gln Leu Leu Gly Leu Leu Met Leu Trp Val Pro
1               5                   10                  15

Gly Ser Ser Gly
            20

<210> SEQ ID NO 335
<211> LENGTH: 18
<212> TYPE: PRT
<213> ORGANISM: Homo sapiens

<400> SEQUENCE: 335

Met Lys Trp Val Thr Phe Ile Ser Leu Leu Phe Leu Phe Ser Ser Ala
1               5                   10                  15

Tyr Ser

<210> SEQ ID NO 336
<211> LENGTH: 20
<212> TYPE: PRT
<213> ORGANISM: Homo sapiens

<400> SEQUENCE: 336

Met Ser Leu Phe Pro Ser Leu Pro Leu Leu Leu Leu Ser Met Val Ala
1               5                   10                  15

Ala Ser Tyr Ser
            20

<210> SEQ ID NO 337
<211> LENGTH: 20
<212> TYPE: PRT
<213> ORGANISM: Homo sapiens

<400> SEQUENCE: 337

Met Ala Ser His Arg Leu Leu Leu Leu Cys Leu Ala Gly Leu Val Phe
1               5                   10                  15

Val Ser Glu Ala
            20

<210> SEQ ID NO 338
<211> LENGTH: 19
<212> TYPE: PRT
<213> ORGANISM: Homo sapiens

<400> SEQUENCE: 338

Met Asp Trp Thr Trp Arg Ile Leu Phe Leu Val Ala Ala Ala Thr Gly
1               5                   10                  15

Ala His Ser

<210> SEQ ID NO 339
<211> LENGTH: 19
<212> TYPE: PRT
<213> ORGANISM: Homo sapiens

<400> SEQUENCE: 339

Met Asn Lys Pro Leu Leu Trp Ile Ser Val Leu Thr Ser Leu Leu Glu
1               5                   10                  15

Ala Phe Ala

<210> SEQ ID NO 340
<211> LENGTH: 20
<212> TYPE: PRT
<213> ORGANISM: Homo sapiens
```

```
<400> SEQUENCE: 340

Met Lys Phe Leu Ala Val Leu Val Leu Leu Gly Val Ser Ile Phe Leu
1               5                   10                  15

Val Ser Ala Gln
            20

<210> SEQ ID NO 341
<211> LENGTH: 19
<212> TYPE: PRT
<213> ORGANISM: Homo sapiens

<400> SEQUENCE: 341

Met Phe Cys Pro Leu Lys Leu Ile Leu Leu Pro Val Leu Leu Asp Tyr
1               5                   10                  15

Ser Leu Gly

<210> SEQ ID NO 342
<211> LENGTH: 20
<212> TYPE: PRT
<213> ORGANISM: Homo sapiens

<400> SEQUENCE: 342

Met Asp Pro Arg Leu Pro Ala Trp Ala Leu Val Leu Gly Pro Ala
1               5                   10                  15

Leu Val Phe Ala
            20

<210> SEQ ID NO 343
<211> LENGTH: 19
<212> TYPE: PRT
<213> ORGANISM: Homo sapiens

<400> SEQUENCE: 343

Met Leu Leu Trp Ser Leu Leu Val Ile Phe Asp Ala Val Thr Glu Gln
1               5                   10                  15

Ala Asp Ser

<210> SEQ ID NO 344
<211> LENGTH: 19
<212> TYPE: PRT
<213> ORGANISM: Homo sapiens

<400> SEQUENCE: 344

Met Glu His Lys Glu Val Val Leu Leu Leu Leu Phe Leu Lys Ser
1               5                   10                  15

Ala Ala Pro

<210> SEQ ID NO 345
<211> LENGTH: 20
<212> TYPE: PRT
<213> ORGANISM: Homo sapiens

<400> SEQUENCE: 345

Met Ala Trp Thr Pro Leu Phe Leu Phe Leu Leu Thr Cys Cys Pro Gly
1               5                   10                  15

Gly Ser Asn Ser
            20

<210> SEQ ID NO 346
<211> LENGTH: 21
<212> TYPE: PRT
```

<213> ORGANISM: Homo sapiens

<400> SEQUENCE: 346

Met Arg Leu Leu Leu Ala Leu Leu Gly Val Leu Leu Ser Val Pro Gly
1               5                   10                  15

Pro Pro Val Leu Ser
            20

<210> SEQ ID NO 347
<211> LENGTH: 21
<212> TYPE: PRT
<213> ORGANISM: Homo sapiens

<400> SEQUENCE: 347

Met Ser Gly Ala Arg Ser Lys Leu Ala Leu Phe Leu Cys Gly Cys Tyr
1               5                   10                  15

Val Val Ala Leu Gly
            20

<210> SEQ ID NO 348
<211> LENGTH: 20
<212> TYPE: PRT
<213> ORGANISM: Homo sapiens

<400> SEQUENCE: 348

Met Glu Pro Trp Pro Leu Leu Leu Phe Ser Leu Cys Ser Ala Gly
1               5                   10                  15

Leu Val Leu Gly
            20

<210> SEQ ID NO 349
<211> LENGTH: 19
<212> TYPE: PRT
<213> ORGANISM: Homo sapiens

<400> SEQUENCE: 349

Met Ser Arg Leu Pro Val Leu Leu Leu Gln Leu Val Arg Pro
1               5                   10                  15

Gly Leu Gln

<210> SEQ ID NO 350
<211> LENGTH: 19
<212> TYPE: PRT
<213> ORGANISM: Homo sapiens

<400> SEQUENCE: 350

Met Asp Trp Thr Trp Arg Val Phe Cys Leu Leu Ala Val Ala Pro Gly
1               5                   10                  15

Ala His Ser

<210> SEQ ID NO 351
<211> LENGTH: 20
<212> TYPE: PRT
<213> ORGANISM: Homo sapiens

<400> SEQUENCE: 351

Met Glu Met Leu Gln Gly Leu Leu Leu Leu Leu Leu Ser Met Gly
1               5                   10                  15

Gly Ala Trp Ala
            20

-continued

<210> SEQ ID NO 352
<211> LENGTH: 20
<212> TYPE: PRT
<213> ORGANISM: Homo sapiens

<400> SEQUENCE: 352

Met Lys Ser Phe Leu Leu Val Val Asn Ala Leu Ala Leu Thr Leu Pro
1               5                   10                  15

Phe Leu Ala Val
            20

<210> SEQ ID NO 353
<211> LENGTH: 20
<212> TYPE: PRT
<213> ORGANISM: Homo sapiens

<400> SEQUENCE: 353

Met Lys Leu Met Val Leu Val Phe Thr Ile Gly Leu Thr Leu Leu Leu
1               5                   10                  15

Gly Val Gln Ala
            20

<210> SEQ ID NO 354
<211> LENGTH: 19
<212> TYPE: PRT
<213> ORGANISM: Homo sapiens

<400> SEQUENCE: 354

Met Asp Leu Arg Gln Phe Leu Met Cys Leu Ser Leu Cys Thr Ala Phe
1               5                   10                  15

Ala Leu Ser

<210> SEQ ID NO 355
<211> LENGTH: 19
<212> TYPE: PRT
<213> ORGANISM: Homo sapiens

<400> SEQUENCE: 355

Met Ile Phe Leu Thr Ala Leu Pro Leu Phe Trp Ile Met Ile Ser Ala
1               5                   10                  15

Ser Arg Gly

<210> SEQ ID NO 356
<211> LENGTH: 21
<212> TYPE: PRT
<213> ORGANISM: Homo sapiens

<400> SEQUENCE: 356

Met Leu Pro Cys Leu Val Val Leu Leu Ala Leu Leu Ser Leu Arg
1               5                   10                  15

Leu Gly Ser Asp Ala
            20

<210> SEQ ID NO 357
<211> LENGTH: 19
<212> TYPE: PRT
<213> ORGANISM: Homo sapiens

<400> SEQUENCE: 357

Met Ile Leu Phe Lys Gln Ala Thr Tyr Phe Ile Ser Leu Phe Ala Thr
1               5                   10                  15

Val Ser Cys

<210> SEQ ID NO 358
<211> LENGTH: 21
<212> TYPE: PRT
<213> ORGANISM: Homo sapiens

<400> SEQUENCE: 358

Met Ala Pro Leu Ala Leu His Leu Leu Val Leu Val Pro Ile Leu Leu
1               5                   10                  15

Ser Leu Val Ala Ser
            20

<210> SEQ ID NO 359
<211> LENGTH: 19
<212> TYPE: PRT
<213> ORGANISM: Homo sapiens

<400> SEQUENCE: 359

Met Val Val Ala Leu Arg Tyr Val Trp Pro Leu Leu Leu Cys Ser Pro
1               5                   10                  15

Cys Leu Leu

<210> SEQ ID NO 360
<211> LENGTH: 22
<212> TYPE: PRT
<213> ORGANISM: Homo sapiens

<400> SEQUENCE: 360

Met Arg Ala Pro Gly Cys Gly Arg Leu Val Leu Pro Leu Leu Leu Leu
1               5                   10                  15

Ala Ala Ala Ala Leu Ala
            20

<210> SEQ ID NO 361
<211> LENGTH: 19
<212> TYPE: PRT
<213> ORGANISM: Homo sapiens

<400> SEQUENCE: 361

Met Arg Leu Phe Leu Trp Asn Ala Val Leu Thr Leu Phe Val Thr Ser
1               5                   10                  15

Leu Ile Gly

<210> SEQ ID NO 362
<211> LENGTH: 21
<212> TYPE: PRT
<213> ORGANISM: Homo sapiens

<400> SEQUENCE: 362

Met Ala Leu Pro Val Thr Ala Leu Leu Leu Pro Leu Ala Leu Leu Leu
1               5                   10                  15

His Ala Ala Arg Pro
            20

<210> SEQ ID NO 363
<211> LENGTH: 19
<212> TYPE: PRT
<213> ORGANISM: Homo sapiens

<400> SEQUENCE: 363

Met Ile Phe Leu Leu Leu Met Leu Ser Leu Glu Leu Gln Leu His Gln
1               5                   10                  15

Ile Ala Ala

<210> SEQ ID NO 364
<211> LENGTH: 22
<212> TYPE: PRT
<213> ORGANISM: Homo sapiens

<400> SEQUENCE: 364

Met Arg Gly Met Lys Leu Leu Gly Ala Leu Leu Ala Leu Ala Ala Leu
1               5                   10                  15

Leu Gln Gly Ala Val Ser
            20

<210> SEQ ID NO 365
<211> LENGTH: 21
<212> TYPE: PRT
<213> ORGANISM: Homo sapiens

<400> SEQUENCE: 365

Met Lys Leu Val Ser Val Ala Leu Met Tyr Leu Gly Ser Leu Ala Phe
1               5                   10                  15

Leu Gly Ala Asp Thr
            20

<210> SEQ ID NO 366
<211> LENGTH: 20
<212> TYPE: PRT
<213> ORGANISM: Homo sapiens

<400> SEQUENCE: 366

Met Gly Pro Leu Met Val Leu Phe Cys Leu Leu Phe Leu Tyr Pro Gly
1               5                   10                  15

Leu Ala Asp Ser
            20

<210> SEQ ID NO 367
<211> LENGTH: 21
<212> TYPE: PRT
<213> ORGANISM: Homo sapiens

<400> SEQUENCE: 367

Met Lys Ala Leu Leu Ala Leu Pro Leu Leu Leu Leu Ser Thr Pro
1               5                   10                  15

Pro Cys Ala Pro Gln
            20

<210> SEQ ID NO 368
<211> LENGTH: 21
<212> TYPE: PRT
<213> ORGANISM: Homo sapiens

<400> SEQUENCE: 368

Met Ile Ala Ser Gln Phe Leu Ser Ala Leu Thr Leu Val Leu Leu Ile
1               5                   10                  15

Lys Glu Ser Gly Ala
            20

<210> SEQ ID NO 369
<211> LENGTH: 21
<212> TYPE: PRT
<213> ORGANISM: Homo sapiens -continued

<400> SEQUENCE: 369

Met Gly Leu Ser Thr Val Pro Asp Leu Leu Pro Leu Val Leu Leu
1               5                   10                  15

Glu Leu Leu Val Gly
            20

<210> SEQ ID NO 370
<211> LENGTH: 20
<212> TYPE: PRT
<213> ORGANISM: Homo sapiens

<400> SEQUENCE: 370

Met Lys Thr Leu Gln Ser Thr Leu Leu Leu Leu Leu Val Pro Leu
1               5                   10                  15

Ile Lys Pro Ala
            20

<210> SEQ ID NO 371
<211> LENGTH: 18
<212> TYPE: PRT
<213> ORGANISM: Homo sapiens

<400> SEQUENCE: 371

Met Lys Trp Val Glu Ser Ile Phe Leu Ile Phe Leu Leu Asn Phe Thr
1               5                   10                  15

Glu Ser

<210> SEQ ID NO 372
<211> LENGTH: 22
<212> TYPE: PRT
<213> ORGANISM: Homo sapiens

<400> SEQUENCE: 372

Met Ala Pro Val Ala Val Trp Ala Ala Leu Ala Val Gly Leu Glu Leu
1               5                   10                  15

Trp Ala Ala Ala His Ala
            20

<210> SEQ ID NO 373
<211> LENGTH: 20
<212> TYPE: PRT
<213> ORGANISM: Homo sapiens

<400> SEQUENCE: 373

Met Arg Trp Ala Leu Leu Val Leu Leu Ala Phe Leu Ser Pro Ala Ser
1               5                   10                  15

Gln Lys Ser Ser
            20

<210> SEQ ID NO 374
<211> LENGTH: 20
<212> TYPE: PRT
<213> ORGANISM: Homo sapiens

<400> SEQUENCE: 374

Met Lys Gly Phe Thr Ala Thr Leu Phe Leu Trp Thr Leu Ile Phe Pro
1               5                   10                  15

Ser Cys Ser Gly
            20

<210> SEQ ID NO 375

```
<211> LENGTH: 21
<212> TYPE: PRT
<213> ORGANISM: Homo sapiens

<400> SEQUENCE: 375

Met Gly Thr Ser Leu Leu Cys Trp Met Ala Leu Cys Leu Leu Gly Ala
1               5                   10                  15

Asp His Ala Asp Thr
            20

<210> SEQ ID NO 376
<211> LENGTH: 21
<212> TYPE: PRT
<213> ORGANISM: Homo sapiens

<400> SEQUENCE: 376

Met Glu His Ser Thr Phe Leu Ser Gly Leu Val Leu Ala Thr Leu Leu
1               5                   10                  15

Ser Gln Val Ser Pro
            20

<210> SEQ ID NO 377
<211> LENGTH: 18
<212> TYPE: PRT
<213> ORGANISM: Homo sapiens

<400> SEQUENCE: 377

Met Lys Thr Leu Gln Phe Phe Phe Leu Phe Cys Cys Trp Lys Ala Ile
1               5                   10                  15

Cys Cys

<210> SEQ ID NO 378
<211> LENGTH: 20
<212> TYPE: PRT
<213> ORGANISM: Homo sapiens

<400> SEQUENCE: 378

Met Val Leu Gln Thr Gln Val Phe Ile Ser Leu Leu Leu Trp Ile Ser
1               5                   10                  15

Gly Ala Tyr Gly
            20

<210> SEQ ID NO 379
<211> LENGTH: 20
<212> TYPE: PRT
<213> ORGANISM: Homo sapiens

<400> SEQUENCE: 379

Met Val Leu Gln Thr Gln Val Phe Ile Ser Leu Leu Leu Trp Ile Ser
1               5                   10                  15

Gly Ala Tyr Gly
            20

<210> SEQ ID NO 380
<211> LENGTH: 20
<212> TYPE: PRT
<213> ORGANISM: Homo sapiens

<400> SEQUENCE: 380

Met Val Leu Gln Thr Gln Val Phe Ile Ser Leu Leu Leu Trp Ile Ser
1               5                   10                  15

Gly Ala Tyr Gly
```

<210> SEQ ID NO 381
<211> LENGTH: 20
<212> TYPE: PRT
<213> ORGANISM: Homo sapiens

<400> SEQUENCE: 381

Met Met Trp Pro Met His Thr Pro Leu Leu Leu Thr Ala Leu Met
1               5                   10                  15

Val Ala Val Ala
            20

<210> SEQ ID NO 382
<211> LENGTH: 20
<212> TYPE: PRT
<213> ORGANISM: Homo sapiens

<400> SEQUENCE: 382

Met Ser Pro Phe Leu Tyr Leu Val Leu Leu Val Leu Gly Leu His Ala
1               5                   10                  15

Thr Ile His Cys
            20

<210> SEQ ID NO 383
<211> LENGTH: 21
<212> TYPE: PRT
<213> ORGANISM: Homo sapiens

<400> SEQUENCE: 383

Met Arg Pro Ala Phe Ala Leu Cys Leu Leu Trp Gln Ala Leu Trp Pro
1               5                   10                  15

Gly Pro Gly Gly Gly
            20

<210> SEQ ID NO 384
<211> LENGTH: 20
<212> TYPE: PRT
<213> ORGANISM: Homo sapiens

<400> SEQUENCE: 384

Met Glu Ala Pro Ala Gln Leu Leu Phe Leu Leu Leu Leu Trp Leu Pro
1               5                   10                  15

Asp Thr Thr Gly
            20

<210> SEQ ID NO 385
<211> LENGTH: 20
<212> TYPE: PRT
<213> ORGANISM: Homo sapiens

<400> SEQUENCE: 385

Met Glu Ala Pro Ala Gln Leu Leu Phe Leu Leu Leu Leu Trp Leu Pro
1               5                   10                  15

Asp Thr Thr Gly
            20

<210> SEQ ID NO 386
<211> LENGTH: 22
<212> TYPE: PRT
<213> ORGANISM: Homo sapiens

<400> SEQUENCE: 386

```
Met Trp Ala Thr Leu Pro Leu Leu Cys Ala Gly Ala Trp Leu Leu Gly
1               5                   10                  15

Val Pro Val Cys Gly Ala
            20

<210> SEQ ID NO 387
<211> LENGTH: 20
<212> TYPE: PRT
<213> ORGANISM: Homo sapiens

<400> SEQUENCE: 387

Met Val Arg Leu Pro Leu Gln Cys Val Leu Trp Gly Cys Leu Leu Thr
1               5                   10                  15

Ala Val His Pro
            20

<210> SEQ ID NO 388
<211> LENGTH: 21
<212> TYPE: PRT
<213> ORGANISM: Homo sapiens

<400> SEQUENCE: 388

Met Asn Gln Thr Ala Ile Leu Ile Cys Cys Leu Ile Phe Leu Thr Leu
1               5                   10                  15

Ser Gly Ile Gln Gly
            20

<210> SEQ ID NO 389
<211> LENGTH: 23
<212> TYPE: PRT
<213> ORGANISM: Homo sapiens

<400> SEQUENCE: 389

Met Ile Leu Asn Lys Ala Leu Leu Leu Gly Ala Leu Ala Leu Thr Ala
1               5                   10                  15

Val Met Ser Pro Cys Gly Gly
            20

<210> SEQ ID NO 390
<211> LENGTH: 21
<212> TYPE: PRT
<213> ORGANISM: Homo sapiens

<400> SEQUENCE: 390

Met Trp Arg Cys Pro Leu Gly Leu Leu Leu Leu Pro Leu Ala Gly
1               5                   10                  15

His Leu Ala Leu Gly
            20

<210> SEQ ID NO 391
<211> LENGTH: 20
<212> TYPE: PRT
<213> ORGANISM: Homo sapiens

<400> SEQUENCE: 391

Met Arg Pro Ala Asp Leu Leu Gln Leu Val Leu Leu Leu Asp Leu Pro
1               5                   10                  15

Arg Asp Leu Gly
            20

<210> SEQ ID NO 392
```

-continued

```
<211> LENGTH: 23
<212> TYPE: PRT
<213> ORGANISM: Homo sapiens

<400> SEQUENCE: 392

Met Lys Ala Ser Ala Ala Leu Leu Cys Leu Leu Leu Thr Ala Ala Ala
1               5                   10                  15

Phe Ser Pro Gln Gly Leu Ala
            20

<210> SEQ ID NO 393
<211> LENGTH: 21
<212> TYPE: PRT
<213> ORGANISM: Homo sapiens

<400> SEQUENCE: 393

Met Arg Leu Leu Ile Leu Ala Leu Leu Gly Ile Cys Ser Leu Thr Ala
1               5                   10                  15

Tyr Ile Val Glu Gly
            20

<210> SEQ ID NO 394
<211> LENGTH: 21
<212> TYPE: PRT
<213> ORGANISM: Homo sapiens

<400> SEQUENCE: 394

Met Lys Val Val Pro Ser Leu Leu Ser Val Leu Leu Ala Gln Val
1               5                   10                  15

Trp Leu Val Pro Gly
            20

<210> SEQ ID NO 395
<211> LENGTH: 23
<212> TYPE: PRT
<213> ORGANISM: Homo sapiens

<400> SEQUENCE: 395

Met Ala Ala Ala Gly Gln Leu Cys Leu Leu Tyr Leu Ser Ala Gly Leu
1               5                   10                  15

Leu Ser Arg Leu Gly Ala Ala
            20

<210> SEQ ID NO 396
<211> LENGTH: 22
<212> TYPE: PRT
<213> ORGANISM: Homo sapiens

<400> SEQUENCE: 396

Met Glu Gln Gly Lys Gly Leu Ala Val Leu Ile Leu Ala Ile Ile Leu
1               5                   10                  15

Leu Gln Gly Thr Leu Ala
            20

<210> SEQ ID NO 397
<211> LENGTH: 21
<212> TYPE: PRT
<213> ORGANISM: Homo sapiens

<400> SEQUENCE: 397

Met Ala Leu Pro Phe Val Leu Leu Met Ala Leu Val Val Leu Asn Cys
1               5                   10                  15
```

Lys Ser Ile Cys Ser
            20

<210> SEQ ID NO 398
<211> LENGTH: 19
<212> TYPE: PRT
<213> ORGANISM: Homo sapiens

<400> SEQUENCE: 398

Met Arg Leu Leu Trp Gly Leu Ile Trp Ala Ser Ser Phe Phe Thr Leu
1               5                   10                  15

Ser Leu Gln

<210> SEQ ID NO 399
<211> LENGTH: 19
<212> TYPE: PRT
<213> ORGANISM: Homo sapiens

<400> SEQUENCE: 399

Met Arg Leu Leu Trp Gly Leu Ile Trp Ala Ser Ser Phe Phe Thr Leu
1               5                   10                  15

Ser Leu Gln

<210> SEQ ID NO 400
<211> LENGTH: 23
<212> TYPE: PRT
<213> ORGANISM: Homo sapiens

<400> SEQUENCE: 400

Met Met Gly Leu Ser Leu Ala Ser Ala Val Leu Leu Ala Ser Leu Leu
1               5                   10                  15

Ser Leu His Leu Gly Thr Ala
            20

<210> SEQ ID NO 401
<211> LENGTH: 21
<212> TYPE: PRT
<213> ORGANISM: Homo sapiens

<400> SEQUENCE: 401

Met Ser Leu Leu Val Val Ser Met Ala Cys Val Gly Phe Phe Leu Leu
1               5                   10                  15

Gln Gly Ala Trp Pro
            20

<210> SEQ ID NO 402
<211> LENGTH: 20
<212> TYPE: PRT
<213> ORGANISM: Homo sapiens

<400> SEQUENCE: 402

Met Ser Asp Leu Leu Ser Val Phe Leu His Leu Leu Leu Leu Phe Lys
1               5                   10                  15

Leu Val Ala Pro
            20

<210> SEQ ID NO 403
<211> LENGTH: 18
<212> TYPE: PRT
<213> ORGANISM: Homo sapiens

<400> SEQUENCE: 403

```
Met Lys Leu Leu His Val Phe Leu Leu Phe Leu Cys Phe His Leu Arg
1               5                   10                  15

Phe Cys

<210> SEQ ID NO 404
<211> LENGTH: 24
<212> TYPE: PRT
<213> ORGANISM: Homo sapiens

<400> SEQUENCE: 404

Met Arg Pro Ser Gly Thr Ala Gly Ala Ala Leu Leu Ala Leu Leu Ala
1               5                   10                  15

Ala Leu Cys Pro Ala Ser Arg Ala
            20

<210> SEQ ID NO 405
<211> LENGTH: 21
<212> TYPE: PRT
<213> ORGANISM: Homo sapiens

<400> SEQUENCE: 405

Met Thr Asn Lys Cys Leu Leu Gln Ile Ala Leu Leu Leu Cys Phe Ser
1               5                   10                  15

Thr Thr Ala Leu Ser
            20

<210> SEQ ID NO 406
<211> LENGTH: 21
<212> TYPE: PRT
<213> ORGANISM: Homo sapiens

<400> SEQUENCE: 406

Met Asp Met Trp Thr Ala Leu Leu Ile Leu Gln Ala Leu Leu Leu Pro
1               5                   10                  15

Ser Leu Ala Asp Gly
            20

<210> SEQ ID NO 407
<211> LENGTH: 20
<212> TYPE: PRT
<213> ORGANISM: Homo sapiens

<400> SEQUENCE: 407

Met Gly Ser Gln Val His Leu Leu Ser Phe Leu Leu Leu Trp Ile Ser
1               5                   10                  15

Asp Thr Arg Ala
            20

<210> SEQ ID NO 408
<211> LENGTH: 22
<212> TYPE: PRT
<213> ORGANISM: Homo sapiens

<400> SEQUENCE: 408

Met Gly Ser Pro Gly Met Val Leu Gly Leu Leu Val Gln Ile Trp Ala
1               5                   10                  15

Leu Gln Glu Ala Ser Ser
            20

<210> SEQ ID NO 409
<211> LENGTH: 23
<212> TYPE: PRT
```

-continued

<213> ORGANISM: Homo sapiens

<400> SEQUENCE: 409

Met Ile Leu Asn Lys Ala Leu Leu Gly Ala Leu Ala Leu Thr Thr
1               5                   10                  15
Val Met Ser Pro Cys Gly Gly
            20

<210> SEQ ID NO 410
<211> LENGTH: 23
<212> TYPE: PRT
<213> ORGANISM: Homo sapiens

<400> SEQUENCE: 410

Met Glu Ala Pro Ala Ala Gly Leu Phe Leu Leu Leu Leu Gly Thr
1               5                   10                  15
Trp Ala Pro Ala Pro Gly Ser
            20

<210> SEQ ID NO 411
<211> LENGTH: 21
<212> TYPE: PRT
<213> ORGANISM: Homo sapiens

<400> SEQUENCE: 411

Met Gly Pro Trp Gly Trp Lys Leu Arg Trp Thr Val Ala Leu Leu
1               5                   10                  15
Ala Ala Ala Gly Thr
            20

<210> SEQ ID NO 412
<211> LENGTH: 20
<212> TYPE: PRT
<213> ORGANISM: Homo sapiens

<400> SEQUENCE: 412

Met Phe Ser Leu Lys Thr Leu Pro Phe Leu Leu Leu His Val Gln
1               5                   10                  15
Ile Ser Lys Ala
            20

<210> SEQ ID NO 413
<211> LENGTH: 21
<212> TYPE: PRT
<213> ORGANISM: Homo sapiens

<400> SEQUENCE: 413

Met Leu Gly Gln Val Val Thr Leu Ile Leu Leu Leu Leu Lys Val
1               5                   10                  15
Tyr Gln Gly Lys Gly
            20

<210> SEQ ID NO 414
<211> LENGTH: 20
<212> TYPE: PRT
<213> ORGANISM: Homo sapiens

<400> SEQUENCE: 414

Met Val Tyr Lys Thr Leu Phe Ala Leu Cys Ile Leu Thr Ala Gly Trp
1               5                   10                  15
Arg Val Gln Ser
            20

```
<210> SEQ ID NO 415
<211> LENGTH: 19
<212> TYPE: PRT
<213> ORGANISM: Homo sapiens

<400> SEQUENCE: 415

Met Gln Ile Glu Leu Ser Thr Cys Phe Phe Leu Cys Leu Leu Arg Phe
1               5                   10                  15

Cys Phe Ser

<210> SEQ ID NO 416
<211> LENGTH: 21
<212> TYPE: PRT
<213> ORGANISM: Homo sapiens

<400> SEQUENCE: 416

Met Val Pro Pro Lys Leu His Val Leu Phe Cys Leu Cys Gly Cys Leu
1               5                   10                  15

Ala Val Val Tyr Pro
            20

<210> SEQ ID NO 417
<211> LENGTH: 20
<212> TYPE: PRT
<213> ORGANISM: Homo sapiens

<400> SEQUENCE: 417

Met Lys Ser Ile Tyr Phe Val Ala Gly Leu Phe Val Met Leu Val Gln
1               5                   10                  15

Gly Ser Trp Gln
            20

<210> SEQ ID NO 418
<211> LENGTH: 23
<212> TYPE: PRT
<213> ORGANISM: Homo sapiens

<400> SEQUENCE: 418

Met Ile Leu Asn Lys Ala Leu Met Leu Gly Ala Leu Ala Leu Thr Thr
1               5                   10                  15

Val Met Ser Pro Cys Gly Gly
            20

<210> SEQ ID NO 419
<211> LENGTH: 23
<212> TYPE: PRT
<213> ORGANISM: Homo sapiens

<400> SEQUENCE: 419

Met Ile Leu Asn Lys Ala Leu Met Leu Gly Ala Leu Ala Leu Thr Thr
1               5                   10                  15

Val Met Ser Pro Cys Gly Gly
            20

<210> SEQ ID NO 420
<211> LENGTH: 23
<212> TYPE: PRT
<213> ORGANISM: Homo sapiens

<400> SEQUENCE: 420

Met Ile Leu Asn Lys Ala Leu Met Leu Gly Ala Leu Ala Leu Thr Thr
```

```
1               5                   10                  15
Val Met Ser Pro Cys Gly Gly
            20

<210> SEQ ID NO 421
<211> LENGTH: 23
<212> TYPE: PRT
<213> ORGANISM: Homo sapiens

<400> SEQUENCE: 421

Met Gln Met Ser Pro Ala Leu Thr Cys Leu Val Leu Gly Leu Ala Leu
1               5                   10                  15

Val Phe Gly Glu Gly Ser Ala
            20

<210> SEQ ID NO 422
<211> LENGTH: 21
<212> TYPE: PRT
<213> ORGANISM: Homo sapiens

<400> SEQUENCE: 422

Met Arg Ala Leu Trp Val Leu Gly Leu Cys Cys Val Leu Leu Thr Phe
1               5                   10                  15

Gly Ser Val Arg Ala
            20

<210> SEQ ID NO 423
<211> LENGTH: 19
<212> TYPE: PRT
<213> ORGANISM: Homo sapiens

<400> SEQUENCE: 423

Met Met Trp Thr Trp Ala Leu Trp Met Leu Pro Ser Leu Cys Lys Phe
1               5                   10                  15

Ser Leu Ala

<210> SEQ ID NO 424
<211> LENGTH: 26
<212> TYPE: PRT
<213> ORGANISM: Homo sapiens

<400> SEQUENCE: 424

Met Thr Ala Ala Ala Gly Ser Ala Gly Arg Ala Ala Val Pro Leu Leu
1               5                   10                  15

Leu Cys Ala Leu Leu Ala Pro Gly Gly Ala
            20                  25

<210> SEQ ID NO 425
<211> LENGTH: 20
<212> TYPE: PRT
<213> ORGANISM: Homo sapiens

<400> SEQUENCE: 425

Met Trp Lys Arg Trp Leu Ala Leu Ala Leu Ala Leu Val Ala Val Ala
1               5                   10                  15

Trp Val Arg Ala
            20

<210> SEQ ID NO 426
<211> LENGTH: 21
<212> TYPE: PRT
<213> ORGANISM: Homo sapiens
```

<400> SEQUENCE: 426

Met Arg Leu Ser Val Cys Leu Leu Met Val Ser Leu Ala Leu Cys Cys
1               5                   10                  15

Tyr Gln Ala His Ala
            20

<210> SEQ ID NO 427
<211> LENGTH: 23
<212> TYPE: PRT
<213> ORGANISM: Homo sapiens

<400> SEQUENCE: 427

Met Ala Leu Thr Phe Ala Leu Leu Val Ala Leu Leu Val Leu Ser Cys
1               5                   10                  15

Lys Ser Ser Cys Ser Val Gly
            20

<210> SEQ ID NO 428
<211> LENGTH: 22
<212> TYPE: PRT
<213> ORGANISM: Homo sapiens

<400> SEQUENCE: 428

Met Asp Ala Met Lys Arg Gly Leu Cys Cys Val Leu Leu Leu Cys Gly
1               5                   10                  15

Ala Val Phe Val Ser Pro
            20

<210> SEQ ID NO 429
<211> LENGTH: 22
<212> TYPE: PRT
<213> ORGANISM: Homo sapiens

<400> SEQUENCE: 429

Met Ala Ser Arg Leu Thr Leu Leu Thr Leu Leu Leu Leu Leu Leu Ala
1               5                   10                  15

Gly Asp Arg Ala Ser Ser
            20

<210> SEQ ID NO 430
<211> LENGTH: 21
<212> TYPE: PRT
<213> ORGANISM: Homo sapiens

<400> SEQUENCE: 430

Met Leu Leu Ala Trp Val Gln Ala Phe Leu Val Ser Asn Met Leu Leu
1               5                   10                  15

Ala Glu Ala Tyr Gly
            20

<210> SEQ ID NO 431
<211> LENGTH: 21
<212> TYPE: PRT
<213> ORGANISM: Homo sapiens

<400> SEQUENCE: 431

Met Arg Leu Ser Val Cys Leu Leu Leu Leu Thr Leu Ala Leu Cys Cys
1               5                   10                  15

Tyr Arg Ala Asn Ala
            20

<210> SEQ ID NO 432
<211> LENGTH: 22
<212> TYPE: PRT
<213> ORGANISM: Homo sapiens

<400> SEQUENCE: 432

Met Thr Ser Ser Arg Leu Trp Phe Ser Leu Leu Ala Ala Ala Phe
1               5                   10                  15
Ala Gly Arg Ala Thr Ala
            20

<210> SEQ ID NO 433
<211> LENGTH: 20
<212> TYPE: PRT
<213> ORGANISM: Homo sapiens

<400> SEQUENCE: 433

Met Glu Ala Pro Ala Gln Leu Leu Phe Leu Leu Leu Leu Trp Leu Pro
1               5                   10                  15
Asp Thr Thr Arg
            20

<210> SEQ ID NO 434
<211> LENGTH: 21
<212> TYPE: PRT
<213> ORGANISM: Homo sapiens

<400> SEQUENCE: 434

Met Lys Trp Lys Ala Leu Phe Thr Ala Ala Ile Leu Gln Ala Gln Leu
1               5                   10                  15
Pro Ile Thr Glu Ala
            20

<210> SEQ ID NO 435
<211> LENGTH: 21
<212> TYPE: PRT
<213> ORGANISM: Homo sapiens

<400> SEQUENCE: 435

Met Glu Ile Lys His Leu Leu Phe Leu Val Ala Ala Cys Leu Leu
1               5                   10                  15
Pro Met Leu Ser Met
            20

<210> SEQ ID NO 436
<211> LENGTH: 23
<212> TYPE: PRT
<213> ORGANISM: Homo sapiens

<400> SEQUENCE: 436

Met Pro Arg Pro Arg Leu Leu Ala Ala Leu Cys Gly Ala Leu Leu Cys
1               5                   10                  15
Ala Pro Ser Leu Leu Val Ala
            20

<210> SEQ ID NO 437
<211> LENGTH: 23
<212> TYPE: PRT
<213> ORGANISM: Homo sapiens

<400> SEQUENCE: 437

Met Ala Ser Pro Phe Ala Leu Leu Met Val Leu Val Val Leu Ser Cys

-continued

```
                1               5                  10                 15

Lys Ser Ser Cys Ser Leu Gly
                20

<210> SEQ ID NO 438
<211> LENGTH: 23
<212> TYPE: PRT
<213> ORGANISM: Homo sapiens

<400> SEQUENCE: 438

Met Lys Val Ser Ala Ala Leu Leu Cys Leu Leu Leu Ile Ala Ala Thr
1               5                   10                  15

Phe Ile Pro Gln Gly Leu Ala
                20

<210> SEQ ID NO 439
<211> LENGTH: 22
<212> TYPE: PRT
<213> ORGANISM: Homo sapiens

<400> SEQUENCE: 439

Met Gly His Pro Pro Leu Leu Pro Leu Leu Leu Leu Leu Leu His Thr Cys
1               5                   10                  15

Val Pro Ala Ser Trp Gly
                20

<210> SEQ ID NO 440
<211> LENGTH: 21
<212> TYPE: PRT
<213> ORGANISM: Homo sapiens

<400> SEQUENCE: 440

Met Arg Leu Ser Trp Phe Arg Val Leu Thr Val Leu Ser Ile Cys Leu
1               5                   10                  15

Ser Ala Val Ala Thr
                20

<210> SEQ ID NO 441
<211> LENGTH: 23
<212> TYPE: PRT
<213> ORGANISM: Homo sapiens

<400> SEQUENCE: 441

Met Gly Leu Pro Arg Leu Val Cys Ala Phe Leu Leu Ala Ala Cys Cys
1               5                   10                  15

Cys Cys Pro Arg Val Ala Gly
                20

<210> SEQ ID NO 442
<211> LENGTH: 21
<212> TYPE: PRT
<213> ORGANISM: Homo sapiens

<400> SEQUENCE: 442

Met Glu Ser Arg Val Leu Leu Arg Thr Phe Cys Leu Ile Phe Gly Leu
1               5                   10                  15

Gly Ala Val Trp Gly
                20

<210> SEQ ID NO 443
<211> LENGTH: 21
<212> TYPE: PRT
```

<213> ORGANISM: Homo sapiens

<400> SEQUENCE: 443

Met Val Gly Lys Met Trp Pro Val Leu Trp Thr Leu Cys Ala Val Arg
1               5                   10                  15

Val Thr Val Asp Ala
            20

<210> SEQ ID NO 444
<211> LENGTH: 22
<212> TYPE: PRT
<213> ORGANISM: Homo sapiens

<400> SEQUENCE: 444

Met Arg Val Leu Ser Gly Thr Ser Leu Met Leu Cys Ser Leu Leu Leu
1               5                   10                  15

Leu Leu Gln Ala Leu Cys
            20

<210> SEQ ID NO 445
<211> LENGTH: 23
<212> TYPE: PRT
<213> ORGANISM: Homo sapiens

<400> SEQUENCE: 445

Met Gln Val Ser Thr Ala Ala Leu Ala Val Leu Leu Cys Thr Met Ala
1               5                   10                  15

Leu Cys Asn Gln Val Leu Ser
            20

<210> SEQ ID NO 446
<211> LENGTH: 22
<212> TYPE: PRT
<213> ORGANISM: Homo sapiens

<400> SEQUENCE: 446

Met Leu Gly Pro Cys Met Leu Leu Leu Leu Leu Leu Gly Leu Arg
1               5                   10                  15

Leu Gln Leu Ser Leu Gly
            20

<210> SEQ ID NO 447
<211> LENGTH: 21
<212> TYPE: PRT
<213> ORGANISM: Homo sapiens

<400> SEQUENCE: 447

Met Ala Arg Arg Ser Val Leu Tyr Phe Ile Leu Leu Asn Ala Leu Ile
1               5                   10                  15

Asn Lys Gly Gln Ala
            20

<210> SEQ ID NO 448
<211> LENGTH: 19
<212> TYPE: PRT
<213> ORGANISM: Homo sapiens

<400> SEQUENCE: 448

Met Arg Arg Leu Leu Glu Pro Cys Trp Trp Ile Leu Phe Leu Lys Ile
1               5                   10                  15

Thr Ser Ser

<210> SEQ ID NO 449
<211> LENGTH: 23
<212> TYPE: PRT
<213> ORGANISM: Homo sapiens

<400> SEQUENCE: 449

Met Leu Leu Leu Ala Arg Cys Leu Leu Val Leu Val Ser Ser Leu
1               5                   10                  15

Leu Val Cys Ser Gly Leu Ala
            20

<210> SEQ ID NO 450
<211> LENGTH: 22
<212> TYPE: PRT
<213> ORGANISM: Homo sapiens

<400> SEQUENCE: 450

Met Asp Thr Ser Pro Leu Cys Phe Ser Ile Leu Val Leu Cys Ile
1               5                   10                  15

Phe Ile Gln Ser Ser Ala
            20

<210> SEQ ID NO 451
<211> LENGTH: 23
<212> TYPE: PRT
<213> ORGANISM: Homo sapiens

<400> SEQUENCE: 451

Met Glu Arg Met Leu Pro Leu Leu Ala Leu Gly Leu Leu Ala Ala Gly
1               5                   10                  15

Phe Cys Pro Ala Val Leu Cys
            20

<210> SEQ ID NO 452
<211> LENGTH: 21
<212> TYPE: PRT
<213> ORGANISM: Homo sapiens

<400> SEQUENCE: 452

Met Leu Trp Leu Phe Gln Ser Leu Leu Phe Val Phe Cys Phe Gly Pro
1               5                   10                  15

Gly Asn Val Val Ser
            20

<210> SEQ ID NO 453
<211> LENGTH: 27
<212> TYPE: PRT
<213> ORGANISM: Homo sapiens

<400> SEQUENCE: 453

Met Gly Thr Gly Gly Arg Arg Gly Ala Ala Ala Ala Pro Leu Leu Val
1               5                   10                  15

Ala Val Ala Ala Leu Leu Leu Gly Ala Ala Gly
            20                  25

<210> SEQ ID NO 454
<211> LENGTH: 24
<212> TYPE: PRT
<213> ORGANISM: Homo sapiens

<400> SEQUENCE: 454

Met Leu Ser Cys Arg Leu Gln Cys Ala Leu Ala Ala Leu Ser Ile Val

-continued

```
                1               5                  10                 15

Leu Ala Leu Gly Cys Val Thr Gly
            20

<210> SEQ ID NO 455
<211> LENGTH: 21
<212> TYPE: PRT
<213> ORGANISM: Homo sapiens

<400> SEQUENCE: 455

Met Lys Pro Val Trp Val Ala Thr Leu Leu Trp Met Leu Leu Leu Val
1               5                  10                 15

Pro Arg Leu Gly Ala
            20

<210> SEQ ID NO 456
<211> LENGTH: 23
<212> TYPE: PRT
<213> ORGANISM: Homo sapiens

<400> SEQUENCE: 456

Met Lys Leu Cys Val Thr Val Leu Ser Leu Leu Met Leu Val Ala Ala
1               5                  10                 15

Phe Cys Ser Pro Ala Leu Ser
            20

<210> SEQ ID NO 457
<211> LENGTH: 23
<212> TYPE: PRT
<213> ORGANISM: Homo sapiens

<400> SEQUENCE: 457

Met Ala Gln Ser Leu Ala Leu Ser Leu Leu Ile Leu Val Leu Ala Phe
1               5                  10                 15

Gly Ile Pro Arg Thr Gln Gly
            20

<210> SEQ ID NO 458
<211> LENGTH: 22
<212> TYPE: PRT
<213> ORGANISM: Homo sapiens

<400> SEQUENCE: 458

Met Ala Leu Lys Asn Lys Phe Ser Cys Leu Trp Ile Leu Gly Leu Cys
1               5                  10                 15

Leu Val Ala Thr Thr Ser
            20

<210> SEQ ID NO 459
<211> LENGTH: 21
<212> TYPE: PRT
<213> ORGANISM: Homo sapiens

<400> SEQUENCE: 459

Met Glu Leu Trp Gly Ala Tyr Leu Leu Leu Cys Leu Phe Ser Leu Leu
1               5                  10                 15

Thr Gln Val Thr Thr
            20

<210> SEQ ID NO 460
<211> LENGTH: 22
<212> TYPE: PRT
```

<213> ORGANISM: Homo sapiens

<400> SEQUENCE: 460

Met Phe Ser Phe Val Asp Leu Arg Leu Leu Leu Leu Ala Ala Thr
1               5                   10                  15
Ala Leu Leu Thr His Gly
            20

<210> SEQ ID NO 461
<211> LENGTH: 23
<212> TYPE: PRT
<213> ORGANISM: Homo sapiens

<400> SEQUENCE: 461

Met Lys Val Ser Glu Ala Ala Leu Ser Leu Leu Val Leu Ile Leu Ile
1               5                   10                  15
Ile Thr Ser Ala Ser Arg Ser
            20

<210> SEQ ID NO 462
<211> LENGTH: 23
<212> TYPE: PRT
<213> ORGANISM: Homo sapiens

<400> SEQUENCE: 462

Met Ala Gly Cys Val Pro Leu Leu Gln Gly Leu Val Leu Val Leu Ala
1               5                   10                  15
Leu His Arg Val Glu Pro Ser
            20

<210> SEQ ID NO 463
<211> LENGTH: 24
<212> TYPE: PRT
<213> ORGANISM: Homo sapiens

<400> SEQUENCE: 463

Met Ala Arg Ser Leu Val Cys Leu Gly Val Ile Ile Leu Leu Ser Ala
1               5                   10                  15
Phe Ser Gly Pro Gly Val Arg Gly
            20

<210> SEQ ID NO 464
<211> LENGTH: 24
<212> TYPE: PRT
<213> ORGANISM: Homo sapiens

<400> SEQUENCE: 464

Met Pro Ser Ser Val Ser Trp Gly Ile Leu Leu Leu Ala Gly Leu Cys
1               5                   10                  15
Cys Leu Val Pro Val Ser Leu Ala
            20

<210> SEQ ID NO 465
<211> LENGTH: 21
<212> TYPE: PRT
<213> ORGANISM: Homo sapiens

<400> SEQUENCE: 465

Met Ala Gln His His Leu Trp Ile Leu Leu Leu Cys Leu Gln Thr Trp
1               5                   10                  15
Pro Glu Ala Ala Gly
            20

<210> SEQ ID NO 466
<211> LENGTH: 24
<212> TYPE: PRT
<213> ORGANISM: Homo sapiens

<400> SEQUENCE: 466

Met Ser Arg Thr Ala Tyr Thr Val Gly Ala Leu Leu Leu Leu Leu Gly
1               5                   10                  15

Thr Leu Leu Pro Ala Ala Glu Gly
            20

<210> SEQ ID NO 467
<211> LENGTH: 23
<212> TYPE: PRT
<213> ORGANISM: Homo sapiens

<400> SEQUENCE: 467

Met Gly Val Pro Arg Pro Gln Pro Trp Ala Leu Gly Leu Leu Leu Phe
1               5                   10                  15

Leu Leu Pro Gly Ser Leu Gly
            20

<210> SEQ ID NO 468
<211> LENGTH: 23
<212> TYPE: PRT
<213> ORGANISM: Homo sapiens

<400> SEQUENCE: 468

Met Pro Ser Pro Gly Thr Val Cys Ser Leu Leu Leu Leu Gly Met Leu
1               5                   10                  15

Trp Leu Asp Leu Ala Met Ala
            20

<210> SEQ ID NO 469
<211> LENGTH: 22
<212> TYPE: PRT
<213> ORGANISM: Homo sapiens

<400> SEQUENCE: 469

Met Asp Met Arg Val Leu Ala Gln Leu Leu Gly Leu Leu Leu Leu Cys
1               5                   10                  15

Phe Pro Gly Ala Arg Cys
            20

<210> SEQ ID NO 470
<211> LENGTH: 22
<212> TYPE: PRT
<213> ORGANISM: Homo sapiens

<400> SEQUENCE: 470

Met Asp Met Arg Val Pro Ala Gln Leu Leu Gly Leu Leu Leu Leu Trp
1               5                   10                  15

Leu Pro Gly Ala Lys Cys
            20

<210> SEQ ID NO 471
<211> LENGTH: 21
<212> TYPE: PRT
<213> ORGANISM: Homo sapiens

<400> SEQUENCE: 471

-continued

Met Asn Lys Leu Leu Cys Cys Ala Leu Val Phe Leu Asp Ile Ser Ile
1               5                   10                  15

Lys Trp Thr Thr Gln
            20

<210> SEQ ID NO 472
<211> LENGTH: 22
<212> TYPE: PRT
<213> ORGANISM: Homo sapiens

<400> SEQUENCE: 472

Met Ala Asn Leu Gly Cys Trp Met Leu Val Leu Phe Val Ala Thr Trp
1               5                   10                  15

Ser Asp Leu Gly Leu Cys
            20

<210> SEQ ID NO 473
<211> LENGTH: 24
<212> TYPE: PRT
<213> ORGANISM: Homo sapiens

<400> SEQUENCE: 473

Met Leu Gln Gly Pro Gly Ser Leu Leu Leu Leu Phe Leu Ala Ser His
1               5                   10                  15

Cys Cys Leu Gly Ser Ala Arg Gly
            20

<210> SEQ ID NO 474
<211> LENGTH: 24
<212> TYPE: PRT
<213> ORGANISM: Homo sapiens

<400> SEQUENCE: 474

Met Ala Arg Arg Ala Gly Gly Ala Arg Met Phe Gly Ser Leu Leu Leu
1               5                   10                  15

Phe Ala Leu Leu Ala Ala Gly Val
            20

<210> SEQ ID NO 475
<211> LENGTH: 22
<212> TYPE: PRT
<213> ORGANISM: Homo sapiens

<400> SEQUENCE: 475

Met Met Lys Thr Leu Leu Leu Phe Val Gly Leu Leu Leu Thr Trp Glu
1               5                   10                  15

Ser Gly Gln Val Leu Gly
            20

<210> SEQ ID NO 476
<211> LENGTH: 24
<212> TYPE: PRT
<213> ORGANISM: Homo sapiens

<400> SEQUENCE: 476

Met Arg Val Leu Gly Gly Arg Cys Gly Ala Leu Leu Ala Cys Leu Leu
1               5                   10                  15

Leu Val Leu Pro Val Ser Glu Ala
            20

<210> SEQ ID NO 477
<211> LENGTH: 23

```
<212> TYPE: PRT
<213> ORGANISM: Homo sapiens

<400> SEQUENCE: 477

Met Arg Gly Ala Asn Ala Trp Ala Pro Leu Cys Leu Leu Leu Ala Ala
1               5                   10                  15

Ala Thr Gln Leu Ser Arg Gln
            20

<210> SEQ ID NO 478
<211> LENGTH: 22
<212> TYPE: PRT
<213> ORGANISM: Homo sapiens

<400> SEQUENCE: 478

Met Gly Glu Leu Met Ala Phe Leu Leu Pro Leu Ile Ile Val Leu Met
1               5                   10                  15

Val Lys His Ser Asp Ser
            20

<210> SEQ ID NO 479
<211> LENGTH: 26
<212> TYPE: PRT
<213> ORGANISM: Homo sapiens

<400> SEQUENCE: 479

Met Ala Gly Pro Leu Arg Ala Pro Leu Leu Leu Ala Ile Leu Ala
1               5                   10                  15

Val Ala Leu Ala Val Ser Pro Ala Ala Gly
            20                  25

<210> SEQ ID NO 480
<211> LENGTH: 23
<212> TYPE: PRT
<213> ORGANISM: Homo sapiens

<400> SEQUENCE: 480

Met Thr Pro Trp Leu Gly Leu Ile Val Leu Leu Gly Ser Trp Ser Leu
1               5                   10                  15

Gly Asp Trp Gly Ala Glu Ala
            20

<210> SEQ ID NO 481
<211> LENGTH: 23
<212> TYPE: PRT
<213> ORGANISM: Homo sapiens

<400> SEQUENCE: 481

Met Phe Ala Arg Met Ser Asp Leu His Val Leu Leu Leu Met Ala Leu
1               5                   10                  15

Val Gly Lys Thr Ala Cys Gly
            20

<210> SEQ ID NO 482
<211> LENGTH: 23
<212> TYPE: PRT
<213> ORGANISM: Homo sapiens

<400> SEQUENCE: 482

Met Ala Pro Phe Glu Pro Leu Ala Ser Gly Ile Leu Leu Leu Leu Trp
1               5                   10                  15

Leu Ile Ala Pro Ser Arg Ala
```

-continued

20

<210> SEQ ID NO 483
<211> LENGTH: 24
<212> TYPE: PRT
<213> ORGANISM: Homo sapiens

<400> SEQUENCE: 483

Met Pro Met Gly Ser Leu Gln Pro Leu Ala Thr Leu Tyr Leu Leu Gly
1               5                   10                  15

Met Leu Val Ala Ser Cys Leu Gly
            20

<210> SEQ ID NO 484
<211> LENGTH: 25
<212> TYPE: PRT
<213> ORGANISM: Homo sapiens

<400> SEQUENCE: 484

Met Ala His Arg Pro Pro Ser Pro Ala Leu Ala Ser Val Leu Leu Ala
1               5                   10                  15

Leu Leu Leu Ser Gly Ala Ala Arg Ala
            20                  25

<210> SEQ ID NO 485
<211> LENGTH: 24
<212> TYPE: PRT
<213> ORGANISM: Homo sapiens

<400> SEQUENCE: 485

Met Lys Gly Pro Pro Thr Phe Cys Ser Leu Leu Leu Ser Leu Leu
1               5                   10                  15

Leu Ser Pro Asp Pro Thr Ala Ala
            20

<210> SEQ ID NO 486
<211> LENGTH: 23
<212> TYPE: PRT
<213> ORGANISM: Homo sapiens

<400> SEQUENCE: 486

Met Gly Lys Asn Lys Leu Leu His Pro Ser Leu Val Leu Leu Leu Leu
1               5                   10                  15

Val Leu Leu Pro Thr Asp Ala
            20

<210> SEQ ID NO 487
<211> LENGTH: 26
<212> TYPE: PRT
<213> ORGANISM: Homo sapiens

<400> SEQUENCE: 487

Met Gly Leu Gly Ala Arg Gly Ala Trp Ala Leu Leu Leu Gly Thr
1               5                   10                  15

Leu Gln Val Leu Ala Leu Leu Gly Ala Ala
            20                  25

<210> SEQ ID NO 488
<211> LENGTH: 24
<212> TYPE: PRT
<213> ORGANISM: Homo sapiens

<400> SEQUENCE: 488

```
Met Ala Arg Leu Gln Thr Ala Leu Leu Val Val Leu Val Leu Leu Ala
1               5                   10                  15

Val Ala Leu Gln Ala Thr Glu Ala
            20

<210> SEQ ID NO 489
<211> LENGTH: 25
<212> TYPE: PRT
<213> ORGANISM: Homo sapiens

<400> SEQUENCE: 489

Met Ala Gly Pro Pro Arg Leu Leu Leu Pro Leu Leu Ala Leu
1               5                   10                  15

Ala Arg Gly Leu Pro Gly Ala Leu Ala
            20                  25

<210> SEQ ID NO 490
<211> LENGTH: 24
<212> TYPE: PRT
<213> ORGANISM: Homo sapiens

<400> SEQUENCE: 490

Met Asp His Leu Gly Ala Ser Leu Trp Pro Gln Val Gly Ser Leu Cys
1               5                   10                  15

Leu Leu Leu Ala Gly Ala Ala Trp
            20

<210> SEQ ID NO 491
<211> LENGTH: 27
<212> TYPE: PRT
<213> ORGANISM: Homo sapiens

<400> SEQUENCE: 491

Met Gly Pro Pro His Ser Gly Pro Gly Gly Val Arg Val Gly Ala Leu
1               5                   10                  15

Leu Leu Leu Gly Val Leu Gly Leu Val Ser Gly
            20                  25

<210> SEQ ID NO 492
<211> LENGTH: 22
<212> TYPE: PRT
<213> ORGANISM: Homo sapiens

<400> SEQUENCE: 492

Met Leu Thr Leu Gln Thr Trp Leu Val Gln Ala Leu Phe Ile Phe Leu
1               5                   10                  15

Thr Thr Glu Ser Thr Gly
            20

<210> SEQ ID NO 493
<211> LENGTH: 24
<212> TYPE: PRT
<213> ORGANISM: Homo sapiens

<400> SEQUENCE: 493

Met Glu Arg Gly Ala Gly Ala Lys Leu Leu Pro Leu Leu Leu Leu Leu
1               5                   10                  15

Arg Ala Thr Gly Phe Thr Cys Ala
            20

<210> SEQ ID NO 494
```

-continued

<211> LENGTH: 23
<212> TYPE: PRT
<213> ORGANISM: Homo sapiens

<400> SEQUENCE: 494

Met Ala Arg Ser Phe Ser Leu Leu Met Val Val Leu Val Leu Ser Tyr
1               5                   10                  15

Lys Ser Ile Cys Ser Leu Gly
            20

<210> SEQ ID NO 495
<211> LENGTH: 24
<212> TYPE: PRT
<213> ORGANISM: Homo sapiens

<400> SEQUENCE: 495

Met Gly Ile Pro Met Gly Lys Ser Met Leu Val Leu Leu Thr Phe Leu
1               5                   10                  15

Ala Phe Ala Ser Cys Cys Ile Ala
            20

<210> SEQ ID NO 496
<211> LENGTH: 26
<212> TYPE: PRT
<213> ORGANISM: Homo sapiens

<400> SEQUENCE: 496

Met Gly Ser Gly Pro Arg Gly Ala Leu Ser Leu Leu Leu Leu Leu Leu
1               5                   10                  15

Ala Pro Pro Ser Arg Pro Ala Ala Gly Cys
            20                  25

<210> SEQ ID NO 497
<211> LENGTH: 23
<212> TYPE: PRT
<213> ORGANISM: Homo sapiens

<400> SEQUENCE: 497

Met Gln Ile Ile Thr Thr Ala Leu Val Cys Leu Leu Leu Ala Gly Met
1               5                   10                  15

Trp Pro Glu Asp Val Asp Ser
            20

<210> SEQ ID NO 498
<211> LENGTH: 22
<212> TYPE: PRT
<213> ORGANISM: Homo sapiens

<400> SEQUENCE: 498

Met Pro Leu Leu Leu Tyr Thr Cys Leu Leu Trp Leu Pro Thr Ser Gly
1               5                   10                  15

Leu Trp Thr Val Gln Ala
            20

<210> SEQ ID NO 499
<211> LENGTH: 23
<212> TYPE: PRT
<213> ORGANISM: Homo sapiens

<400> SEQUENCE: 499

Met Gln Leu Pro Leu Ala Leu Cys Leu Val Cys Leu Leu Val His Thr
1               5                   10                  15

```
Ala Phe Arg Val Val Glu Gly
            20

<210> SEQ ID NO 500
<211> LENGTH: 22
<212> TYPE: PRT
<213> ORGANISM: Homo sapiens

<400> SEQUENCE: 500

Met Asp Met Arg Val Pro Ala Gln Leu Gly Leu Leu Leu Trp
1               5                   10                  15

Leu Arg Gly Ala Arg Cys
            20

<210> SEQ ID NO 501
<211> LENGTH: 24
<212> TYPE: PRT
<213> ORGANISM: Homo sapiens

<400> SEQUENCE: 501

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 502
<211> LENGTH: 24
<212> TYPE: PRT
<213> ORGANISM: Homo sapiens

<400> SEQUENCE: 502

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 503
<211> LENGTH: 24
<212> TYPE: PRT
<213> ORGANISM: Homo sapiens

<400> SEQUENCE: 503

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 504
<211> LENGTH: 24
<212> TYPE: PRT
<213> ORGANISM: Homo sapiens

<400> SEQUENCE: 504

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 505
<211> LENGTH: 24
<212> TYPE: PRT
<213> ORGANISM: Homo sapiens
```

-continued

<400> SEQUENCE: 505

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 506
<211> LENGTH: 24
<212> TYPE: PRT
<213> ORGANISM: Homo sapiens

<400> SEQUENCE: 506

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 507
<211> LENGTH: 24
<212> TYPE: PRT
<213> ORGANISM: Homo sapiens

<400> SEQUENCE: 507

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 508
<211> LENGTH: 24
<212> TYPE: PRT
<213> ORGANISM: Homo sapiens

<400> SEQUENCE: 508

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 509
<211> LENGTH: 23
<212> TYPE: PRT
<213> ORGANISM: Homo sapiens

<400> SEQUENCE: 509

Met Lys Ser Ile Ile Leu Phe Val Leu Ser Leu Leu Leu Ile Leu Glu
1               5                   10                  15

Lys Gln Ala Ala Val Met Gly
            20

<210> SEQ ID NO 510
<211> LENGTH: 22
<212> TYPE: PRT
<213> ORGANISM: Homo sapiens

<400> SEQUENCE: 510

Met Gly Arg Gly Leu Leu Arg Gly Leu Trp Pro Leu His Ile Val Leu
1               5                   10                  15

Trp Thr Arg Ile Ala Ser
            20

```
<210> SEQ ID NO 511
<211> LENGTH: 24
<212> TYPE: PRT
<213> ORGANISM: Homo sapiens

<400> SEQUENCE: 511

Met Gly Leu Thr Ser Gln Leu Leu Pro Pro Leu Phe Phe Leu Leu Ala
1               5                   10                  15

Cys Ala Gly Asn Phe Val His Gly
            20

<210> SEQ ID NO 512
<211> LENGTH: 22
<212> TYPE: PRT
<213> ORGANISM: Homo sapiens

<400> SEQUENCE: 512

Met Arg Ile His Tyr Leu Leu Phe Ala Leu Leu Phe Leu Phe Leu Val
1               5                   10                  15

Pro Val Pro Gly His Gly
            20

<210> SEQ ID NO 513
<211> LENGTH: 24
<212> TYPE: PRT
<213> ORGANISM: Homo sapiens

<400> SEQUENCE: 513

Met Ala Arg Leu Gly Asn Cys Ser Leu Thr Trp Ala Ala Leu Ile Ile
1               5                   10                  15

Leu Leu Leu Pro Gly Ser Leu Glu
            20

<210> SEQ ID NO 514
<211> LENGTH: 23
<212> TYPE: PRT
<213> ORGANISM: Homo sapiens

<400> SEQUENCE: 514

Met Ala Phe Asp Val Ser Cys Phe Phe Trp Val Val Leu Phe Ser Ala
1               5                   10                  15

Gly Cys Lys Val Ile Thr Ser
            20

<210> SEQ ID NO 515
<211> LENGTH: 24
<212> TYPE: PRT
<213> ORGANISM: Homo sapiens

<400> SEQUENCE: 515

Met Gln Arg Gly Ala Ala Leu Cys Leu Arg Leu Trp Leu Cys Leu Gly
1               5                   10                  15

Leu Leu Asp Gly Leu Val Ser Gly
            20

<210> SEQ ID NO 516
<211> LENGTH: 23
<212> TYPE: PRT
<213> ORGANISM: Homo sapiens

<400> SEQUENCE: 516

Met Leu Pro Pro Ala Ile His Phe Tyr Leu Leu Pro Leu Ala Cys Ile
1               5                   10                  15
```

```
Leu Met Lys Ser Cys Leu Ala
            20

<210> SEQ ID NO 517
<211> LENGTH: 26
<212> TYPE: PRT
<213> ORGANISM: Homo sapiens

<400> SEQUENCE: 517

Met Cys Pro Arg Ala Ala Arg Ala Pro Ala Thr Leu Leu Ala Leu
1               5                   10                  15

Gly Ala Val Leu Trp Pro Ala Ala Gly Ala
            20                  25

<210> SEQ ID NO 518
<211> LENGTH: 24
<212> TYPE: PRT
<213> ORGANISM: Homo sapiens

<400> SEQUENCE: 518

Met Lys Ala Ser Ser Leu Ala Phe Ser Leu Leu Ser Ala Ala Phe Tyr
1               5                   10                  15

Leu Leu Trp Thr Pro Ser Thr Gly
            20

<210> SEQ ID NO 519
<211> LENGTH: 24
<212> TYPE: PRT
<213> ORGANISM: Homo sapiens

<400> SEQUENCE: 519

Met Ala Pro Arg Gly Cys Ile Val Ala Val Phe Ala Ile Phe Cys Ile
1               5                   10                  15

Ser Arg Leu Leu Cys Ser His Gly
            20

<210> SEQ ID NO 520
<211> LENGTH: 25
<212> TYPE: PRT
<213> ORGANISM: Homo sapiens

<400> SEQUENCE: 520

Met Ala Pro Ala Met Glu Ser Pro Thr Leu Leu Cys Val Ala Leu Leu
1               5                   10                  15

Phe Phe Ala Pro Asp Gly Val Leu Ala
            20                  25

<210> SEQ ID NO 521
<211> LENGTH: 24
<212> TYPE: PRT
<213> ORGANISM: Homo sapiens

<400> SEQUENCE: 521

Met Ser Phe Pro Cys Lys Phe Val Ala Ser Phe Leu Leu Ile Phe Asn
1               5                   10                  15

Val Ser Ser Lys Gly Ala Val Ser
            20

<210> SEQ ID NO 522
<211> LENGTH: 24
<212> TYPE: PRT
<213> ORGANISM: Homo sapiens
```

```
<400> SEQUENCE: 522

Met Arg Val Met Ala Pro Gln Ala Leu Leu Leu Leu Ser Gly Ala
1               5                   10                  15

Leu Ala Leu Ile Glu Thr Trp Ala
            20

<210> SEQ ID NO 523
<211> LENGTH: 23
<212> TYPE: PRT
<213> ORGANISM: Homo sapiens

<400> SEQUENCE: 523

Met Met Ser Phe Val Gln Lys Gly Ser Trp Leu Leu Leu Ala Leu Leu
1               5                   10                  15

His Pro Thr Ile Ile Leu Ala
            20

<210> SEQ ID NO 524
<211> LENGTH: 24
<212> TYPE: PRT
<213> ORGANISM: Homo sapiens

<400> SEQUENCE: 524

Met Arg Val Thr Ala Pro Arg Thr Val Leu Leu Leu Leu Ser Gly Ala
1               5                   10                  15

Leu Ala Leu Thr Glu Thr Trp Ala
            20

<210> SEQ ID NO 525
<211> LENGTH: 24
<212> TYPE: PRT
<213> ORGANISM: Homo sapiens

<400> SEQUENCE: 525

Met Arg Val Thr Ala Pro Arg Thr Val Leu Leu Leu Leu Ser Gly Ala
1               5                   10                  15

Leu Ala Leu Thr Glu Thr Trp Ala
            20

<210> SEQ ID NO 526
<211> LENGTH: 24
<212> TYPE: PRT
<213> ORGANISM: Homo sapiens

<400> SEQUENCE: 526

Met Arg Val Met Ala Pro Arg Ala Leu Leu Leu Leu Leu Ser Gly Gly
1               5                   10                  15

Leu Ala Leu Thr Glu Thr Trp Ala
            20

<210> SEQ ID NO 527
<211> LENGTH: 24
<212> TYPE: PRT
<213> ORGANISM: Homo sapiens

<400> SEQUENCE: 527

Met Arg Val Met Ala Pro Arg Ala Leu Leu Leu Leu Leu Ser Gly Gly
1               5                   10                  15

Leu Ala Leu Thr Glu Thr Trp Ala
            20
```

<210> SEQ ID NO 528
<211> LENGTH: 24
<212> TYPE: PRT
<213> ORGANISM: Homo sapiens

<400> SEQUENCE: 528

Met Leu Val Met Ala Pro Arg Thr Val Leu Leu Leu Ser Ala Ala
1               5                   10                  15

Leu Ala Leu Thr Glu Thr Trp Ala
            20

<210> SEQ ID NO 529
<211> LENGTH: 24
<212> TYPE: PRT
<213> ORGANISM: Homo sapiens

<400> SEQUENCE: 529

Met Leu Val Met Ala Pro Arg Thr Val Leu Leu Leu Ser Ala Ala
1               5                   10                  15

Leu Ala Leu Thr Glu Thr Trp Ala
            20

<210> SEQ ID NO 530
<211> LENGTH: 24
<212> TYPE: PRT
<213> ORGANISM: Homo sapiens

<400> SEQUENCE: 530

Met Leu Val Met Ala Pro Arg Thr Val Leu Leu Leu Ser Ala Ala
1               5                   10                  15

Leu Ala Leu Thr Glu Thr Trp Ala
            20

<210> SEQ ID NO 531
<211> LENGTH: 24
<212> TYPE: PRT
<213> ORGANISM: Homo sapiens

<400> SEQUENCE: 531

Met Leu Val Met Ala Pro Arg Thr Val Leu Leu Leu Ser Ala Ala
1               5                   10                  15

Leu Ala Leu Thr Glu Thr Trp Ala
            20

<210> SEQ ID NO 532
<211> LENGTH: 24
<212> TYPE: PRT
<213> ORGANISM: Homo sapiens

<400> SEQUENCE: 532

Met Leu Val Met Ala Pro Arg Thr Val Leu Leu Leu Ser Ala Ala
1               5                   10                  15

Leu Ala Leu Thr Glu Thr Trp Ala
            20

<210> SEQ ID NO 533
<211> LENGTH: 24
<212> TYPE: PRT
<213> ORGANISM: Homo sapiens

<400> SEQUENCE: 533

Met Leu Val Met Ala Pro Arg Thr Val Leu Leu Leu Ser Ala Ala

-continued

```
                1               5                  10                  15
Leu Ala Leu Thr Glu Thr Trp Ala
            20

<210> SEQ ID NO 534
<211> LENGTH: 24
<212> TYPE: PRT
<213> ORGANISM: Homo sapiens

<400> SEQUENCE: 534

Met Leu Val Met Ala Pro Arg Thr Val Leu Leu Leu Leu Ser Ala Ala
1               5                  10                  15

Leu Ala Leu Thr Glu Thr Trp Ala
            20

<210> SEQ ID NO 535
<211> LENGTH: 24
<212> TYPE: PRT
<213> ORGANISM: Homo sapiens

<400> SEQUENCE: 535

Met Leu Val Met Ala Pro Arg Thr Val Leu Leu Leu Leu Ser Ala Ala
1               5                  10                  15

Leu Ala Leu Thr Glu Thr Trp Ala
            20

<210> SEQ ID NO 536
<211> LENGTH: 24
<212> TYPE: PRT
<213> ORGANISM: Homo sapiens

<400> SEQUENCE: 536

Met Leu Val Met Ala Pro Arg Thr Val Leu Leu Leu Leu Ser Ala Ala
1               5                  10                  15

Leu Ala Leu Thr Glu Thr Trp Ala
            20

<210> SEQ ID NO 537
<211> LENGTH: 23
<212> TYPE: PRT
<213> ORGANISM: Homo sapiens

<400> SEQUENCE: 537

Met Ala Arg Lys Ser Asn Leu Pro Val Leu Leu Val Pro Phe Leu Leu
1               5                  10                  15

Cys Gln Ala Leu Val Arg Cys
            20

<210> SEQ ID NO 538
<211> LENGTH: 23
<212> TYPE: PRT
<213> ORGANISM: Homo sapiens

<400> SEQUENCE: 538

Met Arg Gly Thr Pro Lys Thr His Leu Leu Ala Phe Ser Leu Leu Cys
1               5                  10                  15

Leu Leu Ser Lys Val Arg Thr
            20

<210> SEQ ID NO 539
<211> LENGTH: 23
<212> TYPE: PRT
```

<213> ORGANISM: Homo sapiens

<400> SEQUENCE: 539

Met Lys Tyr Thr Ser Tyr Ile Leu Ala Phe Gln Leu Cys Ile Val Leu
1               5                   10                  15
Gly Ser Leu Gly Cys Tyr Cys
            20

<210> SEQ ID NO 540
<211> LENGTH: 24
<212> TYPE: PRT
<213> ORGANISM: Homo sapiens

<400> SEQUENCE: 540

Met Arg Leu Pro Arg Arg Ala Ala Leu Gly Leu Leu Pro Leu Leu Leu
1               5                   10                  15
Leu Leu Pro Pro Ala Pro Glu Ala
            20

<210> SEQ ID NO 541
<211> LENGTH: 25
<212> TYPE: PRT
<213> ORGANISM: Homo sapiens

<400> SEQUENCE: 541

Met Gln Thr Pro Arg Ala Ser Pro Pro Arg Pro Ala Leu Leu Leu Leu
1               5                   10                  15
Leu Leu Leu Leu Gly Gly Ala His Gly
            20                  25

<210> SEQ ID NO 542
<211> LENGTH: 25
<212> TYPE: PRT
<213> ORGANISM: Homo sapiens

<400> SEQUENCE: 542

Met Gly Ser Arg Ala Glu Leu Cys Thr Leu Leu Gly Gly Phe Ser Phe
1               5                   10                  15
Leu Leu Leu Leu Ile Pro Gly Glu Gly
            20                  25

<210> SEQ ID NO 543
<211> LENGTH: 25
<212> TYPE: PRT
<213> ORGANISM: Homo sapiens

<400> SEQUENCE: 543

Met Ala Ala Ala Ala Thr Lys Ile Leu Leu Cys Leu Pro Leu Leu
1               5                   10                  15
Leu Leu Leu Ser Gly Trp Ser Arg Ala
            20                  25

<210> SEQ ID NO 544
<211> LENGTH: 24
<212> TYPE: PRT
<213> ORGANISM: Homo sapiens

<400> SEQUENCE: 544

Met Ala Leu Trp Met Arg Leu Leu Pro Leu Leu Ala Leu Leu Ala Leu
1               5                   10                  15
Trp Gly Pro Asp Pro Ala Ala Ala
            20

<210> SEQ ID NO 545
<211> LENGTH: 23
<212> TYPE: PRT
<213> ORGANISM: Homo sapiens

<400> SEQUENCE: 545

Met Arg Gln Thr Leu Pro Cys Ile Tyr Phe Trp Gly Gly Leu Leu Pro
1               5                   10                  15

Phe Gly Met Leu Cys Ala Ser
            20

<210> SEQ ID NO 546
<211> LENGTH: 24
<212> TYPE: PRT
<213> ORGANISM: Homo sapiens

<400> SEQUENCE: 546

Met Lys Glu Asn Val Ala Ser Ala Thr Val Phe Thr Leu Leu Leu Phe
1               5                   10                  15

Leu Asn Thr Cys Leu Leu Asn Gly
            20

<210> SEQ ID NO 547
<211> LENGTH: 23
<212> TYPE: PRT
<213> ORGANISM: Homo sapiens

<400> SEQUENCE: 547

Met Gly Asn Ser Cys Tyr Asn Ile Val Ala Thr Leu Leu Leu Val Leu
1               5                   10                  15

Asn Phe Glu Arg Thr Arg Ser
            20

<210> SEQ ID NO 548
<211> LENGTH: 22
<212> TYPE: PRT
<213> ORGANISM: Homo sapiens

<400> SEQUENCE: 548

Met Glu Lys Lys Cys Thr Leu Tyr Phe Leu Val Leu Leu Pro Phe Phe
1               5                   10                  15

Met Ile Leu Val Thr Ala
            20

<210> SEQ ID NO 549
<211> LENGTH: 27
<212> TYPE: PRT
<213> ORGANISM: Homo sapiens

<400> SEQUENCE: 549

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala
            20                  25

<210> SEQ ID NO 550
<211> LENGTH: 23
<212> TYPE: PRT
<213> ORGANISM: Homo sapiens

<400> SEQUENCE: 550

Met Arg Gln Ser His Gln Leu Pro Leu Val Gly Leu Leu Leu Phe Ser
1               5                   10                  15

Phe Ile Pro Ser Gln Leu Cys
            20

<210> SEQ ID NO 551
<211> LENGTH: 24
<212> TYPE: PRT
<213> ORGANISM: Homo sapiens

<400> SEQUENCE: 551

Met Arg Val Met Ala Pro Arg Thr Leu Ile Leu Leu Leu Ser Gly Ala
1               5                   10                  15

Leu Ala Leu Thr Glu Thr Trp Ala
            20

<210> SEQ ID NO 552
<211> LENGTH: 24
<212> TYPE: PRT
<213> ORGANISM: Homo sapiens

<400> SEQUENCE: 552

Met Arg Val Met Ala Pro Arg Thr Leu Ile Leu Leu Leu Ser Gly Ala
1               5                   10                  15

Leu Ala Leu Thr Glu Thr Trp Ala
            20

<210> SEQ ID NO 553
<211> LENGTH: 24
<212> TYPE: PRT
<213> ORGANISM: Homo sapiens

<400> SEQUENCE: 553

Met Arg Val Met Ala Pro Arg Thr Leu Ile Leu Leu Leu Ser Gly Ala
1               5                   10                  15

Leu Ala Leu Thr Glu Thr Trp Ala
            20

<210> SEQ ID NO 554
<211> LENGTH: 24
<212> TYPE: PRT
<213> ORGANISM: Homo sapiens

<400> SEQUENCE: 554

Met Arg Val Met Ala Pro Arg Thr Leu Ile Leu Leu Leu Ser Gly Ala
1               5                   10                  15

Leu Ala Leu Thr Glu Thr Trp Ala
            20

<210> SEQ ID NO 555
<211> LENGTH: 24
<212> TYPE: PRT
<213> ORGANISM: Homo sapiens

<400> SEQUENCE: 555

Met Arg Val Met Ala Pro Arg Thr Leu Leu Leu Leu Leu Ser Gly Ala
1               5                   10                  15

Leu Ala Leu Thr Glu Thr Trp Ala
            20

<210> SEQ ID NO 556
<211> LENGTH: 24

```
<212> TYPE: PRT
<213> ORGANISM: Homo sapiens

<400> SEQUENCE: 556

Met Arg Val Met Ala Pro Arg Thr Leu Ile Leu Leu Ser Gly Ala
1               5                   10                  15

Leu Ala Leu Thr Glu Thr Trp Ala
            20

<210> SEQ ID NO 557
<211> LENGTH: 24
<212> TYPE: PRT
<213> ORGANISM: Homo sapiens

<400> SEQUENCE: 557

Met Arg Val Met Ala Pro Arg Thr Leu Ile Leu Leu Ser Gly Ala
1               5                   10                  15

Leu Ala Leu Thr Glu Thr Trp Ala
            20

<210> SEQ ID NO 558
<211> LENGTH: 24
<212> TYPE: PRT
<213> ORGANISM: Homo sapiens

<400> SEQUENCE: 558

Met Arg Val Met Ala Pro Arg Thr Leu Ile Leu Leu Ser Gly Ala
1               5                   10                  15

Leu Ala Leu Thr Glu Thr Trp Ala
            20

<210> SEQ ID NO 559
<211> LENGTH: 24
<212> TYPE: PRT
<213> ORGANISM: Homo sapiens

<400> SEQUENCE: 559

Met Arg Val Met Ala Pro Arg Thr Leu Ile Leu Leu Ser Gly Ala
1               5                   10                  15

Leu Ala Leu Thr Glu Thr Trp Ala
            20

<210> SEQ ID NO 560
<211> LENGTH: 26
<212> TYPE: PRT
<213> ORGANISM: Homo sapiens

<400> SEQUENCE: 560

Met Ala Ala Val Val Ala Ala Thr Arg Trp Trp Gln Leu Leu Leu Val
1               5                   10                  15

Leu Ser Ala Ala Gly Met Gly Ala Ser Gly
            20                  25

<210> SEQ ID NO 561
<211> LENGTH: 25
<212> TYPE: PRT
<213> ORGANISM: Homo sapiens

<400> SEQUENCE: 561

Met Ala Gly Pro Ala Ile His Thr Ala Pro Met Leu Phe Leu Val Leu
1               5                   10                  15

Leu Leu Pro Leu Glu Leu Ser Leu Ala
```

```
            20                  25

<210> SEQ ID NO 562
<211> LENGTH: 25
<212> TYPE: PRT
<213> ORGANISM: Homo sapiens

<400> SEQUENCE: 562

Met Ser Glu Val Pro Val Ala Arg Val Trp Leu Val Leu Leu Leu
1               5                   10                  15

Thr Val Gln Val Gly Val Thr Ala Gly
            20                  25

<210> SEQ ID NO 563
<211> LENGTH: 26
<212> TYPE: PRT
<213> ORGANISM: Homo sapiens

<400> SEQUENCE: 563

Met Ala Leu Pro Pro Gly Pro Ala Ala Leu Arg His Thr Leu Leu Leu
1               5                   10                  15

Leu Pro Ala Leu Leu Ser Ser Gly Trp Gly
            20                  25

<210> SEQ ID NO 564
<211> LENGTH: 27
<212> TYPE: PRT
<213> ORGANISM: Homo sapiens

<400> SEQUENCE: 564

Met Ala Ser Ser Pro Trp Gly Cys Val Cys Gly Leu Leu Leu Leu
1               5                   10                  15

Leu Pro Leu Leu Gly Thr Gly Pro Ala Leu Gly
            20                  25

<210> SEQ ID NO 565
<211> LENGTH: 22
<212> TYPE: PRT
<213> ORGANISM: Homo sapiens

<400> SEQUENCE: 565

Met Asp Met Arg Val Pro Ala Gln Leu Leu Gly Leu Leu Leu Leu Trp
1               5                   10                  15

Leu Arg Arg Val Arg Cys
            20

<210> SEQ ID NO 566
<211> LENGTH: 24
<212> TYPE: PRT
<213> ORGANISM: Homo sapiens

<400> SEQUENCE: 566

Met Leu Val Met Ala Pro Arg Thr Val Leu Leu Leu Trp Gly Ala
1               5                   10                  15

Val Ala Leu Thr Glu Thr Trp Ala
            20

<210> SEQ ID NO 567
<211> LENGTH: 27
<212> TYPE: PRT
<213> ORGANISM: Homo sapiens

<400> SEQUENCE: 567
```

```
Met Ala Val Thr Asp Ser Leu Ser Arg Ala Ala Thr Val Leu Ala Thr
1               5                   10                  15

Val Leu Leu Leu Ser Phe Gly Ser Val Ala Ala
            20                  25
```

<210> SEQ ID NO 568
<211> LENGTH: 24
<212> TYPE: PRT
<213> ORGANISM: Homo sapiens

<400> SEQUENCE: 568

```
Met Ser Ala Pro Lys Leu Leu Ser Leu Gly Cys Ile Phe Phe Pro Leu
1               5                   10                  15

Leu Leu Phe Gln Gln Ala Arg Ala
            20
```

<210> SEQ ID NO 569
<211> LENGTH: 24
<212> TYPE: PRT
<213> ORGANISM: Homo sapiens

<400> SEQUENCE: 569

```
Met Arg Val Thr Ala Pro Arg Thr Val Leu Leu Leu Trp Gly Ala
1               5                   10                  15

Val Ala Leu Thr Glu Thr Trp Ala
            20
```

<210> SEQ ID NO 570
<211> LENGTH: 24
<212> TYPE: PRT
<213> ORGANISM: Homo sapiens

<400> SEQUENCE: 570

```
Met Arg Val Thr Ala Pro Arg Thr Val Leu Leu Leu Trp Gly Ala
1               5                   10                  15

Val Ala Leu Thr Glu Thr Trp Ala
            20
```

<210> SEQ ID NO 571
<211> LENGTH: 24
<212> TYPE: PRT
<213> ORGANISM: Homo sapiens

<400> SEQUENCE: 571

```
Met Arg Val Thr Ala Pro Arg Thr Val Leu Leu Leu Trp Gly Ala
1               5                   10                  15

Val Ala Leu Thr Glu Thr Trp Ala
            20
```

<210> SEQ ID NO 572
<211> LENGTH: 24
<212> TYPE: PRT
<213> ORGANISM: Homo sapiens

<400> SEQUENCE: 572

```
Met Arg Val Thr Ala Pro Arg Thr Val Leu Leu Leu Trp Gly Ala
1               5                   10                  15

Val Ala Leu Thr Glu Thr Trp Ala
            20
```

<210> SEQ ID NO 573

<211> LENGTH: 24
<212> TYPE: PRT
<213> ORGANISM: Homo sapiens

<400> SEQUENCE: 573

Met Arg Val Thr Ala Pro Arg Thr Val Leu Leu Leu Leu Trp Gly Ala
1               5                   10                  15

Val Ala Leu Thr Glu Thr Trp Ala
            20

<210> SEQ ID NO 574
<211> LENGTH: 24
<212> TYPE: PRT
<213> ORGANISM: Homo sapiens

<400> SEQUENCE: 574

Met Arg Val Thr Ala Pro Arg Thr Val Leu Leu Leu Leu Trp Gly Ala
1               5                   10                  15

Val Ala Leu Thr Glu Thr Trp Ala
            20

<210> SEQ ID NO 575
<211> LENGTH: 24
<212> TYPE: PRT
<213> ORGANISM: Homo sapiens

<400> SEQUENCE: 575

Met Arg Val Thr Ala Pro Arg Thr Val Leu Leu Leu Leu Trp Gly Ala
1               5                   10                  15

Val Ala Leu Thr Glu Thr Trp Ala
            20

<210> SEQ ID NO 576
<211> LENGTH: 28
<212> TYPE: PRT
<213> ORGANISM: Homo sapiens

<400> SEQUENCE: 576

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala
            20                  25

<210> SEQ ID NO 577
<211> LENGTH: 23
<212> TYPE: PRT
<213> ORGANISM: Homo sapiens

<400> SEQUENCE: 577

Met Tyr Leu Trp Leu Lys Leu Leu Ala Phe Gly Phe Ala Phe Leu Asp
1               5                   10                  15

Thr Glu Val Phe Val Thr Gly
            20

<210> SEQ ID NO 578
<211> LENGTH: 24
<212> TYPE: PRT
<213> ORGANISM: Homo sapiens

<400> SEQUENCE: 578

Met Arg Val Thr Ala Pro Arg Thr Leu Leu Leu Leu Leu Trp Gly Ala
1               5                   10                  15

-continued

Val Ala Leu Thr Glu Thr Trp Ala
            20

<210> SEQ ID NO 579
<211> LENGTH: 24
<212> TYPE: PRT
<213> ORGANISM: Homo sapiens

<400> SEQUENCE: 579

Met Arg Val Thr Ala Pro Arg Thr Leu Leu Leu Leu Trp Gly Ala
1               5                   10                  15

Val Ala Leu Thr Glu Thr Trp Ala
            20

<210> SEQ ID NO 580
<211> LENGTH: 24
<212> TYPE: PRT
<213> ORGANISM: Homo sapiens

<400> SEQUENCE: 580

Met Arg Val Thr Ala Pro Arg Thr Leu Leu Leu Leu Trp Gly Ala
1               5                   10                  15

Val Ala Leu Thr Glu Thr Trp Ala
            20

<210> SEQ ID NO 581
<211> LENGTH: 24
<212> TYPE: PRT
<213> ORGANISM: Homo sapiens

<400> SEQUENCE: 581

Met Arg Val Thr Ala Pro Arg Thr Leu Leu Leu Leu Trp Gly Ala
1               5                   10                  15

Val Ala Leu Thr Glu Thr Trp Ala
            20

<210> SEQ ID NO 582
<211> LENGTH: 24
<212> TYPE: PRT
<213> ORGANISM: Homo sapiens

<400> SEQUENCE: 582

Met Arg Val Thr Ala Pro Arg Thr Leu Leu Leu Leu Trp Gly Ala
1               5                   10                  15

Val Ala Leu Thr Glu Thr Trp Ala
            20

<210> SEQ ID NO 583
<211> LENGTH: 24
<212> TYPE: PRT
<213> ORGANISM: Homo sapiens

<400> SEQUENCE: 583

Met Arg Val Thr Ala Pro Arg Thr Leu Leu Leu Leu Trp Gly Ala
1               5                   10                  15

Val Ala Leu Thr Glu Thr Trp Ala
            20

<210> SEQ ID NO 584
<211> LENGTH: 24
<212> TYPE: PRT
<213> ORGANISM: Homo sapiens -continued

<400> SEQUENCE: 584

Met Arg Val Thr Ala Pro Arg Thr Leu Leu Leu Leu Trp Gly Ala
1               5                   10                  15

Val Ala Leu Thr Glu Thr Trp Ala
            20

<210> SEQ ID NO 585
<211> LENGTH: 26
<212> TYPE: PRT
<213> ORGANISM: Homo sapiens

<400> SEQUENCE: 585

Met Ala Gly Leu Met Thr Ile Val Thr Ser Leu Leu Phe Leu Gly Val
1               5                   10                  15

Cys Ala His His Ile Ile Pro Thr Gly Ser
            20                  25

<210> SEQ ID NO 586
<211> LENGTH: 26
<212> TYPE: PRT
<213> ORGANISM: Homo sapiens

<400> SEQUENCE: 586

Met Ala Ala Gly Ser Arg Thr Ser Leu Leu Leu Ala Phe Gly Leu Leu
1               5                   10                  15

Cys Leu Ser Trp Leu Gln Glu Gly Ser Ala
            20                  25

<210> SEQ ID NO 587
<211> LENGTH: 29
<212> TYPE: PRT
<213> ORGANISM: Homo sapiens

<400> SEQUENCE: 587

Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys
            20                  25

<210> SEQ ID NO 588
<211> LENGTH: 13
<212> TYPE: PRT
<213> ORGANISM: Homo sapiens

<400> SEQUENCE: 588

Val Val Phe Leu Thr Leu Ser Val Thr Trp Ile Gly Ala
1               5                   10

<210> SEQ ID NO 589
<211> LENGTH: 13
<212> TYPE: PRT
<213> ORGANISM: Homo sapiens

<400> SEQUENCE: 589

Val Val Phe Leu Thr Leu Ser Val Thr Trp Ile Gly Ala
1               5                   10

<210> SEQ ID NO 590
<211> LENGTH: 13
<212> TYPE: PRT
<213> ORGANISM: Homo sapiens

<400> SEQUENCE: 590

Val Val Phe Leu Thr Leu Ser Val Thr Trp Ile Gly Ala
1               5                   10

<210> SEQ ID NO 591
<211> LENGTH: 14
<212> TYPE: PRT
<213> ORGANISM: Homo sapiens

<400> SEQUENCE: 591

Met Gly Ser Arg Phe Leu Leu Val Leu Leu Ser Gly Ala Ser
1               5                   10

<210> SEQ ID NO 592
<211> LENGTH: 13
<212> TYPE: PRT
<213> ORGANISM: Homo sapiens

<400> SEQUENCE: 592

Met Leu Arg Leu Tyr Val Leu Val Met Gly Val Ser Ala
1               5                   10

<210> SEQ ID NO 593
<211> LENGTH: 14
<212> TYPE: PRT
<213> ORGANISM: Homo sapiens

<400> SEQUENCE: 593

Met Arg Ala Leu Ala Val Leu Ser Val Thr Leu Val Met Ala
1               5                   10

<210> SEQ ID NO 594
<211> LENGTH: 15
<212> TYPE: PRT
<213> ORGANISM: Homo sapiens

<400> SEQUENCE: 594

Met Ala Leu Leu Leu Leu Ser Leu Gly Leu Ser Leu Ile Ala Ala
1               5                   10                  15

<210> SEQ ID NO 595
<211> LENGTH: 15
<212> TYPE: PRT
<213> ORGANISM: Homo sapiens

<400> SEQUENCE: 595

Met Asn Arg Val Leu Cys Ala Pro Ala Gly Ala Val Arg Ala
1               5                   10                  15

<210> SEQ ID NO 596
<211> LENGTH: 15
<212> TYPE: PRT
<213> ORGANISM: Homo sapiens

<400> SEQUENCE: 596

Met Asn Pro Leu Leu Ile Leu Ala Phe Val Gly Ala Ala Val Ala
1               5                   10                  15

<210> SEQ ID NO 597
<211> LENGTH: 15
<212> TYPE: PRT
<213> ORGANISM: Homo sapiens

<400> SEQUENCE: 597

Met Lys Thr Leu Phe Leu Gly Val Thr Leu Gly Leu Ala Ala Ala

<210> SEQ ID NO 598
<211> LENGTH: 15
<212> TYPE: PRT
<213> ORGANISM: Homo sapiens

<400> SEQUENCE: 598

Met Lys Thr Leu Phe Leu Gly Val Thr Leu Gly Leu Ala Ala Ala
1               5                   10                  15

<210> SEQ ID NO 599
<211> LENGTH: 15
<212> TYPE: PRT
<213> ORGANISM: Homo sapiens

<400> SEQUENCE: 599

Met Gln Ser Arg Leu Leu Leu Gly Ala Pro Gly Gly His Gly
1               5                   10                  15

<210> SEQ ID NO 600
<211> LENGTH: 15
<212> TYPE: PRT
<213> ORGANISM: Homo sapiens

<400> SEQUENCE: 600

Met Leu Leu Leu Pro Leu Leu Leu Pro Val Leu Gly Ala Gly Ser
1               5                   10                  15

<210> SEQ ID NO 601
<211> LENGTH: 15
<212> TYPE: PRT
<213> ORGANISM: Homo sapiens

<400> SEQUENCE: 601

Met Lys Leu Gly Leu Leu Cys Ala Leu Leu Ser Leu Leu Ala Gly
1               5                   10                  15

<210> SEQ ID NO 602
<211> LENGTH: 16
<212> TYPE: PRT
<213> ORGANISM: Homo sapiens

<400> SEQUENCE: 602

Met Leu Gly Ile Thr Val Leu Ala Ala Leu Leu Ala Cys Ala Ser Ser
1               5                   10                  15

<210> SEQ ID NO 603
<211> LENGTH: 15
<212> TYPE: PRT
<213> ORGANISM: Homo sapiens

<400> SEQUENCE: 603

Met Arg Thr Leu Leu Thr Ile Leu Thr Val Gly Ser Leu Ala Ala
1               5                   10                  15

<210> SEQ ID NO 604
<211> LENGTH: 15
<212> TYPE: PRT
<213> ORGANISM: Homo sapiens

<400> SEQUENCE: 604

Met Arg Leu Leu Thr Leu Leu Gly Leu Leu Cys Gly Ser Val Ala
1               5                   10                  15

<210> SEQ ID NO 605
<211> LENGTH: 15
<212> TYPE: PRT
<213> ORGANISM: Homo sapiens

<400> SEQUENCE: 605

Met Gly Leu Leu Leu Val Leu Ile Leu Thr Pro Ser Leu Ala
1               5                   10                  15

<210> SEQ ID NO 606
<211> LENGTH: 15
<212> TYPE: PRT
<213> ORGANISM: Homo sapiens

<400> SEQUENCE: 606

Met Gly Leu Thr Leu Leu Leu Leu Leu Gly Leu Glu Gly
1               5                   10                  15

<210> SEQ ID NO 607
<211> LENGTH: 16
<212> TYPE: PRT
<213> ORGANISM: Homo sapiens

<400> SEQUENCE: 607

Met Val Pro Leu Val Pro Ala Leu Val Met Leu Gly Leu Val Ala Gly
1               5                   10                  15

<210> SEQ ID NO 608
<211> LENGTH: 15
<212> TYPE: PRT
<213> ORGANISM: Homo sapiens

<400> SEQUENCE: 608

Met Lys Ile Ile Ile Leu Leu Gly Phe Leu Gly Ala Thr Leu Ser
1               5                   10                  15

<210> SEQ ID NO 609
<211> LENGTH: 15
<212> TYPE: PRT
<213> ORGANISM: Homo sapiens

<400> SEQUENCE: 609

Met Lys Val Leu Leu Leu Thr Gly Leu Gly Ala Leu Phe Phe Ala
1               5                   10                  15

<210> SEQ ID NO 610
<211> LENGTH: 16
<212> TYPE: PRT
<213> ORGANISM: Homo sapiens

<400> SEQUENCE: 610

Met Leu Leu Ala Thr Leu Leu Leu Leu Leu Gly Gly Ala Leu Ala
1               5                   10                  15

<210> SEQ ID NO 611
<211> LENGTH: 15
<212> TYPE: PRT
<213> ORGANISM: Homo sapiens

<400> SEQUENCE: 611

Met Ala Met Gly Leu Phe Arg Val Cys Leu Val Val Val Thr Ala
1               5                   10                  15

<210> SEQ ID NO 612

```
<211> LENGTH: 15
<212> TYPE: PRT
<213> ORGANISM: Homo sapiens

<400> SEQUENCE: 612

Met Lys Leu Leu Val Ile Leu Leu Phe Ser Gly Leu Ile Thr Gly
1               5                   10                  15

<210> SEQ ID NO 613
<211> LENGTH: 16
<212> TYPE: PRT
<213> ORGANISM: Homo sapiens

<400> SEQUENCE: 613

Met Leu Pro Leu Leu Leu Gly Leu Leu Gly Pro Ala Ala Cys Trp Ala
1               5                   10                  15

<210> SEQ ID NO 614
<211> LENGTH: 16
<212> TYPE: PRT
<213> ORGANISM: Homo sapiens

<400> SEQUENCE: 614

Met Arg Val Leu Ala Cys Leu Leu Ala Ala Leu Val Gly Ile Gln Ala
1               5                   10                  15

<210> SEQ ID NO 615
<211> LENGTH: 16
<212> TYPE: PRT
<213> ORGANISM: Homo sapiens

<400> SEQUENCE: 615

Met Leu Leu Val Leu Leu Ser Val Val Leu Leu Ala Leu Ser Ser Ala
1               5                   10                  15

<210> SEQ ID NO 616
<211> LENGTH: 15
<212> TYPE: PRT
<213> ORGANISM: Homo sapiens

<400> SEQUENCE: 616

Met Thr Val Phe Leu Ser Phe Ala Phe Leu Ala Ala Ile Leu Thr
1               5                   10                  15

<210> SEQ ID NO 617
<211> LENGTH: 14
<212> TYPE: PRT
<213> ORGANISM: Homo sapiens

<400> SEQUENCE: 617

Met Asn Phe Ile Leu Phe Ile Phe Ile Pro Gly Val Phe Ser
1               5                   10

<210> SEQ ID NO 618
<211> LENGTH: 15
<212> TYPE: PRT
<213> ORGANISM: Homo sapiens

<400> SEQUENCE: 618

Met Asn Tyr Ser Pro Gly Leu Val Ser Leu Ile Leu Leu Leu Leu
1               5                   10                  15

<210> SEQ ID NO 619
<211> LENGTH: 15
<212> TYPE: PRT
```

<213> ORGANISM: Homo sapiens

<400> SEQUENCE: 619

Met Glu Leu Arg Val Leu Leu Cys Trp Ala Ser Leu Ala Ala Ala
1               5                   10                  15

<210> SEQ ID NO 620
<211> LENGTH: 17
<212> TYPE: PRT
<213> ORGANISM: Homo sapiens

<400> SEQUENCE: 620

Met Ala Ala Pro Ala Leu Leu Leu Ala Leu Leu Leu Pro Val Gly
1               5                   10                  15

Ala

<210> SEQ ID NO 621
<211> LENGTH: 16
<212> TYPE: PRT
<213> ORGANISM: Homo sapiens

<400> SEQUENCE: 621

Met Val Leu Ala Gln Gly Leu Leu Ser Met Ala Leu Leu Ala Leu Cys
1               5                   10                  15

<210> SEQ ID NO 622
<211> LENGTH: 19
<212> TYPE: PRT
<213> ORGANISM: Homo sapiens

<400> SEQUENCE: 622

Met Ala Ala Gln Ala Ala Ala Ala Gln Ala Ala Ala Ala Gln Ala
1               5                   10                  15

Ala Gln Ala

<210> SEQ ID NO 623
<211> LENGTH: 16
<212> TYPE: PRT
<213> ORGANISM: Homo sapiens

<400> SEQUENCE: 623

Met Lys Thr Gly Leu Phe Phe Leu Cys Leu Leu Gly Thr Ala Ala
1               5                   10                  15

<210> SEQ ID NO 624
<211> LENGTH: 16
<212> TYPE: PRT
<213> ORGANISM: Homo sapiens

<400> SEQUENCE: 624

Met Pro Val Thr Phe Ala Leu Leu Leu Leu Gly Gln Ala Thr Ala
1               5                   10                  15

<210> SEQ ID NO 625
<211> LENGTH: 16
<212> TYPE: PRT
<213> ORGANISM: Homo sapiens

<400> SEQUENCE: 625

Met Ser Val Pro Leu Leu Lys Ile Gly Val Val Leu Ser Thr Met Ala
1               5                   10                  15

<210> SEQ ID NO 626

```
<211> LENGTH: 16
<212> TYPE: PRT
<213> ORGANISM: Homo sapiens

<400> SEQUENCE: 626

Met Ala Ile Leu Pro Leu Leu Cys Leu Leu Pro Leu Ala Pro Ala
1               5                   10                  15

<210> SEQ ID NO 627
<211> LENGTH: 17
<212> TYPE: PRT
<213> ORGANISM: Homo sapiens

<400> SEQUENCE: 627

Met Asn Leu Ser Leu Val Leu Ala Ala Phe Cys Leu Gly Ile Ala Ser
1               5                   10                  15

Ala

<210> SEQ ID NO 628
<211> LENGTH: 19
<212> TYPE: PRT
<213> ORGANISM: Homo sapiens

<400> SEQUENCE: 628

Met Gly Gly Ala Gly Ile Leu Leu Leu Leu Ala Gly Ala Gly Val
1               5                   10                  15

Val Val Ala

<210> SEQ ID NO 629
<211> LENGTH: 16
<212> TYPE: PRT
<213> ORGANISM: Homo sapiens

<400> SEQUENCE: 629

Met Trp Pro Leu Ala Leu Val Ile Ala Ser Leu Thr Leu Ala Leu Ser
1               5                   10                  15

<210> SEQ ID NO 630
<211> LENGTH: 16
<212> TYPE: PRT
<213> ORGANISM: Homo sapiens

<400> SEQUENCE: 630

Met Leu Arg Gly Thr Leu Leu Cys Ala Val Leu Gly Leu Leu Arg Ala
1               5                   10                  15

<210> SEQ ID NO 631
<211> LENGTH: 17
<212> TYPE: PRT
<213> ORGANISM: Homo sapiens

<400> SEQUENCE: 631

Met Ala Ala Gly Val Val Phe Leu Ala Leu Ser Ala Gln Leu Leu Gln
1               5                   10                  15

Ala

<210> SEQ ID NO 632
<211> LENGTH: 17
<212> TYPE: PRT
<213> ORGANISM: Homo sapiens

<400> SEQUENCE: 632

Met Ala Ala Gly Val Val Phe Leu Ala Leu Ser Ala Gln Leu Leu Gln
```

-continued

```
  1               5                   10                  15

Ala

<210> SEQ ID NO 633
<211> LENGTH: 17
<212> TYPE: PRT
<213> ORGANISM: Homo sapiens

<400> SEQUENCE: 633

Met His Leu Leu Pro Ala Leu Ala Gly Val Leu Ala Thr Leu Val Leu
  1               5                   10                  15

Ala

<210> SEQ ID NO 634
<211> LENGTH: 16
<212> TYPE: PRT
<213> ORGANISM: Homo sapiens

<400> SEQUENCE: 634

Met Lys Pro Pro Phe Leu Leu Ala Leu Val Val Cys Ser Val Val Ser
  1               5                   10                  15

<210> SEQ ID NO 635
<211> LENGTH: 16
<212> TYPE: PRT
<213> ORGANISM: Homo sapiens

<400> SEQUENCE: 635

Met Pro Trp Pro Leu Leu Leu Leu Ala Val Ser Gly Ala Gln Thr
  1               5                   10                  15

<210> SEQ ID NO 636
<211> LENGTH: 17
<212> TYPE: PRT
<213> ORGANISM: Homo sapiens

<400> SEQUENCE: 636

Met Leu Leu Leu Gly Ile Leu Thr Leu Ala Phe Ala Gly Arg Thr Ala
  1               5                   10                  15

Gly

<210> SEQ ID NO 637
<211> LENGTH: 16
<212> TYPE: PRT
<213> ORGANISM: Homo sapiens

<400> SEQUENCE: 637

Met Asp Val Leu Phe Val Ala Ile Phe Ala Val Pro Leu Ile Leu Gly
  1               5                   10                  15

<210> SEQ ID NO 638
<211> LENGTH: 16
<212> TYPE: PRT
<213> ORGANISM: Homo sapiens

<400> SEQUENCE: 638

Met Phe Val Leu Leu Tyr Val Thr Ser Phe Ala Ile Cys Ala Ser Gly
  1               5                   10                  15

<210> SEQ ID NO 639
<211> LENGTH: 14
<212> TYPE: PRT
<213> ORGANISM: Homo sapiens
```

-continued

<400> SEQUENCE: 639

Met Ala Arg Thr Arg Asp Arg Val Arg Leu Leu Leu Leu Leu
1               5                   10

<210> SEQ ID NO 640
<211> LENGTH: 16
<212> TYPE: PRT
<213> ORGANISM: Homo sapiens

<400> SEQUENCE: 640

Met Lys Phe Thr Ile Val Phe Ala Gly Leu Leu Gly Val Phe Leu Ala
1               5                   10                  15

<210> SEQ ID NO 641
<211> LENGTH: 16
<212> TYPE: PRT
<213> ORGANISM: Homo sapiens

<400> SEQUENCE: 641

Met Arg Ile Ala Val Ile Cys Phe Cys Leu Leu Gly Ile Thr Cys Ala
1               5                   10                  15

<210> SEQ ID NO 642
<211> LENGTH: 17
<212> TYPE: PRT
<213> ORGANISM: Homo sapiens

<400> SEQUENCE: 642

Met Ser Ser Ser Ser Trp Leu Leu Leu Ser Leu Val Ala Val Thr Ala
1               5                   10                  15

Ala

<210> SEQ ID NO 643
<211> LENGTH: 16
<212> TYPE: PRT
<213> ORGANISM: Homo sapiens

<400> SEQUENCE: 643

Met Ala Pro Lys Leu Ile Thr Val Leu Cys Leu Gly Phe Cys Leu Asn
1               5                   10                  15

<210> SEQ ID NO 644
<211> LENGTH: 16
<212> TYPE: PRT
<213> ORGANISM: Homo sapiens

<400> SEQUENCE: 644

Met Ala Val Leu Phe Leu Leu Leu Phe Leu Cys Gly Thr Pro Gln Ala
1               5                   10                  15

<210> SEQ ID NO 645
<211> LENGTH: 17
<212> TYPE: PRT
<213> ORGANISM: Homo sapiens

<400> SEQUENCE: 645

Met Arg Leu Ala Leu Leu Trp Ala Leu Gly Leu Leu Gly Ala Gly Ser
1               5                   10                  15

Pro

<210> SEQ ID NO 646
<211> LENGTH: 18

```
<212> TYPE: PRT
<213> ORGANISM: Homo sapiens

<400> SEQUENCE: 646

Met Val Gly Cys Gly Val Ala Val Leu Cys Leu Trp Val Ser Cys Gly
1               5                   10                  15

Ala Ala

<210> SEQ ID NO 647
<211> LENGTH: 16
<212> TYPE: PRT
<213> ORGANISM: Homo sapiens

<400> SEQUENCE: 647

Met Ala Phe Leu Gly Leu Phe Ser Leu Leu Val Leu Gln Ser Met Ala
1               5                   10                  15

<210> SEQ ID NO 648
<211> LENGTH: 17
<212> TYPE: PRT
<213> ORGANISM: Homo sapiens

<400> SEQUENCE: 648

Met Leu Gly Ser Leu Gly Leu Trp Ala Leu Leu Pro Thr Ala Val Glu
1               5                   10                  15

Ala

<210> SEQ ID NO 649
<211> LENGTH: 16
<212> TYPE: PRT
<213> ORGANISM: Homo sapiens

<400> SEQUENCE: 649

Met Lys Lys Leu Met Val Val Leu Ser Leu Ile Ala Ala Ala Trp Ala
1               5                   10                  15

<210> SEQ ID NO 650
<211> LENGTH: 18
<212> TYPE: PRT
<213> ORGANISM: Homo sapiens

<400> SEQUENCE: 650

Met Trp Pro Leu Val Ala Ala Leu Leu Leu Gly Ser Ala Cys Cys Gly
1               5                   10                  15

Ser Ala

<210> SEQ ID NO 651
<211> LENGTH: 18
<212> TYPE: PRT
<213> ORGANISM: Homo sapiens

<400> SEQUENCE: 651

Met Pro Leu Ser Pro Gly Leu Leu Leu Leu Leu Ser Gly Ala Thr
1               5                   10                  15

Ala Thr

<210> SEQ ID NO 652
<211> LENGTH: 16
<212> TYPE: PRT
<213> ORGANISM: Homo sapiens

<400> SEQUENCE: 652
```

Met Gly Trp Leu Phe Leu Lys Val Leu Leu Ala Gly Val Ser Phe Ser
1               5                   10                  15

<210> SEQ ID NO 653
<211> LENGTH: 19
<212> TYPE: PRT
<213> ORGANISM: Homo sapiens

<400> SEQUENCE: 653

Met Gly Ala Ala Gly Leu Leu Gly Val Phe Leu Ala Leu Val Ala Pro
1               5                   10                  15

Gly Val Leu

<210> SEQ ID NO 654
<211> LENGTH: 17
<212> TYPE: PRT
<213> ORGANISM: Homo sapiens

<400> SEQUENCE: 654

Met Gly Leu Leu Leu Leu Val Pro Leu Leu Leu Pro Gly Ser Tyr
1               5                   10                  15

Gly

<210> SEQ ID NO 655
<211> LENGTH: 17
<212> TYPE: PRT
<213> ORGANISM: Homo sapiens

<400> SEQUENCE: 655

Met Ile Ala Phe Leu Leu Thr Ser Val Leu Met Ile Pro His Ala Gly
1               5                   10                  15

Gly

<210> SEQ ID NO 656
<211> LENGTH: 16
<212> TYPE: PRT
<213> ORGANISM: Homo sapiens

<400> SEQUENCE: 656

Met Lys Ala Thr Ile Ile Leu Leu Leu Ala Gln Val Ser Trp Ala
1               5                   10                  15

<210> SEQ ID NO 657
<211> LENGTH: 17
<212> TYPE: PRT
<213> ORGANISM: Homo sapiens

<400> SEQUENCE: 657

Met Ala Ala Arg Ala Val Phe Leu Ala Leu Ser Ala Gln Leu Leu Gln
1               5                   10                  15

Ala

<210> SEQ ID NO 658
<211> LENGTH: 17
<212> TYPE: PRT
<213> ORGANISM: Homo sapiens

<400> SEQUENCE: 658

Met Trp Thr Leu Val Ser Trp Val Ala Leu Thr Ala Gly Leu Val Ala
1               5                   10                  15

Gly

```
<210> SEQ ID NO 659
<211> LENGTH: 18
<212> TYPE: PRT
<213> ORGANISM: Homo sapiens

<400> SEQUENCE: 659

Met Ser Gln Val Met Ser Ser Pro Leu Leu Ala Gly Gly His Ala Val
1               5                   10                  15

Ser Leu

<210> SEQ ID NO 660
<211> LENGTH: 17
<212> TYPE: PRT
<213> ORGANISM: Homo sapiens

<400> SEQUENCE: 660

Met Leu Leu Pro Ala Leu Leu Phe Gly Met Ala Trp Ala Leu Ala Asp
1               5                   10                  15

Gly

<210> SEQ ID NO 661
<211> LENGTH: 17
<212> TYPE: PRT
<213> ORGANISM: Homo sapiens

<400> SEQUENCE: 661

Met Val Leu Leu Cys Leu Phe Leu Ala Ser Leu Ala Ala Thr Pro Arg
1               5                   10                  15

Ala

<210> SEQ ID NO 662
<211> LENGTH: 15
<212> TYPE: PRT
<213> ORGANISM: Homo sapiens

<400> SEQUENCE: 662

Met Trp Phe Leu Thr Thr Leu Leu Leu Trp Val Pro Val Asp Gly
1               5                   10                  15

<210> SEQ ID NO 663
<211> LENGTH: 15
<212> TYPE: PRT
<213> ORGANISM: Homo sapiens

<400> SEQUENCE: 663

Met Trp Phe Leu Thr Thr Leu Leu Leu Trp Val Pro Val Asp Gly
1               5                   10                  15

<210> SEQ ID NO 664
<211> LENGTH: 16
<212> TYPE: PRT
<213> ORGANISM: Homo sapiens

<400> SEQUENCE: 664

Met Leu Leu Leu Leu Leu Leu Leu Pro Leu Leu Trp Gly Thr Lys Gly
1               5                   10                  15

<210> SEQ ID NO 665
<211> LENGTH: 17
<212> TYPE: PRT
<213> ORGANISM: Homo sapiens

<400> SEQUENCE: 665
```

Met Ser Ala Val Gly Leu Val Leu Leu Val Leu Ala Leu Arg Leu Arg
1               5                   10                  15
Ala

<210> SEQ ID NO 666
<211> LENGTH: 16
<212> TYPE: PRT
<213> ORGANISM: Homo sapiens

<400> SEQUENCE: 666

Met Leu Pro Arg Leu Leu Leu Ile Cys Ala Pro Leu Cys Glu Pro
1               5                   10                  15

<210> SEQ ID NO 667
<211> LENGTH: 17
<212> TYPE: PRT
<213> ORGANISM: Homo sapiens

<400> SEQUENCE: 667

Met Leu Ala Arg Ala Leu Leu Leu Cys Ala Val Leu Ala Leu Ser His
1               5                   10                  15
Thr

<210> SEQ ID NO 668
<211> LENGTH: 17
<212> TYPE: PRT
<213> ORGANISM: Homo sapiens

<400> SEQUENCE: 668

Met Arg Leu His Leu Leu Leu Leu Ala Leu Cys Gly Ala Gly Thr
1               5                   10                  15
Thr

<210> SEQ ID NO 669
<211> LENGTH: 15
<212> TYPE: PRT
<213> ORGANISM: Homo sapiens

<400> SEQUENCE: 669

Leu Ser Lys Gln Gln Ala Ser Gln Val Leu Val Arg Lys Arg Arg
1               5                   10                  15

<210> SEQ ID NO 670
<211> LENGTH: 17
<212> TYPE: PRT
<213> ORGANISM: Homo sapiens

<400> SEQUENCE: 670

Met Trp Pro Leu Thr Ala Leu Leu Leu Val Pro Ser Ser Gly Gln
1               5                   10                  15
Ala

<210> SEQ ID NO 671
<211> LENGTH: 20
<212> TYPE: PRT
<213> ORGANISM: Homo sapiens

<400> SEQUENCE: 671

Met Ala Gly Leu Ala Ala Arg Leu Val Leu Leu Ala Gly Ala Ala Ala
1               5                   10                  15
Leu Ala Ser Gly

<210> SEQ ID NO 672
<211> LENGTH: 17
<212> TYPE: PRT
<213> ORGANISM: Homo sapiens

<400> SEQUENCE: 672

Met Trp Leu Phe Phe Gly Ile Thr Gly Leu Leu Thr Ala Ala Leu Ser
1               5                   10                  15

Gly

<210> SEQ ID NO 673
<211> LENGTH: 18
<212> TYPE: PRT
<213> ORGANISM: Homo sapiens

<400> SEQUENCE: 673

Met Ala Val Pro Ala Arg Thr Cys Gly Ala Ser Arg Pro Gly Pro Ala
1               5                   10                  15

Arg Thr

<210> SEQ ID NO 674
<211> LENGTH: 17
<212> TYPE: PRT
<213> ORGANISM: Homo sapiens

<400> SEQUENCE: 674

Met Trp Ala Gln Leu Leu Leu Gly Met Leu Ala Leu Ser Pro Ala Ile
1               5                   10                  15

Ala

<210> SEQ ID NO 675
<211> LENGTH: 18
<212> TYPE: PRT
<213> ORGANISM: Homo sapiens

<400> SEQUENCE: 675

Met Asp Phe Gly Leu Ala Leu Leu Leu Ala Gly Leu Leu Gly Leu Leu
1               5                   10                  15

Leu Gly

<210> SEQ ID NO 676
<211> LENGTH: 16
<212> TYPE: PRT
<213> ORGANISM: Homo sapiens

<400> SEQUENCE: 676

Met Arg Thr Leu Leu Leu Val Leu Trp Leu Ala Thr Arg Gly Ser Ala
1               5                   10                  15

<210> SEQ ID NO 677
<211> LENGTH: 16
<212> TYPE: PRT
<213> ORGANISM: Homo sapiens

<400> SEQUENCE: 677

Met Val Pro His Leu Leu Leu Cys Leu Leu Pro Leu Val Arg Ala
1               5                   10                  15

<210> SEQ ID NO 678
<211> LENGTH: 16

<212> TYPE: PRT
<213> ORGANISM: Homo sapiens

<400> SEQUENCE: 678

Met Phe Leu Leu Leu Ala Leu Leu Thr Glu Leu Gly Arg Leu Gln Ala
1               5                   10                  15

<210> SEQ ID NO 679
<211> LENGTH: 17
<212> TYPE: PRT
<213> ORGANISM: Homo sapiens

<400> SEQUENCE: 679

Met Trp Leu Leu Gly Pro Leu Cys Leu Leu Leu Ser Ser Ala Ala Glu
1               5                   10                  15

Ser

<210> SEQ ID NO 680
<211> LENGTH: 16
<212> TYPE: PRT
<213> ORGANISM: Homo sapiens

<400> SEQUENCE: 680

Met Leu Leu Gly Trp Ala Ser Leu Leu Leu Cys Ala Phe Arg Leu Pro
1               5                   10                  15

<210> SEQ ID NO 681
<211> LENGTH: 18
<212> TYPE: PRT
<213> ORGANISM: Homo sapiens

<400> SEQUENCE: 681

Met Ala Leu Arg His Leu Ala Leu Leu Ala Gly Leu Leu Val Gly Val
1               5                   10                  15

Ala Ser

<210> SEQ ID NO 682
<211> LENGTH: 17
<212> TYPE: PRT
<213> ORGANISM: Homo sapiens

<400> SEQUENCE: 682

Met Pro Leu Gln Leu Leu Leu Leu Ile Leu Leu Gly Pro Gly Asn
1               5                   10                  15

Ser

<210> SEQ ID NO 683
<211> LENGTH: 17
<212> TYPE: PRT
<213> ORGANISM: Homo sapiens

<400> SEQUENCE: 683

Met Thr Phe Gly Thr Val Leu Leu Leu Ser Val Leu Ala Ser Tyr His
1               5                   10                  15

Gly

<210> SEQ ID NO 684
<211> LENGTH: 16
<212> TYPE: PRT
<213> ORGANISM: Homo sapiens

<400> SEQUENCE: 684

Met Arg Leu Leu Phe Leu Ala Val Leu Arg Pro His Thr Gly Asn Ala
1               5                   10                  15

<210> SEQ ID NO 685
<211> LENGTH: 18
<212> TYPE: PRT
<213> ORGANISM: Homo sapiens

<400> SEQUENCE: 685

Met Leu Gln Gly Leu Leu Pro Val Ser Leu Leu Ser Val Ala Val
1               5                   10                  15

Ser Ala

<210> SEQ ID NO 686
<211> LENGTH: 19
<212> TYPE: PRT
<213> ORGANISM: Homo sapiens

<400> SEQUENCE: 686

Met Ala Leu Gly Ala Cys Gly Leu Leu Leu Leu Ala Val Pro Gly
1               5                   10                  15

Val Ser Leu

<210> SEQ ID NO 687
<211> LENGTH: 16
<212> TYPE: PRT
<213> ORGANISM: Homo sapiens

<400> SEQUENCE: 687

Met Arg Ile Met Leu Leu Phe Thr Ala Ile Leu Ala Phe Ser Leu Ala
1               5                   10                  15

<210> SEQ ID NO 688
<211> LENGTH: 18
<212> TYPE: PRT
<213> ORGANISM: Homo sapiens

<400> SEQUENCE: 688

Met Pro Pro Pro Pro Leu Leu Leu Thr Val Leu Val Val Ala
1               5                   10                  15

Ala Ala

<210> SEQ ID NO 689
<211> LENGTH: 19
<212> TYPE: PRT
<213> ORGANISM: Homo sapiens

<400> SEQUENCE: 689

Met Cys Leu Leu Ser Ser Ser Ala Ala Ser Asp Leu Ala Ala Thr Ser
1               5                   10                  15

Leu Thr Ala

<210> SEQ ID NO 690
<211> LENGTH: 15
<212> TYPE: PRT
<213> ORGANISM: Homo sapiens

<400> SEQUENCE: 690

Met Ser Lys Gln Gln Ala Ser Gln Val Leu Val Arg Lys Arg Arg
1               5                   10                  15

<210> SEQ ID NO 691

```
<211> LENGTH: 17
<212> TYPE: PRT
<213> ORGANISM: Homo sapiens

<400> SEQUENCE: 691

Met Arg Ala Leu Val Leu Leu Ser Leu Phe Leu Leu Gly Gly Gln
1               5                   10                  15

Ala

<210> SEQ ID NO 692
<211> LENGTH: 15
<212> TYPE: PRT
<213> ORGANISM: Homo sapiens

<400> SEQUENCE: 692

Met Lys Ile Ile Thr Tyr Phe Cys Ile Trp Ala Val Ala Trp Ala
1               5                   10                  15

<210> SEQ ID NO 693
<211> LENGTH: 16
<212> TYPE: PRT
<213> ORGANISM: Homo sapiens

<400> SEQUENCE: 693

Met Leu Val Ile Trp Ile Leu Thr Leu Ala Leu Arg Leu Cys Ala Ser
1               5                   10                  15

<210> SEQ ID NO 694
<211> LENGTH: 16
<212> TYPE: PRT
<213> ORGANISM: Homo sapiens

<400> SEQUENCE: 694

Met Val Leu Leu Arg Leu Leu Val Phe Leu Phe Ala Pro Val Val Ser
1               5                   10                  15

<210> SEQ ID NO 695
<211> LENGTH: 18
<212> TYPE: PRT
<213> ORGANISM: Homo sapiens

<400> SEQUENCE: 695

Met Ala Pro Arg Pro Leu Leu Leu Leu Leu Leu Leu Gly Gly Ser
1               5                   10                  15

Ala Ala

<210> SEQ ID NO 696
<211> LENGTH: 17
<212> TYPE: PRT
<213> ORGANISM: Homo sapiens

<400> SEQUENCE: 696

Met Leu Leu Phe Ala Leu Leu Leu Ala Met Glu Leu Pro Leu Val Ala
1               5                   10                  15

Ala

<210> SEQ ID NO 697
<211> LENGTH: 18
<212> TYPE: PRT
<213> ORGANISM: Homo sapiens

<400> SEQUENCE: 697

Met Pro Pro Leu Leu Ala Pro Leu Leu Cys Leu Ala Leu Leu Pro Ala
```

```
                1               5                   10                  15

Leu Ala

<210> SEQ ID NO 698
<211> LENGTH: 19
<212> TYPE: PRT
<213> ORGANISM: Homo sapiens

<400> SEQUENCE: 698

Met His Ala Ala Leu Ala Gly Pro Leu Leu Ala Ala Leu Leu Ala Thr
1               5                   10                  15

Ala Arg Ala

<210> SEQ ID NO 699
<211> LENGTH: 19
<212> TYPE: PRT
<213> ORGANISM: Homo sapiens

<400> SEQUENCE: 699

Met Ala Ala Ala Val Val Leu Ala Ala Gly Leu Arg Ala Ala Arg Arg
1               5                   10                  15

Ala Val Ala

<210> SEQ ID NO 700
<211> LENGTH: 19
<212> TYPE: PRT
<213> ORGANISM: Homo sapiens

<400> SEQUENCE: 700

Met Gly Val Gln Ala Gly Leu Phe Gly Met Leu Gly Phe Leu Gly Val
1               5                   10                  15

Ala Leu Gly

<210> SEQ ID NO 701
<211> LENGTH: 16
<212> TYPE: PRT
<213> ORGANISM: Homo sapiens

<400> SEQUENCE: 701

Met Leu Ser Leu Leu Val Trp Ile Leu Thr Leu Ser Asp Thr Phe Ser
1               5                   10                  15

<210> SEQ ID NO 702
<211> LENGTH: 17
<212> TYPE: PRT
<213> ORGANISM: Homo sapiens

<400> SEQUENCE: 702

Met Val Pro Pro Val Trp Thr Leu Leu Leu Leu Val Gly Ala Ala Leu
1               5                   10                  15

Phe

<210> SEQ ID NO 703
<211> LENGTH: 17
<212> TYPE: PRT
<213> ORGANISM: Homo sapiens

<400> SEQUENCE: 703

Met Ala Pro Lys Leu Leu Leu Leu Leu Cys Leu Phe Ser Gly Leu His
1               5                   10                  15

Ala
```

<210> SEQ ID NO 704
<211> LENGTH: 18
<212> TYPE: PRT
<213> ORGANISM: Homo sapiens

<400> SEQUENCE: 704

Met Arg Asp Leu Pro Leu Thr Ser Leu Ala Leu Val Leu Ser Ala Leu
1               5                   10                  15

Gly Ala

<210> SEQ ID NO 705
<211> LENGTH: 16
<212> TYPE: PRT
<213> ORGANISM: Homo sapiens

<400> SEQUENCE: 705

Met Pro Met Asp Leu Ile Leu Val Val Trp Phe Cys Val Cys Thr Ala
1               5                   10                  15

<210> SEQ ID NO 706
<211> LENGTH: 19
<212> TYPE: PRT
<213> ORGANISM: Homo sapiens

<400> SEQUENCE: 706

Met Lys Gly Ile Leu Val Ala Gly Ile Thr Ala Val Leu Val Ala Ala
1               5                   10                  15

Val Glu Ser

<210> SEQ ID NO 707
<211> LENGTH: 19
<212> TYPE: PRT
<213> ORGANISM: Homo sapiens

<400> SEQUENCE: 707

Met Ala Arg Gly Ser Ala Leu Leu Leu Ala Ser Leu Leu Leu Ala Ala
1               5                   10                  15

Ala Leu Ser

<210> SEQ ID NO 708
<211> LENGTH: 19
<212> TYPE: PRT
<213> ORGANISM: Homo sapiens

<400> SEQUENCE: 708

Met Lys Ala Ala Gly Ile Leu Thr Leu Ile Gly Cys Leu Val Thr Gly
1               5                   10                  15

Ala Glu Ser

<210> SEQ ID NO 709
<211> LENGTH: 19
<212> TYPE: PRT
<213> ORGANISM: Homo sapiens

<400> SEQUENCE: 709

Met Lys Ala Ala Gly Ile Leu Thr Leu Ile Gly Cys Leu Val Thr Gly
1               5                   10                  15

Ala Glu Ser

<210> SEQ ID NO 710

<211> LENGTH: 17
<212> TYPE: PRT
<213> ORGANISM: Homo sapiens

<400> SEQUENCE: 710

Met Trp Leu Pro Pro Ala Leu Leu Leu Ser Leu Ser Gly Cys Phe
1               5                   10                  15

Ser

<210> SEQ ID NO 711
<211> LENGTH: 17
<212> TYPE: PRT
<213> ORGANISM: Homo sapiens

<400> SEQUENCE: 711

Met Ala Arg Lys Ala Leu Lys Leu Ala Ser Trp Thr Ser Met Ala Leu
1               5                   10                  15

Ala

<210> SEQ ID NO 712
<211> LENGTH: 17
<212> TYPE: PRT
<213> ORGANISM: Homo sapiens

<400> SEQUENCE: 712

Met Leu His Leu Leu Ala Leu Phe Leu His Cys Leu Pro Leu Ala Ser
1               5                   10                  15

Gly

<210> SEQ ID NO 713
<211> LENGTH: 16
<212> TYPE: PRT
<213> ORGANISM: Homo sapiens

<400> SEQUENCE: 713

Met Trp Arg Val Leu Phe Leu Leu Ser Gly Leu Gly Gly Leu Arg Met
1               5                   10                  15

<210> SEQ ID NO 714
<211> LENGTH: 19
<212> TYPE: PRT
<213> ORGANISM: Homo sapiens

<400> SEQUENCE: 714

Met Arg Pro Gly Pro Ala Leu Leu Leu Gly Val Gly Leu Ser Leu
1               5                   10                  15

Ser Val Gly

<210> SEQ ID NO 715
<211> LENGTH: 16
<212> TYPE: PRT
<213> ORGANISM: Homo sapiens

<400> SEQUENCE: 715

Met Asp Trp Thr Trp Arg Ile Leu Phe Leu Val Ala Ala Ala Thr Gly
1               5                   10                  15

<210> SEQ ID NO 716
<211> LENGTH: 17
<212> TYPE: PRT
<213> ORGANISM: Homo sapiens

<400> SEQUENCE: 716

```
Met Leu Pro Pro Trp Thr Leu Gly Leu Leu Leu Ala Thr Val Arg
1               5                   10                  15

Gly

<210> SEQ ID NO 717
<211> LENGTH: 18
<212> TYPE: PRT
<213> ORGANISM: Homo sapiens

<400> SEQUENCE: 717

Met Leu Leu Arg Gly Val Leu Leu Ala Leu Gln Ala Leu Gln Leu Ala
1               5                   10                  15

Gly Ala

<210> SEQ ID NO 718
<211> LENGTH: 18
<212> TYPE: PRT
<213> ORGANISM: Homo sapiens

<400> SEQUENCE: 718

Met Gly Ala Ile Gly Leu Leu Trp Leu Leu Pro Leu Leu Leu Ser Thr
1               5                   10                  15

Ala Ala

<210> SEQ ID NO 719
<211> LENGTH: 17
<212> TYPE: PRT
<213> ORGANISM: Homo sapiens

<400> SEQUENCE: 719

Met Ala Cys Pro Gly Phe Leu Trp Ala Leu Val Ile Ser Thr Cys Leu
1               5                   10                  15

Glu

<210> SEQ ID NO 720
<211> LENGTH: 18
<212> TYPE: PRT
<213> ORGANISM: Homo sapiens

<400> SEQUENCE: 720

Met Trp Leu Pro Ala Leu Val Leu Ala Thr Leu Ala Ala Ser Ala Ala
1               5                   10                  15

Trp Ala

<210> SEQ ID NO 721
<211> LENGTH: 17
<212> TYPE: PRT
<213> ORGANISM: Homo sapiens

<400> SEQUENCE: 721

Met Gly Ser Leu Met Leu Leu Phe Val Glu Thr Thr Arg Asn Ser Ser
1               5                   10                  15

Ala

<210> SEQ ID NO 722
<211> LENGTH: 16
<212> TYPE: PRT
<213> ORGANISM: Homo sapiens

<400> SEQUENCE: 722
```

Met Asn Tyr Ser Leu His Leu Ala Phe Val Cys Leu Ser Leu Phe Thr
1               5                   10                  15

<210> SEQ ID NO 723
<211> LENGTH: 18
<212> TYPE: PRT
<213> ORGANISM: Homo sapiens

<400> SEQUENCE: 723

Met Thr Ala Pro Trp Val Ala Leu Ala Leu Leu Trp Gly Ser Leu Cys
1               5                   10                  15

Ala Gly

<210> SEQ ID NO 724
<211> LENGTH: 20
<212> TYPE: PRT
<213> ORGANISM: Homo sapiens

<400> SEQUENCE: 724

Met Ala Pro Ala Pro Val Thr Leu Leu Ala Pro Gly Ala Ala Ser Ser
1               5                   10                  15

Met Ser Cys Ser
            20

<210> SEQ ID NO 725
<211> LENGTH: 18
<212> TYPE: PRT
<213> ORGANISM: Homo sapiens

<400> SEQUENCE: 725

Met Thr Ser Ser Leu Leu Leu Ala Phe Leu Leu Leu Ala Pro Thr Thr
1               5                   10                  15

Val Ala

<210> SEQ ID NO 726
<211> LENGTH: 18
<212> TYPE: PRT
<213> ORGANISM: Homo sapiens

<400> SEQUENCE: 726

Met Gly Ser Cys Ala Arg Leu Leu Leu Leu Trp Gly Cys Thr Val Val
1               5                   10                  15

Ala Ala

<210> SEQ ID NO 727
<211> LENGTH: 21
<212> TYPE: PRT
<213> ORGANISM: Homo sapiens

<400> SEQUENCE: 727

Met Ala Ala Ala Gly Ala Ala Val Ala Arg Ser Pro Gly Ile Gly Ala
1               5                   10                  15

Gly Pro Ala Leu Arg
            20

<210> SEQ ID NO 728
<211> LENGTH: 16
<212> TYPE: PRT
<213> ORGANISM: Homo sapiens

<400> SEQUENCE: 728

Met Lys Ile Leu Cys Ile Phe Leu Thr Phe Val Phe Thr Val Ser Cys

-continued

<210> SEQ ID NO 729
<211> LENGTH: 18
<212> TYPE: PRT
<213> ORGANISM: Homo sapiens

<400> SEQUENCE: 729

Met Arg Leu Leu Val Ala Pro Leu Leu Leu Ala Trp Val Ala Gly Ala
1               5                   10                  15

Thr Ala

<210> SEQ ID NO 730
<211> LENGTH: 18
<212> TYPE: PRT
<213> ORGANISM: Homo sapiens

<400> SEQUENCE: 730

Met Lys Pro Leu Leu Leu Ala Ile Ser Leu Ser Leu Ile Ala Ala Leu
1               5                   10                  15

Gln Ala

<210> SEQ ID NO 731
<211> LENGTH: 17
<212> TYPE: PRT
<213> ORGANISM: Homo sapiens

<400> SEQUENCE: 731

Met Leu Phe Leu Gln Phe Leu Leu Leu Ala Leu Leu Leu Pro Gly Gly
1               5                   10                  15

Asp

<210> SEQ ID NO 732
<211> LENGTH: 19
<212> TYPE: PRT
<213> ORGANISM: Homo sapiens

<400> SEQUENCE: 732

Met Ala Gly Ser Leu Thr Gly Leu Leu Leu Leu Gln Ala Val Ser Trp
1               5                   10                  15

Ala Ser Gly

<210> SEQ ID NO 733
<211> LENGTH: 17
<212> TYPE: PRT
<213> ORGANISM: Homo sapiens

<400> SEQUENCE: 733

Leu Gly Leu Cys Trp Val Phe Leu Val Ala Leu Leu Arg Gly Val Leu
1               5                   10                  15

Cys

<210> SEQ ID NO 734
<211> LENGTH: 15
<212> TYPE: PRT
<213> ORGANISM: Homo sapiens

<400> SEQUENCE: 734

Met Lys Leu Phe Trp Leu Leu Phe Thr Ile Gly Phe Cys Trp Ala
1               5                   10                  15

```
<210> SEQ ID NO 735
<211> LENGTH: 18
<212> TYPE: PRT
<213> ORGANISM: Homo sapiens

<400> SEQUENCE: 735

Met Ala Leu Arg Arg Leu Gly Ala Ala Leu Leu Leu Leu Pro Leu Leu
1               5                   10                  15

Ala Ala

<210> SEQ ID NO 736
<211> LENGTH: 18
<212> TYPE: PRT
<213> ORGANISM: Homo sapiens

<400> SEQUENCE: 736

Met Ile Pro Ala Val Val Leu Leu Leu Leu Leu Val Glu Gln Ala
1               5                   10                  15

Ala Ala

<210> SEQ ID NO 737
<211> LENGTH: 17
<212> TYPE: PRT
<213> ORGANISM: Homo sapiens

<400> SEQUENCE: 737

Met Pro Pro Met Leu Trp Leu Leu Leu His Phe Ala Ala Pro Ala Leu
1               5                   10                  15

Gly

<210> SEQ ID NO 738
<211> LENGTH: 17
<212> TYPE: PRT
<213> ORGANISM: Homo sapiens

<400> SEQUENCE: 738

Met Ala Leu Leu Ala Leu Leu Leu Val Val Ala Leu Pro Arg Val Trp
1               5                   10                  15

Thr

<210> SEQ ID NO 739
<211> LENGTH: 19
<212> TYPE: PRT
<213> ORGANISM: Homo sapiens

<400> SEQUENCE: 739

Met Gln Glu Ala Ile Ile Leu Leu Ala Leu Leu Gly Ala Met Ser Gly
1               5                   10                  15

Gly Glu Ala

<210> SEQ ID NO 740
<211> LENGTH: 17
<212> TYPE: PRT
<213> ORGANISM: Homo sapiens

<400> SEQUENCE: 740

Met Gly Thr Leu Pro Trp Leu Leu Ala Phe Phe Ile Leu Gly Leu Gln
1               5                   10                  15

Ala

<210> SEQ ID NO 741
```

<211> LENGTH: 17
<212> TYPE: PRT
<213> ORGANISM: Homo sapiens

<400> SEQUENCE: 741

Met Leu Thr Thr Leu Leu Pro Ile Leu Leu Ser Gly Trp Ala Phe
1               5                   10                  15
Cys

<210> SEQ ID NO 742
<211> LENGTH: 18
<212> TYPE: PRT
<213> ORGANISM: Homo sapiens

<400> SEQUENCE: 742

Met Ala Pro Ala Arg Leu Phe Ala Leu Leu Phe Phe Val Gly Gly
1               5                   10                  15
Val Ala

<210> SEQ ID NO 743
<211> LENGTH: 17
<212> TYPE: PRT
<213> ORGANISM: Homo sapiens

<400> SEQUENCE: 743

Met Leu Lys Ala Leu Phe Leu Thr Met Leu Thr Leu Ala Leu Val Lys
1               5                   10                  15
Ser

<210> SEQ ID NO 744
<211> LENGTH: 17
<212> TYPE: PRT
<213> ORGANISM: Homo sapiens

<400> SEQUENCE: 744

Met Leu Leu Trp Ile Leu Leu Leu Glu Thr Ser Leu Cys Phe Ala Ala
1               5                   10                  15
Gly

<210> SEQ ID NO 745
<211> LENGTH: 20
<212> TYPE: PRT
<213> ORGANISM: Homo sapiens

<400> SEQUENCE: 745

Met Ala Pro Leu Ala Leu Val Gly Val Thr Leu Leu Leu Ala Ala Pro
1               5                   10                  15
Pro Cys Ser Gly
            20

<210> SEQ ID NO 746
<211> LENGTH: 20
<212> TYPE: PRT
<213> ORGANISM: Homo sapiens

<400> SEQUENCE: 746

Met Arg Gly Leu Gly Thr Cys Leu Ala Thr Leu Ala Gly Leu Leu Leu
1               5                   10                  15
Thr Ala Ala Gly
            20

```
<210> SEQ ID NO 747
<211> LENGTH: 19
<212> TYPE: PRT
<213> ORGANISM: Homo sapiens

<400> SEQUENCE: 747

Met Val Ala Ala Thr Val Ala Ala Ala Trp Leu Leu Leu Trp Ala Ala
1               5                   10                  15

Ala Cys Ala

<210> SEQ ID NO 748
<211> LENGTH: 18
<212> TYPE: PRT
<213> ORGANISM: Homo sapiens

<400> SEQUENCE: 748

Met Leu Leu Leu Ser Leu Thr Leu Ser Leu Val Leu Leu Gly Ser Ser
1               5                   10                  15

Trp Gly

<210> SEQ ID NO 749
<211> LENGTH: 19
<212> TYPE: PRT
<213> ORGANISM: Homo sapiens

<400> SEQUENCE: 749

Met Lys Ala Ser Val Val Leu Ser Leu Leu Gly Tyr Leu Val Val Pro
1               5                   10                  15

Ser Gly Ala

<210> SEQ ID NO 750
<211> LENGTH: 18
<212> TYPE: PRT
<213> ORGANISM: Homo sapiens

<400> SEQUENCE: 750

Met Leu Leu Leu Leu Leu Leu Pro Pro Leu Leu Cys Gly Arg Val
1               5                   10                  15

Gly Ala

<210> SEQ ID NO 751
<211> LENGTH: 17
<212> TYPE: PRT
<213> ORGANISM: Homo sapiens

<400> SEQUENCE: 751

Met Trp Pro Arg Leu Ala Phe Cys Cys Trp Gly Leu Ala Leu Val Ser
1               5                   10                  15

Gly

<210> SEQ ID NO 752
<211> LENGTH: 19
<212> TYPE: PRT
<213> ORGANISM: Homo sapiens

<400> SEQUENCE: 752

Met Thr Ala Leu Pro Gly Pro Leu Trp Leu Leu Gly Leu Ala Leu Cys
1               5                   10                  15

Ala Leu Gly

<210> SEQ ID NO 753
```

-continued

```
<211> LENGTH: 18
<212> TYPE: PRT
<213> ORGANISM: Homo sapiens

<400> SEQUENCE: 753

Met Leu Val Ala Gly Leu Leu Leu Trp Ala Ser Leu Leu Thr Gly Ala
1               5                   10                  15

Trp Pro

<210> SEQ ID NO 754
<211> LENGTH: 17
<212> TYPE: PRT
<213> ORGANISM: Homo sapiens

<400> SEQUENCE: 754

Met Arg Val Phe Cys Val Gly Leu Leu Leu Phe Ser Val Thr Trp Ala
1               5                   10                  15

Ala

<210> SEQ ID NO 755
<211> LENGTH: 17
<212> TYPE: PRT
<213> ORGANISM: Homo sapiens

<400> SEQUENCE: 755

Met Leu Gly Ile Trp Ile Val Ala Phe Leu Phe Phe Gly Thr Ser Arg
1               5                   10                  15

Gly

<210> SEQ ID NO 756
<211> LENGTH: 19
<212> TYPE: PRT
<213> ORGANISM: Homo sapiens

<400> SEQUENCE: 756

Met Lys Pro Gln Phe Val Gly Ile Leu Leu Ser Ser Leu Leu Gly Ala
1               5                   10                  15

Ala Leu Gly

<210> SEQ ID NO 757
<211> LENGTH: 18
<212> TYPE: PRT
<213> ORGANISM: Homo sapiens

<400> SEQUENCE: 757

Met Leu Ser Leu Leu Leu Leu Ala Leu Pro Val Leu Ala Ser Arg Ala
1               5                   10                  15

Tyr Ala

<210> SEQ ID NO 758
<211> LENGTH: 20
<212> TYPE: PRT
<213> ORGANISM: Homo sapiens

<400> SEQUENCE: 758

Met Val Pro Asp Thr Ala Cys Val Leu Leu Leu Thr Leu Ala Ala Leu
1               5                   10                  15

Gly Ala Ser Gly
            20

<210> SEQ ID NO 759
```

```
<211> LENGTH: 18
<212> TYPE: PRT
<213> ORGANISM: Homo sapiens

<400> SEQUENCE: 759

Met Ala Arg Ala Gln Ala Leu Val Leu Ala Leu Thr Phe Gln Leu Cys
1               5                   10                  15

Ala Pro

<210> SEQ ID NO 760
<211> LENGTH: 18
<212> TYPE: PRT
<213> ORGANISM: Homo sapiens

<400> SEQUENCE: 760

Met Ala Arg Ala Gln Ala Leu Val Leu Ala Leu Thr Phe Gln Leu Cys
1               5                   10                  15

Ala Pro

<210> SEQ ID NO 761
<211> LENGTH: 20
<212> TYPE: PRT
<213> ORGANISM: Homo sapiens

<400> SEQUENCE: 761

Met Thr Thr Gln Leu Gly Pro Ala Leu Val Leu Gly Val Ala Leu Cys
1               5                   10                  15

Leu Gly Cys Gly
            20

<210> SEQ ID NO 762
<211> LENGTH: 18
<212> TYPE: PRT
<213> ORGANISM: Homo sapiens

<400> SEQUENCE: 762

Met Gly Leu Lys Ala Leu Cys Leu Gly Leu Leu Cys Val Leu Phe Val
1               5                   10                  15

Ser His

<210> SEQ ID NO 763
<211> LENGTH: 18
<212> TYPE: PRT
<213> ORGANISM: Homo sapiens

<400> SEQUENCE: 763

Met Lys Val His Met Leu Val Gly Val Leu Val Met Val Gly Phe Thr
1               5                   10                  15

Val Gly

<210> SEQ ID NO 764
<211> LENGTH: 18
<212> TYPE: PRT
<213> ORGANISM: Homo sapiens

<400> SEQUENCE: 764

Met Asp Leu Trp Gln Leu Leu Leu Thr Leu Ala Leu Ala Gly Ser Ser
1               5                   10                  15

Asp Ala

<210> SEQ ID NO 765
```

<211> LENGTH: 17
<212> TYPE: PRT
<213> ORGANISM: Homo sapiens

<400> SEQUENCE: 765

Met Trp Val Pro Val Val Phe Leu Thr Leu Ser Val Thr Trp Ile Gly
1               5                   10                  15

Ala

<210> SEQ ID NO 766
<211> LENGTH: 17
<212> TYPE: PRT
<213> ORGANISM: Homo sapiens

<400> SEQUENCE: 766

Met Trp Val Pro Val Val Phe Leu Thr Leu Ser Val Thr Trp Ile Gly
1               5                   10                  15

Ala

<210> SEQ ID NO 767
<211> LENGTH: 17
<212> TYPE: PRT
<213> ORGANISM: Homo sapiens

<400> SEQUENCE: 767

Met Trp Val Pro Val Val Phe Leu Thr Leu Ser Val Thr Trp Ile Gly
1               5                   10                  15

Ala

<210> SEQ ID NO 768
<211> LENGTH: 17
<212> TYPE: PRT
<213> ORGANISM: Homo sapiens

<400> SEQUENCE: 768

Met Trp Val Pro Val Val Phe Leu Thr Leu Ser Val Thr Trp Ile Gly
1               5                   10                  15

Ala

<210> SEQ ID NO 769
<211> LENGTH: 15
<212> TYPE: PRT
<213> ORGANISM: Homo sapiens

<400> SEQUENCE: 769

Met Arg Val Tyr Ile Phe Leu Cys Leu Met Cys Trp Val Arg Ser
1               5                   10                  15

<210> SEQ ID NO 770
<211> LENGTH: 20
<212> TYPE: PRT
<213> ORGANISM: Homo sapiens

<400> SEQUENCE: 770

Met Thr Ala Gly Ala Gly Val Leu Leu Leu Leu Ser Leu Ser Gly
1               5                   10                  15

Ala Leu Arg Ala
            20

<210> SEQ ID NO 771
<211> LENGTH: 18
<212> TYPE: PRT

-continued

<213> ORGANISM: Homo sapiens

<400> SEQUENCE: 771

Met Lys Phe Phe Met Val Leu Leu Pro Ala Ser Leu Ala Ser Thr Ser
1               5                   10                  15

Leu Ala

<210> SEQ ID NO 772
<211> LENGTH: 19
<212> TYPE: PRT
<213> ORGANISM: Homo sapiens

<400> SEQUENCE: 772

Met Arg Ala Ala Gly Thr Leu Leu Ala Phe Cys Cys Leu Val Leu Ser
1               5                   10                  15

Thr Thr Gly

<210> SEQ ID NO 773
<211> LENGTH: 18
<212> TYPE: PRT
<213> ORGANISM: Homo sapiens

<400> SEQUENCE: 773

Met Leu Cys Ser Leu Leu Leu Cys Glu Cys Leu Leu Leu Val Ala Gly
1               5                   10                  15

Tyr Ala

<210> SEQ ID NO 774
<211> LENGTH: 18
<212> TYPE: PRT
<213> ORGANISM: Homo sapiens

<400> SEQUENCE: 774

Met Trp Leu Leu Val Ser Val Ile Leu Ile Ser Arg Ile Ser Ser Val
1               5                   10                  15

Gly Gly

<210> SEQ ID NO 775
<211> LENGTH: 17
<212> TYPE: PRT
<213> ORGANISM: Homo sapiens

<400> SEQUENCE: 775

Met Lys Phe Ile Leu Leu Trp Ala Leu Leu Asn Leu Thr Val Ala Leu
1               5                   10                  15

Ala

<210> SEQ ID NO 776
<211> LENGTH: 19
<212> TYPE: PRT
<213> ORGANISM: Homo sapiens

<400> SEQUENCE: 776

Met Lys Thr Leu Ala Gly Leu Val Leu Gly Leu Val Ile Phe Asp Ala
1               5                   10                  15

Ala Val Thr

<210> SEQ ID NO 777
<211> LENGTH: 19
<212> TYPE: PRT

<400> SEQUENCE: 777

Met Gly Pro Gly Val Leu Leu Leu Leu Val Ala Thr Ala Trp His
1               5                   10                  15

Gly Gln Gly

<210> SEQ ID NO 778
<211> LENGTH: 18
<212> TYPE: PRT
<213> ORGANISM: Homo sapiens

<400> SEQUENCE: 778

Met Ala Arg Val Pro Pro Val Gly Ala Leu Leu Leu Leu Arg Gly Ser
1               5                   10                  15

Arg Gln

<210> SEQ ID NO 779
<211> LENGTH: 18
<212> TYPE: PRT
<213> ORGANISM: Homo sapiens

<400> SEQUENCE: 779

Met Leu Leu Leu Phe Ser Val Ile Leu Ile Ser Trp Val Ser Thr Val
1               5                   10                  15

Gly Gly

<210> SEQ ID NO 780
<211> LENGTH: 17
<212> TYPE: PRT
<213> ORGANISM: Homo sapiens

<400> SEQUENCE: 780

Met Trp Gln Leu Trp Ala Ser Leu Cys Cys Leu Leu Val Leu Ala Asn
1               5                   10                  15

Ala

<210> SEQ ID NO 781
<211> LENGTH: 17
<212> TYPE: PRT
<213> ORGANISM: Homo sapiens

<400> SEQUENCE: 781

Met Leu Met Leu Phe Val Phe Gly Val Leu Leu His Glu Val Ser Leu
1               5                   10                  15

Ser

<210> SEQ ID NO 782
<211> LENGTH: 18
<212> TYPE: PRT
<213> ORGANISM: Homo sapiens

<400> SEQUENCE: 782

Met Arg Ser Leu Leu Leu Leu Ser Ala Phe Cys Leu Leu Glu Ala Ala
1               5                   10                  15

Leu Ala

<210> SEQ ID NO 783
<211> LENGTH: 19
<212> TYPE: PRT
<213> ORGANISM: Homo sapiens -continued

```
<400> SEQUENCE: 783

Met Gln Gln Arg Gly Leu Ala Ile Val Ala Leu Ala Val Cys Ala Ala
1               5                   10                  15

Leu His Ala

<210> SEQ ID NO 784
<211> LENGTH: 19
<212> TYPE: PRT
<213> ORGANISM: Homo sapiens

<400> SEQUENCE: 784

Met Gly Ala Arg Gly Ala Leu Leu Leu Ala Leu Leu Leu Ala Arg Ala
1               5                   10                  15

Gly Leu Arg

<210> SEQ ID NO 785
<211> LENGTH: 20
<212> TYPE: PRT
<213> ORGANISM: Homo sapiens

<400> SEQUENCE: 785

Met Pro Leu Ala Leu Thr Leu Leu Leu Ser Gly Leu Gly Ala Pro
1               5                   10                  15

Gly Gly Trp Gly
            20

<210> SEQ ID NO 786
<211> LENGTH: 22
<212> TYPE: PRT
<213> ORGANISM: Homo sapiens

<400> SEQUENCE: 786

Met Ala Ala Ala Gly Leu Val Ala Val Ala Ala Ala Ala Glu Tyr Ser
1               5                   10                  15

Gly Thr Val Ala Ser Gly
            20

<210> SEQ ID NO 787
<211> LENGTH: 18
<212> TYPE: PRT
<213> ORGANISM: Homo sapiens

<400> SEQUENCE: 787

Met Thr Ile Ala Leu Leu Gly Phe Ala Ile Phe Leu Leu His Cys Ala
1               5                   10                  15

Thr Cys

<210> SEQ ID NO 788
<211> LENGTH: 19
<212> TYPE: PRT
<213> ORGANISM: Homo sapiens

<400> SEQUENCE: 788

Met Ile Ala Ile Ser Ala Val Ser Ser Ala Leu Leu Phe Ser Leu Leu
1               5                   10                  15

Cys Glu Ala

<210> SEQ ID NO 789
<211> LENGTH: 20
<212> TYPE: PRT
<213> ORGANISM: Homo sapiens
```

```
<400> SEQUENCE: 789

Met Trp Gly Leu Leu Leu Ala Leu Ala Ala Phe Ala Pro Ala Val Gly
1               5                   10                  15

Pro Ala Leu Gly
            20

<210> SEQ ID NO 790
<211> LENGTH: 20
<212> TYPE: PRT
<213> ORGANISM: Homo sapiens

<400> SEQUENCE: 790

Met Gly Gly Pro Arg Ala Leu Leu Ala Ala Leu Trp Ala Leu Glu Ala
1               5                   10                  15

Ala Gly Thr Ala
            20

<210> SEQ ID NO 791
<211> LENGTH: 19
<212> TYPE: PRT
<213> ORGANISM: Homo sapiens

<400> SEQUENCE: 791

Met Asn Gly Leu Ser Leu Ser Glu Leu Cys Cys Leu Cys Cys Pro Pro
1               5                   10                  15

Cys Pro Gly

<210> SEQ ID NO 792
<211> LENGTH: 17
<212> TYPE: PRT
<213> ORGANISM: Homo sapiens

<400> SEQUENCE: 792

Met Trp Gly Arg Leu Trp Pro Leu Leu Ser Ile Leu Thr Ala Thr
1               5                   10                  15

Ala

<210> SEQ ID NO 793
<211> LENGTH: 18
<212> TYPE: PRT
<213> ORGANISM: Homo sapiens

<400> SEQUENCE: 793

Met Leu Asn Leu Leu Leu Leu Ala Leu Pro Val Leu Ala Ser Arg Ala
1               5                   10                  15

Tyr Ala

<210> SEQ ID NO 794
<211> LENGTH: 18
<212> TYPE: PRT
<213> ORGANISM: Homo sapiens

<400> SEQUENCE: 794

Met Leu Asn Leu Leu Leu Leu Ala Leu Pro Val Leu Ala Ser Arg Ala
1               5                   10                  15

Tyr Ala

<210> SEQ ID NO 795
<211> LENGTH: 18
<212> TYPE: PRT
```

<213> ORGANISM: Homo sapiens

<400> SEQUENCE: 795

Met Ile His Leu Gly His Ile Leu Phe Leu Leu Leu Pro Val Ala
1               5                   10                  15

Ala Ala

<210> SEQ ID NO 796
<211> LENGTH: 18
<212> TYPE: PRT
<213> ORGANISM: Homo sapiens

<400> SEQUENCE: 796

Met Ala Ser His Arg Leu Leu Leu Leu Cys Leu Ala Gly Leu Val Phe
1               5                   10                  15

Val Ser

<210> SEQ ID NO 797
<211> LENGTH: 18
<212> TYPE: PRT
<213> ORGANISM: Homo sapiens

<400> SEQUENCE: 797

Met His Tyr Pro Thr Ala Leu Leu Phe Leu Ile Leu Ala Asn Gly Ala
1               5                   10                  15

Gln Ala

<210> SEQ ID NO 798
<211> LENGTH: 18
<212> TYPE: PRT
<213> ORGANISM: Homo sapiens

<400> SEQUENCE: 798

Met Gln His Ile Phe Ala Phe Phe Cys Thr Gly Phe Leu Gly Ala Val
1               5                   10                  15

Val Gly

<210> SEQ ID NO 799
<211> LENGTH: 19
<212> TYPE: PRT
<213> ORGANISM: Homo sapiens

<400> SEQUENCE: 799

Cys Met Thr Ala Leu Thr Val Thr Leu Met Val Leu Ser Ser Pro Leu
1               5                   10                  15

Ala Leu Ser

<210> SEQ ID NO 800
<211> LENGTH: 17
<212> TYPE: PRT
<213> ORGANISM: Homo sapiens

<400> SEQUENCE: 800

Met Gly Leu Ile Trp Leu Leu Leu Ser Leu Leu Glu Pro Gly Trp
1               5                   10                  15

Pro

<210> SEQ ID NO 801
<211> LENGTH: 19
<212> TYPE: PRT
<213> ORGANISM: Homo sapiens

<400> SEQUENCE: 801

Met Ala Ala Arg Pro Gly Pro Leu Trp Leu Leu Gly Leu Thr Leu Cys
1               5                   10                  15

Ala Leu Gly

<210> SEQ ID NO 802
<211> LENGTH: 19
<212> TYPE: PRT
<213> ORGANISM: Homo sapiens

<400> SEQUENCE: 802

Met Pro Trp Thr Ile Leu Leu Phe Ala Ala Gly Ser Leu Ala Ile Pro
1               5                   10                  15

Ala Pro Ser

<210> SEQ ID NO 803
<211> LENGTH: 20
<212> TYPE: PRT
<213> ORGANISM: Homo sapiens

<400> SEQUENCE: 803

Met Ala Pro Pro Thr Gly Val Leu Ser Ser Leu Leu Leu Leu Val Thr
1               5                   10                  15

Ile Ala Gly Cys
            20

<210> SEQ ID NO 804
<211> LENGTH: 18
<212> TYPE: PRT
<213> ORGANISM: Homo sapiens

<400> SEQUENCE: 804

Met Ser Thr Met Arg Leu Leu Thr Leu Ala Leu Leu Phe Ser Cys Ser
1               5                   10                  15

Val Ala

<210> SEQ ID NO 805
<211> LENGTH: 20
<212> TYPE: PRT
<213> ORGANISM: Homo sapiens

<400> SEQUENCE: 805

Met Ser Ile Ser Ser Ala Leu Ala Met Val Phe Met Gly Ala Lys Gly
1               5                   10                  15

Asn Thr Ala Ala
            20

<210> SEQ ID NO 806
<211> LENGTH: 18
<212> TYPE: PRT
<213> ORGANISM: Homo sapiens

<400> SEQUENCE: 806

Met Lys Leu His Cys Cys Leu Phe Thr Leu Val Ala Ser Ile Ile Val
1               5                   10                  15

Pro Ala

<210> SEQ ID NO 807
<211> LENGTH: 19
<212> TYPE: PRT

-continued

<213> ORGANISM: Homo sapiens

<400> SEQUENCE: 807

Met Leu Thr Pro Pro Leu Leu Leu Leu Pro Leu Leu Ser Ala Leu
1               5                   10                  15

Val Ala Ala

<210> SEQ ID NO 808
<211> LENGTH: 18
<212> TYPE: PRT
<213> ORGANISM: Homo sapiens

<400> SEQUENCE: 808

Met Leu Leu Phe Ser Val Leu Leu Leu Ser Leu Val Thr Gly Thr
1               5                   10                  15

Gln Leu

<210> SEQ ID NO 809
<211> LENGTH: 18
<212> TYPE: PRT
<213> ORGANISM: Homo sapiens

<400> SEQUENCE: 809

Met Glu Leu Val Leu Val Phe Leu Cys Ser Leu Leu Ala Pro Met Val
1               5                   10                  15

Leu Ala

<210> SEQ ID NO 810
<211> LENGTH: 19
<212> TYPE: PRT
<213> ORGANISM: Homo sapiens

<400> SEQUENCE: 810

Met Ala Pro Trp Leu Gln Leu Leu Ser Leu Leu Gly Leu Leu Pro Gly
1               5                   10                  15

Ala Val Ala

<210> SEQ ID NO 811
<211> LENGTH: 18
<212> TYPE: PRT
<213> ORGANISM: Homo sapiens

<400> SEQUENCE: 811

Met Phe Leu Leu Leu Thr Ala Leu Gln Val Leu Ala Ile Ala Met Thr
1               5                   10                  15

Gln Ser

<210> SEQ ID NO 812
<211> LENGTH: 19
<212> TYPE: PRT
<213> ORGANISM: Homo sapiens

<400> SEQUENCE: 812

Met Ala Leu Leu Val Leu Gly Leu Val Ser Cys Thr Phe Phe Leu Ala
1               5                   10                  15

Val Asn Gly

<210> SEQ ID NO 813
<211> LENGTH: 18
<212> TYPE: PRT
<213> ORGANISM: Homo sapiens

```
<400> SEQUENCE: 813

Met Ser Leu Leu Leu Leu Leu Leu Val Ser Tyr Tyr Val Gly Thr
1               5                   10                  15

Leu Gly

<210> SEQ ID NO 814
<211> LENGTH: 19
<212> TYPE: PRT
<213> ORGANISM: Homo sapiens

<400> SEQUENCE: 814

Met Ser Ala Thr Thr Ala Cys Trp Pro Ala Phe Thr Val Leu Gly Glu
1               5                   10                  15

Ala Arg Gly

<210> SEQ ID NO 815
<211> LENGTH: 17
<212> TYPE: PRT
<213> ORGANISM: Homo sapiens

<400> SEQUENCE: 815

Met Glu Lys Ile Leu Phe Tyr Leu Phe Leu Ile Gly Ile Ala Val Lys
1               5                   10                  15

Ala

<210> SEQ ID NO 816
<211> LENGTH: 19
<212> TYPE: PRT
<213> ORGANISM: Homo sapiens

<400> SEQUENCE: 816

Met Arg Ala Pro Leu Leu Pro Pro Ala Pro Val Val Leu Ser Leu Leu
1               5                   10                  15

Ile Leu Gly

<210> SEQ ID NO 817
<211> LENGTH: 19
<212> TYPE: PRT
<213> ORGANISM: Homo sapiens

<400> SEQUENCE: 817

Met Gly Ser Pro Val Ser His Leu Leu Ala Gly Phe Cys Val Trp Val
1               5                   10                  15

Val Leu Gly

<210> SEQ ID NO 818
<211> LENGTH: 18
<212> TYPE: PRT
<213> ORGANISM: Homo sapiens

<400> SEQUENCE: 818

Met Ala Pro Ala Phe Leu Leu Leu Leu Leu Trp Pro Gln Gly Cys
1               5                   10                  15

Val Ser

<210> SEQ ID NO 819
<211> LENGTH: 18
<212> TYPE: PRT
<213> ORGANISM: Homo sapiens
```

<400> SEQUENCE: 819

Met Leu Leu Leu Ile Asn Val Ile Leu Thr Leu Trp Val Ser Cys Ala
1               5                   10                  15

Asn Gly

<210> SEQ ID NO 820
<211> LENGTH: 18
<212> TYPE: PRT
<213> ORGANISM: Homo sapiens

<400> SEQUENCE: 820

Met Arg Arg Ala Trp Ile Leu Leu Thr Leu Gly Leu Val Ala Cys Val
1               5                   10                  15

Ser Ala

<210> SEQ ID NO 821
<211> LENGTH: 17
<212> TYPE: PRT
<213> ORGANISM: Homo sapiens

<400> SEQUENCE: 821

Met Leu Lys Thr Phe Thr Val Leu Leu Phe Cys Ile Arg Met Ser Leu
1               5                   10                  15

Gly

<210> SEQ ID NO 822
<211> LENGTH: 17
<212> TYPE: PRT
<213> ORGANISM: Homo sapiens

<400> SEQUENCE: 822

Met Trp Ile Leu Ala Leu Ser Leu Phe Gln Ser Phe Ala Asn Val Phe
1               5                   10                  15

Ser

<210> SEQ ID NO 823
<211> LENGTH: 20
<212> TYPE: PRT
<213> ORGANISM: Homo sapiens

<400> SEQUENCE: 823

Met Ala Gly Val Val His Val Ser Leu Ala Ala Leu Leu Leu Leu Pro
1               5                   10                  15

Met Ala Pro Ala
            20

<210> SEQ ID NO 824
<211> LENGTH: 18
<212> TYPE: PRT
<213> ORGANISM: Homo sapiens

<400> SEQUENCE: 824

Met Leu Gln Leu Trp Lys Leu Val Leu Leu Cys Gly Val Leu Thr Gly
1               5                   10                  15

Thr Ser

<210> SEQ ID NO 825
<211> LENGTH: 18
<212> TYPE: PRT
<213> ORGANISM: Homo sapiens

```
<400> SEQUENCE: 825

Met Lys Thr Leu Pro Val Leu Val Leu Ser Leu Thr Leu Leu Thr Val
1               5                   10                  15

Phe Ser

<210> SEQ ID NO 826
<211> LENGTH: 19
<212> TYPE: PRT
<213> ORGANISM: Homo sapiens

<400> SEQUENCE: 826

Met Thr Leu Leu Leu Leu Pro Leu Leu Leu Ala Ser Leu Leu Ala Ser
1               5                   10                  15

Cys Ser Cys

<210> SEQ ID NO 827
<211> LENGTH: 18
<212> TYPE: PRT
<213> ORGANISM: Homo sapiens

<400> SEQUENCE: 827

Met Arg Leu Gly Ser Pro Gly Leu Leu Phe Leu Leu Phe Ser Ser Leu
1               5                   10                  15

Arg Ala

<210> SEQ ID NO 828
<211> LENGTH: 18
<212> TYPE: PRT
<213> ORGANISM: Homo sapiens

<400> SEQUENCE: 828

Met Ile Leu Leu Ala Val Leu Phe Leu Cys Phe Ile Ser Ser Tyr Ser
1               5                   10                  15

Ala Ser

<210> SEQ ID NO 829
<211> LENGTH: 17
<212> TYPE: PRT
<213> ORGANISM: Homo sapiens

<400> SEQUENCE: 829

Met Leu Leu Leu Leu Leu Pro Leu Leu Trp Gly Arg Glu Arg Ala Glu
1               5                   10                  15

Gly

<210> SEQ ID NO 830
<211> LENGTH: 19
<212> TYPE: PRT
<213> ORGANISM: Homo sapiens

<400> SEQUENCE: 830

Met Arg Thr Ile Ala Ile Leu Ala Ala Ile Leu Leu Val Ala Leu Gln
1               5                   10                  15

Ala Gln Ala

<210> SEQ ID NO 831
<211> LENGTH: 18
<212> TYPE: PRT
<213> ORGANISM: Homo sapiens

<400> SEQUENCE: 831
```

-continued

Met Trp Leu Ser Pro Ser Leu Leu Leu Ile Leu Pro Gly Tyr Ser
1               5                   10                  15

Ile Ala

<210> SEQ ID NO 832
<211> LENGTH: 20
<212> TYPE: PRT
<213> ORGANISM: Homo sapiens

<400> SEQUENCE: 832

Met Leu Pro Leu Leu Ala Ala Leu Leu Ala Ala Ala Cys Pro Leu Pro
1               5                   10                  15

Pro Val Arg Gly
            20

<210> SEQ ID NO 833
<211> LENGTH: 17
<212> TYPE: PRT
<213> ORGANISM: Homo sapiens

<400> SEQUENCE: 833

Met Trp Gly Arg Leu Leu Leu Trp Pro Leu Val Leu Gly Phe Ser Leu
1               5                   10                  15

Ser

<210> SEQ ID NO 834
<211> LENGTH: 19
<212> TYPE: PRT
<213> ORGANISM: Homo sapiens

<400> SEQUENCE: 834

Met Trp Ser Leu Leu Leu Cys Gly Leu Ser Ile Ala Leu Pro Leu Ser
1               5                   10                  15

Val Thr Ala

<210> SEQ ID NO 835
<211> LENGTH: 19
<212> TYPE: PRT
<213> ORGANISM: Homo sapiens

<400> SEQUENCE: 835

Met Lys Ser Val Leu Leu Leu Thr Thr Leu Leu Val Pro Ala His Leu
1               5                   10                  15

Val Ala Ala

<210> SEQ ID NO 836
<211> LENGTH: 19
<212> TYPE: PRT
<213> ORGANISM: Homo sapiens

<400> SEQUENCE: 836

Met Lys Gly Ala Arg Leu Phe Val Leu Leu Ser Ser Leu Trp Ser Gly
1               5                   10                  15

Gly Ile Gly

<210> SEQ ID NO 837
<211> LENGTH: 18
<212> TYPE: PRT
<213> ORGANISM: Homo sapiens

<400> SEQUENCE: 837

Met Lys Ala Leu Met Leu Leu Thr Leu Ser Val Leu Leu Cys Trp Val
1               5                   10                  15

Ser Ala

<210> SEQ ID NO 838
<211> LENGTH: 18
<212> TYPE: PRT
<213> ORGANISM: Homo sapiens

<400> SEQUENCE: 838

Met Trp Leu Pro Leu Val Leu Leu Ala Val Leu Leu Ala Val
1               5                   10                  15

Leu Cys

<210> SEQ ID NO 839
<211> LENGTH: 20
<212> TYPE: PRT
<213> ORGANISM: Homo sapiens

<400> SEQUENCE: 839

Met Arg Ala Gly Pro Gly Pro Thr Val Thr Leu Ala Leu Val Leu Ala
1               5                   10                  15

Val Ala Trp Ala
            20

<210> SEQ ID NO 840
<211> LENGTH: 19
<212> TYPE: PRT
<213> ORGANISM: Homo sapiens

<400> SEQUENCE: 840

Met Ala Gly Ile Pro Gly Leu Leu Phe Leu Leu Phe Phe Leu Leu Cys
1               5                   10                  15

Ala Val Gly

<210> SEQ ID NO 841
<211> LENGTH: 19
<212> TYPE: PRT
<213> ORGANISM: Homo sapiens

<400> SEQUENCE: 841

Met Val Leu Ser Leu Thr Gly Leu Ile Ala Phe Ser Phe Leu Gln Ala
1               5                   10                  15

Thr Leu Ala

<210> SEQ ID NO 842
<211> LENGTH: 17
<212> TYPE: PRT
<213> ORGANISM: Homo sapiens

<400> SEQUENCE: 842

Met Leu Leu Trp Leu Leu Leu Leu Ile Leu Thr Pro Gly Arg Glu Gln
1               5                   10                  15

Ser

<210> SEQ ID NO 843
<211> LENGTH: 20
<212> TYPE: PRT
<213> ORGANISM: Homo sapiens

<400> SEQUENCE: 843

Met Val Leu Leu Leu Val Ile Leu Ile Pro Val Leu Ser Ser Ala
1               5                   10                  15

Gly Thr Ser Ala
            20

<210> SEQ ID NO 844
<211> LENGTH: 19
<212> TYPE: PRT
<213> ORGANISM: Homo sapiens

<400> SEQUENCE: 844

Met Pro Ala Leu Gly Pro Ala Leu Leu Gln Ala Leu Trp Ala Gly Trp
1               5                   10                  15

Val Leu Thr

<210> SEQ ID NO 845
<211> LENGTH: 19
<212> TYPE: PRT
<213> ORGANISM: Homo sapiens

<400> SEQUENCE: 845

Met Lys Phe Val Pro Cys Leu Leu Leu Val Thr Leu Ser Cys Leu Gly
1               5                   10                  15

Thr Leu Gly

<210> SEQ ID NO 846
<211> LENGTH: 18
<212> TYPE: PRT
<213> ORGANISM: Homo sapiens

<400> SEQUENCE: 846

Met Phe Pro Leu Arg Ala Leu Trp Leu Val Trp Ala Leu Leu Gly Val
1               5                   10                  15

Ala Gly

<210> SEQ ID NO 847
<211> LENGTH: 18
<212> TYPE: PRT
<213> ORGANISM: Homo sapiens

<400> SEQUENCE: 847

Met Phe Leu Ser Ile Leu Val Ala Leu Cys Leu Trp Leu His Leu Ala
1               5                   10                  15

Leu Gly

<210> SEQ ID NO 848
<211> LENGTH: 19
<212> TYPE: PRT
<213> ORGANISM: Homo sapiens

<400> SEQUENCE: 848

Met Val Leu Leu Arg Val Leu Ile Leu Leu Leu Ser Trp Ala Ala Gly
1               5                   10                  15

Met Gly Gly

<210> SEQ ID NO 849
<211> LENGTH: 19
<212> TYPE: PRT
<213> ORGANISM: Homo sapiens

<400> SEQUENCE: 849

```
Met Lys Leu Leu Pro Ser Val Val Lys Leu Phe Leu Ala Ala Val
1               5                   10                  15

Leu Ser Ala

<210> SEQ ID NO 850
<211> LENGTH: 18
<212> TYPE: PRT
<213> ORGANISM: Homo sapiens

<400> SEQUENCE: 850

Met Glu Pro Leu Arg Leu Leu Ile Leu Leu Phe Val Thr Glu Leu Ser
1               5                   10                  15

Gly Ala

<210> SEQ ID NO 851
<211> LENGTH: 20
<212> TYPE: PRT
<213> ORGANISM: Homo sapiens

<400> SEQUENCE: 851

Met Val Leu Leu Thr Ala Val Leu Leu Leu Ala Ala Tyr Ala Gly
1               5                   10                  15

Pro Ala Gln Ser
            20

<210> SEQ ID NO 852
<211> LENGTH: 19
<212> TYPE: PRT
<213> ORGANISM: Homo sapiens

<400> SEQUENCE: 852

Met Cys Cys Trp Pro Leu Leu Leu Leu Trp Gly Leu Leu Pro Gly Thr
1               5                   10                  15

Ala Ala Gly

<210> SEQ ID NO 853
<211> LENGTH: 18
<212> TYPE: PRT
<213> ORGANISM: Homo sapiens

<400> SEQUENCE: 853

Met Arg Val Val Thr Ile Val Ile Leu Leu Cys Phe Cys Lys Ala Ala
1               5                   10                  15

Glu Leu

<210> SEQ ID NO 854
<211> LENGTH: 20
<212> TYPE: PRT
<213> ORGANISM: Homo sapiens

<400> SEQUENCE: 854

Met Leu Asn Val Ser Gly Leu Phe Val Leu Leu Cys Gly Leu Leu Val
1               5                   10                  15

Ser Ser Ser Ala
            20

<210> SEQ ID NO 855
<211> LENGTH: 18
<212> TYPE: PRT
<213> ORGANISM: Homo sapiens
```

<400> SEQUENCE: 855

Met Val Pro Ala Trp Leu Trp Leu Leu Cys Val Ser Val Pro Gln Ala
1               5                   10                  15

Leu Pro

<210> SEQ ID NO 856
<211> LENGTH: 19
<212> TYPE: PRT
<213> ORGANISM: Homo sapiens

<400> SEQUENCE: 856

Met Gly Ala Val Leu Arg Ser Leu Leu Ala Cys Ser Phe Cys Val Leu
1               5                   10                  15

Leu Arg Ala

<210> SEQ ID NO 857
<211> LENGTH: 20
<212> TYPE: PRT
<213> ORGANISM: Homo sapiens

<400> SEQUENCE: 857

Met Lys Leu Leu Ser Leu Val Ala Val Val Gly Cys Leu Leu Val Pro
1               5                   10                  15

Pro Ala Glu Ala
            20

<210> SEQ ID NO 858
<211> LENGTH: 19
<212> TYPE: PRT
<213> ORGANISM: Homo sapiens

<400> SEQUENCE: 858

Met Asp Ser Trp Phe Ile Leu Val Leu Leu Gly Ser Gly Leu Ile Cys
1               5                   10                  15

Val Ser Ala

<210> SEQ ID NO 859
<211> LENGTH: 19
<212> TYPE: PRT
<213> ORGANISM: Homo sapiens

<400> SEQUENCE: 859

Met Gly Pro Ala Trp Leu Trp Leu Gly Thr Gly Ile Leu Ala Ser
1               5                   10                  15

Val His Cys

<210> SEQ ID NO 860
<211> LENGTH: 17
<212> TYPE: PRT
<213> ORGANISM: Homo sapiens

<400> SEQUENCE: 860

Met Leu Phe Trp Val Leu Gly Leu Leu Ile Leu Cys Gly Phe Leu Trp
1               5                   10                  15

Thr

<210> SEQ ID NO 861
<211> LENGTH: 20
<212> TYPE: PRT
<213> ORGANISM: Homo sapiens

```
<400> SEQUENCE: 861

Met Glu Thr Leu Leu Gly Gly Leu Leu Ala Phe Gly Met Ala Phe Ala
1               5                   10                  15

Val Val Asp Ala
            20

<210> SEQ ID NO 862
<211> LENGTH: 19
<212> TYPE: PRT
<213> ORGANISM: Homo sapiens

<400> SEQUENCE: 862

Met Arg Thr Leu Thr Ile Leu Thr Ala Val Leu Leu Val Ala Leu Gln
1               5                   10                  15

Ala Lys Ala

<210> SEQ ID NO 863
<211> LENGTH: 17
<212> TYPE: PRT
<213> ORGANISM: Homo sapiens

<400> SEQUENCE: 863

Met Tyr Glu Leu Leu Val Leu Phe Met Leu Ile Gln Pro Gln Ser Met
1               5                   10                  15

Ala

<210> SEQ ID NO 864
<211> LENGTH: 20
<212> TYPE: PRT
<213> ORGANISM: Homo sapiens

<400> SEQUENCE: 864

Met Val Arg Cys Leu Gly Pro Ala Leu Leu Leu Leu Leu Leu Leu Gly
1               5                   10                  15

Ser Ala Ser Ser
            20

<210> SEQ ID NO 865
<211> LENGTH: 20
<212> TYPE: PRT
<213> ORGANISM: Homo sapiens

<400> SEQUENCE: 865

Met Glu Leu Ala Leu Leu Cys Gly Leu Val Val Met Ala Gly Val Ile
1               5                   10                  15

Pro Ile Gln Gly
            20

<210> SEQ ID NO 866
<211> LENGTH: 18
<212> TYPE: PRT
<213> ORGANISM: Homo sapiens

<400> SEQUENCE: 866

Met Ala Trp Phe Ala Leu Tyr Leu Leu Ser Leu Leu Trp Ala Thr Ala
1               5                   10                  15

Gly Thr

<210> SEQ ID NO 867
<211> LENGTH: 18
<212> TYPE: PRT
```

-continued

<213> ORGANISM: Homo sapiens

<400> SEQUENCE: 867

Met Trp Gln Ile Val Phe Phe Thr Leu Ser Cys Asp Leu Val Leu Ala
1               5                   10                  15

Ala Ala

<210> SEQ ID NO 868
<211> LENGTH: 19
<212> TYPE: PRT
<213> ORGANISM: Homo sapiens

<400> SEQUENCE: 868

Met Val Leu Cys Trp Leu Leu Leu Val Met Ala Leu Pro Pro Gly
1               5                   10                  15

Thr Thr Gly

<210> SEQ ID NO 869
<211> LENGTH: 19
<212> TYPE: PRT
<213> ORGANISM: Homo sapiens

<400> SEQUENCE: 869

Met Gly Phe Leu Gly Thr Gly Thr Trp Ile Leu Val Leu Val Leu Pro
1               5                   10                  15

Ile Gln Ala

<210> SEQ ID NO 870
<211> LENGTH: 18
<212> TYPE: PRT
<213> ORGANISM: Homo sapiens

<400> SEQUENCE: 870

Met Glu Val Thr Cys Leu Leu Leu Ala Leu Ile Pro Phe His Cys
1               5                   10                  15

Arg Gly

<210> SEQ ID NO 871
<211> LENGTH: 20
<212> TYPE: PRT
<213> ORGANISM: Homo sapiens

<400> SEQUENCE: 871

Met Val Trp Cys Leu Gly Leu Ala Val Leu Ser Leu Val Ile Ser Gln
1               5                   10                  15

Gly Ala Asp Gly
            20

<210> SEQ ID NO 872
<211> LENGTH: 19
<212> TYPE: PRT
<213> ORGANISM: Homo sapiens

<400> SEQUENCE: 872

Met Met His Leu Arg Leu Phe Cys Ile Leu Leu Ala Ala Val Ser Gly
1               5                   10                  15

Ala Glu Gly

<210> SEQ ID NO 873
<211> LENGTH: 20
<212> TYPE: PRT

<213> ORGANISM: Homo sapiens

<400> SEQUENCE: 873

Met Ser Pro Ser Pro Thr Ala Leu Phe Cys Leu Gly Leu Cys Leu Gly
1               5                   10                  15

Arg Val Pro Ala
            20

<210> SEQ ID NO 874
<211> LENGTH: 18
<212> TYPE: PRT
<213> ORGANISM: Homo sapiens

<400> SEQUENCE: 874

Met Ser Met Leu Phe Tyr Thr Leu Ile Thr Ala Phe Leu Ile Gly Ile
1               5                   10                  15

Gln Ala

<210> SEQ ID NO 875
<211> LENGTH: 19
<212> TYPE: PRT
<213> ORGANISM: Homo sapiens

<400> SEQUENCE: 875

Met Leu Pro Cys Leu Ala Leu Leu Leu Met Glu Leu Ser Val Cys
1               5                   10                  15

Thr Val Ala

<210> SEQ ID NO 876
<211> LENGTH: 19
<212> TYPE: PRT
<213> ORGANISM: Homo sapiens

<400> SEQUENCE: 876

Met Arg Gln Gly Leu Leu Val Leu Ala Leu Val Leu Val Leu Val Leu
1               5                   10                  15

Val Leu Ala

<210> SEQ ID NO 877
<211> LENGTH: 19
<212> TYPE: PRT
<213> ORGANISM: Homo sapiens

<400> SEQUENCE: 877

Met Asp Phe Leu Leu Ala Leu Val Leu Val Ser Ser Leu Tyr Leu Gln
1               5                   10                  15

Ala Ala Ala

<210> SEQ ID NO 878
<211> LENGTH: 18
<212> TYPE: PRT
<213> ORGANISM: Homo sapiens

<400> SEQUENCE: 878

Met Asn Cys Gln Gln Leu Trp Leu Gly Phe Leu Leu Pro Met Thr Val
1               5                   10                  15

Ser Gly

<210> SEQ ID NO 879
<211> LENGTH: 19
<212> TYPE: PRT

<213> ORGANISM: Homo sapiens

<400> SEQUENCE: 879

Met Tyr Gly Lys Ile Ile Phe Val Leu Leu Leu Ser Ala Ile Val Ser
1               5                   10                  15

Ile Ser Ala

<210> SEQ ID NO 880
<211> LENGTH: 19
<212> TYPE: PRT
<213> ORGANISM: Homo sapiens

<400> SEQUENCE: 880

Met Tyr Gly Lys Ile Ile Phe Val Leu Leu Leu Ser Ala Ile Val Ser
1               5                   10                  15

Ile Ser Ala

<210> SEQ ID NO 881
<211> LENGTH: 17
<212> TYPE: PRT
<213> ORGANISM: Homo sapiens

<400> SEQUENCE: 881

Met Pro Pro Phe Leu Ile Thr Leu Phe Leu Phe His Ser Cys Cys Leu
1               5                   10                  15

Arg

<210> SEQ ID NO 882
<211> LENGTH: 21
<212> TYPE: PRT
<213> ORGANISM: Homo sapiens

<400> SEQUENCE: 882

Met Ala Ala Arg Val Ala Ala Val Arg Ala Ala Ala Trp Leu Leu Leu
1               5                   10                  15

Gly Ala Ala Thr Gly
            20

<210> SEQ ID NO 883
<211> LENGTH: 18
<212> TYPE: PRT
<213> ORGANISM: Homo sapiens

<400> SEQUENCE: 883

Met Phe Leu Trp Leu Phe Leu Ile Leu Ser Ala Leu Ile Ser Ser Thr
1               5                   10                  15

Asn Ala

<210> SEQ ID NO 884
<211> LENGTH: 19
<212> TYPE: PRT
<213> ORGANISM: Homo sapiens

<400> SEQUENCE: 884

Met Glu Pro Leu Cys Pro Leu Leu Leu Val Gly Phe Ser Leu Pro Leu
1               5                   10                  15

Ala Arg Ala

<210> SEQ ID NO 885
<211> LENGTH: 19
<212> TYPE: PRT

<213> ORGANISM: Homo sapiens

<400> SEQUENCE: 885

Met Lys Ser Pro His Val Leu Val Phe Leu Cys Leu Leu Val Ala Leu
1               5                   10                  15

Val Thr Gly

<210> SEQ ID NO 886
<211> LENGTH: 21
<212> TYPE: PRT
<213> ORGANISM: Homo sapiens

<400> SEQUENCE: 886

Met Arg Pro Leu Leu Cys Ala Leu Ala Gly Leu Ala Leu Leu Cys Ala
1               5                   10                  15

Val Gly Ala Leu Ala
            20

<210> SEQ ID NO 887
<211> LENGTH: 21
<212> TYPE: PRT
<213> ORGANISM: Homo sapiens

<400> SEQUENCE: 887

Met Gln Ala Cys Met Val Pro Gly Leu Ala Leu Cys Leu Leu Leu Gly
1               5                   10                  15

Pro Leu Ala Gly Ala
            20

<210> SEQ ID NO 888
<211> LENGTH: 18
<212> TYPE: PRT
<213> ORGANISM: Homo sapiens

<400> SEQUENCE: 888

Met Ala Trp Thr Lys Tyr Gln Leu Phe Leu Ala Gly Leu Met Leu Val
1               5                   10                  15

Thr Gly

<210> SEQ ID NO 889
<211> LENGTH: 18
<212> TYPE: PRT
<213> ORGANISM: Homo sapiens

<400> SEQUENCE: 889

Met Thr Leu Leu Pro Gly Leu Leu Phe Leu Thr Trp Leu His Thr Cys
1               5                   10                  15

Leu Ala

<210> SEQ ID NO 890
<211> LENGTH: 18
<212> TYPE: PRT
<213> ORGANISM: Homo sapiens

<400> SEQUENCE: 890

Met Lys Ala Pro Ile Pro His Leu Ile Leu Leu Tyr Ala Thr Phe Thr
1               5                   10                  15

Gln Ser

<210> SEQ ID NO 891
<211> LENGTH: 19

<212> TYPE: PRT
<213> ORGANISM: Homo sapiens

<400> SEQUENCE: 891

Met Arg Ala Asn Asp Ala Leu Gln Val Leu Gly Leu Leu Phe Ser Leu
1               5                   10                  15

Ala Arg Gly

<210> SEQ ID NO 892
<211> LENGTH: 17
<212> TYPE: PRT
<213> ORGANISM: Homo sapiens

<400> SEQUENCE: 892

Met Lys Arg Leu Leu Leu Leu Phe Leu Phe Phe Ile Thr Phe Ser Ser
1               5                   10                  15

Ala

<210> SEQ ID NO 893
<211> LENGTH: 19
<212> TYPE: PRT
<213> ORGANISM: Homo sapiens

<400> SEQUENCE: 893

Met Lys Pro Leu Val Leu Leu Val Ala Leu Leu Leu Trp Pro Ser Ser
1               5                   10                  15

Val Pro Ala

<210> SEQ ID NO 894
<211> LENGTH: 17
<212> TYPE: PRT
<213> ORGANISM: Homo sapiens

<400> SEQUENCE: 894

Met Gln Leu Val Ile Leu Arg Val Thr Ile Phe Leu Pro Trp Cys Phe
1               5                   10                  15

Ala

<210> SEQ ID NO 895
<211> LENGTH: 19
<212> TYPE: PRT
<213> ORGANISM: Homo sapiens

<400> SEQUENCE: 895

Met Arg Ala Pro Leu Cys Leu Leu Leu Val Ala His Ala Val Asp
1               5                   10                  15

Met Leu Ala

<210> SEQ ID NO 896
<211> LENGTH: 19
<212> TYPE: PRT
<213> ORGANISM: Homo sapiens

<400> SEQUENCE: 896

Met Gly Ile Val Cys Ala Gln Cys Ser Phe Ile Leu Leu Ser Ile
1               5                   10                  15

Ile Arg Ala

<210> SEQ ID NO 897
<211> LENGTH: 20
<212> TYPE: PRT

<213> ORGANISM: Homo sapiens

<400> SEQUENCE: 897

Met Ala Pro Ser Leu Trp Lys Gly Leu Val Gly Ile Gly Leu Phe Ala
1               5                   10                  15

Leu Ala His Ala
            20

<210> SEQ ID NO 898
<211> LENGTH: 19
<212> TYPE: PRT
<213> ORGANISM: Homo sapiens

<400> SEQUENCE: 898

Met Gly Leu Gly Leu Leu Pro Leu Leu Leu Trp Thr Arg Gly
1               5                   10                  15

Thr Gln Gly

<210> SEQ ID NO 899
<211> LENGTH: 18
<212> TYPE: PRT
<213> ORGANISM: Homo sapiens

<400> SEQUENCE: 899

Met Ile Pro Val Glu Leu Leu Leu Cys Tyr Leu Leu Leu His Pro Val
1               5                   10                  15

Asp Ala

<210> SEQ ID NO 900
<211> LENGTH: 20
<212> TYPE: PRT
<213> ORGANISM: Homo sapiens

<400> SEQUENCE: 900

Met Leu Pro Gly Arg Leu Cys Trp Val Pro Leu Leu Leu Ala Leu Gly
1               5                   10                  15

Val Gly Ser Gly
            20

<210> SEQ ID NO 901
<211> LENGTH: 18
<212> TYPE: PRT
<213> ORGANISM: Homo sapiens

<400> SEQUENCE: 901

Met Arg Ser Glu Ala Leu Leu Leu Tyr Phe Thr Leu Leu His Phe Ala
1               5                   10                  15

Gly Ala

<210> SEQ ID NO 902
<211> LENGTH: 20
<212> TYPE: PRT
<213> ORGANISM: Homo sapiens

<400> SEQUENCE: 902

Met Ala Gly Thr Gly Leu Leu Ala Leu Arg Thr Leu Pro Gly Pro Ser
1               5                   10                  15

Trp Val Arg Gly
            20

<210> SEQ ID NO 903

```
<211> LENGTH: 21
<212> TYPE: PRT
<213> ORGANISM: Homo sapiens

<400> SEQUENCE: 903

Met Leu Arg Thr Ser Gly Leu Ala Leu Leu Ala Leu Val Ser Ala Val
1               5                   10                  15

Gly Pro Ser Gln Ala
            20

<210> SEQ ID NO 904
<211> LENGTH: 17
<212> TYPE: PRT
<213> ORGANISM: Homo sapiens

<400> SEQUENCE: 904

Met Asp Phe Trp Leu Trp Pro Leu Tyr Phe Leu Pro Val Ser Gly Ala
1               5                   10                  15

Leu

<210> SEQ ID NO 905
<211> LENGTH: 18
<212> TYPE: PRT
<213> ORGANISM: Homo sapiens

<400> SEQUENCE: 905

Met Val Gly Leu Leu Phe Phe Phe Pro Ala Ile Phe Leu Glu Val
1               5                   10                  15

Ser Leu

<210> SEQ ID NO 906
<211> LENGTH: 20
<212> TYPE: PRT
<213> ORGANISM: Homo sapiens

<400> SEQUENCE: 906

Met Thr Arg Ala Leu Cys Ser Ala Leu Arg Gln Ala Leu Leu Leu Leu
1               5                   10                  15

Ala Ala Ala Ala
            20

<210> SEQ ID NO 907
<211> LENGTH: 19
<212> TYPE: PRT
<213> ORGANISM: Homo sapiens

<400> SEQUENCE: 907

Met Arg Leu Leu Leu Leu Leu Val Ala Ala Ser Ala Met Val Arg
1               5                   10                  15

Ser Glu Ala

<210> SEQ ID NO 908
<211> LENGTH: 18
<212> TYPE: PRT
<213> ORGANISM: Homo sapiens

<400> SEQUENCE: 908

Met Leu Pro Gly Cys Ile Phe Leu Met Ile Leu Leu Ile Pro Gln Val
1               5                   10                  15

Lys Glu
```

```
<210> SEQ ID NO 909
<211> LENGTH: 21
<212> TYPE: PRT
<213> ORGANISM: Homo sapiens

<400> SEQUENCE: 909

Met Arg Leu Ala Val Leu Phe Ser Gly Ala Leu Leu Gly Leu Leu Ala
1               5                   10                  15

Ala Gln Gly Thr Gly
            20

<210> SEQ ID NO 910
<211> LENGTH: 18
<212> TYPE: PRT
<213> ORGANISM: Homo sapiens

<400> SEQUENCE: 910

Met Arg Leu Leu Ala Trp Leu Ile Phe Leu Ala Asn Trp Gly Gly Ala
1               5                   10                  15

Arg Ala

<210> SEQ ID NO 911
<211> LENGTH: 21
<212> TYPE: PRT
<213> ORGANISM: Homo sapiens

<400> SEQUENCE: 911

Met Ala Leu Gly Leu Leu Ile Ala Val Pro Leu Leu Leu Gln Ala Ala
1               5                   10                  15

Pro Arg Gly Ala Ala
            20

<210> SEQ ID NO 912
<211> LENGTH: 19
<212> TYPE: PRT
<213> ORGANISM: Homo sapiens

<400> SEQUENCE: 912

Met Thr Cys Ser Pro Leu Leu Leu Thr Leu Leu Ile His Cys Thr Gly
1               5                   10                  15

Ser Trp Ala

<210> SEQ ID NO 913
<211> LENGTH: 19
<212> TYPE: PRT
<213> ORGANISM: Homo sapiens

<400> SEQUENCE: 913

Met Phe Gln Thr Gly Gly Leu Ile Val Phe Tyr Gly Leu Leu Ala Gln
1               5                   10                  15

Thr Met Ala

<210> SEQ ID NO 914
<211> LENGTH: 20
<212> TYPE: PRT
<213> ORGANISM: Homo sapiens

<400> SEQUENCE: 914

Met Gly Ser Gly Arg Val Pro Gly Leu Cys Leu Leu Val Leu Leu Val
1               5                   10                  15

His Ala Arg Ala
            20
```

<210> SEQ ID NO 915
<211> LENGTH: 18
<212> TYPE: PRT
<213> ORGANISM: Homo sapiens

<400> SEQUENCE: 915

Met Met Leu Asn Leu Val Arg Tyr Val Cys Val Leu Gly Asn Met Val
1               5                   10                  15

His Ala

<210> SEQ ID NO 916
<211> LENGTH: 19
<212> TYPE: PRT
<213> ORGANISM: Homo sapiens

<400> SEQUENCE: 916

Met Val Pro Arg Ile Ser Ala Ala Ile Phe Ile Phe Glu Leu Leu Gly
1               5                   10                  15

Ser Asn Ser

<210> SEQ ID NO 917
<211> LENGTH: 18
<212> TYPE: PRT
<213> ORGANISM: Homo sapiens

<400> SEQUENCE: 917

Met Val Leu Leu Trp Leu Thr Leu Leu Leu Ile Ala Leu Pro Cys Leu
1               5                   10                  15

Leu Gln

<210> SEQ ID NO 918
<211> LENGTH: 20
<212> TYPE: PRT
<213> ORGANISM: Homo sapiens

<400> SEQUENCE: 918

Met Asp Ser Arg Gln Ala Ala Ala Leu Leu Val Leu Leu Leu Leu Ile
1               5                   10                  15

Asp Gly Gly Cys
            20

<210> SEQ ID NO 919
<211> LENGTH: 18
<212> TYPE: PRT
<213> ORGANISM: Homo sapiens

<400> SEQUENCE: 919

Met Cys Ala Phe Pro Trp Leu Leu Leu Leu Leu Leu Gln Glu Gly
1               5                   10                  15

Ser Gln

<210> SEQ ID NO 920
<211> LENGTH: 19
<212> TYPE: PRT
<213> ORGANISM: Homo sapiens

<400> SEQUENCE: 920

Met Ser Ala Leu Trp Leu Leu Leu Gly Leu Leu Ala Leu Met Asp Leu
1               5                   10                  15

Ser Glu Ser

<210> SEQ ID NO 921
<211> LENGTH: 20
<212> TYPE: PRT
<213> ORGANISM: Homo sapiens

<400> SEQUENCE: 921

Met Arg Ala Leu Val Leu Leu Gly Cys Leu Leu Ala Ser Leu Leu Phe
1               5                   10                  15

Ser Gly Gln Ala
            20

<210> SEQ ID NO 922
<211> LENGTH: 20
<212> TYPE: PRT
<213> ORGANISM: Homo sapiens

<400> SEQUENCE: 922

Met Lys Lys Phe Phe Thr Val Ala Ile Leu Ala Gly Ser Val Leu Ser
1               5                   10                  15

Thr Ala His Gly
            20

<210> SEQ ID NO 923
<211> LENGTH: 18
<212> TYPE: PRT
<213> ORGANISM: Homo sapiens

<400> SEQUENCE: 923

Met Ala Leu Val Leu Ile Leu Gln Leu Leu Thr Leu Trp Pro Leu Cys
1               5                   10                  15

His Thr

<210> SEQ ID NO 924
<211> LENGTH: 20
<212> TYPE: PRT
<213> ORGANISM: Homo sapiens

<400> SEQUENCE: 924

Met Lys Leu Ala Leu Leu Leu Pro Trp Ala Cys Cys Cys Leu Cys Gly
1               5                   10                  15

Ser Ala Leu Ala
            20

<210> SEQ ID NO 925
<211> LENGTH: 18
<212> TYPE: PRT
<213> ORGANISM: Homo sapiens

<400> SEQUENCE: 925

Met Ile Val Leu Leu Leu Phe Ala Leu Leu Trp Met Val Glu Gly Val
1               5                   10                  15

Phe Ser

<210> SEQ ID NO 926
<211> LENGTH: 20
<212> TYPE: PRT
<213> ORGANISM: Homo sapiens

<400> SEQUENCE: 926

Met His Ser Trp Glu Arg Leu Ala Val Leu Val Leu Leu Gly Ala Ala
1               5                   10                  15

Ala Cys Ala Ala
            20

<210> SEQ ID NO 927
<211> LENGTH: 18
<212> TYPE: PRT
<213> ORGANISM: Homo sapiens

<400> SEQUENCE: 927

Met Pro His Thr Leu Trp Met Val Trp Val Leu Gly Val Ile Ile Ser
1               5                   10                  15

Leu Ser

<210> SEQ ID NO 928
<211> LENGTH: 19
<212> TYPE: PRT
<213> ORGANISM: Homo sapiens

<400> SEQUENCE: 928

Met Gly Ile Gly Cys Trp Arg Asn Pro Leu Leu Leu Ile Ala Leu
1               5                   10                  15

Val Leu Ser

<210> SEQ ID NO 929
<211> LENGTH: 19
<212> TYPE: PRT
<213> ORGANISM: Homo sapiens

<400> SEQUENCE: 929

Met Ala Ile Leu Met Leu Ser Leu Gln Leu Ile Leu Leu Ile Pro
1               5                   10                  15

Ser Ile Ser

<210> SEQ ID NO 930
<211> LENGTH: 20
<212> TYPE: PRT
<213> ORGANISM: Homo sapiens

<400> SEQUENCE: 930

Met Thr Pro Ala Cys Pro Leu Leu Leu Ser Val Ile Leu Ser Leu Arg
1               5                   10                  15

Leu Ala Thr Ala
            20

<210> SEQ ID NO 931
<211> LENGTH: 20
<212> TYPE: PRT
<213> ORGANISM: Homo sapiens

<400> SEQUENCE: 931

Met Leu Leu Ala Leu Ala Leu Leu Ala Phe Leu Pro Pro Ala Ser
1               5                   10                  15

Gln Lys Ser Ser
            20

<210> SEQ ID NO 932
<211> LENGTH: 19
<212> TYPE: PRT
<213> ORGANISM: Homo sapiens

<400> SEQUENCE: 932

Met Gly Arg Pro Leu Leu Leu Pro Leu Leu Leu Pro Pro
1               5                   10                  15

Ala Phe Leu

<210> SEQ ID NO 933
<211> LENGTH: 20
<212> TYPE: PRT
<213> ORGANISM: Homo sapiens

<400> SEQUENCE: 933

Met Ala Phe Leu Pro Ser Trp Val Cys Val Leu Val Gly Ser Phe Ser
1               5                   10                  15

Ala Ser Leu Ala
            20

<210> SEQ ID NO 934
<211> LENGTH: 21
<212> TYPE: PRT
<213> ORGANISM: Homo sapiens

<400> SEQUENCE: 934

Met Gly Pro His Phe Thr Leu Leu Cys Ala Ala Leu Ala Gly Cys Leu
1               5                   10                  15

Leu Pro Ala Glu Gly
            20

<210> SEQ ID NO 935
<211> LENGTH: 19
<212> TYPE: PRT
<213> ORGANISM: Homo sapiens

<400> SEQUENCE: 935

Met Gly Val Leu Gly Arg Val Leu Leu Trp Leu Gln Leu Cys Ala Leu
1               5                   10                  15

Thr Gln Ala

<210> SEQ ID NO 936
<211> LENGTH: 20
<212> TYPE: PRT
<213> ORGANISM: Homo sapiens

<400> SEQUENCE: 936

Met Leu Gln Gly Thr Cys Ser Val Leu Leu Leu Trp Gly Ile Leu Gly
1               5                   10                  15

Ala Ile Gln Ala
            20

<210> SEQ ID NO 937
<211> LENGTH: 20
<212> TYPE: PRT
<213> ORGANISM: Homo sapiens

<400> SEQUENCE: 937

Met Asn Gly Leu Ser Leu Ser Glu Leu Cys Cys Leu Phe Cys Cys Pro
1               5                   10                  15

Pro Cys Pro Gly
            20

<210> SEQ ID NO 938
<211> LENGTH: 20
<212> TYPE: PRT
<213> ORGANISM: Homo sapiens

```
<400> SEQUENCE: 938

Met Asn Gly Leu Ser Leu Ser Glu Leu Cys Cys Leu Phe Cys Cys Pro
1               5                   10                  15
Pro Cys Pro Gly
            20

<210> SEQ ID NO 939
<211> LENGTH: 22
<212> TYPE: PRT
<213> ORGANISM: Homo sapiens

<400> SEQUENCE: 939

Met Ala Leu Pro Ser Leu Leu Leu Val Ala Ala Leu Ala Gly Gly
1               5                   10                  15
Val Arg Pro Pro Gly Ala
            20

<210> SEQ ID NO 940
<211> LENGTH: 19
<212> TYPE: PRT
<213> ORGANISM: Homo sapiens

<400> SEQUENCE: 940

Met Pro Ala Leu Arg Pro Leu Leu Pro Leu Leu Leu Leu Arg Leu
1               5                   10                  15
Thr Ser Gly

<210> SEQ ID NO 941
<211> LENGTH: 18
<212> TYPE: PRT
<213> ORGANISM: Homo sapiens

<400> SEQUENCE: 941

Met Arg Pro Arg Leu Trp Leu Leu Leu Ala Ala Gln Leu Thr Val Leu
1               5                   10                  15
His Gly

<210> SEQ ID NO 942
<211> LENGTH: 19
<212> TYPE: PRT
<213> ORGANISM: Homo sapiens

<400> SEQUENCE: 942

Met Ser Trp Ala Pro Val Leu Leu Met Leu Phe Val Tyr Cys Thr Gly
1               5                   10                  15
Cys Gly Pro

<210> SEQ ID NO 943
<211> LENGTH: 19
<212> TYPE: PRT
<213> ORGANISM: Homo sapiens

<400> SEQUENCE: 943

Met Ala Gly Ile Phe Tyr Phe Ala Leu Phe Ser Cys Leu Phe Gly Ile
1               5                   10                  15
Cys Asp Ala

<210> SEQ ID NO 944
<211> LENGTH: 18
<212> TYPE: PRT
```

<213> ORGANISM: Homo sapiens

<400> SEQUENCE: 944

Met Glu Leu Leu Pro Leu Trp Leu Cys Leu Gly Phe His Phe Leu Thr
1               5                   10                  15

Val Gly

<210> SEQ ID NO 945
<211> LENGTH: 19
<212> TYPE: PRT
<213> ORGANISM: Homo sapiens

<400> SEQUENCE: 945

Met Thr Trp Leu Val Leu Leu Gly Thr Leu Leu Cys Met Leu Arg Val
1               5                   10                  15

Gly Leu Gly

<210> SEQ ID NO 946
<211> LENGTH: 19
<212> TYPE: PRT
<213> ORGANISM: Homo sapiens

<400> SEQUENCE: 946

Met Ser Asp Leu Gly Ala Val Ile Ser Leu Leu Leu Trp Gly Arg Gln
1               5                   10                  15

Leu Phe Ala

<210> SEQ ID NO 947
<211> LENGTH: 19
<212> TYPE: PRT
<213> ORGANISM: Homo sapiens

<400> SEQUENCE: 947

Met Thr Lys Ala Leu Leu Ile Tyr Leu Val Ser Ser Phe Leu Ala Leu
1               5                   10                  15

Asn Gln Ala

<210> SEQ ID NO 948
<211> LENGTH: 18
<212> TYPE: PRT
<213> ORGANISM: Homo sapiens

<400> SEQUENCE: 948

Met Arg Gly Glu Leu Trp Leu Leu Val Leu Val Leu Arg Glu Ala Ala
1               5                   10                  15

Arg Ala

<210> SEQ ID NO 949
<211> LENGTH: 19
<212> TYPE: PRT
<213> ORGANISM: Homo sapiens

<400> SEQUENCE: 949

Met Arg Ala Ala Leu Trp Thr Leu Gly Leu Gly Pro Leu Leu Leu Asn
1               5                   10                  15

Leu Trp Ala

<210> SEQ ID NO 950
<211> LENGTH: 21
<212> TYPE: PRT
<213> ORGANISM: Homo sapiens

```
<400> SEQUENCE: 950

Met Leu Pro Gln Gln Val Gly Phe Val Cys Ala Val Leu Ala Leu Val
1               5                   10                  15

Cys Cys Ala Ser Gly
            20

<210> SEQ ID NO 951
<211> LENGTH: 22
<212> TYPE: PRT
<213> ORGANISM: Homo sapiens

<400> SEQUENCE: 951

Met Arg Leu Gly Pro Arg Thr Ala Ala Leu Gly Leu Leu Leu Leu Cys
1               5                   10                  15

Ala Ala Ala Ala Gly Ala
            20

<210> SEQ ID NO 952
<211> LENGTH: 19
<212> TYPE: PRT
<213> ORGANISM: Homo sapiens

<400> SEQUENCE: 952

Met Lys Phe Ser Pro Ala His Tyr Leu Leu Pro Leu Leu Pro Ala Leu
1               5                   10                  15

Val Leu Ser

<210> SEQ ID NO 953
<211> LENGTH: 19
<212> TYPE: PRT
<213> ORGANISM: Homo sapiens

<400> SEQUENCE: 953

Met Met Leu Ser Trp Lys Gln Leu Ile Leu Leu Ser Phe Ile Gly Cys
1               5                   10                  15

Leu Gly Gly

<210> SEQ ID NO 954
<211> LENGTH: 20
<212> TYPE: PRT
<213> ORGANISM: Homo sapiens

<400> SEQUENCE: 954

Met Ala Arg Ala Met Ala Ala Ala Trp Pro Leu Leu Leu Val Ala Leu
1               5                   10                  15

Leu Val Leu Ser
            20

<210> SEQ ID NO 955
<211> LENGTH: 19
<212> TYPE: PRT
<213> ORGANISM: Homo sapiens

<400> SEQUENCE: 955

Met Lys Ile Leu Val Ala Leu Ala Val Phe Phe Leu Val Ser Thr Gln
1               5                   10                  15

Leu Phe Ala

<210> SEQ ID NO 956
<211> LENGTH: 23
```

```
<212> TYPE: PRT
<213> ORGANISM: Homo sapiens

<400> SEQUENCE: 956

Met Ala Pro Arg Ala Leu Pro Gly Ser Ala Val Leu Ala Ala Ala Val
1               5                   10                  15

Phe Val Gly Gly Ala Val Ser
            20

<210> SEQ ID NO 957
<211> LENGTH: 20
<212> TYPE: PRT
<213> ORGANISM: Homo sapiens

<400> SEQUENCE: 957

Met Glu Arg Val Thr Leu Ala Leu Leu Leu Ala Gly Leu Thr Ala
1               5                   10                  15

Leu Glu Ala Asn
            20

<210> SEQ ID NO 958
<211> LENGTH: 20
<212> TYPE: PRT
<213> ORGANISM: Homo sapiens

<400> SEQUENCE: 958

Met His Pro Gln Val Val Ile Leu Ser Leu Ile Leu His Leu Ala Asp
1               5                   10                  15

Ser Val Ala Gly
            20

<210> SEQ ID NO 959
<211> LENGTH: 19
<212> TYPE: PRT
<213> ORGANISM: Homo sapiens

<400> SEQUENCE: 959

Met Ala Phe Cys Ala Leu Thr Ile Val Ala Leu Tyr Ile Leu Ser Leu
1               5                   10                  15

Lys Asp Gln

<210> SEQ ID NO 960
<211> LENGTH: 18
<212> TYPE: PRT
<213> ORGANISM: Homo sapiens

<400> SEQUENCE: 960

Met Val Arg Pro Tyr Pro Leu Ile Tyr Phe Leu Phe Leu Pro Leu Gly
1               5                   10                  15

Ala Cys

<210> SEQ ID NO 961
<211> LENGTH: 19
<212> TYPE: PRT
<213> ORGANISM: Homo sapiens

<400> SEQUENCE: 961

Met Thr Glu Arg Arg Arg Ala Leu Ser Leu Ala Ala Val Val Asp Ser
1               5                   10                  15

Ile Asn Leu
```

```
<210> SEQ ID NO 962
<211> LENGTH: 20
<212> TYPE: PRT
<213> ORGANISM: Homo sapiens

<400> SEQUENCE: 962

Met Lys Pro Leu Leu Glu Thr Leu Tyr Leu Gly Met Leu Val Pro
1               5                   10                  15

Gly Gly Leu Gly
            20

<210> SEQ ID NO 963
<211> LENGTH: 20
<212> TYPE: PRT
<213> ORGANISM: Homo sapiens

<400> SEQUENCE: 963

Met Val Ser Gln Ala Leu Arg Leu Leu Cys Leu Leu Leu Gly Leu Gln
1               5                   10                  15

Gly Cys Leu Ala
            20

<210> SEQ ID NO 964
<211> LENGTH: 19
<212> TYPE: PRT
<213> ORGANISM: Homo sapiens

<400> SEQUENCE: 964

Met Gly Arg Pro Leu Leu Leu Pro Leu Leu Leu Leu Gln Pro Pro
1               5                   10                  15

Ala Phe Leu

<210> SEQ ID NO 965
<211> LENGTH: 19
<212> TYPE: PRT
<213> ORGANISM: Homo sapiens

<400> SEQUENCE: 965

Met Lys Leu Leu Leu Leu Ala Leu Pro Met Leu Val Leu Leu Pro Gln
1               5                   10                  15

Val Ile Pro

<210> SEQ ID NO 966
<211> LENGTH: 20
<212> TYPE: PRT
<213> ORGANISM: Homo sapiens

<400> SEQUENCE: 966

Met Leu Cys Cys Cys Pro Leu Ala Asp Ala Leu Leu Ile Phe Leu Glu
1               5                   10                  15

Thr Gly Ser Cys
            20

<210> SEQ ID NO 967
<211> LENGTH: 19
<212> TYPE: PRT
<213> ORGANISM: Homo sapiens

<400> SEQUENCE: 967

Met Glu Lys Ser Ile Trp Leu Leu Ala Cys Leu Ala Trp Val Leu Pro
1               5                   10                  15

Thr Gly Ser
```

<210> SEQ ID NO 968
<211> LENGTH: 21
<212> TYPE: PRT
<213> ORGANISM: Homo sapiens

<400> SEQUENCE: 968

Met Ser Arg Val Val Ser Leu Leu Leu Gly Ala Ala Leu Leu Cys Gly
1               5                   10                  15

His Gly Ala Phe Cys
            20

<210> SEQ ID NO 969
<211> LENGTH: 19
<212> TYPE: PRT
<213> ORGANISM: Homo sapiens

<400> SEQUENCE: 969

Met Gly Trp Thr Trp Arg Ile Leu Phe Leu Val Val Ile Ala Ala Gly
1               5                   10                  15

Ala Gln Ser

<210> SEQ ID NO 970
<211> LENGTH: 22
<212> TYPE: PRT
<213> ORGANISM: Homo sapiens

<400> SEQUENCE: 970

Met Ala Ala Pro Val Pro Trp Ala Cys Cys Ala Val Leu Ala Ala Ala
1               5                   10                  15

Ala Ala Val Val Tyr Ala
            20

<210> SEQ ID NO 971
<211> LENGTH: 19
<212> TYPE: PRT
<213> ORGANISM: Homo sapiens

<400> SEQUENCE: 971

Met Trp Gly Leu Val Arg Leu Leu Leu Ala Trp Leu Gly Gly Trp Gly
1               5                   10                  15

Cys Met Gly

<210> SEQ ID NO 972
<211> LENGTH: 21
<212> TYPE: PRT
<213> ORGANISM: Homo sapiens

<400> SEQUENCE: 972

Met Leu Gly Val Leu Glu Leu Leu Leu Gly Ala Ala Trp Leu Ala
1               5                   10                  15

Gly Pro Ala Arg Gly
            20

<210> SEQ ID NO 973
<211> LENGTH: 18
<212> TYPE: PRT
<213> ORGANISM: Homo sapiens

<400> SEQUENCE: 973

Met Leu Leu Leu Leu Leu Leu Pro Leu Leu Trp Gly Arg Glu Arg Val
1               5                   10                  15

-continued

Glu Gly

<210> SEQ ID NO 974
<211> LENGTH: 21
<212> TYPE: PRT
<213> ORGANISM: Homo sapiens

<400> SEQUENCE: 974

Met Ala Thr Ser Met Gly Leu Leu Leu Leu Leu Leu Leu Leu Leu Thr
1               5                   10                  15

Gln Pro Gly Ala Gly
            20

<210> SEQ ID NO 975
<211> LENGTH: 19
<212> TYPE: PRT
<213> ORGANISM: Homo sapiens

<400> SEQUENCE: 975

Met Arg Gly Cys Leu Arg Leu Ala Leu Leu Cys Ala Leu Pro Trp Leu
1               5                   10                  15

Leu Leu Ala

<210> SEQ ID NO 976
<211> LENGTH: 20
<212> TYPE: PRT
<213> ORGANISM: Homo sapiens

<400> SEQUENCE: 976

Met Trp Val Leu Gly Ile Ala Ala Thr Phe Cys Gly Leu Phe Leu Leu
1               5                   10                  15

Pro Gly Phe Ala
            20

<210> SEQ ID NO 977
<211> LENGTH: 22
<212> TYPE: PRT
<213> ORGANISM: Homo sapiens

<400> SEQUENCE: 977

Met Leu Leu Leu Trp Val Ser Val Val Ala Ala Leu Ala Leu Ala Val
1               5                   10                  15

Leu Ala Pro Gly Ala Gly
            20

<210> SEQ ID NO 978
<211> LENGTH: 21
<212> TYPE: PRT
<213> ORGANISM: Homo sapiens

<400> SEQUENCE: 978

Met Ala Cys Leu Gly Phe Leu Pro Val Gly Phe Leu Leu Leu Ile
1               5                   10                  15

Ser Thr Val Ala Gly
            20

<210> SEQ ID NO 979
<211> LENGTH: 20
<212> TYPE: PRT
<213> ORGANISM: Homo sapiens

<400> SEQUENCE: 979

```
Met Ala Ser Gly Leu Leu Leu Leu Leu Leu Thr Ala Leu Pro
1               5                   10                  15

Pro Leu Trp Ser
            20
```

<210> SEQ ID NO 980
<211> LENGTH: 18
<212> TYPE: PRT
<213> ORGANISM: Homo sapiens

<400> SEQUENCE: 980

```
Met Val Leu Leu Ser Ile Leu Arg Ile Leu Phe Leu Cys Glu Leu Val
1               5                   10                  15

Leu Phe
```

<210> SEQ ID NO 981
<211> LENGTH: 20
<212> TYPE: PRT
<213> ORGANISM: Homo sapiens

<400> SEQUENCE: 981

```
Met Ser Pro Ala Pro Arg Pro Ser Arg Cys Leu Leu Leu Pro Leu Leu
1               5                   10                  15

Thr Leu Gly Thr
            20
```

<210> SEQ ID NO 982
<211> LENGTH: 19
<212> TYPE: PRT
<213> ORGANISM: Homo sapiens

<400> SEQUENCE: 982

```
Met Arg Leu Leu Trp Lys Leu Val Ile Leu Leu Pro Leu Ile Asn Ser
1               5                   10                  15

Ser Ala Gly
```

<210> SEQ ID NO 983
<211> LENGTH: 21
<212> TYPE: PRT
<213> ORGANISM: Homo sapiens

<400> SEQUENCE: 983

```
Met Arg Phe Val Val Ala Leu Val Leu Leu Asn Val Ala Ala Ala Gly
1               5                   10                  15

Ala Val Pro Leu Leu
            20
```

<210> SEQ ID NO 984
<211> LENGTH: 18
<212> TYPE: PRT
<213> ORGANISM: Homo sapiens

<400> SEQUENCE: 984

```
Met Gln His Ser Leu Val Phe Phe Ala Val Ile Leu His Leu Ser
1               5                   10                  15

His Leu
```

<210> SEQ ID NO 985
<211> LENGTH: 20
<212> TYPE: PRT
<213> ORGANISM: Homo sapiens -continued

```
<400> SEQUENCE: 985

Met Ala Thr Ser Trp Gly Thr Val Phe Phe Met Leu Val Val Ser Cys
1               5                   10                  15

Val Cys Ser Ala
            20

<210> SEQ ID NO 986
<211> LENGTH: 19
<212> TYPE: PRT
<213> ORGANISM: Homo sapiens

<400> SEQUENCE: 986

Met Ala Leu Pro Ser Arg Ile Leu Leu Trp Lys Leu Val Leu Leu Gln
1               5                   10                  15

Ser Ser Ala

<210> SEQ ID NO 987
<211> LENGTH: 20
<212> TYPE: PRT
<213> ORGANISM: Homo sapiens

<400> SEQUENCE: 987

Met Ile Trp Tyr Val Ala Thr Phe Ile Ala Ser Val Ile Gly Thr Arg
1               5                   10                  15

Gly Leu Ala Ala
            20

<210> SEQ ID NO 988
<211> LENGTH: 20
<212> TYPE: PRT
<213> ORGANISM: Homo sapiens

<400> SEQUENCE: 988

Met Gly His Leu Trp Leu Leu Gly Ile Trp Gly Leu Cys Gly Leu Leu
1               5                   10                  15

Leu Cys Ala Ala
            20

<210> SEQ ID NO 989
<211> LENGTH: 23
<212> TYPE: PRT
<213> ORGANISM: Homo sapiens

<400> SEQUENCE: 989

Met Gln Ser His Leu Ala Pro Leu Ala Cys Ala Ala Ala Ala Gly Arg
1               5                   10                  15

Ala Gly Gly Ser Cys Gln Ala
            20

<210> SEQ ID NO 990
<211> LENGTH: 19
<212> TYPE: PRT
<213> ORGANISM: Homo sapiens

<400> SEQUENCE: 990

Met His Tyr Cys Val Leu Ser Ala Phe Leu Ile Leu His Leu Val Thr
1               5                   10                  15

Val Ala Leu

<210> SEQ ID NO 991
```

```
<211> LENGTH: 21
<212> TYPE: PRT
<213> ORGANISM: Homo sapiens

<400> SEQUENCE: 991

Met Leu Leu Leu Leu Leu Pro Ser Leu Leu Leu Leu Leu Leu Leu Pro
1               5                   10                  15

Gly Pro Gly Ser Gly
            20

<210> SEQ ID NO 992
<211> LENGTH: 21
<212> TYPE: PRT
<213> ORGANISM: Homo sapiens

<400> SEQUENCE: 992

Met Ser Pro Leu Leu Phe Gly Ala Gly Leu Val Val Leu Asn Leu Val
1               5                   10                  15

Thr Ser Ala Arg Ser
            20

<210> SEQ ID NO 993
<211> LENGTH: 22
<212> TYPE: PRT
<213> ORGANISM: Homo sapiens

<400> SEQUENCE: 993

Met Leu Leu Gly Gln Leu Ser Thr Leu Leu Cys Leu Leu Ser Gly Ala
1               5                   10                  15

Leu Pro Thr Gly Ser Gly
            20

<210> SEQ ID NO 994
<211> LENGTH: 19
<212> TYPE: PRT
<213> ORGANISM: Homo sapiens

<400> SEQUENCE: 994

Met Trp Thr Leu Lys Ser Ser Leu Val Leu Leu Leu Cys Leu Thr Cys
1               5                   10                  15

Ser Tyr Ala

<210> SEQ ID NO 995
<211> LENGTH: 19
<212> TYPE: PRT
<213> ORGANISM: Homo sapiens

<400> SEQUENCE: 995

Met Trp Thr Leu Lys Ser Ser Leu Val Leu Leu Leu Cys Leu Thr Cys
1               5                   10                  15

Ser Tyr Ala

<210> SEQ ID NO 996
<211> LENGTH: 21
<212> TYPE: PRT
<213> ORGANISM: Homo sapiens

<400> SEQUENCE: 996

Met Gly Ser Leu Val Leu Thr Leu Cys Ala Leu Phe Cys Leu Ala Ala
1               5                   10                  15

Tyr Leu Val Ser Gly
            20
```

```
<210> SEQ ID NO 997
<211> LENGTH: 18
<212> TYPE: PRT
<213> ORGANISM: Homo sapiens

<400> SEQUENCE: 997

Met Arg Leu Pro Trp Glu Leu Leu Val Leu Gln Ser Phe Ile Leu Cys
1               5                   10                  15

Leu Ala

<210> SEQ ID NO 998
<211> LENGTH: 18
<212> TYPE: PRT
<213> ORGANISM: Homo sapiens

<400> SEQUENCE: 998

Met Glu Met Phe Thr Phe Leu Leu Thr Cys Ile Phe Leu Pro Leu Leu
1               5                   10                  15

Arg Gly

<210> SEQ ID NO 999
<211> LENGTH: 19
<212> TYPE: PRT
<213> ORGANISM: Homo sapiens

<400> SEQUENCE: 999

Met Thr Arg Cys Ala Leu Leu Leu Met Val Leu Met Leu Gly Arg
1               5                   10                  15

Val Leu Val

<210> SEQ ID NO 1000
<211> LENGTH: 19
<212> TYPE: PRT
<213> ORGANISM: Homo sapiens

<400> SEQUENCE: 1000

Met Asp Trp Thr Trp Arg Ile Leu Phe Leu Val Ala Ala Ala Thr Gly
1               5                   10                  15

Ala His Ser

<210> SEQ ID NO 1001
<211> LENGTH: 17
<212> TYPE: PRT
<213> ORGANISM: Homo sapiens

<400> SEQUENCE: 1001

Met Trp Trp Arg Val Leu Ser Leu Leu Ala Trp Phe Pro Leu Gln Glu
1               5                   10                  15

Ala

<210> SEQ ID NO 1002
<211> LENGTH: 21
<212> TYPE: PRT
<213> ORGANISM: Homo sapiens

<400> SEQUENCE: 1002

Met Leu Arg Gln Leu Leu Leu Ala Ala Leu Cys Leu Ala Gly Pro Pro
1               5                   10                  15

Ala Pro Ala Arg Ala
            20
```

```
<210> SEQ ID NO 1003
<211> LENGTH: 20
<212> TYPE: PRT
<213> ORGANISM: Homo sapiens

<400> SEQUENCE: 1003

Met Thr Leu Phe Pro Val Leu Leu Phe Leu Val Ala Gly Leu Leu Pro
1               5                   10                  15

Ser Phe Pro Ala
            20

<210> SEQ ID NO 1004
<211> LENGTH: 21
<212> TYPE: PRT
<213> ORGANISM: Homo sapiens

<400> SEQUENCE: 1004

Met Gly Thr Ala Arg Trp Leu Ala Leu Gly Ser Leu Phe Ala Leu Ala
1               5                   10                  15

Gly Leu Leu Glu Gly
            20

<210> SEQ ID NO 1005
<211> LENGTH: 20
<212> TYPE: PRT
<213> ORGANISM: Homo sapiens

<400> SEQUENCE: 1005

Met Asn Gly Leu Ser Leu Ser Glu Leu Cys Cys Leu Phe Cys Tyr Pro
1               5                   10                  15

Pro Cys Pro Gly
            20

<210> SEQ ID NO 1006
<211> LENGTH: 20
<212> TYPE: PRT
<213> ORGANISM: Homo sapiens

<400> SEQUENCE: 1006

Met Val Pro Lys Ala Asp Ser Gly Ala Phe Leu Leu Leu Phe Leu Leu
1               5                   10                  15

Val Leu Thr Val
            20

<210> SEQ ID NO 1007
<211> LENGTH: 18
<212> TYPE: PRT
<213> ORGANISM: Homo sapiens

<400> SEQUENCE: 1007

Met Leu Arg Phe Tyr Leu Phe Ile Ser Leu Leu Cys Leu Ser Arg Ser
1               5                   10                  15

Asp Ala

<210> SEQ ID NO 1008
<211> LENGTH: 21
<212> TYPE: PRT
<213> ORGANISM: Homo sapiens

<400> SEQUENCE: 1008

Met Asp Ala Ala Phe Leu Leu Val Leu Gly Leu Leu Ala Gln Ser Leu
```

```
1               5                   10                  15

Cys Leu Ser Leu Gly
            20

<210> SEQ ID NO 1009
<211> LENGTH: 20
<212> TYPE: PRT
<213> ORGANISM: Homo sapiens

<400> SEQUENCE: 1009

Met Met Ser Phe Leu Leu Gly Ala Ile Leu Thr Leu Leu Trp Ala Pro
1               5                   10                  15

Thr Ala Gln Ala
            20

<210> SEQ ID NO 1010
<211> LENGTH: 21
<212> TYPE: PRT
<213> ORGANISM: Homo sapiens

<400> SEQUENCE: 1010

Met Asn Gly Asn Leu Asp Gly Trp Val Val Leu Ala Ala Pro Leu
1               5                   10                  15

Leu Pro Ala Ala Gln
            20

<210> SEQ ID NO 1011
<211> LENGTH: 20
<212> TYPE: PRT
<213> ORGANISM: Homo sapiens

<400> SEQUENCE: 1011

Met Arg Arg Gln Trp Gly Ala Leu Leu Leu Gly Ala Leu Leu Cys Ala
1               5                   10                  15

His Ala Val Ala
            20

<210> SEQ ID NO 1012
<211> LENGTH: 19
<212> TYPE: PRT
<213> ORGANISM: Homo sapiens

<400> SEQUENCE: 1012

Met Gly Pro Arg Ala Lys Thr Ile Ser Ser Leu Phe Phe Leu Leu Trp
1               5                   10                  15

Val Leu Ala

<210> SEQ ID NO 1013
<211> LENGTH: 21
<212> TYPE: PRT
<213> ORGANISM: Homo sapiens

<400> SEQUENCE: 1013

Met Gly Gly Leu Glu Pro Cys Ser Arg Leu Leu Leu Leu Pro Leu Leu
1               5                   10                  15

Leu Ala Val Ser Gly
            20

<210> SEQ ID NO 1014
<211> LENGTH: 20
<212> TYPE: PRT
<213> ORGANISM: Homo sapiens
```

```
<400> SEQUENCE: 1014

Met Ala Pro Ala Val Thr Arg Leu Leu Phe Leu Gln Leu Val Leu Gly
1               5                   10                  15

Pro Thr Leu Val
            20

<210> SEQ ID NO 1015
<211> LENGTH: 20
<212> TYPE: PRT
<213> ORGANISM: Homo sapiens

<400> SEQUENCE: 1015

Met Glu Thr Leu Gly Ala Leu Leu Val Leu Glu Phe Leu Leu Leu Ser
1               5                   10                  15

Pro Val Glu Ala
            20

<210> SEQ ID NO 1016
<211> LENGTH: 21
<212> TYPE: PRT
<213> ORGANISM: Homo sapiens

<400> SEQUENCE: 1016

Met Ala Ser Ser Leu Thr Cys Thr Gly Val Ile Trp Ala Leu Leu Ser
1               5                   10                  15

Phe Leu Cys Ala Ala
            20

<210> SEQ ID NO 1017
<211> LENGTH: 21
<212> TYPE: PRT
<213> ORGANISM: Homo sapiens

<400> SEQUENCE: 1017

Met Ala Val Gly Lys Phe Leu Leu Gly Ser Leu Leu Leu Leu Ser Leu
1               5                   10                  15

Gln Leu Gly Gln Gly
            20

<210> SEQ ID NO 1018
<211> LENGTH: 19
<212> TYPE: PRT
<213> ORGANISM: Homo sapiens

<400> SEQUENCE: 1018

Met Trp Gln Leu Leu Ala Ala Ala Cys Trp Met Leu Leu Gly Ser
1               5                   10                  15

Met Tyr Gly

<210> SEQ ID NO 1019
<211> LENGTH: 23
<212> TYPE: PRT
<213> ORGANISM: Homo sapiens

<400> SEQUENCE: 1019

Met Gly Thr Gly Gly Ser Leu Cys Gly Cys Ser Leu Val Leu Ser
1               5                   10                  15

Cys Leu Cys Pro Ser Ala Ser
            20
```

-continued

```
<210> SEQ ID NO 1020
<211> LENGTH: 17
<212> TYPE: PRT
<213> ORGANISM: Homo sapiens

<400> SEQUENCE: 1020

Met Trp Leu Tyr Leu Ala Ala Phe Val Gly Leu Tyr Tyr Leu His
1               5                   10                  15

Trp

<210> SEQ ID NO 1021
<211> LENGTH: 19
<212> TYPE: PRT
<213> ORGANISM: Homo sapiens

<400> SEQUENCE: 1021

Met Asp Trp Thr Trp Arg Ile Leu Phe Leu Val Ala Ala Ala Thr Gly
1               5                   10                  15

Thr His Ala

<210> SEQ ID NO 1022
<211> LENGTH: 21
<212> TYPE: PRT
<213> ORGANISM: Homo sapiens

<400> SEQUENCE: 1022

Asp Leu Arg Val Ala Thr Val Thr Leu Met Leu Ala Ile Leu Ser Ser
1               5                   10                  15

Ser Leu Ala Glu Gly
            20

<210> SEQ ID NO 1023
<211> LENGTH: 20
<212> TYPE: PRT
<213> ORGANISM: Homo sapiens

<400> SEQUENCE: 1023

Met Leu Asn Asn Leu Leu Leu Phe Ser Leu Gln Ile Ser Leu Ile Gly
1               5                   10                  15

Thr Thr Leu Gly
            20

<210> SEQ ID NO 1024
<211> LENGTH: 24
<212> TYPE: PRT
<213> ORGANISM: Homo sapiens

<400> SEQUENCE: 1024

Met Ala Ala Gly Leu Ala Arg Leu Leu Leu Leu Leu Gly Leu Ser Ala
1               5                   10                  15

Gly Gly Pro Ala Pro Ala Gly Ala
            20

<210> SEQ ID NO 1025
<211> LENGTH: 21
<212> TYPE: PRT
<213> ORGANISM: Homo sapiens

<400> SEQUENCE: 1025

Met Arg Pro Gly Thr Ala Leu Gln Ala Val Leu Leu Ala Val Leu Leu
1               5                   10                  15

Val Gly Leu Arg Ala
```

-continued

```
<210> SEQ ID NO 1026
<211> LENGTH: 20
<212> TYPE: PRT
<213> ORGANISM: Homo sapiens

<400> SEQUENCE: 1026

Met Val Leu Gln Thr Gln Val Phe Ile Ser Leu Leu Trp Ile Ser
1               5                   10                  15

Gly Ala Ser Gly
            20

<210> SEQ ID NO 1027
<211> LENGTH: 20
<212> TYPE: PRT
<213> ORGANISM: Homo sapiens

<400> SEQUENCE: 1027

Met Arg Leu Gly Leu Leu Ser Val Ala Leu Leu Phe Val Gly Ser Ser
1               5                   10                  15

His Leu Tyr Ser
            20

<210> SEQ ID NO 1028
<211> LENGTH: 21
<212> TYPE: PRT
<213> ORGANISM: Homo sapiens

<400> SEQUENCE: 1028

Met Ser Ser Thr Leu Pro Ala Leu Leu Cys Val Gly Leu Cys Leu Ser
1               5                   10                  15

Gln Arg Ile Ser Ala
            20

<210> SEQ ID NO 1029
<211> LENGTH: 22
<212> TYPE: PRT
<213> ORGANISM: Homo sapiens

<400> SEQUENCE: 1029

Met Ala Val Ala Pro Leu Arg Gly Ala Leu Leu Leu Trp Gln Leu Leu
1               5                   10                  15

Ala Ala Gly Gly Ala Ala
            20

<210> SEQ ID NO 1030
<211> LENGTH: 21
<212> TYPE: PRT
<213> ORGANISM: Homo sapiens

<400> SEQUENCE: 1030

Met Arg Gly Pro Gly His Pro Leu Leu Leu Gly Leu Leu Leu Val Leu
1               5                   10                  15

Gly Pro Ser Pro Glu
            20

<210> SEQ ID NO 1031
<211> LENGTH: 19
<212> TYPE: PRT
<213> ORGANISM: Homo sapiens

<400> SEQUENCE: 1031
```

Met Glu Gln Ile Trp Leu Leu Leu Leu Thr Ile Arg Val Leu Pro
1               5                   10                  15

Gly Ser Ala

<210> SEQ ID NO 1032
<211> LENGTH: 22
<212> TYPE: PRT
<213> ORGANISM: Homo sapiens

<400> SEQUENCE: 1032

Met Ala Thr Val Arg Ala Ser Leu Arg Gly Ala Leu Leu Leu Leu
1               5                   10                  15

Ala Val Ala Gly Val Ala
            20

<210> SEQ ID NO 1033
<211> LENGTH: 20
<212> TYPE: PRT
<213> ORGANISM: Homo sapiens

<400> SEQUENCE: 1033

Met Pro Arg Val Ser Ala Pro Leu Val Leu Pro Ala Trp Leu Val
1               5                   10                  15

Met Val Ala Cys
            20

<210> SEQ ID NO 1034
<211> LENGTH: 20
<212> TYPE: PRT
<213> ORGANISM: Homo sapiens

<400> SEQUENCE: 1034

Met Gly Gly Arg Val Phe Leu Ala Phe Cys Val Trp Leu Thr Leu Pro
1               5                   10                  15

Gly Ala Glu Thr
            20

<210> SEQ ID NO 1035
<211> LENGTH: 19
<212> TYPE: PRT
<213> ORGANISM: Homo sapiens

<400> SEQUENCE: 1035

Met Glu Phe Gly Leu Ser Trp Val Phe Leu Val Ala Leu Leu Arg Gly
1               5                   10                  15

Val Gln Cys

<210> SEQ ID NO 1036
<211> LENGTH: 21
<212> TYPE: PRT
<213> ORGANISM: Homo sapiens

<400> SEQUENCE: 1036

Met Arg Val Gly Gly Ala Phe His Leu Leu Leu Val Cys Leu Ser Pro
1               5                   10                  15

Ala Leu Leu Ser Ala
            20

<210> SEQ ID NO 1037
<211> LENGTH: 19
<212> TYPE: PRT

-continued

<213> ORGANISM: Homo sapiens

<400> SEQUENCE: 1037

Met Ala Gln Ser Arg Val Leu Leu Leu Leu Leu Leu Pro Pro Gln
1               5                   10                  15

Leu His Leu

<210> SEQ ID NO 1038
<211> LENGTH: 20
<212> TYPE: PRT
<213> ORGANISM: Homo sapiens

<400> SEQUENCE: 1038

Met Ala Leu Arg Ala Pro Ala Leu Leu Pro Leu Leu Leu Leu Leu
1               5                   10                  15

Pro Leu Arg Ala
            20

<210> SEQ ID NO 1039
<211> LENGTH: 20
<212> TYPE: PRT
<213> ORGANISM: Homo sapiens

<400> SEQUENCE: 1039

Met Asp Pro Lys Gly Leu Leu Ser Leu Thr Phe Val Leu Phe Leu Ser
1               5                   10                  15

Leu Ala Phe Gly
            20

<210> SEQ ID NO 1040
<211> LENGTH: 18
<212> TYPE: PRT
<213> ORGANISM: Homo sapiens

<400> SEQUENCE: 1040

Met Val Trp Arg Leu Val Leu Leu Ala Leu Trp Val Trp Pro Ser Thr
1               5                   10                  15

Gln Ala

<210> SEQ ID NO 1041
<211> LENGTH: 20
<212> TYPE: PRT
<213> ORGANISM: Homo sapiens

<400> SEQUENCE: 1041

Met Asp Leu Leu Trp Met Pro Leu Leu Leu Val Ala Ala Cys Val Ser
1               5                   10                  15

Ala Val His Ser
            20

<210> SEQ ID NO 1042
<211> LENGTH: 18
<212> TYPE: PRT
<213> ORGANISM: Homo sapiens

<400> SEQUENCE: 1042

Met Trp Gly Phe Leu Val Leu Lys Ala Arg Trp Leu Val Thr Pro Val
1               5                   10                  15

Arg Thr

<210> SEQ ID NO 1043

```
<211> LENGTH: 21
<212> TYPE: PRT
<213> ORGANISM: Homo sapiens

<400> SEQUENCE: 1043

Met Glu Trp Pro Ala Arg Leu Cys Gly Leu Trp Ala Leu Leu Leu Cys
1               5                   10                  15

Ala Gly Gly Gly Gly
            20

<210> SEQ ID NO 1044
<211> LENGTH: 22
<212> TYPE: PRT
<213> ORGANISM: Homo sapiens

<400> SEQUENCE: 1044

Met His Gly Gly Gln Gly Pro Leu Leu Leu Leu Leu Leu Ala Val
1               5                   10                  15

Cys Leu Gly Ala Gln Gly
            20

<210> SEQ ID NO 1045
<211> LENGTH: 20
<212> TYPE: PRT
<213> ORGANISM: Homo sapiens

<400> SEQUENCE: 1045

Met Thr Cys Ser Pro Leu Leu Thr Leu Leu Ile His Cys Thr Gly
1               5                   10                  15

Ser Trp Ala Gln
            20

<210> SEQ ID NO 1046
<211> LENGTH: 18
<212> TYPE: PRT
<213> ORGANISM: Homo sapiens

<400> SEQUENCE: 1046

Met Val Phe Leu Lys Phe Phe Cys Met Ser Phe Phe Cys His Leu Cys
1               5                   10                  15

Gln Gly

<210> SEQ ID NO 1047
<211> LENGTH: 18
<212> TYPE: PRT
<213> ORGANISM: Homo sapiens

<400> SEQUENCE: 1047

Met Leu Met Pro Leu Cys Gly Leu Leu Trp Trp Trp Cys Cys Cys
1               5                   10                  15

Ser Gly

<210> SEQ ID NO 1048
<211> LENGTH: 20
<212> TYPE: PRT
<213> ORGANISM: Homo sapiens

<400> SEQUENCE: 1048

Met Ala Arg Leu Leu Gly Leu Cys Ala Trp Ala Arg Lys Ser Val Arg
1               5                   10                  15

Leu Ala Ser Ser
            20
```

<210> SEQ ID NO 1049
<211> LENGTH: 19
<212> TYPE: PRT
<213> ORGANISM: Homo sapiens

<400> SEQUENCE: 1049

Met Asp Trp Asn Trp Arg Ile Leu Phe Leu Val Val Ile Ala Ala Gly
1               5                   10                  15

Ala Gln Ser

<210> SEQ ID NO 1050
<211> LENGTH: 21
<212> TYPE: PRT
<213> ORGANISM: Homo sapiens

<400> SEQUENCE: 1050

Met Gln Gly Pro Leu Leu Pro Gly Leu Cys Phe Leu Leu Ser Leu
1               5                   10                  15

Phe Gly Ala Val Thr
            20

<210> SEQ ID NO 1051
<211> LENGTH: 20
<212> TYPE: PRT
<213> ORGANISM: Homo sapiens

<400> SEQUENCE: 1051

Met Glu Gly Lys Trp Leu Leu Cys Met Leu Leu Val Leu Gly Thr Ala
1               5                   10                  15

Ile Val Glu Ala
            20

<210> SEQ ID NO 1052
<211> LENGTH: 20
<212> TYPE: PRT
<213> ORGANISM: Homo sapiens

<400> SEQUENCE: 1052

Met Gly Ala Leu Ala Arg Ala Leu Leu Leu Pro Leu Leu Ala Gln Trp
1               5                   10                  15

Leu Leu Arg Ala
            20

<210> SEQ ID NO 1053
<211> LENGTH: 21
<212> TYPE: PRT
<213> ORGANISM: Homo sapiens

<400> SEQUENCE: 1053

Met Ala Gly Pro Trp Thr Phe Thr Leu Leu Cys Gly Leu Leu Ala Ala
1               5                   10                  15

Thr Leu Ile Gln Ala
            20

<210> SEQ ID NO 1054
<211> LENGTH: 21
<212> TYPE: PRT
<213> ORGANISM: Homo sapiens

<400> SEQUENCE: 1054

Met Gly Phe Cys Leu Ala Leu Ala Trp Thr Leu Leu Val Gly Ala Trp

-continued

```
1               5                   10                  15

Thr Pro Leu Gly Ala
            20

<210> SEQ ID NO 1055
<211> LENGTH: 20
<212> TYPE: PRT
<213> ORGANISM: Homo sapiens

<400> SEQUENCE: 1055

Met Tyr Arg Arg Lys Ser Gly Trp Thr Gly Cys Ala Ile Thr Cys Ser
1               5                   10                  15

Pro Cys Thr Ala
            20

<210> SEQ ID NO 1056
<211> LENGTH: 21
<212> TYPE: PRT
<213> ORGANISM: Homo sapiens

<400> SEQUENCE: 1056

Met Pro Phe Ser Val Ser Trp Gly Val Leu Leu Leu Ala Gly Leu Cys
1               5                   10                  15

Cys Leu Val Pro Ser
            20

<210> SEQ ID NO 1057
<211> LENGTH: 21
<212> TYPE: PRT
<213> ORGANISM: Homo sapiens

<400> SEQUENCE: 1057

Met Ala Leu Leu Pro Val Leu Phe Leu Val Thr Val Leu Leu Pro Ser
1               5                   10                  15

Leu Pro Ala Glu Gly
            20

<210> SEQ ID NO 1058
<211> LENGTH: 19
<212> TYPE: PRT
<213> ORGANISM: Homo sapiens

<400> SEQUENCE: 1058

Met Phe Gln Gln Phe Gln Ala Ser Cys Leu Val Leu Phe Phe Leu Val
1               5                   10                  15

Gly Phe Ala

<210> SEQ ID NO 1059
<211> LENGTH: 21
<212> TYPE: PRT
<213> ORGANISM: Homo sapiens

<400> SEQUENCE: 1059

Met Ala Leu Ala Ala Leu Met Ile Ala Leu Gly Ser Leu Gly Leu His
1               5                   10                  15

Thr Trp Gln Ala Gln
            20

<210> SEQ ID NO 1060
<211> LENGTH: 24
<212> TYPE: PRT
<213> ORGANISM: Homo sapiens
```

```
<400> SEQUENCE: 1060

Met Ala Gly Ala Val Ser Leu Leu Gly Val Val Gly Leu Leu Leu Val
1               5                   10                  15

Ser Ala Leu Ser Gly Val Leu Gly
            20

<210> SEQ ID NO 1061
<211> LENGTH: 21
<212> TYPE: PRT
<213> ORGANISM: Homo sapiens

<400> SEQUENCE: 1061

Met Asp Thr Ser Arg Leu Gly Val Leu Leu Ser Leu Pro Val Leu Leu
1               5                   10                  15

Gln Leu Ala Thr Gly
            20

<210> SEQ ID NO 1062
<211> LENGTH: 21
<212> TYPE: PRT
<213> ORGANISM: Homo sapiens

<400> SEQUENCE: 1062

Met Ser Pro Ser Gly Arg Leu Cys Leu Leu Thr Ile Val Gly Leu Ile
1               5                   10                  15

Leu Pro Thr Arg Gly
            20

<210> SEQ ID NO 1063
<211> LENGTH: 21
<212> TYPE: PRT
<213> ORGANISM: Homo sapiens

<400> SEQUENCE: 1063

Met Ala Ala Ala Ala Trp Leu Gln Val Leu Pro Val Ile Leu Leu Leu
1               5                   10                  15

Leu Gly Ala His Pro
            20

<210> SEQ ID NO 1064
<211> LENGTH: 19
<212> TYPE: PRT
<213> ORGANISM: Homo sapiens

<400> SEQUENCE: 1064

Met Lys Arg Leu Pro Leu Leu Val Val Phe Ser Thr Leu Leu Asn Cys
1               5                   10                  15

Ser Tyr Thr

<210> SEQ ID NO 1065
<211> LENGTH: 22
<212> TYPE: PRT
<213> ORGANISM: Homo sapiens

<400> SEQUENCE: 1065

Met Arg Gly Val Ser Cys Leu Gln Val Leu Leu Leu Leu Val Leu Gly
1               5                   10                  15

Ala Ala Gly Thr Gln Gly
            20
```

-continued

```
<210> SEQ ID NO 1066
<211> LENGTH: 22
<212> TYPE: PRT
<213> ORGANISM: Homo sapiens

<400> SEQUENCE: 1066

Met Gly Leu Leu Ala Ser Ala Gly Leu Leu Leu Leu Val Ile Gly
1               5                   10                  15

His Pro Arg Ser Leu Gly
            20

<210> SEQ ID NO 1067
<211> LENGTH: 19
<212> TYPE: PRT
<213> ORGANISM: Homo sapiens

<400> SEQUENCE: 1067

Met Gln Arg Trp Thr Leu Trp Ala Ala Ala Phe Leu Thr Leu His Ser
1               5                   10                  15

Ala Gln Ala

<210> SEQ ID NO 1068
<211> LENGTH: 20
<212> TYPE: PRT
<213> ORGANISM: Homo sapiens

<400> SEQUENCE: 1068

Met Ala Phe Arg Thr Ile Cys Val Leu Val Gly Val Phe Ile Cys Ser
1               5                   10                  15

Ile Cys Val Lys
            20

<210> SEQ ID NO 1069
<211> LENGTH: 19
<212> TYPE: PRT
<213> ORGANISM: Homo sapiens

<400> SEQUENCE: 1069

Met Ala Phe Tyr Ser Cys Cys Trp Val Leu Leu Ala Leu Thr Trp His
1               5                   10                  15

Thr Ser Ala

<210> SEQ ID NO 1070
<211> LENGTH: 20
<212> TYPE: PRT
<213> ORGANISM: Homo sapiens

<400> SEQUENCE: 1070

Met His Leu Ile Asp Tyr Leu Leu Leu Leu Val Gly Leu Leu Ala
1               5                   10                  15

Leu Ser His Gly
            20

<210> SEQ ID NO 1071
<211> LENGTH: 23
<212> TYPE: PRT
<213> ORGANISM: Homo sapiens

<400> SEQUENCE: 1071

Met Gly Phe Pro Ala Ala Ala Leu Leu Cys Ala Leu Cys Cys Gly Leu
1               5                   10                  15

Leu Ala Pro Ala Ala Arg Ala
```

```
                    20

<210> SEQ ID NO 1072
<211> LENGTH: 21
<212> TYPE: PRT
<213> ORGANISM: Homo sapiens

<400> SEQUENCE: 1072

Met Lys Ala Trp Gly Thr Val Val Thr Leu Ala Thr Leu Met Val
1               5                   10                  15

Val Thr Val Asp Ala
            20

<210> SEQ ID NO 1073
<211> LENGTH: 19
<212> TYPE: PRT
<213> ORGANISM: Homo sapiens

<400> SEQUENCE: 1073

Met Leu Cys Leu Gly Trp Ile Phe Leu Trp Leu Val Ala Gly Glu Arg
1               5                   10                  15

Ile Lys Gly

<210> SEQ ID NO 1074
<211> LENGTH: 22
<212> TYPE: PRT
<213> ORGANISM: Homo sapiens

<400> SEQUENCE: 1074

Met Ala Gln Leu Phe Leu Pro Leu Leu Ala Ala Leu Val Leu Ala Gln
1               5                   10                  15

Ala Pro Ala Ala Leu Ala
            20

<210> SEQ ID NO 1075
<211> LENGTH: 20
<212> TYPE: PRT
<213> ORGANISM: Homo sapiens

<400> SEQUENCE: 1075

Met Leu Leu Cys Thr Ala Arg Leu Val Gly Leu Gln Leu Leu Ile Ser
1               5                   10                  15

Cys Cys Trp Ala
            20

<210> SEQ ID NO 1076
<211> LENGTH: 23
<212> TYPE: PRT
<213> ORGANISM: Homo sapiens

<400> SEQUENCE: 1076

Met Gly Ala Ala Ala Arg Leu Ser Ala Pro Arg Ala Leu Val Leu Trp
1               5                   10                  15

Ala Ala Leu Gly Ala Ala Ala
            20

<210> SEQ ID NO 1077
<211> LENGTH: 20
<212> TYPE: PRT
<213> ORGANISM: Homo sapiens

<400> SEQUENCE: 1077
```

```
Met Ala Cys Arg Cys Leu Ser Phe Leu Leu Met Gly Thr Phe Leu Ser
1               5                   10                  15

Val Ser Gln Thr
            20
```

<210> SEQ ID NO 1078
<211> LENGTH: 19
<212> TYPE: PRT
<213> ORGANISM: Homo sapiens

<400> SEQUENCE: 1078

```
Met Asn Leu Val Ile Cys Val Leu Leu Ser Ile Trp Lys Asn Asn
1               5                   10                  15

Cys Met Thr
```

<210> SEQ ID NO 1079
<211> LENGTH: 19
<212> TYPE: PRT
<213> ORGANISM: Homo sapiens

<400> SEQUENCE: 1079

```
Met Met Leu Gln His Leu Val Ile Phe Cys Leu Gly Leu Val Val Gln
1               5                   10                  15

Asn Phe Cys
```

<210> SEQ ID NO 1080
<211> LENGTH: 21
<212> TYPE: PRT
<213> ORGANISM: Homo sapiens

<400> SEQUENCE: 1080

```
Met Ala Pro Arg Thr Leu Trp Ser Cys Tyr Leu Cys Cys Leu Leu Thr
1               5                   10                  15

Ala Ala Ala Gly Ala
            20
```

<210> SEQ ID NO 1081
<211> LENGTH: 23
<212> TYPE: PRT
<213> ORGANISM: Homo sapiens

<400> SEQUENCE: 1081

```
Met Ala Pro Pro Gln Val Leu Ala Phe Gly Leu Leu Leu Ala Ala Ala
1               5                   10                  15

Thr Ala Thr Phe Ala Ala Ala
            20
```

<210> SEQ ID NO 1082
<211> LENGTH: 21
<212> TYPE: PRT
<213> ORGANISM: Homo sapiens

<400> SEQUENCE: 1082

```
Met Ser Pro His Pro Thr Ala Leu Leu Gly Leu Val Leu Cys Leu Ala
1               5                   10                  15

Gln Thr Ile His Thr
            20
```

<210> SEQ ID NO 1083
<211> LENGTH: 21
<212> TYPE: PRT
<213> ORGANISM: Homo sapiens

```
<400> SEQUENCE: 1083

Met Gln Leu Leu Gly Leu Leu Ser Ile Leu Trp Met Leu Lys Ser Ser
1               5                   10                  15

Pro Gly Ala Thr Gly
            20

<210> SEQ ID NO 1084
<211> LENGTH: 21
<212> TYPE: PRT
<213> ORGANISM: Homo sapiens

<400> SEQUENCE: 1084

Met Gly Trp Arg Ala Ala Gly Ala Leu Leu Ala Leu Leu Leu His
1               5                   10                  15

Gly Arg Leu Leu Ala
            20

<210> SEQ ID NO 1085
<211> LENGTH: 21
<212> TYPE: PRT
<213> ORGANISM: Homo sapiens

<400> SEQUENCE: 1085

Met Gly Trp Arg Ala Ala Gly Ala Leu Leu Ala Leu Leu Leu His
1               5                   10                  15

Gly Arg Leu Leu Ala
            20

<210> SEQ ID NO 1086
<211> LENGTH: 22
<212> TYPE: PRT
<213> ORGANISM: Homo sapiens

<400> SEQUENCE: 1086

Met Gly Pro Gly Arg Cys Leu Leu Thr Ala Leu Leu Leu Leu Ala Leu
1               5                   10                  15

Ala Pro Pro Pro Glu Ala
            20

<210> SEQ ID NO 1087
<211> LENGTH: 20
<212> TYPE: PRT
<213> ORGANISM: Homo sapiens

<400> SEQUENCE: 1087

Met Ala Pro His Trp Ala Val Trp Leu Leu Ala Ala Arg Leu Trp Gly
1               5                   10                  15

Leu Gly Ile Gly
            20

<210> SEQ ID NO 1088
<211> LENGTH: 22
<212> TYPE: PRT
<213> ORGANISM: Homo sapiens

<400> SEQUENCE: 1088

Met Phe Arg Thr Ala Val Met Met Ala Ala Ser Leu Ala Leu Thr Gly
1               5                   10                  15

Ala Val Val Ala His Ala
            20
```

<210> SEQ ID NO 1089
<211> LENGTH: 21
<212> TYPE: PRT
<213> ORGANISM: Homo sapiens

<400> SEQUENCE: 1089

Met Thr Pro Ile Val Thr Val Leu Ile Cys Leu Gly Leu Ser Leu Gly
1               5                   10                  15

Pro Arg Thr His Val
            20

<210> SEQ ID NO 1090
<211> LENGTH: 21
<212> TYPE: PRT
<213> ORGANISM: Homo sapiens

<400> SEQUENCE: 1090

Met Ala Pro Gln Thr Leu Leu Pro Val Leu Val Leu Cys Val Leu Leu
1               5                   10                  15

Leu Gln Ala Gln Gly
            20

<210> SEQ ID NO 1091
<211> LENGTH: 20
<212> TYPE: PRT
<213> ORGANISM: Homo sapiens

<400> SEQUENCE: 1091

Met Arg Val Pro Ala Gln Leu Leu Gly Leu Leu Leu Leu Trp Leu Pro
1               5                   10                  15

Gly Ala Arg Cys
            20

<210> SEQ ID NO 1092
<211> LENGTH: 21
<212> TYPE: PRT
<213> ORGANISM: Homo sapiens

<400> SEQUENCE: 1092

Met Lys Ala Leu Ile Phe Ala Ala Ala Gly Leu Leu Leu Leu Leu Pro
1               5                   10                  15

Thr Phe Cys Gln Ser
            20

<210> SEQ ID NO 1093
<211> LENGTH: 24
<212> TYPE: PRT
<213> ORGANISM: Homo sapiens

<400> SEQUENCE: 1093

Met Gly Arg Ala Gly Ala Ala Ala Val Ile Pro Gly Leu Ala Leu Leu
1               5                   10                  15

Trp Ala Val Gly Leu Gly Ser Ala
            20

<210> SEQ ID NO 1094
<211> LENGTH: 20
<212> TYPE: PRT
<213> ORGANISM: Homo sapiens

<400> SEQUENCE: 1094

Met Leu Arg Leu Leu Arg Pro Leu Leu Leu Leu Leu Leu Leu Pro Pro

```
1               5                   10                  15
Pro Gly Ser Pro
            20
```

<210> SEQ ID NO 1095
<211> LENGTH: 19
<212> TYPE: PRT
<213> ORGANISM: Homo sapiens

<400> SEQUENCE: 1095

```
Met Ala Ser Val Phe His Tyr Phe Leu Leu Val Leu Val Phe Leu Asp
1               5                   10                  15

Thr His Ala
```

<210> SEQ ID NO 1096
<211> LENGTH: 19
<212> TYPE: PRT
<213> ORGANISM: Homo sapiens

<400> SEQUENCE: 1096

```
Met His Phe Gln Ala Phe Trp Leu Cys Leu Gly Leu Leu Phe Ile Ser
1               5                   10                  15

Ile Asn Ala
```

<210> SEQ ID NO 1097
<211> LENGTH: 22
<212> TYPE: PRT
<213> ORGANISM: Homo sapiens

<400> SEQUENCE: 1097

```
Met Gly Leu Gly Arg Val Leu Leu Phe Leu Ala Val Ala Phe Pro Phe
1               5                   10                  15

Ala Pro Pro Ala Ala Ala
            20
```

<210> SEQ ID NO 1098
<211> LENGTH: 19
<212> TYPE: PRT
<213> ORGANISM: Homo sapiens

<400> SEQUENCE: 1098

```
Met Arg Leu Ile Arg Asn Ile Tyr Ile Phe Cys Ser Ile Val Met Thr
1               5                   10                  15

Ala Glu Gly
```

<210> SEQ ID NO 1099
<211> LENGTH: 21
<212> TYPE: PRT
<213> ORGANISM: Homo sapiens

<400> SEQUENCE: 1099

```
Met Thr Leu Gly Ser Pro Arg Lys Gly Leu Leu Met Leu Leu Met Ala
1               5                   10                  15

Leu Val Thr Gln Gly
            20
```

<210> SEQ ID NO 1100
<211> LENGTH: 23
<212> TYPE: PRT
<213> ORGANISM: Homo sapiens

<400> SEQUENCE: 1100

```
Met Ala Gly Ala Pro Gly Pro Leu Arg Leu Ala Leu Leu Leu Gly
1               5                   10                  15

Met Val Gly Arg Ala Gly Pro
                20

<210> SEQ ID NO 1101
<211> LENGTH: 20
<212> TYPE: PRT
<213> ORGANISM: Homo sapiens

<400> SEQUENCE: 1101

Met Gly Pro Ala Pro Leu Pro Leu Leu Gly Leu Phe Leu Pro Ala
1               5                   10                  15

Leu Trp Arg Arg
            20

<210> SEQ ID NO 1102
<211> LENGTH: 21
<212> TYPE: PRT
<213> ORGANISM: Homo sapiens

<400> SEQUENCE: 1102

Met Ser Pro His Leu Thr Ala Leu Leu Gly Leu Val Leu Cys Leu Ala
1               5                   10                  15

Gln Thr Ile His Thr
                20

<210> SEQ ID NO 1103
<211> LENGTH: 21
<212> TYPE: PRT
<213> ORGANISM: Homo sapiens

<400> SEQUENCE: 1103

Met Ala Gln Ala Leu Pro Trp Leu Leu Leu Trp Met Gly Ala Gly Val
1               5                   10                  15

Leu Pro Ala His Gly
                20

<210> SEQ ID NO 1104
<211> LENGTH: 20
<212> TYPE: PRT
<213> ORGANISM: Homo sapiens

<400> SEQUENCE: 1104

Met Gly Lys Pro Trp Leu Arg Ala Leu Gln Leu Leu Leu Leu Leu Gly
1               5                   10                  15

Ala Ser Trp Ala
            20

<210> SEQ ID NO 1105
<211> LENGTH: 23
<212> TYPE: PRT
<213> ORGANISM: Homo sapiens

<400> SEQUENCE: 1105

Met Val Ala Gly Thr Arg Cys Leu Leu Ala Leu Leu Leu Pro Gln Val
1               5                   10                  15

Leu Leu Gly Gly Ala Ala Gly
                20

<210> SEQ ID NO 1106
```

-continued

```
<211> LENGTH: 20
<212> TYPE: PRT
<213> ORGANISM: Homo sapiens

<400> SEQUENCE: 1106

Met Asn Ile Leu Met Leu Thr Phe Ile Ile Cys Gly Leu Leu Thr Arg
1               5                   10                  15

Val Thr Lys Gly
            20

<210> SEQ ID NO 1107
<211> LENGTH: 20
<212> TYPE: PRT
<213> ORGANISM: Homo sapiens

<400> SEQUENCE: 1107

Met Arg Arg Leu Leu Leu Val Thr Ser Leu Val Val Leu Leu Trp
1               5                   10                  15

Glu Ala Gly Ala
            20

<210> SEQ ID NO 1108
<211> LENGTH: 22
<212> TYPE: PRT
<213> ORGANISM: Homo sapiens

<400> SEQUENCE: 1108

Met Ala Pro Ser Ala Trp Ala Ile Cys Trp Leu Leu Gly Gly Leu Leu
1               5                   10                  15

Leu His Gly Gly Ser Ser
            20

<210> SEQ ID NO 1109
<211> LENGTH: 25
<212> TYPE: PRT
<213> ORGANISM: Homo sapiens

<400> SEQUENCE: 1109

Met Val Thr Arg Ala Gly Ala Gly Thr Ala Val Ala Gly Ala Val Val
1               5                   10                  15

Val Ala Leu Leu Ser Ala Ala Leu Ala
            20                  25

<210> SEQ ID NO 1110
<211> LENGTH: 20
<212> TYPE: PRT
<213> ORGANISM: Homo sapiens

<400> SEQUENCE: 1110

Met Thr Ala Arg Ala Trp Ala Ser Trp Arg Ser Ser Ala Leu Leu Leu
1               5                   10                  15

Leu Leu Val Pro
            20

<210> SEQ ID NO 1111
<211> LENGTH: 21
<212> TYPE: PRT
<213> ORGANISM: Homo sapiens

<400> SEQUENCE: 1111

Met Ala Ala His Leu Leu Pro Ile Cys Ala Leu Phe Leu Thr Leu Leu
1               5                   10                  15
```

-continued

Asp Met Ala Gln Gly
              20

<210> SEQ ID NO 1112
<211> LENGTH: 23
<212> TYPE: PRT
<213> ORGANISM: Homo sapiens

<400> SEQUENCE: 1112

Met Pro Pro Ala Ala Pro Ala Arg Leu Ala Leu Ala Leu Gly Leu Gly
1               5                   10                  15

Leu Trp Leu Gly Ala Leu Ala
            20

<210> SEQ ID NO 1113
<211> LENGTH: 21
<212> TYPE: PRT
<213> ORGANISM: Homo sapiens

<400> SEQUENCE: 1113

Met Ala Leu His Ile His Glu Ala Cys Ile Leu Leu Val Ile Pro
1               5                   10                  15

Gly Leu Val Thr Ser
            20

<210> SEQ ID NO 1114
<211> LENGTH: 22
<212> TYPE: PRT
<213> ORGANISM: Homo sapiens

<400> SEQUENCE: 1114

Met Gln Ala Pro Arg Ala Ala Leu Val Phe Ala Leu Val Ile Ala Leu
1               5                   10                  15

Val Pro Val Gly Arg Gly
            20

<210> SEQ ID NO 1115
<211> LENGTH: 21
<212> TYPE: PRT
<213> ORGANISM: Homo sapiens

<400> SEQUENCE: 1115

Met Asn Leu Cys Leu Ser Ala Leu Leu Phe Phe Leu Val Ile Leu Leu
1               5                   10                  15

Pro Ser Gly Lys Gly
            20

<210> SEQ ID NO 1116
<211> LENGTH: 21
<212> TYPE: PRT
<213> ORGANISM: Homo sapiens

<400> SEQUENCE: 1116

Met Pro Ala Leu Trp Leu Gly Cys Cys Leu Cys Phe Ser Leu Leu Leu
1               5                   10                  15

Pro Ala Ala Arg Ala
            20

<210> SEQ ID NO 1117
<211> LENGTH: 22
<212> TYPE: PRT
<213> ORGANISM: Homo sapiens -continued

```
<400> SEQUENCE: 1117

Met Lys Pro Gly Gly Phe Trp Leu His Leu Thr Leu Leu Gly Ala Ser
1               5                   10                  15

Leu Pro Ala Ala Leu Gly
            20

<210> SEQ ID NO 1118
<211> LENGTH: 23
<212> TYPE: PRT
<213> ORGANISM: Homo sapiens

<400> SEQUENCE: 1118

Met Ala Ala Met Ala Ser Leu Gly Ala Leu Ala Leu Leu Leu Leu Ser
1               5                   10                  15

Ser Leu Ser Arg Cys Ser Ala
            20

<210> SEQ ID NO 1119
<211> LENGTH: 21
<212> TYPE: PRT
<213> ORGANISM: Homo sapiens

<400> SEQUENCE: 1119

Met Leu Ser Gly Val Trp Phe Leu Ser Val Leu Thr Val Ala Gly Ile
1               5                   10                  15

Leu Gln Thr Glu Ser
            20

<210> SEQ ID NO 1120
<211> LENGTH: 21
<212> TYPE: PRT
<213> ORGANISM: Homo sapiens

<400> SEQUENCE: 1120

Met Gly Leu Arg Pro Gly Ile Phe Leu Leu Glu Leu Leu Leu Leu
1               5                   10                  15

Gly Gln Gly Thr Pro
            20

<210> SEQ ID NO 1121
<211> LENGTH: 19
<212> TYPE: PRT
<213> ORGANISM: Homo sapiens

<400> SEQUENCE: 1121

Met Leu Ala Pro Leu Phe Leu Cys Cys Leu Arg Asn Leu Phe Arg Lys
1               5                   10                  15

Leu Ile Ser

<210> SEQ ID NO 1122
<211> LENGTH: 22
<212> TYPE: PRT
<213> ORGANISM: Homo sapiens

<400> SEQUENCE: 1122

Met Gln Ile Pro Arg Ala Ala Leu Leu Pro Leu Leu Leu Leu Leu
1               5                   10                  15

Ala Ala Pro Ala Ser Ala
            20

<210> SEQ ID NO 1123
```

```
<211> LENGTH: 19
<212> TYPE: PRT
<213> ORGANISM: Homo sapiens

<400> SEQUENCE: 1123

Met Arg Leu Leu Cys Gly Leu Trp Leu Trp Leu Ser Leu Leu Lys Val
1               5                   10                  15

Leu Gln Ala

<210> SEQ ID NO 1124
<211> LENGTH: 21
<212> TYPE: PRT
<213> ORGANISM: Homo sapiens

<400> SEQUENCE: 1124

Met Ser Leu Thr Val Val Ser Met Ala Cys Val Gly Phe Phe Leu Leu
1               5                   10                  15

Gln Gly Ala Trp Pro
            20

<210> SEQ ID NO 1125
<211> LENGTH: 19
<212> TYPE: PRT
<213> ORGANISM: Homo sapiens

<400> SEQUENCE: 1125

Met Lys Leu Leu Phe Pro Ile Phe Ala Ser Leu Met Leu Gln Tyr Gln
1               5                   10                  15

Val Asn Thr

<210> SEQ ID NO 1126
<211> LENGTH: 23
<212> TYPE: PRT
<213> ORGANISM: Homo sapiens

<400> SEQUENCE: 1126

Met Val Pro Ser Ala Gly Gln Leu Ala Leu Phe Ala Leu Gly Ile Val
1               5                   10                  15

Leu Ala Ala Cys Gln Ala Leu
            20

<210> SEQ ID NO 1127
<211> LENGTH: 22
<212> TYPE: PRT
<213> ORGANISM: Homo sapiens

<400> SEQUENCE: 1127

Met Leu Arg Leu Gly Leu Cys Ala Ala Ala Leu Leu Cys Val Cys Arg
1               5                   10                  15

Pro Gly Ala Val Arg Ala
            20

<210> SEQ ID NO 1128
<211> LENGTH: 20
<212> TYPE: PRT
<213> ORGANISM: Homo sapiens

<400> SEQUENCE: 1128

Met Val Phe Ser Leu Lys Val Ile Leu Phe Leu Ser Leu Leu Leu Ser
1               5                   10                  15

Pro Val Leu Lys
            20
```

<210> SEQ ID NO 1129
<211> LENGTH: 20
<212> TYPE: PRT
<213> ORGANISM: Homo sapiens

<400> SEQUENCE: 1129

Met Leu Met Leu Met Leu Val Ala Ala Val Thr Met Trp Leu Arg Pro
1               5                   10                  15

Leu Val Thr Ala
            20

<210> SEQ ID NO 1130
<211> LENGTH: 22
<212> TYPE: PRT
<213> ORGANISM: Homo sapiens

<400> SEQUENCE: 1130

Met Thr Ser Gln Arg Ser Pro Leu Ala Pro Leu Leu Leu Ser Leu
1               5                   10                  15

His Gly Val Ala Ala Ser
            20

<210> SEQ ID NO 1131
<211> LENGTH: 22
<212> TYPE: PRT
<213> ORGANISM: Homo sapiens

<400> SEQUENCE: 1131

Met Ala Ala Arg Gly Ser Gly Pro Arg Ala Leu Arg Leu Leu Leu Leu
1               5                   10                  15

Val Gln Leu Val Ala Gly
            20

<210> SEQ ID NO 1132
<211> LENGTH: 22
<212> TYPE: PRT
<213> ORGANISM: Homo sapiens

<400> SEQUENCE: 1132

Met Leu Gly Ala Arg Ala Trp Leu Gly Arg Val Leu Leu Leu Pro Arg
1               5                   10                  15

Ala Gly Ala Gly Leu Ala
            20

<210> SEQ ID NO 1133
<211> LENGTH: 21
<212> TYPE: PRT
<213> ORGANISM: Homo sapiens

<400> SEQUENCE: 1133

Met Arg Leu Leu Ile Leu Ala Leu Leu Gly Ile Cys Ser Leu Thr Ala
1               5                   10                  15

Tyr Ile Val Glu Gly
            20

<210> SEQ ID NO 1134
<211> LENGTH: 23
<212> TYPE: PRT
<213> ORGANISM: Homo sapiens

<400> SEQUENCE: 1134

Met Arg Leu Leu Ala Leu Ala Ala Ala Leu Leu Ala Arg Ala Pro
1               5                   10                  15

Ala Pro Glu Val Cys Ala Ala
            20

<210> SEQ ID NO 1135
<211> LENGTH: 19
<212> TYPE: PRT
<213> ORGANISM: Homo sapiens

<400> SEQUENCE: 1135

Met Asn Ile Ile Leu Glu Ile Leu Leu Leu Ile Thr Ile Ile Tyr
1               5                   10                  15

Ser Tyr Leu

<210> SEQ ID NO 1136
<211> LENGTH: 22
<212> TYPE: PRT
<213> ORGANISM: Homo sapiens

<400> SEQUENCE: 1136

Met Ala Ala Ala Pro Leu Leu Leu Leu Leu Leu Val Pro Val Pro
1               5                   10                  15

Leu Leu Pro Leu Leu Ala
            20

<210> SEQ ID NO 1137
<211> LENGTH: 22
<212> TYPE: PRT
<213> ORGANISM: Homo sapiens

<400> SEQUENCE: 1137

Met Leu Ser His Gly Ala Gly Leu Ala Leu Trp Ile Thr Leu Ser Leu
1               5                   10                  15

Leu Gln Thr Gly Leu Ala
            20

<210> SEQ ID NO 1138
<211> LENGTH: 22
<212> TYPE: PRT
<213> ORGANISM: Homo sapiens

<400> SEQUENCE: 1138

Met Glu Leu Ala Ala Leu Cys Arg Trp Gly Leu Leu Leu Ala Leu Leu
1               5                   10                  15

Pro Pro Gly Ala Ala Ser
            20

<210> SEQ ID NO 1139
<211> LENGTH: 22
<212> TYPE: PRT
<213> ORGANISM: Homo sapiens

<400> SEQUENCE: 1139

Met Pro Leu Ser Ser His Leu Leu Pro Ala Leu Val Leu Phe Leu Ala
1               5                   10                  15

Gly Ser Ser Gly Trp Ala
            20

<210> SEQ ID NO 1140
<211> LENGTH: 22
<212> TYPE: PRT

```
<213> ORGANISM: Homo sapiens

<400> SEQUENCE: 1140

Met Ala Leu Ala Ala Leu Met Ile Ala Leu Gly Ser Leu Gly Leu His
1               5                   10                  15

Thr Trp Gln Ala Gln Ala
            20

<210> SEQ ID NO 1141
<211> LENGTH: 20
<212> TYPE: PRT
<213> ORGANISM: Homo sapiens

<400> SEQUENCE: 1141

Met Pro Arg Gly Phe Thr Trp Leu Arg Tyr Leu Gly Ile Phe Leu Gly
1               5                   10                  15

Val Ala Leu Gly
            20

<210> SEQ ID NO 1142
<211> LENGTH: 23
<212> TYPE: PRT
<213> ORGANISM: Homo sapiens

<400> SEQUENCE: 1142

Met Ser Leu Ala Ser Gly Pro Gly Pro Gly Trp Leu Leu Phe Ser Phe
1               5                   10                  15

Gly Met Gly Leu Val Ser Gly
            20

<210> SEQ ID NO 1143
<211> LENGTH: 20
<212> TYPE: PRT
<213> ORGANISM: Homo sapiens

<400> SEQUENCE: 1143

Met Lys Met His Leu Gln Arg Ala Leu Val Val Leu Ala Leu Leu Asn
1               5                   10                  15

Phe Ala Thr Val
            20

<210> SEQ ID NO 1144
<211> LENGTH: 18
<212> TYPE: PRT
<213> ORGANISM: Homo sapiens

<400> SEQUENCE: 1144

Met Arg Ile Phe Ala Val Phe Ile Phe Met Thr Tyr Trp His Leu Leu
1               5                   10                  15

Asn Ala

<210> SEQ ID NO 1145
<211> LENGTH: 21
<212> TYPE: PRT
<213> ORGANISM: Homo sapiens

<400> SEQUENCE: 1145

Met His Val His Val Cys Val Cys Leu Cys Val Cys Ile Tyr Thr Ser
1               5                   10                  15

Ser Cys Val Cys Ala
            20
```

<210> SEQ ID NO 1146
<211> LENGTH: 21
<212> TYPE: PRT
<213> ORGANISM: Homo sapiens

<400> SEQUENCE: 1146

Met Leu Val Asn Phe Ile Leu Arg Cys Gly Leu Leu Val Thr Leu
1               5                   10                  15

Ser Leu Ala Ile Ala
            20

<210> SEQ ID NO 1147
<211> LENGTH: 23
<212> TYPE: PRT
<213> ORGANISM: Homo sapiens

<400> SEQUENCE: 1147

Met Val Pro Ala Ala Gly Ala Leu Leu Trp Val Leu Leu Asn Leu
1               5                   10                  15

Gly Pro Arg Ala Ala Gly Ala
            20

<210> SEQ ID NO 1148
<211> LENGTH: 21
<212> TYPE: PRT
<213> ORGANISM: Homo sapiens

<400> SEQUENCE: 1148

Met Lys Leu Val Thr Ile Phe Leu Leu Val Thr Ile Ser Leu Cys Ser
1               5                   10                  15

Tyr Ser Ala Thr Ala
            20

<210> SEQ ID NO 1149
<211> LENGTH: 22
<212> TYPE: PRT
<213> ORGANISM: Homo sapiens

<400> SEQUENCE: 1149

Met Arg Leu Ser Leu Pro Leu Leu Leu Leu Leu Gly Ala Trp Ala
1               5                   10                  15

Ile Pro Gly Gly Leu Gly
            20

<210> SEQ ID NO 1150
<211> LENGTH: 20
<212> TYPE: PRT
<213> ORGANISM: Homo sapiens

<400> SEQUENCE: 1150

Met Ala Leu Met Phe Thr Gly His Leu Leu Phe Leu Ala Leu Leu Met
1               5                   10                  15

Phe Ala Phe Ser
            20

<210> SEQ ID NO 1151
<211> LENGTH: 20
<212> TYPE: PRT
<213> ORGANISM: Homo sapiens

<400> SEQUENCE: 1151

Met Arg Thr Leu Trp Met Ala Leu Cys Ala Leu Ser Arg Leu Trp Pro

```
                1               5                   10                  15

Gly Ala Gln Ala
            20

<210> SEQ ID NO 1152
<211> LENGTH: 22
<212> TYPE: PRT
<213> ORGANISM: Homo sapiens

<400> SEQUENCE: 1152

Met Lys Ala Leu Arg Leu Ser Ala Ser Ala Leu Phe Cys Leu Leu Leu
1               5                   10                  15

Ile Asn Gly Leu Gly Ala
            20

<210> SEQ ID NO 1153
<211> LENGTH: 23
<212> TYPE: PRT
<213> ORGANISM: Homo sapiens

<400> SEQUENCE: 1153

Met Glu Gly Ala Pro Pro Gly Ser Leu Ala Leu Arg Leu Leu Leu Phe
1               5                   10                  15

Val Ala Leu Pro Ala Ser Gly
            20

<210> SEQ ID NO 1154
<211> LENGTH: 21
<212> TYPE: PRT
<213> ORGANISM: Homo sapiens

<400> SEQUENCE: 1154

Met Ser Ser Phe Gly Tyr Arg Thr Leu Thr Val Ala Leu Phe Thr Leu
1               5                   10                  15

Ile Cys Cys Pro Gly
            20

<210> SEQ ID NO 1155
<211> LENGTH: 20
<212> TYPE: PRT
<213> ORGANISM: Homo sapiens

<400> SEQUENCE: 1155

Met Pro Pro Phe Leu Ile Thr Leu Phe Leu Phe His Ser Cys Cys Leu
1               5                   10                  15

Arg Ala Asn Gly
            20

<210> SEQ ID NO 1156
<211> LENGTH: 22
<212> TYPE: PRT
<213> ORGANISM: Homo sapiens

<400> SEQUENCE: 1156

Met Val Thr Ser Ser Phe Pro Ile Ser Val Ala Val Phe Ala Leu Ile
1               5                   10                  15

Thr Leu Gln Val Gly Thr
            20

<210> SEQ ID NO 1157
<211> LENGTH: 21
<212> TYPE: PRT
```

<213> ORGANISM: Homo sapiens

<400> SEQUENCE: 1157

Met Asp His Cys Gly Ala Leu Phe Leu Cys Leu Cys Leu Leu Thr Leu
1               5                   10                  15
Gln Asn Ala Thr Thr
            20

<210> SEQ ID NO 1158
<211> LENGTH: 22
<212> TYPE: PRT
<213> ORGANISM: Homo sapiens

<400> SEQUENCE: 1158

Met Leu Pro Trp Thr Ala Leu Gly Leu Ala Leu Ser Leu Arg Leu Ala
1               5                   10                  15
Leu Ala Arg Ser Gly Ala
            20

<210> SEQ ID NO 1159
<211> LENGTH: 22
<212> TYPE: PRT
<213> ORGANISM: Homo sapiens

<400> SEQUENCE: 1159

Met Lys Val Leu Pro Ala Ser Gly Leu Ala Val Phe Leu Ile Met Ala
1               5                   10                  15
Leu Thr Phe Ser Thr Ala
            20

<210> SEQ ID NO 1160
<211> LENGTH: 21
<212> TYPE: PRT
<213> ORGANISM: Homo sapiens

<400> SEQUENCE: 1160

Met Arg Ala Leu Leu Ala Leu Cys Leu Leu Gly Trp Leu Arg Trp
1               5                   10                  15
Gly Pro Ala Gly Ala
            20

<210> SEQ ID NO 1161
<211> LENGTH: 23
<212> TYPE: PRT
<213> ORGANISM: Homo sapiens

<400> SEQUENCE: 1161

Met Met Ala Ala Gly Ala Ala Leu Ala Leu Trp Leu Leu Met
1               5                   10                  15
Pro Pro Val Glu Val Gly Gly
            20

<210> SEQ ID NO 1162
<211> LENGTH: 23
<212> TYPE: PRT
<213> ORGANISM: Homo sapiens

<400> SEQUENCE: 1162

Met Ser Ala Leu Arg Pro Leu Leu Leu Leu Leu Pro Leu Cys Pro
1               5                   10                  15
Gly Pro Gly Pro Gly Pro Gly
            20

-continued

<210> SEQ ID NO 1163
<211> LENGTH: 22
<212> TYPE: PRT
<213> ORGANISM: Homo sapiens

<400> SEQUENCE: 1163

Met Ala Leu Leu Thr Asn Leu Pro Leu Cys Cys Leu Ala Leu Leu
1               5                   10                  15

Ala Leu Pro Ala Gln Ser
            20

<210> SEQ ID NO 1164
<211> LENGTH: 19
<212> TYPE: PRT
<213> ORGANISM: Homo sapiens

<400> SEQUENCE: 1164

Met Gln Phe Gln Leu Thr Leu Phe Leu His Leu Gly Trp Leu Ser Tyr
1               5                   10                  15

Ser Lys Ala

<210> SEQ ID NO 1165
<211> LENGTH: 21
<212> TYPE: PRT
<213> ORGANISM: Homo sapiens

<400> SEQUENCE: 1165

Met Val Gly Thr Lys Ala Trp Val Phe Ser Phe Leu Val Leu Glu Val
1               5                   10                  15

Thr Ser Val Leu Gly
            20

<210> SEQ ID NO 1166
<211> LENGTH: 21
<212> TYPE: PRT
<213> ORGANISM: Homo sapiens

<400> SEQUENCE: 1166

Met Arg Met Cys Thr Pro Ile Arg Gly Leu Leu Met Ala Leu Ala Val
1               5                   10                  15

Met Phe Gly Thr Ala
            20

<210> SEQ ID NO 1167
<211> LENGTH: 20
<212> TYPE: PRT
<213> ORGANISM: Homo sapiens

<400> SEQUENCE: 1167

Met Gly Arg Ala Arg Arg Phe Gln Trp Pro Leu Leu Leu Leu Trp Ala
1               5                   10                  15

Ala Ala Ala Gly
            20

<210> SEQ ID NO 1168
<211> LENGTH: 21
<212> TYPE: PRT
<213> ORGANISM: Homo sapiens

<400> SEQUENCE: 1168

Met Thr Asn Lys Cys Leu Leu Gln Ile Ala Leu Leu Leu Cys Phe Ser

```
1               5                  10                 15

Thr Thr Ala Leu Ser
            20

<210> SEQ ID NO 1169
<211> LENGTH: 23
<212> TYPE: PRT
<213> ORGANISM: Homo sapiens

<400> SEQUENCE: 1169

Met Ser Leu Leu Leu Pro Pro Leu Ala Leu Leu Leu Leu Ala Ala
1               5                  10                 15

Leu Val Ala Pro Ala Thr Ala
            20

<210> SEQ ID NO 1170
<211> LENGTH: 22
<212> TYPE: PRT
<213> ORGANISM: Homo sapiens

<400> SEQUENCE: 1170

Met Lys Tyr Ser Cys Cys Ala Leu Val Leu Ala Val Leu Gly Thr Glu
1               5                  10                 15

Leu Leu Gly Ser Leu Cys
            20

<210> SEQ ID NO 1171
<211> LENGTH: 22
<212> TYPE: PRT
<213> ORGANISM: Homo sapiens

<400> SEQUENCE: 1171

Met Ile Ile Ser His Phe Pro Lys Cys Val Ala Val Phe Ala Leu Leu
1               5                  10                 15

Ala Leu Ser Val Gly Ala
            20

<210> SEQ ID NO 1172
<211> LENGTH: 21
<212> TYPE: PRT
<213> ORGANISM: Homo sapiens

<400> SEQUENCE: 1172

Met Ser Leu Met Val Val Ser Met Ala Cys Val Gly Phe Phe Leu Leu
1               5                  10                 15

Gln Gly Ala Trp Pro
            20

<210> SEQ ID NO 1173
<211> LENGTH: 21
<212> TYPE: PRT
<213> ORGANISM: Homo sapiens

<400> SEQUENCE: 1173

Met Ser Leu Met Val Val Ser Met Ala Cys Val Gly Phe Phe Leu Leu
1               5                  10                 15

Gln Gly Ala Trp Pro
            20

<210> SEQ ID NO 1174
<211> LENGTH: 21
<212> TYPE: PRT
```

<213> ORGANISM: Homo sapiens

<400> SEQUENCE: 1174

Met Ser Leu Met Val Val Ser Met Ala Cys Val Gly Phe Phe Leu Leu
1               5                   10                  15

Gln Gly Ala Trp Pro
            20

<210> SEQ ID NO 1175
<211> LENGTH: 20
<212> TYPE: PRT
<213> ORGANISM: Homo sapiens

<400> SEQUENCE: 1175

Met Arg Arg Leu Pro Arg Ala Leu Leu Gln Leu Arg Leu Ala Leu
1               5                   10                  15

Leu Val Ala Ala
            20

<210> SEQ ID NO 1176
<211> LENGTH: 20
<212> TYPE: PRT
<213> ORGANISM: Homo sapiens

<400> SEQUENCE: 1176

Met Asp Thr Arg Asn Lys Ala Gln Leu Leu Val Leu Leu Thr Leu Leu
1               5                   10                  15

Ser Val Leu Phe
            20

<210> SEQ ID NO 1177
<211> LENGTH: 22
<212> TYPE: PRT
<213> ORGANISM: Homo sapiens

<400> SEQUENCE: 1177

Met Ala Gly Gln Arg Val Leu Leu Leu Val Gly Phe Leu Leu Pro Gly
1               5                   10                  15

Val Leu Leu Ser Glu Ala
            20

<210> SEQ ID NO 1178
<211> LENGTH: 21
<212> TYPE: PRT
<213> ORGANISM: Homo sapiens

<400> SEQUENCE: 1178

Met Val Ser Trp Gly Arg Phe Ile Cys Leu Val Val Val Thr Met Ala
1               5                   10                  15

Thr Leu Ser Leu Ala
            20

<210> SEQ ID NO 1179
<211> LENGTH: 22
<212> TYPE: PRT
<213> ORGANISM: Homo sapiens

<400> SEQUENCE: 1179

Met Ser Ser Gly Asp Pro Ala His Leu Gly Leu Cys Leu Trp Leu Trp
1               5                   10                  15

Leu Gly Ala Thr Leu Gly
            20

<210> SEQ ID NO 1180
<211> LENGTH: 22
<212> TYPE: PRT
<213> ORGANISM: Homo sapiens

<400> SEQUENCE: 1180

Met Lys Ile Pro Val Leu Pro Ala Val Val Leu Leu Ser Leu Leu Val
1               5                   10                  15

Leu His Ser Ala Gln Gly
            20

<210> SEQ ID NO 1181
<211> LENGTH: 21
<212> TYPE: PRT
<213> ORGANISM: Homo sapiens

<400> SEQUENCE: 1181

Met Phe Leu Ala Thr Leu Ser Phe Leu Leu Pro Phe Ala His Pro Phe
1               5                   10                  15

Gly Thr Val Ser Cys
            20

<210> SEQ ID NO 1182
<211> LENGTH: 21
<212> TYPE: PRT
<213> ORGANISM: Homo sapiens

<400> SEQUENCE: 1182

Met Gln Leu Leu Gly Leu Leu Gly Leu Leu Trp Met Leu Lys Ala Ser
1               5                   10                  15

Pro Trp Ala Thr Gly
            20

<210> SEQ ID NO 1183
<211> LENGTH: 20
<212> TYPE: PRT
<213> ORGANISM: Homo sapiens

<400> SEQUENCE: 1183

Met Asp Trp Pro His Asn Leu Leu Phe Leu Leu Thr Ile Ser Ile Phe
1               5                   10                  15

Leu Gly Leu Gly
            20

<210> SEQ ID NO 1184
<211> LENGTH: 22
<212> TYPE: PRT
<213> ORGANISM: Homo sapiens

<400> SEQUENCE: 1184

Met Thr Ala Arg Gly Leu Ala Leu Gly Leu Leu Leu Leu Leu Leu Cys
1               5                   10                  15

Pro Ala Gln Val Phe Ser
            20

<210> SEQ ID NO 1185
<211> LENGTH: 21
<212> TYPE: PRT
<213> ORGANISM: Homo sapiens

<400> SEQUENCE: 1185

Met Asn Cys Val Cys Arg Leu Val Leu Val Val Leu Ser Leu Trp Pro
1               5                   10                  15

Asp Thr Ala Val Ala
            20

<210> SEQ ID NO 1186
<211> LENGTH: 21
<212> TYPE: PRT
<213> ORGANISM: Homo sapiens

<400> SEQUENCE: 1186

Met Ser Arg Ser Ala Thr Leu Leu Cys Leu Leu Gly Cys His Val
1               5                   10                  15

Trp Lys Ala Val Thr
            20

<210> SEQ ID NO 1187
<211> LENGTH: 22
<212> TYPE: PRT
<213> ORGANISM: Homo sapiens

<400> SEQUENCE: 1187

Met Ala Thr Trp Ala Leu Leu Leu Leu Ala Ala Met Leu Leu Gly Asn
1               5                   10                  15

Pro Gly Leu Val Phe Ser
            20

<210> SEQ ID NO 1188
<211> LENGTH: 23
<212> TYPE: PRT
<213> ORGANISM: Homo sapiens

<400> SEQUENCE: 1188

Met Pro Ser Trp Ile Gly Ala Val Ile Leu Pro Leu Gly Leu Leu
1               5                   10                  15

Leu Ser Leu Pro Ala Gly Ala
            20

<210> SEQ ID NO 1189
<211> LENGTH: 25
<212> TYPE: PRT
<213> ORGANISM: Homo sapiens

<400> SEQUENCE: 1189

Met Ala Gly Arg Gly Gly Ser Ala Leu Leu Ala Leu Cys Gly Ala Leu
1               5                   10                  15

Ala Ala Cys Gly Trp Leu Leu Gly Ala
            20                  25

<210> SEQ ID NO 1190
<211> LENGTH: 20
<212> TYPE: PRT
<213> ORGANISM: Homo sapiens

<400> SEQUENCE: 1190

Met Trp Thr Ala Leu Val Leu Ile Trp Ile Phe Ser Leu Ser Leu Ser
1               5                   10                  15

Glu Ser His Ala
            20

<210> SEQ ID NO 1191
<211> LENGTH: 20

```
<212> TYPE: PRT
<213> ORGANISM: Homo sapiens

<400> SEQUENCE: 1191

Met Phe Lys Cys Trp Ser Val Val Leu Val Leu Gly Phe Ile Phe Leu
1               5                   10                  15

Glu Ser Glu Gly
            20

<210> SEQ ID NO 1192
<211> LENGTH: 20
<212> TYPE: PRT
<213> ORGANISM: Homo sapiens

<400> SEQUENCE: 1192

Met Met Trp Arg Pro Ser Val Leu Leu Leu Leu Leu Leu Leu Arg His
1               5                   10                  15

Gly Ala Gln Gly
            20

<210> SEQ ID NO 1193
<211> LENGTH: 21
<212> TYPE: PRT
<213> ORGANISM: Homo sapiens

<400> SEQUENCE: 1193

Met Leu Met Pro Val His Phe Leu Leu Leu Leu Leu Leu Leu Leu Gly
1               5                   10                  15

Gly Pro Arg Thr Gly
            20

<210> SEQ ID NO 1194
<211> LENGTH: 21
<212> TYPE: PRT
<213> ORGANISM: Homo sapiens

<400> SEQUENCE: 1194

Met Ser Leu Met Val Ile Ser Met Ala Cys Val Gly Phe Phe Leu Leu
1               5                   10                  15

Gln Gly Ala Trp Thr
            20

<210> SEQ ID NO 1195
<211> LENGTH: 21
<212> TYPE: PRT
<213> ORGANISM: Homo sapiens

<400> SEQUENCE: 1195

Met Ser Leu Met Val Ile Ser Met Ala Cys Val Gly Phe Phe Leu Leu
1               5                   10                  15

Gln Gly Ala Trp Thr
            20

<210> SEQ ID NO 1196
<211> LENGTH: 21
<212> TYPE: PRT
<213> ORGANISM: Homo sapiens

<400> SEQUENCE: 1196

Met Ser Leu Met Val Ile Ser Met Ala Cys Val Gly Phe Phe Leu Leu
1               5                   10                  15

Gln Gly Ala Trp Thr
```

-continued

20

<210> SEQ ID NO 1197
<211> LENGTH: 20
<212> TYPE: PRT
<213> ORGANISM: Homo sapiens

<400> SEQUENCE: 1197

Met Gly Trp Leu Thr Arg Ile Val Cys Leu Phe Trp Gly Val Leu Leu
1               5                   10                  15

Thr Ala Arg Ala
            20

<210> SEQ ID NO 1198
<211> LENGTH: 22
<212> TYPE: PRT
<213> ORGANISM: Homo sapiens

<400> SEQUENCE: 1198

Met Ala Arg Glu Met Thr Ile Leu Gly Ser Ala Val Leu Thr Leu Leu
1               5                   10                  15

Leu Ala Gly Tyr Leu Ala
            20

<210> SEQ ID NO 1199
<211> LENGTH: 24
<212> TYPE: PRT
<213> ORGANISM: Homo sapiens

<400> SEQUENCE: 1199

Met Ser Ala Ala Trp Ile Pro Ala Leu Gly Leu Gly Val Cys Leu Leu
1               5                   10                  15

Leu Leu Pro Gly Pro Ala Gly Ser
            20

<210> SEQ ID NO 1200
<211> LENGTH: 23
<212> TYPE: PRT
<213> ORGANISM: Homo sapiens

<400> SEQUENCE: 1200

Met Ala Ala Ala Thr Ala Ser Pro Arg Ser Leu Leu Val Leu Leu Gln
1               5                   10                  15

Val Val Val Leu Ala Leu Ala
            20

<210> SEQ ID NO 1201
<211> LENGTH: 25
<212> TYPE: PRT
<213> ORGANISM: Homo sapiens

<400> SEQUENCE: 1201

Met Ala Pro Gly Met Ser Gly Arg Gly Gly Ala Ala Leu Leu Cys Leu
1               5                   10                  15

Ser Ala Leu Leu Ala His Ala Ser Gly
            20                  25

<210> SEQ ID NO 1202
<211> LENGTH: 23
<212> TYPE: PRT
<213> ORGANISM: Homo sapiens

<400> SEQUENCE: 1202

```
Met Gly Arg Arg Asp Ala Gln Leu Leu Ala Ala Leu Leu Val Leu Gly
1               5                   10                  15

Leu Cys Ala Leu Ala Gly Ser
            20

<210> SEQ ID NO 1203
<211> LENGTH: 22
<212> TYPE: PRT
<213> ORGANISM: Homo sapiens

<400> SEQUENCE: 1203

Met Lys Ala Gln Thr Ala Leu Ser Phe Phe Leu Ile Leu Ile Thr Ser
1               5                   10                  15

Leu Ser Gly Ser Gln Gly
            20

<210> SEQ ID NO 1204
<211> LENGTH: 21
<212> TYPE: PRT
<213> ORGANISM: Homo sapiens

<400> SEQUENCE: 1204

Met Ser Arg Arg Ser Met Leu Leu Ala Trp Ala Leu Pro Ser Leu Leu
1               5                   10                  15

Arg Leu Gly Ala Ala
            20

<210> SEQ ID NO 1205
<211> LENGTH: 18
<212> TYPE: PRT
<213> ORGANISM: Homo sapiens

<400> SEQUENCE: 1205

Met Arg Leu Arg Phe Trp Leu Leu Ile Trp Leu Leu Leu Gly Phe Ile
1               5                   10                  15

Ser His

<210> SEQ ID NO 1206
<211> LENGTH: 18
<212> TYPE: PRT
<213> ORGANISM: Homo sapiens

<400> SEQUENCE: 1206

Met Arg Leu Arg Phe Trp Leu Leu Ile Trp Leu Leu Leu Gly Phe Ile
1               5                   10                  15

Ser His

<210> SEQ ID NO 1207
<211> LENGTH: 20
<212> TYPE: PRT
<213> ORGANISM: Homo sapiens

<400> SEQUENCE: 1207

Met Asp Thr Lys Leu Met Cys Leu Leu Phe Phe Phe Ser Leu Pro Pro
1               5                   10                  15

Leu Leu Val Ser
            20

<210> SEQ ID NO 1208
<211> LENGTH: 22
<212> TYPE: PRT
```

<213> ORGANISM: Homo sapiens

<400> SEQUENCE: 1208

Met Ala Leu Trp Arg Gly Ser Ala Tyr Ala Gly Phe Leu Ala Leu Ala
1               5                   10                  15

Val Gly Cys Val Phe Leu
            20

<210> SEQ ID NO 1209
<211> LENGTH: 22
<212> TYPE: PRT
<213> ORGANISM: Homo sapiens

<400> SEQUENCE: 1209

Met Lys Phe Leu Leu Leu Val Leu Ala Ala Leu Gly Phe Leu Thr Gln
1               5                   10                  15

Val Ile Pro Ala Ser Ala
            20

<210> SEQ ID NO 1210
<211> LENGTH: 22
<212> TYPE: PRT
<213> ORGANISM: Homo sapiens

<400> SEQUENCE: 1210

Met Val Gly Ala Met Trp Lys Val Ile Val Ser Leu Val Leu Leu Met
1               5                   10                  15

Pro Gly Pro Cys Asp Gly
            20

<210> SEQ ID NO 1211
<211> LENGTH: 19
<212> TYPE: PRT
<213> ORGANISM: Homo sapiens

<400> SEQUENCE: 1211

Met Pro Pro Pro Arg Leu Leu Phe Phe Leu Leu Phe Leu Thr Pro Met
1               5                   10                  15

Glu Val Arg

<210> SEQ ID NO 1212
<211> LENGTH: 26
<212> TYPE: PRT
<213> ORGANISM: Homo sapiens

<400> SEQUENCE: 1212

Met Ala Gly Val Gly Ala Ala Ala Leu Ser Leu Leu Leu His Leu Gly
1               5                   10                  15

Ala Leu Ala Leu Ala Ala Gly Ala Glu Gly
            20                  25

<210> SEQ ID NO 1213
<211> LENGTH: 21
<212> TYPE: PRT
<213> ORGANISM: Homo sapiens

<400> SEQUENCE: 1213

Met Lys Leu Thr Phe Phe Leu Gly Leu Leu Ala Leu Ile Ser Cys Phe
1               5                   10                  15

Thr Pro Ser Glu Ser
            20

```
<210> SEQ ID NO 1214
<211> LENGTH: 22
<212> TYPE: PRT
<213> ORGANISM: Homo sapiens

<400> SEQUENCE: 1214

Met Lys Val Phe Lys Phe Ile Gly Leu Met Ile Leu Leu Thr Ser Ala
1               5                   10                  15

Phe Ser Ala Gly Ser Gly
            20

<210> SEQ ID NO 1215
<211> LENGTH: 21
<212> TYPE: PRT
<213> ORGANISM: Homo sapiens

<400> SEQUENCE: 1215

Met Gln Pro Leu Trp Leu Cys Trp Ala Leu Trp Val Leu Pro Leu Ala
1               5                   10                  15

Ser Pro Gly Ala Ala
            20

<210> SEQ ID NO 1216
<211> LENGTH: 21
<212> TYPE: PRT
<213> ORGANISM: Homo sapiens

<400> SEQUENCE: 1216

Met Arg Arg Ala Pro Ser Leu Val Leu Phe Phe Leu Val Ala Leu Cys
1               5                   10                  15

Gly Arg Gly Asn Cys
            20

<210> SEQ ID NO 1217
<211> LENGTH: 20
<212> TYPE: PRT
<213> ORGANISM: Homo sapiens

<400> SEQUENCE: 1217

Met Ala Leu Pro Tyr His Ile Phe Leu Phe Thr Val Leu Leu Pro Ser
1               5                   10                  15

Phe Thr Leu Thr
            20

<210> SEQ ID NO 1218
<211> LENGTH: 23
<212> TYPE: PRT
<213> ORGANISM: Homo sapiens

<400> SEQUENCE: 1218

Met Ala Ser Met Ala Ala Val Leu Thr Trp Ala Leu Ala Leu Leu Ser
1               5                   10                  15

Ala Phe Ser Ala Thr Gln Ala
            20

<210> SEQ ID NO 1219
<211> LENGTH: 22
<212> TYPE: PRT
<213> ORGANISM: Homo sapiens

<400> SEQUENCE: 1219

Val Met Ala Pro Arg Thr Leu Val Leu Leu Leu Ser Gly Ala Leu Ala
```

-continued

```
                 1               5              10              15

Leu Thr Gln Thr Trp Ala
            20

<210> SEQ ID NO 1220
<211> LENGTH: 21
<212> TYPE: PRT
<213> ORGANISM: Homo sapiens

<400> SEQUENCE: 1220

Met Ser Ser Asn Thr Met Leu Gln Lys Thr Leu Leu Ile Leu Ile Ser
1               5                   10                  15

Phe Ser Val Val Thr
            20

<210> SEQ ID NO 1221
<211> LENGTH: 21
<212> TYPE: PRT
<213> ORGANISM: Homo sapiens

<400> SEQUENCE: 1221

Met Gly Arg Arg Ala Leu Leu Leu Leu Leu Ser Phe Leu Ala Pro
1               5                   10                  15

Trp Ala Thr Ile Ala
            20

<210> SEQ ID NO 1222
<211> LENGTH: 21
<212> TYPE: PRT
<213> ORGANISM: Homo sapiens

<400> SEQUENCE: 1222

Met Thr Thr Ser Pro Ile Leu Gln Leu Leu Leu Arg Leu Ser Leu Cys
1               5                   10                  15

Gly Leu Leu Leu Gln
            20

<210> SEQ ID NO 1223
<211> LENGTH: 19
<212> TYPE: PRT
<213> ORGANISM: Homo sapiens

<400> SEQUENCE: 1223

Met Trp Ser His Leu Asn Arg Leu Leu Phe Trp Ser Ile Phe Ser Ser
1               5                   10                  15

Val Thr Cys

<210> SEQ ID NO 1224
<211> LENGTH: 19
<212> TYPE: PRT
<213> ORGANISM: Homo sapiens

<400> SEQUENCE: 1224

Met Lys His Leu Trp Phe Phe Leu Leu Leu Val Ala Ala Pro Arg Trp
1               5                   10                  15

Val Leu Ser

<210> SEQ ID NO 1225
<211> LENGTH: 19
<212> TYPE: PRT
<213> ORGANISM: Homo sapiens
```

-continued

<400> SEQUENCE: 1225

Met Lys His Leu Trp Phe Phe Leu Leu Leu Val Ala Ala Pro Arg Trp
1               5                   10                  15

Val Leu Ser

<210> SEQ ID NO 1226
<211> LENGTH: 19
<212> TYPE: PRT
<213> ORGANISM: Homo sapiens

<400> SEQUENCE: 1226

Met Lys His Leu Trp Phe Phe Leu Leu Leu Val Ala Ala Pro Arg Trp
1               5                   10                  15

Val Leu Ser

<210> SEQ ID NO 1227
<211> LENGTH: 20
<212> TYPE: PRT
<213> ORGANISM: Homo sapiens

<400> SEQUENCE: 1227

Met Pro Leu Trp Val Phe Phe Phe Val Ile Leu Thr Leu Ser Asn Ser
1               5                   10                  15

Ser His Cys Ser
            20

<210> SEQ ID NO 1228
<211> LENGTH: 22
<212> TYPE: PRT
<213> ORGANISM: Homo sapiens

<400> SEQUENCE: 1228

Met Val Gly Gln Arg Val Leu Leu Val Ala Phe Leu Leu Ser Gly
1               5                   10                  15

Val Leu Leu Ser Glu Ala
            20

<210> SEQ ID NO 1229
<211> LENGTH: 19
<212> TYPE: PRT
<213> ORGANISM: Homo sapiens

<400> SEQUENCE: 1229

Met Val Leu Leu His Trp Cys Leu Leu Trp Leu Leu Phe Pro Leu Ser
1               5                   10                  15

Ser Arg Thr

<210> SEQ ID NO 1230
<211> LENGTH: 21
<212> TYPE: PRT
<213> ORGANISM: Homo sapiens

<400> SEQUENCE: 1230

Met Thr Asp Lys Ser Ile Val Ile Leu Ser Leu Met Val Phe His Ser
1               5                   10                  15

Ser Phe Ile Asn Gly
            20

<210> SEQ ID NO 1231
<211> LENGTH: 21
<212> TYPE: PRT

```
<213> ORGANISM: Homo sapiens

<400> SEQUENCE: 1231

Met Pro Phe Arg Leu Leu Ile Pro Leu Gly Leu Leu Cys Ala Leu Leu
1               5                   10                  15

Pro Gln His His Gly
            20

<210> SEQ ID NO 1232
<211> LENGTH: 21
<212> TYPE: PRT
<213> ORGANISM: Homo sapiens

<400> SEQUENCE: 1232

Met Ser Leu Met Val Val Ser Met Ala Arg Val Gly Phe Phe Leu Leu
1               5                   10                  15

Gln Gly Ala Trp Pro
            20

<210> SEQ ID NO 1233
<211> LENGTH: 20
<212> TYPE: PRT
<213> ORGANISM: Homo sapiens

<400> SEQUENCE: 1233

Met Val His Val Ala Arg Leu Leu Leu Leu Leu Thr Phe Phe Leu
1               5                   10                  15

Arg Thr Asp Ala
            20

<210> SEQ ID NO 1234
<211> LENGTH: 21
<212> TYPE: PRT
<213> ORGANISM: Homo sapiens

<400> SEQUENCE: 1234

Met Asp Ser Trp Thr Phe Cys Cys Val Ser Leu Cys Ile Leu Val Ala
1               5                   10                  15

Lys His Thr Asp Ala
            20

<210> SEQ ID NO 1235
<211> LENGTH: 22
<212> TYPE: PRT
<213> ORGANISM: Homo sapiens

<400> SEQUENCE: 1235

Met Ala Gly Ala Ser Arg Leu Leu Phe Leu Trp Leu Gly Cys Phe Cys
1               5                   10                  15

Val Ser Leu Ala Gln Gly
            20

<210> SEQ ID NO 1236
<211> LENGTH: 21
<212> TYPE: PRT
<213> ORGANISM: Homo sapiens

<400> SEQUENCE: 1236

Met Glu Ala Ser Arg Trp Trp Leu Leu Val Thr Val Leu Met Ala Gly
1               5                   10                  15

Ala His Cys Val Ala
            20
```

-continued

<210> SEQ ID NO 1237
<211> LENGTH: 21
<212> TYPE: PRT
<213> ORGANISM: Homo sapiens

<400> SEQUENCE: 1237

Met Asp Pro Lys Gln Thr Thr Leu Leu Cys Leu Val Leu Cys Leu Gly
1               5                   10                  15

Gln Arg Ile Gln Ala
            20

<210> SEQ ID NO 1238
<211> LENGTH: 22
<212> TYPE: PRT
<213> ORGANISM: Homo sapiens

<400> SEQUENCE: 1238

Met Pro Gly Val Ala Arg Leu Pro Leu Leu Gly Leu Leu Leu Leu Leu
1               5                   10                  15

Pro Arg Pro Gly Arg Pro
            20

<210> SEQ ID NO 1239
<211> LENGTH: 18
<212> TYPE: PRT
<213> ORGANISM: Homo sapiens

<400> SEQUENCE: 1239

Met Arg Thr Tyr Arg Tyr Phe Leu Leu Leu Phe Trp Val Gly Gln Pro
1               5                   10                  15

Tyr Pro

<210> SEQ ID NO 1240
<211> LENGTH: 25
<212> TYPE: PRT
<213> ORGANISM: Homo sapiens

<400> SEQUENCE: 1240

Met Ser Arg Pro Gly Thr Ala Thr Pro Ala Leu Ala Leu Val Leu Leu
1               5                   10                  15

Ala Val Thr Leu Ala Gly Val Gly Ala
            20                  25

<210> SEQ ID NO 1241
<211> LENGTH: 21
<212> TYPE: PRT
<213> ORGANISM: Homo sapiens

<400> SEQUENCE: 1241

Met Arg Val Ala Leu Gly Met Leu Trp Leu Leu Ala Leu Ala Trp Pro
1               5                   10                  15

Pro Gln Ala Arg Gly
            20

<210> SEQ ID NO 1242
<211> LENGTH: 23
<212> TYPE: PRT
<213> ORGANISM: Homo sapiens

<400> SEQUENCE: 1242

Met Gly Ser Ser Ser Phe Leu Val Leu Met Val Ser Leu Val Leu Val

-continued

```
                1               5                  10                 15

Thr Leu Val Ala Val Glu Gly
            20

<210> SEQ ID NO 1243
<211> LENGTH: 20
<212> TYPE: PRT
<213> ORGANISM: Homo sapiens

<400> SEQUENCE: 1243

Met Gly Phe Leu Ser Pro Ile Tyr Val Ile Phe Phe Phe Phe Gly Val
1               5                  10                 15

Lys Val His Cys
            20

<210> SEQ ID NO 1244
<211> LENGTH: 21
<212> TYPE: PRT
<213> ORGANISM: Homo sapiens

<400> SEQUENCE: 1244

Met Trp Pro Leu Trp Leu Cys Trp Ala Leu Trp Val Leu Pro Leu Ala
1               5                  10                 15

Gly Pro Gly Ala Ala
            20

<210> SEQ ID NO 1245
<211> LENGTH: 20
<212> TYPE: PRT
<213> ORGANISM: Homo sapiens

<400> SEQUENCE: 1245

Met Val Arg Ile Trp Thr Thr Ile Met Ile Val Leu Ile Leu Leu Leu
1               5                  10                 15

Arg Ile Gly Pro
            20

<210> SEQ ID NO 1246
<211> LENGTH: 21
<212> TYPE: PRT
<213> ORGANISM: Homo sapiens

<400> SEQUENCE: 1246

Met Gly Pro Val Arg Leu Gly Ile Leu Leu Phe Leu Phe Leu Ala Val
1               5                  10                 15

His Glu Ala Trp Ala
            20

<210> SEQ ID NO 1247
<211> LENGTH: 21
<212> TYPE: PRT
<213> ORGANISM: Homo sapiens

<400> SEQUENCE: 1247

Met Lys Leu Trp Val Ser Ala Leu Leu Met Ala Trp Phe Gly Val Leu
1               5                  10                 15

Ser Cys Val Gln Ala
            20

<210> SEQ ID NO 1248
<211> LENGTH: 20
<212> TYPE: PRT
```

-continued

<213> ORGANISM: Homo sapiens

<400> SEQUENCE: 1248

Met Arg Val Phe Leu Leu Cys Ala Tyr Ile Leu Leu Leu Met Val Ser
1               5                   10                  15

Gln Leu Arg Ala
            20

<210> SEQ ID NO 1249
<211> LENGTH: 23
<212> TYPE: PRT
<213> ORGANISM: Homo sapiens

<400> SEQUENCE: 1249

Met Ser Ala Pro Arg Leu Leu Ile Ser Ile Ile Met Val Ser Ala
1               5                   10                  15

Ser Ser Ser Ser Cys Met Gly
            20

<210> SEQ ID NO 1250
<211> LENGTH: 20
<212> TYPE: PRT
<213> ORGANISM: Homo sapiens

<400> SEQUENCE: 1250

Met Leu Arg Tyr Leu Leu Lys Thr Leu Leu Gln Met Asn Leu Phe Ala
1               5                   10                  15

Asp Ser Leu Ala
            20

<210> SEQ ID NO 1251
<211> LENGTH: 22
<212> TYPE: PRT
<213> ORGANISM: Homo sapiens

<400> SEQUENCE: 1251

Met Gly Arg Arg Arg Leu Leu Val Trp Leu Cys Ala Val Ala Ala Leu
1               5                   10                  15

Leu Ser Gly Ala Gln Ala
            20

<210> SEQ ID NO 1252
<211> LENGTH: 20
<212> TYPE: PRT
<213> ORGANISM: Homo sapiens

<400> SEQUENCE: 1252

Met Lys Pro Pro Leu Leu Val Phe Ile Val Cys Leu Leu Trp Leu Lys
1               5                   10                  15

Asp Ser His Cys
            20

<210> SEQ ID NO 1253
<211> LENGTH: 24
<212> TYPE: PRT
<213> ORGANISM: Homo sapiens

<400> SEQUENCE: 1253

Met Arg Pro Ala Ala Leu Arg Gly Ala Leu Leu Gly Cys Leu Cys Leu
1               5                   10                  15

Ala Leu Leu Cys Leu Gly Gly Ala
            20

```
<210> SEQ ID NO 1254
<211> LENGTH: 22
<212> TYPE: PRT
<213> ORGANISM: Homo sapiens

<400> SEQUENCE: 1254

Met Asp Leu Leu Gln Phe Leu Ala Phe Leu Phe Val Leu Leu Leu Ser
1               5                   10                  15

Gly Met Gly Ala Thr Gly
            20

<210> SEQ ID NO 1255
<211> LENGTH: 21
<212> TYPE: PRT
<213> ORGANISM: Homo sapiens

<400> SEQUENCE: 1255

Met Val Phe Ala Phe Trp Lys Val Phe Ile Leu Ser Cys Leu Ala
1               5                   10                  15

Gly Gln Val Ser Val
            20

<210> SEQ ID NO 1256
<211> LENGTH: 21
<212> TYPE: PRT
<213> ORGANISM: Homo sapiens

<400> SEQUENCE: 1256

Met Gly Gly Met Lys Tyr Ile Phe Ser Leu Leu Phe Phe Leu Leu Leu
1               5                   10                  15

Glu Gly Gly Lys Thr
            20

<210> SEQ ID NO 1257
<211> LENGTH: 21
<212> TYPE: PRT
<213> ORGANISM: Homo sapiens

<400> SEQUENCE: 1257

Met Glu Leu Gly Cys Trp Thr Gln Leu Gly Leu Thr Phe Leu Gln Leu
1               5                   10                  15

Leu Leu Ile Ser Ser
            20

<210> SEQ ID NO 1258
<211> LENGTH: 20
<212> TYPE: PRT
<213> ORGANISM: Homo sapiens

<400> SEQUENCE: 1258

Met Lys Ile Ala Val Leu Phe Cys Phe Leu Leu Ile Ile Phe Gln
1               5                   10                  15

Thr Asp Phe Gly
            20

<210> SEQ ID NO 1259
<211> LENGTH: 21
<212> TYPE: PRT
<213> ORGANISM: Homo sapiens

<400> SEQUENCE: 1259
```

-continued

```
Met Ile Leu Ile Pro Arg Met Leu Leu Val Leu Phe Leu Leu Pro
1               5                   10                  15

Ile Leu Ser Ser Ala
            20

<210> SEQ ID NO 1260
<211> LENGTH: 24
<212> TYPE: PRT
<213> ORGANISM: Homo sapiens

<400> SEQUENCE: 1260

Met Gly Ala Pro Leu Ala Val Ala Leu Gly Ala Leu His Tyr Leu Ala
1               5                   10                  15

Leu Phe Leu Gln Leu Gly Gly Ala
            20

<210> SEQ ID NO 1261
<211> LENGTH: 22
<212> TYPE: PRT
<213> ORGANISM: Homo sapiens

<400> SEQUENCE: 1261

Met Lys Thr Leu Pro Leu Phe Val Cys Ile Cys Ala Leu Ser Ala Cys
1               5                   10                  15

Phe Ser Phe Ser Glu Gly
            20

<210> SEQ ID NO 1262
<211> LENGTH: 22
<212> TYPE: PRT
<213> ORGANISM: Homo sapiens

<400> SEQUENCE: 1262

Met Arg Leu Trp Ser Trp Val Leu His Leu Gly Leu Leu Ser Ala Ala
1               5                   10                  15

Leu Gly Cys Gly Leu Ala
            20

<210> SEQ ID NO 1263
<211> LENGTH: 24
<212> TYPE: PRT
<213> ORGANISM: Homo sapiens

<400> SEQUENCE: 1263

Met Ser Ala Pro Ser Leu Arg Ala Arg Ala Ala Gly Leu Gly Leu Leu
1               5                   10                  15

Leu Cys Ala Val Leu Gly Arg Ala
            20

<210> SEQ ID NO 1264
<211> LENGTH: 21
<212> TYPE: PRT
<213> ORGANISM: Homo sapiens

<400> SEQUENCE: 1264

Met Gly Ile Arg Gly Met Leu Arg Ala Ala Val Ile Leu Leu Leu Ile
1               5                   10                  15

Arg Thr Trp Leu Ala
            20

<210> SEQ ID NO 1265
<211> LENGTH: 27
```

```
<212> TYPE: PRT
<213> ORGANISM: Homo sapiens

<400> SEQUENCE: 1265

Met Ala Gly Trp Pro Gly Ala Gly Pro Leu Cys Val Leu Gly Gly Ala
1               5                   10                  15

Ala Leu Gly Val Cys Leu Ala Gly Val Ala Gly
            20                  25

<210> SEQ ID NO 1266
<211> LENGTH: 21
<212> TYPE: PRT
<213> ORGANISM: Homo sapiens

<400> SEQUENCE: 1266

Met Ala Glu Ala Gly Leu Arg Gly Trp Leu Leu Trp Ala Leu Leu Leu
1               5                   10                  15

Arg Leu Ala Gln Ser
            20

<210> SEQ ID NO 1267
<211> LENGTH: 22
<212> TYPE: PRT
<213> ORGANISM: Homo sapiens

<400> SEQUENCE: 1267

Met Ala Leu Val Arg Ala Leu Val Cys Cys Leu Leu Thr Ala Trp His
1               5                   10                  15

Cys Arg Ser Gly Leu Gly
            20

<210> SEQ ID NO 1268
<211> LENGTH: 23
<212> TYPE: PRT
<213> ORGANISM: Homo sapiens

<400> SEQUENCE: 1268

Met Cys Ser Arg Val Pro Leu Leu Pro Leu Leu Leu Leu Leu Leu Ala
1               5                   10                  15

Leu Gly Pro Gly Val Gln Gly
            20

<210> SEQ ID NO 1269
<211> LENGTH: 21
<212> TYPE: PRT
<213> ORGANISM: Homo sapiens

<400> SEQUENCE: 1269

Met Ala Ala Glu Trp Ala Ser Arg Phe Trp Leu Trp Ala Thr Leu Leu
1               5                   10                  15

Ile Pro Ala Ala Ala
            20

<210> SEQ ID NO 1270
<211> LENGTH: 20
<212> TYPE: PRT
<213> ORGANISM: Homo sapiens

<400> SEQUENCE: 1270

Met Gln Ile Pro Gln Ala Pro Trp Pro Val Val Trp Ala Val Leu Gln
1               5                   10                  15

Leu Gly Trp Arg
```

-continued

```
                20

<210> SEQ ID NO 1271
<211> LENGTH: 23
<212> TYPE: PRT
<213> ORGANISM: Homo sapiens

<400> SEQUENCE: 1271

Met Thr Leu Thr Leu Ser Val Leu Ile Cys Leu Gly Leu Ser Val Gly
1               5                   10                  15

Pro Arg Thr Cys Val Gln Ala
            20

<210> SEQ ID NO 1272
<211> LENGTH: 22
<212> TYPE: PRT
<213> ORGANISM: Homo sapiens

<400> SEQUENCE: 1272

Met Trp Lys Val Ser Ala Leu Leu Phe Val Leu Gly Ser Ala Ser Leu
1               5                   10                  15

Trp Val Leu Ala Glu Gly
            20

<210> SEQ ID NO 1273
<211> LENGTH: 22
<212> TYPE: PRT
<213> ORGANISM: Homo sapiens

<400> SEQUENCE: 1273

Met Met Cys Leu Lys Ile Leu Arg Ile Ser Leu Ala Ile Leu Ala Gly
1               5                   10                  15

Trp Ala Leu Cys Ser Ala
            20

<210> SEQ ID NO 1274
<211> LENGTH: 23
<212> TYPE: PRT
<213> ORGANISM: Homo sapiens

<400> SEQUENCE: 1274

Met Pro Gly Ile Lys Arg Ile Leu Thr Val Thr Ile Leu Ala Leu Cys
1               5                   10                  15

Leu Pro Ser Pro Gly Asn Ala
            20

<210> SEQ ID NO 1275
<211> LENGTH: 22
<212> TYPE: PRT
<213> ORGANISM: Homo sapiens

<400> SEQUENCE: 1275

Met Gly Ala Pro Phe Val Trp Ala Leu Gly Leu Leu Met Leu Gln Met
1               5                   10                  15

Leu Leu Phe Val Ala Gly
            20

<210> SEQ ID NO 1276
<211> LENGTH: 22
<212> TYPE: PRT
<213> ORGANISM: Homo sapiens

<400> SEQUENCE: 1276
```

```
Met Asp Pro Glu Cys Ala Gln Leu Leu Pro Ala Leu Cys Ala Val Leu
1               5                   10                  15

Val Asp Pro Arg Gln Pro
            20

<210> SEQ ID NO 1277
<211> LENGTH: 22
<212> TYPE: PRT
<213> ORGANISM: Homo sapiens

<400> SEQUENCE: 1277

Met Thr Asn Val Tyr Ser Leu Asp Gly Ile Leu Val Phe Gly Leu Leu
1               5                   10                  15

Phe Val Cys Thr Cys Ala
            20

<210> SEQ ID NO 1278
<211> LENGTH: 21
<212> TYPE: PRT
<213> ORGANISM: Homo sapiens

<400> SEQUENCE: 1278

Met Ser Arg Gln Leu Leu Pro Val Leu Leu Leu Leu Leu Leu Arg Ala
1               5                   10                  15

Ser Cys Pro Trp Gly
            20

<210> SEQ ID NO 1279
<211> LENGTH: 22
<212> TYPE: PRT
<213> ORGANISM: Homo sapiens

<400> SEQUENCE: 1279

Met Arg Pro His Leu Ser Pro Pro Leu Gln Gln Leu Leu Leu Pro Val
1               5                   10                  15

Leu Leu Ala Cys Ala Ala
            20

<210> SEQ ID NO 1280
<211> LENGTH: 21
<212> TYPE: PRT
<213> ORGANISM: Homo sapiens

<400> SEQUENCE: 1280

Met Met Cys Pro Leu Trp Arg Leu Leu Ile Phe Leu Gly Leu Leu Ala
1               5                   10                  15

Leu Pro Leu Ala Pro
            20

<210> SEQ ID NO 1281
<211> LENGTH: 22
<212> TYPE: PRT
<213> ORGANISM: Homo sapiens

<400> SEQUENCE: 1281

Met Leu Leu Thr Leu Ile Ile Leu Leu Pro Val Val Ser Lys Phe Ser
1               5                   10                  15

Phe Val Ser Leu Ser Ala
            20

<210> SEQ ID NO 1282
```

<211> LENGTH: 22
<212> TYPE: PRT
<213> ORGANISM: Homo sapiens

<400> SEQUENCE: 1282

Met Leu Ser Lys Val Leu Pro Val Leu Leu Gly Ile Leu Leu Ile Leu
1               5                   10                  15

Gln Ser Arg Val Glu Gly
            20

<210> SEQ ID NO 1283
<211> LENGTH: 24
<212> TYPE: PRT
<213> ORGANISM: Homo sapiens

<400> SEQUENCE: 1283

Met Arg Gly Ser Gly Pro Arg Gly Ala Gly Arg Arg Pro Pro Ser
1               5                   10                  15

Gly Gly Gly Asp Thr Pro Ile Thr
            20

<210> SEQ ID NO 1284
<211> LENGTH: 24
<212> TYPE: PRT
<213> ORGANISM: Homo sapiens

<400> SEQUENCE: 1284

Met Glu Leu Gln Ala Ala Arg Ala Cys Phe Ala Leu Leu Trp Gly Cys
1               5                   10                  15

Ala Leu Ala Ala Ala Ala Ala Ala
            20

<210> SEQ ID NO 1285
<211> LENGTH: 23
<212> TYPE: PRT
<213> ORGANISM: Homo sapiens

<400> SEQUENCE: 1285

Met Gly Pro Ser Ser Cys Leu Leu Leu Ile Leu Ile Pro Leu Leu Gln
1               5                   10                  15

Leu Ile Asn Pro Gly Ser Thr
            20

<210> SEQ ID NO 1286
<211> LENGTH: 21
<212> TYPE: PRT
<213> ORGANISM: Homo sapiens

<400> SEQUENCE: 1286

Met Val Phe Leu Val Ala Cys Ala Leu His Ile Ala Leu Asp Leu Leu
1               5                   10                  15

Pro Arg Leu Glu Arg
            20

<210> SEQ ID NO 1287
<211> LENGTH: 20
<212> TYPE: PRT
<213> ORGANISM: Homo sapiens

<400> SEQUENCE: 1287

Met Gly Phe His Phe Cys Ile Trp Ile Ile Phe Leu Leu Pro Pro Pro
1               5                   10                  15

Cys Lys Lys Cys
        20

<210> SEQ ID NO 1288
<211> LENGTH: 22
<212> TYPE: PRT
<213> ORGANISM: Homo sapiens

<400> SEQUENCE: 1288

Met Gly Ala Ala Arg Leu Leu Pro Asn Leu Thr Leu Cys Leu Gln Leu
1               5                   10                  15

Leu Ile Leu Cys Cys Gln
        20

<210> SEQ ID NO 1289
<211> LENGTH: 24
<212> TYPE: PRT
<213> ORGANISM: Homo sapiens

<400> SEQUENCE: 1289

Met Arg His Gly Val Ala Trp Ala Leu Leu Val Ala Ala Ala Leu Gly
1               5                   10                  15

Leu Gly Ala Arg Gly Val Arg Gly
        20

<210> SEQ ID NO 1290
<211> LENGTH: 22
<212> TYPE: PRT
<213> ORGANISM: Homo sapiens

<400> SEQUENCE: 1290

Met Leu Thr Arg Leu Val Leu Ser Ala His Leu Ser Ser Thr Thr Ser
1               5                   10                  15

Pro Pro Trp Thr His Ala
        20

<210> SEQ ID NO 1291
<211> LENGTH: 21
<212> TYPE: PRT
<213> ORGANISM: Homo sapiens

<400> SEQUENCE: 1291

Met Gly Arg His Leu Ala Leu Leu Leu Leu Leu Leu Leu Phe Gln
1               5                   10                  15

His Phe Gly Asp Ser
        20

<210> SEQ ID NO 1292
<211> LENGTH: 23
<212> TYPE: PRT
<213> ORGANISM: Homo sapiens

<400> SEQUENCE: 1292

Met Gly Ser Ser Arg Leu Ala Ala Leu Leu Pro Leu Leu Leu Ile
1               5                   10                  15

Val Ile Asp Leu Ser Asp Ser
        20

<210> SEQ ID NO 1293
<211> LENGTH: 21
<212> TYPE: PRT
<213> ORGANISM: Homo sapiens

```
<400> SEQUENCE: 1293

Met Glu His Lys Glu Val Val Leu Leu Leu Leu Phe Leu Lys Ser
1               5                   10                  15

Ala Pro Thr Glu Thr
            20

<210> SEQ ID NO 1294
<211> LENGTH: 22
<212> TYPE: PRT
<213> ORGANISM: Homo sapiens

<400> SEQUENCE: 1294

Met Arg Arg Pro Ala Ala Val Pro Leu Leu Leu Leu Cys Phe Gly
1               5                   10                  15

Ser Gln Arg Ala Lys Ala
            20

<210> SEQ ID NO 1295
<211> LENGTH: 20
<212> TYPE: PRT
<213> ORGANISM: Homo sapiens

<400> SEQUENCE: 1295

Met Leu His Val Glu Met Leu Thr Leu Val Phe Leu Val Leu Trp Met
1               5                   10                  15

Cys Val Phe Ser
            20

<210> SEQ ID NO 1296
<211> LENGTH: 24
<212> TYPE: PRT
<213> ORGANISM: Homo sapiens

<400> SEQUENCE: 1296

Met Ala Ser Cys Leu Ala Leu Arg Met Ala Leu Leu Leu Val Ser Gly
1               5                   10                  15

Val Leu Ala Pro Ala Val Leu Thr
            20

<210> SEQ ID NO 1297
<211> LENGTH: 21
<212> TYPE: PRT
<213> ORGANISM: Homo sapiens

<400> SEQUENCE: 1297

Met Arg Val Thr Leu Ala Thr Ile Ala Trp Met Val Ser Phe Val Ser
1               5                   10                  15

Asn Tyr Ser His Thr
            20

<210> SEQ ID NO 1298
<211> LENGTH: 22
<212> TYPE: PRT
<213> ORGANISM: Homo sapiens

<400> SEQUENCE: 1298

Met Glu Thr Gln Glu Leu Arg Gly Ala Leu Ala Leu Leu Leu Leu Cys
1               5                   10                  15

Phe Phe Thr Ser Ala Ser
            20
```

```
<210> SEQ ID NO 1299
<211> LENGTH: 21
<212> TYPE: PRT
<213> ORGANISM: Homo sapiens

<400> SEQUENCE: 1299

Met Lys Met Lys Ser Gln Ala Thr Met Ile Cys Cys Leu Val Phe Phe
1               5                   10                  15

Leu Ser Thr Glu Cys
            20

<210> SEQ ID NO 1300
<211> LENGTH: 21
<212> TYPE: PRT
<213> ORGANISM: Homo sapiens

<400> SEQUENCE: 1300

Met Asp Trp Thr Trp Arg Val Phe Cys Leu Leu Ala Val Ala Pro Gly
1               5                   10                  15

Val His Ser Gln Val
            20

<210> SEQ ID NO 1301
<211> LENGTH: 23
<212> TYPE: PRT
<213> ORGANISM: Homo sapiens

<400> SEQUENCE: 1301

Met Ala Arg Arg Gly Pro Gly Trp Arg Pro Leu Leu Leu Val Leu
1               5                   10                  15

Leu Ala Gly Ala Ala Gln Gly
            20

<210> SEQ ID NO 1302
<211> LENGTH: 22
<212> TYPE: PRT
<213> ORGANISM: Homo sapiens

<400> SEQUENCE: 1302

Met Arg Ala Ala Arg Ala Ala Pro Leu Leu Gln Leu Leu Leu Leu Leu
1               5                   10                  15

Gly Pro Trp Leu Glu Ala
            20

<210> SEQ ID NO 1303
<211> LENGTH: 22
<212> TYPE: PRT
<213> ORGANISM: Homo sapiens

<400> SEQUENCE: 1303

Met Ala Arg His Leu Leu Leu Pro Leu Val Met Leu Val Ile Ser Pro
1               5                   10                  15

Ile Pro Gly Ala Phe Gln
            20

<210> SEQ ID NO 1304
<211> LENGTH: 24
<212> TYPE: PRT
<213> ORGANISM: Homo sapiens

<400> SEQUENCE: 1304

Met Met Arg Ala Val Trp Glu Ala Leu Ala Ala Leu Ala Ala Val Ala
1               5                   10                  15
```

```
Cys Leu Val Gly Ala Val Arg Gly
            20

<210> SEQ ID NO 1305
<211> LENGTH: 22
<212> TYPE: PRT
<213> ORGANISM: Homo sapiens

<400> SEQUENCE: 1305

Met Glu Pro Ala Val Ser Leu Ala Val Cys Ala Leu Leu Phe Leu Leu
1               5                   10                  15

Trp Val Arg Leu Lys Gly
            20

<210> SEQ ID NO 1306
<211> LENGTH: 22
<212> TYPE: PRT
<213> ORGANISM: Homo sapiens

<400> SEQUENCE: 1306

Met Asn Leu Arg Leu Cys Val Gln Ala Leu Leu Leu Trp Leu Ser
1               5                   10                  15

Leu Thr Ala Val Cys Gly
            20

<210> SEQ ID NO 1307
<211> LENGTH: 24
<212> TYPE: PRT
<213> ORGANISM: Homo sapiens

<400> SEQUENCE: 1307

Met Pro Gly Pro Trp Leu Leu Leu Ala Leu Ala Leu Thr Leu Asn Leu
1               5                   10                  15

Thr Gly Val Pro Gly Gly Arg Ala
            20

<210> SEQ ID NO 1308
<211> LENGTH: 25
<212> TYPE: PRT
<213> ORGANISM: Homo sapiens

<400> SEQUENCE: 1308

Met Ala Gly Gly Ser Ala Thr Thr Trp Gly Tyr Pro Val Ala Leu Leu
1               5                   10                  15

Leu Leu Val Ala Thr Leu Gly Leu Gly
            20                  25

<210> SEQ ID NO 1309
<211> LENGTH: 21
<212> TYPE: PRT
<213> ORGANISM: Homo sapiens

<400> SEQUENCE: 1309

Met Glu Cys Leu Tyr Tyr Phe Leu Gly Phe Leu Leu Leu Ala Ala Arg
1               5                   10                  15

Leu Pro Leu Asp Ala
            20

<210> SEQ ID NO 1310
<211> LENGTH: 21
<212> TYPE: PRT
<213> ORGANISM: Homo sapiens
```

```
<400> SEQUENCE: 1310

Met Lys Met Arg Phe Leu Gly Leu Val Val Cys Leu Val Leu Trp Thr
1               5                   10                  15

Leu His Ser Glu Gly
            20

<210> SEQ ID NO 1311
<211> LENGTH: 23
<212> TYPE: PRT
<213> ORGANISM: Homo sapiens

<400> SEQUENCE: 1311

Met Lys Gly Arg Gly Met Leu Val Leu Leu His Ala Val Val Leu
1               5                   10                  15

Gly Leu Pro Ser Ala Trp Ala
            20

<210> SEQ ID NO 1312
<211> LENGTH: 23
<212> TYPE: PRT
<213> ORGANISM: Homo sapiens

<400> SEQUENCE: 1312

Met Thr Pro Ile Leu Thr Val Leu Ile Cys Leu Gly Leu Ser Leu Gly
1               5                   10                  15

Pro Arg Thr His Val Gln Ala
            20

<210> SEQ ID NO 1313
<211> LENGTH: 23
<212> TYPE: PRT
<213> ORGANISM: Homo sapiens

<400> SEQUENCE: 1313

Met Thr Pro Ile Leu Thr Val Leu Ile Cys Leu Gly Leu Ser Leu Gly
1               5                   10                  15

Pro Arg Thr His Val Gln Ala
            20

<210> SEQ ID NO 1314
<211> LENGTH: 22
<212> TYPE: PRT
<213> ORGANISM: Homo sapiens

<400> SEQUENCE: 1314

Met Lys Asp Met Pro Leu Arg Ile His Val Leu Leu Gly Leu Ala Ile
1               5                   10                  15

Thr Thr Leu Val Gln Ala
            20

<210> SEQ ID NO 1315
<211> LENGTH: 24
<212> TYPE: PRT
<213> ORGANISM: Homo sapiens

<400> SEQUENCE: 1315

Met Thr Cys Trp Leu Cys Val Leu Ser Leu Pro Leu Leu Leu Leu Pro
1               5                   10                  15

Ala Ala Pro Pro Ala Gly Gly
            20
```

```
<210> SEQ ID NO 1316
<211> LENGTH: 24
<212> TYPE: PRT
<213> ORGANISM: Homo sapiens

<400> SEQUENCE: 1316

Met Leu Arg Ala Gly Trp Leu Arg Gly Ala Ala Ala Leu Ala Leu Leu
1               5                   10                  15

Leu Ala Ala Arg Val Val Ala Ala
            20

<210> SEQ ID NO 1317
<211> LENGTH: 22
<212> TYPE: PRT
<213> ORGANISM: Homo sapiens

<400> SEQUENCE: 1317

Met Lys Glu Asn Tyr Cys Leu Gln Ala Ala Leu Val Cys Leu Gly Met
1               5                   10                  15

Leu Cys His Ser His Ala
            20

<210> SEQ ID NO 1318
<211> LENGTH: 23
<212> TYPE: PRT
<213> ORGANISM: Homo sapiens

<400> SEQUENCE: 1318

Met Gly Ala Ala Ala Val Arg Trp His Leu Cys Val Leu Leu Ala Leu
1               5                   10                  15

Gly Thr Arg Gly Arg Leu Ala
            20

<210> SEQ ID NO 1319
<211> LENGTH: 20
<212> TYPE: PRT
<213> ORGANISM: Homo sapiens

<400> SEQUENCE: 1319

Met Pro Tyr Phe Thr Arg Leu Ile Leu Phe Leu Phe Cys Leu Met Val
1               5                   10                  15

Leu Val Glu Ser
            20

<210> SEQ ID NO 1320
<211> LENGTH: 21
<212> TYPE: PRT
<213> ORGANISM: Homo sapiens

<400> SEQUENCE: 1320

Met Pro Arg Cys Arg Trp Leu Ser Leu Ile Leu Leu Thr Ile Pro Leu
1               5                   10                  15

Ala Leu Val Ala Arg
            20

<210> SEQ ID NO 1321
<211> LENGTH: 23
<212> TYPE: PRT
<213> ORGANISM: Homo sapiens

<400> SEQUENCE: 1321

Met Leu Arg Asp Val Arg Gly Arg Arg Arg Ala Gly Ala Ala Leu Val
```

-continued

```
                1               5                  10                  15

Gly Val Leu Val Ala Glu Ala
            20

<210> SEQ ID NO 1322
<211> LENGTH: 23
<212> TYPE: PRT
<213> ORGANISM: Homo sapiens

<400> SEQUENCE: 1322

Met Arg Pro Arg Ser Ala Leu Pro Arg Leu Leu Leu Pro Leu Leu Leu
1               5                  10                  15

Leu Pro Ala Ala Gly Pro Ala
            20

<210> SEQ ID NO 1323
<211> LENGTH: 23
<212> TYPE: PRT
<213> ORGANISM: Homo sapiens

<400> SEQUENCE: 1323

Met Ala Gly Ala Trp Leu Arg Trp Gly Leu Leu Leu Trp Ala Gly Leu
1               5                  10                  15

Leu Ala Ser Ser Ala His Gly
            20

<210> SEQ ID NO 1324
<211> LENGTH: 23
<212> TYPE: PRT
<213> ORGANISM: Homo sapiens

<400> SEQUENCE: 1324

Met Ala Ser Tyr Leu Tyr Gly Val Leu Phe Ala Val Gly Leu Cys Ala
1               5                  10                  15

Pro Ile Tyr Cys Val Ser Pro
            20

<210> SEQ ID NO 1325
<211> LENGTH: 24
<212> TYPE: PRT
<213> ORGANISM: Homo sapiens

<400> SEQUENCE: 1325

Met Pro Leu Leu Pro Ser Thr Val Gly Leu Ala Gly Leu Leu Phe Trp
1               5                  10                  15

Ala Gly Gln Ala Val Asn Ala Leu
            20

<210> SEQ ID NO 1326
<211> LENGTH: 20
<212> TYPE: PRT
<213> ORGANISM: Homo sapiens

<400> SEQUENCE: 1326

Val Leu His Cys Thr Lys Ser Cys Thr Cys His Lys Gln Cys Thr Tyr
1               5                  10                  15

Phe Lys Phe Tyr
            20

<210> SEQ ID NO 1327
<211> LENGTH: 25
<212> TYPE: PRT
```

<213> ORGANISM: Homo sapiens

<400> SEQUENCE: 1327

Met Leu Pro Ala Ala Thr Ala Ser Leu Leu Gly Pro Leu Leu Thr Ala
1               5                   10                  15

Cys Ala Leu Leu Pro Phe Ala Gln Gly
            20                  25

<210> SEQ ID NO 1328
<211> LENGTH: 23
<212> TYPE: PRT
<213> ORGANISM: Homo sapiens

<400> SEQUENCE: 1328

Met Met Gly Leu Phe Pro Arg Thr Thr Gly Ala Leu Ala Ile Phe Val
1               5                   10                  15

Val Val Ile Leu Val His Gly
            20

<210> SEQ ID NO 1329
<211> LENGTH: 21
<212> TYPE: PRT
<213> ORGANISM: Homo sapiens

<400> SEQUENCE: 1329

Met Trp Ser Trp Lys Cys Leu Leu Phe Trp Ala Val Leu Val Thr Ala
1               5                   10                  15

Thr Leu Cys Thr Ala
            20

<210> SEQ ID NO 1330
<211> LENGTH: 20
<212> TYPE: PRT
<213> ORGANISM: Homo sapiens

<400> SEQUENCE: 1330

Met Pro Arg Trp Leu Leu Leu Ser Leu Thr Phe Ala Gly Leu Phe Pro
1               5                   10                  15

Leu Arg Arg Arg
            20

<210> SEQ ID NO 1331
<211> LENGTH: 22
<212> TYPE: PRT
<213> ORGANISM: Homo sapiens

<400> SEQUENCE: 1331

Met Ala Lys Phe Gly Val His Arg Ile Leu Leu Leu Ala Ile Ser Leu
1               5                   10                  15

Thr Lys Cys Leu Glu Ser
            20

<210> SEQ ID NO 1332
<211> LENGTH: 21
<212> TYPE: PRT
<213> ORGANISM: Homo sapiens

<400> SEQUENCE: 1332

Met Phe Ser His Leu Pro Phe Asp Cys Val Leu Leu Leu Leu Leu Leu
1               5                   10                  15

Leu Leu Thr Arg Ser
            20

<210> SEQ ID NO 1333
<211> LENGTH: 22
<212> TYPE: PRT
<213> ORGANISM: Homo sapiens

<400> SEQUENCE: 1333

Met Asp Leu Pro Arg Gly Leu Val Val Ala Trp Ala Leu Ser Leu Trp
1               5                   10                  15

Pro Gly Phe Thr Asp Thr
            20

<210> SEQ ID NO 1334
<211> LENGTH: 21
<212> TYPE: PRT
<213> ORGANISM: Homo sapiens

<400> SEQUENCE: 1334

Met Lys Ser Pro Arg Arg Thr Thr Leu Cys Leu Met Phe Ile Val Ile
1               5                   10                  15

Tyr Ser Ser Lys Ala
            20

<210> SEQ ID NO 1335
<211> LENGTH: 23
<212> TYPE: PRT
<213> ORGANISM: Homo sapiens

<400> SEQUENCE: 1335

Met Met Pro Ala Gln Tyr Ala Leu Thr Ser Ser Leu Val Leu Leu Val
1               5                   10                  15

Leu Leu Ser Thr Ala Arg Ala
            20

<210> SEQ ID NO 1336
<211> LENGTH: 25
<212> TYPE: PRT
<213> ORGANISM: Homo sapiens

<400> SEQUENCE: 1336

Met Val Ser Ala Ala Ala Pro Ser Leu Leu Ile Leu Leu Leu Leu
1               5                   10                  15

Leu Gly Ser Val Pro Ala Thr Asp Ala
            20                  25

<210> SEQ ID NO 1337
<211> LENGTH: 24
<212> TYPE: PRT
<213> ORGANISM: Homo sapiens

<400> SEQUENCE: 1337

Met Arg Ser Arg Leu Pro Pro Ala Leu Ala Ala Leu Gly Ala Ala Leu
1               5                   10                  15

Leu Leu Ser Ser Ile Glu Ala Glu
            20

<210> SEQ ID NO 1338
<211> LENGTH: 24
<212> TYPE: PRT
<213> ORGANISM: Homo sapiens

<400> SEQUENCE: 1338

```
Met Glu Gln Arg Pro Arg Gly Cys Ala Ala Val Ala Ala Ala Leu Leu
1               5                   10                  15

Leu Val Leu Leu Gly Ala Arg Ala
            20
```

<210> SEQ ID NO 1339
<211> LENGTH: 23
<212> TYPE: PRT
<213> ORGANISM: Homo sapiens

<400> SEQUENCE: 1339

```
Met Ser Arg Leu Ser Arg Ser Leu Leu Trp Ala Ala Thr Cys Leu Gly
1               5                   10                  15

Val Leu Cys Val Leu Ser Ala
            20
```

<210> SEQ ID NO 1340
<211> LENGTH: 25
<212> TYPE: PRT
<213> ORGANISM: Homo sapiens

<400> SEQUENCE: 1340

```
Met Val Cys Ser Ala Ala Pro Leu Leu Leu Ala Thr Thr Leu Pro
1               5                   10                  15

Leu Leu Gly Ser Pro Val Ala Gln Ala
            20                  25
```

<210> SEQ ID NO 1341
<211> LENGTH: 22
<212> TYPE: PRT
<213> ORGANISM: Homo sapiens

<400> SEQUENCE: 1341

```
Met Ile Leu Asn Trp Lys Leu Leu Gly Ile Leu Val Leu Cys Leu His
1               5                   10                  15

Thr Arg Gly Ile Ser Gly
            20
```

<210> SEQ ID NO 1342
<211> LENGTH: 23
<212> TYPE: PRT
<213> ORGANISM: Homo sapiens

<400> SEQUENCE: 1342

```
Met Ala Pro Tyr Pro Cys Gly Cys His Ile Leu Leu Leu Leu Phe Cys
1               5                   10                  15

Cys Leu Ala Ala Ala Arg Ala
            20
```

<210> SEQ ID NO 1343
<211> LENGTH: 20
<212> TYPE: PRT
<213> ORGANISM: Homo sapiens

<400> SEQUENCE: 1343

```
Met Ile Ile Met Val Ile Ile Phe Leu Val Leu Leu Phe Trp Glu Asn
1               5                   10                  15

Glu Val Asn Asp
            20
```

<210> SEQ ID NO 1344
<211> LENGTH: 22

```
<212> TYPE: PRT
<213> ORGANISM: Homo sapiens

<400> SEQUENCE: 1344

Met Lys Leu His Ser Leu Ile Ser Val Leu Leu Phe Val Thr Leu
1               5                   10                  15

Ile Pro Lys Gly Lys Thr
            20

<210> SEQ ID NO 1345
<211> LENGTH: 22
<212> TYPE: PRT
<213> ORGANISM: Homo sapiens

<400> SEQUENCE: 1345

Met Ile Met Phe Pro Leu Phe Gly Lys Ile Ser Leu Gly Ile Leu Ile
1               5                   10                  15

Phe Val Leu Ile Glu Gly
            20

<210> SEQ ID NO 1346
<211> LENGTH: 23
<212> TYPE: PRT
<213> ORGANISM: Homo sapiens

<400> SEQUENCE: 1346

Met Thr Pro Ile Leu Thr Val Leu Ile Cys Leu Gly Leu Ser Leu Gly
1               5                   10                  15

Pro Arg Thr Arg Val Gln Ala
            20

<210> SEQ ID NO 1347
<211> LENGTH: 24
<212> TYPE: PRT
<213> ORGANISM: Homo sapiens

<400> SEQUENCE: 1347

Met Pro Ser Pro Pro Gly Leu Arg Ala Leu Trp Leu Cys Ala Ala Leu
1               5                   10                  15

Cys Ala Ser Arg Arg Ala Gly Gly
            20

<210> SEQ ID NO 1348
<211> LENGTH: 23
<212> TYPE: PRT
<213> ORGANISM: Homo sapiens

<400> SEQUENCE: 1348

Met Asn Leu Trp Leu Leu Ala Cys Leu Val Ala Gly Phe Leu Gly Ala
1               5                   10                  15

Trp Ala Pro Ala Val His Thr
            20

<210> SEQ ID NO 1349
<211> LENGTH: 24
<212> TYPE: PRT
<213> ORGANISM: Homo sapiens

<400> SEQUENCE: 1349

Met Arg Thr Gln Ser Leu Leu Leu Leu Gly Ala Leu Leu Ala Val Gly
1               5                   10                  15

Ser Gln Leu Pro Ala Val Phe Gly
```

20

<210> SEQ ID NO 1350
<211> LENGTH: 24
<212> TYPE: PRT
<213> ORGANISM: Homo sapiens

<400> SEQUENCE: 1350

Met Gly Arg Arg Met Arg Gly Ala Ala Thr Ala Gly Leu Trp Leu
1               5                   10                  15

Leu Ala Leu Gly Ser Leu Leu Ala
            20

<210> SEQ ID NO 1351
<211> LENGTH: 25
<212> TYPE: PRT
<213> ORGANISM: Homo sapiens

<400> SEQUENCE: 1351

Met Pro Arg Ala Thr Ala Leu Gly Ala Leu Val Ser Leu Leu Leu
1               5                   10                  15

Leu Pro Leu Pro Arg Gly Ala Gly Gly
            20                  25

<210> SEQ ID NO 1352
<211> LENGTH: 22
<212> TYPE: PRT
<213> ORGANISM: Homo sapiens

<400> SEQUENCE: 1352

Met Val Ala Arg Val Gly Leu Leu Leu Arg Ala Leu Gln Leu Leu
1               5                   10                  15

Trp Gly His Leu Asp Ala
            20

<210> SEQ ID NO 1353
<211> LENGTH: 23
<212> TYPE: PRT
<213> ORGANISM: Homo sapiens

<400> SEQUENCE: 1353

Met Asp Pro Gln Cys Thr Met Gly Leu Ser Asn Ile Leu Phe Val Met
1               5                   10                  15

Ala Phe Leu Leu Ser Gly Ala
            20

<210> SEQ ID NO 1354
<211> LENGTH: 23
<212> TYPE: PRT
<213> ORGANISM: Homo sapiens

<400> SEQUENCE: 1354

Met Ala Glu Thr Leu Phe Trp Thr Pro Leu Leu Val Val Leu Leu Ala
1               5                   10                  15

Gly Leu Gly Asp Thr Glu Ala
            20

<210> SEQ ID NO 1355
<211> LENGTH: 22
<212> TYPE: PRT
<213> ORGANISM: Homo sapiens

<400> SEQUENCE: 1355

```
Met Gly Pro Trp Ser Arg Ser Leu Ser Ala Leu Leu Leu Leu Gln
1               5                   10                  15

Val Ser Ser Trp Leu Cys
            20
```

<210> SEQ ID NO 1356
<211> LENGTH: 24
<212> TYPE: PRT
<213> ORGANISM: Homo sapiens

<400> SEQUENCE: 1356

```
Met Ala His Val Arg Gly Leu Gln Leu Pro Gly Cys Leu Ala Leu Ala
1               5                   10                  15

Ala Leu Cys Ser Leu Val His Ser
            20
```

<210> SEQ ID NO 1357
<211> LENGTH: 22
<212> TYPE: PRT
<213> ORGANISM: Homo sapiens

<400> SEQUENCE: 1357

```
Met Lys Leu Cys Ser Leu Ala Val Leu Val Pro Ile Val Leu Phe Cys
1               5                   10                  15

Glu Gln His Val Phe Ala
            20
```

<210> SEQ ID NO 1358
<211> LENGTH: 23
<212> TYPE: PRT
<213> ORGANISM: Homo sapiens

<400> SEQUENCE: 1358

```
Met Ala Ala Ala Leu Trp Gly Phe Phe Pro Val Leu Leu Leu Leu Leu
1               5                   10                  15

Leu Ser Gly Asp Val Gln Ser
            20
```

<210> SEQ ID NO 1359
<211> LENGTH: 22
<212> TYPE: PRT
<213> ORGANISM: Homo sapiens

<400> SEQUENCE: 1359

```
Met Ile Leu Gln Ala His Leu His Ser Leu Cys Leu Leu Met Leu Tyr
1               5                   10                  15

Leu Ala Thr Gly Tyr Gly
            20
```

<210> SEQ ID NO 1360
<211> LENGTH: 21
<212> TYPE: PRT
<213> ORGANISM: Homo sapiens

<400> SEQUENCE: 1360

```
Met Gln Ala Ala Cys Trp Tyr Val Leu Phe Leu Leu Gln Pro Thr Val
1               5                   10                  15

Tyr Leu Val Thr Cys
            20
```

<210> SEQ ID NO 1361

```
<211> LENGTH: 22
<212> TYPE: PRT
<213> ORGANISM: Homo sapiens

<400> SEQUENCE: 1361

Met Leu Gly Met Asn Met Leu Leu Ile Thr Leu Phe Leu Leu Leu Pro
1               5                   10                  15

Leu Ser Met Leu Lys Gly
            20

<210> SEQ ID NO 1362
<211> LENGTH: 21
<212> TYPE: PRT
<213> ORGANISM: Homo sapiens

<400> SEQUENCE: 1362

Met Ile Leu Ala Asn Val Phe Cys Leu Phe Phe Phe Leu Asp Glu Thr
1               5                   10                  15

Leu Arg Ser Leu Ala
            20

<210> SEQ ID NO 1363
<211> LENGTH: 25
<212> TYPE: PRT
<213> ORGANISM: Homo sapiens

<400> SEQUENCE: 1363

Met Ala Ala Val Arg Gly Ala Pro Leu Leu Ser Cys Leu Leu Ala Leu
1               5                   10                  15

Leu Ala Leu Cys Pro Gly Gly Arg Pro
            20                  25

<210> SEQ ID NO 1364
<211> LENGTH: 24
<212> TYPE: PRT
<213> ORGANISM: Homo sapiens

<400> SEQUENCE: 1364

Met Ala Gly Thr Val Arg Thr Ala Cys Leu Val Val Ala Met Leu Leu
1               5                   10                  15

Ser Leu Asp Phe Pro Gly Gln Ala
            20

<210> SEQ ID NO 1365
<211> LENGTH: 24
<212> TYPE: PRT
<213> ORGANISM: Homo sapiens

<400> SEQUENCE: 1365

Met Asp Leu Ile Arg Gly Val Leu Leu Arg Leu Leu Leu Leu Ala Ser
1               5                   10                  15

Ser Leu Gly Pro Gly Ala Val Ser
            20

<210> SEQ ID NO 1366
<211> LENGTH: 23
<212> TYPE: PRT
<213> ORGANISM: Homo sapiens

<400> SEQUENCE: 1366

Met Glu Thr Gly Ala Leu Arg Arg Pro Gln Leu Leu Pro Leu Leu Leu
1               5                   10                  15
```

Leu Leu Cys Gly Gly Cys Pro
            20

<210> SEQ ID NO 1367
<211> LENGTH: 21
<212> TYPE: PRT
<213> ORGANISM: Homo sapiens

<400> SEQUENCE: 1367

Met Glu Ser Trp Trp Gly Leu Pro Cys Leu Ala Phe Leu Cys Phe Leu
1               5                   10                  15

Met His Ala Arg Gly
            20

<210> SEQ ID NO 1368
<211> LENGTH: 22
<212> TYPE: PRT
<213> ORGANISM: Homo sapiens

<400> SEQUENCE: 1368

Met Gly Arg Val Gly Tyr Trp Thr Leu Leu Val Leu Pro Ala Leu Leu
1               5                   10                  15

Val Trp Arg Gly Pro Ala
            20

<210> SEQ ID NO 1369
<211> LENGTH: 24
<212> TYPE: PRT
<213> ORGANISM: Homo sapiens

<400> SEQUENCE: 1369

Met Leu Arg Lys Gly Cys Cys Val Glu Leu Leu Leu Leu Val Ala
1               5                   10                  15

Ala Glu Leu Pro Leu Gly Gly Gly
            20

<210> SEQ ID NO 1370
<211> LENGTH: 23
<212> TYPE: PRT
<213> ORGANISM: Homo sapiens

<400> SEQUENCE: 1370

Met Lys Gly Ser Arg Ala Leu Leu Leu Val Ala Leu Thr Leu Phe Cys
1               5                   10                  15

Ile Cys Arg Met Ala Thr Gly
            20

<210> SEQ ID NO 1371
<211> LENGTH: 23
<212> TYPE: PRT
<213> ORGANISM: Homo sapiens

<400> SEQUENCE: 1371

Met Gln Gly Leu Leu Phe Ser Thr Leu Leu Leu Ala Gly Leu Ala Gln
1               5                   10                  15

Phe Cys Cys Arg Val Gln Gly
            20

<210> SEQ ID NO 1372
<211> LENGTH: 23
<212> TYPE: PRT
<213> ORGANISM: Homo sapiens

```
<400> SEQUENCE: 1372

Met Pro Gly Arg Thr Trp Glu Leu Cys Leu Leu Leu Leu Gly Leu
1               5                   10                  15

Gly Leu Gly Ser Gln Glu Ala
            20

<210> SEQ ID NO 1373
<211> LENGTH: 24
<212> TYPE: PRT
<213> ORGANISM: Homo sapiens

<400> SEQUENCE: 1373

Met Ala Ser Asp Leu Ile Arg Thr Ile Leu Val Val Ala Leu Ile Ser
1               5                   10                  15

Lys Leu Gly Thr Ala Val Asp Ala
            20

<210> SEQ ID NO 1374
<211> LENGTH: 24
<212> TYPE: PRT
<213> ORGANISM: Homo sapiens

<400> SEQUENCE: 1374

Met Trp Cys Ala Ser Pro Val Ala Val Val Ala Phe Cys Ala Gly Leu
1               5                   10                  15

Leu Val Ser His Pro Val Leu Thr
            20

<210> SEQ ID NO 1375
<211> LENGTH: 22
<212> TYPE: PRT
<213> ORGANISM: Homo sapiens

<400> SEQUENCE: 1375

Met Leu Ile Asn Lys Leu Trp Leu Leu Leu Val Thr Leu Cys Leu Thr
1               5                   10                  15

Glu Glu Leu Ala Ala Ala
            20

<210> SEQ ID NO 1376
<211> LENGTH: 25
<212> TYPE: PRT
<213> ORGANISM: Homo sapiens

<400> SEQUENCE: 1376

Met Arg Gly Ala Ala Arg Leu Gly Arg Pro Gly Arg Ser Cys Leu Pro
1               5                   10                  15

Gly Pro Ala Leu Arg Ala Ala Ala Ala
            20                  25

<210> SEQ ID NO 1377
<211> LENGTH: 22
<212> TYPE: PRT
<213> ORGANISM: Homo sapiens

<400> SEQUENCE: 1377

Met Glu Arg Ile Val Ile Cys Leu Met Val Ile Phe Leu Gly Thr Leu
1               5                   10                  15

Val His Lys Ser Ser Ser
            20
```

```
<210> SEQ ID NO 1378
<211> LENGTH: 23
<212> TYPE: PRT
<213> ORGANISM: Homo sapiens

<400> SEQUENCE: 1378

Met Ser Pro Leu Trp Trp Gly Phe Leu Leu Ser Leu Gly Cys Lys
1               5                   10                  15

Ile Leu Pro Gly Ala Gln Gly
            20

<210> SEQ ID NO 1379
<211> LENGTH: 23
<212> TYPE: PRT
<213> ORGANISM: Homo sapiens

<400> SEQUENCE: 1379

Met Arg Pro Pro Gly Phe Arg Asn Phe Leu Leu Ala Ser Ser Leu
1               5                   10                  15

Leu Phe Ala Gly Leu Ser Ala
            20

<210> SEQ ID NO 1380
<211> LENGTH: 23
<212> TYPE: PRT
<213> ORGANISM: Homo sapiens

<400> SEQUENCE: 1380

Met Ser Pro Pro Leu Leu Lys Leu Gly Ala Val Leu Ser Thr Met Ala
1               5                   10                  15

Met Ile Ser Asn Trp Met Ser
            20

<210> SEQ ID NO 1381
<211> LENGTH: 22
<212> TYPE: PRT
<213> ORGANISM: Homo sapiens

<400> SEQUENCE: 1381

Met Arg Leu Arg Pro Leu Pro Leu Val Val Pro Gly Leu Leu Gln
1               5                   10                  15

Leu Leu Phe Cys Asp Ser
            20

<210> SEQ ID NO 1382
<211> LENGTH: 24
<212> TYPE: PRT
<213> ORGANISM: Homo sapiens

<400> SEQUENCE: 1382

Met Val Ser Val Pro Thr Thr Trp Cys Ser Val Ala Leu Ala Leu Leu
1               5                   10                  15

Val Ala Leu His Glu Gly Lys Gly
            20

<210> SEQ ID NO 1383
<211> LENGTH: 22
<212> TYPE: PRT
<213> ORGANISM: Homo sapiens

<400> SEQUENCE: 1383

Met Asp Arg Arg Met Trp Gly Ala His Val Phe Cys Val Leu Ser Pro
1               5                   10                  15
```

Leu Pro Thr Val Leu Gly
            20

<210> SEQ ID NO 1384
<211> LENGTH: 21
<212> TYPE: PRT
<213> ORGANISM: Homo sapiens

<400> SEQUENCE: 1384

Met Asn Lys His Phe Leu Phe Leu Phe Leu Leu Tyr Cys Leu Ile Val
1               5                   10                  15

Ala Val Thr Ser Leu
            20

<210> SEQ ID NO 1385
<211> LENGTH: 22
<212> TYPE: PRT
<213> ORGANISM: Homo sapiens

<400> SEQUENCE: 1385

Met Val Val Leu Asn Pro Met Thr Leu Gly Ile Tyr Leu Gln Leu Phe
1               5                   10                  15

Phe Leu Ser Ile Val Ser
            20

<210> SEQ ID NO 1386
<211> LENGTH: 23
<212> TYPE: PRT
<213> ORGANISM: Homo sapiens

<400> SEQUENCE: 1386

Met Ala Ile His Lys Ala Leu Val Met Cys Leu Gly Leu Pro Leu Phe
1               5                   10                  15

Leu Phe Pro Gly Ala Trp Ala
            20

<210> SEQ ID NO 1387
<211> LENGTH: 23
<212> TYPE: PRT
<213> ORGANISM: Homo sapiens

<400> SEQUENCE: 1387

Met Leu Leu Trp Val Gln Gln Ala Leu Leu Ala Leu Leu Leu Pro Thr
1               5                   10                  15

Leu Leu Ala Gln Gly Glu Ala
            20

<210> SEQ ID NO 1388
<211> LENGTH: 22
<212> TYPE: PRT
<213> ORGANISM: Homo sapiens

<400> SEQUENCE: 1388

Met Arg Arg Arg Leu Trp Leu Gly Leu Ala Trp Leu Leu Leu Ala Arg
1               5                   10                  15

Ala Pro Asp Ala Ala Gly
            20

<210> SEQ ID NO 1389
<211> LENGTH: 20
<212> TYPE: PRT
<213> ORGANISM: Homo sapiens

<400> SEQUENCE: 1389

Met Arg Lys Thr Arg Leu Trp Gly Leu Leu Trp Met Leu Phe Val Ser
1               5                   10                  15

Glu Leu Arg Ala
            20

<210> SEQ ID NO 1390
<211> LENGTH: 21
<212> TYPE: PRT
<213> ORGANISM: Homo sapiens

<400> SEQUENCE: 1390

Met Lys Phe Tyr Ser Leu Leu Leu Cys Ser Leu Leu Phe Ser Phe Pro
1               5                   10                  15

Phe Leu Cys His Pro
            20

<210> SEQ ID NO 1391
<211> LENGTH: 25
<212> TYPE: PRT
<213> ORGANISM: Homo sapiens

<400> SEQUENCE: 1391

Met Ala Val Glu Ser Gln Gly Gly Arg Pro Leu Val Leu Gly Leu Leu
1               5                   10                  15

Leu Cys Val Leu Gly Pro Val Val Ser
            20                  25

<210> SEQ ID NO 1392
<211> LENGTH: 24
<212> TYPE: PRT
<213> ORGANISM: Homo sapiens

<400> SEQUENCE: 1392

Met Lys Ala Pro Ala Val Leu Ala Pro Gly Ile Leu Val Leu Leu Phe
1               5                   10                  15

Thr Leu Val Gln Arg Ser Asn Gly
            20

<210> SEQ ID NO 1393
<211> LENGTH: 21
<212> TYPE: PRT
<213> ORGANISM: Homo sapiens

<400> SEQUENCE: 1393

Met Lys Leu Leu Lys Leu Thr Gly Phe Ile Phe Phe Leu Phe Phe Leu
1               5                   10                  15

Thr Glu Ser Leu Thr
            20

<210> SEQ ID NO 1394
<211> LENGTH: 23
<212> TYPE: PRT
<213> ORGANISM: Homo sapiens

<400> SEQUENCE: 1394

Met Arg Gly Ser Gln Glu Val Leu Leu Met Trp Leu Leu Val Leu Ala
1               5                   10                  15

Val Gly Gly Thr Glu His Ala
            20

```
<210> SEQ ID NO 1395
<211> LENGTH: 22
<212> TYPE: PRT
<213> ORGANISM: Homo sapiens

<400> SEQUENCE: 1395

Met Lys Met Leu Thr Arg Leu Gln Val Leu Thr Ala Leu Phe Ser
1               5                   10                  15

Lys Gly Phe Leu Leu Ser
            20

<210> SEQ ID NO 1396
<211> LENGTH: 26
<212> TYPE: PRT
<213> ORGANISM: Homo sapiens

<400> SEQUENCE: 1396

Met Ala Ala Ala Thr Arg Gly Cys Arg Pro Trp Gly Ser Leu Leu Gly
1               5                   10                  15

Leu Leu Gly Leu Val Ser Ala Ala Ala Ala
            20                  25

<210> SEQ ID NO 1397
<211> LENGTH: 26
<212> TYPE: PRT
<213> ORGANISM: Homo sapiens

<400> SEQUENCE: 1397

Met Ala Ala Ala Thr Arg Gly Cys Arg Pro Trp Gly Ser Leu Leu Gly
1               5                   10                  15

Leu Leu Gly Leu Val Ser Ala Ala Ala Ala
            20                  25

<210> SEQ ID NO 1398
<211> LENGTH: 25
<212> TYPE: PRT
<213> ORGANISM: Homo sapiens

<400> SEQUENCE: 1398

Met Gly Ala Pro Ser Ala Cys Arg Thr Leu Val Leu Ala Leu Ala Ala
1               5                   10                  15

Met Leu Val Val Pro Gln Ala Glu Thr
            20                  25

<210> SEQ ID NO 1399
<211> LENGTH: 24
<212> TYPE: PRT
<213> ORGANISM: Homo sapiens

<400> SEQUENCE: 1399

Met Ala Gly Leu Gly Ala Ser Leu His Val Trp Gly Trp Leu Met Leu
1               5                   10                  15

Gly Ser Cys Leu Leu Ala Arg Ala
            20

<210> SEQ ID NO 1400
<211> LENGTH: 24
<212> TYPE: PRT
<213> ORGANISM: Homo sapiens

<400> SEQUENCE: 1400

Met Ala Ser Leu Gly Gln Ile Leu Phe Trp Ser Ile Ile Ser Ile Ile
```

```
1               5                  10                 15
Ile Ile Leu Ala Gly Ala Ile Ala
            20

<210> SEQ ID NO 1401
<211> LENGTH: 23
<212> TYPE: PRT
<213> ORGANISM: Homo sapiens

<400> SEQUENCE: 1401

Met Gly Gln Leu Cys Trp Leu Pro Leu Leu Ala Pro Leu Leu Leu Leu
1               5                  10                 15

Arg Pro Pro Gly Val Gln Ser
            20

<210> SEQ ID NO 1402
<211> LENGTH: 21
<212> TYPE: PRT
<213> ORGANISM: Homo sapiens

<400> SEQUENCE: 1402

Met Cys Leu Thr Asp Glu Trp Gly Phe Leu Phe Phe Phe Phe Phe Leu
1               5                  10                 15

Gly Val Pro Glu Ala
            20

<210> SEQ ID NO 1403
<211> LENGTH: 22
<212> TYPE: PRT
<213> ORGANISM: Homo sapiens

<400> SEQUENCE: 1403

Met Arg Thr His Thr Arg Gly Ala Pro Ser Val Phe Phe Ile Tyr Leu
1               5                  10                 15

Leu Cys Phe Val Ser Ala
            20

<210> SEQ ID NO 1404
<211> LENGTH: 23
<212> TYPE: PRT
<213> ORGANISM: Homo sapiens

<400> SEQUENCE: 1404

Met Ser Asp Leu Leu Ser Ile Tyr Ser Ala Pro Val Val Val Ser Thr
1               5                  10                 15

Val Leu His Met Leu Gln Ile
            20

<210> SEQ ID NO 1405
<211> LENGTH: 22
<212> TYPE: PRT
<213> ORGANISM: Homo sapiens

<400> SEQUENCE: 1405

Met Phe Leu Ser Lys Pro Ser Val Tyr Ile Cys Leu Phe Thr Cys Val
1               5                  10                 15

Leu Gln Leu Ser His Ser
            20

<210> SEQ ID NO 1406
<211> LENGTH: 20
<212> TYPE: PRT
```

<213> ORGANISM: Homo sapiens

<400> SEQUENCE: 1406

Met Tyr Leu Glu Thr Arg Arg Ala Ile Phe Val Phe Trp Ile Phe Leu
1               5                   10                  15

Gln Val Gln Gly
            20

<210> SEQ ID NO 1407
<211> LENGTH: 24
<212> TYPE: PRT
<213> ORGANISM: Homo sapiens

<400> SEQUENCE: 1407

Met Pro Arg Lys Gln Pro Ala Gly Cys Ile Phe Leu Leu Thr Phe Leu
1               5                   10                  15

Gly Leu Ser Gly Leu Val Gly Thr
            20

<210> SEQ ID NO 1408
<211> LENGTH: 22
<212> TYPE: PRT
<213> ORGANISM: Homo sapiens

<400> SEQUENCE: 1408

Met Arg Pro Arg Arg Pro Leu Val Phe Met Ser Leu Val Cys Ala Leu
1               5                   10                  15

Leu Asn Thr Cys Gln Ala
            20

<210> SEQ ID NO 1409
<211> LENGTH: 21
<212> TYPE: PRT
<213> ORGANISM: Homo sapiens

<400> SEQUENCE: 1409

Met Asp Pro Lys Tyr Phe Ile Leu Ile Leu Phe Cys Gly His Leu Asn
1               5                   10                  15

Asn Thr Phe Phe Ser
            20

<210> SEQ ID NO 1410
<211> LENGTH: 23
<212> TYPE: PRT
<213> ORGANISM: Homo sapiens

<400> SEQUENCE: 1410

Met Arg Gly His Pro Ser Leu Leu Leu Leu Tyr Met Ala Leu Thr Thr
1               5                   10                  15

Cys Leu Asp Thr Ser Pro Ser
            20

<210> SEQ ID NO 1411
<211> LENGTH: 23
<212> TYPE: PRT
<213> ORGANISM: Homo sapiens

<400> SEQUENCE: 1411

Met Gly Tyr Cys Gln Gly Val Ser Gln Val Ala Val Val Leu Leu Met
1               5                   10                  15

Phe Pro Lys Glu Lys Glu Ala
            20

<210> SEQ ID NO 1412
<211> LENGTH: 23
<212> TYPE: PRT
<213> ORGANISM: Homo sapiens

<400> SEQUENCE: 1412

Met Gly Gly Arg Val Phe Leu Val Phe Leu Ala Phe Cys Val Trp Leu
1               5                   10                  15

Thr Leu Pro Gly Ala Glu Thr
            20

<210> SEQ ID NO 1413
<211> LENGTH: 24
<212> TYPE: PRT
<213> ORGANISM: Homo sapiens

<400> SEQUENCE: 1413

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 1414
<211> LENGTH: 24
<212> TYPE: PRT
<213> ORGANISM: Homo sapiens

<400> SEQUENCE: 1414

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 1415
<211> LENGTH: 24
<212> TYPE: PRT
<213> ORGANISM: Homo sapiens

<400> SEQUENCE: 1415

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 1416
<211> LENGTH: 24
<212> TYPE: PRT
<213> ORGANISM: Homo sapiens

<400> SEQUENCE: 1416

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 1417
<211> LENGTH: 24
<212> TYPE: PRT
<213> ORGANISM: Homo sapiens

<400> SEQUENCE: 1417

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 1418
<211> LENGTH: 24
<212> TYPE: PRT
<213> ORGANISM: Homo sapiens

<400> SEQUENCE: 1418

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 1419
<211> LENGTH: 24
<212> TYPE: PRT
<213> ORGANISM: Homo sapiens

<400> SEQUENCE: 1419

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 1420
<211> LENGTH: 24
<212> TYPE: PRT
<213> ORGANISM: Homo sapiens

<400> SEQUENCE: 1420

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 1421
<211> LENGTH: 24
<212> TYPE: PRT
<213> ORGANISM: Homo sapiens

<400> SEQUENCE: 1421

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 1422
<211> LENGTH: 24
<212> TYPE: PRT
<213> ORGANISM: Homo sapiens

<400> SEQUENCE: 1422

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 1423
<211> LENGTH: 24

```
<212> TYPE: PRT
<213> ORGANISM: Homo sapiens

<400> SEQUENCE: 1423

Met Ala Val Met Ala Pro Arg Thr Leu Val Leu Leu Ser Gly Ala
1               5                   10                  15

Leu Ala Leu Thr Gln Thr Trp Ala
            20

<210> SEQ ID NO 1424
<211> LENGTH: 24
<212> TYPE: PRT
<213> ORGANISM: Homo sapiens

<400> SEQUENCE: 1424

Met Ala Val Met Ala Pro Arg Thr Leu Val Leu Leu Ser Gly Ala
1               5                   10                  15

Leu Ala Leu Thr Gln Thr Trp Ala
            20

<210> SEQ ID NO 1425
<211> LENGTH: 22
<212> TYPE: PRT
<213> ORGANISM: Homo sapiens

<400> SEQUENCE: 1425

Met Arg Ile Ala Val Leu Leu Phe Ala Ile Phe Phe Phe Met Ser Gln
1               5                   10                  15

Val Leu Pro Ala Arg Gly
            20

<210> SEQ ID NO 1426
<211> LENGTH: 22
<212> TYPE: PRT
<213> ORGANISM: Homo sapiens

<400> SEQUENCE: 1426

Met Arg Ile Ala Val Leu Leu Phe Ala Ile Phe Phe Phe Met Ser Gln
1               5                   10                  15

Val Leu Pro Ala Arg Gly
            20

<210> SEQ ID NO 1427
<211> LENGTH: 22
<212> TYPE: PRT
<213> ORGANISM: Homo sapiens

<400> SEQUENCE: 1427

Met Trp His Leu Lys Leu Cys Ala Val Leu Met Ile Phe Leu Leu Leu
1               5                   10                  15

Leu Gly Gln Ile Asp Gly
            20

<210> SEQ ID NO 1428
<211> LENGTH: 25
<212> TYPE: PRT
<213> ORGANISM: Homo sapiens

<400> SEQUENCE: 1428

Met Glu Pro Arg Ala Leu Val Thr Ala Leu Ser Leu Gly Leu Ser Leu
1               5                   10                  15

Cys Ser Leu Gly Leu Leu Val Thr Ala
```

```
            20                  25

<210> SEQ ID NO 1429
<211> LENGTH: 22
<212> TYPE: PRT
<213> ORGANISM: Homo sapiens

<400> SEQUENCE: 1429

Met Arg Leu His Leu Leu Leu Ile Leu Leu Leu Phe Ser Ile Leu
1               5                   10                  15

Leu Ser Pro Val Arg Gly
            20

<210> SEQ ID NO 1430
<211> LENGTH: 24
<212> TYPE: PRT
<213> ORGANISM: Homo sapiens

<400> SEQUENCE: 1430

Met Leu Ser Gln Leu Ala Met Leu Gln Gly Ser Leu Leu Leu Val Val
1               5                   10                  15

Ala Thr Met Ser Val Ala Gln Gln
            20

<210> SEQ ID NO 1431
<211> LENGTH: 25
<212> TYPE: PRT
<213> ORGANISM: Homo sapiens

<400> SEQUENCE: 1431

Met Pro Ala Gly Val Pro Met Ser Thr Tyr Leu Lys Met Phe Ala Ala
1               5                   10                  15

Ser Leu Leu Ala Met Cys Ala Gly Ala
            20                  25

<210> SEQ ID NO 1432
<211> LENGTH: 23
<212> TYPE: PRT
<213> ORGANISM: Homo sapiens

<400> SEQUENCE: 1432

Met Gln Ser Pro Trp Lys Ile Leu Thr Val Ala Pro Leu Phe Leu Leu
1               5                   10                  15

Leu Ser Leu Gln Ser Ser Ala
            20

<210> SEQ ID NO 1433
<211> LENGTH: 23
<212> TYPE: PRT
<213> ORGANISM: Homo sapiens

<400> SEQUENCE: 1433

Met Gln Pro Pro Ser Leu Leu Leu Leu Leu Leu Leu Leu Leu Leu Leu
1               5                   10                  15

Cys Val Ser Val Val Arg Pro
            20

<210> SEQ ID NO 1434
<211> LENGTH: 22
<212> TYPE: PRT
<213> ORGANISM: Homo sapiens

<400> SEQUENCE: 1434
```

Met Arg Thr Pro Gln Leu Ala Leu Leu Gln Val Phe Phe Leu Val Phe
1               5                   10                  15

Pro Asp Gly Val Arg Pro
            20

<210> SEQ ID NO 1435
<211> LENGTH: 24
<212> TYPE: PRT
<213> ORGANISM: Homo sapiens

<400> SEQUENCE: 1435

Met Ala Arg Gln Pro Pro Pro Trp Val His Ala Ala Phe Leu Leu
1               5                   10                  15

Cys Leu Leu Ser Leu Gly Gly Ala
            20

<210> SEQ ID NO 1436
<211> LENGTH: 21
<212> TYPE: PRT
<213> ORGANISM: Homo sapiens

<400> SEQUENCE: 1436

Met Gln Phe Arg Leu Phe Ser Phe Ala Leu Ile Ile Leu Asn Cys Met
1               5                   10                  15

Asp Tyr Ser His Cys
            20

<210> SEQ ID NO 1437
<211> LENGTH: 25
<212> TYPE: PRT
<213> ORGANISM: Homo sapiens

<400> SEQUENCE: 1437

Met Gly Ser Arg Gly Gln Gly Leu Leu Leu Ala Tyr Cys Leu Leu Leu
1               5                   10                  15

Ala Phe Ala Ser Gly Leu Val Leu Ser
            20                  25

<210> SEQ ID NO 1438
<211> LENGTH: 24
<212> TYPE: PRT
<213> ORGANISM: Homo sapiens

<400> SEQUENCE: 1438

Met Phe Leu Ala Thr Leu Tyr Phe Ala Leu Pro Leu Leu Asp Leu Leu
1               5                   10                  15

Leu Ser Ala Glu Val Ser Gly Gly
            20

<210> SEQ ID NO 1439
<211> LENGTH: 22
<212> TYPE: PRT
<213> ORGANISM: Homo sapiens

<400> SEQUENCE: 1439

Met Gln Arg Leu Val Leu Leu Leu Ala Ile Ser Leu Leu Leu Tyr Gln
1               5                   10                  15

Asp Leu Pro Val Arg Ser
            20

<210> SEQ ID NO 1440

-continued

```
<211> LENGTH: 23
<212> TYPE: PRT
<213> ORGANISM: Homo sapiens

<400> SEQUENCE: 1440

Met Arg Leu Trp Lys Ala Val Val Thr Leu Ala Phe Met Ser Val
1               5                   10                  15

Asp Ile Cys Val Thr Thr Ala
            20

<210> SEQ ID NO 1441
<211> LENGTH: 25
<212> TYPE: PRT
<213> ORGANISM: Homo sapiens

<400> SEQUENCE: 1441

Met Arg Lys Pro Ala Ala Gly Phe Leu Pro Ser Leu Leu Lys Val Leu
1               5                   10                  15

Leu Leu Pro Leu Ala Pro Ala Ala Ala
            20                  25

<210> SEQ ID NO 1442
<211> LENGTH: 25
<212> TYPE: PRT
<213> ORGANISM: Homo sapiens

<400> SEQUENCE: 1442

Met Gln Ala Ala Val Ala Val Ser Val Pro Phe Leu Leu Leu Cys Val
1               5                   10                  15

Leu Gly Thr Cys Pro Pro Ala Arg Cys
            20                  25

<210> SEQ ID NO 1443
<211> LENGTH: 24
<212> TYPE: PRT
<213> ORGANISM: Homo sapiens

<400> SEQUENCE: 1443

Met Ser Arg Leu Arg Ala Leu Leu Gly Leu Gly Leu Leu Val Ala Gly
1               5                   10                  15

Ser Arg Val Pro Arg Ile Lys Ser
            20

<210> SEQ ID NO 1444
<211> LENGTH: 22
<212> TYPE: PRT
<213> ORGANISM: Homo sapiens

<400> SEQUENCE: 1444

Met Arg Ile Ala Val Leu Phe Phe Thr Ile Phe Phe Phe Met Ser Gln
1               5                   10                  15

Val Leu Pro Ala Lys Gly
            20

<210> SEQ ID NO 1445
<211> LENGTH: 25
<212> TYPE: PRT
<213> ORGANISM: Homo sapiens

<400> SEQUENCE: 1445

Met Leu Pro Cys Ala Ser Cys Leu Pro Gly Ser Leu Leu Leu Trp Ala
1               5                   10                  15
```

```
Leu Leu Leu Leu Leu Gly Ser Ala
            20                  25

<210> SEQ ID NO 1446
<211> LENGTH: 23
<212> TYPE: PRT
<213> ORGANISM: Homo sapiens

<400> SEQUENCE: 1446

Met Lys Pro Trp Ile Leu Leu Leu Val Met Phe Ile Ser Gly Val Val
1               5                   10                  15

Met Leu Leu Pro Val Leu Gly
            20

<210> SEQ ID NO 1447
<211> LENGTH: 27
<212> TYPE: PRT
<213> ORGANISM: Homo sapiens

<400> SEQUENCE: 1447

Met Thr Arg Gly Arg Ala Trp Gly Met Arg Arg Ala Ala Ala Gly Ala
1               5                   10                  15

Gly Gly Ala Arg Ala Ala Gly Pro Thr Gly Gly
            20                  25

<210> SEQ ID NO 1448
<211> LENGTH: 23
<212> TYPE: PRT
<213> ORGANISM: Homo sapiens

<400> SEQUENCE: 1448

Met Ser Arg Lys Ile Glu Gly Phe Leu Leu Leu Leu Phe Gly Tyr
1               5                   10                  15

Glu Ala Thr Leu Gly Leu Ser
            20

<210> SEQ ID NO 1449
<211> LENGTH: 23
<212> TYPE: PRT
<213> ORGANISM: Homo sapiens

<400> SEQUENCE: 1449

Met Pro Pro Phe Leu Leu Leu Glu Ala Val Cys Val Phe Leu Phe Ser
1               5                   10                  15

Arg Val Pro Pro Ser Leu Pro
            20

<210> SEQ ID NO 1450
<211> LENGTH: 24
<212> TYPE: PRT
<213> ORGANISM: Homo sapiens

<400> SEQUENCE: 1450

Met Gly Val Arg Val His Val Val Ala Ala Ser Ala Leu Leu Tyr Phe
1               5                   10                  15

Ile Leu Leu Ser Gly Thr Arg Cys
            20

<210> SEQ ID NO 1451
<211> LENGTH: 24
<212> TYPE: PRT
<213> ORGANISM: Homo sapiens
```

```
<400> SEQUENCE: 1451

Met Val Leu Ala Ala Pro Leu Leu Gly Phe Leu Leu Ala Leu
1               5                   10                  15

Glu Leu Arg Pro Arg Gly Glu Ala
            20

<210> SEQ ID NO 1452
<211> LENGTH: 23
<212> TYPE: PRT
<213> ORGANISM: Homo sapiens

<400> SEQUENCE: 1452

Met Met Ala Gly Met Lys Ile Gln Leu Val Cys Met Leu Leu Leu Ala
1               5                   10                  15

Phe Ser Ser Trp Ser Leu Cys
            20

<210> SEQ ID NO 1453
<211> LENGTH: 25
<212> TYPE: PRT
<213> ORGANISM: Homo sapiens

<400> SEQUENCE: 1453

Met Pro Arg Pro Gly Thr Met Ala Leu Cys Leu Leu Thr Leu Val Leu
1               5                   10                  15

Ser Leu Leu Pro Pro Gln Ala Ala Ala
            20                  25

<210> SEQ ID NO 1454
<211> LENGTH: 24
<212> TYPE: PRT
<213> ORGANISM: Homo sapiens

<400> SEQUENCE: 1454

Met Met Gln Leu Leu Gln Leu Leu Gly Leu Gly Pro Gly Gly
1               5                   10                  15

Tyr Leu Phe Leu Leu Gly Asp Cys
            20

<210> SEQ ID NO 1455
<211> LENGTH: 23
<212> TYPE: PRT
<213> ORGANISM: Homo sapiens

<400> SEQUENCE: 1455

Met Arg Glu Leu Val Asn Ile Pro Leu Val His Ile Leu Thr Leu Val
1               5                   10                  15

Ala Phe Ser Gly Thr Glu Lys
            20

<210> SEQ ID NO 1456
<211> LENGTH: 23
<212> TYPE: PRT
<213> ORGANISM: Homo sapiens

<400> SEQUENCE: 1456

Met Ala Ala Phe Pro His Lys Ile Ile Phe Phe Leu Val Cys Ser Thr
1               5                   10                  15

Leu Thr His Val Ala Phe Ser
            20
```

```
<210> SEQ ID NO 1457
<211> LENGTH: 25
<212> TYPE: PRT
<213> ORGANISM: Homo sapiens

<400> SEQUENCE: 1457

Met Arg Gln Ala Gly Arg Ala Ala Leu Leu Ala Leu Leu Leu Leu
1               5                   10                  15

Val Gln Leu Cys Pro Gly Ser Ser Gln
            20                  25

<210> SEQ ID NO 1458
<211> LENGTH: 25
<212> TYPE: PRT
<213> ORGANISM: Homo sapiens

<400> SEQUENCE: 1458

Met Lys Leu Asp Met Thr Gly Asp Cys Met Pro Val Leu Val Met
1               5                   10                  15

Ala Ala Val Leu Thr Val Thr Gly Ala
            20                  25

<210> SEQ ID NO 1459
<211> LENGTH: 25
<212> TYPE: PRT
<213> ORGANISM: Homo sapiens

<400> SEQUENCE: 1459

Met Ala Pro Leu Leu Pro Ile Arg Thr Leu Pro Leu Ile Leu Ile
1               5                   10                  15

Leu Ala Leu Leu Ser Pro Gly Ala Ala
            20                  25

<210> SEQ ID NO 1460
<211> LENGTH: 25
<212> TYPE: PRT
<213> ORGANISM: Homo sapiens

<400> SEQUENCE: 1460

Met Ala Leu Ala Arg Gly Ser Arg Gln Leu Gly Ala Leu Val Trp Gly
1               5                   10                  15

Ala Cys Leu Cys Val Leu Val His Gly
            20                  25

<210> SEQ ID NO 1461
<211> LENGTH: 23
<212> TYPE: PRT
<213> ORGANISM: Homo sapiens

<400> SEQUENCE: 1461

Met Trp Met Phe Ser Trp Leu Cys Ala Ile Leu Ile Ile Leu Ala Ile
1               5                   10                  15

Ala Gly Met Asn Thr Ile Ala
            20

<210> SEQ ID NO 1462
<211> LENGTH: 23
<212> TYPE: PRT
<213> ORGANISM: Homo sapiens

<400> SEQUENCE: 1462

Met Asp Ile Leu Val Pro Leu Leu Gln Leu Leu Val Leu Leu Leu Thr
1               5                   10                  15
```

Leu Pro Leu His Leu Met Ala
            20

<210> SEQ ID NO 1463
<211> LENGTH: 24
<212> TYPE: PRT
<213> ORGANISM: Homo sapiens

<400> SEQUENCE: 1463

Met Arg Val Thr Ala Pro Arg Thr Val Leu Leu Leu Leu Ser Gly Ala
1               5                   10                  15

Leu Ala Leu Thr Glu Thr Trp Ala
            20

<210> SEQ ID NO 1464
<211> LENGTH: 24
<212> TYPE: PRT
<213> ORGANISM: Homo sapiens

<400> SEQUENCE: 1464

Met Arg Val Thr Ala Pro Arg Thr Val Leu Leu Leu Leu Ser Gly Ala
1               5                   10                  15

Leu Ala Leu Thr Glu Thr Trp Ala
            20

<210> SEQ ID NO 1465
<211> LENGTH: 24
<212> TYPE: PRT
<213> ORGANISM: Homo sapiens

<400> SEQUENCE: 1465

Met Arg Val Thr Ala Pro Arg Thr Val Leu Leu Leu Leu Ser Gly Ala
1               5                   10                  15

Leu Ala Leu Thr Glu Thr Trp Ala
            20

<210> SEQ ID NO 1466
<211> LENGTH: 24
<212> TYPE: PRT
<213> ORGANISM: Homo sapiens

<400> SEQUENCE: 1466

Met Arg Val Thr Ala Pro Arg Thr Val Leu Leu Leu Leu Ser Gly Ala
1               5                   10                  15

Leu Ala Leu Thr Glu Thr Trp Ala
            20

<210> SEQ ID NO 1467
<211> LENGTH: 24
<212> TYPE: PRT
<213> ORGANISM: Homo sapiens

<400> SEQUENCE: 1467

Met Arg Val Met Ala Pro Arg Ala Leu Leu Leu Leu Leu Ser Gly Gly
1               5                   10                  15

Leu Ala Leu Thr Glu Thr Trp Ala
            20

<210> SEQ ID NO 1468
<211> LENGTH: 24
<212> TYPE: PRT
<213> ORGANISM: Homo sapiens

<400> SEQUENCE: 1468

Met Arg Val Met Ala Pro Arg Ala Leu Leu Leu Leu Ser Gly Gly
1               5                   10                  15

Leu Ala Leu Thr Glu Thr Trp Ala
            20

<210> SEQ ID NO 1469
<211> LENGTH: 24
<212> TYPE: PRT
<213> ORGANISM: Homo sapiens

<400> SEQUENCE: 1469

Met Arg Val Met Ala Pro Arg Ala Leu Leu Leu Leu Ser Gly Gly
1               5                   10                  15

Leu Ala Leu Thr Glu Thr Trp Ala
            20

<210> SEQ ID NO 1470
<211> LENGTH: 24
<212> TYPE: PRT
<213> ORGANISM: Homo sapiens

<400> SEQUENCE: 1470

Met Arg Val Met Ala Pro Arg Ala Leu Leu Leu Leu Ser Gly Gly
1               5                   10                  15

Leu Ala Leu Thr Glu Thr Trp Ala
            20

<210> SEQ ID NO 1471
<211> LENGTH: 26
<212> TYPE: PRT
<213> ORGANISM: Homo sapiens

<400> SEQUENCE: 1471

Met Gly Ala Ser Arg Asp Arg Gly Leu Ala Ala Leu Trp Cys Leu Gly
1               5                   10                  15

Leu Leu Gly Gly Leu Ala Arg Val Ala Gly
            20                  25

<210> SEQ ID NO 1472
<211> LENGTH: 25
<212> TYPE: PRT
<213> ORGANISM: Homo sapiens

<400> SEQUENCE: 1472

Met Ala Val Met Ala Pro Arg Thr Leu Val Leu Leu Leu Ser Gly Ala
1               5                   10                  15

Leu Ala Leu Thr Gln Thr Trp Ala Gly
            20                  25

<210> SEQ ID NO 1473
<211> LENGTH: 25
<212> TYPE: PRT
<213> ORGANISM: Homo sapiens

<400> SEQUENCE: 1473

Met Ala Val Met Ala Pro Arg Thr Leu Val Leu Leu Leu Ser Gly Ala
1               5                   10                  15

Leu Ala Leu Thr Gln Thr Trp Ala Gly
            20                  25

<210> SEQ ID NO 1474
<211> LENGTH: 25
<212> TYPE: PRT
<213> ORGANISM: Homo sapiens

<400> SEQUENCE: 1474

Met Ala Val Met Ala Pro Arg Thr Leu Val Leu Leu Leu Ser Gly Ala
1               5                   10                  15

Leu Ala Leu Thr Gln Thr Trp Ala Gly
            20                  25

<210> SEQ ID NO 1475
<211> LENGTH: 25
<212> TYPE: PRT
<213> ORGANISM: Homo sapiens

<400> SEQUENCE: 1475

Met Glu Ala Cys Cys Leu Leu Gln Leu Pro Gln Arg Leu Leu Leu Leu
1               5                   10                  15

Gly Ala Ala Ala Leu Thr Ala Thr Ala
            20                  25

<210> SEQ ID NO 1476
<211> LENGTH: 24
<212> TYPE: PRT
<213> ORGANISM: Homo sapiens

<400> SEQUENCE: 1476

Met Leu Val Met Ala Pro Arg Thr Val Leu Leu Leu Leu Ser Ala Ala
1               5                   10                  15

Leu Ala Leu Thr Glu Thr Trp Ala
            20

<210> SEQ ID NO 1477
<211> LENGTH: 24
<212> TYPE: PRT
<213> ORGANISM: Homo sapiens

<400> SEQUENCE: 1477

Met Leu Val Met Ala Pro Arg Thr Val Leu Leu Leu Leu Ser Ala Ala
1               5                   10                  15

Leu Ala Leu Thr Glu Thr Trp Ala
            20

<210> SEQ ID NO 1478
<211> LENGTH: 24
<212> TYPE: PRT
<213> ORGANISM: Homo sapiens

<400> SEQUENCE: 1478

Met Leu Val Met Ala Pro Arg Thr Val Leu Leu Leu Leu Ser Ala Ala
1               5                   10                  15

Leu Ala Leu Thr Glu Thr Trp Ala
            20

<210> SEQ ID NO 1479
<211> LENGTH: 24
<212> TYPE: PRT
<213> ORGANISM: Homo sapiens

<400> SEQUENCE: 1479

Met Leu Val Met Ala Pro Arg Thr Val Leu Leu Leu Leu Ser Ala Ala
1               5                   10                  15

-continued

```
                1               5                   10                  15
Leu Ala Leu Thr Glu Thr Trp Ala
            20

<210> SEQ ID NO 1480
<211> LENGTH: 24
<212> TYPE: PRT
<213> ORGANISM: Homo sapiens

<400> SEQUENCE: 1480

Met Leu Val Met Ala Pro Arg Thr Val Leu Leu Leu Ser Ala Ala
1               5                   10                  15

Leu Ala Leu Thr Glu Thr Trp Ala
            20

<210> SEQ ID NO 1481
<211> LENGTH: 24
<212> TYPE: PRT
<213> ORGANISM: Homo sapiens

<400> SEQUENCE: 1481

Met Ala Leu Lys Trp Thr Ser Val Leu Leu Ile His Leu Gly Cys
1               5                   10                  15

Tyr Phe Ser Ser Gly Ser Cys Gly
            20

<210> SEQ ID NO 1482
<211> LENGTH: 27
<212> TYPE: PRT
<213> ORGANISM: Homo sapiens

<400> SEQUENCE: 1482

Met Gly Ser Gly Gly Asp Ser Leu Leu Gly Gly Arg Gly Ser Leu Pro
1               5                   10                  15

Leu Leu Leu Leu Leu Ile Met Gly Gly Met Ala
            20                  25

<210> SEQ ID NO 1483
<211> LENGTH: 27
<212> TYPE: PRT
<213> ORGANISM: Homo sapiens

<400> SEQUENCE: 1483

Met Ala Gly Ala Gly Gly Gly Leu Gly Val Trp Gly Asn Leu Val Leu
1               5                   10                  15

Leu Gly Leu Cys Ser Trp Thr Gly Ala Arg Ala
            20                  25

<210> SEQ ID NO 1484
<211> LENGTH: 24
<212> TYPE: PRT
<213> ORGANISM: Homo sapiens

<400> SEQUENCE: 1484

Met His Val Ala Glu Val Ala Val Asn Val Ile Leu Leu Leu Ser Met
1               5                   10                  15

Gly Trp Thr Ser Asp Ser Leu Cys
            20

<210> SEQ ID NO 1485
<211> LENGTH: 23
<212> TYPE: PRT
```

<213> ORGANISM: Homo sapiens

<400> SEQUENCE: 1485

Met Leu Thr Arg Asn Cys Leu Ser Leu Leu Leu Trp Val Leu Phe Asp
1               5                   10                  15

Gly Gly Leu Leu Thr Pro Leu
            20

<210> SEQ ID NO 1486
<211> LENGTH: 24
<212> TYPE: PRT
<213> ORGANISM: Homo sapiens

<400> SEQUENCE: 1486

Met Ala Pro Ala Gln Arg Pro Leu Leu Pro Leu Leu Leu Leu Leu Leu
1               5                   10                  15

Pro Leu Pro Pro Pro Pro Phe Ala
            20

<210> SEQ ID NO 1487
<211> LENGTH: 25
<212> TYPE: PRT
<213> ORGANISM: Homo sapiens

<400> SEQUENCE: 1487

Met Ala Ala Ile Arg Met Gly Lys Leu Thr Thr Met Pro Ala Gly Leu
1               5                   10                  15

Ile Tyr Ala Ser Val Ser Val His Ala
            20                  25

<210> SEQ ID NO 1488
<211> LENGTH: 22
<212> TYPE: PRT
<213> ORGANISM: Homo sapiens

<400> SEQUENCE: 1488

Met Lys Val Leu Gly Arg Ser Phe Phe Trp Val Leu Phe Pro Val Leu
1               5                   10                  15

Pro Trp Ala Val Gln Ala
            20

<210> SEQ ID NO 1489
<211> LENGTH: 23
<212> TYPE: PRT
<213> ORGANISM: Homo sapiens

<400> SEQUENCE: 1489

Met Arg Gln Lys Ala Val Ser Leu Phe Leu Cys Tyr Leu Leu Leu Phe
1               5                   10                  15

Thr Cys Ser Gly Val Glu Ala
            20

<210> SEQ ID NO 1490
<211> LENGTH: 25
<212> TYPE: PRT
<213> ORGANISM: Homo sapiens

<400> SEQUENCE: 1490

Met Pro Pro Pro Arg Thr Gly Arg Gly Leu Leu Trp Leu Gly Leu Val
1               5                   10                  15

Leu Ser Ser Val Cys Val Ala Leu Gly
            20                  25

<210> SEQ ID NO 1491
<211> LENGTH: 23
<212> TYPE: PRT
<213> ORGANISM: Homo sapiens

<400> SEQUENCE: 1491

Met Leu Phe Arg Asn Arg Phe Leu Leu Leu Ala Leu Ala Ala Leu
1               5                   10                  15

Leu Ala Phe Val Ser Leu Ser
            20

<210> SEQ ID NO 1492
<211> LENGTH: 24
<212> TYPE: PRT
<213> ORGANISM: Homo sapiens

<400> SEQUENCE: 1492

Met Leu Pro Leu Pro Ser Cys Ser Leu Pro Ile Leu Leu Phe Leu
1               5                   10                  15

Leu Pro Ser Val Pro Ile Glu Ser
            20

<210> SEQ ID NO 1493
<211> LENGTH: 23
<212> TYPE: PRT
<213> ORGANISM: Homo sapiens

<400> SEQUENCE: 1493

Met Lys Ala Met Pro Trp Asn Trp Thr Cys Leu Leu Ser His Leu Leu
1               5                   10                  15

Met Val Gly Met Gly Ser Ser
            20

<210> SEQ ID NO 1494
<211> LENGTH: 27
<212> TYPE: PRT
<213> ORGANISM: Homo sapiens

<400> SEQUENCE: 1494

Met Ala Leu Gly Lys Val Leu Ala Met Ala Leu Val Leu Ala Leu Ala
1               5                   10                  15

Val Leu Gly Ser Leu Ser Pro Gly Ala Arg Ala
            20                  25

<210> SEQ ID NO 1495
<211> LENGTH: 24
<212> TYPE: PRT
<213> ORGANISM: Homo sapiens

<400> SEQUENCE: 1495

Met Val Pro Ser Ser Pro Arg Ala Leu Phe Leu Leu Leu Ile Leu
1               5                   10                  15

Ala Cys Pro Glu Pro Arg Ala Ser
            20

<210> SEQ ID NO 1496
<211> LENGTH: 25
<212> TYPE: PRT
<213> ORGANISM: Homo sapiens

<400> SEQUENCE: 1496

Met Cys Arg Ile Ala Gly Ala Leu Arg Thr Leu Leu Pro Leu Leu Ala
1               5                   10                  15

Ala Leu Leu Gln Ala Ser Val Glu Ala
            20                  25

<210> SEQ ID NO 1497
<211> LENGTH: 24
<212> TYPE: PRT
<213> ORGANISM: Homo sapiens

<400> SEQUENCE: 1497

Met Asn Asn Phe Arg Ala Thr Ile Leu Phe Trp Ala Ala Ala Ala Trp
1               5                   10                  15

Ala Lys Ser Gly Lys Pro Ser Gly
            20

<210> SEQ ID NO 1498
<211> LENGTH: 21
<212> TYPE: PRT
<213> ORGANISM: Homo sapiens

<400> SEQUENCE: 1498

Met His Leu Arg Leu Ile Ser Trp Leu Phe Ile Ile Leu Asn Phe Met
1               5                   10                  15

Glu Tyr Ile Gly Ser
            20

<210> SEQ ID NO 1499
<211> LENGTH: 23
<212> TYPE: PRT
<213> ORGANISM: Homo sapiens

<400> SEQUENCE: 1499

Met Lys Leu Ala Asn Trp Tyr Trp Leu Ser Ser Ala Val Leu Ala Thr
1               5                   10                  15

Tyr Gly Phe Leu Val Val Ala
            20

<210> SEQ ID NO 1500
<211> LENGTH: 24
<212> TYPE: PRT
<213> ORGANISM: Homo sapiens

<400> SEQUENCE: 1500

Met Thr Met Cys Ser Gly Ala Arg Leu Ala Leu Leu Val Tyr Gly Ile
1               5                   10                  15

Ile Met His Ser Ser Val Tyr Ser
            20

<210> SEQ ID NO 1501
<211> LENGTH: 24
<212> TYPE: PRT
<213> ORGANISM: Homo sapiens

<400> SEQUENCE: 1501

Met Gly Leu Arg Ser His His Leu Ser Leu Gly Leu Leu Leu Leu Phe
1               5                   10                  15

Leu Leu Pro Ala Glu Cys Leu Gly
            20

<210> SEQ ID NO 1502
<211> LENGTH: 26

```
<212> TYPE: PRT
<213> ORGANISM: Homo sapiens

<400> SEQUENCE: 1502

Met Gly Thr Ala Arg Ile Ala Pro Gly Leu Ala Leu Leu Cys Cys
1               5                   10                  15

Pro Val Leu Ser Ser Ala Tyr Ala Leu Val
            20                  25

<210> SEQ ID NO 1503
<211> LENGTH: 24
<212> TYPE: PRT
<213> ORGANISM: Homo sapiens

<400> SEQUENCE: 1503

Met Asp Ala Gln Thr Trp Pro Val Gly Phe Arg Cys Leu Leu Leu
1               5                   10                  15

Ala Leu Val Gly Ser Ala Arg Ser
            20

<210> SEQ ID NO 1504
<211> LENGTH: 21
<212> TYPE: PRT
<213> ORGANISM: Homo sapiens

<400> SEQUENCE: 1504

Met Tyr Arg Glu Trp Val Val Val Asn Val Phe Met Met Leu Tyr Val
1               5                   10                  15

Gln Leu Val Gln Gly
            20

<210> SEQ ID NO 1505
<211> LENGTH: 24
<212> TYPE: PRT
<213> ORGANISM: Homo sapiens

<400> SEQUENCE: 1505

Met Ser Ser Arg Ile Ala Arg Ala Leu Ala Leu Val Val Thr Leu Leu
1               5                   10                  15

His Leu Thr Arg Leu Ala Leu Ser
            20

<210> SEQ ID NO 1506
<211> LENGTH: 26
<212> TYPE: PRT
<213> ORGANISM: Homo sapiens

<400> SEQUENCE: 1506

Met Ala Arg Gly Pro Gly Leu Ala Pro Pro Pro Leu Arg Leu Pro Leu
1               5                   10                  15

Leu Leu Leu Val Leu Ala Ala Val Thr Gly
            20                  25

<210> SEQ ID NO 1507
<211> LENGTH: 24
<212> TYPE: PRT
<213> ORGANISM: Homo sapiens

<400> SEQUENCE: 1507

Met Gly Ser Leu Ser Asn Tyr Ala Leu Leu Gln Leu Thr Leu Thr Ala
1               5                   10                  15

Phe Leu Thr Ile Leu Val Gln Pro
```

<210> SEQ ID NO 1508
<211> LENGTH: 25
<212> TYPE: PRT
<213> ORGANISM: Homo sapiens

<400> SEQUENCE: 1508

Met Ala Ala Pro Thr Pro Ala Arg Pro Val Leu Thr His Leu Leu Val
1               5                   10                  15

Ala Leu Phe Gly Met Gly Ser Trp Ala
            20                  25

<210> SEQ ID NO 1509
<211> LENGTH: 21
<212> TYPE: PRT
<213> ORGANISM: Homo sapiens

<400> SEQUENCE: 1509

Met Lys Ile Gln Leu Phe Phe Phe Ile Leu His Phe Trp Val Thr Ile
1               5                   10                  15

Leu Pro Ala Arg Ser
            20

<210> SEQ ID NO 1510
<211> LENGTH: 24
<212> TYPE: PRT
<213> ORGANISM: Homo sapiens

<400> SEQUENCE: 1510

Met Glu Leu Arg Pro Trp Leu Leu Trp Val Val Ala Ala Thr Gly Thr
1               5                   10                  15

Leu Val Leu Leu Ala Ala Asp Ala
            20

<210> SEQ ID NO 1511
<211> LENGTH: 25
<212> TYPE: PRT
<213> ORGANISM: Homo sapiens

<400> SEQUENCE: 1511

Met Ala Arg Ala Gly Trp Thr Ser Pro Val Pro Leu Cys Val Cys Leu
1               5                   10                  15

Leu Leu Thr Cys Gly Phe Ala Glu Ala
            20                  25

<210> SEQ ID NO 1512
<211> LENGTH: 25
<212> TYPE: PRT
<213> ORGANISM: Homo sapiens

<400> SEQUENCE: 1512

Met Lys Gly Gly Cys Val Ser Gln Trp Lys Ala Ala Ala Gly Phe Leu
1               5                   10                  15

Phe Cys Val Met Val Phe Ala Ser Ala
            20                  25

<210> SEQ ID NO 1513
<211> LENGTH: 24
<212> TYPE: PRT
<213> ORGANISM: Homo sapiens

<400> SEQUENCE: 1513

Met Cys Ala Glu Arg Leu Gly Gln Phe Met Thr Leu Ala Leu Val Leu
1               5                   10                  15

Ala Thr Phe Asp Pro Ala Arg Gly
            20

<210> SEQ ID NO 1514
<211> LENGTH: 24
<212> TYPE: PRT
<213> ORGANISM: Homo sapiens

<400> SEQUENCE: 1514

Met Leu Ser Phe Val Asp Thr Arg Thr Leu Leu Leu Ala Val Thr
1               5                   10                  15

Leu Cys Leu Ala Thr Cys Gln Ser
            20

<210> SEQ ID NO 1515
<211> LENGTH: 24
<212> TYPE: PRT
<213> ORGANISM: Homo sapiens

<400> SEQUENCE: 1515

Met Arg Thr Ala Pro Ser Leu Arg Arg Cys Val Cys Leu Leu Leu Ala
1               5                   10                  15

Ala Ile Leu Asp Leu Ala Arg Gly
            20

<210> SEQ ID NO 1516
<211> LENGTH: 25
<212> TYPE: PRT
<213> ORGANISM: Homo sapiens

<400> SEQUENCE: 1516

Met Lys Pro Ala Thr Gly Leu Trp Val Trp Val Ser Leu Leu Val Ala
1               5                   10                  15

Ala Gly Thr Val Gln Pro Ser Asp Ser
            20                  25

<210> SEQ ID NO 1517
<211> LENGTH: 23
<212> TYPE: PRT
<213> ORGANISM: Homo sapiens

<400> SEQUENCE: 1517

Met Gly Ile Phe Leu Val Tyr Val Gly Phe Val Phe Phe Ser Val Leu
1               5                   10                  15

Tyr Val Gln Gln Gly Leu Ser
            20

<210> SEQ ID NO 1518
<211> LENGTH: 26
<212> TYPE: PRT
<213> ORGANISM: Homo sapiens

<400> SEQUENCE: 1518

Met Pro Ser Leu Pro Ala Pro Pro Ala Pro Leu Leu Leu Gly Leu
1               5                   10                  15

Leu Leu Leu Gly Ser Arg Pro Ala Arg Gly
            20                  25

<210> SEQ ID NO 1519

```
<211> LENGTH: 24
<212> TYPE: PRT
<213> ORGANISM: Homo sapiens

<400> SEQUENCE: 1519

Met Arg Lys His Val Leu Ala Ala Ser Phe Ser Met Leu Ser Leu Leu
1               5                   10                  15

Val Ile Met Gly Asp Thr Asp Ser
            20

<210> SEQ ID NO 1520
<211> LENGTH: 24
<212> TYPE: PRT
<213> ORGANISM: Homo sapiens

<400> SEQUENCE: 1520

Met Asn Val Asp Ala Glu Ala Ser Met Ala Val Ile Ser Leu Leu Phe
1               5                   10                  15

Leu Ala Val Met Tyr Val Val His
            20

<210> SEQ ID NO 1521
<211> LENGTH: 25
<212> TYPE: PRT
<213> ORGANISM: Homo sapiens

<400> SEQUENCE: 1521

Met Ser Pro Pro Pro Leu Leu Gln Pro Leu Leu Leu Leu Pro Leu
1               5                   10                  15

Leu Asn Val Glu Pro Ser Gly Ala Thr
            20                  25

<210> SEQ ID NO 1522
<211> LENGTH: 24
<212> TYPE: PRT
<213> ORGANISM: Homo sapiens

<400> SEQUENCE: 1522

Met Arg Val Met Ala Pro Arg Thr Leu Ile Leu Leu Leu Ser Gly Ala
1               5                   10                  15

Leu Ala Leu Thr Glu Thr Trp Ala
            20

<210> SEQ ID NO 1523
<211> LENGTH: 24
<212> TYPE: PRT
<213> ORGANISM: Homo sapiens

<400> SEQUENCE: 1523

Met Arg Val Met Ala Pro Arg Thr Leu Ile Leu Leu Leu Ser Gly Ala
1               5                   10                  15

Leu Ala Leu Thr Glu Thr Trp Ala
            20

<210> SEQ ID NO 1524
<211> LENGTH: 24
<212> TYPE: PRT
<213> ORGANISM: Homo sapiens

<400> SEQUENCE: 1524

Met Arg Val Met Ala Pro Arg Thr Leu Ile Leu Leu Leu Ser Gly Ala
1               5                   10                  15
```

-continued

Leu Ala Leu Thr Glu Thr Trp Ala
            20

<210> SEQ ID NO 1525
<211> LENGTH: 24
<212> TYPE: PRT
<213> ORGANISM: Homo sapiens

<400> SEQUENCE: 1525

Met Arg Val Met Ala Pro Arg Thr Leu Ile Leu Leu Leu Ser Gly Ala
1               5                   10                  15

Leu Ala Leu Thr Glu Thr Trp Ala
            20

<210> SEQ ID NO 1526
<211> LENGTH: 24
<212> TYPE: PRT
<213> ORGANISM: Homo sapiens

<400> SEQUENCE: 1526

Met Arg Val Met Ala Pro Arg Thr Leu Ile Leu Leu Leu Ser Gly Ala
1               5                   10                  15

Leu Ala Leu Thr Glu Thr Trp Ala
            20

<210> SEQ ID NO 1527
<211> LENGTH: 25
<212> TYPE: PRT
<213> ORGANISM: Homo sapiens

<400> SEQUENCE: 1527

Met Thr Ser Cys Gly Gln Gln Ser Leu Asn Val Leu Ala Val Leu Phe
1               5                   10                  15

Ser Leu Leu Phe Ser Ala Val Leu Ser
            20                  25

<210> SEQ ID NO 1528
<211> LENGTH: 24
<212> TYPE: PRT
<213> ORGANISM: Homo sapiens

<400> SEQUENCE: 1528

Met Ala Thr Arg Ser Val Leu Leu Ala Leu Val Val Leu Asn Leu Leu
1               5                   10                  15

Phe Tyr Val Pro Pro Gly Arg Ser
            20

<210> SEQ ID NO 1529
<211> LENGTH: 24
<212> TYPE: PRT
<213> ORGANISM: Homo sapiens

<400> SEQUENCE: 1529

Met Ala Arg Phe Leu Thr Leu Cys Thr Trp Leu Leu Leu Leu Gly Pro
1               5                   10                  15

Gly Leu Leu Ala Thr Val Arg Ala
            20

<210> SEQ ID NO 1530
<211> LENGTH: 23
<212> TYPE: PRT
<213> ORGANISM: Homo sapiens

```
<400> SEQUENCE: 1530

Met His Thr Leu Thr Gly Phe Ser Leu Val Ser Leu Leu Ser Phe Gly
1               5                   10                  15

Tyr Leu Ser Trp Asp Trp Ala
            20

<210> SEQ ID NO 1531
<211> LENGTH: 21
<212> TYPE: PRT
<213> ORGANISM: Homo sapiens

<400> SEQUENCE: 1531

Met His Trp Gly Thr Leu Cys Gly Phe Leu Trp Leu Trp Pro Tyr Leu
1               5                   10                  15

Phe Tyr Val Gln Ala
            20

<210> SEQ ID NO 1532
<211> LENGTH: 26
<212> TYPE: PRT
<213> ORGANISM: Homo sapiens

<400> SEQUENCE: 1532

Met Arg Ala Val Pro Leu Pro Ala Pro Leu Leu Pro Leu Leu Leu Leu
1               5                   10                  15

Ala Leu Leu Ala Ala Pro Ala Ala Arg Ala
            20                  25

<210> SEQ ID NO 1533
<211> LENGTH: 24
<212> TYPE: PRT
<213> ORGANISM: Homo sapiens

<400> SEQUENCE: 1533

Met Val Val Met Ala Pro Arg Thr Leu Phe Leu Leu Leu Ser Gly Ala
1               5                   10                  15

Leu Thr Leu Thr Glu Thr Trp Ala
            20

<210> SEQ ID NO 1534
<211> LENGTH: 23
<212> TYPE: PRT
<213> ORGANISM: Homo sapiens

<400> SEQUENCE: 1534

Met Ile Ser Ser Val Lys Leu Asn Leu Ile Leu Val Leu Ser Leu Ser
1               5                   10                  15

Thr Met His Val Phe Trp Cys
            20

<210> SEQ ID NO 1535
<211> LENGTH: 23
<212> TYPE: PRT
<213> ORGANISM: Homo sapiens

<400> SEQUENCE: 1535

Met Lys Thr Phe Thr Trp Thr Leu Gly Val Leu Phe Phe Leu Leu Val
1               5                   10                  15

Asp Thr Gly His Cys Arg Gly
            20
```

<210> SEQ ID NO 1536
<211> LENGTH: 25
<212> TYPE: PRT
<213> ORGANISM: Homo sapiens

<400> SEQUENCE: 1536

Met Ala Ser Val Ala Trp Ala Val Leu Lys Val Leu Leu Leu Pro
1               5                   10                  15

Thr Gln Thr Trp Ser Pro Val Gly Ala
            20                  25

<210> SEQ ID NO 1537
<211> LENGTH: 25
<212> TYPE: PRT
<213> ORGANISM: Homo sapiens

<400> SEQUENCE: 1537

Met Ala Ser Val Ala Trp Ala Val Leu Lys Val Leu Leu Leu Pro
1               5                   10                  15

Thr Gln Thr Trp Ser Pro Val Gly Ala
            20                  25

<210> SEQ ID NO 1538
<211> LENGTH: 25
<212> TYPE: PRT
<213> ORGANISM: Homo sapiens

<400> SEQUENCE: 1538

Met Arg Trp Leu Trp Pro Leu Ala Val Ser Leu Ala Val Ile Leu Ala
1               5                   10                  15

Val Gly Leu Ser Arg Val Ser Gly Gly
            20                  25

<210> SEQ ID NO 1539
<211> LENGTH: 27
<212> TYPE: PRT
<213> ORGANISM: Homo sapiens

<400> SEQUENCE: 1539

Met Ala Ala Ala Ser Ala Gly Ala Thr Arg Leu Leu Leu Leu Leu
1               5                   10                  15

Met Ala Val Ala Ala Pro Ser Arg Ala Arg Gly
            20                  25

<210> SEQ ID NO 1540
<211> LENGTH: 25
<212> TYPE: PRT
<213> ORGANISM: Homo sapiens

<400> SEQUENCE: 1540

Met Gly Thr Arg Gly Ala Val Met Pro Pro Met Trp Gly Leu Leu
1               5                   10                  15

Gly Cys Cys Phe Val Cys Ala Trp Ala
            20                  25

<210> SEQ ID NO 1541
<211> LENGTH: 27
<212> TYPE: PRT
<213> ORGANISM: Homo sapiens

<400> SEQUENCE: 1541

Met Lys Pro Ala Leu Leu Pro Trp Ala Leu Leu Leu Leu Ala Thr Ala
1               5                   10                  15

Leu Gly Pro Gly Pro Gly Pro Thr Ala Asp Ala
            20                  25

<210> SEQ ID NO 1542
<211> LENGTH: 24
<212> TYPE: PRT
<213> ORGANISM: Homo sapiens

<400> SEQUENCE: 1542

Met Gln Lys Ile Met His Ile Ser Val Leu Leu Ser Pro Val Leu Trp
1               5                   10                  15

Gly Leu Ile Phe Gly Val Ser Ser
            20

<210> SEQ ID NO 1543
<211> LENGTH: 25
<212> TYPE: PRT
<213> ORGANISM: Homo sapiens

<400> SEQUENCE: 1543

Met His Pro Asp Leu Gly Pro Leu Cys Thr Leu Leu Tyr Val Thr Leu
1               5                   10                  15

Thr Ile Leu Cys Ser Ser Val Ser Ser
            20                  25

<210> SEQ ID NO 1544
<211> LENGTH: 25
<212> TYPE: PRT
<213> ORGANISM: Homo sapiens

<400> SEQUENCE: 1544

Met Ser Leu Met Val Val Ser Met Ala Cys Val Gly Phe Phe Leu Leu
1               5                   10                  15

Glu Gly Pro Trp Pro His Val Gly Gly
            20                  25

<210> SEQ ID NO 1545
<211> LENGTH: 23
<212> TYPE: PRT
<213> ORGANISM: Homo sapiens

<400> SEQUENCE: 1545

Met Glu Pro Arg Leu Phe Cys Trp Thr Thr Leu Phe Leu Leu Ala Gly
1               5                   10                  15

Trp Cys Leu Pro Gly Leu Pro
            20

<210> SEQ ID NO 1546
<211> LENGTH: 23
<212> TYPE: PRT
<213> ORGANISM: Homo sapiens

<400> SEQUENCE: 1546

Met Lys Cys Thr Ala Arg Glu Trp Leu Arg Val Thr Thr Val Leu Phe
1               5                   10                  15

Met Ala Arg Ala Ile Pro Ala
            20

<210> SEQ ID NO 1547
<211> LENGTH: 27
<212> TYPE: PRT
<213> ORGANISM: Homo sapiens

```
<400> SEQUENCE: 1547

Met Pro Pro Ala Gly Leu Arg Arg Ala Ala Pro Leu Thr Ala Ile Ala
1               5                   10                  15

Leu Leu Val Leu Gly Ala Pro Leu Val Leu Ala
            20                  25

<210> SEQ ID NO 1548
<211> LENGTH: 25
<212> TYPE: PRT
<213> ORGANISM: Homo sapiens

<400> SEQUENCE: 1548

Met Glu Ala Leu Leu Gly Ala Gly Leu Leu Gly Ala Tyr Val
1               5                   10                  15

Leu Val Tyr Tyr Asn Leu Val Lys Ala
            20                  25

<210> SEQ ID NO 1549
<211> LENGTH: 24
<212> TYPE: PRT
<213> ORGANISM: Homo sapiens

<400> SEQUENCE: 1549

Met Lys Ile Thr Ser Thr Ser Cys Ile Cys Pro Val Leu Val Cys Leu
1               5                   10                  15

Cys Phe Val Gln Arg Cys Tyr Gly
            20

<210> SEQ ID NO 1550
<211> LENGTH: 24
<212> TYPE: PRT
<213> ORGANISM: Homo sapiens

<400> SEQUENCE: 1550

Met Arg Val Thr Ala Pro Arg Thr Val Leu Leu Leu Trp Gly Ala
1               5                   10                  15

Val Ala Leu Thr Glu Thr Trp Ala
            20

<210> SEQ ID NO 1551
<211> LENGTH: 24
<212> TYPE: PRT
<213> ORGANISM: Homo sapiens

<400> SEQUENCE: 1551

Met Arg Val Thr Ala Pro Arg Thr Val Leu Leu Leu Trp Gly Ala
1               5                   10                  15

Val Ala Leu Thr Glu Thr Trp Ala
            20

<210> SEQ ID NO 1552
<211> LENGTH: 24
<212> TYPE: PRT
<213> ORGANISM: Homo sapiens

<400> SEQUENCE: 1552

Met Arg Val Thr Ala Pro Arg Thr Val Leu Leu Leu Trp Gly Ala
1               5                   10                  15

Val Ala Leu Thr Glu Thr Trp Ala
            20
```

<210> SEQ ID NO 1553
<211> LENGTH: 25
<212> TYPE: PRT
<213> ORGANISM: Homo sapiens

<400> SEQUENCE: 1553

Met Ala Arg Ala Gly Trp Thr Gly Leu Leu Pro Leu Tyr Val Cys Leu
1               5                   10                  15

Leu Leu Thr Cys Gly Phe Ala Lys Ala
            20                  25

<210> SEQ ID NO 1554
<211> LENGTH: 28
<212> TYPE: PRT
<213> ORGANISM: Homo sapiens

<400> SEQUENCE: 1554

Met Ala Gly Pro Gly Ser Pro Arg Arg Ala Ser Arg Gly Ala Ser Ala
1               5                   10                  15

Leu Leu Ala Ala Ala Leu Leu Tyr Ala Ala Leu Gly
            20                  25

<210> SEQ ID NO 1555
<211> LENGTH: 25
<212> TYPE: PRT
<213> ORGANISM: Homo sapiens

<400> SEQUENCE: 1555

Met Leu Gly Ile Trp Thr Leu Leu Pro Leu Val Leu Thr Ser Val Ala
1               5                   10                  15

Arg Leu Ser Ser Lys Ser Val Asn Ala
            20                  25

<210> SEQ ID NO 1556
<211> LENGTH: 23
<212> TYPE: PRT
<213> ORGANISM: Homo sapiens

<400> SEQUENCE: 1556

Met Val Leu Ala Phe Gln Leu Val Ser Phe Thr Tyr Ile Trp Ile Ile
1               5                   10                  15

Leu Lys Pro Asn Val Cys Ala
            20

<210> SEQ ID NO 1557
<211> LENGTH: 24
<212> TYPE: PRT
<213> ORGANISM: Homo sapiens

<400> SEQUENCE: 1557

Met Asp Ser Leu Pro Arg Leu Thr Ser Val Leu Thr Leu Leu Phe Ser
1               5                   10                  15

Gly Leu Trp His Leu Gly Leu Thr
            20

<210> SEQ ID NO 1558
<211> LENGTH: 23
<212> TYPE: PRT
<213> ORGANISM: Homo sapiens

<400> SEQUENCE: 1558

Met Ala His Thr Phe Arg Gly Cys Ser Leu Ala Phe Met Phe Ile Ile

-continued

```
1               5                   10                  15

Thr Trp Leu Leu Ile Lys Ala
            20

<210> SEQ ID NO 1559
<211> LENGTH: 23
<212> TYPE: PRT
<213> ORGANISM: Homo sapiens

<400> SEQUENCE: 1559

Met Gln Lys Leu Gln Leu Cys Val Tyr Ile Tyr Leu Phe Met Leu Ile
1               5                   10                  15

Val Ala Gly Pro Val Asp Leu
            20

<210> SEQ ID NO 1560
<211> LENGTH: 26
<212> TYPE: PRT
<213> ORGANISM: Homo sapiens

<400> SEQUENCE: 1560

Met Ser Gln Ala Trp Val Pro Gly Leu Ala Pro Thr Leu Leu Phe Ser
1               5                   10                  15

Leu Leu Ala Gly Pro Gln Lys Ile Ala Ala
            20                  25

<210> SEQ ID NO 1561
<211> LENGTH: 23
<212> TYPE: PRT
<213> ORGANISM: Homo sapiens

<400> SEQUENCE: 1561

Met Tyr Phe Leu Thr Pro Ile Leu Val Ala Ile Leu Cys Ile Leu Val
1               5                   10                  15

Val Trp Ile Phe Lys Asn Ala
            20

<210> SEQ ID NO 1562
<211> LENGTH: 26
<212> TYPE: PRT
<213> ORGANISM: Homo sapiens

<400> SEQUENCE: 1562

Met Gln Gly Ala Gln Glu Ala Ser Ala Ser Glu Met Leu Pro Leu Leu
1               5                   10                  15

Leu Pro Leu Leu Trp Ala Gly Ala Leu Ala
            20                  25

<210> SEQ ID NO 1563
<211> LENGTH: 26
<212> TYPE: PRT
<213> ORGANISM: Homo sapiens

<400> SEQUENCE: 1563

Met Pro Gly Pro Pro Ala Leu Arg Arg Arg Leu Leu Leu Leu Leu Leu
1               5                   10                  15

Val Leu Leu Ile Ala Gly Ser Ala Gly Ala
            20                  25

<210> SEQ ID NO 1564
<211> LENGTH: 24
<212> TYPE: PRT
```

<213> ORGANISM: Homo sapiens

<400> SEQUENCE: 1564

Met Arg Val Thr Ala Pro Arg Thr Leu Leu Leu Leu Trp Gly Ala
1               5                   10                  15

Val Ala Leu Thr Glu Thr Trp Ala
            20

<210> SEQ ID NO 1565
<211> LENGTH: 25
<212> TYPE: PRT
<213> ORGANISM: Homo sapiens

<400> SEQUENCE: 1565

Met Val Ala Trp Arg Ser Ala Phe Leu Val Cys Leu Ala Phe Ser Leu
1               5                   10                  15

Ala Thr Leu Val Gln Arg Gly Ser Gly
            20                  25

<210> SEQ ID NO 1566
<211> LENGTH: 27
<212> TYPE: PRT
<213> ORGANISM: Homo sapiens

<400> SEQUENCE: 1566

Cys Leu Lys Phe Pro Gly Gly Ser Cys Met Ala Ala Leu Thr Val Thr
1               5                   10                  15

Leu Met Val Leu Ser Ser Pro Leu Ala Leu Ala
            20                  25

<210> SEQ ID NO 1567
<211> LENGTH: 26
<212> TYPE: PRT
<213> ORGANISM: Homo sapiens

<400> SEQUENCE: 1567

Met Ala Ala Gly Ser Arg Thr Ser Leu Leu Leu Ala Phe Gly Leu Leu
1               5                   10                  15

Cys Leu Ser Trp Leu Gln Glu Gly Ser Ala
            20                  25

<210> SEQ ID NO 1568
<211> LENGTH: 26
<212> TYPE: PRT
<213> ORGANISM: Homo sapiens

<400> SEQUENCE: 1568

Met Ala Ala Gly Ser Arg Thr Ser Leu Leu Leu Ala Phe Gly Leu Leu
1               5                   10                  15

Cys Leu Ser Trp Leu Gln Glu Gly Ser Ala
            20                  25

<210> SEQ ID NO 1569
<211> LENGTH: 28
<212> TYPE: PRT
<213> ORGANISM: Homo sapiens

<400> SEQUENCE: 1569

Met Tyr Ser Phe Asn Thr Leu Arg Leu Tyr Leu Trp Glu Thr Ile Val
1               5                   10                  15

Phe Phe Ser Leu Ala Ala Ser Lys Glu Ala Glu Ala
            20                  25

<210> SEQ ID NO 1570
<211> LENGTH: 31
<212> TYPE: PRT
<213> ORGANISM: Homo sapiens

<400> SEQUENCE: 1570

Met Glu Pro Gly Pro Thr Ala Ala Gln Arg Arg Cys Ser Leu Pro Pro
1               5                   10                  15

Trp Leu Pro Leu Gly Leu Leu Leu Trp Ser Gly Leu Ala Leu Gly
            20                  25                  30

<210> SEQ ID NO 1571
<211> LENGTH: 30
<212> TYPE: PRT
<213> ORGANISM: Homo sapiens

<400> SEQUENCE: 1571

Met Lys Thr Gln Arg Asp Gly His Ser Leu Gly Arg Trp Ser Leu Val
1               5                   10                  15

Leu Leu Leu Leu Gly Leu Val Met Pro Leu Ala Ile Ile Ala
            20                  25                  30

<210> SEQ ID NO 1572
<211> LENGTH: 29
<212> TYPE: PRT
<213> ORGANISM: Homo sapiens

<400> SEQUENCE: 1572

Met Ser Pro Val Arg Arg Trp Gly Ser Pro Cys Leu Phe Pro Leu Gln
1               5                   10                  15

Leu Phe Ser Leu Cys Trp Val Leu Ser Val Ala Gln Ser
            20                  25

<210> SEQ ID NO 1573
<211> LENGTH: 30
<212> TYPE: PRT
<213> ORGANISM: Homo sapiens

<400> SEQUENCE: 1573

Met Cys Phe Pro Lys Val Leu Ser Asp Asp Met Lys Lys Leu Lys Ala
1               5                   10                  15

Arg Met Val Met Leu Leu Pro Thr Ser Ala Gln Gly Leu Gly
            20                  25                  30

<210> SEQ ID NO 1574
<211> LENGTH: 30
<212> TYPE: PRT
<213> ORGANISM: Homo sapiens

<400> SEQUENCE: 1574

Met Leu Arg Gly Ile Ser Gln Leu Pro Ala Val Ala Thr Met Ser Trp
1               5                   10                  15

Val Leu Leu Pro Val Leu Trp Leu Ile Val Gln Thr Gln Ala
            20                  25                  30

<210> SEQ ID NO 1575
<211> LENGTH: 30
<212> TYPE: PRT
<213> ORGANISM: Homo sapiens

<400> SEQUENCE: 1575

-continued

Met Arg Arg Ile Ser Leu Thr Ser Ser Pro Val Arg Leu Leu Leu Phe
1               5                   10                  15

Leu Leu Leu Leu Leu Ile Ala Leu Glu Ile Met Val Gly Gly
            20                  25                  30

<210> SEQ ID NO 1576
<211> LENGTH: 30
<212> TYPE: PRT
<213> ORGANISM: Homo sapiens

<400> SEQUENCE: 1576

Met Cys Ser Tyr Tyr His Met Lys Lys Arg Ser Val Ser Gly Cys Asn
1               5                   10                  15

Ile Thr Ile Phe Ala Val Met Phe Ser His Leu Ser Ala Gly
            20                  25                  30

<210> SEQ ID NO 1577
<211> LENGTH: 28
<212> TYPE: PRT
<213> ORGANISM: Homo sapiens

<400> SEQUENCE: 1577

Met Asn Trp Glu Leu Leu Leu Trp Leu Leu Val Leu Cys Ala Leu Leu
1               5                   10                  15

Leu Leu Leu Val Gln Leu Leu Arg Phe Leu Arg Ala
            20                  25

<210> SEQ ID NO 1578
<211> LENGTH: 30
<212> TYPE: PRT
<213> ORGANISM: Homo sapiens

<400> SEQUENCE: 1578

Met Lys Cys Leu Gly Lys Arg Gly Gln Ala Ala Ala Phe Leu Pro
1               5                   10                  15

Leu Cys Trp Leu Phe Leu Lys Ile Leu Gln Pro Gly His Ser
            20                  25                  30

<210> SEQ ID NO 1579
<211> LENGTH: 28
<212> TYPE: PRT
<213> ORGANISM: Homo sapiens

<400> SEQUENCE: 1579

Met Lys Thr Lys Leu Asn Ile Tyr Asn Met Gln Phe Leu Leu Phe Val
1               5                   10                  15

Phe Leu Val Trp Asp Pro Ala Arg Leu Val Leu Ala
            20                  25

<210> SEQ ID NO 1580
<211> LENGTH: 29
<212> TYPE: PRT
<213> ORGANISM: Homo sapiens

<400> SEQUENCE: 1580

Met Ala Trp Lys Ser Ser Val Ile Met Gln Met Gly Arg Phe Leu Leu
1               5                   10                  15

Leu Val Ile Leu Phe Leu Pro Arg Glu Met Thr Ser Ser
            20                  25